US007888558B2

(12) United States Patent
Gutterson et al.

(10) Patent No.: US 7,888,558 B2
(45) Date of Patent: Feb. 15, 2011

(54) CONFERRING BIOTIC AND ABIOTIC STRESS TOLERANCE IN PLANTS

(75) Inventors: Neal I. Gutterson, Oakland, CA (US); Oliver Ratcliffe, Oakland, CA (US); Emily L. Queen, San Bruno, CA (US); T. Lynne Reuber, San Mateo, CA (US); Karen S. Century, Albany, CA (US); Roger Canales, Westerly, RI (US)

(73) Assignee: Mendel Biotechnology, Inc., Hayward, CA (US)

( * ) Notice: Subject to any disclaimer, the term of this patent is extended or adjusted under 35 U.S.C. 154(b) by 218 days.

(21) Appl. No.: 11/981,576

(22) Filed: Oct. 30, 2007

(65) Prior Publication Data

US 2008/0301840 A1    Dec. 4, 2008

Related U.S. Application Data

(60) Continuation-in-part of application No. 11/479,226, filed on Jun. 30, 2006, which is a continuation-in-part of application No. 09/713,994, filed on Nov. 16, 2000, (Continued)

(60) Provisional application No. 60/961,403, filed on Jul. 20, 2007, provisional application No. 60/166,228, (Continued)

(30) Foreign Application Priority Data

Aug. 31, 2006   (WO) .................. PCT/US2006/03461

(51) Int. Cl.
*C12N 15/82* (2006.01)
*A01H 5/00* (2006.01)
*A01H 5/10* (2006.01)

(52) U.S. Cl. ....................... 800/289; 800/298; 800/320; 435/320.1; 435/252.3

(58) Field of Classification Search ........................ None
See application file for complete search history.

(56) References Cited

U.S. PATENT DOCUMENTS

| | | | |
|---|---|---|---|
| 5,892,009 | A | 4/1999 | Thomashow et al. |
| 5,981,729 | A | 11/1999 | Chun et al. |
| 5,994,622 | A | 11/1999 | Jofuku et al. |
| 6,093,874 | A | 7/2000 | Jofuku et al. |
| 6,121,513 | A | 9/2000 | Zhang et al. |
| 6,248,937 | B1 | 6/2001 | Finkelstein et al. |

(Continued)

FOREIGN PATENT DOCUMENTS

| | | |
|---|---|---|
| EP | 1033405 | 9/2000 |
| JP | 2005-013214 | 1/2005 |
| KR | 1020040050633 | 6/2004 |
| WO | WO9632007 | 10/1996 |
| WO | WO9747183 | 12/1997 |
| WO | WO9807842 | 2/1998 |

(Continued)

OTHER PUBLICATIONS

Asamizu, et al. (2000) Generation of 7137 non-redundant expressed sequence tags from a legume, *Lotus japonicus*. DNA Res. 7 (2), 127-130.
Ayele, et al. (2005) Whole genome shotgun sequencing of *Brassica oleracea* and its application to gene discovery and annotation in *Arabidopsis*. Genome Res. 15 (4), 487-495.
Baerson, et al. (1994) Identification of domains in an *Arabidopsis acyl* carrier protein gene promoter required for maximal organ-specific expression. Plant Mol Biol. Dec. 1994;26(6):1947-59.
Baerson, et al. (1993) Developmental regulation of an acyl carrier protein gene promoter in vegetative and reproductive tissues. Plant Mol Biol. May 1993;22(2):255-67.
Balciunas, et al. (200). Evidence of domain swapping within the jumonji family of transcription factors. Trends Biochem Sci. Jun. 2000;25(6):274-6.
Baumann, et al. (1999) The DNA binding site of the Dof protein NtBBF1 is essential for tissue-specific and auxin-regulated expression of the rolB oncogene in plants. Plant Cell. Mar. 1999;11(3):323-34.
Berrocal-Lobo, M., et al. (2002). Constitutive expression of Ethylene-Response-Factor1 in *Arabidopsis* confers resistance to several necrotrophic fungi. Plant J 29, 23-32.
Bird, et al. (1988) Plant Mol. Biol. 11:651-662.
Boggon et al. (Dec. 1999). Implication of tubby proteins as transcription factors by structure-based functional analysis. Science 286:2119-2125.
Bohmert et al., AGO1 defines a novel locus of *Arabidopsis* controlling leaf development, EMBO J. (Jan. 2, 1998).
Bowman et al., Crabs Claw, a gene that regulates carpel and nectary developments in *Arabidopsis*, encodes a novel protein . . . , Development (Jun. 1999) 126:2387-2396.
Buchel, et al. (1999) Mutation of GT-1 binding sites in the Pr-1A promoter influences the level of inducible gene expression in vivo. Plant Mol Biol. Jun. 1999;40(3):387-96.
Bustin and Reeves (1996) High-mobility-group chromosomal proteins: architectural components that facilitate chromatin function. Prog. Nucl. Acids Res. Mol. Biol. 54:35-100.
Cao, et al. (2001) Effect of two conserved amino acid residues on DREB1A function. Biochemistry (Mosc). Jun. 2001;66(6):623-7.
Chao et al., Activation of the Ethylene Gas Response Pathway in *Arabidopsis* by the Nuclear Protein . . . , Cell (Jun. 27, 1997) 89:1133-1144.
Cheong, Y.H., et al. (2003). BWMK1, a rice mitogen-activated protein kinase, locates in the nucleus and mediates pathogenesis-related gene expression by activation of a transcription factor. Plant Physiol 132, 1961-1972.
Christiansen, et al. (1996) A novel type of DNA-binding protein interacts with a conserved sequence in an early nodulin ENOD12 promoter, Plant Mol Biol. Dec. 1996;32(5):809-21.

(Continued)

*Primary Examiner*—Cynthia Collins
(74) *Attorney, Agent, or Firm*—Jeffrey M. Libby; Yifan Mao

(57) ABSTRACT

The invention relates to plant transcription factor polypeptides, polynucleotides that encode them, homologs from a variety of plant species, and methods of using the polynucleotides and polypeptides to produce transgenic plants having advantageous properties, tolerance low nitrogen, cold and water deficit conditions, and resistance to disease, as compared to wild-type or other control plants.

20 Claims, 16 Drawing Sheets

Figure 1:
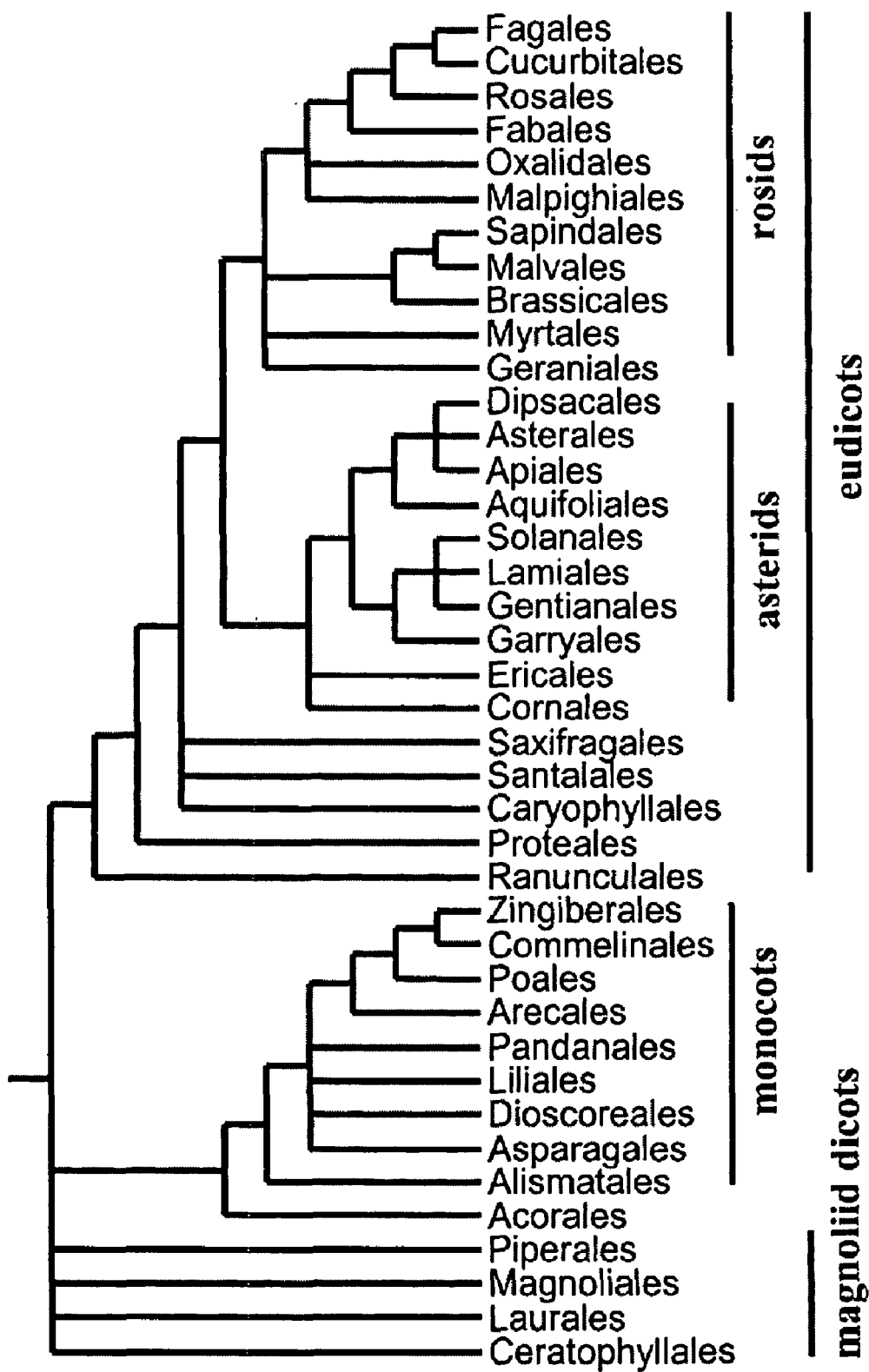

Related U.S. Application Data now abandoned, and a continuation-in-part of application No. 11/725,235, filed on Mar. 16, 2007, now Pat. No. 7,601,893, which is a division of application No. 10/225,068, filed on Aug. 9, 2002, now Pat. No. 7,193,129, and a continuation-in-part of application No. 09/837,944, filed on Apr. 18, 2001, now abandoned, and a continuation-in-part of application No. 10/171,468, filed on Jun. 14, 2002, now abandoned, application No. 11/981,576, which is a continuation-in-part of application No. 11/728,567, filed on Mar. 26, 2007, now Pat. No. 7,635,800, which is a division of application No. 10/225,066, filed on Aug. 9, 2002, now Pat. No. 7,238,860, and a continuation-in-part of application No. 10/171,468, filed on Jun. 14, 2002, now abandoned, application No. 11/981,576, which is a continuation-in-part of application No. 10/374,780, filed on Feb. 25, 2003, now Pat. No. 7,511,190, which is a continuation-in-part of application No. 09/934,455, filed on Aug. 22, 2001, now abandoned, and a continuation-in-part of application No. 09/713,994, filed on Nov. 16, 2000, now abandoned, which is a continuation-in-part of application No. 09/837,944, filed on Apr. 18, 2001, now abandoned, said application No. 10/374,780 is a continuation-in-part of application No. 10/225,068, filed on Aug. 9, 2002, now Pat. No. 7,193,129, and a continuation-in-part of application No. 10/225,066, filed on Aug. 9, 2002, now Pat. No. 7,238,860, application No. 11/981,576, which is a continuation-in-part of application No. 10/546,266, filed as application No. PCT/US2004/005654 on Feb. 25, 2004, now Pat. No. 7,659,446, which is a continuation-in-part of application No. 10/374,780, filed on Feb. 25, 2003, now Pat. No. 7,511,190, application No. 11/981,576, which is a continuation-in-part of application No. 10/559,441, filed as application No. PCT/US2004/017768 on Jun. 4, 2004, now abandoned, which is a continuation-in-part of application No. 10/456,882, filed on Jun. 6, 2003, now abandoned, application No. 11/981,576, which is a continuation-in-part of application No. 11/642,814, filed on Dec. 20, 2006, which is a division of application No. 10/666,642, filed on Sep. 18, 2003, now Pat. No. 7,196,245, application No. 11/981,576, which is a continuation-in-part of application No. 10/714,887, filed on Nov. 13, 2003, which is a continuation-in-part of application No. 10/456,882, filed on Jun. 6, 2003, now abandoned, and a continuation-in-part of application No. 10/666,642, filed on Sep. 18, 2003, now Pat. No. 7,196,245, application No. 11/981,576, which is a continuation-in-part of application No. 11/435,388, filed on May 16, 2006, now Pat. No. 7,663,025, which is a continuation-in-part of application No. PCT/US2004/037584, filed on Nov. 12, 2004, which is a continuation-in-part of application No. 10/714,887, filed on Nov. 13, 2003, application No. 11/981,576, which is a continuation-in-part of application No. 11/632,390, filed as application No. PCT/US2005/025010 on Jul. 14, 2005, and a continuation-in-part of application No. PCT/US2006/034615, filed on Aug. 31, 2006, application No. 11/981,576, which is a continuation-in-part of application No. 10/903,236, filed on Jul. 30, 2004, which is a continuation-in-part of application No. 10/456,882, filed on Jun. 6, 2003, now abandoned, and a continuation-in-part of application No. 10/666,642, filed on Sep. 18, 2003, now Pat. No. 7,196,245, application No. 11/981,576, which is a continuation-in-part of application No. 11/699,973, filed on Jan. 29, 2007, now abandoned, which is a continuation-in-part of application No. PCT/US2005/027151, filed on Mar. 30, 2006, which is a continuation-in-part of application No. 10/903,236, filed on Jul. 30, 2004.

(60) filed on Nov. 17, 1999, provisional application No. 60/310,847, filed on Aug. 9, 2001, provisional application No. 60/336,049, filed on Nov. 19, 2001, provisional application No. 60/338,692, filed on Dec. 11, 2001, provisional application No. 60/310,847, filed on Aug. 9, 2001, provisional application No. 60/336,049, filed on Nov. 19, 2001, provisional application No. 60/338,692, filed on Dec. 11, 2001, provisional application No. 60/411,837, filed on Sep. 18, 2002, provisional application No. 60/465,809, filed on Apr. 24, 2003, provisional application No. 60/713,952, filed on Aug. 31, 2005.

(56) References Cited

U.S. PATENT DOCUMENTS

| | | |
|---|---|---|
| 6,329,567 B1 | 12/2001 | Jofuku et al. |
| 6,417,428 B1 | 7/2002 | Thomashow et al. |
| 6,664,446 B2 | 12/2003 | Heard et al. |
| 6,706,866 B1 | 3/2004 | Thomashow et al. |
| 6,717,034 B2 | 4/2004 | Jiang et al. |
| 6,835,540 B2 | 12/2004 | Broun |
| 6,846,669 B1 | 1/2005 | Jofuku et al. |
| 6,946,586 B1 | 9/2005 | Fromm et al. |
| 7,109,393 B2 | 9/2006 | Gutterson et al. |
| 7,135,616 B2 | 11/2006 | Heard et al. |
| 7,196,245 B2 | 3/2007 | Jiang et al. |
| 7,223,904 B2 | 5/2007 | Heard et al. |
| 7,238,860 B2 | 7/2007 | Ratcliffe et al. |
| 7,345,217 B2 | 3/2008 | Zhang et al. |
| 2002/0138882 A1 | 9/2002 | Cahoon |
| 2003/0093837 A1 | 5/2003 | Keddie et al. |
| 2003/0121070 A1 | 6/2003 | Adam et al. |
| 2003/0135888 A1 | 7/2003 | Zhu et al. |
| 2003/0217383 A1 | 11/2003 | Reuber et al. |
| 2003/0226170 A1 | 12/2003 | Lammers et al. |
| 2003/0233670 A1 | 12/2003 | Edgerton et al. |
| 2003/0233680 A1 | 12/2003 | Thomashow et al. |
| 2004/0010815 A1 | 1/2004 | Lange et al. |
| 2004/0016025 A1 | 1/2004 | Budworth et al. |
| 2004/0019927 A1 | 1/2004 | Sherman et al. |
| 2004/0031072 A1 | 2/2004 | La Rosa et al. |
| 2004/0034888 A1 | 2/2004 | Liu et al. |
| 2004/0091874 A1 | 5/2004 | Yamasaki |
| 2004/0123343 A1 | 6/2004 | La Rosa et al. |
| 2004/0128712 A1 | 7/2004 | Jiang et al. |
| 2004/0143098 A1 | 7/2004 | Pages et al. |
| 2004/0172684 A1 | 9/2004 | Kovalic et al. |
| 2004/0214272 A1 | 10/2004 | La Rosa et al. |
| 2004/0216190 A1 | 10/2004 | Kovalic et al. |
| 2005/0070697 A1 | 3/2005 | Hu et al. |
| 2005/0086718 A1 | 4/2005 | Heard et al. |
| 2005/0097638 A1 | 5/2005 | Jiang et al. |
| 2005/0108791 A1 | 5/2005 | Edgerton et al. |
| 2005/0155117 A1 | 7/2005 | Century et al. |
| 2005/0172364 A1 | 8/2005 | Heard |
| 2006/0008874 A1 | 1/2006 | Creelman et al. |
| 2006/0015972 A1 | 1/2006 | Heard et al. |
| 2006/0162018 A1 | 7/2006 | Gutterson et al. |
| 2006/0195944 A1 | 8/2006 | Heard et al. |

| | | | |
|---|---|---|---|
| 2006/0236419 A1* | 10/2006 | La Rosa et al. | 800/278 |
| 2006/0242738 A1 | 10/2006 | Sherman et al. | |
| 2006/0272060 A1 | 11/2006 | Heard et al. | |
| 2007/0022495 A1 | 1/2007 | Reuber | |
| 2007/0044171 A1 | 2/2007 | Kovalic et al. | |
| 2007/0101454 A1 | 5/2007 | Jiang et al. | |
| 2007/0186308 A1 | 8/2007 | Reuber et al. | |
| 2007/0192889 A1 | 8/2007 | La Rosa et al. | |
| 2007/0199107 A1 | 8/2007 | Ratcliffe et al. | |
| 2007/0209086 A1 | 9/2007 | Ratcliffe et al. | |
| 2007/0226839 A1 | 9/2007 | Gutterson et al. | |
| 2008/0010703 A1 | 1/2008 | Creelman et al. | |
| 2008/0155706 A1 | 6/2008 | Riechmann et al. | |
| 2008/0163397 A1 | 7/2008 | Ratcliffe et al. | |
| 2008/0229439 A1 | 9/2008 | La Rosa et al. | |
| 2008/0229448 A1 | 9/2008 | Libby et al. | |
| 2008/0301836 A1 | 12/2008 | Century et al. | |
| 2008/0301841 A1 | 12/2008 | Ratcliffe et al. | |
| 2008/0313756 A1 | 12/2008 | Zhang et al. | |
| 2009/0044297 A1 | 2/2009 | Andersen et al. | |
| 2009/0049566 A1 | 2/2009 | Zhang et al. | |
| 2009/0049573 A1 | 2/2009 | Dotson et al. | |
| 2009/0100536 A1 | 4/2009 | Adams et al. | |
| 2009/0158452 A1 | 6/2009 | Johnson et al. | |
| 2009/0217414 A1 | 8/2009 | La Rosa et al. | |

FOREIGN PATENT DOCUMENTS

| | | |
|---|---|---|
| WO | WO99/41974 | 8/1999 |
| WO | WO9955840 | 11/1999 |
| WO | WO0032761 | 6/2000 |
| WO | WO0046383 | 8/2000 |
| WO | WO0215675 A1 | 2/2002 |
| WO | WO0222675 A2 | 3/2002 |
| WO | WO02079245 | 10/2002 |
| WO | WO03008540 | 1/2003 |
| WO | WO03013227 A2 | 2/2003 |
| WO | WO03014327 A2 | 2/2003 |
| WO | WO03044190 | 5/2003 |
| WO | WO03048319 | 6/2003 |
| WO | WO 03081978 | 10/2003 |
| WO | WO03097790 | 11/2003 |
| WO | WO2004029222 | 4/2004 |
| WO | WO2004031349 | 4/2004 |
| WO | WO 2004035798 | 4/2004 |
| WO | WO2004076638 | 9/2004 |
| WO | WO2005001050 | 1/2005 |
| WO | WO2005047516 A2 | 5/2005 |
| WO | WO2006033708 A2 | 3/2006 |
| WO | WO2006069201 A2 | 6/2006 |
| WO | WO2006130156 A2 | 12/2006 |
| WO | WO2007028165 A2 | 3/2007 |
| WO | WO2007127186 A1 | 11/2007 |

OTHER PUBLICATIONS

Collingwood, et al. (Dec. 1999). Nuclear receptors: coactivators, corepressors and chromatin remodeling in the control of transcription. J Mol Endocrinol. Dec. 1999;23(3):255-75.
Cubas, et al. (1999)The TCP domain: a motif found in proteins regulating plant growth and development. Plant J. Apr. 1999;18(2):215-22.
Cvitanich, et al. (2000) CPP1, a DNA-binding protein involved in the expression of a soybean leghemoglobin c3 gene. Proc Natl Acad Sci U S A. Jul. 5, 2000;97(14):8163-8.
Da Costa e Silva, et al. (1994) CG-1, a parsley light-induced DNA-binding protein. Plant Mol Biol. Aug. 1994;25(5):921-4.
Dehesh et al (Dec. 1990) A trans-acting factor that binds to a GT-motif in a phytochrome gene promoter. Science 250:1397-1399.
Dubouzet J G et al: OsDREB genes in rice, Oryza sativa L., encode transcription activators that function in drought. Plant Journal, vol. 33, No. 4, Feb. 2003, pp. 751-763.

Durrant, et al. (2000) cDNA-AFLP reveals a striking overlap in race-specific resistance and wound response gene expression profiles. Plant Cell 12 (6), 963-977.
Feng, et al., (2002) Sequence and analysis of rice chromosome 4. Nature 420 (6913), 316-320.
Fischer, U., and Droge-Laser, W. (Oct. 2004). Overexpression of NtERF5, a new member of the tobacco ethylene response transcription factor family enhances resistance to tobacco mosaic virus. Mol Plant Microbe Interact 17, 1162-1171.
Forsburg and Guarente, Identification and characterization of HAP4: a third component of the . . . , Genes Dev. (Aug. 1989) 3:1166-1178.
Fromm, et al. (1989) An octopine synthase enhancer element directs tissue-specific expression and binds ASF-1, a factor from tobacco nuclear extracts. Plant Cell. Oct. 1989;1(10):977-84.
Gan and Amasino (1995) Inhibition of leaf senescence by autoregulated production of cytokinin. Science. Dec. 22, 1995;270(5244):1986-8.
Gatz (1997) Chemical Control of Gene Expression. Annu Rev Plant Physiol Plant Mol Biol. Jun. 1997;48-89-108.
Giniger and Ptashne (1987) Transcription in yeast activated by a putative amphipathic alpha helix linked to a DNA binding unit. Nature. Dec. 17-23, 1987;330(6149):670-2.
Giovannoni, et al. (1999) Genetic mapping of ripening and ethylene related loci in tomato. Theor. Appl. Genet. 98 (6/7), 1005-1013.
Giraudat et al. (Oct. 1992) Isolation of the Arabidopsis ABI3 gene by positional cloning. Plant Cell 4:1251-1261.
Gong, et al. (Jun. 2004). Genome-wide ORFeome cloning and analysis of Arabidopsis transcription factor genes Plant Physiology (2004), 135(2), 773-782.
Gu, Y.Q., et al. (2000). Pti4 is induced by ethylene and salicylic acid, and its product is phosphorylated by the Pto kinase. Plant Cell 12, 771-786.
Gu, Y.Q., et al. (2002). Tomato transcription factors pti4, pti5, and pti6 activate defense responses when expressed in Arabidopsis. Plant Cell 14, 817-831.
Guevara-Garcia, et al. (1998) A 42 by fragment of the pmas1' promoter containing an ocs-like element confers a developmental, wound- and chemically inducible expression pattern. Plant Mol Biol. Nov. 1998;38(5):743-53.
Guo, et al. (2004) Protein tolerance to random amino acid change. Proc Natl Acad Sci U S A. Jun. 22, 2004;101 (25):9205-10. Epub Jun. 14, 2004.
Hall et al., GOLDEN 2: A Novel Transcriptional Regulator of Cellular Differentiation in the Maize Leaf. The Plant Cell (Jun. 1998) 10:925-936.
Hill, et al. (1998) Functional analysis of conserved histidines in ADP-glucose pyrophosphorylase from Escherichia coli. Biochem Biophys Res Commun. Mar. 17, 1998;244(2):573-577.
Lee, S.C., et al. (Aug. 2004). Ectopic expression of a cold-inducible transcription factor, CBF1/DREB1b, in transgenic rice (Oryza sativa L.). Mol Cells 18, 107-114.
Lee, J. H. et al: "Derepression of the Activity of Genetically Engineered Heat Shock Factor Causes Constitutive Synthesis of Heat Shock Proteins and Increased thermottolerance in Transgenic Arabidopsis" Plant Journal, Blackwell Scientific Publications, OXFORD, GB, vol. 8, No. 4, Oct. 1, 1995, pp. 603-612.
Littlewood et al. (1994) Transcription factors 2: helix-loop-helix. Prot. Profile 1:639-709.
Lui et al (1999) Transcription factors and their genes in higher plants functional domains, evolution and regulation. Eur J Biochem. Jun. 1999;262(2):247-57.
Lu and Ferl (Oct. 1995) The Electronic Plant Gene Register. Plant Physiol. 109:721-723.
Luo et al. (1996) Origin of floral asymmetry in Antirrhinum. Nature 383:794-799.
Ma and Ptashne (1987) A new class of yeast transcriptional activators. Cell. Oct. 9, 1987;51(1):113-9.
Manners, et al. (1998) the promoter of the plant defensin gene PDF1.2 from Arabidopsis is systemically activated by fungal pathogens and responds to methyl jasmonate but not to salicylic acid. Plant Mol Biol. Dec. 1998;38 (6):1071-80.

Mayer, K. et al. (2001) Conservation of microstructure between a sequenced region of the genome of rice and multiple segments of the genome of *Arabidopsis thaliana*. Genome Res. 11 (7), 1167-1174 (2001).

Millar, A.A., et al. (1999). CUT1, an *Arabidopsis* gene required for cuticular wax biosynthesis and pollen fertility, encodes a very-long-chain fatty acid condensing enzyme. Plant Cell 11, 825-838.

Moore, et al. (1998) A transcription activation system for regulated gene expression in transgenic plants. Proc Natl Acad Sci U S A. Jan. 6, 1998;95(1):376-81.

Nieva, et al. (2000). Plant tolerance to abiotic stressed in Agriculture: Role of genetic engineering. Kluwer Academic Pub., pp. 157-180.

Odell, et al. (1985) Identification of DNA sequences required for activity of the cauliflower mosaic virus 35S promoter. Nautre. Feb. 28-Mar. 6, 1985;313(6005):810-12

Odell, et al. (1994) Seed-specific gene activation mediated by the Cre/lox site-specific recombination system. Plant Physiol. Oct. 1994;106(2):477-58.

Ohl, et al. (1990) Functional properties of a phenylalanine ammonia-lyase promoter from *Arabidopsis*. Plant Cell. Sep. 1990;2(9):837-48.

Park, J.M., et al. (2001). Overexpression of the tobacco Tsi1 gene encoding an EREBP/AP2-type transcription factor enhances resistance against pathogen attack and osmotic stress in tobacco. Plant Cell 13, 1035-1046.

Reeves and Nissen (1990) J. Biol. Chem. 265:8573-8582.

Rouse et al., Changes in Auxin Response from Mutations in an AUX/IAA Gene, Science 279:1371 (Feb. 1998). 279:1371-1373.

Sasaki, T. et al. (2002) The genome sequence and structure of rice chromosome 1. Nature 420 (6913), 312-316.

Sato, et. al. (Apr. 28, 2000) Structural analysis of Arabidopsis thaliana chromosome 3. I. Sequence features of the regions of 4,504,864 bp covered by sixty P1 and TAC clones. DNA Res. 7(2):131-5.

U.S. Appl. No. 11/986,992, Kumimoto, R. et al.

U.S. Appl. No. 12/077,535, filed May 28, 2009, Repetti, P. et al.

Sato, et al. (2000) Structural analysis of *Arabidopsis thaliana* chromosome 5. X. Sequence features of the regions of 3,076,755 by covered by sixty P1 and TAC clones. DNA Res. 7(1), 31-63 (2000).

Schaffner and Sheen (1991) Maize rbcS promoter activity depends on sequence elements not found in dicot rbcS promoters. Plant Cell. Sep. 1991;3(9):997-1012.

Schauser, et al. (1999) A plant regulator controlling development of symbiotic root nodules. Nature. Nov. 11, 1999;402(6758):191-5.

Seguin, et al. (1997) Characterization of a gene encoding a DNA-binding protein that interacts in vitro with vascular specific cis elements of the phenylalanine ammonia-lyase promoter. Plant Mol Biol. Oct. 1997:35(3):281-91.

Seki et al. (epub Mar. 21, 2002). Functional annotation of a full-length *Arabidopsis* cDNA collection. Science (2002), 296(5565), 141-145.

Shi, et al. (1998) Gibberellin and abscisic acid regulate GAST1 expression at the level of transcription. Plant Mol Biol. Dec. 1998;38(6):1053-60.

Shin, R., et al. (2002). Ectopic expression of Tsi1 in transgenic hot pepper plants enhances host resistance to viral, bacterial, and oomycete pathogenes. Mol Plant Microbe Interact 15, 983-989.

Siebertz, et al. (1989) cis-analysis of the wound-inducible promoter wun1 in transgenic tobacco plants and histochemical localization off its expression. Plant Cell. Oct. 1989;1(10):961-8.

Souer et al., The No Apical Meristem Gene of Petunia is Required for Pattern Formation in Embryos and . . . , Cell (Apr. 19, 1996) 85: 159-170.

Stemmer, et al. (1994) Rapid evolution of a protein in vitro by DNA shuffling. Nature. Aug. 4, 1994;370(6488):389-91.

Smalle J. et al.: 'The trihelix DNA-binding motif in higher plants is not restricted to the transcription factors GT-1 and GT-2' Proc. Natl. Acad. Sci. USA vol. 95, 1998, pp. 3318-3322, XP002906573.

White J.A. et al.: 'A new set of *Arabidopsis* expressed sequence tags from developing seeds. The metabolic pathway from carbohydrates to seed oil', XP002906628 Retrieved from NCBI Database accesssion No. BE522812 & Plant Physiol. vol. 124, No. 4, pp. 1582-1594.

Elomaa, P. et al.: 'Transformation of antisense constructs of the chalcone synthase gene superfamily into *Gerbera hybrida*: differential effect on the expression of family members' Molecular Breeding vol. 2, 1966, pp. 41-50, XP002906572.

Quattrocchio F. et al.: 'Analysis of bHLH and MYB domain proteins: species-specific regulatory differences are caused by divergent evolution of target anthocyanin genes' The Plant Journal vol. 13, No. 4, 1998, pp. 475-488, XP002906572.

Non-Final Office Action of Jul. 10, 2008 for U.S. Appl. No. 10/903,236.

Non-Final Office Action of Jul. 6, 2006 for U.S. Appl. No. 10/903,236.

Final Rejection of May 14, 2007 for U.S. Appl. No. 10/903,236.

Final Rejection of May 22, 2009 for U.S. Appl. No. 10/903,236.

Non-Final Office Action of Sep. 15, 2008 for U.S. Appl. No. 11/699,973.

Non-Final Office Action of Apr. 16, 2008 for U.S. Appl. No. 11/435,388.

Stemmer, et al. (1994) DNA shuffling by random fragmentation and reassembly: in vitro recombination for molecular evolution. Proc Natl Acad Sci U S A. Oct. 25, 1994;91(22):10747-51

Tournier, B., et al. (2003). New members of the tomato ERF family show specific expression pattern and diverse DNA-binding capacity to the GCC box element. FEBS Lett 550, 149-154

Tucker et al. (Jul. 1994) Crystal structure of the adenovirus DNA binding protein reveals a hook-on model for cooperative DNA binding. EMBO J. 13:2994-3002.

Ujino-Ihara, et al. (Jul. 2000). Expression analysis of ESTs derived from the inner bark of *Cryptomeria japonica* . Plant Mol. Biol. 43 (4), 451-457.

Ulmasov, et al. (May 1999). Activation and repression of transcription by auxin-response factors. Proc Natl Acad Sci U S A. May 11, 1999;96(10):5844-9.

van der Knaap E, et al. (2000) A novel gibberellin-induced gene from rice and its potential regulatory role in stem growth. Plant physiol. Mar. 2000;122(3):695-704.

Van der Kop, et al. (1999) Selection of *Arabidopsis* mutants overexpressing genes driven by the promoter of an auxin-inducible glutathione S-transferase gene. Plant Mol. Biol. Mar. 1999;39(5):979-90.

Vazquez, et al. (1999) The trithorax group gene osa encodes an ARID-domain protein that genetically interacts with the brahma chromatin-remodeling factor to regulate transcription. Development. Feb. 1999;126(4):733-42.

Willmott, et al. (1998) DNase1 footprints suggest the involvement of at least three types of transcription factors in the regulation of alpha-Amy2/A by gibberellin. Plant Mol Biol. Nov. 1998;38(5):817-25.

Wu et al., The *Arabidopsis* 14-3-3 Multigene Family, Plant Physiol. (Aug. 1997) 114:1421-1431.

U.S. Appl. No. 12/064,961, filed Dec. 22, 2008, Gutterson, N. et al.

U.S. Appl. No. 11/632,390, filed Dec. 17, 2008, Zhang, James et al.

Hovarth, et al. (1998) Four classes of salicylate-induced tobacco genes. Mol. Plant Microbe Interact. 11 (9), 895-905.

Hsieh, M.H. et al. (1998). A PII-like protein in *Arabidopsis*: putative role in nitrogen sensing. Proc Natl Acad Sci U S A 95, 13965-13970.

Ishiguro and Nakamura, Characterization of cDNA encoding a novel DNA-binding protein, SPF1, that . . . , Mol. Gen. Genet. (Sep. 28, 1994), 244: 563-571.

Kaelin, et al. (1992) Expression cloning of a cDNA encoding a retinoblastoma-binding protein with E2F-like properties. Cell. Jul. 24, 1992;70(2):351-64.

Kaiser, et al. (1995) Cis-acting elements of the CHS1 gene from white mustard controlling promoter activity and spatial patterns of expression. Plant Mol Biol. May 1995;28(2):231-43.

Kikuchi, et al. (2003); Collection, mapping, and annotation of over 28,000 cDNA clones from japonica rice. Science. Jul. 18, 2003;301(5631):376-9, Erratum in: Science Sep. 2003;301(5641);1849.

Klein et al., A new family of DNA binding proteins includes putative transcriptional regulators of . . . , Mol. Gen. Genet. (Jan. 15, 1996) 250:7-16.

Kuhlemeier, et al. (1989) The Pea rbcS-3A Promoter Mediates Light Responsiveness but not Organ Specificity Plant Cell. Apr. 1989;1(4):471-478.

Lamb, C.J., et al. (1992). Emerging strategies for enhancing crop resistance to microbial pathogens Biotechnology (N Y) 10, 1436-1445.

Lazar, et al. (1988) Transforming growth factor alpha: mutation of aspartic acid 47 and leucine 48 results in different biological activities. Mol Cell Biol. Mar. 1988;8(3):1247-52.

AA556800 NCBI acc. No. AA556800 (gi: 3365814) (Aug. 14, 1997); Allona,I., et al. "642 *Loblolly pine* C *Pinus taeda* cDNA clone 6C11C, mRNA sequence"; source: *Pinus taeda* (*Loblolly pine*); Title: "Analysis of xylem formation in pine by cDNA sequencing" (Proc. Natl. Acad. Sci. U.S.A. 95 (16), 9693-9698 (1998)).

AAAA01000537 NCBI acc. No. AAAA01000537 (gi: 19924846) (Apr. 4, 2002); Yu,J., et al. "*Oryza sativa* (indica cultivar-group) scaffold000537, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01000764 NCBI acc. No. AAAA01000764 (gi: 19925073) (Apr. 4, 2002); Yu,J., et al. "*Oryza sativa* (indica cultivar-group) scaffold000764, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01001138 NCBI acc. No. AAAA01001138 (gi: 19925447) (Apr. 4, 2002); Yu,J., et al. "*Oryza sativa* (indica cultivar-group) scaffold001138, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01001242 NCBI acc. No. AAAA01001242 (gi: 19925551) (Apr. 4, 2002); Yu,J., et al. "*Oryza sativa* (indica cultivar-group) scaffold001242, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01002144 NCBI acc. No. AAAA01002144 (gi: 19926453) (Apr. 4, 2002); Yu,J., et al. "*Oryza sativa* (indica cultivar-group) scaffold002144, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01002491 NCBI acc. No. AAAA01002491 (gi: 19926800) (Apr. 4, 2002); Yu,J., et al. "*Oryza sativa* (indica cultivar-group) scaffold002491, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01002646 NCBI acc. No. AAAA01002646 (gi: 19926955) (Apr. 4, 2002); Yu,J., et al. "*Oryza sativa* (indica cultivar-group) scaffold002646, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01003158 NCBI acc. No. AAAA01003158 (gi: 19927467) (Apr. 4, 2002); Yu,J., et al. "*Oryza sativa* (indica cultivar-group) scaffold003158, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01004215 NCBI acc. No. AAAA01004215 (gi: 19928525) (Apr. 4, 2002); Yu,J., et al. "*Oryza sativa* (indica cultivar-group) scaffold004215, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01005323 NCBI acc. No. AAAA01005323 (gi: 19929633) (Apr. 4, 2002); Yu,J., et al. "*Oryza sativa* indica cultivar-group) scaffold005323, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01006298 NCBI acc. No. AAAA01006298 (gi: 19930608) (Apr. 4, 2002); Yu,J., et al. "*Oryza sativa* (indica cultivar-group) scaffold006298, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01008724 NCBI acc. no. AAAA01008724 (gi: 19933034) (Apr. 4, 2002); Yu,J., et al. "*Oryza sativa* (indica cultivar-group) scaffold008724, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01010631 NCBI acc. No. AAAA01010631 (gi: 19936489) (Apr. 4, 2002); Yu,J., et al. "*Oryza sativa* (indica cultivar-group) scaffold010631, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01012531 NCBI acc. No. AAAA01012531 (gi: 19939938) (Apr. 4, 2002); Yu,J., et al. "*Oryza sativa* (indica cultivar-group) scaffold012531, whole genome shotgun sequence"; source: *Oryza sativa* (indica cultivar-group); Title: "The Genomes of *Oryza sativa*: A History of Duplications" (PLoS Biol. 3 (2), E38 (2005)).

AAAA01035494 NCBI acc. No. AAAA01035494 (gi: 19975076) (Apr. 4, 2002); Yu,J., et al. "*Oryza sativa* (indica cultivar-group) scaffold035494, whole genome shotgun sequence"; source: *Oryza sativa* (indica cultivar-group); Title: "The Genomes of *Oryza sativa*: A History of diplications" (PLoS Biol. 3 (2), E38 (2005)).

AB016264 NCBI acc. No. AB016264 (gi: 8809570) (Jun. 28, 2000); Kitajima,S., et al. "*Nicotiana sylvestris* nserf2 gene for ethylene-responsive element binding factor, complete cds"; source: *Nicotiana sylvestris* (wood tobacco); Title: Characterization of gene expression of NsERFs, transcription factors of basic PR genes from *Nicotiana*.

AB035270 NCBI acc. No. AB035270 (gi: 6478844) (Nov. 30, 1999); Ashida,Y., et al. "*Matricaria chamomilla* McEREBP1 mRNA for ethylene-responsive element binding protein1 homolog, partial cds"; source: *Matricaria chamomilla*; Title: ethylene-responsive element binding protein1 (EREBP) homolog, *Matricaria*.

AB036883 NCBI acc. No. AB036883 (gi: 10567105) (Oct. 3, 2000); Ohta,M., et al. "*Oryza sativa* mRNA for osERF3, complete cds"; source: *Oryza sativa*; Title: "A nobel repression domain of class Ii Erf transcriptional repressors" (Unpublished (2000)).

AB037183 NCBI acc. No. AB037183 (gi: 9309341) (Jul. 20, 2000); Ohta,M., et al. "*Oryza sativa* osERF3 mRNA for ethylene responsive element binding factor3, complete cds"; source: *Oryza sativa*; Title: "Novel transcriptional repression in plants" (Unpublished (2000)).

ACO25907 NCBI acc. No. ACO25907 (gi: 7249444) (Mar. 16, 2000); Llaca,V., et al. "*Oryza sativa* chromosome 10 clone nbxb0094K20, * Sequencing in Progress *, 2 ordered pieces"; source: *Oryza sativa*; Title: "Rice Chromosome 10" (Unpublished).

AC079890 NCBI acc. No. AC079890 (gi: 10179366) (Sep. 16, 2000); Buell,R., et al. "*Oryza sativa* chromosome 10 clone OSJNBb0089A17, * Sequencing in Progress *, 12 unordered pieces"; source: *Oryza sativa*; Title: "*Oryza sativa* ssp. japonica cv. Nipponbare OSJNBb0089A17 BAC genomic sequence" (Unpublished).

AC084763 NCBI acc. No. AC084763 (gi: 11178087) (Nov. 15, 2000); Buell,R., et al. "*Oryza sativa* chromosome 10 clone OSJNBa0027P10, * Sequencing in Progress *, 9 unordered pieces"; source: *Oryza sativa*; Title: "*Oryza sativa* ssp. japonica cv. Nipponbare OSJNBa0027P10 BAC genomic sequence" (Unpublished).

AC092263 NCBI acc. No. AC092263 (gi: 14578167) (Jun. 30, 2001); Buell,R., et al. "*Oryza sativa* chromosome 3 clone OSJNBa0033PO4, * Sequencing in Progress *, 15 unordered pieces"; source: *Oryza sativa*; Title: "*Oryza sativa* ssp. japonica cv. Nipponbare OSJNBa0033PO4 BAC genomic sequence" (Unpublished).

AC105318 NCBI acc. No. AC105318 (gi: 17998701) (Dec. 30, 2001); Chow,T.-Y., et al. "*Oryza sativa* chromosome 5 clone OJ1058F05, * Sequencing in Progress *, 3 ordered pieces"; source: *Oryza sativa*; Title: "*Oryza sativa* BAC OJ1058F05 genomic sequence" (Unpublished).

AC105734 NCBI acc. No. AC105734 (gi: 18092960) (Jan. 9, 2002); Wing, R.A., et al. "*Oryza sativa* chromosome 3 clone OSJNBb0050NO2, * Sequencing in Progress *, 11 ordered pieces"; source: *Oryza sativa*; Title: "Rice Genomic Sequence" (Unpublished).

AC137635 NCBI acc. No. AC137635 (gi: 25697839) (Nov. 27, 2002); McCOMBIE,W.R., et al. "*Oryza sativa* (japonica cultivar-group) chromosome 3 clone OSJNBa0038D20, * Sequencing in Progress *, 2 ordered pieces"; source: *Oryza sativa* (japonica cultivar-group); Title: "Rice genomic sequence" (Unpublished).

AF057373 NCBI acc. No. AF057373 (gi: 3695033) (Oct. 6, 1998); Horvath,D.M., et al. "*Nicotiana tabacum* ethylene response element binding protein 1 (EREBP1) mRNA, EREBP1-2 allele, partial cds"; source: *Nicotiana tabacum* (common tobacco); (Mol. Plant Microbe Interact. 11 (9), 895-905 (1998)).

AF204784 NCBI acc. No. AF204784 (gi: 12231293) (Jan. 16, 2001); Giovannoni,J.J., et al. "*Lycopersicon esculentum* ripening regulated protein DDTFR10/A (DDTFR10/A) mRNA, partial cds"; source: *Solanum lycopersicum* (*Lycopersicon esculentum*); (Theor. Appl. Genet. 98 (6/7), 1005-1013 (1999)).

AF211527 NCBI acc. No. AF211527 (gi: 12003375) (Jan. 2, 2001); Durrant, W.E., et al. "*Nicotiana tabacum* Avr9/Cf-9 rapidly elicited protein 1 (ACRE1) mRNA, complete cds"; source: *Nicotiana tabacum* (common tobacco); Title: "cDNA expression profiling reveals rapid, resistance gene-dependent, active oxygen-independent, gene induction during the plant defense response" (Unpublished).

AF245119 NCBI acc. No. AF245119 (gi: 7528275) (Apr. 9, 2000); Scharte,J., et al. "*Mesembryanthemum crystallinum* AP2-related transcription factor (CDBP) mRNA, complete cds"; source: *Mesembryanthemum crystallinum* (common iceplant); Title: "A stress induced transcription factor of the AP2 gene family from the inducible CAM-plant *Mesembryanthemum crystallinum* L." (Unpublished).

AF357211 NCBI acc. No. AF357211 (gi: 21304711) (Jun. 1, 2002); Mazarei,M., et al. "*Glycine max* ethylene-responsive element binding protein 1 (EREBP1) mRNA, complete cds"; source: *Glycine max* (soybean); (Mol. Plant Microbe Interact. 15 (6), 577-586 (2002)).

AF494201 NCBI acc. No. AF494201 (gi: 23452023) (Oct. 2, 2002); Zhang,H., et al. "*Lycopersicon esculentum* transcription factor TSRF1 (TSRF1) mRNA, complete cds"; source: *Lycopersicon esculentum* (tomato); Title: "A tomato transcription factor regulating expression of stress responsive genes" (Unpublished).

AF502085 NCBI acc. No. AF502085 (gi: 25992125) (Dec. 2, 2002); Cheng, X.G., et al. "*Lycopersicon esculentum* ethylene responsive element binding protein (EREB) mRNA, complete cds"; source: *Solanum lycopersicum* (*Lycopersicon esculentum*); Title: "Direct Submission" (Submitted (Apr. 13, 2002).

AI442716 NCBI acc. No. AI442716 (gi: 4298124) (Feb. 19, 1999); Shoemaker,R., et al. "sa85d10.y1 Gm-c1004 *Glycine max* cDNA clone Genome Systems Clone ID: Gm-c1004-6092 5 similar to TR:O04680 O04680 PTI4. ;, mRNA sequence"; source: *Glycine max* (soybean); Title: "Public Soybean EST Project" (Unpublished (1999)).

AI483501 NCBI acc. No. AI483501 (gi: 4387425) (Mar. 9, 1999); Alcala,J., et al. "EST249322 tomato ovary, TAMU *Solanum lycopersicum* cDNA clone cLED24G10, mRNA sequence"; source: *Solanum lycopersicum* (*Lycopersicon esculentum*); Title: "Generation of ESTs from tomato carpel tissue" (Unpublished (1999)).

AI483510 NCBI acc. No. AI483510 (gi: 4387434) (Mar. 9, 1999); Alcala,J., et al. "EST249359 tomato ovary, TAMU *Solanum lycopersicum* cDNA clone cLED25A22, mRNA sequence"; source: *Solanum lycopersicum* (*Lycopersicon esculentum*); Title: "Generation of ESTs from tomato carpel tissue" (Unpublished (1999)).

AI483636 NCBI acc. No. AI483636 (gi: 4387560) (Mar. 9, 1999); Alcala,J., et al. "EST249507 tomato ovary, TAMU *Solanum lycopersicum* cDNA clone cLED25J16, mRNA sequence"; source: *Solanum lycopersicum* (*Lycopersicon esculentum*); Title: "Generation of ESTs from tomato carpel tissue" (Unpublished (1999)).

AI483741 NCBI acc. No. AI483741 (gi: 4387665) (Mar. 9, 1999); Alcala,J., et al. "EST249612 tomato ovary, TAMU *Solanum lycopersicum* cDNA clone cLED23L11, mRNA sequence"; source: *Solanum lycopersicum* (*Lycopersicon esculentum*); Title: "Generation of ESTs from tomato carpel tissue" (Unpublished (1999)).

AI484961 NCBI acc. No. AI484961 (gi: 4380332) (Mar. 9, 1999); Alcala,J., et al. "EST243224 tomato ovary, TAMU *Solanum lycopersicum* cDNA clone cLED2F21, mRNA sequence"; source: *Solanum lycopersicum* (*Lycopersicon esculentum*); Title: "Generation of ESTs from tomato carpel tissue" (Unpublished (1999)).

AI485175 NCBI acc. No. AI485175 (gi: 4380546) (Mar. 9, 1999); Alcala,J., et al. "EST243479 tomato ovary, TAMU *Solanum lycopersicum* cDNA clone cLED6D8, mRNA sequence"; source: *Solanum lycopersicum* (*Lycopersicon esculentum*); Title: "Generation of ESTs from tomato carpel tissue" (Unpublished (1999)).

AI485460 NCBI acc. No. AI485460 (gi: 4380831) (Mar. 9, 1999); Alcala,J., et al. "EST243781 tomato ovary, TAMU *Solanum lycopersicum* cDNA clone cLED4J9, mRNA sequence"; source: *Solanum lycopersicum* (*Lycopersicon esculentum*); Title: "Generation of ESTs from tomato carpel tissue" (Unpublished (1999)).

AI485634 NCBI acc. No. AI485634 (gi: 4381005) (Mar. 9, 1999); Alcala,J., et al. "EST243955 tomato ovary, TAMU *Solanum lycopersicum* cDNA clone cLED6J8, mRNA sequence"; source: *Solanum lycopersicum* (*Lycopersicon esculentum*); Title: "Generation of ESTs from tomato carpel tissue" (Unpublished (1999)).

AI486689 NCBI acc. No. AI486689 (gi: 4382060) (Mar. 9, 1999); Alcala,J., et al. "EST245011 tomato ovary, TAMU *Solanum lycopersicum* cDNA clone cLED11H4, mRNA sequence"; source: *Solanum lycopersicum* (*Lycopersicon esculentum*); Title: "Generation of ESTs from tomato carpel tissue" (Unpublished (1999)).

AI486798 NCBI acc. No. AI486798 (gi: 4382169) (Mar. 9, 1999); Alcala,J., et al. "EST245120 tomato ovary, TAMU *Solanum lycopersicum* cDNA clone cLED11D21, mRNA sequence"; source: *Solanum lycopersicum* (*Lycopersicon esculentum*); Title: "Generation of ESTs from tomato carpel tissue" (Unpublished (1999)).

AI486929 NCBI acc. No. AI486929 (gi: 4382300) (Mar. 9, 1999); Alcala,J., et al. "EST245251 tomato ovary, TAMU *Solanum lycopersicum* cDNA clone cLED6L21, mRNA sequence"; source: *Solanum lycopersicum* (*Lycopersicon esculentum*); Title: "Generation of ESTs from tomato carpel tissue" (Unpublished (1999)).

AI487698 NCBI acc. No. AI487698 (gi: 4383069) (Mar. 9, 1999); Alcala,J., et al. "EST246020 tomato ovary, TAMU *Solanum lycopersicum* cDNA clone cLED14C15, mRNA sequence"; source: *Solanum lycopersicum* (*Lycopersicon esculentum*); Title: "Generation of ESTs from tomato carpel tissue" (Unpublished (1999)).

AI489199 NCBI acc. No. AI489199 (gi: 4384570) (Mar. 9, 1999); Alcala,J., et al. "EST247538 tomato ovary, TAMU *Solanum lycopersicum* cDNA clone cLED17M16, mRNA sequence"; source: *Solanum lycopersicum* (*Lycopersicon esculentum*); Title: "Generation of ESTs from tomato carpel tissue" (Unpublished (1999)).

AI490296 NCBI acc. No. AI490296 (gi: 4385606) (Mar. 9, 1999); Alcala,J., et al. "EST248622 tomato ovary, TAMU *Solanum lycopersicum* cDNA clone cLED24J8, mRNA sequence"; source: *Solanum lycopersicum* (*Lycopersicon esculentum*); Title: "Generation of ESTs from tomato carpel tissue" (Unpublished (1999)).

AI495036 NCBI acc. No. AI495036 (gi: 4396039) (Mar. 11, 1999); Shoemaker,R., et al. "sa90a09.y1 Gm-c1004 *Glycine max* cDNA clone Genome Systems Clone ID: Gm-c1004-6545 5 similar to TR:O22167 O22167 Erebp Isolog. ;, mRNA sequence"; source: *Glycine max* (soybean); Title: "Public Soybean EST Project" (Unpublished (1999)).

AI771213 NCBI acc. No. AI771213 (gi: 5269350) (Jun. 29, 1999); Alcala,J., et al. "EST252409 tomato ovary, TAMU *Solanum lycopersicum* cDNA clone cLED29K9, mRNA sequence"; source: *Solanum lycopersicum* (*Lycopersicon esculentum*); Title: "Generation of ESTs from tomato carpel tissue" (Unpublished (1999)).

AI771245 NCBI acc. No. AI771245 (gi: 5269202) (Jun. 29, 1999); Alcala,J., et al. "EST252261 tomato ovary, TAMU *Solanum lycopersicum* cDNA clone cLED28N15, mRNA sequence"; source: *Solanum lycopersicum* (*Lycopersicon esculentum*); Title: "Generation of ESTs from tomato carpel tissue" (Unpublished (1999)).

AI771755 NCBI acc. No. AI771755 (gi: 5269796) (Jun. 29, 1999); Alcala,J., et al. "EST252855 tomato ovary, TAMU *Solanum lycopersicum* cDNA clone cLED35M15, mRNA sequence"; source: *Solanum lycopersicum* (*Lycopersicon esculentum*); Title: "Generation of ESTs from tomato carpel tissue" (Unpublished (1999)).

AI771795 NCBI acc. No. AI771795 (gi: 5269836) (Jun. 29, 1999); Alcala,J., et al. "EST252895 tomato ovary, TAMU *Solanum lycopersicum* cDNA clone cLED38A15, mRNA sequence"; source: *Solanum lycopersicum* (*Lycopersicon esculentum*); Title: "Generation of ESTs from tomato carpel tissue" (Unpublished (1999)).

AI771834 NCBI acc. No. AI771834 (gi: 5269875) (Jun. 29, 1999); Alcala,J., et al. "EST252934 tomato ovary, TAMU *Solanum lycopersicum* cDNA clone cLED38I1, mRNA sequence"; source: *Solanum lycopersicum* (*Lycopersicon esculentum*); Title: "Generation of ESTs from tomato carpel tissue" (Unpublished (1999)).

AI772620 NCBI acc. No. AI772620 (gi: 5270661) (Jun. 29, 1999); D'Ascenzo, M., et al. "EST253720 tomato resistant, Cornell *Solanum lycopersicum* cDNA clone cLER3I2, mRNA sequence";

source: *Solanum lycopersicum* (*Lycopersicon esculentum*); Title: "Generation of ESTs from *Pseudomonas* resistant tomato" (Unpublished (1999)).
AI775562 NCBI acc. No. AI775562 (gi: 5273603) (Jun. 29, 1999); D'Ascenzo, M. et al. "EST256662 tomato resistant, Cornell *Solanum lycopersicum* cDNA clone cLER15L16, mRNA sequence"; source: *Solanum lycopersicum* (*Lycopersicon esculentum*); Title: "Generation of ESTs *Pseudomonas* resistant tomato" (Unpublished (1999)).
AI776626 NCBI acc. No. AI776626 (gi: 5274667) (Jun. 29, 1999); D'Ascenzo, M. et al. "EST257726 tomato resistant, Cornell *Solanum lycopersicum* cDNA clone cLER15L16, mRNA sequence"; source: *Solanum lycopersicum* (*Lycopersicon esculentum*); Title: "Generation of ESTs from *Pseudomonas* resistant tomato" (Unpublished (1999)).
AI778498 NCBI acc. No. AI778498 (gi: 5276539) (Jun. 29, 1999); D'Ascenzo, M. et al. "EST259377 tomato susceptible, Cornell *Solanum lycopersicum* cDNA clone cLES5D19, mRNA sequence"; source: *Solanum lycopersicum* (*Lycopersicon esculentum*); Title: "Generation of ESTs from *Pseudomonas* sceptible tomato" (Unpublished (1999)).
AI778693 NCBI acc. No. AI778693 (gi: 5276734) (Jun. 29, 1999); D'Ascenzo, M. et al. "EST259572 tomato susceptible, Cornell *Solanum lycopersicum* cDNA clone cLES6I9, mRNA sequence"; source: *Solanum lycopersicum* (*Lycopersicon esculentum*); Title: "Generation of ESTs from *Pseudomonas* susceptible tomato" (Unpublished (1999)).
AI779791 NCBI acc. No. AI779791 (gi: 5277832) (Jun. 29, 1999); D'Ascenzo, M. et al. "EST260670 tomato susceptible, Cornell *Solanum lycopersicum* cDNA clone cLES9K15, mRNA sequence"; source: *Solanum lycopersicum* (*Lycopersicon esculentum*); Title: "Generation of ESTs from *Pseudomonas* susceptible tomato" (Unpublished (1999)).
AI780258 NCBI acc. No. AI780258 (gi: 5278299) (Jun. 29, 1999); D'Ascenzo, M. et al. "EST261137 tomato susceptible, Cornell *Solanum lycopersicum* cDNA clone cLES11B13, mRNA sequence"; source: *Solanum lycopersicum* (*Lycopersicon esculentum*); Title: "Generation of ESTs from *Pseudomonas* susceptible tomato" (Unpublished (1999)).
AI782381 NCBI acc. No. AI1782381 (gi: 5280422) (Jun. 29, 1999); D'Ascenzo, M., et al. "EST263260 tomato susceptible, Cornell *Solanum lycopersicum* cDNA clone cLES18P16, mRNA sequence"; source: *Solanum lycopersicum* (*Lycopersicon esculentum*); Title: "Generation of ESTs from *Pseudomonas* susceptible tomato" (Unpublished (1999)).
AI794657 NCBI acc. No. AI794657 (gi: 5342373) (Jul. 2, 1999); Shoemaker,R., et al. "sb67b03.y1 Gm-c1019 *Glycine max* cDNA clone Genome Systems Clone ID: Gm-c1019-6 5' similar to TR:Q40478 Q40478 EREBP-4. ;, mRNA sequence"; source: *Glycine max* (soybean); Title: "Public Soybean EST Project" (Unpublished (1999)).
AI855585 NCBI acc. No. AI855585 (gi: 5509027) (Jul. 16, 1999); Shoemaker,R., et al. "sc28b12.y1 Gm-c1014 *Glycine max* cDNA clone Genome Systems Clone ID: Gm-c1014-408 5' similar to TR:O81365 O81365 AP2 Domain Containing Protein ;, mRNA sequence"; source: *Glycine max* (soybean); Title: "Public Soybean EST Project" (Unpublished (1999)).
AI894515 NCBI acc. No. AI894515 (gi: 5600417) (Jul. 27, 1999); Alcala,J., et al. "EST263958 tomato callus, TAMU *Solanum lycopersicum* cDNA clone cLEC4M24, mRNA sequence"; source: *Solanum lycopersicum* (*Lycopersicon esculentum*); Title: "Generation of ESTs from tomato callus tissue" (Unpublished (1999)).
AI894873 NCBI acc. No. AI894873 (gi: 5600775) (Jul. 27, 1999); Alcala,J., et al. "EST264316 tomato callus, TAMU *Solanum lycopersicum* cDNA clone cLEC6K7, mRNA sequence"; source: *Solanum lycopersicum* (*Lycopersicon esculentum*); Title: "Generation of ESTs from tomato callus tissue" (Unpublished (1999)).
AI895391 NCBI acc. No. AI895391 (gi: 5601293) (Jul. 27, 1999); Alcala,J., et al. "EST264834 tomato callus, TAMU *Solanum lycopersicum* cDNA clone cLEC7L3, mRNA sequence"; source: *Solanum lycopersicum* (*Lycopersicon esculentum*); Title: "Generation of ESTs from tomato callus tissue" (Unpublished (1999)).
AI895742 NCBI acc. No. AI895742 (gi: 5601644) (Jul. 27, 1999); Alcala,J., et al. "EST265185 tomato callus, TAMU *Solanum lycopersicum* cDNA clone cLEC10A3, mRNA sequence"; source: *Solanum lycopersicum* (*Lycopersicon esculentum*); Title: "Generation of ESTs from tomato callus tissue" (Unpublished (1999)).
AI896308 NCBI acc. No. AI896308 (gi: 5602210) (Jul. 27, 1999); Alcala,J., et al. "EST265751 tomato callus, TAMU *Solanum lycopersicum* cDNA clone cLEC14N19, mRNA sequence"; source: *Solanum lycopersicum* (*Lycopersicon esculentum*); Title: "Generation of ESTs from tomato callus tissue" (Unpublished (1999)).
AI897787 NCBI acc. No. AI897787 (gi: 5603689) (Jul. 27, 1999); Alcala,J., et al. "EST267230 tomato ovary, TAMU *Solanum lycopersicum* cDNA clone cLED3ON5, mRNA sequence"; source: *Solanum lycopersicum* (*Lycopersicon esculentum*); Title: "Generation of ESTs from tomato carpel tissue" (Unpublished (1999)).
AI897797 NCBI acc. No. AI897797 (gi: 5603699) (Jul. 27, 1999); Alcala,J., et al. "EST267240 tomato ovary, TAMU *Solanum lycopersicum* cDNA clone cLED30P1, mRNA sequence"; source: *Solanum lycopersicum* (*Lycopersicon esculentum*); Title: "Generation of ESTs from tomato carpel tissue" (Unpublished (1999)).
AI897834 NCBI acc. No. AI897834 (gi: 5603736) (Jul. 27, 1999); Alcala,J., et al. "EST267277 tomato ovary, TAMU *Solanum lycopersicum* cDNA clone cLED30F18, mRNA sequence"; source: *Solanum lycopersicum* (*Lycopersicon esculentum*); Title: "Generation of ESTs from tomato carpel tissue" (Unpublished (1999)).
AI899000 NCBI acc. No. AI899000 (gi: 5604902) (Jul. 27, 1999); Alcala,J., et al. "EST268443 tomato ovary, TAMU *Solanum lycopersicum* cDNA clone cLED36J9, mRNA sequence"; source: *Solanum lycopersicum* (*Lycopersicon esculentum*); Title: "Generation of ESTs from tomato carpel tissue" (Unpublished (1999)).
AI899889 NCBI acc. No. AI899889 (gi: 5605791) (Jul. 27, 1999); Shoemaker,R., et al. "sb94g05.y1 Gm-c1017 *Glycine max* cDNA clone Genome Systems Clone ID: Gm-c1017-1137 5' similar to TR:Q40478 Q40478 EREBP-4. ;, mRNA sequence"; source: *lycine max* (soybean); Title: "Public Soybean EST Project" (Unpublished (1999)).
AI965917 NCBI acc. No. AI965917 (gi: 5760554) (Aug. 23, 1999); Shoemaker,R., et al. "sc79f12.y1 Gm-c1018 *Glycine max* cDNA clone Genome Systems Clone ID: Gm-c1018-1128 5' similar to TR:O80341 O80341 Ethylene Responsive Element Binding Factor 5. ;, mRNA sequence"; source: *Glycine max* (soybean); Title: "Public Soybean EST Project" (Unpublished (1999)).
AI966369 NCBI acc. No. AI966369 (gi: 5761006) (Aug. 23, 1999); Shoemaker, R., et al. "sc37h09.y1 Gm-c1014 *Glycine max* cDNA clone Genome Systems Clone ID: Gm-c1014-1338 5' similar to TR:O81365 O81365 AP2 Domain Containing Protein ;, mRNA sequence"; source: *Glycine max* (soybean); Title: "Public Soybean EST Project" (Unpublished (1999)).
AI966559 NCBI acc. No. AI966559 (gi: 5761196) (Aug. 23, 1999); Shoemaker,R., et al. "sc52a04.y1 Gm-c1015 *Glycine max* cDNA clone Genome Systems Clone ID: Gm-c1015-1159 5' similar to TR:O23591 O23591 EREBP-4 Homolog. ;, mRNA sequence"; source: *Glycine max* (soybean); Title: "Public Soybean EST Project" (Unpublished (1999)).
AI967551 NCBI acc. No. AI967551 (gi: 5762854) (Aug. 24, 1999); Poulsen,C., et al. "Ljirnpest05-400-d11 Ljirnp Lambda HybriZap two-hybrid library *Lotus japonicus* cDNA clone LP400-05-d11 5' similar to ethylene response factor 1, mRNA sequence"; source: *Lotus japonicus*; Title: "Expressed sequence tags from *Mesorhizobium loti* infected roots of *Lotus japonicus*" (Unpublished (1999)).
AI973653 NCBI acc. No. AI973653 (gi: 5770479) (Aug. 25, 1999); Shoemaker, R., et al. "sdO7h05.y1 Gm-c1020 *Glycine max* cDNA clone Genome Systems Clone ID: Gm-c1020-1042 5' similar to TR:O22167 O22167 EREBP ISOLOG. ;, mRNA sequence"; source: *Glycine max* (soybean); Title: "Public Soybean EST Project" (Unpublished (1999)).
AJ503278 NCBI acc. No. AJ503278 (gi: 22084206) (Aug. 1, 2002); Manthey,K., et al. "*Medicago truncatula* EST, clone mtgmadc120032c02"; source: *Medicago truncatula*; Title: "Detection of transcript sequences from mycorrhizal roots of the model mycorrhiza *Medicago truncatula* genotype A17—Glomus mosseae using the approach of an EST genome project" (Unpublished).
AL367092 NCBI acc. No. AL367092 (gi: 9666845) (Aug. 3, 2000); Journet,E.P., et al. "MtBAl2B12F1 MtBA *Medicago truncatula* cDNA clone MtBA12B12 T3, mRNA sequence"; source: *Medicago truncatula* (barrel medic); Title: "*Medicago truncatula* ESTs from nitrogen-starved roots" (Unpublished (2000)).
AL374803 NCBI acc. No. AL374803 (gi: 9674555) (Aug. 3, 2000); Journet,E.P., et al. "MtBBO9D02F1 MtBB *Medicago truncatula* cDNA clone MtBBO9D02 T3, mRNA sequence"; source: *Medicago truncatula* (barrel medic); Title: "*Medicago truncatula* ESTs from Sinorhizobium meliloti-induced root nodules" (Unpublished (2000)).
AL378570 NCBI acc. No. AL378570 (gi: 9678322) (Aug. 3, 2000); Journet,E.P., et al. "MtBB39B01F1 MtBB *Medicago truncatula* cDNA clone MtBB39B01 T3, mRNA sequence"; source: *Medicago truncatula* (barrel medic); Title: "*Medicago truncatula* ESTs from Sinorhizobium meliloti-induced root nodules" (Unpublished (2000)).
AL378571 NCBI acc. No. AL378571 (gi: 9678323) (Aug. 3, 2000); Journet,E.P., et al. "MtBB39B01 R1 MtBB *Medicago truncatula* cDNA clone MtBB39B01 T7, mRNA sequence"; source: *Medicago truncatula* (barrel medic); Title: "*Medicago truncatula* ESTs from Sinorhizobium meliloti-induced root nodules" (Unpublished (2000)).
AL381730 NCBI acc. No. AL381730 (gi: 9681481) (Aug. 3, 2000); Journet,E.P., et al. "MtBCO2F03F3 MtBC *Medicago truncatula* cDNA clone MtBCO2F03 T3, mRNA sequence"; source: *Medicago truncatula* (barrel medic); Title: "*Medicago truncatula* ESTs from endomycorrhizal roots" (Unpublished (2000)).
AL387924 NCBI acc. No. AL387924 (gi: 9687675) (Aug. 3, 2000); Journet,E.P., et al. "MtBC45F03F1 MtBC *Medicago truncatula* cDNA clone MtBC45F03 T3, mRNA sequence"; source: *Medicago truncatula* (barrel medic); Title: " *Medicago truncatula* ESTs from endomycorrhizal roots" (Unpublished (2000)).
AL388234 NCBI acc. No. AL388234 (gi: 9687985) (Aug. 3, 2000); Journet,E.P., et al. "MtBC47D08F1 MtBC *Medicago truncatula* cDNA clone MtBC47D08 T3, mRNA sequence"; source: *Medicago truncatula* (barrel medic); Title: "*Medicago truncatula* ESTs from endomycorrhizal roots" (Unpublished (2000)).
AL750652 NCBI acc. No. AL750652 (gi: 21491890) (Jun. 20, 2002); Frigerio,J., et al. "AL750652 RN *Pinus pinaster* cDNA clone RNO5H01 similar to Ethylene Responsive Element Binding Factor, mRNA sequence"; source: *Pinus pinaster*; Title: "Identification of water-deficit responsive genes in *Maritime pine* (*Pinus pinaster* Ait.) using an EST approach" (Unpublished (2002)).
AP003237 NCBI acc. No. AP003237 (gi: 13027267) (Feb. 21, 2001); Sasaki,T., et al. "*Oryza sativa* chromosome 1 clone P0046E05, * Sequencing in Progress *"; source: *Oryza sativa*; Title: "*Oryza sativa* nipponbare(GA3) genomic DNA, chromosome 1, PAC clone:P0046E05" (Published Only in DataBase (2001) in press).
AP003249 NCBI acc. No. AP003249 (gi: 13027279) (Feb. 21, 2001); Sasaki,T., et al. "*Oryza sativa* chromosome 1 clone PO435B05, * Sequencing in Progress *"; source: *Oryza sativa*; Title: "*Oryza sativa* nipponbare(GA3) genomic DNA, chromosome 1, PAC clone:P0435B05" (Published Only in DataBase (2001) In press).
AP003286 NCBI acc. No. AP003286 (gi: 13027316) (Feb. 21, 2001); Sasaki,T., et al. "*Oryza sativa* chromosome 1 clone P0677H08, * Sequencing in Progress *"; source: *Oryza sativa*; Title: "*Oryza sativa* nipponbare(GA3) genomic DNA, chromosome 1, PAC clone:P0677H08" (Published Only in DataBase (2001) In press).
AP003294 NCBI acc. No. AP003294 (gi: 13027324) (Feb. 21, 2001); Sasaki,T., et al. "*Oryza sativa* chromosome 1 clone P0694A04, * Sequencing in Progress *"; source: *Oryza sativa*; Title: "*Oryza sativa* nipponbare(GA3) genomic DNA, chromosome 1, PAC clone:P0694A04" (Published Only in DataBase (2001) In press).
AP003820 NCBI acc. No. AP003820 (gi: 14595160) (Jul. 3, 2001); Sasaki,T., et al. "*Oryza sativa* chromosome 7 clone OJ1235_H07, * Sequencing in Progress *"; source: *Oryza sativa*; Title: "*Oryza sativa* nipponbare(GA3) genomic DNA, chromosome 7, BAC clone:OJ1235_H07" (Published Only in Database (2001) In press).
AP003891 NCBI acc. No. AP003891 (gi: 14646849) (Jul. 9, 2001); Sasaki,T., et al. "*Oryza sativa* chromosome 8 clone OJ1314_F06, * Sequencing in Progress *"; source: *Oryza sativa*; Title: "*Oryza sativa* nipponbare(GA3) genomic DNA, chromosome 8, BAC clone:OJ1314_F06" (Published Only in Database (2001) In press).

AP004623 NCBI acc. No. AP004623 (gi: 18157388) (Jan. 15, 2002); Sasaki,T., et al. "*Oryza sativa* chromosome 8 clone P0705A05, * Sequencing in Progress, *"; source: *Oryza sativa*; Title: "*Oryza sativa* nipponbare(GA3) genomic DNA, chromosome 8, PAC clone:P0705A05" (Published Only in Database (2002)).
AP005006 NCBI acc. No. AP005006 (gi: 19773546) (Mar. 27, 2002); Sasaki,T., et al. "*Oryza sativa* (japonica cultivar-group) chromosome 2 clone P0519E06, * Sequencing in Progress *"; source: *Oryza sativa* (japonica cultivar-group); Title: "*Oryza sativa* nipponbare(GA3) genomic DNA, chromosome 2, PAC clone:P0519E06" (Published Only in Database (2002)).
AP006162 NCBI acc. No. AP006162 (gi: 27884274) (Jan. 23, 2003); Sasaki,T., et al. "*Oryza sativa* (japonica cultivar-group) chromosome 9 clone B1331 F11, * Sequencing in Progress *"; source: *Oryza sativa* (japonica cultivar-group); Title: "*Oryza sativa* nipponbare(GA3) genomic DNA, chromosome 9, BAC clone:B1331F11" (Published Only in Database (2003)).
AU083457 NCBI acc. No. AU083457 (gi: 7273913) (Mar. 21, 2000); Sasaki,T., et al. "AU083457 Rice panicle at flowering stage *Oryza sativa* (japonica cultivar-group) cDNA clone E4394, mRNA sequence"; source: *Oryza sativa* (japonica cultivar-group); Title: "Rice cDNA from panicle at flowering stage (2000)" (Unpublished (2000)).
AU083511 NCBI acc. No. AU083511 (gi: 7273967) (Mar. 21, 2000); Sasaki,T., et al. "AU083511 Rice cDNA from young root *Oryza sativa* (japonica cultivar-group) cDNA clone R10838, mRNA sequence"; source: *Oryza sativa* (japonica cultivar-group); Title: "Rice cDNA from young root (2000 " (Unpublished (2000)).
AU173832 NCBI acc. No. AU173832 (gi: 13165035) (Feb. 28, 2001); Sasaki,T., et al. "AU173832 Rice cDNA from young root *Oryza sativa* (japonica cultivar-group) cDNA clone R10061, mRNA sequence"; source: *Oryza sativa* (japonica cultivar-group); Title: "Rice cDNA from young root (2001)" (Unpublished (2001)).
AU181580 NCBI acc. No. AU181580 (gi: 13806594) (Apr. 26, 2001); Sasaki,T., et al. "AU181580 Rice callus (2001) *Oryza sativa* (japonica cultivar-group) cDNA clone C50458, mRNA sequence"; source: *Oryza sativa* (japonica cultivar-group); Title: "Rice cDNA from callus (2001)" (Unpublished (2001)).
AV407462 NCBI acc. No. AV407462 (gi: 7720316) (May 8, 2000); Asamizu,E., et al. "AV407462 *Lotus japonicus* young plants (two-week old) *Lotus japonicus* cDNA clone MWL024d04_r 5', mRNA sequence"; source: *Lotus japonicus*; (DNA Res. 7 (2), 127-130 (2000)).
AV417624 NCBI acc. No. AV417624 (gi: 7746802) (May 9, 2000); Asamizu,E., et al. "AV417624 *Lotus japonicus* young plants (two-week old) *Lotus japonicus* cDNA clone MWM146e09_r 5', mRNA sequence"; source: *Lotus japonicus*;(DNA Res. 7 (2), 127-130 (2000)).
AV421566 NCBI acc. No. AV421566 (gi: 7775366) (May 12, 2000); Asamizu,E., et al. "AV421566 *Lotus japonicus* young plants (two-week old) *Lotus japonicus* cDNA clone MWM196a01_r 5', mRNA sequence"; source: *Lotus japonicus*; (DNA Res. 7 (2), 127-130 (2000)).
AV422393 NCBI acc. No. AV422393 (gi: 7777209) (May 12, 2000); Asamizu,E., et al. "AV422393 *Lotus Japonicus* young plants (two-week old) *Lotus japonicus* cDNA clone MWM012d12_r 5', mRNA sequence"; source: *Lotus japonicus*; (DNA res. 7 (2), 127-130 (2000)).
AV422603 NCBI acc. No. AV422603 (gi: 7777670) (May 12, 2000); Asamizu,E., et al. "AV422603 *Lotus japonicus* young plants (two-week old) *Lotus japonicus* cDNA clone MWM015a04_r 5', mRNA sequence"; source: *Lotus japonicus*; (DNA Res. 7 (2), 127-130 (2000)).
AV423260 NCBI acc. No. AV423260 (gi: 7778996) (May 12, 2000); Asamizu,E., et al. "AV423260 *Lotus japonicus* young plants (two-week old) *Lotus japonicus* cDNA clone MWMO24b09_r 5', mRNA sequence"; source: *Lotus japonicus*; (DNA Res. 7 (2), 127-130 (2000)).
AV425560 NCBI acc. No. AV425560 (gi: 7783624) (May 12, 2000); Asamizu,E., et al. "AV425560 *Lotus japonicus* young plants (two-week old) *Lotus japonicus* cDNA clone MWM055f07_r 5', mRNA sequence"; source: *Lotus japonicus*; (DNA Res. 7 (2), 127-130 (2000)).

AV425829 NCBI acc. No. AV425829 (gi: 7784155) (May 12, 2000); Asamizu,E., et al. "AV425829 *Lotus japonicus* young plants (two-week old) *Lotus japonicus* cDNA clone MWM059g11_r 5';, mRNA sequence"; source: *Lotus japonicus*; (DNA Res. 7 (2), 127-130 (2000)).

AV426605 NCBI acc. No. AV426605 (gi: 7785709) (May 12, 2000); Asamizu,E., et al. "AV426605 *Lotus japonicus* young plants (two-week old) *Lotus japonicus* cDNA clone MWM070e11_r 5';, mRNA sequence"; source: *Lotus japonicus*; (DNA Res. 7 (2), 127-130 (2000)).

AV428124 NCBI acc. No. AV428124 (gi: 7788764) (May 12, 2000); Asamizu,E., et al. "AV428124 *Lotus japonicus* young plants (two-week old) *Lotus japonicus* cDNA clone MWM092d01_r 5, mRNA sequence"; source: *Lotus japonicus*;(DNA Res. 7 (2), 127-130 (2000)).

AW030009 NCBI acc. No. AW030009 (gi: 5888765) (Sep. 15, 1999); Alcala,J., et al. "EST273264 tomato callus, TAMU *Solanum lycopersicum* cDNA clone cLEC11J16, mRNA sequence"; source: *Solanum lycopersicum* (*Lycopersicon esculentum*); Title: "Generation of ESTs from tomato callus tissue" (Unpublished (1999)).

AW030386 NNCBI acc. No. AW030386 (gi: 5889142) (Sep. 15, 1999); Alcala,J., et al. "EST273641 tomato callus, TAMU *Solanum lycopersicum* cDNA clone cLEC20112, mRNA sequence"; source: *Solanum lycopersicum* (*Lycopersicon esculentum*); Title: "Generation of ESTs from tomato callus tissue" (Unpublished (1999)).

AW031184 NCBI acc. No. AW031184 (gi: 5890024) (Sep. 15, 1999); Alcala,J., et al. "EST274722 tomato callus, TAMU *Solanum lycopersicum* cDNA clone cLEC18K13, mRNA sequence"; source: *Solanum lycopersicum* (*Lycopersicon esculentum*); Title: "Generation of ESTs from tomato callus tissue" (Unpublished (1999)).

AW032555 NCBI acc. No. AW032555 (gi: 5891311) (Sep. 15, 1999); Alcala,J., et al. "EST276114 tomato callus, TAMU *Solanum lycopersicum* cDNA clone cLEC8C12, mRNA sequence"; source: *Solanum lycopersicum* (*Lycopersicon esculentum*); Title: "Generation of ESTs from tomato callus tissue" (Unpublished (1999)).

AW032633 NCBI acc. No. AW032633 (gi: 5891389) (Sep. 15, 1999); Alcala,J., et al. "EST276192 tomato callus, TAMU *Solanum lycopersicum* cDNA clone cLEC20L6, mRNA sequence"; source: *Solanum lycopersicum* (*Lycopersicon esculentum*); Title: "Generation of ESTs from tomato callus tissue" (Unpublished (1999)).

AW033743 NCBI acc. No. AW033743 (gi: 5892499) (Sep. 15, 1999); Alcala,J., et al. "EST277314 tomato callus, TAMU *Solanum lycopersicum* cDNA clone cLEC29G11 similar to AP2 domain-containing protein, putative, mRNA sequence"; source: *Solanum lycopersicum* (*Lycopersicon esculentum*); Title: "Generation of ESTs from tomato callus tissue" (Unpublished (1999)).

AW034216 NCBI acc. No. AW034216 (gi: 5892972) (Sep. 15, 1999); Alcala,J., et al. "EST277787 tomato callus, TAMU *Solanum lycopersicum* cDNA clone cLEC32P18 similar to Pti4, mRNA sequence"; source: *Solanum lycopersicum* (*Lycopersicon esculentum*); Title: "Generation of ESTs from tomato callus tissue" (Unpublished (1999)).

AW034241 NCBI acc. No. AW034241 (gi: 5892997) (Sep. 15, 1999); Alcala,J., et al. "EST277812 tomato callus, TAMU *Solanum lycopersicum* cDNA clone cLEC33C21 similar to DNA binding protein homolog, putative, mRNA sequence"; source: *Solanum lycopersicum* (*Lycopersicon esculentum*); Title: "Generation of ESTs from tomato callus tissue" (Unpublished (1999)).

AW035648 NCBI acc. No. AW035648 (gi: 5894404) (Sep. 15, 1999); Alcala,J., et al. "EST281480 tomato callus, TAMU *Solanum lycopersicum* cDNA clone cLEC34P21 similar to EREBP-3 homolog, putative, mRNA sequence"; source: *Solanum lycopersicum* (*Lycopersicon esculentum*); Title: "Generation of ESTs from tomato callus tissue" (Unpublished (1999)).

AW040234 NCBI acc. No. AW040234 (gi: 5898988) (Sep. 15, 1999); D'Ascenzo, M. et al. "EST282740 tomato mixed elicitor, BTI *Solanum lycopersicum* cDNA clone cLET19L2, mRNA sequence"; source: *Solanum lycopersicum* (*Lycopersicon esculentum*); Title: "Generation of ESTs from tomato leaf tissue" (Unpublished (1999)).

AW101483 NCBI acc. No. AW101483 (gi: 6072036) (Oct. 19, 1999); SHOEMAKERr,R., et al. "sd78g09.y1 Gm-c1009 *Glycine max* cDNA clone Genome Systems Clone ID: Gm-c1009-569 5'; similar to TR:O23107 O23107 AP2 Domain Containing Protein RAP2.5. [1] ;, mRNA sequence"; source: *Glycine max* (soybean); Title: "Public Soyeban EST Project" (Unpublished (1999)).

AW156366 NCBI acc. No. AW156366 (gi: 6227767) (Nov. 4, 1999); Shoemaker,R., et al. "se25b08.y1 Gm-c1015 *Glycine max* cDNA clone Genome Systems Clone ID: Gm-c1015-2224 5' similar to TR:O23108 O23108 RAP2.6 ;, mRNA sequence"; source: *Glycine max* (soybean); Title: "Public Soybean EST Project" (Unpublished (1999)).

AW164527 NCBI acc. No. AW164527 (gi: 6341778) (Nov. 10, 1999); Shoemaker,R., et al. "se75a02.y1 Gm-c1023 *Glycine max* cDNA clone Genome Systems Clone ID: Gm-c1023-483 5' similar to TR:P93589 P93589 DNA Binding Protein Homolog. ;, mRNA sequence"; source: *Glycine max* (soybean); Title: "Public Soybean EST Project" (Unpublished (1999)).

AW185126 NCBI acc. No. AW185126 (gi: 6454443) (Nov .19, 1999); Shoemaker,R., et al. "se87b08.y1 Gm-c1023 Glycine max cDNA clone Genome Systems Clone ID: Gm-c1023-1648 5' similar to TR:O23108 O23108 RAP2.6 ;, mRNA sequence"; source: *Glycine max* (soybean); Title: "Public Soybean EST Project" (Unpublished (1999)).

AW185128 NCBI acc. No. AW185128 (gi: 6454445) (Nov. 19, 1999); Shoemaker,R., et al. "se87b10.y1 Gm-c1023 *Glycine max* cDNA clone Genome Systems Clone ID: Gm-c1023-1652 5' similar to TR:O80341 O80341 Ethylene Responsive Element Binding Factor 5. ;, mRNA sequence"; source: *Glycine max* (soybean); Title: "Public Soybean EST Project" (Unpublished (1999)).

AW186005 NCBI acc. No. AW186005 (gi: 6455322) (Nov. 19, 1999); Shoemaker,R., et al. "se62d09.y1 Gm-c1019 *Glycine max* cDNA clone Genome Systems Clone ID: Gm-c1019-1578 5' similar to TR:O23107 O23107 AP2 Domain Containing Protein RAP2.5. [1] ;, mRNA sequence"; source: *Glycine max* (soybean): Title: "Public Soybean EST Project" (Unpublished (1999)).

AW200919 NCBI acc. No. AW200919 (gi: 6481648) (Nov. 30, 1999); Shoemaker,R., et al. "se95c12.y1 Gm-c1027 *Glycine max* cDNA clone Genome Systems Clone ID: Gm-c1027-527 5' similar to TR:O80341 O80341 Ethylene Responsive Element Binding Factor 5. ;, mRNA sequence"; source: *Glycine max* (soybean); Title: "Public Soybean EST Project" (Unpublished (1999)).

AW219198 NCBI acc. No. AW219198 (gi: 6530072) (Dec. 6, 1999); Van Der Hoeven,R.S., et al. "EST301680 tomato root during/after fruit set, Cornell University *Solanum lycopersicum* cDNA clone cLEX3G6, mRNA sequence"; source: *Solanum lycopersicum* (*Lycopersicon esculentum*); Title: "Generation of ESTs from tomato root tissue" (Unpublished (1999)).

AW220395 NCBI acc. No. AW220395 (gi: 6531269) (Dec. 6, 1999); Van Der Hoeven,R.S., et al. "EST302878 tomato root during/after fruit set, Cornell University *Solanum lycopersicum* cDNA clone cLEX10F20, mRNA sequence"; source: *Solanum lycopersicum* (*Lycopersicon esculentum*); Title: "Generation of ESTs from tomato root tissue" (Unpublished (1999)).

AW221854 NCBI acc. No. AW221854 (gi: 6533538) (Dec. 7, 1999); Alcala,J., et al. "EST298665 tomato fruit red ripe, TAMU *Solanum lycopersicum* cDNA clone cLEN4I21, mRNA sequence"; source: *Solanum lycopersicum* (*Lycopersicon esculentum*); Title: "Generation of ESTs from tomato fruit tissue" (Unpublished (1999)).

AW233956 NCBI acc. No. AW233956 (gi: 6566281) (Dec. 13, 1999); Shoemaker,R., et al. "sf32e02.y1.Gm-c1028 *Glycine max* cDNA clone Genome Systems Clone ID: Gm-c1028-1683 5&apos similar to TR:O80337 O80337 Ethylene Responsive Element Binding Factor 1. ;, mRNA sequence"; source: *Glycine max* (soybean); Title: "Public Soybean EST Project" (Unpublished (1999)).

AW234175 NCBI acc. No. AW234175 (gi: 6566532) (Dec. 13, 1999); Shoemaker,R., et al. "sf22b03.y1 Gm-c1028 *Glycine max* cDNA clone Genome Systems Clone ID: Gm-c1028-678 5' similar to TR:O81365 O81365 AP2 Domain Containing Protein ;, mRNA sequence"; source: *Glycine max* (soybean); Title: "Public Soybean EST Project" (Unpublished (1999)).

AW256448 NCBI acc. No. AW256448 (gi: 6604705) (Dec. 20, 1999); Vandenbosch,K., et al. "EST304585 KV2 *Medicago truncatula* cDNA clone KV2-4N11, mRNA sequence"; source: *Medicago truncatula* (barrel medic); Title: "ESTs from roots of *Medicago truncatula* after *Rhizobium inoculation*" (Unpublished (1999)).

AW267756 NCBI acc. No. AW267756 (gi: 6654712) (Jan. 3, 2000); Fedorova,M., et al. "EST305884 DSIR *Medicago truncatula* cDNA clone pDSIR-7O1, mRNA sequence"; source: *Medicago truncatula* (barrel medic); Title: "ESTs from roots of *Medicago truncatula* after inoculation with *Phytophthora medicaginis*" (Unpublished (1999)).

AW267820 NCBI acc. No. AW267820 (gi: 6654776) (Jan. 3, 2000); Fedorova,M., et al. "EST305948 DSIR *Medicago truncatula* cDNA clone pDSIR-8M17, mRNA sequence"; source: *Medicago truncatula* (barrel medic); Title: "ESTs from roots of *Medicago truncatula* after inoculation with *Phytophthora medicaginis*" (Unpublished (1999)).

AW267914 NCBI acc. No. AW267914 (gi: 6654934) (Jan. 3, 2000); Fedorova,M., et al. "EST306256 DSIR *Medicago truncatula* cDNA clone pDSIR-8D12, mRNA sequence"; source: *Medicago truncatula* (barrel medic); Title: "ESTs from roots of *Medicago truncatula* after inoculation with *Phytophthora medicaginis*" (Unpublished (1999)).

AW278190 NCBI acc. No. AW278190 (gi: 6666731) (Jan. 4, 2000); Shoemaker,R., et al. "sf40g11.y1 Gm-c1009 *Glycine max* cDNA clone Genome Systems Clone ID: Gm-c1009-2493 5' similar to TR:Q40476 Q40476 ERF1. ;, mRNA sequence"; source: *Glycine max* (soybean); Title: "Public Soybean EST Project" (Unpublished (1999)).

AW308784 NCBI acc. No. AW308784 (gi: 6724385) (Jan. 21, 2000); Shoemaker,R., et al. "sf71h01.y1 Gm-c1013 *Glycine max* cDNA clone Genome Systems Clone ID: Gm-c1013-5066 5 similar to TR:P93822 P93822 F19P19.18. ;, mRNA sequence"; source: *Glycine max* (soybean); Title: "Public Soybean EST Project" (Unpublished (1999)).

AW329209 NCBI acc. No. AW329209 (gi: 7675608) (Jan. 28, 2000); Harrison,M.J., et al. "N200421e rootphos(-) *Medicago truncatula* cDNA clone MHRP-17E1, mRNA sequence"; source: *Medicago truncatula* (barrel medic); Title: "ESTs from phosphate starved roots" (Unpublished (1999)).

AW348322 NCBI acc. No. AW348322 (gi: 6846032) (Feb. 1, 2000); Vodkin,L., et al. "GM210001B23F6 Gm-r1021 *Glycine max* cDNA clone Gm-r1021-276 3,', mRNA sequence"; source: *Glycine max* (soybean); Title: "A Functional Genomics Program for Soybean (NSF 9872565)" (Unpublished (1999)).

AW349516 NCBI acc. No. AW349516 (gi: 6847226) (Feb. 1, 2000); Vodkin,L., et al. "GM210007B10A12 Gm-r1021 *Glycine max* cDNA clone Gm-r1021-2351 3', mRNA sequence"; source: *Glycine max* (soybean); Title: "A Functional Genomics Program for Soybean (NSF 9872565)" (Unpublished (1999)).

AW349638 NCBI acc. No. AW349638 (gi: 6847348) (Feb. 1, 2000); Vodkin,L., et al. "GM210005B21A4 Gm-r1021 *Glycine max* cDNA clone Gm-r1021-1568 3', mRNA sequence"; source: *Glycine max* (soybean); Title: "A Functional Genomics Program for Soybean (NSF 9872565)" (Unpublished (1999)).

AW396250 NCBI acc. No. AW396250 (gi: 6914720) (Feb. 7, 2000); Shoemaker,R., et al. "sh26c01.y1 Gm-c1016 *Glycine max* cDNA clone Genome Systems Clone ID: Gm-c1016-5881 5', similar to TR:O80341 O80341 Ethylene Responsive Element Binding Factor 5. ;, mRNA sequence"; source : *Glycine max* (soybean); Title: "Public Soybean EST Project" (Unpublished (1999)).

AW396612 NCBI acc. No. AW396612 (gi: 6915151) (Feb. 7, 2000); Shoemaker,R., et al. "sg80c07.y1 Gm-c1026 *Glycine max* cDNA clone Genome Systems Clone ID: Gm-c1026-37 5', similar to TR:080339 080339 Ethylene Responsive Element Binding Factor 3. ;, mRNA sequence"; source: *Glycine max* (soybean); Title: "Public Soybean EST Project" (Unpublished (1999)).

AW441715 NCBI acc. No. AW441715 (gi: 6976966) (Feb. 14, 2000); Alcala,J., et al. "EST311111 tomato fruit red ripe, TAMU *Solanum lycopersicum* cDNA clone cLEN18A16 5', mRNA sequence"; source: *Solanum lycopersicum* (*Lycopersicon esculentum*); Title: "Generation of ESTs from tomato fruit tissue" (Unpublished (1999).

AW441775 NCBI acc. No. AW441775 (gi: 6977026) (Feb. 14, 2000); Alcala,J., et al. "EST311171 tomato fruit red ripe, TAMU *Solanum lycopersicum* cDNA clone cLEN18018 5', mRNA sequence"; source: *Solanum lycopersicum* (*Lycopersicon esculentum*); Title: "Generation of ESTs from tomato fruit tissue" (Unpublished (1999).

AW507860 NCBI acc. No. AW507860 (gi: 7145938) (Mar. 3, 2000); Shoemaker,R., et al. "si45h05.y1 Gm-r1030 *Glycine max* cDNA clone Genome Systems Clone ID: Gm-r1030-1906 5', similar to TR:Q40478 Q40478 EREBP-4. ;, mRNA sequence"; source: *Glycine max* (soybean); Title: "Public Soybean EST Project" (Unpublished (1999)).

AW507898 NCBI acc. No. AW507898 (gi: 7145976) (Mar. 3, 2000); Shoemaker,R., et al. "si46f03.y1 Gm-r1030 *Glycine max* cDNA clone Genome Systems Clone ID: Gm-r1030-1974 5', similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

AW559315 NCBI acc. No. AW559315 (gi: 7204741) (Mar. 7, 2000); Fedorova,M., et al. "EST306358 DSIR *Medicago truncatula* cDNA clone pDSIR-2515, mRNA sequence"; source: *Medicago truncatula* (barrel medic); Title: "ESTs from roots of *Medicago truncatula* after inoculation with *Phytophthora medicaginis*" (Unpublished (1999)).

AW559374 NCBI acc. No. AW559374 (gi: 7204800) (Mar. 7, 2000); Fedorova,M., et al. "EST314422 DSIR *Medicago truncatula* cDNA clone pDSIR-7J9, mRNA sequence"; source: *Medicago truncatula* (barrel medic); Title: "ESTs from roots of *Medicago truncatula* after inoculation with *Phytophthora medicaginis*" (Unpublished (1999)).

AW559641 NCBI acc. No. AW559641 (gi: 7205131) (Mar. 7, 2000); Fedorova,M., et al. "EST314753 DSIR *Medicago truncatula* cDNA clone pDSIR-24B7, mRNA sequence"; source: *Medicago truncatula* (barrel medic); Title: "ESTs from roots of *Medicago truncatula* after inoculation with *Phytophthora medicaginis*" (Unpublished (1999)).

AW560134 NCBI acc. No. AW560134 (gi: 7205560) (Mar. 7, 2000); Fedorova,M., et al. "EST315182 DSIR *Medicago truncatula* cDNA clone pDSIR-26023, mRNA sequence"; source: *Medicago truncatula* (barrel medic); Title: "ESTs from roots of *Medicago truncatula* after inoculation with *Phytophthora medicaginis*" (Unpublished (1999)).

AW560135 NCBI acc. No. AW560135 (gi: 7205561) (Mar. 7, 2000); Fedorova,M., et al. "EST315183 DSIR *Medicago truncatula* cDNA clone pDSIR-26023, mRNA sequence"; source: *Medicago truncatula* (barrel medic); Title: "ESTs from roots of *Medicago truncatula* after inoculation with *Phytophthora medicaginis*" (Unpublished (1999)).

AW560196 NCBI acc. No. AW560196 (gi: 7205622) (Mar. 7, 2000); Fedorova,M., et al. "EST315244 DSIR *Medicago truncatula* cDNA clone pDSIR-26K12, mRNA sequence"; source: *Medicago truncatula* (barrel medic); Title: "ESTs from roots of *Medicago truncatula* after inoculation with *Phytophthora medicaginis*" (Unpublished (1999)).

AW560968 NCBI acc. No. AW560968 (gi: 7206394) (Mar. 7, 2000); Fedorova,M., et al. "EST316016 DSIR *Medicago truncatula* cDNA clone pDSIR-30N21, mRNA sequence"; source: *Medicago truncatula* (barrel medic); Title: "ESTs from roots of *Medicago truncatula* after inoculation with *Phytophthora medicaginis*" (Unpublished (1999)).

AW568194 NCBI acc. No. AW568194 (gi: 7232842) (Mar. 13, 2000); Shoemaker,R., et al. "si57g03.y1 Gm-r1030 *Glycine max* cDNA clone Genome Systems Clone ID: Gm-r1030-3053 5', similar to TR:O23107 O23107 AP2 Domain Containing Protein RAP2.5. [1] ;, mRNA sequence"; source: *Glycine max* (soybean); Title: "Public Soybean EST Project" (Unpublished (1999)).

AW574073 NCBI acc. No. AW574073 (gi: 7238806) (Mar. 13, 2000); Fedorova,M., et al. "EST316664 GVN *Medicago truncatula* cDNA clone pGVN-51 E4, mRNA sequence"; source: *Medicago truncatula* (barrel medic); Title: "ESTs from one month old nitrogen-fixing root nodules of *Medicago truncatula*" (Unpublished (2000)).

AW574222 NCBI acc. No. AW574222 (gi: 7238955) (Mar. 13, 2000); Fedorova,M., et al. "EST316813 GVN *Medicago truncatula* cDNA clone pGVN-52B10, mRNA sequence"; source: *Medicago truncatula* (barrel medic); Title: "ESTs from one month old nitrogen-fixing root nodules of *Medicago truncatula*" (Unpublished (2000)).

AW596384 NCBI acc. No. AW596384 (gi: 7283781) (Mar. 22, 2000); Shoemaker,R., et al. "sjO2f12.y1 Gm-c1032 *Glycine max* cDNA clone Genome Systems Clone ID: Gm-c1032-744 5', similar to TR:Q40478 Q40478 EREBP-4. ;, mRNA sequence"; source: *Glycine max* (soybean); Title: "Public Soybean EST Project" (Unpublished (1999)).

AW618112 NCBI acc. No. AW618112 (gi: 7324339) (Mar. 24, 2000); Alcala,J., et al. "EST314162 *L. pennellii* trichome, Cornell University *Solanum pennellii* cDNA clone cLPT12K17 5', mRNA sequence"; source: *Solanum pennellii* (*Lycopersicon pennellii*); Title: "Generation of ESTs from wild tomato (*Lycopersicon pennellii*) trichomes" (Unpublished (1999)).

AW618245 NCBI acc. No. AW618245 (gi: 7324479) (Mar. 24, 2000); Alcala,J., et al. "EST314295 *L. pennellii* trichome, Cornell University *Solanum pennellii* cDNA clone cLPT15H2O 5', mRNA sequence"; source: *Solanum pennellii* (*Lycopersicon pennellii*); Title: "Generation of ESTs from wild tomato (*Lycopersicon pennellii*) trichomes" (Unpublished (1999)).

AW620490 NCBI acc. No. AW620490 (gi: 7326692) (Mar. 24, 2000); Shoemaker,R., et al. "sjO5h02.y1 Gm-c1032 Glycine max cDNA clone Genome Systems Clone ID: Gm-c1032-1036 5', similar to TR:080387 080387 Ethylene Responsive Element Binding Factor. ;, mRNA sequence"; source: *Glycine max* (soybean); Title: "Public Soybean EST Project" (Unpublished (1999)).

AW622531 NCBI acc. No. AW622531 (gi: 7334178) (Mar. 28, 2000); Van Der Hoeven,R.S., et al. "EST313331 tomato root during/ after fruit set, Cornell University *Solanum lycopersicum* cDNA clone cLEX15D17 5', mRNA sequence"; source: *Solanum lycopersicum* (*Lycopersicon esculentum*); Title: "Generation of ESTs from tomato root, during and after fruit set" (Unpublished (1999)).

AW647824 NCBI acc. No. AW647824 (gi: 7409062) (Apr. 4, 2000); Alcala,J., et al. "EST326278 tomato germinating seedlings, Tamu *Solanum lycopersicum* cDNA clone cLEI2M8 5', mRNA sequence"; source: *Solanum lycopersicum* (*Lycopersicon esculentum*); Title: "Generation of ESTs from germinating tomato seed" (Unpublished 2000)).

AW685799 NCBI acc. No. AW685799 (gi: 7560535) (Apr. 14, 2000); Watson,B.S., et al. "NFO3ODO9NR1F1000 Nodulated root *Medicago truncatula* cDNA clone NFO3ODO9NR 5', mRNA sequence"; source: *Medicago truncatula* (barrel medic); Title: "Expressed Sequence Tags from the Samuel Roberts Noble Foundation *Medicago truncatula* nodulated root library" (Unpublished 2000)).

AW686013 NCBI acc. No. AW686013 (gi: 11930899) (Apr. 14, 2000); Watson,B.S., et al. "NF033DO4NR1F1000 Nodulated root *Medicago truncatula* cDNA clone NF033DO4NR 5', mRNA sequence"; source: *Medicago truncatula* (barrel medic); Title: "Expressed Sequence Tags from the Samuel Roberts Noble Foundation *Medicago truncatula* nodulated root library" (Unpublished 2000)).

AW686992 NCBI acc. No. AW686992 (gi: 11930183) (Apr. 14, 2000); Watson,B.S., et al. "NFOO4GO7RT1F1055 Developing root *Medicago truncatula* cDNA clone NFOO4GO7RT 5', mRNA sequence"; source: *Medicago truncatula* (barrel medic); Title: "Expressed Sequence Tags from the Samuel Roberts Noble Foundation *Medicago truncatula* root library" (Unpublished 2000)).

AW706554 NCBI acc. No. AW706554 (gi: 7590810) (Apr. 18, 2000); Shoemaker,R., et al. "sj58h12.y1 Gm-c1033 *Glycine max* cDNA clone Genome Systems Clone ID: Gm-c1033-1536 5' similar to TR:Q9ZR85 Q9ZR85 Ethylene-Responsive Element Binding Protein Homolog. ;, mRNA sequence"; source: *Glycine max* (soybean); Title: "Publication Soybean EST Project" (Unpublished 1999)).

AW737966 NCBI acc. No. AW737966 (gi: 7646911) (Apr. 25, 2000); Van Der Hoeven,R.S., et al. "EST339393 tomato flower buds, anthesis, Cornell University *Solanum lycopersicum* cDNA clone cTOD4F22 5', mRNA sequence"; source: *Solanum lycopersicum* (*Lycopersicon esculentum*); Title: "Generation of ESTs from tomato flower tissue, anthesis" (Unpublished (1999)).

AW759181 NCBI acc. No. AW759181 (gi: 7691047) (May 4, 2000); Shoemaker,R., et al. "s138a09.y1 Gm-c1027 *Glycine max* cDNA clone Genome Systems Clone ID: Gm-c1027-3569 5' similar to TR:O80387 O80387 Ethylene Responsive Element Binding Factor. ;, mRNA sequence"; source: *Glycine max* (soybean); Title: "Public Soybean EST Project" (Unpublished (1999)).

AW760204 NCBI acc. No. AW760204 (gi: 7692089) (May 4, 2000); Shoemaker,R., et al. "s159d04.y1 Gm-c1027 *Glycine max* cDNA clone Genome Systems Clone ID: Gm-c1027-5600 5' similar to TR:O23143 O23143 Putative CKC2. ;, mRNA sequence"; source: *Glycine max* (soybean); Title: "Public Soybean EST Project" (Unpublished (1999)).

AW774176 NCBI acc. No. AW774176 (gi: 7718021) (May 8, 2000); Vandenbosch,K., et al. "EST333259 KV3 *Medicago truncatula* cDNA clone pKV3-21J17, mRNA sequence"; source: *Medicago truncatula* (barrel medic); Title: "ESTs from roots of *Medicago truncatula* after *Rhizobium* inoculation" (Unpublished (1999)).

AW776668 NCBI acc. No. AW776668 (gi: 7766481) (May 9, 2000); Fedorova,M., et al. "EST335733 DSIL *Medicago truncatula* cDNA clone pDSIL-13B14, mRNA sequence"; source: *Medicago truncatula* (barrel medic); Title: "ESTs from leaves of *Medicago truncatula* after inoculation with *Colletotrichum trifolii*" (Unpublished (2000)).

AW781602 NCBI acc. No. AW781602 (gi: 7796205) (May 12, 2000); Shoemaker,R., et al. "s182d06.y1 Gm-c1037 *Glycine max* cDNA clone Genome Systems Clone ID: Gm-c1037-516 5' similar to Tr:Q40478 Q40478 EREBP-4. ;, mRNA sequence"; source: *Glycine max* (soybean); Title: "Public Soybean EST Project" (Unpublished (1999)).

AW782252 NCBI acc. No. AW782252 (gi: 7796858) (May 12, 2000); Shoemaker,R., et al. "sm03d11.y1 Gm-c1027 *Glycine max* cDNA clone Genome Systems Clone ID: Gm-c1027-7822 5' similar to TR:P93007 P93007 Cadmium-Induced Protein Isolog. ;, mRNA sequence"; source: *Glycine max* (soybean); Title: "Public Soybean EST Project" (Unpublished (1999)).

AW840600 NCBI acc. No. AW840600 (gi: 7934583) (May 18, 2000); Anderson,J.V., et al. "00058 leafy spurge Lambda HybriZAP 2.1 two-hybrid vector cDNA Library *Euphorbia esula* cDNA clone 16G 5' similar to DNA-binding Protein/AP2-Domain Containing Protein, mRNA sequence"; source: *Euphorbia esula* (leafy spurge); Title: "Identification of mRNAs expressed in underground adventitious buds of *Euphorbia esula* (leafy spurge)" (Unpublished (2000)).

AW840611 NCBI acc. No. AW840611 (gi: 7934594) (May 18, 2000); Anderson,J.V., et al. "00057 leafy spurge Lambda HybriZAP 2.1 two-hybrid vector cDNA Library *Euphorbia esula* cDNA clone 1G 5' similar to DNA-binding Protein-Ethylene Responsive Factor, mRNA sequence"; source: *Euphorbia esula* (leafy spurge); Title: "Identification of mRNAs expressed in underground adventitious buds of *Euphorbia esula* (leafy spurge)" (Unpublished (2000)).

AW930351 NCBI acc. No. AW930351 (gi: 8105848) (May 30, 2000); Alcala,J., et al. "EST340904 tomato fruit mature green, TAMU *Solanum lycopersicum* cDNA clone cLEF43H15 5, mRNA sequence"; source: *Solanum lycopersicum* (*Lycopersicon esculentum*); Title: "Generation of ESTs from tomato fruit tissue" (Unpublished (1999)).

AW931292 NCBI acc. No. AW931292 (gi: 8106693) (May 30, 2000); Alcala,J., et al. "EST357135 tomato fruit mature green, TAMU *Solanum lycopersicum* cDNA clone cLEF44J15 5', mRNA sequence"; source: *Solanum lycopersicum* (*Lycopersicon esculentum*); Title: "Generation of ESTs from tomato fruit tissue" (Unpublished (1999)).

AW933517 NCBI acc. No. AW933517 (gi: 8108834) (May 30, 2000); Alcala,J., et al. "EST359276 tomato fruit mature green, TAMU *Solanum lycopersicum* cDNA clone cLEF54C10 5', mRNA sequence"; source: *Solanum lycopersicum* (*Lycopersic esculentum*); Title: "Generation of ESTs from tomato fruit tissue" (Unpublished (1999)).

AW980654 NCBI acc. No. AW980654 (gi: 8172193) (Jun. 2, 2000); Fedorova,M., et al. "EST391807 GVN *Medicago truncatula* cDNA clone pGVN-55D7, mRNA sequence"; source: *Medicago truncatula* (barrel medic); Title: "ESTs from one month old nitrogen-fixing root nodules of *Medicago truncatula*" (Unpublished (2000)).

AW980969 NCBI acc. No. AW980969 (gi: 8172507) (Jun. 2, 2000); Fedorova,M., et al. "EST392114 GVN *Medicago truncatula* cDNA clone pGVN-60017, mRNA sequence"; source: *Medicago truncatula* (barrel medic); Title: "ESTs from one month old nitrogen-fixing root nodules of *Medicago truncatula*" (Unpublished (2000)).

AW981151 NCBI acc. No. AW981151 (gi: 8172743) (Jun. 2, 2000); Fedorova,M., et al. "EST392345 DSIL *Medicago truncatula* cDNA clone pDSIL-12111, mRNA sequence"; source: *Medicago*

*truncatula* (barrel medic); Title: "ESTs from leaves of *Medicago truncatula* after inoculation with *Colletotrichum trifolii*" (Unpublished (2000)).

AX033191 NCBI acc. No. AX033191 (gi: 10280046) (Sep. 22, 2000); Memelink,J., et al. "Sequence 2 from Patent WO0046383"; source: *Catharanthus reseus (Madagascar periwinkle)*; Title "Method of modulating metabolite biosynthesis in recombinant cells" (Patent: WO 0046383-A Aug. 10, 2000; Univ Leiden (NL); Memelink Johan (NL); Fits Cornelia Theodora Elisabe (NL); Kijne Jan Willem (NL); Menke Frank Leonardus Hendriku (NL)).

AX033192 NCBI acc. No. AX033192 (gi: 10280047) (Sep. 22, 2000); Memelink,J., et al. "Sequence 3 from Patent WO0046383"; source *Catharanthus reseus (Madagascar periwinkle)*; Title: "Method of modulating metabolitie biosynthesis in recombinant cells" (Patent: WO 0046383-A Aug. 10, 2000; Univ Leiden (NL); Memelink Johan (NL); Fits Cornelia Theodora Elisabe (NL); Kijne Jan Willem (NL); Menke Frank Leonardus Hendriku (NL)).

AX573798 NCBI acc. No. AX573798 (gi: 27551457) (Jan. 9, 2003); Pages,M., et al. "Sequence 15 from Patent WO002079245"; source: *Oryza sativa*; Title: "Method for improving plant tolerance to environmental stress" (Patent: WO 02079245-A 15 Oct. 10, 2002; Consejo Superior Investigaciones Cientificas (CSIC) (ES)).

AY192370 NCBI acc. No. AY192370 (gi: 28274833) (Feb. 9, 2003); Tournier,B., et al. "*Lycopersicon esculentum* ethylene response factor 4 (ERF4) mRNA, complete cds"; source: *Lycopersicon esculentum* (tomato); Title: "LeERF2 defines a novel class of ethylene response factors and confers enhanced tolerance to cold stress when overexpressed in the tomato" (Unpublished).

BE057468 NCBI acc. No. BE057468 (gi: 8401834) (Jun. 9, 2000); Shoemaker,R., et al. "sm58e08.y1 Gm-c1028 *Glycine max* cDNA clone Genome Systems Clone ID: Gm-c1028-8127 5' similar to TR:O23105 O23105 AP2 Domain Containing Protein RAP2.3. ;, mRNA sequence"; source: *Glycine max* (soybean); Title: "Public Soybean EST Project" (Unpublished (1999)).

BE191029 NCBI acc. No. BE191029 (gi: 8669922) (Jun. 22, 2000); Shoemaker,R., et al. "sn83h08.y1 Gm-c1038 Glycine max cDNA clone Genome Systems Clone ID: Gm-c1038-1240 5' similar to TR:Q9ZR85 Q9ZR85 Ethylene-Responsive Element Binding Protein Homolog. ;, mRNA sequence"; source: *Glycine max* (soybean); Title: "Public Soubean EST Project" (Unpublished (1999)).

BE203165 NCBI acc. No. BE203165 (gi: 8746436) (Jun. 27, 2000); Vandenbosch,K., et al. "EST403187 KV1 *Medicago truncatula* cDNA clone pKV1-4L15, mRNA sequence"; source: *Medicago truncatula* (barrel medic); Title: "ESTs from roots of *Medicago truncatula* 24 hours after inoculation with *Sinorhizobiu meliloti*"; (Unpublished (1999)).

BE203296 NCBI acc. No. BE203296 (gi: 8746567) (Jun. 27, 2000); Vandenbosch,K., et al. "EST403318 KV1 *Medicago truncatula* cDNA clone pKV1-5G15, mRNA sequence"; source: *Medicago truncatula* (barrel medic); Title: "ESTs from roots of *Medicago truncatula* 24 hours after inoculation with *Sinorhizobiu meliloti*"; (Unpublished (1999)).

BE318516 NCBI acc. No. BE318516 (gi: 11960607) (Jul. 14, 2000); Torres-Jerez,I., et al."NF071G07LF1F1053 Developing leaf *Medicago truncatula* cDNA clone NF071 G07LF 5', mRNA sequence"; source: *Medicago truncatula* (barrel medic); Title: "Expressed Sequence Tags from the Samuel Roberts Noble Foundation *Medicago truncatula* leaf library" (Unpublished (2000)).

BE325359 NCBI acc. No. BE325359 (gi: 11935917) (Jul. 14, 2000); He,X.-Z., et al. "NF087B10ST1F1077 Developing stem *Medicago truncatula* cDNA clone NF087B10ST 5', mRNA sequence"; source: *Medicago truncatula* (barrel medic); Title: "Expressed Sequence Tags from the Samuel Roberst Noble Foundation *Medicago truncatula* stem library" (Unpublished (2000)).

BE326131 NCBI acc. No. BE326131 (gi: 11934119) (Jul. 14, 2000); He,X.-Z., et al. "NF085C08ST1F1055 Developing stem *Medicago truncatula* cDNA clone NF085C08ST 5', mRNA sequence"; source: *Medicago truncatula* (barrel medic); Title: "Expressed Sequence Tags from the Samuel Roberts Noble Foundation *Medicago truncatula* stem library" (Unpublished (2000)).

BE330726 NCBI acc. No. BE330726 (gi: 9204502) (Jul. 14, 2000); Shoemaker,R., et al. "so84a08.y1 Gm-c1041 *Glycine max* cDNA clone Genome Systems Clone ID: Gm-c1041-15 5', similar to TR:O81365 O81365 AP2 Domain Containing Protein:, mRNA sequence"; source: *Glycine max* (soybean); Title: "Public Soybean EST Project" (Unpublished (1999)).

BE331593 NCBI acc. No. BE331593 (gi: 9205369) (Jul. 14, 2000); Shoemaker,R., et al. "sp16c03.y1 Gm-c1042 *Glycine max* cDNA clone Genome Systems Clone ID: Gm-c1042-701 5' similar to Tr:Q40478 Q40478 EREBP-4. ;, mRNA sequence"; source: *Glycine max* (soybean); Title: "Public Soybean EST Project" (Unpublished (1999)).

BE357795 NCBI acc. No. BE357795 (gi: 9299352) (Jul. 20, 2000); Cordonnier-Pratt,M.-M., et al. "DG1_22_A02.b1_A002 Dark Grown 1 (DG1) *Sorghum bicolor* cDNA, mRNA sequence"; source: *Sorghum bicolor* (sorghum); Title: "An EST database from *Sorghum*: dark-grown seedlings" (Unpublished (2000)).

BE365169 NCBI acc. No. BE365169 (gi: 9306726) (Jul. 20, 2000); Cordonnier-Pratt,M.-M., et al."P11_25_F08.b1_A002 Pathogen induced 1 (PI1) *Sorghum bicolor* cDNA, mRNA sequence"; source: *Sorghum bicolor* (sorghum); Title: "An EST database from *Sorghum*: pathogen-induced plants" (Unpublished (2000)).

BE427520 NCBI acc. No. BE427520 (gi: 9425363) (Jul. 24, 2000); Anderson,O.A., et al. "PSR7136 ITEC PSR Wheat Pericarp/Testa Library *Triticum aestivum* cDNA clone PSR7136, mRNA sequence"; source: *Triticum aestivum* (bread wheat); Title: "International Triticeae EST Cooperative (ITEC): Production of Expressed Sequence Tags for Species of the Triticeae" (Unpublished (2000)).

BE429439 NCBI acc. No. BE429439 (gi: 9427282) (Jul. 24, 2000); Anderson,O.A., et al. "TAS000.B08R990618 ITEC TAS Wheat cDNA Library *Triticum aestivum* cDNA clone TAS000.B08, mRNA sequence"; source: *Triticum aestivum* (bread wheat); Title: "International Triticeae EST Cooperative (ITEC): Production of Expressed Sequence Tags for Species of the Triticeae" (Unpublished (2000)).

BE432465 NCBI acc. No. BE432465 (gi: 9430308) (Jul. 24, 2000); Alcala,J., et al. "EST398994 tomato breaker fruit, TIGR *Solanum lycopersicum* cDNA clone cLEG8I18, mRNA sequence"; source: *Solanum lycopersicum (Lycopersicon esculentum)*; Title: "Generation of ESTs from tomato fruit tissue, breaker stage" (Unpublished (2000)).

BE433462 NCBI acc. No. BE433462 (gi: 9431305) (Jul. 24, 2000); Alcala,J., et al. "EST399991 tomato breaker fruit, TIGR *Solanum lycopersicum* cDNA clone cLEG14M13, mRNA sequence"; source: *Solanum lycopersicum (Lycopersicon esculentum)*; Title: "Generation of ESTs from tomato fruit tissue, breaker stage" (Unpublished (2000)).

BE435827 NCBI acc. No. BE435827 (gi: 9433670) (Jul. 24, 2000); Alcala,J., et al. "EST406905 tomato breaker fruit, TIGR *Solanum lycopersicum* cDNA clone cLEG29O9, mRNA sequence"; source: *Solanum lycopersicum (Lycopersicon esculentum)*; Title: "Generation of ESTs from tomato fruit tissue, breaker stage" (Unpublished 2000)).

BE436333 NCBI acc. No. BE436333 (gi: 9434176) (Jul. 24, 2000); Alcala,J., et al. "EST407411 tomato breaker fruit, TIGR *Solanum lycopersicum* cDNA clone cLEG32E7, mRNA sequence"; source: *Solanum lycopersicum (Lycopersicon esculentum)*; Title: "Generation of ESTs from tomato fruit tissue, breaker stage" (Unpublished 2000)).

BE436391 NCBI acc. No. BE436391 (gi: 9434234) (Jul. 24, 2000); Alcala,J., et al. "EST407469 tomato breaker fruit, TIGR *Solanum lycopersicum* cDNA clone cLEG32A16, mRNA sequence"; source: *Solanum lycopersicum (Lycopersicon esculentum)*; Title: "Generation of ESTs from tomato fruit tissue, breaker stage" (Unpublished 2000)).

BE436556 NCBI acc. No. BE436556 (gi: 9434399) (Jul. 24, 2000); Alcala,J., et al. "EST407634 tomato breaker fruit, TIGR *Solanum lycopersicum* cDNA clone cLEG33I3, mRNA sequence"; source: *Solanum lycopersicum (Lycopersicon esculentum)*; Title: "Generation of ESTs from tomato fruit tissue, breaker stage" (Unpublished 2000)).

BE449392 NCBI acc. No. BE449392 (gi: 9454895) (Jul. 26, 2000); Van Der Hoeven,R.S., et al. "EST356151 *L. hirsutum* trichome, Cornell University *Solanum habrochaites* cDNA clone cLHT31 K6, mRNA sequence"; source: *Solanum habrochaites (Lycopersicon hirsutum)*; Title: Generation of ESTs from wild tomato (*Lycopersicon hirsutum*); Title: "Generation of ESTs from tomato fruit tissue, immature green" (Unpublished (2000)).
BE459781 NCBI acc. No. BE459781 (gi: 9504083) (Jul. 27, 2000); Alcala,J., et al. "EST415073 tomato developing/immature green fruit *Solanum lycopersicum* cDNA clone cLEM8C19, mRNA sequence"; source: *Solanum lycopersicum* (*Lycopersicon esculentum*); Title: "Generation of ESTs from tomato fruit tissue, immature green" (Unpublished (2000)).
BE461852 NCBI acc. No. BE461852 (gi: 9506154) (Jul. 27, 2000); Alcala,J., et al. "EST413271 tomato breaker fruit, TIGR *Solanum lycopersicum* cDNA clone cLEG40O17, mRNA sequence"; source: *Solanum lycopersicum* (*Lycopersicon esculentum*); Title: "Generation of ESTs from tomato fruit tissue, breaker stage" (Unpublished 2000)).
BE474049 NCBI acc. No. BE474049 (gi: 9564540) (Jul. 28, 2000); Shoemaker,R., et al. "sp58d12.y1 Gm-c1044 *Glycine max* cDNA clone Genome Systems Clone ID: Gm-c1044-144 5' similar to TR:081365 081365 AP2 Domain Containing Protein ;, mRNA sequence"; source: *Glycine max* (soybean); Title; "Public Soybean EST Project" (Unpublished (1999)).
BE494041 NCBI acc. No. BE494041 (gi: 9660634) (Aug. 2, 2000); Anderson,O.D., et al. "WHE1277_B09_D17ZS Secale cereale anther cDNA library Secale cereale cDNA clone WHE1277_B09_D17, mRNA sequence"; source: *Secale cereale* (rye); Title: "The structure and function of the expressed portion of the wheat genomes—Anther cDNA library from rye" (Unpublished (2000)).
BE554898 NCBI acc. No. BE554898 (gi: 9819385) (Aug. 15, 2000); Shoemaker,R., et al. "sp82c07.y1 Gm-c1045 *Glycine max* cDNA clone Genome Systems Clone ID: Gm-c1045-133 5' similar to TR:Q40478 Q40478 EREBP-4. ;, mRNA sequence"; source: *Glycine max* (soybean); Title: "Public Soybean EST Project" (Unpublished (1999)).
BE555398 NCBI acc. No. BE555398 (gi: 9819822) (Aug. 15, 2000); Shoemaker,R., et al. "sp88c01.y1 Gm-c1045 *Glycine max* cDNA clone Genome Systems Clone ID: Gm-c1045-697 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).
BE599413 NCBI acc. No. BE599413 (gi: 9854486) (Aug. 18, 2000); Cordonnier-Pratt,M.-M., et al. "PI1_87_C-4/n2_A002 Pathogen induced 1 (PI1) *Sorghum bicolor* cDNA, mRNA sequence"; source: *Sorghum bicolor* (sorghum); Title: "An EST database from *Sorghum*: pathogen-induced plants" (Unpublished (2000)).
BE610114 NCBI acc. No. BE610114 (gi: 9901146) (Aug. 24, 2000); Shoemaker,R., et al. "sp80h02.y1 Gm-c1044 *Glycine max* cDNA clone Genome Systems Clone ID: Gm-c1044-2284 5' similar to TR:Q40478 Q40478 EREBP-4. ;, mRNA sequence"; source: *Glycine max* (soybean); Title: "Public Soybean EST Project" (Unpublished (1999)).
BE801560 NCBI acc. No. BE801560 (gi: 10232672) (Sep. 20, 2000); Shoemaker,R., et al. "sr16a08.y1 Gm-c1050 *Glycine max* cDNA clone Genome Systems Clone ID: Gm-c1050-495 5' similar to TR:O80387 O80387 Ethylene Responsive Element Binding Factor. ;, mRNA sequence"; source *Glycine max* (soybean); Title: "Public Soybean EST Project" (Unpublished (1999)).
BE804368 NCBI acc. No. BE804368 (gi: 10235480) (Sep. 20, 2000); Shoemaker,R., et al. "sr78h05.y1 Gm-c1052 *Glycine max* cDNA clone Genome Systems Clone ID: Gm-c1052-1906 5' similar to TR:Q40478 Q40478 EREBP-4. ;, mRNA sequence"; source: *Glycine max* (soybean); Title: "Public Soybean EST Project" (Unpublished (1999)).
BE805304 NCBI acc. No. BE805304 (gi: 10236416) (Sep. 20, 2000); Shoemaker,R., et al. "ss40h06.y1 Gm-c1061 *Glycine max* cDNA clone Genome Systems Clone ID: Gm-c1061-1236 5' similar to TR:Q40478 Q40478 EREBP-4. ;, mRNA sequence"; source: *Glycine max* (soybean); Title: "Public Soybean EST Project" (Unpublished (1999)).
BE820195 NCBI acc. No. BE820195 (gi: 10252429) (Sep. 21, 2000); Vodkin,L., et al. "GM700006A11G12 Gm-r1070 *Glycine MAX* cDNA clone Gm-r1070-2231 3', mRNA sequence"; source: *Glycine max* (soybean); Title: "A Functional Genomics Program for Soybean (NSF 9872565)" (Unpublished (1999)).

BE941508 NCBI acc. No. BE941508 (gi: 10519339) (Oct. 3, 2000); Cote,F., et al. "EST421159 MGHG *Medicago truncatula* cDNA clone pMGHG-4M14, mRNA sequence"; source: *Medicago truncatula* (barrel medic); Title: "ESTs from seedling roots of *Medicago truncatula* after treatment with beta glucan elicitor preparation from *Phytophthora sojae*" (Unpublished (2000)).
BE941864 NCBI acc. No. BE941864 (gi: 10519623) (Oct. 3, 2000); Cote,F., et al. "EST421443 MGHG *Medicago truncatula* cDNA clone pMGHG-6D2, mRNA sequence"; source: *Medicago truncatula* (barrel medic); Title: "ESTs from seedling roots of *Medicago truncatula* after treatment with beta glucan elicitor preparation from *Phytophthora sojae*" (Unpublished (2000)).
BE942996 NCBI acc. No. BE942996 (gi: 10520755) (Oct. 3, 2000); Cote,F., et al. "EST422575 MGHG *Medicago truncatula* cDNA clone pMGHG-14B1, mRNA sequence"; source: *Medicago truncatula* (barrel medic); Title: "ESTs from seedling roots of *Medicago truncatula* after treatment with beta glucan elicitor preparation from *Phytophthora sojae*" (Unpublished (2000)).
BE997398 NCBI acc. No. BE997398 (gi: 10697674) (Oct. 6, 2000); Fedorova,M., et al. "EST429121 GVSN *Medicago truncatula* cDNA clone pGVSN-1 C3, mRNA sequence"; source: *Medicago truncatula* (barrel medic); Title: "ESTs from senescent nodules of *Medicago truncatula*" (Unpublished (2000)).
BE997780 NCBI acc. No. BE997780 (gi: 10698056) (Oct. 6, 2000); Fedorova,M., et al. "EST429503 GVSN *Medicago truncatula* cDNA clone pGVSN-4M3, mRNA sequence"; source: *Medicago truncatula* (barrel medic); Title: "ESTs from senescent nodules of *Medicago truncatula*" (Unpublished 2000)).
BE997834 NCBI acc. No. BE997834 (gi: 10698110) (Oct. 6, 2000); Fedorova,M., et al. "EST429557 GVSN *Medicago truncatula* cDNA clone pGVSN-8G17, mRNA sequence"; source: *Medicago truncatula* (barrel medic); Title: "ESTs from senescent nodules of *Medicago truncatula*" (Unpublished (2000)).
BE999493 NCBI acc. No. BE999493 (gi: 10699769) (Oct. 6, 2000); Fedorova,M., et al. "EST431216 GVSN *Medicago truncatula* cDNA clone pGVSN-16L15, mRNA sequence"; source: *Medicago truncatula* (barrel medic); Title: "ESTs from senescent nodules of *Medicago truncatula*" (Unpublished (2000)).
BF006068 NCBI acc. No. BF006068 (gi: 10706343) (Oct. 6, 2000); Fedorova,M., et al. "EST434566 DSLC *Medicago truncatula* cDNA clone pDSLC-39F7, mRNA sequence"; source: *Medicago truncatula* (barrel medic); Title: "ESTs from *Medicago truncatula* leaves and cotyledons" (Unpublished (2000)).
BF006539 NCBI acc. No. BF006539 (gi: 10706814) (Oct. 6, 2000); Fedorova,M., et al. "EST435037 DSLC *Medicago truncatula* cDNA clone pDSLC-41L18, mRNA sequence"; source: *Medicago truncatula* (barrel medic); Title: "ESTs from *Medicago truncatula* leaves and cotyledons" (Unpublished (2000)).
BF008875 NCBI acc. No. BF008875 (gi: 10709151) (Oct. 6, 2000); Shoemaker,R., et al. "ss70e04.y1 Gm-c1062 *Glycine max* cDNA clone Genome Systems Clone ID: Gm-c1062-1783 5' similar to TR:O81365 O81365 AP2 Domain Containing Protein ;, mRNA sequence"; source: *Glycine max* (soybean); Title; "Public Soybean EST Project" (Unpublished (1999)).
BF009446 NCBI acc. No. BF009446 (gi: 10709722) (Oct .6, 2000); Shoemaker,R., et al. "ss78g12.y1 Gm-c1064 *Glycine max* cDNA clone Genome Systems Clone ID: Gm-c1064-287 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).
BF068784 NCBI acc. No. BF068784 (gi: 10845722) (Oct. 17, 2000); Shoemaker,R., et al. "st02e12.y1 Gm-c1065 *Glycine max* cDNA clone Genome Systems Clone ID: Gm-c1065-167 5' similar to TR:P93589 P93589 DNA Binding Protein Homolog. ;, mRNA sequence"; source: *Glycine max* (soybean); Title: "Public Soybean EST Project" (Unpublished (1999)).
BF070873 NCBI acc. No. BF070873 (gi: 10843956) (Oct. 17, 2000); Shoemaker,R., et al. "st38c09.y1 Gm-c1067 *Glycine max* cDNA clone Genome Systems Clone ID: Gm-c1067-1266 5' similar to TR:023143 0231 43 Putative CKC2. ;, mRNA sequence"; source: *Glycine max* (soybean); Title: "Public Soybean EST Project" (Unpublished (1999)).

BF096818 NCBI acc. No. BF096818 (gi: 10902528) (Oct. 19, 2000); Van Der Hoeven,R.S., et al. "EST360845 tomato nutrient deficient roots *Solanum lycopersicum* cDNA clone cLEW17I10 5 sequence, mRNA sequence"; source: *Solanum lycopersicum* (*Lycopersicon esculentum*); Title: "Generation of ESTs from tomato nutrient-deficient roots" (Unpublished (1999)).

BF112878 NCBI acc. No. BF112878 (gi: 10942568) (Oct. 20, 2000); Alcala,J., et al. "EST440468 tomato breaker fruit *Solanum lycopersicum* cDNA clone cLEG42N7 5' sequence, mRNA sequence"; source: *Solanum lycopersicum* (*Lycopersicon esculentum*); Title: "Generation of ESTs from Tomato fruit tissue, breaker stage" (Unpublished (2000)).

BF113172 NCBI acc. No. BF113172 (gi: 10942862) (Oct. 20, 2000); Alcala,J., et al. "EST440762 tomato breaker fruit *Solanum lycopersicum* cDNA clone cLEG43D8 5 sequence, mRNA sequence"; source: *Solanum lycopersicum* (*Lycopersicon esculentum*); Title: "Generation of ESTs from tomato fruit tissue, breaker stage" (Unpublished (2000)).

BF263411 NCBI acc. No. BF263411 (gi: 13260800) (Nov. 17, 2000); Wing,R., et al. "HV_CEa0006K20f *Hordeum vulgare* seedling green leaf EST library HVcDNA0004 (Blumeria challenged) *Hordeum vulgare* subsp. vulgare cDNA clone HV_CEa0006K20f, mRNA sequence"; source: *Hordeum vulgare* subsp. vulgare; Title: "Development of a genetically and physically anchored EST resource for barley genomics: Blumeria infected incompatible (Mla13) seeding leaf cDNA library" (Unpublished (2001)).

BF275458 NCBI acc. No. BF275458 (gi: 11206528) (Nov. 17, 2000); Wing,R.A., et al. "GA_Eb0024B16f *Gossypium arboreum* 7-10 dpa fiber library *Gossypium arboreum* cDNA clone GA_Eb0024B16f, mRNA sequence"; source: *Gossypium arboreum*; Title: "An integrated analysis of the genetics, development, and evolution of the cotton fiber" (Unpublished (2000)).

BF275652 NCBI acc. No. BF275652 (gi: 11206722) (Nov. 17, 2000); Wing,R.A., et al. "GA_Eb0024J23f *Gossypium arobeum* 7-10 dpa fiber library *Gossypium arboreum* cDNA clone GA_Eb0024J23f, mRNA sequence"; source: *Gossypium arboreum*; Title: "An integrated analysis of the genetics, development, and evolution of the cotton fiber" (Unpublished (2000)).

BC277659 NCBI acc. No. BF277659 (gi: 11208729); (Nov. 17, 2000) Wing,R.A., et al. "GA_Eb0031C19f *Gossypium arboreum* 7-10 dpa fiber library *Gossypium arboreum* cDNA clone GA_Eb0031C19f, mRNA sequence"; source: *Gossypium arboreum*; Title: "An integrated analysis of the genetics, development, and evolution of the cotton fiber" (Unpublished 2000)).

BF324075 NCBI acc. No. BF324075 (gi: 11273699) (Nov. 21, 2000); Shoemaker,R., et al. "su22c11.y1.Gm-c1068 *Glycine max* cDNA clone Genome Systems Clone ID: Gm-c1068-117 5' similar to TR:P93589 P93589 DNA Binding Protein Homolog. ;, mRNA sequence"; source: *Glycine max* (soybean); Title: "Public Soybean EST Project" (Unpublished (1999)).

BF518896 NCBI acc. No. BF518896 (gi: 11607651) (Dec. 8, 2000); Fedorova,M., et al. "EST456428 DSIL *Medicago truncatula* cDNA clone pDSIL-19G12, mRNA sequence"; source: *Medicago truncatula* (barrel medic); Title: "ESTs from leaves of *Medicago truncatula* after inoculation with *Colletotrichum trifolii*" (Unpublished (2000)).

BF520727 NCBI acc. No. BF520727 (gi: 11609410) (Dec. 8, 2000); Fedorova,M., et al. "EST458200 DSIL *Medicago truncatula* cDNA clone pDSIL-39A6, mRNA sequence"; source: *Medicago truncatula* (barrel medic); Title: "ESTs from leaves of *Medicago truncatula* after inoculation with *Colletotrichum trifolii*" (Unpublished (2000)).

BF596417 NCBI acc. No. BF596417 (gi: 11688741) (Dec. 12, 2000); Shoemaker,R., et al. "su51a06.y1 Gm-c1069 *Glycine max* cDNA clone Genome Systems Clone ID: Gm-c1069-396 5' similar to TR:O81365 O81365 AP2 Domain Containing Protein ;, mRNA sequence"; source: *Glycine max* (soybean); Title: "Public Soybean EST Project" (Unpublished (1999)).

BF617601 NCBI acc. No. BF617601 (gi: 13109111) (Dec. 18, 2000); Wing,R., et al. "HVSMEc0018D19f *Hordeum vulgare* seedling shoot EST library HVcDNA0003 (Etiolated and unstressed) *Hordeum vulgare* subsp. vulgare cDNA clone HVSMEc0018D19f, mRNA sequence"; source: *Hordeum vulgare* subsp. vulgare; Title: "Development of a genetically and physically anchored EST resource for barley genomics: Morex unstressed seedling shoot cDNA library" (Unpublished (2001)).

BF618047 NCBI acc. No. BF618047 (gi: 13106669) (Dec. 18, 2000); Wing,R., et al. "HVSMEc0003G22f *Hordeum vulgare* seedling shoot EST library HVcDNA0003 (Etiolated and unstressed) *Hordeum vulgare* subsp. vulgare cDNA clone HVSMEc0003G22f, mRNA sequence"; source: *Hordeum vulgare* subsp. vulgare; Title: "Development of a genetically and physically anchored EST resource for barley genomics: Morex unstressed seedling shoot cDNA library" (Unpublished (2001)).

BF621655 NCBI acc. No. BF621655 (gi: 13083645) (Dec.18, 2000); Wing,R., et al. "HVSMEa0011L23f *Hordeum vulgare* seedling shoot Est library HVcDNA0001 (Cold stress) *Hordeum vulgare* subsp. vulgare cDNA clone HVSMEa0011 L23f, mRNA sequence"; source: *Hordeum vulgare* subsp. vulgare; Title: "Development of a genetically and physically anchored EST resource for barley genomics: Morex cold-stressed seedling shoot cDNA library" (Unpublished (2001)).

BF624177 NCBI acc. No. BF624177 (gi: 13083964) (Dec. 18, 2000); Wing,R., et al. "HVSMEa0012F2of *Hordeum vulgare* seedling shoot EST library HVcDNA0001 (Cold stress) *Hordeum vulgare* subsp. vulgare cDNA clone HVSMEa0012F20f, mRNA sequence"; source: *Hordeum vulgare* subsp. vulgare; Title: "Development of a genetically and physically anchored EST resource for barley genomics: Morex cold-stressed seedling shoot cDNA library" (Unpublished (2001)).

BF634482 NCBI acc. No. BF634482 (gi: 11898640) (Dec. 19, 2000); Torres-Jerez,I., et al. Title: "Expressed Sequence Tags from the Samuel Roberts Noble Foundation *Medicago truncatula* drought library" (Unpublished (2000)).

BF637755 NCBI acc. No. BF637755 (gi: 11901913) (Dec. 19, 2000); Liu,J., et al. "NF041B03PL1F1027 Phosphate starved leaf *Medicago truncatula* cDNA clone NF041 B03PL 5', mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).

BF637999 NCBI acc. No. BF637999 (gi: 11902157) (Dec. 19, 2000); Liu,J., et al. "NF028F04PL1F1041 Phosphate starved leaf *Medicago truncatula* cDNA clone NF028F04PL 5', mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).

BF643225 NCBI acc. No. BF643225 (gi: 11908350) (Dec. 20, 2000); Torres-Jerez,I., et al. "NFOO1G02EC1F1017 Elicited cell culture *Medicago truncatula* cDNA clone NFOO1G02EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF644716 NCBI acc. No. BF644716 (gi: 11909845) (Dec. 20, 2000); Torres-Jerez,I., et al. "NF019F07EC1F1062 Elicited cell culture *Medicago truncatula* cDNA clone NF019F07EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF645474 NCBI acc. No. BF645474 (gi: 11910603) (Dec. 20, 2000); Torres-Jerez,I., et al. "NF019D04EC1F1041 Elicited cell culture *Medicago truncatula* cDNA clone NF019D04EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF645999 NCBI acc. No. BF645999 (gi: 11911128) (Dec. 20, 2000); Torres-Jerez,I., et al. "NF043B08EC1F1064 Elicited cell culture *Medicago truncatula* cDNA clone NF043B08EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF646324 NCBI acc. No. BF646324 (gi: 11911454) (Dec. 20, 2000); Torres-Jerez,I., et al. "NF074E05EC1 F1038 Elicited cell culture *Medicago truncatula* cDNA clone NF074E05EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF647222 NCBI acc. No. BF647222 (gi: 11912352) (Dec. 20, 2000); Torres-Jerez,I., et al. "NF033B03EC1 F1028 Elicited cell culture *Medicago truncatula* cDNA clone NF033B03EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF647376 NCBI acc. No. BF647376 (gi: 11912506) (Dec. 20, 2000); Torres-Jerez,I., et al. "NF033B02EC1 F1016 Elicited cell culture *Medicago truncatula* cDNA clone NF033B02EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF648210 NCBI acc. No. BF648210 (gi: 11913340) (Dec. 20, 2000); Torres-Jerez,I., et al. "NF045C04EC1F1033 Elicited cell culture *Medicago truncatula* cDNA clone NF045C04EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF648225 NCBI acc. No. BF648225 (gi: 11913355) (Dec. 20, 2000); Torres-Jerez,I., et al. "NF045D1OEC1F1089 Elicited cell culture *Medicago truncatula* cDNA clone NF045D1 Oec 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF648429 NCBI acc. No. BF648429 (gi: 11913559) (Dec. 20, 2000); Torres-Jerez,I., et al."NF045H02EC1 F1027 Elicited cell culture *Medicago truncatula* cDNA clone NF045H02EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF649047 NCBI acc. No. BF649047 (gi: 11914093) (Dec. 20, 2000); Torres-Jerez,I., et al. "NF053B11EC1F1091 Elicited cell culture *Medicago truncatula* cDNA clone NF053B11EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF649327 NCBI acc. No. BF649327 (gi: 11914457) (Dec. 20, 2000); Torres-Jerez,I., et al. "NF056E12EC1F1097 Elicited cell culture *Medicago truncatula* cDNA clone NF056E12EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF649790 NCBI acc. No. BF649790 (gi: 11914920) (Dec. 20, 2000); Torres-Jerez,I., et al. "NF084C07EC1F1052 Elicited cell culture *Medicago truncatula* cDNA clone NF084C07EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF649879 NCBI acc. No. BF649879 (gi: 11915009) (Dec. 20, 2000); Torres-Jerez,I., et al. "NF086A05EC1F1035 Elicited cell culture *Medicago truncatula* cDNA clone NF086A05EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF650089 NCBI acc. No. BF650089 (gi: 11915219) (Dec. 20, 2000); Torres-Jerez,I., et al. "NF088B12EC1F1095 Elicited cell culture *Medicago truncatula* cDNA clone NF088B12EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF650178 NCBI acc. No. BF650178 (gi: 11915308) (Dec. 20, 2000); Torres-Jerez,I., et al. "NF085H09EC1F1078 Elicited cell culture *Medicago truncatula* cDNA clone NF085H09EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF650547 NCBI acc. No. BF650547 (gi: 11915677) (Dec. 20, 2000); Torres-Jerez,I., et al. "NF097H02EC1F1026 Elicited cell culture *Medicago truncatula* cDNA clone NF097H02EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF650930 NCBI acc. No. BF650930 (gi: 11916060) (Dec. 20, 2000); Torres-Jerez,I., et al. Title: "Expressed Sequence Tags from the Samuel Roberts Noble Foundation—Center for *Medicago* Genomics Research" (Unpublished 2000)).

BF651153 NCBI acc. No. BF651153 (gi: 11916283) (Dec. 20, 2000); Torres-Jerez,I., et al. "NF102B10EC1F1079 Elicited cell culture *Medicago truncatula* cDNA clone NF102B10EC 5, mRNA sequence"; source: *Medicago truncatula* (barrel medic); Title: "Expressed Sequence Tags from the Samuel Roberts Noble Foundation—Center for *Medicago* Genomics Research" (Unpublished (2000)).

BF729336 NCBI acc. No. BF729336 (gi: 12047197) (Jan. 8, 2001); Walbot,V., et al. "1000076Al2.x1 1000—Unigene i from Maize Genome Project *Zea mays* cDNA, mRNA sequence"; source: *Zea mays*; Title: "Maize ESTs from various cDNA libraries sequenced at Stanford University" (Unpublished (1999)).

BG046680 NCBI acc. No. BG046680 (gi: 12495682) (Jan. 25, 2001); Shoemaker,R., et al. "saa58c10.y1 Gm-c1060 *Glycine soja* cDNA clone Genome Systems Clone ID: Gm-c1060-884 5' similar to TR:Q40478 Q40478 EREBP-4. ;, mRNA sequence"; source: *Glycine soja*; Title: "Public Soybean EST Project" (Unpublished (1999)).

BG103305 NCBI acc. No. BG103305 (gi: 12618124) (Jan. 30, 2001); Cordonnier-Pratt,M.-M., et al. "RHIZ2__18__D08.b1__A003 Rhizome2 (RHIZ2) *Sorghum propinquum* cDNA, mRNA sequence"; source: *Sorghum propinquum*; Title: "An EST database from Sorghum: *Sorghum propinquum* rhizomes" (Unpublished (2000)).

BG128566 NCBI acc. No. BG128566 (gi: 12628754) (Jan. 31, 2001); Van Der Hoeven,R., et al. "EST474212 tomato shoot/meristem *Solanum lycopersicum* cDNA clone cTOF21 K4 5' sequence, mRNA sequence"; source: *Solanum lycopersicum* (*Lycopersicon esculentum*); Title: "Generation of ESTs from tomato shoot/meristem tissue" (Unpubished (2001)).

BG129573 NCBI acc. No. BG129573 (gi: 12629761) (Jan. 31, 2001); Van Der Hoeven,R., et al. "EST475219 tomato shoot/meristem *Solanum lycopersicum* cDNA clone cTOF25A11 5' sequence, mRNA sequence"; source: *Solanum lycopersicum* (*Lycopersicon esculentum*); Title: "Generation of ESTs from tomato shhot/meristem tissue" (Unpublished (2001)).

BG155935 NCBI acc. No. BG155935 (gi: 12689599) (Feb. 6, 2001); Shoemaker,R., et al. "saa66d04.y1 Gm-c1060 *Glycine soja* cDNA clone Genome Systems Clone ID: Gm-c1060-1688 5' similar to TR:Q40478 Q40478 EREBP-4. ;, mRNA sequence"; source: *Glycine soja*; Title: "Public Soybean EST Project" (Unpublished (1999)).

BG239157 NCBI acc. No. BG239157 (gi: 12774230) (Feb. 13, 2001); Shoemaker,R., et al. "sab66d01.y1 Unknown Library Type *Glycine max* cDNA clone Genome Systems Clone ID: Gm-c1043-4369 5' similar to TR:Q9ZR85 Q9ZR85 Ethylene-Responsive Element Binding Protein Homolog. ;, mRNA sequence"; source: *Glycine max* (soubean); Title: "Public Soybean EST Project" (Unpublished (1999)).

BG368839 NCBI acc. No. BG368839 (gi: 13257940) (Mar. 8, 2001); Wing,R., et al. "HVSMEi0020012f *Hordeum vulgare* 20 DAP spike EST library HVcDNA0010 (20 DAP) *Hordeum vulgare* subsp.

vulgare cDNA clone HVSMEi0020O12f, mRNA sequence"; source: *Hordeum vulgare* subsp. vulgare; Title: "Development of a geneticaly and physically anchored EST resource for barley genomics: Morex 20 DAP spike cDNA library" (Unpublished (2001)).
BG381764 NCBI acc. No. BG381764 (gi: 13306236) (Mar. 12, 2001); Anderson,J.V., et al. "00735 leafy spurge Lambda HybriZAP 2.1 two-hybrid vector cDNA Library *Euphorbia esula* cDNA clone 5AC 5' similar to ethylene-responsive element binding factor, mRNA sequence"; source: *Euphorbia esula* (leafy spurge); Title: "Identification of mRNAs expressed in underground adventitious buds of *Euphorbia esula* (leafy spurge)" (Unpublished 2000)).
BG411150 NCBI acc. No. BG411150 (gi: 13316703) (Mar. 13, 2001); Reid,S.P., et al. "EM1_26_C09.b1_A002 Embryo 1 (EM1) *Sorghum bicolor* cDNA, mRNA sequence"; source: *Sorghum bicolor* (sorghum); Title: "An EST database from *Sorghum*: developing embryos" (Unpublished (2000)).
BG417325 NCBI acc. No. BG417325 (gi: 13322972) (Mar. 13, 2001); Wing,R., et al. "HVSMEk0017I08f *Hordeum vulgare* testa/pericarp EST library HVcDNA0013 (normal) *Hordeum vulgare* subsp. vulgare cDNA clone HVSMEk0017I08f, mRNA sequence"; source: *Hordeum vulgare* subsp. vulgare; Title: "Development of a geneticaly and physically anchored EST resource for barley genomics: Morex testa/pericarp cDNA library" (Unpublished 2001)).
BG444654 NCBI acc. No. BG444654 (gi: 13354306) (Mar. 15, 2001); Wing,R., et al. "GA_Ea0025B11f *Gossypium arboreum* 7-10 dpa fiber library *Gossypium arboreum* cDNA clone GA_Ea0025B11f, mRNA sequence"; source: *Gossypium arboreum*; Title: "An integrated analysis of the genetics, development, and evolution of the cotton fiber" (Unpublished (2000)).
BG447769 NCBI acc. No. BG447769 (gi: 13366548) (Mar. 16, 2001); Torres-Jerez,I., et al. "NF093H08EC1F1076 Elicited cell culture *Medicago truncatula* cDNA clone NF093H08EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).
BG448225 NCBI acc. No. BG448225 (gi: 13367006) (Mar. 16, 2001); Torres-Jerez,I., et al. "NF107H09EC1F1078 Elicited cell culture *Medicago truncatula* cDNA clone NF107H09EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).
BG448686 NCBI acc. No. BG448686 (gi: 13367383) (Mar. 16, 2001); Watson,B.S., et al. "NF023A03NR1F1000 Nodulated root *Medicago truncatula* cDNA clone NF023A03NR 5', mRNA sequence"; source: *Medicago truncatula* (barrel medic); Title: "Expressed Sequence Tags from the Samuel Roberts Noble Foundation *Medicago truncatula* nodulated root library" (Unpublished (2000)).
BG449954 NCBI acc. No. BG449954 (gi: 13368736) (Mar. 16, 2001); Torres-Jerez,I., et al. "NF013A10DT1F1081 Drought *Medicago truncatula* cDNA clone NF013A10DT 5', mRNA sequence"; source: *Medicago truncatula* (barrel medic); Title: "Expressed Sequence Tags from the Samuel Roberts Noble Foundation *Medicago truncatula* drought library" (Unpublished 2000)).
BG450588 NCBI acc. No. BG450588 (gi: 13369358) (Mar. 16, 2001); Torres-Jerez,I., et al."NF031F1ODT1F1091 Drought *Medicago truncatula* cDNA clone NF031F1ODT 5', mRNA sequence"; source: *Medicago truncatula* (barrel medic); Title: "Expressed Sequence Tags from the Samuel Roberts Noble Foundation *Medicago truncatula* drought library" (Unpublished 2000)).
BG451892 NCBI acc. No. BG451892 (gi: 13370674) (Mar. 16, 2001); Torres-Jerez,I., et al."NF101E12DT1F1088 Drought *Medicago truncatula* cDNA clone NF101E12DT 5', mRNA sequence"; source: *Medicago truncatula* (barrel medic); Title: "Expressed Sequence Tags from the Samuel Roberts Noble Foundation *Medicago truncatula* drought library" (Unpublished 2000)).
BG455325 NCBI acc. No. BG455325 (gi: 13378650) (Mar. 19, 2001); Liu,J., et al. "NF046F09PL1F1077 Phosphate starved leaf *Medicago truncatula* cDNA clone NF046F09PL 5', mRNA sequence"; source: *Medicago truncatula* (barrel medic); Title:

"Expressed Sequence Tags from the Samuel Roberts Noble Foundation *Medicago truncatula* phosphate-starved leaf library" (Unpublished 2000)).
BG457772 NCBI acc. No. BG457772 (gi: 13381097) (Mar. 19, 2001); Liu,J., et al. "NF033D11PL1F1091 Phosphate starved leaf *Medicago truncatula* cDNA clone NF033D11PL 5', mRNA sequence"; source: *Medicago truncatula* (barrel medic); Title: "Expressed Sequence Tags from the Samuel Roberts Noble Foundation *Medicago truncatula* phosphate-starved leaf library" (Unpublished 2000)).
BG459073 NCBI acc. No. BG459073 (gi: 13382398) (Mar. 19, 2001); Anderson,J.V., et al. "00846 leafy spurge Lambda HybriZAP 2.1 two-hybrid vector cDNA Library *Euphorbia esula* cDNA clone 18AF 5' similar to putative Ckc2 [*Arabidopsis thaliana*], accession# CAA05084, mRNA sequence"; source: *Euphorbia esula* (leafy spurge); Title: "Identification of mRNAs expressed in underground adventitious buds of *Euphorbia esua* (leaf spurge)" (Unpublished (2000)).
BG507541 NCBI acc. No. BG507541 (gi: 13477813) (Mar. 28, 2001); Shoemaker,R., et al. "sac60g11.y1 Gm-c1062 *Glycine max* cDNA clone Genome Systems Clone ID: Gm-c1062-4534 5' similar to TR:O81365 O81365 AP2 Domain Containing Protein ;, mRNA sequence"; source: *Glycine max* (soybean); Title: "Public Soybean EST Project" (Unpublished (1999)).
BG507761 NCBI acc. No. BG507761 (gi: 13478178) (Mar. 28, 2001); Shoemaker,R., et al. "sac89a05.y1 Gm-c1073 *Glycine max* cDNA clone Genome Systems Clone ID: Gm-c1073-33 5' similar to TR:P93392 P93392 S25-XP1 DNA Binding Protein. ;, mRNA sequence"; source: *Glycine max* (soybean); Title: "Public Soybean EST Project" (Unpublished (1999)).
BG508757 NCBI acc. No. BG508757 (gi: 13479414) (Mar. 28, 2001); Shoemaker,R., et al. "sac90a05.y1 Gm-c1073 *Glycine max* cDNA clone Genome Systems Clone ID: Gm-c1073-34 5' similar to TR:P93392 P93392 S25-XP1 DNA Binding Protein. ;, mRNA sequence"; source: *Glycine max* (soybean): Title: "Public Soybean EST Project" (Unpublished (1999)).
BG510218 NCBI acc. No. BG510218 (gi: 13480875) (Mar. 28, 2001); Shoemaker,R., et al. "sac64a08.y1 Gm-c1072 *Glycine max* cDNA clone Genome Systems Clone ID: Gm-c1072-16 5' similar to TR:O80387 O80387 Ethylene Responsive Element Binding Factor. ;, mRNA sequence"; source: *Glycine max* (soybean); Title: "Public Soybean EST Project" (Unpublished (1999)).
BG518375 NCBI acc. No. BG518375 (gi: 13516099) (Apr. 2, 2001); Walbot,V., et al. "947066G11.y1 947—2 week shoot from Barkan lab *Zea mays* cDNA, mRNA sequence"; source: *Zea mays*; Title: "Maize ESTs from various cDNA libraries sequenced at Stanford University" (Unpublished (1999)).
BG581520 NCBI acc. No. BG581520 (gi: 13596584) (Apr. 11, 2001); Fedorova,M., et al. "EST483254 GVN *Medicago truncatula* cDNA clone pGVN-6513 5' end, mRNA sequence"; source: *Medicago truncatula* (barrel medic); Title: "ESTs from one month old nitrogen-fixing root nodules of *Medicago truncatula*, 2001" (Unpublished (2001)).
BG581532 NCBI acc. No. BG581532 (gi: 13596596) (Apr. 11, 2001); Fedorova,M., et al. "EST483266 GVN *Medicago truncatula* cDNA clone pGVN-65K5 5' end, mRNA sequence"; source: *Medicago truncatula* (barrel medic); Title: "ESTs from one month old nitrogen-fixing root nodules of *Medicago truncatula*, 2001" (Unpublished (2001)).
BG582281 NCBI acc. No. BG582281 (gi: 13597345) (Apr. 11, 2001); Fedorova,M., et al. "EST484022 GVN *Medicago truncatula* cDNA clone pGVN-69O23 5' end, mRNA sequence"; source: *Medicago truncatula* (barrel medic); Title: "ESTs from one month old nitrogen-fixing root nodules of *Medicago truncatula*, 2001" (Unpublished (2001)).
BG582759 NCBI acc. No. BG582759 (gi: 13597823) (Apr. 11, 2001); Fedorova,M., et al. "EST484505 GVN *Medicago truncatula* cDNA clone pGVN-70J21 5' end, mRNA sequence"; source: *Medicago truncatula* (barrel medic); Title: "ESTs from one month old nitrogen-fixing root nodules of *Medicago truncatula*, 2001" (Unpublished (2001)).
BG582854 NCBI acc. No. BG582854 (gi: 13597918) (Apr. 11, 2001); Fedorova,M., et al. "EST484600 GVN *Medicago truncatula* cDNA clone pGVN-70L24 5' end, mRNA sequence"; source: *Medicago truncatula* (barrel medic); Title: "ESTs from one month old nitrogen-fixing root nodules of *Medicago truncatula*, 2001" (Unpublished (2001)).

BG582869 NCBI acc. No. BG582869 (gi: 13597933) (Apr. 11, 2001); Fedorova,M., et al. "EST484615 GVN *Medicago truncatula* cDNA clone pGVN-70P6 5' end, mRNA sequence"; source: *Medicago truncatula* (barrel medic); Title: "ESTs from one month old nitrogen-fixing root nodules of *Medicago truncatula*, 2001" (Unpublished (2001)).

BG583042 NCBI acc. No. BG583042 (gi: 13598098) (Apr. 11, 2001); Fedorova,M., et al. "EST484784 GVN *Medicago truncatula* cDNA clone pGVN-7104 5' end, mRNA sequence"; source: *Medicago truncatula* (barrel medic); Title: "ESTs from one month old nitrogen-fixing root nodules of *Medicago truncatula*, 2001" (Unpublished (2001)).

BG583111 NCBI acc. No. BG583111 (gi: 13598175) (Apr. 11, 2001); Fedorova,M., et al. "EST484861 GVN *Medicago truncatula* cDNA clone pGVN-71N15 5' end, mRNA sequence"; source: *Medicago truncatula* (barrel medic); Title: "ESTs from one month old nitrogen-fixing root nodules of *Medicago truncatula*, 2001" (Unpublished (2001)).

BG583265 NCBI acc. No. BG583265 (gi: 13598329) (Apr. 11, 2001); Fedorova,M., et al. "EST485016 GVN *Medicago truncatula* cDNA clone pGVN-72M9 5' end, mRNA sequence"; source: *Medicago truncatula*(barrel medic); Title: "ESTs from one month old nitrogen-fixing root nodules of *Medicago truncatula*, 2001" (Unpublished (2001)).

BG583402 NCBI acc. No. BG583402 (gi: 13598466) (Apr. 11, 2001 ; Fedorova,M., et al. "EST485154 GNV *Medicago truncatula* cDNA clone pGVN-73K11 5' end, mRNA sequence"; source: *Medicago truncatula* (barrel medic); Title: "ESTs from one month old nitrogen-fixing root nodules of *Medicago truncatula*, 2001" (Unpublished (2001)).

BG583604 NCBI acc. No. BG583604 (gi: 13598668) (Apr. 11, 2001) ; Fedorova,M., et al. "EST485356 GVN *Medicago truncatula* cDNA clone pGVN-73L16 5' end, mRNA sequence"; source: *Medicago truncatula* (barrel medic); Title: "ESTs from one month old nitrogen-fixing root nodules of *Medicago truncatula*, 2001" (Unpublished (2001)).

BG583626 NCBI acc. No. BG583626 (gi: 13598690) (Apr. 11, 2001); Fedorova,M., et al. "EST485378 GVN *Medicago truncatula* cDNA clone pGVN-73P18 5' end, mRNA sequence"; source: *Medicago truncatula* (barrel medic); Title: "ESTs from one month old nitrogen-fixing root nodules of *Medicago truncatula*, 2001" (Unpublished (2001)).

BG583711 NCBI acc. No. BG583711 (gi: 13598775) (Apr. 11 2001); Fedorova,M., et al. "EST485464 GVN *Medicago truncatula* cDNA clone pGVN-74C14 5' end, mRNA sequence"; source: *Medicago truncatula* (barrel medic); Title: "ESTs from one month old nitrogen-fixing root nodules of *Medicago truncatula*, 2001" (Unpublished (2001)).

BG583745 NCBI acc. No. BG583745 (gi: 13598809) (Apr. 11, 2001); Fedorova,M., et al. "EST485500 GVN *Medicago truncatula* cDNA clone pGVN-74I24 5& apos; end, mRNA sequence"; source: *Medicago truncatula* (barrel medic); Title: "ESTs from one month old nitrogen-fixing root nodules of *Medicago truncatula*, 2001" (Unpublished (2001)).

BG583761 NCBI acc. No. BG583761 (gi: 13598825) (Apr. 11, 2001); Fedorova,M., et al. "EST485516 GNV *Medicago truncatula* cDNA clone pGVN-74M12 5' end, mRNA sequence"; source: *Medicago truncatula* (barrel medic); Title: "ESTs from one month old nitrogen-fixing root nodules of *Medicago truncatula*, 2001" (Unpublished (2001)).

BG587841 NCBI acc. No. BG587841 (gi: 13602905) (Apr. 11, 2001); Harrison,M.J., et al. "EST489616 KV3 *Medicago truncatula* cDNA clone pKV3-13E10 5' end, mRNA sequence"; source: *Medicago truncatula* (barrel medic); Title: "ESTs from roots of *Medicago truncatula* after colonization with *Glomus versiforme*, 2001" (Unpublished (2001)).

BG591632 NCBI acc. No. BG591632 (gi: 13609772) (Apr. 12, 2001); Zhang,P., et al. "EST499474 P. infestans-challenged leaf Solanum tuberosum cDNA clone BPLI9N11 5' sequence, mRNA sequence"; source: *Solanum tuberosum* (potato); Title: "Generation of ESTs from Potato Leaves Challenged with *Phytophthora infestans*, Incompatible Reaction" (Unpublished (2000)).

BG592132 NCBI acc. No. BG592132 (gi: 13610272) (Apr. 12, 2001); Zhang,P., et al. "EST499974 P. infestans-challenged leaf Solanum tuberosum cDNA clone BPLI11I10 5' sequence, mRNA sequence"; source: *Solanum tuberosum* (potato); Title: "Generation of ESTs from Potato Leaves Challenged with *Phytophthora infestans*, Incompatible Reaction" (Unpublished (2000)).

BG596455 NCBI acc. No. BG596455 (gi: 13614595) (Apr. 12, 2001); Van Der Hoeven,R., et al. "EST495133 cSTS *solanum tuberosum* cDNA clone CSTS14A18 5' sequence, mRNA sequence"; source: *Solanum tuberosum* (potato); Title: "Generations of ESTs from sprouting potato eyes" (Unpublished (2000)).

BG600086 NCBI acc. No. BG600086 (gi: 13617222) (Apr. 12, 2001); Van Der Hoeven,R., et al. "EST504981cSTS *Solanum tuberosum* cDNA clone cSTS27A2 5' sequence, mRNA sequence"; source: *Solanum tuberosum* (potato); Title: "Generations of ESTs from sprouting potato eyes" (Unpublished (2000)).

BG606428 NCBI acc. No. BG606428 (gi: 13656411) (Apr. 17, 2001); Anderson,O.D., et al. "WHE2956_B01_C02ZS Wheat dormant embryo cDNA library *Triticum aestivum* cDNA clone WHE2956_B01_C02, mRNA sequence"; source: *Triticum aestivum* (bread wheat); Title: "The structure and function of the expressed portion of the wheat genomes—Dormant embryo cDNA library" (Unpublished (2001)).

BG642691 NCBI acc. No. BG642691 (gi: 13777572) (Apr. 24, 2001); van Der Hoeven,R., et al. "EST510885 tomato shoot/meristem *Solanum lycopersicum* cDNA clone cTOF25K14 5' sequence, mRNA sequence"; source: *Solanum lycopersicum* (*Lycopersicon esculentum*); Title: "Generation of ESTs from tomato shoot/meristem tissue" (Unpublished (2001)).

BG643340 NCBI acc. No. BG643340 (gi: 13778565) (Apr. 24, 2001); Van Der Hoeven,R., et al. "EST511534 tomato shoot/meristem *Solanum lycopersicum* cDNA clone cTOF27E22 5 sequence, mRNA sequence"; source: *Solanum lycopersicum* (*Lycopersicon esculentum*); Title: "Generation of ESTs from tomato shoot/meristem tissue" (Unpublished (2001)).

BG644911 NCBI acc. No. BG644911 (gi: 13780023) (Apr. 24, 2001); Vandenbosch,K., et al. "EST506530 KV3 *Medicago truncatula* cDNA clone pKV3-38P9 5' end, mRNA sequence"; source: *Medicago truncatula* (barrel medic); Title: "ESTs from roots of *Medicago truncatula* 72 h after *Rhizobium inoculation*, 2001" (Unpublished (2001)).

BG645028 NCBI acc. No. BG645028 (gi: 13780140) (Apr. 24, 2001); Vandenbosch,K., et al. "EST506647 KV3 *Medicago truncatula* cDNA clone pKV3-39C23 5' end, mRNA sequence"; source: *Medicago truncatula* (barrel medic); Title: "ESTs from roots of *Medicago truncatula* 72 h after *Rhizobium inoculation*, 2001" (Unpublished (2001)).

BG646470 NCBI acc. No. BG646470 (gi: 13781582) (Apr. 24, 2001); Hahn,M.G., et al. "EST508089 HOGA *Medicago truncatula* cDNA clone pHOGA-7L24 5' end, mRNA sequence"; source: *Medicago truncatula* (barrel medic); Title: "ESTs from roots of *Medicago truncatula* treated with oligogalacturonides of DP 6-20" (Unpublished (2001)).

BG646567 NCBI acc. No. BG646567 (gi: 13781679) (Apr. 24, 2001); Hahn,M.G., et al. "EST508186 HOGA *Medicago truncatula* cDNA clone pHOGA-9M7 5' end, mRNA sequence"; source: *Medicago truncatula* (barrel medic); Title: "ESTs from roots of *Medicago truncatula* treated with oligogalacturonides of DP 6-20" (Unpublished (2001)).

BG646774 NCBI acc. No. BG646774 (gi: 13781886) (Apr. 24, 2001); Hahn,M.G., et al. "EST508393 HOGA *Medicago truncatula* cDNA clone pHOGA-9D12 5' end, mRNA sequence"; source: *Medicago truncatula* (barrel medic); TTitle: "ESTs from roots of *Medicago truncatula* treated with oligogalacturonides of DP 6-20" (Unpublished (2001)).

BG647592 NCBI acc. No. BG647592 (gi: 13782704) (Apr. 24, 2001); Hahn,M.G., et al. "EST509211 HOGA *Medicago truncatula* cDNA clone pHOGA-17G24 5' end, mRNA sequence";

source: *Medicago truncatula* (barrel medic); Title: "ESTs from roots of *Medicago truncatula* treated with oligogalacturonides of DP 6-20" (Unpublished (2001)).
BG647771 NCBI acc. No. BG647771 (gi: 13782883) (Apr. 24, 2001); Hahn,M.G., et al. "EST509390 HOGA *Medicago truncatula* cDNA clone pHOGA-17J8 5' end, mRNA sequence"; source: *Medicago truncatula* (barrel medic); Title: "ESTs from roots of *Medicago truncatula* treated with oligogalacturonides of DP 6-20" (Unpublished (2001)).
BG647799 NCBI acc. No. BG647799 (gi: 13782911) (Apr. 24, 2001); Hahn,M.G., et al. "EST509418 HOGA *Medicago truncatula* cDNA clone pHOGA-17N20 5' end, mRNA sequence"; source: *Medicago truncatula* (barrel medic); Title: "ESTs from roots of *Medicago truncatula* treated with oligogalacturonides of DP 6-20" (Unpublished (2001)).
BG647917 NCBI acc. No. BG647917 (gi: 13783029) (Apr. 24, 2001); Hahn,M.G., et al. "EST509536 HOGA *Medicago truncatula* cDNA clone pHOGA-18C12 5' end, mRNA sequence"; source: *Medicago truncatula* (barrel medic); Title: "ESTs from roots of *Medicago truncatula* treated with oligogalacturonides of DP 6-20" (Unpublished (2001)).
BG648548 NCBI acc. No. BG648548 (gi: 13783660) (Apr. 24, 2001); Hahn,M.G., et al. "EST510167 HOGA *Medicago truncatula* cDNA clone pHOGA-2311 5' end, mRNA sequence"; source: *Medicago truncatula* (barrel medic); Title: "ESTs from roots of *Medicago truncatula* treated with oligogalacturonides of DP 6-20" (Unpublished (2001)).
BG650102 NCBI acc. No. BG650102 (gi: 13787510) (Apr. 25, 2001); Shoemaker,R., et al. "sad79h09.y1 Gm-c1051 *Glycine max* cDNA clone Genome Systems Clone ID: Gm-c1051-6522 5' similar to TR:P93822 P93822 F19P19.18. ;, mRNA sequence"; source: *Glycine max* (soybean); Title: "Public Soybean EST Project" (Unpublished (1999)).
BG652103 NCBI acc. No. BG652103 (gi: 13789512) (Apr. 25, 2001); Shoemaker,R., et al. "sad74b10.y1 Gm-c1051 *Glycine max* cDNA clone Genome Systems Clone ID: Gm-c1051-5851 5' similar to TR:Q40477 Q40477 EREBP-3. ;, mRNA sequence"; source: *Glycine max* (soybean); Title: "Public Soybean EST Project" (Unpublished (1999)).
BG726262 NCBI acc. No. BG726262 (gi: 14011340) (May 9, 2001); Shoemaker,R., et al. "sae13f10.y1 Gm-c1067 *Glycine max* cDNA clone Genome Systems Clone ID: Gm-c1067-2947 5' similar to TR:Q9SJX3 Q9SJX3 Ethylene Reponse Factor-Like AP2 Domain Transcription Factor. ;, mRNA sequence" ; source: *Glycine max* (soybean); Title: "Public Soybean EST Project" (Unpublished (1999)).
BG789540 NCBI acc. No. BG789540 (gi: 14125102) (May 16, 2001); Shoemaker,R., et al. "sae65a11.y1 Gm-c1064 *Glycine max* cDNA clone Genome Systems Clone ID: Gm-c1064-3093 5'; similar to TR:Q9ZR85 Q9ZR85 Ethylene-Responsive Element Binding Protein Homolog. ;, mRNA sequence" ; source: *Glycine max* (soybean); Title: "Public Soybean EST Project" (Unpublished (1999)).
BG790680 NCBI acc. No. BG790680 (gi: 14126242) (May 16, 2001); Shoemaker,R., et al. "sae75d09.y1 Gm-c1064 *Glycine max* cDNA clone Genome Systems Clone ID: Gm-c1064-4025 5' similar to TR:P93822 P93822 F19P19.18. ;, mRNA sequence"; source: *Glycine max* (soybean); Title: "Public Soybean EST Project" (Unpublished (1999)).
BG790996 NCBI acc. No. BG790996 (gi: 14126558) (May 16, 2001); Shoemaker,R., et al. "sae72h12.y1 Gm-c1064 *Glycine max* cDNA clone Genome Systems Clone ID: Gm-c1064-3840 5 similar to TR:Q9ZR85 Q9ZR85 Ethylene-Responsive Element Binding Protein Homolog. ;, mRNA sequence" ; source: *Glycine max* (soybean); Title: "Public Soybean EST Project" (Unpublished (1999)).
BG886550 NCBI acc. No. BG886550 (gi: 14263636) (May 30, 2001); Van Der Hoeven,R., et al. "EST512401 cSTD *Solanum tuberosum* cDNA clone cSTD1K11 5' sequence similar to similar to *Prunus armeniaca* AP2 domain containing protein, mRNA sequence"; source: *Solanum tuberosum* (potato); Title: "Generations of ESTs from dormant potato tubers" (Unpublished (2001)).
BG888738 NCBI acc. No. BG888738 (gi: 14265824) (May 30, 2001); van Der Hoeven,R., et al. "EST514589 cSTD *Solanum tuberosum* cDNA clone cSTD11I12 5' sequence, mRNA sequence"; source: *Solanum tuberosum* (potato); Title: "Generations of ESTs from dormant potato tubers" (Unpublished (2001)).
BG890347 NCBI acc. No. BG890347 (gi: 14267448) (May 30, 2001); Van Der Hoeven,R., et al. "EST516198 cSTD *Solanum tuberosum* cDNA clone cSTD18G1 5 sequence, mRNA sequence"; source: *Solanum tuberosum* (potato); Title: "Generations of ESTs from dormant potato tubers" (Unpublished (2001)).
BH454277 NCBI acc. No. BH454277 (gi: 17639988) (Dec. 12, 2001); Ayele,M., et al. "BOGSI45TR BOGS *Brassica oleracea* genomic clone BOGSI45, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH460596 NCBI acc. No. BH460596 (gi: 17650341) (Dec. 13, 2001); Ayele,M., et al. "BOGWG8OTR BOGW *Brassica oleracea* genomic clone BOGWG80, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH517030 NCBI acc. No. BH517030 (gi: 17725120) (Dec. 13, 2001); Ayele,M., et al. "BOHRB76TF BOHR *Brassica oleracea* genomic clone BOHRB76, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH519444 NCBI acc. No. BH519444 (gi: 17727529) (Dec. 13, 2001); Ayele,M., et al. "BOGKI41TF BOGK *Brassica oleracea* genomic clone BOGKI41, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH603154 NCBI acc. No. BH603154 (gi: 17855600) (Dec. 15, 2001); Ayele,M., et al. "BOGDP09TF BOGD *Brassica oleracea* genomic clone BOGDP09, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH672011 NCBI acc. No. BH672011 (gi: 18737461) (Feb. 19, 2002); Ayele,M., et al. "BOHYF95TR BO_2_3_KB *Brassica oleracea* genomic clone BOHYF95, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH683728 NCBI acc. No. BH683728 (gi: 18754171) (Feb. 19, 2002); Ayele,M., et al. "BOHTE23TR BO_2_3_KB *Brassica oleracea* genomic clone BOHTE23, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH715240 NCBI acc. No. BH715240 (gi: 18809815) (Feb. 20, 2002); Ayele,M., et al. "BOHVQ41TR_BO_2_3_KB *Brassica oleracea* genomic clone BOHVQ41, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BH777081 NCBI acc. No. BH777081 (gi: 19779485) (Mar. 28, 2002); Budiman,M.A., et al. "fzmb013f019h09f0 fzmb filtered library *Zea mays* genomic clone fzmb013f019h09 5', genomic survey sequence"; source: *Zea mays*; Title: "GeneThresher methylation filtered genomic sequences from maize" (Unpublished (2002)).
BI263133 NCBI acc. No. BI263133 (gi: 14864047) (Jul. 18, 2001); Liu,J., et al. "NF085D03PL1F1030 Phosphate starved leaf *Medicago truncatula* cDNA clone NF085D03PL 5', mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).
BI265074 NCBI acc. No. BI265074 (gi: 14867921) (Jul. 18, 2001); Korth,K., et al. "NF078F081N1F1075 Insect herbivory *Medicago truncatula* cDNA clone NF078F08IN 5, mRNA sequence"; source: *Medicago truncatula* (barrel medic); Title: "Expressed Sequence Tags from the Samuel Roberts Noble Foundation *Medicago truncatula* insect herbivory library" (Unpublished (2000)).
BI265685 NCBI acc. No. BI265685 (gi: 14869141) (Jul. 18, 2001); Korth,K., et al. "NF083D07IN1F1062 Insect herbivory *Medicago truncatula* cDNA clone NF083D07IN 5', mRNA sequence"; source: *Medicago truncatula* (barrel medic); Title: "Expressed Sequence Tags from the Samuel Roberts Noble Foundation *Medicago truncatula* insect herbivory library" (Unpublished (2000)).
BI266358 NCBI acc. No. BI266358 (gi: 14870395) (Jul. 18, 2001); Korth,K., et al. "NF084D12IN1F1102 Insect herbivory *Medicago truncatula* cDNA clone NF084D12IN 5', mRNA sequence"; source: *Medicago truncatula* (barrel medic); Title: "Expressed Sequence Tags from the Samuel Roberts Noble Foundation *Medicago truncatula* insect herbivory library" (Unpublished (2000)).
BI271853 NCBI acc. No. BI271853 (gi: 14880681) (Jul. 18, 2001); Torres-Jerez,I., et al. "NF013E04FL1F1034 Developing flower *Medicago truncatula* cDNA clone NF013E04FL 5&APOS;, mRNA sequence"; source: *Medicago truncatula* (barrel medic); Title: "Expressed Sequence Tags from the Samuel Roberts Noble Foundation *Medicago truncatula* flower library" (Unpublished (2001)).
BI305323 NCBI acc. No. BI305323 (gi: 14980645) (Jul. 20, 2001); Reddy,A.R., et al. "NRS2R_1_N04 Drought stress (root) *Oryza sativa* (indica cultivar-group) cDNA clone NRS2R 1_N04 3', mRNA sequence"; source: *Oryza sativa* (indica cultivar-group); Title: "Novel EST enrichment with normalized cDNA libraries from drought stressed rice (*Oryza sativa* L. cv Nagina 22)" (Unpublished (2001)).
BI305776 NCBI acc. No. BI305776 (gi: 14981085) (Jul. 20, 2001); Reddy,A.R., et al. "NL_1_L02 Drought stress (leaf) *Oryza sativa* (indica cultivar-group) cDNA clone NL_1_L02 3', mRNA sequence"; source: *Oryza sativa* (indica cultivar-group); Title: "Novel EST enrichment with normalized cDNA libraries from drought stressed rice (*Oryza sativa* L. cv Nagina 22)" (Unpublished (2001)).
BI308635 NCBI acc. No. BI308635 (gi: 14982962) (Jul. 20, 2001); Grusak,M.A., et al. "EST530045 GPOD *Medicago truncatula* cDNA clone pGPOD-7M22 5' end, mRNA sequence"; source: *Medicago truncatula* (barrel medic); Title: "ESTs from developing reproductive tissues of *Medicago truncatula*" (Unpublished (2001)).
BI308895 NCBI acc. No. BI308895 (gi: 14983222) (Jul. 20, 2001); Grusak,M.A., et al. "EST530305 GPOD *Medicago truncatula* cDNA clone pGPOD-10E21 5&APOS; end, mRNA sequence"; source: *Medicago truncatula* (barrel medic); Title: "ESTs from developing reproductive tissues of *Medicago truncatula*" (Unpublished (2001)).
BI310543 NCBI acc. No. BI310543 (gi: 14984870) (Jul. 20, 2001); Grusak,M.A., et al. "EST5312293 GESD *Medicago truncatula* cDNA clone pGESD8I18 5' end, mRNA sequence"; source: *Medicago truncatula* (barrel medic); Title: "ESTs from developing reproductive tissues of *Medicago truncatula*" (Unpublished (2001)).
BI311856 NCBI acc. No. BI311856 (gi: 14986183) (Jul. 20, 2001); Grusak,M.A., et al. "EST5313606 GESD *Medicago truncatula* cDNA clone pGESD15N15 5' end, mRNA sequence"; source: *Medicago truncatula* (barrel medic); Title: "ESTs from developing reproductive tissues of *Medicago truncatula*" (Unpublished (2001)).
BI321594 NCBI acc. No. BI321594 (gi: 15000780) (Jul. 23, 2001); Shoemaker,R., et al. "saf15b09.y3 Gm-c1076 *Glycine max* cDNA clone Genome Systems Clone ID: Gm-c1076-834 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).
BI418604 NCBI acc. No. BI418604 (gi: 15189627) (Aug. 15, 2001); Colebatch,G., et al. "LjNEST43f5r *Lotus japonicus* nodule library 5 and 7 week-old *Lotus japonicus* cDNA 5', mRNA sequence"; source: *Lotus japonicus*; Title: "*Lotus japonicus* root nodule ESTs: tools for functional genomics" (Unpublished (2000)).
BI420305 NCBI acc. No. BI420305 (gi: 15191328) (Aug. 15, 2001); Colebatch,G., et al. "LjNEST55d6r *Lotus japonicus* nodule library 5 and 7 week-old *Lotus japonicus* cDNA 5', mRNA sequence"; source: *Lotus japonicus*; Title: "*Lotus japonicus* root nodule ESTs: tools for functional genomics" (Unpublished (2000)).

BI421270 NCBI acc. No. BI421270 (gi: 15194638) (Aug. 16, 2001); Alcala,J., et al. "EST531936 tomato callus, TAMU *Solanum lycopersicum* cDNA clone cLEC66M2 5' end, mRNA sequence"; source: *Solanum lycopersicum* (*Lycopersicon esculentum*); Title: "Generation of ESTs from tomato callus tissue" (Unpublished (1999)).
BI421507 NCBI acc. No. BI421507 (gi: 15195085) (Aug. 16, 2001); Alcala,J., et al. "EST532173 tomato callus, TAMU *Solanum lycopersicum* cDNA clone cLEC67G17 5' end, mRNA sequence"; source: *Solanum lycopersicum* (*Lycopersicon esculentum*); Title: "Generation of ESTs from tomato callus tissue" (Unpublished (1999)).
BI421558 NCBI acc. No. BI421558 (gi: 15195182) (Aug. 16, 2001); Alcala,J., et al. "EST532224 tomato callus, TAMU *Solanum lycopersicum* cDNA clone cLEC67A22 5' end, mRNA sequence"; source: *Solanum lycopersicum* (*Lycopersicon esculentum*); Title: "Generation of ESTs from tomato callus tissue" (Unpublished (1999)).
BI421895 NCBI acc. No. BI421895 (gi: 15195839) (Aug. 16, 2001); Alcala,J., et al. "EST532561 tomato callus, TAMU *Solanum lycopersicum* cDNA clone cLEC68E16 5' end, mRNA sequence"; source: *Solanum lycopersicum* (*Lycopersicon esculentum*); Title: "Generation of ESTs from tomato callus tissue" (Unpublished (1999)).
BI422101 NCBI acc. No. BI422101 (gi: 15196219) (Aug. 16, 2001); Alcala,J., et al. "EST532767 tomato callus, TAMU *Solanum lycopersicum* cDNA clone cLEC69A23 5' end, mRNA sequence"; source: *Solanum lycopersicum* (*Lycopersicon esculentum*); Title: "Generation of ESTs from tomato callus tissue" (Unpublished (1999)).
BI424734 NCBI acc. No. BI424734 (gi: 15201177) (Aug. 16, 2001); Shoemaker,R., et al. "sah48a08.y2 Gm-c1036 *Glycine max* cDNA clone Genome Systems Clone ID: Gm-c1036-4623 5' similar to TR:O81365 O81365 AP2 Domain Containing Protein ;, mRNA sequence"; source: *Glycine max* (soybean); Title: "Public Soybean EST Project" (Unpublished (1999)).
BI427468 NCBI acc. No. BI427468 (gi: 15204700) (Aug. 16, 2001); Shoemaker,R., et al. "sah80f02.y1 Gm-c1050 *Glycine max* cDNA clone Genome Systems Clone ID: Gm-c1050-2547 5' similar to SW:ERF5_ARATH O80341 Ethylene Responsive Element Binding Factor 5 ;, mRNA sequence"; source: *Glycine max* (soybean); Title: "Public Soybean EST Project" (Unpublished (1999)).
BI436183 NCBI acc. No. BI436183 (gi: 15260873) (Aug. 21, 2001); van der Hoeven,R., et al. "EST538944 cSTE *Solanum tuberosum* cDNA clone cSTE21L16 5' sequence, mRNA sequence"; source: *Solanum tuberosum* (potato); Title: "Generation of ESTs from in vitro grown microtubers" (Unpublished (2001)).
BI436295 NCBI acc. No. BI436295 (gi: 15260985) (Aug. 21, 2001); Van Der Hoeven,R., et al. "EST539056 cSTE *Solanum tuberosum* cDNA clone cSTE22O21 5' sequence, mRNA sequence"; source: *Solanum tuberosum* (potato); Title: "Generation of ESTs from in vitro grown microtubers" (Unpublished (2001)).
BI468669 NCBI acc. No. BI468669 (gi: 15284778) (Aug. 24, 2001); Shoemaker,R., et al. "sai01h08.y1 Gm-c1050 *Glycine max* cDNA clone Genome Systems Clone ID: Gm-c1050-4575 5' similar to TR:Q40478 Q40478 EREBP-4. ;, mRNA sequence"; source: *Glycine max* (soybean); Title: "Public Soybean EST Project" (Unpublished (1999)).
BI469284 NCBI acc. No. BI469284 (gi: 15285393) (Aug. 24, 2001); Shoemaker,R., et al. "sai09h04.y1 Gm-c1053 *Glycine max* cDNA clone Genome Systems Clone ID: Gm-c1053-3031 5' similar to TR:O23143 O23143 Putative CKC2. ;, mRNA sequence"; source: *Glycine max* (soybean); Title: "Public Soybean EST Project" (Unpublished (1999)).
BI784879 NCBI acc. No. BI784879 (gi: 15812604) (Oct. 1, 2001); Shoemaker,R., et al. "saf94g11.y3 Gm-c1079 *Glycine max* cDNA clone Genome Systems Clone ID: Gm-c1079-1845 5' similar to TR:Q40478 Q40478 EREBP-4. ;, mRNA sequence"; source: *Glycine max* (soybean); Title: "Public Soybean EST Project" (Unpublished (1999)).
BI786168 NCBI acc. No. BI786168 (gi: 15813893) (Oct. 1, 2001); Shoemaker,R., et al. "sai33g03.y1 Gm-c1065 *Glycine max* cDNA clone Genome Systems Clone ID: Gm-c1065-5285 5' similar to TR:O80387 O80387 Ethylene Responsive Element Binding Factor. ;, mRNA sequence"; source: *Glycine max* (soybean); Title: "Public Soybean EST Project" (Unpublished (1999)).

BI787734 NCBI acc. No. BI787734 (gi: 15815459) (Oct. 1, 2001); Shoemaker,R., et al. "sag75b04.y1 Gm-c1084 *Glycine max* cDNA clone Genome Systems Clone ID: Gm-c1084-55 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BI893228 NCBI acc. No. BI893228 (gi: 16105488) (Oct. 12, 2001); Shoemaker,R., et al. "sai63b03.y1 Gm-c1068 *Glycine max* cDNA clone Genome Systems Clone ID: Gm-c1068-3149 5' similar to TR:O80387 O80387 Ethylene Responsive Element Binding Factor. ;, mRNA sequence"; source: *Glycine max* (soybean); Title: "Public Soybean EST Project" (Unpublished (1999)).

BI921995 NCBI acc. No. BI921995 (gi: 16218023) (Oct. 17, 2001); Alcala,J., et al. "EST541898 tomato callus *Solanum lycopersicum* cDNA clone cLEC75P13 5' end, mRNA sequence"; source: *Solanum lycopersicum* (*Lycopersicon esculentum*); Title: "Generation of ESTs from tomato callus tissue (2001)" (Unpublished (2001)).

BI968964 NCBI acc. No. BI968964 (gi: 16343369) (Oct. 23, 2001); Vodkin,L., et al. "GM830006B21G05 Gm-r1083 *Glycine max* cDNA clone Gm-r1083-2242 3', mRNA sequence"; source: *Glycine max* (soybean); Title: "A Functional Genomics Program for Soybean (NSF 9872565)" (Unpublished (1999)).

BI973708 NCBI acc. No. BI973708 (gi: 16348113) (Oct. 23, 2001); Shoemaker,R., et al. "sai91g09.y1 Gm-c1065 *Glycine max* cDNA clone Genome Systems Clone ID: Gm-c1065-8393 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BI973872 NCBI acc. No. BI973872 (gi: 16348277) (Oct. 23, 2001); Shoemaker,R., et al. "sai93h12.y1 Gm-c1065 *Glycine max* cDNA clone Genome Systems Clone ID: Gm-c1065-8807 5' similar to SW:ERF1_ARATH O80337 Ethylene Responsive Element Binding Factor 1 ;, mRNA sequence"; source: *Glycine max* (soybean); Title: "Public Soybean EST Project" (Unpublished (1999)).

BM062245 NCBI acc. No. BM062245 (gi: 22782363) (Sep. 11, 2002); Lee,S., et al. "KS01040C11 KS01 *Capsicum annuum* cDNA, mRNA sequence"; source: *Capsicum annuum*; Title: "Generation of Expressed Sequence Tags from Hot Pepper (*Capsicum annuum* L.) and Sequence Analysis in Relation to Hypersensitive Response Against Pathogen" (Unpublished (2001)).

BM075553 NCBI acc. No. BM075553 (gi: 16922376) (Nov. 13, 2001); Wen,T.J., et al. "MEST357-A11.T3 ISUM5-RN *Zea mays* cDNA clone MEST357-A11 3', mRNA sequence"; source: *Zea mays*; Title: "Expressed Sequence Tags from B73 Maize: various stages and tissues including seedlings treated with a variety of hormones" (Unpublished (2001)).

BM093669 NCBI acc. No. BM093669 (gi: 17022635) (Nov. 20, 2001); Shoemaker,R., et al. "saj12f09.y1 Gm-c1066 *Glycine max* cDNA clone Genome Systems Clone ID: Gm-c1066-2585 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BM094577 NCBI acc. No. BM094577 (gi: 17023543) (Nov. 20, 2001); Shoemaker,R., et al. "saj17g07.y1 Gm-c1066 *Glycine max* cDNA clone Genome Systems Clone ID: Gm-c1066-3014 5' similar to TR:O80387 O80387 Ethylene Responsive Element Binding Factor. ;, mRNA sequence"; source: *Glycine max* (soybean); Title: "Public Soybean EST Project" (Unpublished (1999)).

BM110901 NCBI acc. No. BM110901 (gi: 17073001) (Nov. 26, 2001); Van Der Hoeven,R, et al. "EST558437 potato roots *Solanum tuberosum* cDNA clone cPRO9J5 5' end, mRNA sequence"; source: *Solanum tuberosum* (potato); Title: "Generation of ESTs from potato roots" (Unpublished (2001)).

BM110909 NCBI acc. No. BM110909 (gi: 17073016) (Nov. 26, 2001); Van Der Hoeven,R., et al. "EST558445 potato roots *Solanum tuberosum* cDNA clone cPRO9L5 5' end, mRNA sequence"; source: *Solanum tuberosum* (potato); Title: "Generation of ESTs from potato roots" (Unpublished (2001)).

BM110921 NCBI acc. No. BM110921 (gi: 17073038) (Nov. 26, 2001); Van Der Hoeven,R., et al. "EST558457 potato roots *Solanum tuberosum* cDNA clone cPRO9N5 5' end, mRNA sequence"; source: *Solanum tuberosum* (potato); Title: "Generation of ESTs from potato roots" (Unpublished (2001)).

BM143375 NCBI acc. No. BM143375 (gi: 17153433) (Nov. 29, 2001); Shoemaker,R., et al. "saj43b11.y1 Gm-c1072 *Glycine max* cDNA clone Soybean Clone ID: Gm-c1072-2374 5' similar to TR:Q40478 Q40478 EREBP-4. ;, mRNA sequence"; source: *Glycine max* (soybean); Title: "Public Soybean EST Project" (Unpublished (1999)).

BM178361 NCBI acc. No. BM178361 (gi: 17401579) (Dec. 6, 2001); Shoemaker,R., et al. "saj72a10.y1 Gm-c1072 *Glycine max* cDNA clone Soybean Clone ID: Gm-c1072-5035 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BM178875 NCBI acc. No. BM178875 (gi: 17402093) (Dec. 6, 2001); Shoemaker,R., et al. "saj60f01.y1 Gm-c1072 *Glycine max* cDNA clone Soybean Clone ID: Gm-c1072-4105 5' similar to TR:P93822 P93822 F19P19.18. ;, mRNA sequence"; source: *Glycine max* (soybean); Title: "Public Soybean EST Project" (Unpublished (1999)).

BM268956 NCBI acc. No. BM268956 (gi: 17931996) (Dec. 18, 2001); Wen,T.J., et al. "MEST402-H11.univ ISUM5-RN *Zea mays* cDNA clone MEST402-H11 3, mRNA sequence"; source: *Zea mays*; Title: "Expressed Sequence Tags from B73 Maize: various stages and tissues including seedlings treated with a variety of hormones" (Unpublished (2001)).

BM271048 NCBI acc. No. BM271048 (gi: 17964311) (Dec. 20, 2001); Shoemaker,R., et al. "sak04f02.y1 Gm-c1074 *Glycine max* cDNA clone Soybean Clone ID: Gm-c1074-5236 5' similar to TR:Q40478 Q40478 EREBP-4. ;, mRNA sequence"; source: *Glycine max* (soybean); Title: "Public Soybean EST Project" (Unpublished (1999)).

BM332316 NCBI acc. No. BM332316 (gi: 18162477) (Jan. 16, 2002); Wen,T.J., et al. "MEST167-B07.T3 ISUM5-RN *Zea mays* cDNA clone MEST167-B07 3', mRNA sequence"; source: *Zea mays*; Title: "Expressed Sequence Tags from B73 Maize: various stages and tissues including seedlings treated with a variety of hormones" (Unpublished (2001)).

BM332461 NCBI acc. No. BM332461 (gi: 18162622) (Jan. 16, 2002); Wen,T.J., et al. "MEST169-C11.T3 ISUM5-RN *Zea mays* cDNA clone MEST169-C11 3', mRNA sequence"; source: *Zea mays*; Title: "Expressed Sequence Tags from B73 Maize: various stages and tissues including seedlings treated with a variety of hormones" (Unpublished (2001)).

BM348130 NCBI acc. No. BM348130 (gi: 18172742) (Jan. 16, 2002); Wen,T.J., et al. "MEST286-H07.T3 ISUM5-RN *Zea mays* cDNA clone MEST286-H07 3', mRNA sequence"; source: *Zea mays*; Title: "Expressed Sequence Tags from B73 Maize: various stages and tissues including seedling treated with a variety of hormones" (Unpublished (2001)).

BM348921 NCBI acc. No. BM348921 (gi: 18173533) (Jan. 16, 2002); Wen,T.J., et al. "MEST303-H12.T3 ISUM5-RN *Zea mays* cDNA clone MEST303-H12 3', mRNA sequence"; source: *Zea mays*; Title: "Expressed Sequence Tags from B73 Maize: various stages and tissues including seedlings treated with a variety of hormones" (Unpublished (2001)).

BM403974 NCBI acc. No. BM403974 (gi: 18255379) (Jan. 22, 2002); Restrepo,S., et al. "EST578301 P infestans-challenged potato leaf, compatible reaction *Solanum tuberosum* cDNA clone PPCCR61 5 end, mRNA sequence"; source: *Solanum tuberosum* (potato); Title: "Generation of ESTs from Potato Leaves Challenged with Phytophthora infestans, Compatible Interaction" (Unpublished (2000)).

BM409157 NCBI acc. No. BM409157 (gi: 18260787) (Jan. 22, 2002); Alcala,J., et al. "EST583484 tomato breaker fruit *Solanum lycopersicum* cDNA clone cLEG47M16 5' end, mRNA sequence"; source: *Solanum lycopersicum* (*Lycopersicon esculentum*); Title: "Generation of ESTs from tomato fruit tissue, breaker stage (2002)" (Unpublished (2002)).

BM411708 NCBI acc. No. BM411708 (gi: 18263338) (Jan. 22, 2002); Alcala,J., et al. "EST586035 tomato breaker fruit *Solanum lycopersicum* cDNA clone cLEG57L21 5' end, mRNA sequence"; source: *Solanum lycopersicum* (*Lycopersicon esculentum*); Title: "Generation of ESTs from tomato fruit tissue, breaker stage (2002)" (Unpublished (2002)).
BM412823 NCBI acc. No. BM412823 (gi: 18264453) (Jan. 22, 2002); Alcala,J., et al. "EST587150 tomato breaker fruit *Solanum lycopersicum* cDNA clone cLEG61 C12 5' end, mRNA sequence"; source: *Solanum lycopersicum* (*Lycopersicon esculentum*); Title: "Generation of ESTs from tomato fruit tissue, breaker stage (2002)" (Unpublished (2002)).
BM412928 NCBI acc. No. BM412928 (gi: 18264558) (Jan. 22, 2002); Alcala,J., et al. "EST587255 tomato breaker fruit *Solanum lycopersicum* cDNA clone cLEG61 N3 5' end, mRNA sequence"; source: *Solanum lycopersicum* (*Lycopersicon esculentum*); Title: "Generation of ESTs from tomato fruit tissue, breaker stage (2002)" (Unpublished (2002)).
BM436925 NCBI acc. No. BM436925 (gi: 18458647) (Jan. 31, 2002); Cramer,G.R., et al. "VVA011E03_53345 An expressed sequence tag database for abiotic stressed leaves of *Vitis vinifera* var. Chardonnay *Vitis vinifera* cDNA clone VVA011E03 5, mRNA sequence"; source: *Vitis vinifera*; Title: "An expressed sequence tag database for abiotic stressed leaves of *Vitis vinifera* var. Chardonnay" (Unpublished (2002)).
BM437083 NCBI acc. No. BM437083 (gi: 18458805) (Jan. 31, 2002); Cramer,G.R., et al. "VVA014A06_53661 An expressed sequence tag database for abiotic stressed leaves of *Vitis vinifera* var. Chardonnay *Vitis vinifera* cDNA clone VVA014A06 5, mRNA sequence"; source: *Vitis vinifera*; Title: "An expressed sequence tag database for abiotic stressed leaves of *Vitis vinifera* var. Chardonnay" (Unpublished (2002)).
BM437580 NCBI acc. No. BM437580 (gi: 18459302) (Jan. 31, 2002); Cramer,G.R., et al. "VVA021G02_54655 An expressed sequence tag database for abiotic stressed leaves of *Vitis vinifera* var. Chardonnay *Vitis vinifera* cDNA clone VVA021 G02 5, mRNA sequence"; source: *Vitis vinifera*; Title: "An expressed sequence tag database for abiotic stressed leaves of *Vitis vinifera* var. Chardonnay" (Unpublished (2002)).
BM535956 NCBI acc. No. BM535956 (gi: 18814998) (Feb. 20, 2002); Alcala,J., et al. "EST588978 tomato breaker fruit *Solanum lycopersicum* cDNA clone cLEG70J23 5' end, mRNA sequence"; source *Solanum lycopersicum* (*Lycopersicon esculentum*); Title: "Generation of ESTs from tomato fruit tissue, breaker stage (2002)" (Unpublished (2002)).
BM536165 NCBI acc. No. BM536165 (gi: 18815366) (Feb. 20, 2002); Alcala,J., et al. "EST589187 tomato breaker fruit *Solanum lycopersicum* cDNA clone cLEG71 N23 5' end, mRNA sequence"; source: *Solanum lycopersicum* (*Lycopersicon esculentum*); Title: "Generation of ESTs from tomato fruit tissue, breaker stage (2002)" (Unpublished (2002)).
BM779603 NCBI acc. No. BM779603 (gi: 19109483) (Mar. 4, 2002); Vandenbosch,K., et al. "EST590179 KV2 *Medicago truncatula* cDNA clone pKV2-52D13, mRNA sequence"; source: *Medicago truncatula* (barrel medic); Title: "ESTs from roots of *Medicago truncatula* 48 hr after inoculation with *Sinorhizobium meliloti*" (Unpublished (2002)).
BM779692 NCBI acc. No. BM779692 (gi: 19109604) (Mar. 4, 2002); Vandenbosch,K., et al. "EST590268 KV2 *Medicago truncatula* cDNA clone pKV2-52D24, mRNA sequence"; source: *Medicago truncatula* (barrel medic); Title: "ESTs from roots of *Medicago truncatula* 48 hr after inoculation with *Sinorhizobium meliloti*" (Unpublished (2002)).
BM886268 NCBI acc. No. BM886268 (gi: 19270021) (Mar. 8, 2002); Shoemaker,R., et al. "sam14e12.y1 Gm-c1068 *Glycine max* cDNA clone Soybean Clone ID: Gm-c1068-4824 5' similar to TR:O80387 O80387 Ethylene Responsive Element Binding Factor. ;, mRNA sequence"; source: *Glycine max* (soybean); Title: "Public Soybean EST Project" (Unpublished (1999)).
BM891538 NCBI acc. No. BM891538 (gi: 19346658) (Mar. 11, 2002); Shoemaker,R., et al. "sam28e11.y1 Gm-c1068 *Glycine max* cDNA clone Soybean Clone ID: Gm-c1068-5998 5' similar to TR:O80387 O80387 Ethylene Responsive Element Binding Factor. ;, mRNA sequence"; source: *Glycine max* (soybean); Title: "Public Soybean EST Project" (Unpublished (1999)).
BM954448 NCBI acc. No. BM954448 (gi: 19453038) (Mar. 14, 2002); Shoemaker,R., et al. "san03e10.y1 Gm-c1084 *Glycine max* cDNA clone Soybean Clone ID: Gm-c1084-2900 5' similar to SW:ERF5_ARATH 080341 Ethylene Responsive Element Binding Factor 5 ;, mRNA sequence"; source: *Glycine max* (soybean); Title: "Public Soybean EST Project" (Unpublished (1999)).
BP174381 NCBI acc. No. BP174381 (gi: 29056877) (Mar. 18, 2003); Ujino-Ihara,T., et al. "BP174381 *Cryptomeria japonica* inner bark *Cryptomeria japonica* cDNA clone CC1389R 3', mRNA sequence"; source: *Cryptomeria japonica* (Japanese cedar); Title: "Expression analysis of ESTs derived from the inner bark of *Cryptomeria japonica*" (Plant Mol. Biol. 43 (4), 451-457 (2000)).
BQ045702 NCBI acc. No. BQ045702 (gi: 19819688) (Mar. 29, 2002); Zhang,P., et al. "EST594820 P infestans-challenged potato leaf, incompatible reaction *Solanum tuberosum* cDNA clone BPLI12L1 5 end, mRNA sequence"; source: *Solanum tuberosum* (potato); Title: "Generation of ESTs from Potato Leaves Challenged with Phytophthora infestans, incompatible Interaction (2002)" (Unpublished (2002)).
BQ047502 NCBI acc. No. BQ047502 (gi: 19821488) (Mar. 29, 2002); Zhang,P., et al. "EST596620 P. infestans-challenged potato leaf, incompatible reaction *Solanum tuberosum* cDNA clone BPLI17L16 5' end, mRNA sequence"; source: *Solanum tuberosum* (potato); Title: "Generation of ESTs from Potato Leaves Challenged with Phytophthora infestans, incompatible Interaction (2002)" (Unpublished (2002)).
BQ080756 NCBI acc. No. BQ080756 (gi: 19936180) (Apr. 4, 2002); Shoemaker,R., et al. "san37g07.y1 Gm-c1084 *Glycine max* cDNA clone Soybean Clone ID: Gm-c1084-6086 5' similar to TR:Q9SJX3 Q9SJX3 Ethylene Reponse Factor-Like AP2 Domain Transcription Factor. ;, mRNA sequence"; source: *Glycine max* (soybean); Title: "Public Soybean EST Project" (Unpublished (1999)).
BQ081056 NCBI acc. No. BQ081056 (gi: 19936893) (Apr. 4, 2002); Shoemaker,R., et al. "san18g09.y1 Gm-c1084 *Glycine max* cDNA clone Soybean Clone ID: Gm-c1084-4529 5' similar to TR:P93822 P93822 F19P19.18. ;, mRNA sequence"; source: *Glycine max* (soybean); Title: "Public Soybean EST Project" (Unpublished (1999)).
BQ081073 NCBI acc. No. BQ081073 (gi: 19936936) (Apr. 4, 2002); Shoemaker,R., et al. "san19a08.y1 Gm-c1084 *Glycine max* cDNA clone Soybean Clone ID: Gm-c1084-4240 5' similar to TR:P93822 P93822 F19P19.18. ;, mRNA sequence"; source: *Glycine max* (soybean); Title: "Public Soybean EST Project" (Unpublished (1999)).
BQ081329 NCBI acc. No. BQ081329 (gi: 19937535) (Apr. 4, 2002); Shoemaker,R., et al. "san23a04.y1 Gm-c1084 *Glycine max* cDNA clone Soybean Clone ID: Gm-c1084-4616 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).
BQ122054 NCBI acc. No. BQ122054 (gi: 20174016) (Apr. 17, 2002); Buell,C.R., et al. "EST607630 mixed potato tissues *Solanum tuberosum* cDNA clone STMFC37 3' end, mRNA sequence"; source: *Solanum tuberosum* (potato); Title: "Generation of a set of potato cDNA clones for microarray analyses" (Unpublished (2002)).
BQ138491 NCBI acc. No. BQ138491 (gi: 20274617) (Apr. 23, 2002); Watson,B.S., et al. "NF003G09PH1F1070 Phoma-infected *Medicago truncatula* cDNA clone NF003G09PH 5', mRNA sequence"; source: *Medicago truncatula* (barrel medic); Title: "Expressed Sequence Tags from the Samuel Roberts Noble Foundation *Medicago truncatula* Phoma-infected library" (Unpublished (2002)).
BQ165291 NCBI acc. No. BQ165291 (gi: 20307557) (Apr. 25, 2002); Vandenbosch,K., et al. "EST611160 KVKC *Medicago truncatula* cDNA clone pKVKC-7F4, mRNA sequence"; source: *Medicago truncatula* (barrel medic); Title: "The *Medicago truncatula* 'kiloclone' set; ESTs selected and re-arrayed from various libraries" (Unpublished (2002)).
BQ452871 NCBI acc. No. BQ452871 (gi: 21255983) (May 29, 2002); Shoemaker,R., et al. "sao92e10.y1 Gm-c1081 *Glycine max* cDNA clone Soybean Clone ID: Gm-c1081-3284 5' similar to SW:ERFI__ARATH O80337 Ethylene Responsive Element Binding Factor 1 ;, mRNA sequence"; source: *Glycine max* (soybean); Title: "Public Soybean EST Project" (Unpublished (1999)).
BQ469024 NCBI acc. No. BQ469024 (gi: 21276806) (May 30, 2002); Zhang,H., et al. "HM03C08r HM *Hordeum vulgare* subsp. vulgare cDNA clone HM03C08 5-Prime, mRNA sequence"; source: *Hordeum vulgare* subsp. vulgare; Title: "Large-scale analysis of the barley transcriptome based on expressed sequence tags" (Plant J. 40 (2), 276-290 (2004)).
BQ514194 NCBI acc. No. BQ514194 (gi: 21373063) (Jun. 10, 2002); Buell,C.R., et al. "EST621609 Generation of a set of potato cDNA clones for microarray analyses mixed potato tissues *Solanum tuberosum* cDNA clone STMIK39 5' end, mRNA sequence"; source: *Solanum tuberosum* (potato); Title: "Generation of a set of potato cDNA clones for microarray analyses" (Unpublished (2002)).
BQ514195 NCBI acc. No. BQ514195 (gi: 21373064) (Jun. 10, 2002); Buell,C.R., et al. "EST621610 Generation of a set of potato cDNA clones for microarray analyses mixed potato tissues *Solanum tuberosum* cDNA clone STMIK39 3' end, mRNA sequence"; source: *Solanum tuberosum* (potato); Title: "Generation of a set of potato cDNA clones of microarray analyses" (Unpublished (2002)).
BQ517082 NCBI acc. No. BQ517082 (gi: 21375951) (Jun. 10, 2002); Buell,C.R., et al. "EST624497 Generation of a set of potato cDNA clones for microarray analyses mixed potato tissues *Solanum tuberosum* cDNA clone STMJB52 5' end, mRNA sequence"; source: *Solanum tuberosum* (potato); Title: "Generation of a set of potato cDNA clones of microarray analyses" (Unpublished (2002)).
BQ517083 NCBI acc. No. BQ517083 (gi: 21375952) (Jun. 10, 2002); Buell,C.R., et al. "EST624498 Generation of a set of potato cDNA clones for microarray analyses mixed potato tissues *Solanum tuberosum* cDNA clone STMJB52 3' end, mRNA sequence"; source: *Solanum tuberosum* (potato); Title: "Generation of a set of potato cDNA clones of microarray analyses" (Unpublished (2002)).
BQ592225 NCBI acc. No. BQ592225 (gi: 26121808) (Dec. 6, 2002); Herwig,R., et al. "E012698-024-021-H24-SP6 MPIZ-ADIS-024-developing root *Beta vulgaris* cDNA clone 024-021-H24 5-PRIME, mRNA sequence"; source: *Beta vulgaris*; Title: "Construction of a'unigene' cDNA clone set by oligonucleotide fingerprinting allows access to 25 000 potential sugar beet genes" (Plant J. 32 (5), 845-857 (2002)).
BQ623351 NCBI acc. No. BQ623351 (gi: 21650520) (Jul. 1, 2002); Bausher,M., et al. "USDA-FP__00442 Ridge pineapple sweet orange entire seedling *Citrus sinensis* cDNA clone USDA-FP__00442 5', mRNA sequence"; source: *Citrus sinensis*; Title: "Expressed sequence tags isolated from entire sweet orange (*C. sinesis* L. Osbeck) seedling" (Unpublished (2003)).
BQ628375 NCBI acc. No. BQ628375 (gi: 21676024) (Jul. 2, 2002); Shoemaker,R., et al. "sap46b10.y1 Gm-c1087 *Glycine max* cDNA clone Soybean Clone ID: Gm-c1087-3547 5' similar to SW:ERF5__ARATH O80341 Ethylene Responsive Element Binding Factor 5 ;, mRNA sequence"; source: *Glycine max* (soybean); Title: "Public Soybean EST Project" (Unpublished (1999)).
BQ630661 NCBI acc. No. BQ630661 (gi: 21678310) (Jul. 2, 2002); Shoemaker,R., et al. "sap29e09.y1 Gm-c1082 *Glycine max* cDNA clone Soybean Clone ID: Gm-c1082-4050 5' similar to TR:Q40478 Q40478 EREBP-4. ;, mRNA sequence"; source: *Glycine max* (soybean); Title: "Public Soybean EST Project" (Unpublished (1999)).
BQ743147 NCBI acc. No. BQ743147 (gi: 21889934) (Jul. 17, 2002); Shoemaker,R., et al. "saq60g01.y1 Gm-c1076 *Glycine max* cDNA clone Soybean Clone ID: Gm-c1076-4154 5' similar to SW:ERFI__ARATH 080337 Ethylene Responsive Element Binding Factor 1 ;, mRNA sequence"; source: *Glycine max* (soybean); Title: "Public Soybean EST Project" (Unpublished (1999)).
BQ762577 NCBI acc. No. BQ762577 (gi: 21971049) (Jul. 26, 2002); Hedley,P., et al. "EBro02__SQ004__H12__R root, 3 week, hydroponic grown, low nitrogen, cv Optic, EBro02 *Hordeum vulgare* subsp. vulgare cDNA clone EBro02__SQ004__H12 5', mRNA sequence"; source: *Hordeum vulgare* subsp. vulgare; Title: "Development of Barley Transcriptome Resources" (Unpublished (2001)).
BQ785400 NCBI acc. No. B0785400 (gi: 21993872) (Jul. 26, 2002); Shoemaker,R., et al. "saq77c02.y1 Gm-c1076 *Glycine max* cDNA clone Soybean Clone ID: Gm-c1076-5859 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).
B0786714 NCBI acc. No. B0786714 (gi: 21995186) (Jul. 26, 2002); Shoemaker,R., et al. "saq72c10.y1 Gm-c1076 *Glycine max* cDNA clone Soybean Clone ID: Gm-c1076-5132 5' similar to SW:ERF5__ARATH O80341 Ethylene Responsive Element Binding Factor 5 :, mRNA sequence"; source: *Glycine max* (soybean); Title: "Public Soybean EST Project" (Unpublished (1999)).
B0991410 NCBI acc. No. B0991410 (gi: 22410945) (Aug. 21, 2002); Kozik,a., et al. "QGF22M18.yg.ab1 QG__EFGHJ lettuce serriola *Lactuca serriola* cDNA clone QGF22M18, mRNA sequence"; source: *Lactuca serriola*; Title: "Lettuce and Sunflower ESTs from the Compositae Genome Project" (Unpublished (2002)).
BU547894 NCBI acc. No. BU547894 (gi: 22930755) (Sep. 16, 2002); Vodkin,L., et al. "GM880014B10B09 Gm-r1088 *Glycine max* cDNA clone Gm-r1088-5081 3', mRNA sequence"; source: *Glycine max* (soybean); Title: "A Functional Genomics Program for Soybean (NSF 9872565) (2002)" (Unpublished (2002)).
BU763420 NCBI acc. No. BU763420 (gi: 23730658) (Oct. 10, 2002); Shoemaker,R., et al. "sas42d05.y1 Gm-c1080 *Glycine max* cDNA clone Soybean Clone ID: Gm-c1080-6322 5' similar to TR:Q40478 Q40478 EREBP-4. ;, mRNA sequence"; source: *Glycine max* (soybean); Title: "Public Soybean EST Project" (Unpublished (1999)).
BU765444 NCBI acc. No. BU765444 (gi: 23734437) (Oct. 10, 2002); Shoemaker,R., et al. "sas18g12.y1 Gm-c1080 *Glycine max* cDNA clone Soybean Clone ID: Gm-c1080-4176 5' similar to SW:ERF5__ARATH O80341 Ethylene Responsive Element Binding Factor 5 ;, mRNA sequence"; source: *Glycine max* (soybean); Title: "Public Soybean EST Project" (Unpublished (1999)).
BU765819 NCBI acc. No. BU765819 (gi: 23735106) (Oct. 10, 2002); Shoemaker,R., et al. "sas20d07.y1 Gm-c1080 *Glycine max* cDNA clone Soybean Clone ID: Gm-c1080-4382 5' similar to SW:ERF5__ARATH O80341 Ethylene Responsive Element Binding Factor 5 ;, mRNA sequence"; source: *Glycine max* (soybean); Title: "Public Soybean EST Project" (Unpublished (1999)).
BU765920 NCBI acc. No. BU765920 (gi: 23735288) (Oct. 10, 2002); Shoemaker,R., et al. "sar82b04.y1 Gm-c1074 *Glycine max* cDNA clone Soybean Clone ID: Gm-c1074-8887 5' similar to TR:Q40478 Q40478 EREBP-4. ;, mRNA sequence"; source: *Glycine max* (soybean); Title: "Public Soybean EST Project" (Unpublished (1999)).
BU765924 NCBI acc. No. BU765924 (gi: 23735295) (Oct. 10, 2002); Shoemaker,R., et al. "sar82c04.y1 Gm-c1074 *Glycine max* cDNA clone Soybean Clone ID: Gm-c1074-8935 5' similar to TR:Q40478 Q40478 EREBP-4. ;, mRNA sequence"; source: *Glycine max* (soybean); Title: "Public Soybean EST Project" (Unpublished (1999)).
BU814218 NCBI acc. No. BU814218 (gi: 23971351) (Oct. 15, 2002); Unneberg,P., et al. "N026E12 Populus bark cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BU823955 NCBI acc. No. BU823955 (gi: 23993933) (Oct. 15, 2002); Unneberg,P., et al. "UB58DPE07 *Populus tremula* cambium cDNA library *Populus tremula* cDNA 5 prime, mRNA sequence"; source: *Populus tremula*; Title: "The poplar tree transcriptome: Analysis of expressed sequence tags from multiple libraries" (Unpublished (2002)).
BU830292 NCBI acc. No. BU830292 (gi: 24007304) (Oct. 15, 2002);Unneberg,P., et al. "T006E02 *Populus* apical shoot cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BU832225 NCBI acc. No. BU832225 (gi: 24011454) (Oct. 15, 2002); Unneberg,P., et al. "T031A05 *Populus* apical shoot cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).

BU837816 NCBI acc. No. BU837816 (gi: 24020612) (Oct. 16, 2002); Unneberg,P., et al. "T106A05 *Populus* apical shoot cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).

BU871861 NCBI acc. No. BU871861 (gi: 24063385) (Oct. 16, 2002); Unneberg,P., et al. "0035D06 *Populus* flower cDNA library *Populus trichocarpa* cDNA 5 prime, mRNA sequence"; source: *Populus trichocarpa* (*Populus balsamifera* subsp. trichocarpa); Title: "The poplar tree transcriptome: Analysis of expressed sequence tags from multiple libraries" (Unpublished (2002)).

BU874000 NCBI acc. No. BU874000 (gi: 24065524) (Oct. 16, 2002); Unneberg,P., et al. "0063CO2 *Populus* flower cDNA library *Populus trichocarpa* cDNA 5 prime, mRNA sequence"; source: *Populus trichocarpa* (*Populus balsamifera* subsp. trichocarpa); Title: "The poplar tree transcriptome: Analysis of expressed sequence tags from multiple libraries" (Unpublished (2002)).

BU884339 NCBI acc. No. BU884339 (gi: 24075856) (Oct. 17, 2002); Unneberg,P., et al. "R009C12 *Populus* root cDNA library *Populus tremula* x Populus tremuloides cDNA 5 prime, mRNA sequence"; source: *Populus tremula* x Populus tremuloides; Title:"The poplar tree transcriptome: Analysis of expressed sequence tags from multiple libraries" (Unpublished (2002)).

BU884448 NCBI acc. No. BU884448 (gi: 24075965) (Oct .17, 2002); Unneberg,P., et al. "R010G08 *Populus* root cDNA library *Populus tremula* x Populus tremuloides cDNA 5 prime, mRNA sequence"; source: *Populus tremula* x Populus tremuloides; Title:"The poplar tree transcriptome: Analysis of expressed sequence tags from multiple libraries" (Unpublished (2002)).

BU887519 NCBI acc. No. BU887519 (gi: 24080231) (Oct.17, 2002); Unneberg,P., et al. "R062F03 *Populus* root cDNA library *Populus tremula* x Populus tremuloides cDNA 5 prime, mRNA sequence"; source: *Populus tremula* x Populus tremuloides; Title:"The poplar tree transcriptome: Analysis of expressed sequence tags from multiple libraries" (Unpublished (2002)).

BZ020356 NCBI acc. No. BZ020356 (gi: 23580089) (Oct. 8, 2002); Delehaunty,K., et al. "oegO4a10.g1 *B.oleracea*002 *Brassica oleracea* genomic, genomic survey sequence"; source: *Brassica oleracea*; Title: "Whole genome shotgun reads from *Brassica oleracea*" (Unpublished (2002)).

BZ332067 NCBI acc. No. BZ332067 (gi: 24720629) (Nov. 6, 2002); Rabinowicz,P.D., et al. "hx25b08.b1 WGS-SbicolorF (JM107 adapted methyl filtered) *Sorghum bicolor* genomic clone hx25b08 5', genomic survey sequence"; source: *Sorghum bicolor* (*sorghum*); Title: "Genomic shotgun sequences from *Sorghum bicolor* (methyl-filtered)" (Unpublished (2002)).

BZ337899 NCBI acc. No. BZ337899 (gi: 24733043) (Nov. 6, 2002); Rabinowicz,P.D., et al. "ia91f11.b1 WGS-SbicolorF (JM107 adapted methyl filtered) *Sorghum bicolor* genomic clone ia91f11 5', genomic survey sequence"; source: *Sorghum bicolor* (*sorghum*); Title: "Genomic shotgun sequences from *Sorghum bicolor* (methyl-filtered)" (Unpublished (2002)).

BZ359367 NCBI acc. No. BZ359367 (gi: 25059121) (Nov. 18, 2002); Rabinowicz,P.D., et al. "id72f11.b1 WGS-ZmaysF (JM107 adapted methyl filtered) *Zea mays* genomic clone id72f11 5', genomic survey sequence"; source: *Zea mays*; Title: "Genomic shotgun sequences from *Zea mays* (methyl-filtered)" (Unpublished (2002)).

BZ401507 NCBI acc. No. BZ401507 (gi: 26026577) (Dec. 4, 2002); Whitelaw, C.A., et al. "OGABH91TC ZM_0.7_1.5_KB *Zea mays* genomic clone ZMMBMa0022B11, genomic survey sequence"; source: *Zea mays*; Title: "Consortium for Maize Genomics" (Unpublished (2002)).

BZ401512 NBCI acc. No. BZ401512 (gi: 26026582) (Dec. 4, 2002); Whitelaw, C.A., et al. "OGABH91TM ZM_0.7_1.5_KB *Zea mays* genomic clone ZMMBMa0022B11, genomic survey sequence"; source: *Zea mays*; Title: "Consortium for Maize Genomics" (Unpublished (2002)).

BZ489256 NCBI acc. No. BZ489256 (gi: 26995806) (Dec. 16, 2002); Ayele,M., et al. "BOOAWO9TF BO_1.6_2_KB_tot *Brassica oleracea* genomic clone BOOAW09, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BZ489264 NCBI acc. No. BZ489264 (gi: 26995814) (Dec. 16, 2002); Ayele,M., et al. "BOOAWO9TR BO_1.6_2_KB_tot *Brassica oleracea* genomic clone BOOAW09, Ayele,M survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BZ536116 NCBI acc. No. BZ536116 (gi: 27083627) (Dec. 16, 2002); Whitelaw,C.A., et al. "OGAGZO6TC ZM2_0.7_1.5_KB *Zea mays* genomic clone ZMMBMa0059A12, genomic survey sequence"; source: *Zea mays*; Title: "Consortium for Maize Genomics" (Unpublished (2002)).

BZ646476 NCBI acc. No. BZ646476 (gi: 28108680) (Jan. 29, 2003); Whitelaw,C.A., et al. "OGAMK11TC ZM_0.7_1.5_KB *Zea mays* genomic clone ZMMBMa0094B21, genomic survey sequence"; source: *Zea mays*; Title: "Consortium for Maize Genomics" (Unpublished (2002)).

CA019696 NCBI acc. No. CA019696 (gi: 24297040) (Oct. 23, 2002); Zhang,H., et al. "HV12M24r HV *Hordeum vulgare* subsp. vulgare cDNA clone HV12M24 5-PRIME, mRNA sequence"; source: *Hordeum vulgare* subsp. vulgare; Title: "Large-scale analysis of the barley transcriptome based on expressed sequence tags" (Plant J. 40 (2), 287-290 (2004).

CA514062 NCBI acc. No. CA514062 (gi: 25014619) (Nov. 15, 2002); Lee,S., et al. "KS09016D12 KS09 *Capsicum annuum* cDNA, mRNA sequence"; source: *Capsicum annuum*; Title: "Generation of Expressed Sequence Tags from Hot Pepper (*Capsicum annuum* L.) and Sequence Analysis in Relation to Hypersensitive Response Against Pathogen" (Unpublished (2001)).

CA522916 NCBI acc. No. CA522916 (gi: 25036961) (Nov. 15, 2002); Lee,S., et al. "KS12015D10 KS12 *Capsicum annuum* cDNA, mRNA sequence"; source: *Capsicum annuum*; Title: "Generation of Expressed Sequence Tags from Hot Pepper (*Capsicum annuum* L.) and Sequence Analysis in Relation to Hypersensitive Response Against Pathogen" (Unpublished (2001)).

CA723694 NCBI acc. No. CA723694 (gi: 25445487) (Nov. 26, 2002); Tingey,S.V., et al. "wdr1f.pk003.I5 wdrlf *Triticum aestivum* cDNA clone wdr1f.pk003.I5 5' end, mRNA sequence"; source: *Triticum aestivum* (bread wheat); Title: "DuPont Wheat cDNA Sequence" (Unpublished (2002)).

CA783253 NCBI acc. No. CA783253 (gi: 26045764) (Dec. 4, 2002); Shoemaker,R., et al. "sat21f08.y1 Gm-c1036 *Glycine max* cDNA clone Soybean Clone ID: Gm-c1036-14464 5' similar to TR:Q40478 Q40478 EREBP-4. ;, mRNA sequence"; source: *Glycine max* (soybean); Title: "Public Soybean EST Project" (Unpublished (1999)).

CA783313 NCBI acc. No. CA783313 (gi: 26045880) (Dec. 4, 2002); Shoemaker,R., et al. "sat22e09.y1 Gm-c1036 *Glycine max* cDNA clone Soybean Clone ID: Gm-c1036-14441 5' similar to TR:Q40478 Q40478 EREBP-4. ;, mRNA sequence"; source: *Glycine max* (soybean); Title: "Public Soybean EST Project" (Unpublished (1999)).

CA799724 NCBI acc. No. CA799724 (gi: 26056810) (Dec. 5, 2002); Shoemaker,R., et al. "sat61h01.y1 Gm-c1056 *Glycine soja* cDNA clone Soybean Clone ID: Gm-c1056-6098 5' similar to TR:Q40478 Q40478 EREBP-4. ;, mRNA sequence"; source: *Glycine soja*; Title: "Public Soybean EST Project" (Unpublished (1999)).

CA801993 NCBI acc. No. CA801993 (gi: 26059079) (Dec. 5, 2002); Shoemaker,R., et al. "sau28c10.y1 Gm-c1062 *Glycine max* cDNA clone Soybean Clone ID: Gm-c1062-9356 5' similar to TR:Q40478 Q40478 EREBP-4. ;, mRNA sequence"; source: *Glycine max* (soybean); Title: "Public Soybean EST Project" (Unpublished (1999)).

CA918826 NCBI acc. No. CA918826 (gi: 27405756) (Dec. 27, 2002); Vandenbosch,K., et al. "EST636544 MTUS *Medicago truncatula* cDNA clone MTUS-3F12, mRNA sequence"; source: *Medicago truncatula* (barrel medic); Title: "The *Medicago truncatula* 6K unigene set: cDNA clones selected and re-arrayed from various libraries" (Unpublished (2002)).

CA926476 NBCI acc. No. CA926476 (gi: 27414955) (Dec. 30, 2002); Ranjan,P., et al. "MTU6CR.P15.E02 Aspen root cDNA Library *Populus tremuloides* cDNA, mRNA sequence"; source: *Populus tremuloides* (quaking aspen); Title: "Expressed sequence tags from Aspen" (Unpublished (2003)).
CB001513 NCBI acc. No. CB001513 (gi: 27578818) (Jan. 10, 2003); Cramer,G.R., et al. "VVB004H10__124488 An expressed sequence tag database for abiotic stressed leaves of *Vitis vinifera* var. Chardonnay *Vitis vinifera* cDNA clone VVB004H10 5, mRNA sequence"; source: *Vitis vinifera*; Title: "An expressed sequence tag database for abiotic stressed leaves of *Vitis vinifera* var. Chardonnay" (Unpublished (2002)).
CB002777 NCBI acc. No. CB002777 (gi: 27580082) (Jan. 10, 2003); Cramer,G.R., et al. "VVB020G03__132412 An expressed sequence tag database for abiotic stressed leaves of *Vitis vinifera* var. Chardonnay *Vitis vinifera* cDNA clone VVB020G03 5, mRNA sequence"; source: *Vitis vinifera*; Title: "An expressed sequence tag database for abiotic stressed leaves of *Vitis vinifera* var. Chardonnay" (Unpublished (2002)).
CB003172 NCBI acc. No. CB003172 (gi: 27580477) (Jan. 10, 2003); Cramer,G.R., et al. "VVB027C01__133202 An expressed sequence tag database for abiotic stressed leaves of *Vitis vinifera* var. Chardonnay *Vitis vinifera* cDNA clone VVB027C01 5, mRNA sequence"; source: *Vitis vinifera*; Title: "An expressed sequence tag database for abiotic stressed leaves of *Vitis vinifera* var. Chardonnay" (Unpublished (2002)).
CB003334 NCBI acc. No. CB003334 (gi: 27580639) (Jan. 10, 2003); Cramer,G.R., et al. "VVB029A07__33526 An expressed sequence tag database for abiotic stressed leaves of *Vitis vinifera* var. Chardonnay *Vitis vinifera* cDNA clone VVB029A07 5, mRNA sequence"; source: *Vitis vinifera*; Title: "An expressed sequence tag database for abiotic stressed leaves of *Vitis vinifera* var. Chardonnay" (Unpublished (2002)).
CB003997 NCBI acc. No. CB003997 (gi: 27581302) (Jan. 10, 2003); Cramer,G.R., et al. "VVB034F08__134852 An expressed sequence tag database for abiotic stressed leaves of *Vitis vinifera* var. Chardonnay *Vitis vinifera* cDNA clone VVB034F08 5, mRNA sequence"; source: *Vitis vinifera*; Title: "An expressed sequence tag database for abiotic stressed leaves of *Vitis vinifera* var. Chardonnay" (Unpublished (2002)).
CB007463 NCBI acc. No. CB007463 (gi: 27584768) (Jan. 10, 2003); Cushman,J.C., et al. "VVC045F10__141982 An expressed sequence tag database for abiotic stressed berries of *Vitis vinifera* var. Chardonnay *Vitis vinifera* cDNA clone VVC045F10 5, mRNA sequence"; source: *Vitis vinifera*; Title: "An expressed sequence tag database for abiotic stressed leaves of *Vitis vinifera* var. Chardonnay" (Unpublished (2002)).
CB288719 NCBI acc. No. CB288719 (gi: 28602460) (Feb. 27, 2003); Hou,H.S., et al. "V-B-18C10 Van-Baker-1 *Vitis aestivalis* cDNA clone V-B-18C10 5', mRNA sequence"; source: *Vitis aestivalis*; Title: "Expressed sequence tags of young leaf tissues of a disease-resistant *Vitis aestivalis* var. Norton" (Unpublished (2003)).
CB288872 NCBI acc. No. CB288872 (gi: 28602613) (Feb. 27, 2003); Hou,H.S., et al. "V-B-110A09 VAN-Baker-1 *Vitis aestivalis* cDNA clone V-B-110A09 5', mRNA sequence"; source: *Vitis aestivalis*; Title: "Expressed sequence tags of young leaf tissues of a disease-resistant *Vitis aestivalis* var. Norton" (Unpublished (2003)).
CB289287 NCBI acc. No. CB289287 (gi: 28603028) (Feb. 27, 2003); Hou,H.S., et al. "V-B-115B12 VAN-Baker-1 *Vitis aestivalis* cDNA clone V-B-115B12 5', mRNA sequence"; source: *Vitis aestivalis*; Title: "Expressed sequence tags of young leaf tissues of a disease-resistant *Vitis aestivalis* var. Norton" (Unpublished (2003)).
CB289366 NCBI acc. No. CB289366 (gi: 28603107) (Feb. 27, 2003); Hou,H.S., et al. "V-B-116B09 VAN-Baker-1 *Vitis aestivalis* cDNA clone V-B-116B09 5', mRNA sequence"; source: *Vitis aestivalis*; Title: "Expressed sequence tags of young leaf tissues of a disease-resistant *Vitis aestivalis* var. Norton" (Unpublished (2003)).
CB289523 NCBI acc. No. CB289523 (gi: 28603264) (Feb. 27, 2003); Hou,H.S., et al. "V-B-118A07 VAN-Baker-1 *Vitis aestivalis* cDNA clone V-B-118A07 5, mRNA sequence"; source: *Vitis aestivalis*; Title: "Expressed sequence tags of young leaf tissues of a disease-resistant *Vitis aestivalis* var. Norton" (Unpublished (2003)).

CB292286 NCBI acc. No. CB292286 (gi: 28617743) (Feb. 28, 2003); Close,T.J., et al. "UCRCS01__04ba10__g1 Washington Navel orange cold acclimated flavedo & albedo cDNA library *Citrus sinensis* cDNA clone UCRCS01__04ba10, mRNA sequence"; source: *Citrus sinensis*; Title: "Development of Est Resources and New Genetic Markers for California Cirtus" (Unpublished (2003)).
CB322190 NCBI acc. No. CB322190 (gi: 28856848) (Mar. 5, 2003); Burns,J.K., et al. "EST0312 Mature leaf blade cDNA substraction library *Citrus sinensis* cDNA clone 24LB271 similar to pathogensis-related transcriptional activator PTI5 (acc# AAC49740), mRNA sequence"; source: *Citrus sinensis*; Title: "Expressed sequence tags of cDNA clones from a subtracted 'Valencia' orange mature leaf lblade library" (Unpublished (2000)).
CB341794 NCBI acc. No. CB341794 (gi: 28962761) (Mar. 14, 2003); Goes Da Silva,F., et al. "CA32EN0002__IIIbF__A03 Cabernet Sauvignon Leaf—CA32EN *Vitis vinifera* cDNA clone CA32EN0002__IIIbF__A03 5', mRNA sequence"; source: *Vitis vinifera*; Title: "Transcriptional responses of *Vitis vinifera* to infection by the bacterial pathogen *Xylella fastidiosa*" (Unpublished (2003)).
CB342848 NCBI acc. No. CB342848 (gi: 28963815) (Mar. 14, 2003); Goes Da Silva,F., et al. "CA32EN0004__111aF__C01 Cabernet Sauvignon Leaf—CA32EN *Vitis vinifera* cDNA clone CA32EN0004__IIIaF__C01 5', mRNA sequence"; source: *Vitis vinifera*; Title: "Transcriptional responses of *Vitis vinifera* to infection by the bacterial pathogen *Xylella fastidiosa*" (Unpublished (2003)).
CB342920 NCBI acc. No. CB342920 (gi: 28963887) (Mar. 14, 2003); Goes Da Silva,F., et al."CA32EN0004__IIIbR__C01 Cabernet Sauvignon Leaf—CA32EN *Vitis vinifera* cDNA clone CA32EN0004__IIIbR__C01 3', mRNA sequence"; source: *Vitis vinifera*; Title: "Transcriptional responses of *Vitis vinifera* to infection by the bacterial pathogen *Xylella fastidiosa*" (Unpublished (2003)).
CB350627 NCBI acc. No. CB350627 (gi: 28985410) (Mar. 17, 2003); Wen,T.J., et al. "MEST253-F08.univ ISUM5-RN *Zea mays* cDNA clone MEST253-F08 3', mRNA sequence"; source: *Zea mays*; Title: "Expressed Sequence Tags from B73 Maize: various stages and tissues including seedlings treated with a variety of hormones" (Unpublished (2001)).
CRO238740 NCBI acc. No. AJ238740 (gi: 8346774) (Jun. 7, 2000); Menke,F.L.H., et al. "*Catharanthus roseus* mRNA for AP2-domain DNA-binding protein ORCA2"; source: *Catharanthus roseus* (*Madagascar periwinkle*); Title: "A jasmonate- and elicitor-responsive element in the periwinkle secondary metabolite biosynthetic gene Str interacts with a jasmonate- and elicitor-inducible AP2-domain transcription factor, ORCA2" (Unpublished).
CRO251249 NCBI acc. No. AJ251249 (gi: 8980312) (Jul. 8, 2000); Van Der Fits,L., et al. "*Catharanthus roseus* mRNA for AP2-domain DNA-binding protein (orca3 gene)"; source: *Catharanthus roseus* (*Madagascar periwinkle*); Title: "ORCA3, a jasmonate-responsive master regulator of multiple genes in plant primary and secondary metabolism" (Unpublished).
CRO251250 NCBI acc. No. AJ251250 (gi: 8980314) (Jul. 8, 2000); Van Der Fits,L., et al. "*Catharanthus roseus* orca3 gene for AP2-domain DNA-binding protein"; source: *Catharanthus roseus* (*Madagascar periwinkle*); Title: "ORCA3, a jasmonate-responsive master regulator of multiple genes in plant primary and secondary metabolism" (Unpublished).
LEU89255 NCBI acc. No. U89255 (gi: 2213780) (Jun. 25, 1997); Zhou,J., et al. "*Lycopersicon esculentum* DNA-binding protein Pti4 mRNA, complete cds"; source: *Lycopersicon esculentum* (tomato); Title: "The Pto Kinase Conferring Resistance to Tomato Bacterial Speck Disease Interacts with Proteins that Bind a Cis-Element of Pathogenesis-Related Genes" (EMBO J. 16, 3207-3218 (1997).
LEU89256 NCBI acc. No. U89256 (gi: 2213782) (Jun. 25, 1997); Zhou,J., et al. "*Lycopersicon esculentum* DNA-binding protein PtiS mRNA, complete cds"; source: *Lycopersicon esculentum* (tomato); Title: "The Pto Kinase Conferring Resistance to Tomato Bacterial Speck Disease Interacts with Proteins that Bind a Cis-Element of Pathogenesis-Related Genes" (EMBO J. 16, 3207-3218 (1997)).
NTA299252 NCBI acc. No. AJ299252 (gi: 10798643) (Oct .11, 2000); Shen,W.H., et al. "*Nicotiana tabacum* partial mRNA for AP2 domain-containing transcription factor (ap2 gene)"; source: *Nicotiana tabacum* (common tobacco); Title: "*Nicotiana tabacum* cDNA (partial) encoding AP2 domain-containing protein" (Unpublished).
NTU81157 NCBI acc. No. U81157 (gi: 1732405) (Dec. 16, 1996); Xu,P., et al. "*Nicotiana tabacum* S25-XP1 DNA binding protein mRNA, complete cds"; source: *Nicotiana tabacum* (common tobacco); Title: "Direct Submission" (Submitted (Dec. 6, 1996) Biotechnology Institute, Zhejiang Agriculture Unversity, Hangzhou, Zhejiang 310029, P.R.China).
OSA307662 NCBI acc. No. AJ307662 (gi: 14140112) (May 17, 2001); Mayer,K., et al. "*Oryza sativa* genomic DNA fragment, chromosome 2"; source: *Oryza sativa*; Title: "Conservation of microstructure bewtween a sequenced region of the genome of rice and multiple segments of the genome of *Arabidopsis thanliana*" (Unpublished).
OSJN00126 NCBI acc. No. AL607006 (gi: 15799247) (Sep. 27, 2001); Han,B., et al. "*Oryza sativa* chromosome 4 clone OSJNBA0079A21, * Sequencing in Progress *"; source: *Oryza sativa*; Title: "Direct Submission" (Submitted (Jul. 28, 2000) Han Bin, National Center for Gene Research, Chinese Academy of sciendces, 500# Cao Bao Road, Shanghai 200233, CHINA. E-mail enquiries: bhan@ncgr.ac.cn. Clone requests: bhan@ncgr.ac.cn.).
SHU91857 NCBI acc. No. U91857 (gi: 4099913) (Jan. 5, 1999); Gardner,R.C., et al. "*Stylosanthes hamata* ethylene-responsive element binding protein homolog gene, comp ete cds"; source: *Stylosanthes hamata*; Title: "Aluminium Tolerance in Yeast Conferred by Over-expression of *Stylosanthes* genes".(Unpublished).
STU77655 NCBI acc. No. U77655 (gi: 1688232) (Nov. 28, 1996); Stidd,J.E., et al. "*Solanum tuberosum* DNA binding protein homolog (STWAAEIRD) mRNA, complete cds"; source: *Solanum tuberosum* (potato); Title: "cDNA sequence from a log-phase cell suspension culture with similarity to DNA binding proteins" (Unpublished).
TOBBY4A NCBI acc. No. D38123 (gi: 790359) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).
TOBBY4B NCBI acc. No. D38124 (gi: 790360) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).
TOBBY4C NCBI acc. No. D38125 (gi: 790361) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).
TOBBY4D NCBI acc. No. D38126 (gi: 790362) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).
AAG43545 NCBI acc. No. AAG43545 (gi: 12003376) (Jan. 2, 2001); Durrant,W.E., et al. "Avr9/Cf-9 rapidly elicited protein 1 [*Nicotiana tabacum*]"; source: *Nocotiana tabacum* (commom tobacco); Title: "cDNA expression profiling reveals rapid, resistance gene-dependent, active oxygen-independent, gene induction during the plant defense response" (Unpublished).
BAA07324 NCBI acc. No. BAA07324 (gi: 1208498) (Feb. 28, 1996); Ohme-Takagi,M., et al. "EREBP-2"; source: *Nicotiana tabacum* (common tobacco); Title: "Direct Submission" (Submitted (Sep. 1, 1994) Masaru Ohme-Takagi, National Institute of Bioscience and Human Thechnology, Plant Moplecular Biology Laboratory, 1-1 Higashi, Tsukuba, Ibaraki 305, Japan).
AAG60182 NCBI acc. No. AAG60182 (gi: 12597874) (Jan. 30, 2001); Buell,C.R., et al. "putative ethylene-responsive element binding protein [*Oryza sativa*]"; source: *Oryza sativa*; Title: "*Oryza sativa* chromosome 10 BAC OSJNBa0027P10 genomic sequence" (Unpublished).
AAK31279 NCBI acc. No. AAK31279 (gi: 13569995) (Apr. 10, 2001); Buell,C.R., et al. "putative ethylene-responsive element binding protein [*Oryza sativa*]"; source: *Oryza sativa*; Title: "*Oryza sativa* chromosome 10 BAC OSJNBb0089A17 genomic sequence" (Unpublished).
CAC39058 NCBI acc. No. CAC39058 (gi: 14140141) (May 17, 2001); Mayer,K., et al. "putative AP2-related transcription factor [*Oryza sativa*]"; source: *Oryza sativa*; Title: "Conservation of microstructure bewtween a sequenced region of the genome of rice and multiple segments of he genome of *Arabidopsis tbaliana*" (Unpublished).
CAC39060 NCBI acc. No. CAC39060 (gi: 14140143) (May 17, 2001); Mater,K., et al. "putative ethylene responsive element binding factor [*Oryza sativa*]"; source: *Oryza sativa*; Title: "Conservation of microstructure bewtween a sequenced region of the genome of rice and multiple segments of the genome of *Arabidopsis*" (Unpublished).
BAB67922 NCBI acc. No. BAB67922 (gi: 1562863) (Sep. 14, 2001); Sasaki,T., et al. "contains EST~hypothetical protein [Oryza sativa]"; source: *Oryza sativa*; Title: "*Oryza sativa* nipponbare(GA3) genomic DNA, chromosome 1, PAC clone:P0046E05" (Published Only in Database (2001) in press).
AAB38748 NCBI acc. No. AAB38748 (gi: 1732406) (Dec. 16, 1996); Xu,P., et al. "S25-XP1 DNA binding protein [*Nicotiana tabacum*]"; source: *Nicotiana tabacum* (common tobacco); Title: "Direct Submission" (Submitted (Dec. 6, 1996) Biotechnology Institute, Zhejiang Agriculture Unversity, Hangzhou, Zhejiang 310029, P.R.China).
BAA87068 NCBI acc. No. BAA87068 (gi: 6478845) (Nov. 30, 1999); Ashida,Y., et al. "ethylene-responsive element binding protein1 homolog [*Matricaria chamomilla*]"; source: *Matricaria chamomilla*; Title: "ethylene-responsive element binding protein1 (EREBP) homolog, *Matricaria chamomilla*" (Published Only in DataBase (1999) In press).
BAB89538 NCBI acc. No. BAB89538 (gi: 20160591) (Apr. 16, 2002); Sasaki,T., et al. "hypothetical protein [*Oryza sativa* (japonica cultivar-group)]"; source: *Oryza sativa* (japonica cultivar-group); Title: "*Oryza sativa* nipponbare(GA3) genomic DNA, chromosome 1, PAC clone:P0435B05" (Published Only in Database (2001)).
AAC49740 NCBI acc. No. (gi: 2213783) (Jun. 25, 1997); Zhouj., et al. "Pti5 [*Lycopersicon esculentum*]"; source: *Lycopersicon esculentum* (tomato); Title: "The Pto Kinase Conferring Resistance to Tomato Bacterial Speck Disease Interacts with Proteins that Bind a Cis-Element of Pathogenesis-Related Genes" (EMBO J. 16, 3207-3218 (1997)).
AAN32899 NCBI acc. No. AAN32899 (gi: 23452024) (Oct. 2, 2002); Zhang,H., et al. "transcription factor TSRF1 [*Lycopersicon esculentum*]"; source: *Lycopersicon esculentum* (tomato); Title: "A tomato transcription factor regulating expression of stress responsive genes" (Unpublished).
BAC21532 NCBI acc. No. BAC21532 (gi: 24060081) (Oct. 16, 2002); Sasaki,T., et al. "putative ethylene response factor ERF1 [*Oryza sativa* (japonica cultivar-group)]"; source: *Oryza sativa* (japonica cultivar-group); Title: "*Oryza sativa* nipponbare(GA3) genomic DNA, chromosome 7, PAC clone:P0710F09" (Published Only in Database (2002)).
AAN77067 NCBI acc. No. AAN77067 (gi: 25992126) (Dec. 2, 2002); Cheng,X.G., et al. "ethylene responsive element binding protein [*Lycopersicon esculentum*]"; source: *Solanum lycopersicum* (*Lycopersicon esculentum*); Title: "Direct Submission" (Submitted (Apr. 13, 2002) Department of Biological Science and Biotechnology, Tsinghua University, Qinghua Yuan, Beijing 100084, China).
AAN87744 NCBI acc. No. AAN87744 (gi: 27261478) (Dec. 19, 2002); Wing,R.A., et al. "Hypothetical protein [*Oryza sativa* (japonica cultivar-group)]"; source: *Oryza sativa* (japonica cultivar-group); Title: "Rice Genomic Sequence" (Unpublished).
BAC55991 NCBI acc. No. BAC55991 (gi: 28071302) (Jan. 29, 2003); Sasaki,T., et al. "P0705A05.4 [*Oryza sativa* (japonica cultivar-group)]"; source: *Oryza sativa* (japonica cultivar-group); Title: "*Oryza sativa* nipponbare(GA3) genomic DNA, chromosome 8, PAC clone:P0705A05" (Published Only in Database (2002)).
BAA87068 NCBI acc. No. BAA87068 (gi: 6478845) (Nov. 30, 1999); Ashida,Y., et al. "ethylene-responsive element binding protein1 homolog [*Matricaria chamomilla*]"; source: *Matricaria chamomilla*; Title: "ethylene-responsive element binding protein1 (EREBP) homolog, *Matricaria chamomilla*" (Published Only in DataBase (1999) In press).
T07689 NCBI acc. No. T07689 (gi: 7489078) (Apr. 6, 2000); Zhou,J., et al. "transcription factor Pti5—tomato"; source: *Lycopersicon esculentum* (tomato); Title: "The Pto kinase conferring resistance to tomato bacterial speck disease interacts with proteins that bind a cis-element of pathogenesis-related genes" (EMBO J. 16 (11), 3207-3218 (1997)).

T02590 NCBI acc. No. T02590 (gi: 7489113) (Apr. 6, 2000); Ohme-Takagi,M., et al. "DNA binding protein EREBP-2—common tobacco"; source: *Nicotiana tabacum* (common tobacco); Title: "Ethylene-inducible DNA binding proteins that interact with an ethylene-responsive element" (Plant Cell 7 (2), 173-182 (1995)).

T03927 NCBI acc. No. T03927 (gi: 7489116) (Apr. 6, 2000); Xu,P., et al. "DNA binding protein S25-XP1—common tobacco"; source: *Nicotiana tabacum* (common tobacco); Title: "Direct Submission" (Submitted (??-Dec. 1996) to the EMBL Data Library).

AAF63205 NCBI acc. No. AAF63205 (gi: 7528276) (Apr. 9, 2000); Scharte,J., et al. "AP2-related transcription factor [*Mesembryanthemum crystallinum*]"; source: *Mesembryanthemum crystallinum* (common iceplant); Title: "A stress induced transcription factor of the AP2 gene family from the inducible CAM-plant *Mesembryanthemum crystallinum* L." (Unpublished).

O04681 NCBI acc. No. O04681 (gi: 7531180) (Apr. 10, 2000); Zhou,J., et al. "Pathogenesis-Related Genes Transcriptional Activator PTI5"; source: *Lycopersicon esculentum* (tomato); Title: "The Pto kinase conferring resistance to tomato bacterial speck disease interacts with proteins that bind a cis-element of pathogenesis-related genes" (EMBO J. 16 (11), 3207-3218 (1997)).

BAA97122 NCBI acc. No. BAA97122 (gi: 8809571) (Jun. 28, 2000); Kitajima,S., et al. "ethylene-responsive element binding factor [*Nicotiana sylvestris*]"; source: *Nicotiana sylvestris* (wood tobacco); Title: "Characterization of gene expression of NsERFs, transcription factors of basic PR genes from *Nicotiana sylvestris*" (Plant Cell Physiol. 41, 817-824 (2000)).

CAB96899 NCBI acc. No. CAB96899 (gi: 8980313) (Jul. 8, 2000); Van Der Fits,L., et al. "AP2-domain DNA-binding protein [*Catharanthus roseus*]"; source: *Catharanthus roseus* (*Madagascar periwinkle*); Title: "ORCA3, a jasmonate-responsive master regulator of multiple genes in plant primary and secondary metabolism" (Unpublished).

CAB96900 NCBI acc. No. CAB96900 (gi: 8980315) (Jul. 8, 2000); Van Der Fits,L., et al. "AP2-domain DNA-binding protein [*Catharanthus roseus*]"; source: *Catharanthus roseus* (*Madagascar periwinkle*); Title: "ORCA3, a jasmonate-responsive master regulator of multiple genes in plant primary and secondary metabolism" (Unpublished).

AAB70439 NCBI acc. No. AAB70439 (gi: 1903358) (Mar. 21, 1997); Van Den Fits,L., et al. "F19P19.18 [*Arabidopsis thaliana*]"; source: *Arabidopsis thaliana* (thale cress); Title: "Sequence of BAC F19P19 from *Arabidopsis thaliana* chromosome 1" (Unpublished (1997)).

AC000104 CBI acc. No. AC000104 (gi: 1764158) (Jan. 6, 1997); Vysotskaia,V., et al. "*Arabidopsis thaliana* chromosome 1, * Sequencing in Progress *"; source: *Arabidopsis thaliana* (thale cress); Title: "Sequence of BAC F19P19 from *Arabidopsis thaliana* chromosome 1" (Unpublished (1997)).

AB025608 CBI acc. No. AB025608 (gi: 4589414) (Apr. 20, 1999); Nakamura,Y., et al. "*Arabidopsis thaliana* genomic DNA, chromosome 3, TAC clone: K13B15, complete sequence"; source: *Arabidopsis thaliana* (thale cress); Title: "Structural Analysis of *Arabidopsis thaliana* Chromosome 3. II" (Unpublished (1999)).

AB025638 NCBI acc. No. AB025638 (gi: 4589444) (Apr. 20, 1999); Nakamura,Y., et al. "*Arabidopsis thaliana* genomic DNA, chromosome 5, P1 clone: MWF20, complete sequence"; source: *Arabidopsis thaliana* (thale cress); Title: "Structural Analysis of *Arabidopsis thaliana* Chromosome 5. XIII" (Unpublished (1999)).

CC669146 NCBI acc. No. CC669146 (gi: 32073332) (Jun. 19, 2003); Whitelaw,C.A., et al. "OGUBT28TV ZM_0.7_1.5_KB *Zea mays* genomic clone ZMMBMa0403E08, genomic survey sequence"; source: *Zea mays*; Title: "Consortium for Maize Genomics" (Unpublished (2002)).

BT009060 NCBI acc. No. BT009060 (gi: 32128611) (Jun. 20, 2003); Tingey,S.V., et al. "*Triticum aestivum* clone wdr1f.pk003.I5:fis, full insert mRNA sequence"; source: *Triticum aestivum* (bread wheat); Title: "Direct Submission"; (Submitted (Jun. 20, 2003) Crop Genetics, E. I. DuPont de Nemours and Company, 1 Innovation Way, P.O. Box 6104, Newark, DE 19714-6104, USA).

AK107745 NCBI acc. No. AK107745 (gi: 32992954) (Jul. 19, 2003); Kikuchi,S., et al. "*Oryza sativa* (japonica cultivar-group) cDNA clone:002-132-H03, full insert sequence"; source: *Oryza sativa* (japonica cultivar-group); Title: "Rice full-length cDNA" (Unpublished).

CG262446 NCBI acc. No. CG262446 (gi: 34174058) (Aug. 25, 2003); Whitelaw,C.A., et al. "OGWGY72TH. ZM_0.7_1.5_KB *Zea mays* genomic clone ZMMBMa0576K23, genomic survey sequence"; source: *Zea mays*; Title: "Consortium for Maize Genomics" (Unpublished (2002)).

CB967722 NCBI acc. No. CB967722 (gi: 30229857) (Apr. 29, 2003); Kirst,M., et al. "egx20b12_F Differentiating xylem *Eucalyptus* grandis cDNA clone egx20b12 5, mRNA sequence"; source: *Eucalyptus* grandis; Title: "Gene Discovery in *Eucalyptus* grandis Xylem" (Unpublished (2003)).

CC690315 NCBI acc. No. CC690315 (gi: 32095091) (Jun. 19, 2003); Whitelaw, C.A., et al. "OGVBI92TV ZM_0.7_1.5_KB *Zea mays* genomic clone ZMMBMa0495P15, genomic survey sequence"; source: *Zea mays*; Title: "Consortium for Maize Genomics" (Unpublished (2002)).

CAE45639 NCBI acc. No. CAE45639 (gi: 34221729) (Aug. 25, 2003); Gong,W., et al. "putative ethylene responsive element binding protein [*Arabidopsis thaliana*]"; source: *Arabidopsis thaliana* (thale cress); Title: "*Arabidopsis thaliana* putative ethylene responsive element binding protein, similar to the At3g23230 protein encoded by chromosome 3" (Unpublished).

BAA95735 NCBI acc. No. BAA95735 (gi: 7939532) (May 19, 2000); Nakamura,Y., et al. "contains similarity to ethylene response element binding protein EREBP~gene_id:K14B15.13 [*Arabidopsis thaliana*]"; source: *Arabidopsis thaliana* (thale cress); Title: "Structural Analysis of *Arabidopsis thaliana* Chromosome 3. II" (Unpublished (1999)).

AJ580377 EMBL acc. No. AJ580377 (Aug. 24, 2003); Gong W., et al. "*Arabidopsis thaliana* mRNA for putative ethylene responsive element binding protein".

AB008103 EMBL acc. No. AB008103 (Aug. 21, 1998); " *Arabidopsis thaliana* AtERF-1 mRNA for ethylene responsive element binding factor 1, complete cds".

O80337 EMBL acc. No. O80337 (May 30, 2000); "Ethylene responsive element bnding factor 1 (AtERF1) (EREBP-2 proteion)".

AB008104 EMBL acc. No. AB008104 (Aug. 21, 1998); "*Arabidopsis thaliana* AtERF-2 mRNA for ethylene responsive element binding factor 2, complete cds".

AL161546 EMBL acc. No. AL161546 (Mar. 16, 2000); "*Arabidopsis thaliana* DNA chromosome 4, contig fragment No. 46".

AJ307662 (Locus OSA307662) *Oryza sativa* genomic DNA fragment, chromosome 2 (May 15, 2001).

AI776626 EMBL acc. No. AB025608 (Jun. 30, 1999); "EST257726 tomato resistant, Cornell *Lycopersicon esculentum* cDNA clone cLER19A14, mRNA sequence".

AF245119 EMBL acc. No. AF245119 (Apr. 9, 2000); "*Mesembryanthemum crystallinum* AP2-related transciprtion factor (CDBP) mRNA, complete cds".

Allen, M.D., et al. (1998). A novel mode of DNA recognition by a beta-sheet revealed by the solution structure of the GCC-box binding domain in complex with DNA. Embo J 17, 5484-5496.

Ashida, et al. (2002); Molecular cloning and mRNA expression of geraniol-inducible genes in cultured soot primordia of *Matricaria chamomilla*. Biosci. Biotechnol. Biochem. 66 (11), 2511-2514.

Berrocal-Lobo, M., and Molina, A. (Jul. 2004). Ethylene response factor 1 mediates *Arabidopsis* resistance to the soilborne fungus *Fusarium oxysporum*. Mol Plant Microbe Interact 17, 763-770.

Brown, R.L., et al. (2003). A role for the GCC-box in jasmonate-mediated activation of the PDF1.2 gene of *Arabidopsis*. Plant Physiol 132, 1020-1032.

Campbell, et al. (1998) Isolation of a cDNA from potato with structural similarity to the AP2 gene superfamily (Accession No. U77655) (PGR98-129). Plant Physiol. 117 (3), 1127 (1998).

Chakravarthy, S., et al. (2003). The tomato transcription factor Pti4 regulates defense-related gene expression via GCC box and non-GCC box cis elements. Plant Cell 15, 3033-3050.

Chen, W., et al. (2002). Expression profile matrix of *Arabidopsis* transcription factor genes suggests their putative functions in response to environmental stresses. Plant Cell 14, 559-574.

Da Costa E Silva et al. (Jul. 1993) BPF-1, A pathogen-induced DNA-binding protein involved in the plant defense response. Plant J. 4:125-135.

Fujimoto, et al. (Mar. 2000). *Arabidopsis* ethylene-responsive element binding factors act as transcriptional activators or repressors of GCC box-mediated gene expression. Plant Cell (2000), 12(3), 393-404.

Guo, H., and Ecker, J.R. (Feb. 2004). The ethylene signaling pathway: new insights. Curr Opin Plant Biol 7, 40-49.

Guo, Z.J., et al. (Jul. 2004). Overexpression of the AP2/EREBP transcription factor OPBP1 enhances disease resistance and salt tolerance in tobacco. Plant Mol Biol 55, 607-618.

Hao, D., et al. (1998). Unique mode of GCC box recognition by the DNA-binding domain of ethylene-responsive element-binding factor (ERF domain) in plant. J Biol Chem 273, 26857-26861.

Hao, D., et al. (2002). Determinants in the sequence specific binding of two plant transcription factors, CBF1 and NtERF2, to the DRE and GCC motifs. Biochemistry 41, 4202-4208.

He, P., et al. (2001). Overexpression of PtiS in tomato potentiates pathogen-induced defense gene expression and enhances disease resistance to *Pseudomonas syringae* pv. tomato. Mol Plant Microbe Interact 14, 1453-1457.

Kitajima, Sakihito et al (Jun. 2000) "Characterization of gene expression of NsERFs, transcription factors of basic PR genes from *Nicotiana sylvestris*" Plant and Cell Physiology, vol. 41, No. 6, pp. 817-824.

Lee, J.H., et al. (May 2004). The ethylene-responsive factor like protein 1 (CaERFLP1) of hot pepper (*Capsicum annuum* L.) interacts in vitro with both GCC and DRE/CRT sequences with different binding affinities: possible biological roles of CaERFLP1 in response to pathogen infection and high salinity condi . . . Plant Mol Biol 55, 61-81.

Liu, Q., et al. (1998). Two transcription factors, DREB1 and DREB2, with an EREBP/AP2 DNA binding domain separate two cellular signal transduction pathways in drought- and low-temperature-responsive gene expression, respectively, in *Arabidopsis*. Plant Cell 10, 1391-1406.

Lorenzo, O., et al. (2003). Ethylene Response Factor1 integrates signals from ethylene and jasmonate pathways in plant defense. Plant Cell 15, 165-178.

Mazarei, et al. (Jun. 2002) Identification and characterization of a soybean ethylene-responsive element-binding protein gene whose mRNA expression changes during soybean cyst nematode infection. Mol. Plant Microbe Interact. 15(6):577-86.

Menke, et al. (1999) A novel jasmonate-and elicitor-responsive element in the periwinkle secondary metabolite biosynthetic gene Str interacts with a jasmonate-and elicitor-inducible AP2-domain transcription factor, ORCA2. Embo J. 18 (16), 4455-4463.

Ohme-Takagi, M., and Shinshi, H. (1995). Ethylene-inducible DNA binding proteins that interact with an ethylene-responsive element. Plant Cell 7, 173-182.

Ohta, et al. (2001) Repression domains of class II ERF transcriptional repressors share an essential motif for active repression. Plant Cell 13 (8), 1959-1968.

Okamuro et al. (Jun. 24, 1997). The AP2 domain of APETALA2 defines a large new family of NA binding proteins in *Arabidopsis*. Proc. Natl Acad Sci USA (1997), 94(13), 7076-7081.

Onate-Sanchez, L., and Singh, K.B. (2002). Identification of *Arabidopsis* ethylene-responsive element binding factors with distinct induction kinetics after pathogen infection. Plant Physiol 128, 1313-1322.

Riechmann, J.L., et al. (2000). *Arabidopsis* transcription factors: genome-wide comparative analysis among eukaryotes. Science 290, 2105-2110.

Riechmann, J.L., and Meyerowitz, E.M. (June 1998). The AP2/EREBP family of plant transcription factors. Biol. Chem 379, 633-646.

Sakuma, Y., et al. (2002). DNA-binding specificity of the ERF/AP2 domain of *Arabidopsis* DREBs, transcription factors involved in dehydration- and cold-inducible gene expression. Biochem Biophys Res Commun 290, 998-1009.

Solano, et al. (Dec. 1, 1998). Nuclear events in ethylene signaling: a transcriptional cascade mediated by Ethylene-Insensitive3 and Ethylene-Response-Factor1. Genes & Development (1998), 12(23), 3703-3714.

Suzuki, et al. (1998). Immediate early induction of mRNAs for ethylene-responsive transcription factors in tobacco leaf strips after cutting. Plant Journal vol. 15, No. 5, 1998, pp. 657-665.

Tao, Y., et al. (2003). Quantitative nature of *Arabidopsis* responses during compatible and incompatible interactions with the bacterial pathogen *Pseudomonas syringae*. Plant Cell 15, 317-330.

Van Der Fits, L. and Memelink, J. (2000) ORCA3, a jasmonate-responsive transcriptional regulator of plant primary and secondary metabolism. Science 289 (5477), 295-297 (2000).

Van Der Fits, et al. (Jan. 2001). The jasmonate-inducible AP2/ERF-domain transcription factor ORCA3 activates gene expression via interaction with a jasmonate-responsive promoter element. Plant Journal (2001), 25(1), 43-53.

Xu, et al. (Nov. 1998). A nitrilase-like protein interacts with GCC box DNA-binding proteins involved in ethylene and defense responses. Plant Physiology (1998), 118(3), 867-874.

Zhang, et al. (Aug. 2004). Tomato stress-responsive factor TSRF1 interacts with ethylene responsive element GCC box and regulates pathogen resistance to *Ralstonia solanacearum*. Plant Mol. Biol. 55 (6), 825-834.

Zhou, J., et al. (1997). The Pto kinase conferring resistance to tomato bacterial speck disease interacts with proteins that bind a cis-element of pathogenesis-related genes. Embo J 16, 3207-3218.

Daly et al. (Dec. 2001). Plant Systematics in the Age of Genomics. Plant Physiology 127:1328-1333.

Ainley, et al. (1993) Regulatable endogenous production of cytokinins up to 'toxic' levels in transgenic plants and plant issues. Plant Mol Biol. Apr. 1993;22(1):13-23.

Allona, et al. (Aug. 4, 1998); Analysis of xylem formation in pine by cDNA sequencing. Proc. Natl. Acad. Sci. U.S.A. 95 (16), 9693-9698.

An, et al. Organ-Specific and Developmental Regulation of the Nopaline Synthase Promoter in Transgenic Tobacco Plants. Plant Physiol. Nov. 1988;88(3):547-552.

Aoyama, et al. (1995) Ectopic expression of the *Arabidopsis* transcriptional activator Athb-1 alters leaf cell fate in tobacco. Plant Cell. Nov. 1995;7(11):1773-85.

Wu, et al. (1995) Heat shock transcription factors: structure and regulation. Annu Rev Cell Dev Biol. 1995;11:441-69.

Xu, P., Ling, J. Q. Li, D. B. (1998). Identification of a novel DNA-binding protein to osmotin promoter, Science in China, Ser. C, 1998, 41: 657-663.

Yanagisawa, Shuichi et al: "Metabolic engineering with Dof1 transcription factor in plants: Improved nitrogen assimilation and growth under low-nitrogen conditions" PNAS of the USA, vol. 101, No. 20, May 18, 2004, pp. 7833-7838.

Yi, et al. (2004). The Pepper Transcription Factor CaPF1 Confers Pathogen and Freezing Tolerance in *Arabidopsis*. Plant Physiol. Sep. 2004;136(1):2862-74. Epub Sep. 3, 2004.

Yu, J., et al. (Feb. 2005). The Genomes of *Oryza sativa*: A History of Duplications. PloS Biol. 3 (2) E38.

Zhang, et al. (Oct. 2004). Large-scale analysis of the barley transcriptome based on expressed sequence tags Plant J. 40 (2), 276-290.

Zhang et al., Expression of Antisense or Sense RNA of an Ankyrin Repeat-Containing Gene . . . , The Plant Cell (Dec. 1992) 4:1575-1588.

Zhou et al. (1995) Molecular cloning of a small DNA binding protein with specificity for a tissue-specific negative element within the rps1 promoter. Nucleic Acids Res. 23:1165-1169.

Gu et al. (2002) Tomato Transcription Factors Pti4, PtiS, and Pti6 Activate Defense Responses When Expressed in *Arabidopsis*. Plant Cell 14: 817-831.

Kranz H.D. et al.: 'Towards functional characterisation of the members of the R2R3-MYB gene family from *Arabidopsis thaliana*' The Plant Journal vol. 16, No. 2, 1998, pp. 263-276, XP002937951.

U.S. Appl. No. 10/155,881, filed May 22, 2002, Kovalic, et al.
AB016264 NCBI acc. No. AB016264 (gi: 8809570) (Jun. 28, 2000); Kitajima,S., et al. "*Nicotiana sylvestris* nserf2 gene for ethylene-responsive element binding factor, complete cds"; source: *Nicotiana sylvestris* wood tobacco); Title: "Characterization of gene expression of NsERFs, transcription factors of basic PR genes from *Nicotiana sylvestris*" (Plant Cell Physiol. 41, 817-824 (2000)).
AB035270 NCBI acc. No. AB035270 (gi: 6478844) (Nov. 30, 1999); Ashida,Y., et al. "*Matricaria chamomilla* McEREBP1 mRNA for ethylene-responsive element binding protein1 homolog, partial cds"; source: *Matricaria chamomilla*; Title: "ethylene-responsive element binding protein1 (EREBP) homolog, *Matricaria chamomilla*" (Published Only in DataBase (1999) In press).
NCBI acc. No. AB025608 (gi: 4589414) (Apr. 20, 1999); Nakamura,Y., et al. "*Arabidopsis thaliana* genomic DNA, chromosome 3, TAC clone: K13B15, complete sequence"; source: *Arabidopsis thaliana* (thale cress); Title: "Structural Analysis of *Arabidopsis thaliana* Chromosome 3. II" (Unpublished (1999)).
AF211527 NCBI acc. No. AF211527 (gi: 12003375) (Jan. 2, 2001); Durrant, W.E., et al. "*Nicotiana tabacum* Avr9/Cf-9 rapidly elicited protein 1 (ACRE1) mRNA, complete cds"; source: *Nicotiana tabacum* (common tobacco); Title: "cDNA expression profiling reveals rapid, resistance gene-dependent, active oxygen-independent, gene induction during the plant defense response" (Unpublished).
AF245119 NCBI acc. No. AF245119 (gi: 7528275) (Apr. 9, 2000); Scharte,J., et al. "*Mesembryanthemum crystallinum* AP2-related transcription factor (CDBP) mRNA, complete cds"; source: *Mesembryanthemum crystallinum* (common iceplant); Title: "A stress induced transcription factor of the AP2 gene family from the inducible CAM-plant *Mesembryanthemum crystallinum* L." (Unpublished).
AF502085 NCBI acc. No. AF502085 (gi: 25992125) (Dec. 2, 2002); Cheng, X.G., et al. "*Lycopersicon esculentum* ethylene responsive element binding protein (EREB) mRNA, complete cds"; source: *Solanum lycopersicum* (*Lycopersicon esculentum*); Title: "Direct Submission" (Submitted (Apr. 13, 2002) Department of Biological Science and Biotechnology, Tsinghua University, Qinghua Yuan, Beijing 100084, China).
AI442716 NCBI acc. No. AI442716 (gi: 4298124) (Feb. 19, 1999); Shoemaker,R., et al. "sa85d10.y1 Gm-c1004 *Glycine max* cDNA clone Genome Systems Clone ID: Gm-c1004-6092 5&apos similar to TR:O04680 O04680 PTI4. ;, mRNA sequence"; source: *Glycine max* (soybean); Title: "Public Soybean EST Project" (Unpublished (1999)).
AI495036 NCBI acc. No. AI495036 (gi: 4396039) (Mar. 11, 1999); Shoemaker,R., et al. "sa90a09.y1 Gm-c1004 *Glycine max* cDNA clone Genome Systems Clone ID: Gm-c1004-6545 5' similar to TR:O22167 O22167 EREBP ISOLOG. ;, mRNA sequence"; source: *Glycine max* (soybean); Title: "Public Soybean EST Project" (Unpublished (1999)).
AI775562 NCBI acc. No. AI775562 (gi: 5273603) (Jun. 29, 1999); D' Ascenzo,M., et al. "EST256662 tomato resistant, Cornell *Solanum lycopersicum* cDNA clone cLER15L16, mRNA sequence"; source: *Solanum lycopersicum* (*Lycopersicon esculentum*); Title: "Generation of ESTs from Pseudomonas resistant tomato" (Unpublished (1999)).
AI776626 NCBI acc. No. AI776626 (gi: 5274667) (Jun. 29, 1999); D' Ascenzo,M., et al. "EST257726 tomato resistant, Cornell *Solanum lycopersicum* cDNA clone cLER19A14, mRNA sequence"; source: *Solanum lycopersicum* (*Lycopersicon esculentum*); Title: "Generation of ESTs from Pseudomonas resistant tomato" (Unpublished (1999)).
AI778498 NCBI acc. No. AI778498 (gi: 5276539) (Jun. 29, 1999); D' Ascenzo,M., et al. "EST259377 tomato susceptible, Cornell *Solanum lycopersicum* cDNA clone cLES5D19, mRNA sequence"; source: *Solanum lycopersicum* (*Lycopersicon esculentum*); Title: "Generation of ESTs from Pseudomonas susceptible tomato" (Unpublished (1999)).
AI778693 NCBI acc. No. AI778693 (gi: 5276734) (Jun. 29, 1999); D' Ascenzo,M., et al. "EST259572 tomato susceptible, Cornell *Solanum lycopersicum* cDNA clone cLES6I9, mRNA sequence"; source: *Solanum lycopersicum lycopersicum* (*Lycopersicon esculentum*); Title: "Generation of ESTs from Pseudomonas susceptible tomato" (Unpublished (1999)).
AI779791 NCBI acc. No. AI779791 (gi: 5277832) (Jun. 29, 1999); D' Ascenzo,M., et al. "EST260670 tomato susceptible, Cornell *Solanum lycopersicum* cDNA clone cLES9K15, mRNA sequence"; source: *Solanum lycopersicum* (*Lycopersicon esculentum*); Title: "Generation of ESTs from Pseudomonas susceptible tomato" (Unpublished (1999)).
AI780258 NCBI acc. No. AI780258 (gi: 5278299) (Jun. 29, 1999); D' Ascenzo,M., et al. "EST261137 tomato susceptible, Cornell *Solanum lycopersicum* cDNA clone cLES11B13, mRNA sequence"; source: *Solanum lycopersicum* (*Lycopersicon esculentum*); Title: "Generation of ESTs from Pseudomonas susceptible tomato" (Unpublished (1999)).
AI782381 NCBI acc. No. AI782381 (gi: 5280422) (Jun. 29, 1999); D' Ascenzo,M., et al. "EST263260 tomato susceptible, Cornell *Solanum lycopersicum* cDNA clone cLES18P16, mRNA sequence"; source: *Solanum lycopersicum* (*Lycopersicon esculentum*); Title: "Generation of ESTs from Pseudomonas susceptible tomato" (Unpublished (1999)).
AI794657 NCBI acc. No. AI794657 (gi: 5342373) (Jul. 2, 1999); Shoemaker,R., et al. "sb67b03.y1 Gm-c1019 *Glycine max* cDNA clone Genome Systems Clone ID: Gm-c1019-6 5' sililar to TR:Q40478 Q40478 EREBP-4. ;, mRNA sequence"; source: *Glycine max* (soybean); Title: "Public Soybean EST Project" (Unpublished (1999)).
AI855585 NCBI acc. No. AI855585 (gi: 5509027) (Jul. 16, 1999); Shoemaker,R., et al. "sc28b12.y1 Gm-c1014 *Glycine max* cDNA clone Genome Systems Clone ID: Gm-c1014-408 5&pos; similar to TR:O81365 O81365 AP2 Domain Containing Protein ;, mRNA sequence"; source: *Glycine max* (soybean); Title: "Public Soybean EST Project" (Unpublished (1999)).
AI899889 NCBI acc. No. AI899889 (gi: 5605791) (Jul. 27, 1999); Shoemaker,R., et al. "sb94g05.y1 Gm-c1017 *Glycine max* cDNA clone Genome Systems Clone ID: Gm-c1017-1137 5&pos; similar to TR:Q40478 Q40478 EREBP-4. ;, mRNA sequence"; source: *Glycine max* (soybean); Title: "Public Soybean EST Project" (Unpublished (1999)).
AI965917 NCBI acc. No. AI965917 (gi: 5760554) (Aug. 23, 1999); Shoemaker,R., et al. "sc79f12.y1 Gm-c1018 *Glycine max* cDNA clone Genome Systems Clone ID: Gm-c1018-1128 5&pos; similar to TR:O80341 O80341 Ethylene Responsive Element Binding Factor 5. ;, mRNA sequence"; source: *Glycine max* (soybean); Title: "Public Soybean EST Project" (Unpublished (1999)).
AI966369 NCBI acc. No. AI966369 (gi: 5761006) (Aug. 23, 1999); Shoemaker,R., et al. "sc37h09.y1 Gm-c1014 *Glycine max* cDNA clone Genome Systems Clone ID: Gm-c1014-1338 5&pos; similar to TR:O81365 O81365 AP2 Domain Containing Protein ;, mRNA sequence"; source: *Glycine max*(soybean); Title: "Public Soybean EST Project" (Unpublished (1999)).
AI966559 NCBI acc. No. AI966559 (gi: 5761196) (Aug. 23, 1999); Shoemaker,R., et al. "sc52a04.y1 Gm-c1015 *Glycine max* cDNA clone Genome Systems Clone ID: Gm-c1015-1159 5&pos; similar to TR:O23591 O23591 EREBP-4 Homolog. ;, mRNA sequence"; source: *Glycine max* (soybean); Title: "Public Soybean EST Project" (Unpublished (1999)).
AI967551 NCBI acc. No. AI967551 (gi: 5762854) (Aug. 24, 1999); Poulsen,C., et al. "Ljirnpest05-400-d11 Ljirnp Lambda HybriZap two-hybrid library *Lotus japonicus* cDNA clone LP400-05-d11 5&pos; similar to ethylene response factor 1, mRNA sequence"; source: *Lotus japonicus*; Title: "Expressed sequence tags from *Mesorhizobium loti* infected roots of *Lotus japonicus*" (Unpublished (1999)).
AI973653 NCBI acc. No. AI973653 (gi: 5770479) (Aug. 25, 1999); Shoemaker,R., et al. "sd07h05.y1 Gm-c1020 *Glycine max* cDNA clone Genome Systems Clone ID: Gm-c1020-1042 5&pos; similar to TR:O22167 O22167 EREBP ISOLOG. ;, mRNA sequence"; source: *Glycine max* (soybean); Title: "Public Soybean EST Project" (Unpublished (1999)).
AJ503278 NCBI acc. No. AJ503278 (gi: 22084206) (Aug. 1, 2002); Manthey,K., et al. "*Medicago truncatula* EST, clone mtgmadc120032c02"; source: *Medicago truncatula*; Title: "Detection of transcript sequences from mycorrhizal roots of the model mycorrhiza *Medicago truncatula* genotype A17 - *Glomus mosseae* using the approach of an EST genome project" (Unpublished).
AL750652 NCBI acc. No. AL750652 (gi: 21491890) (Jun. 20, 2002); Frigerio,J., et al. "AL750652 RN *Pinus pinaster* cDNA clone RN05H01 similar to Ethylene Responsive Element Binding Factor, mRNA sequence"; source: *Pinus pinaster*; Title: "Identification of water-deficit responsive genes in Maritime pine (*Pinus pinaster* Ait.) using an EST approach" (Unpublished (2002)).
AP003237 NCBI acc. No. AP003237 (gi: 13027267) (Feb. 21, 2001); Sasaki,T., et al. "*Oryza sativa* chromosome 1 clone P0046E05, * Sequencing in Progress *"; source: *Oryza sativa*; Title: "*Oryza sativa* nipponbare(GA3) genomic DNA, chromosome 1, PAC clone:P0046E05" (Published Only in DataBase (2001) In press).
AP003249 NCBI acc. No. AP003249 (gi: 13027279) (Feb. 21, 2001); Sasaki,T., et al. "*Oryza sativa* chromosome 1 clone P0435B05, * Sequencing in Progress *"; source: *Oryza sativa*; Title: "*Oryza sativa* nipponbare(GA3) genomic DNA, chromosome 1, PAC clone:P0435B05" (Published Only in DataBase (2001) In press).
AP003286 NCBI acc. No. AP003286 (gi: 13027316) (Feb. 21, 2001); Sasaki,T., et al. "*Oryza sativa* chromosome 1 clone P0677H08, * Sequencing in Progress  "; source: *Oryza sativa* ; Title: "*Oryza sativa* nipponbare(GA3) genomic DNA, chromosome 1, PAC clone:P0677H08" (Published Only in DataBase (2001) In press).
AP003294 NCBI acc. No. AP003294 (gi: 13027324) (Feb. 21, 2001); Sasaki,T., et al. "*Oryza sativa* chromosome 1 clone P0694A04, * Sequencing in Progress *"; source: *Oryza sativa* ; Title: "*Oryza sativa* nipponbare(GA3) genomic DNA, chromosome 1, PAC clone:P0694A04" (Published Only in DataBase (2001) In press).
AP003820 NCBI acc. No. AP003820 (gi: 14595160) (Jul. 3, 2001); Sasaki,T., et al. "*Oryza sativa* chromosome 7 clone OJ1235__H07, * Sequencing in Progress *"; source: *Oryza sativa* ; Title: "*Oryza sativa* nipponbare(GA3) genomic DNA, chromosome 7, BAC clone:OJ1235__H07" (Published Only in Database (2001) In press).
AP003891 NCBI acc. No. AP003891 (gi: 14646849) (Jul. 9, 2001); Sasaki,T., et al. "*Oryza sativa* chromosome 8 clone OJ1314__F06, * Sequencing in Progress *"; source: *Oryza sativa*; Title: "*Oryza sativa* nipponbare(GA3) genomic DNA, chromosome 8, BAC clone:OJ1314__F06" (Published Only in Database (2001) In press).
AP004122 NCBI acc. No. AP004122 (gi: 15375108) (Aug. 29, 2001); Sasaki,T., et al. "*Oryza sativa* chromosome 2 clone OJ1616__E07, * Sequencing in Progress *"; source: *Oryza sativa*; Title: "*Oryza sativa* nipponbare(GA3) genomic DNA, chromosome 2, BAC clone:OJ1616__E07" (Published Only in Database (2001) In press).
AP004533 NCBI acc. No. AP004533 (gi: 17736900) (Dec. 13, 2001); Sato,S., et al. "*Lotus japonicus* genomic DNA, chromosome 3, clone:LjT14G02, TM0080, complete sequence"; source: *Lotus japonicus*; Title: "Structural Analysis of a *Lotus japonicus* Genome. I. Sequence Features and Mapping of Fifty-six TAC clones which cover the 5.4 Mb Regions of the Genome" (Unpublished).
AP004676 NCBI acc. No. AP004676 (gi: 18447935) (Jan. 30, 2002); Sasaki,T., et al. "*Oryza sativa* chromosome 2 clone OJ1003__B06, * Sequencing in Progress *"; source: *Oryza sativa*; Title: "*Oryza sativa* nipponbare(GA3) genomic DNA, chromosome 2, BAC clone:OJ1003__B06" (Published Only in Database (2002)).
AP005006 NCBI acc. No. AP005006 (gi: 19773546) (Mar. 27, 2002); Sasaki,T., et al. "*Oryza sativa* (japonica cultivar-group) chromosome 2 clone P0519E06, * Sequencing in Progress *"; source: *Oryza sativa* (japonica cultivar-group); Title: "*Oryza sativa* nipponbare(GA3) genomic DNA, chromosome 2, PAC clone:P0519E06" (Published Only in Database (2002)).
AP006162 NCBI acc. No. AP006162 (gi: 27884274) (Jan. 23, 2003); Sasaki,T., et al. "*Oryza sativa* (japonica cultivar-group) chromosome 9 clone B1331F11, * Sequencing in Progress *"; source: *Oryza sativa* (japonica cultivar-group); Title: "*Oryza sativa* nipponbare(GA3) genomic DNA, chromosome 9, BAC clone:B1331F11" (Published Only in Database (2003)).
AV407462 NCBI acc. No. AV407462 (gi: 7720316) (May 8, 2000); Asamizu,E., et al. "AV407462 *Lotus japonicus* young plants (two-week old) *Lotus japonicus* cDNA clone MWL024d04__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV417624 NCBI acc. No. AV417624 (gi: 7746802) (May 9, 2000); Asamizu,E., et al. "AV417624 *Lotus japonicus* young plants (two-week old) *Lotus japonicus* cDNA clone MWM146e09__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV421566 NCBI acc. No. AV421566 (gi: 7775366) (May 12, 2000); Asamizu,E., et al. "AV421566 *Lotus japonicus* young plants (two-week old) *Lotus japonicus* cDNA clone MWM196a01__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV422393 NCBI acc. No. AV422393 (gi: 7777209) (May 12, 2000); Asamizu,E., et al. "AV422393 *Lotus japonicus* young plants (two-week old) *Lotus japonicus* cDNA clone MWM012d12__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV422603 NCBI acc. No. AV422603 (gi: 7777670) (May 12, 2000); Asamizu,E., et al. "AV422603 *Lotus japonicus* young plants (two-week old) *Lotus japonicus* cDNA clone MWM015a04__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV423260 NCBI acc. No. AV423260 (gi: 7778996) (May 12, 2000); Asamizu,E., et al. "AV423260 *Lotus japonicus* young plants (two-week old) *Lotus japonicus* cDNA clone MWM024b09__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV425560 NCBI acc. No. AV425560 (gi: 7783624) (May 12, 2000); Asamizu,E., et al. "AV425560 *Lotus japonicus* young plants (two-week old) *Lotus japonicus* cDNA clone MWM055f07__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV425829 NCBI acc. No. AV425829 (gi: 7784155) (May 12, 2000); Asamizu,E., et al. "AV425829 *Lotus japonicus* young plants (two-week old) *Lotus japonicus* cDNA clone MWM059g11__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV426605 NCBI acc. No. AV426605 (gi: 7785709) (May 12, 2000); Asamizu,E., et al. "AV426605 *Lotus japonicus* young plants (two-week old) *Lotus japonicus* cDNA clone MWM070e11__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AV428124 NCBI acc. No. AV428124 (gi: 7788764) (May 12, 2000); Asamizu,E., et al. "AV428124 *Lotus japonicus* young plants (two-week old) *Lotus japonicus* cDNA clone MWM092d01__r 5', mRNA sequence"; source: *Lotus japonicus*; Title: "Generation of 7137 non-redundant expressed sequence tags from a legume, *Lotus japonicus*" (DNA Res. 7 (2), 127-130 (2000)).
AW033743 NCBI acc. No. AW033743 (gi: 5892499) (Sep. 15, 1999); Alcala,J., et al. "EST277314 tomato callus, TAMU *Solanum lycopersicum* cDNA clone cLEC29G11 similar to AP2 domain-containing protein, putative, mRNA sequence"; source: *Solanum lycopersicum* (*Lycopersicon esculentum*); Title: "Generation of ESTs from tomato callus tissue" (Unpublished (1999)).
AW034216 NCBI acc. No. AW034216 (gi: 5892972) (Sep. 15, 1999); Alcala,J., et al. "EST277787 tomato callus, TAMU *Solanum lycopersicum* cDNA clone cLEC32P18 similar to Pti4, mRNA sequence"; source: *Solanum lycopersicum* (*Lycopersicon esculentum*); Title: "Generation of ESTs from tomato callus tissue" (Unpublished (1999)).
AW034241 NCBI acc. No. AW034241 (gi: 5892997) (Sep. 15, 1999); Alcala,J., et al. "EST277812 tomato callus, TAMU *Solanum lycopersicum* cDNA clone cLEC33C21 similar to DNA binding protein homolog, putative, mRNA sequence"; source: *Solanum* lycopersicum (Lycopersicon esculentum); Title: "Generation of ESTs from tomato callus tissue" (Unpublished (1999)).

AW035648 NCBI acc. No. AW035648 (gi: 5894404) (Sep. 15, 1999); Alcala,J., et al. "EST281480 tomato callus, TAMU Solanum lycopersicum cDNA clone cLEC34P21 similar to EREBP-3 homolog, putative, mRNA sequence"; source: Solanum lycopersicum (Lycopersicon esculentum); Title: "Generation of ESTs from tomato callus tissue" (Unpublished (1999)).

AW040234 NCBI acc. No. AW040234 (gi: 5898988) (Sep. 15, 1999); D'Ascenzo,M., et al. "EST282740 tomato mixed elicitor, BTI Solanum lycopersicum cDNA clone cLET19L2, mRNA sequence"; source: Solanum lycopersicum (Lycopersicon esculentum); Title: "Generation of ESTs from tomato leaf tissue" (Unpublished (1999)).

AW101483 NCBI acc. No. AW101483 (gi: 6072036) (Oct. 19, 1999); Shoemaker,R., et al. "sd78g09.y1 Gm-c1009 Glycine max cDNA clone Genome Systems Clone ID: Gm-c1009-569 5' similar to TR:O23107 O23107 AP2 Domain Containing Protein RAP2.5. [1] ;, mRNA sequence"; source: Glycine max (soybean); Title: "Public Soybean EST Project" (Unpublished (1999)).

AW156366 NCBI acc. No. AW156366 (gi: 6227767) (Nov. 4, 1999); Shoemaker,R., et al. "se25b08.y1 Gm-c1015 Glycine max cDNA clone Genome Systems Clone ID: Gm-c1015-2224 5' similar to TR:O23108 O23108 RAP2.6 ;, mRNA sequence"; source: Glycine max (soybean); Title: "Public Soybean EST Project" (Unpublished (1999)).

AW164527 NCBI acc. No. AW164527 (gi: 6341778) (Nov. 10, 1999); Shoemaker,R., et al. "se75a02.y1 Gm-c1023 Glycine max cDNA clone Genome Systems Clone ID: Gm-c1023-483 5' similar to TR:P93589 P93589 DNA Binding Protein Homolog. ;, mRNA sequence"; source: Glycine max (soybean); Title: "Public Soybean EST Project" (Unpublished (1999)).

AW185126 NCBI acc. No. AW185126 (gi: 6454443) (Nov. 19, 1999); Shoemaker,R., et al. "se87b08.y1 Gm-c1023 Glycine max cDNA clone Genome Systems Clone ID: Gm-c1023-1648 5' similar to TR:O23108 O23108 RAP2.6 ;, mRNA sequence"; source: Glycine max (soybean); Title: "Public Soybean EST Project" (Unpublished (1999)).

AW185128 NCBI acc. No. AW185128 (gi: 6454445) (Nov. 9, 1999); Shoemaker,R., et al. "se87b10.y1 Gm-c1023 Glycine max cDNA clone Genome Systems Clone ID: Gm-c1023-1652 5' similar to TR:O80341 O80341 Ethylene Responsive Element Binding Factor 5. ;, mRNA sequence"; source: Glycine max (soybean); Title: "Public Soybean EST Project" (Unpublished (1999)).

AW186005 NCBI acc. No. AW186005 (gi: 6455322) (Nov. 19, 1999); Shoemaker,R., et al. "se62d09.y1 Gm-c1019 Glycine max cDNA clone Genome Systems Clone ID: Gm-c1019-1578 5' similar to TR:O23107 O23107 AP2 Domain Containing Protein RAP2.5. [1] ;, mRNA sequence"; source: Glycine max (soybean); Title: "Public Soybean EST Project" (Unpublished (1999)).

AW200919 NCBI acc. No. AW200919 (gi: 6481648) (Nov. 30, 1999); Shoemaker,R., et al. "se95c12.y1 Gm-c1027 Glycine max cDNA clone Genome Systems Clone ID: Gm-c1027-527 5' similar to TR:O80341 O80341 Ethylene Responsive Element Binding Factor 5. ;, mRNA sequence"; source: Glycine max (soybean); Title: "Public Soybean EST Project" (Unpublished (1999)).

AW219198 NCBI acc. No. AW219198 (gi: 6530072) (Dec. 6, 1999); van der Hoeven,R.S., et al. "EST301680 tomato root during/after fruit set, Cornell University Solanum lycopersicum cDNA clone cLEX3G6, mRNA sequence"; source: Solanum lycopersicum (Lycopersicon esculentum); Title: "Generation of ESTs from tomato root tissue" (Unpublished (1999)).

AW220395 NCBI acc. No. AW220395 (gi: 6531269) (Dec. 6, 1999); van der Hoeven,R.S., et al. "EST302878 tomato root during/after fruit set, Cornell University Solanum lycopersicum cDNA clone cLEX10F20, mRNA sequence"; source: Solanum lycopersicum (Lycopersicon esculentum); Title: "Generation of ESTs from tomato root tissue" (Unpublished (1999)).

AW221854 NCBI acc. No. AW221854 (gi: 6533538) (Dec. 7, 1999); Alcala,J., et al. "EST298665 tomato fruit red ripe, TAMU Solanum lycopersicum cDNA clone cLEN4I21, mRNA sequence"; source: Solanum lycopersicum (Lycopersicon esculentum); Title: "Generation of ESTs from tomato fruit tissue" (Unpublished (1999)).

AW233956 NCBI acc. No. AW233956 (gi: 6566281) (Dec. 13, 1999); Shoemaker,R., et al. "sf32e02.y1 Gm-c1028 Glycine max cDNA clone Genome Systems Clone ID: Gm-c1028-1683 5' similar to TR:O80337 O80337 Ethylene Responsive Element Binding Factor 1. ;, mRNA sequence"; source: Glycine max (soybean); Title: "Public Soybean EST Project" (Unpublished (1999)).

AW234175 NCBI acc. No. AW234175 (gi: 6566532) (Dec. 13, 1999); Shoemaker,R., et al. "sf22b03.y1 Gm-c1028 Glycine max cDNA clone Genome Systems Clone ID: Gm-c1028-678 5 similar to TR:O81365 O81365 AP2 Domain Containing Protein ;, mRNA sequence"; source: Glycine max (soybean); Title: "Public Soybean EST Project" (Unpublished (1999)).

AW267756 NCBI acc. No. AW267756 (gi: 6654712) (Jan. 3, 2000); Fedorova,M., et al. "EST305884 DSIR Medicago truncatula cDNA clone pDSIR-701, mRNA sequence"; source: Medicago truncatula (barrel medic); Title: "ESTs from roots of Medicago truncatula after inoculation with Phytophthora medicaginis" (Unpublished (1999)).

AW267820 NCBI acc. No. AW267820 (gi: 6654776) (Jan. 3, 2000); Fedorova,M., et al. "EST305948 DSIR Medicago truncatula cDNA clone pDSIR-8M17, mRNA sequence"; source: Medicago truncatula (barrel medic); Title: "ESTs from roots of Medicago truncatula after inoculation with Phytophthora medicaginis" (Unpublished (1999)).

AW267914 NCBI acc. No. AW267914 (gi: 6654934) (Jan. 3, 2000); Fedorova,M., et al. "EST306256 DSIR Medicago truncatula cDNA clone pDSIR-8D12, mRNA sequence"; source: Medicago truncatula (barrel medic); Title: "ESTs from roots of Medicago truncatula after inoculation with Phytophthora medicaginis" (Unpublished (1999)).

AW278190 NCBI acc. No. AW278190 (gi: 6666731) (Jan. 4, 2000); Shoemaker,R., et al. "sf40g11.y1 Gm-c1009 Glycine max cDNA clone Genome Systems Clone ID: Gm-c1009-2493 5' similar to TR:Q40476 Q40476 ERF1. ;, mRNA sequence"; source: Glycine max (soybean); Title: "Public Soybean EST Project" (Unpublished (1999)).

AW308784 NCBI acc. No. AW308784 (gi: 6724385) (Jan. 21, 2000); Shoemaker,R., et al. "sf71h01.y1 Gm-c1013 Glycine max cDNA clone Genome Systems Clone ID: Gm-c1013-5066 5' similar to TR:P93822 P93822 F19P19.18. ;, mRNA sequence"; source: Glycine max (soybean); Title: "Public Soybean EST Project" (Unpublished (1999)).

AW396250 NCBI acc. No. AW396250 (gi: 6914720) (Feb. 7, 2000); Shoemaker,R., et al. "sh26c01.y1 Gm-c1016 Glycine max cDNA clone Genome Systems Clone ID: Gm-c1016-5881 5' similar to TR:O80341 O80341 Ethylene Responsive Element Binding Factor 5. ;, mRNA sequence"; source: Glycine max (soybean); Title: "Public Soybean EST Project" (Unpublished (1999)).

AW396612 NCBI acc. No. AW396612 (gi: 6915151) (Feb. 7, 2000); Shoemaker,R., et al. "sg80c07.y1 Gm-c1026 Glycine max cDNA clone Genome Systems Clone ID: Gm-c1026-37 5' similar to TR:O80339 O80339 Ethylene Responsive Element Binding Factor 3. ;, mRNA sequence"; source: Glycine max (soybean); Title: "Public Soybean EST Project" (Unpublished (1999)).

AW441715 NCBI acc. No. AW441715 (gi: 6976966) (Feb. 14, 2000); Alcala,J., et al. "EST311111 tomato fruit red ripe, TAMU Solanum lycopersicum cDNA clone cLEN18A16 5', mRNA sequence"; source: Solanum lycopersicum (Lycopersicon esculentum); Title: "Generation of ESTs from tomato fruit tissue" (Unpublished (1999)).

AW441775 NCBI acc. No. AW441775 (gi: 6977026) (Feb. 14, 2000); Alcala,J., et al. "EST311171 tomato fruit red ripe, TAMU Solanum lycopersicum cDNA clone cLEN18O18 5', mRNA sequence"; source: Solanum lycopersicum (Lycopersicon esculentum); Title: "Generation of ESTs from tomato fruit tissue" (Unpublished (1999)).

AW507860 NCBI acc. No. AW507860 (gi: 7145938) (Mar. 3, 2000); Shoemaker,R., et al. "si45h05.y1 Gm-r1030 Glycine max cDNA clone Genome Systems Clone ID: Gm-r1030-1906 5' similar to TR:Q40478 Q40478 EREBP-4. ;, mRNA sequence"; source: Glycine max (soybean); Title: "Public Soybean EST Project" (Unpublished (1999)).

AW507898 NCBI acc. No. AW507898 (gi: 7145976) (Mar. 3, 2000); Shoemaker,R., et al. "si46f03.y1 Gm-r1030 Glycine max cDNA clone Genome Systems Clone ID: Gm- r1030-1974 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

AW559315 NCBI acc. No. AW559315 (gi: 7204741) (Mar. 7, 2000); Fedorova,M., et al. "EST306358 DSIR *Medicago truncatula* cDNA clone pDSIR-2515, mRNA sequence"; source: *Medicago truncatula* (barrel medic); Title: "ESTs from roots of *Medicago truncatula* after inoculation with *Phytophthora medicaginis*" (Unpublished (1999)).

AW559374 NCBI acc. No. AW559374 (gi: 7204800) (Mar. 7, 2000); Fedorova,M., et al. "EST314422 DSIR *Medicago truncatula* cDNA clone pDSIR-7J9, mRNA sequence"; source: *Medicago truncatula* (barrel medic); Title: "ESTs from roots of *Medicago truncatula* after inoculation with *Phytophthora medicaginis*" (Unpublished (1999)).

AW559641 NCBI acc. No. AW559641 (gi: 7205131) (Mar. 7, 2000); Fedorova,M., et al. "EST314753 DSIR *Medicago truncatula* cDNA clone pDSIR-24B7, mRNA sequence"; source: *Medicago truncatula* (barrel medic); Title: "ESTs from roots of *Medicago truncatula* after inoculation with *Phytophthora medicaginis*" (Unpublished (1999)).

AW560134 NCBI acc. No. AW560134 (gi: 7205560) (Mar. 7, 2000); Fedorova,M., et al. "EST315182 DSIR *Medicago truncatula* cDNA clone pDSIR-26023, mRNA sequence"; source: *Medicago truncatula* (barrel medic); Title: "ESTs from roots of *Medicago truncatula* after inoculation with *Phytophthora medicaginis*" (Unpublished (1999)).

AW560135 NCBI acc. No. AW560135 (gi: 7205561) (Mar. 7, 2000); Fedorova,M., et al. "EST315183 DSIR *Medicago truncatula* cDNA clone pDSIR-26023, mRNA sequence"; source: *Medicago truncatula* (barrel medic); Title: "ESTs from roots of *Medicago truncatula* after inoculation with *Phytophthora medicaginis*" (Unpublished (1999)).

AW560196 NCBI acc. No. AW560196 (gi: 7205622) (Mar. 7, 2000); Fedorova,M., et al. "EST315244 DSIR *Medicago truncatula* cDNA clone pDSIR-26K12, mRNA sequence"; source: *Medicago truncatula* (barrel medic); Title: "ESTs from roots of *Medicago truncatula* after inoculation with *Phytophthora medicaginis*" (Unpublished (1999)).

AW560968 NCBI acc. No. AW560968 (gi: 7206394) (Mar. 7, 2000); Fedorova,M., et al. "EST316016 DSIR *Medicago truncatula* cDNA clone pDSIR-30N21, mRNA sequence"; source: *Medicago truncatula* (barrel medic); Title: "ESTs from roots of *Medicago truncatula* after inoculation with *Phytophthora medicaginis*" (Unpublished (1999)).

AW568194 NCBI acc. No. AW568194 (gi: 7232842) (Mar. 13, 2000); Shoemaker,R., et al. "si57g03.y1 Gm-r1030 *Glycine max* cDNA clone Genome Systems Clone ID: Gm-r1030-3053 5' similar to TR:O23107 O23107 AP2 Domain Containing Protein RAP2.5. [1] ;, mRNA sequence"; source: *Glycine max* (soybean); Title: "Public Soybean EST Project" (Unpublished (1999)).

AW596384 NCBI acc. No. AW596384 (gi: 7283781) (Mar. 22, 2000); Shoemaker,R., et al. "sjO2f12.y1 Gm-c1032 *Glycine max* cDNA clone Genome Systems Clone ID: Gm-c1032-744 5' similar to TR:Q40478 Q40478 EREBP-4. ;, mRNA sequence"; source: *Glycine max* (soybean); Title: "Public Soybean EST Project" (Unpublished (1999)).

AW618112 NCBI acc. No. AW618112 (gi: 7324339) (Mar. 24, 2000); Alcala,J., et al. "EST314162 *L. pennellii* trichome, Cornell University *Solanum pennellii* cDNA clone cLPT12K17 5', mRNA sequence"; source: *Solanum pennellii* (*Lycopersicon pennellii*); Title: "Generation of ESTs from wild tomato (*Lycopersicon pennellii*) trichomes" (Unpublished (1999)).

AW618245 NCBI acc. No. AW618245 (gi: 7324479) (Mar. 24, 2000); Alcala,J., et al. "EST314295 *L. pennellii* trichome, Cornell University *Solanum pennellii* cDNA clone cLPT15H2O 5', mRNA sequence"; source: *Solanum pennellii* (*Lycopersicon pennellii*); Title: "Generation of ESTs from wild tomato (*Lycopersicon pennellii*) trichomes" (Unpublished (1999)).

AW620490 NCBI acc. No. AW620490 (gi: 7326692) (Mar. 24, 2000); Shoemaker,R., et al. "sjO5h02.y1 Gm-c1032 *Glycine max* cDNA clone Genome Systems Clone ID Gm-c1032-1036 5' similar to TR:O80387 O80387 Ethylene Responsive Element Binding Factor. ;, mRNA sequence"; source: *Glycine max* (soybean); Title: "Public Soybean EST Project" (Unpublished (1999)).

AW622531 NCBI acc. No. AW622531 (gi: 7334178) (Mar. 28, 2000); van der Hoeven,R.S., et al. "EST313331 tomato root during/after fruit set, Cornell University *Solanum lycopersicum* cDNA clone cLEX15D17 5', mRNA sequence"; source: *Solanum lycopersicum* (*Lycopersicon esculentum*); Title: "Generation of ESTs from tomato root, during and after fruit set" (Unpublished (1999)).

AW647824 NCBI acc. No. AW647824 (gi: 7409062) (Apr. 4, 2000); Alcala,J., et al. "EST326278 tomato germinating seedlings, TAMU *Solanum lycopersicum* cDNA clone cLEI2M8 5, mRNA sequence"; source: *Solanum lycopersicum* (*Lycopersicon esculentum*); Title: "Generation of ESTs from germinating tomato seed" (Unpublished (2000)).

AW685799 NCBI acc. No. AW685799 (gi: 7560535) (Apr. 14, 2000); Watson,B.S., et al. "NFO3ODO9NR1F1000 Nodulated root *Medicago truncatula* cDNA clone NFO3ODO9NR 5', mRNA sequence"; source: *Medicago truncatula* (barrel medic); Title: "Expressed Sequence Tags from the Samuel Roberts Noble Foundation *Medicago truncatula* nodulated root library" (Unpublished (2000)).

AW686013 NCBI acc. No. AW686013 (gi: 11930899) (Apr. 14, 2000); Watson,B.S., et al. "NF033DO4NR1F1000 Nodulated root *Medicago truncatula* cDNA clone NF033DO4NR 5', mRNA sequence"; source: *Medicago truncatula* (barrel medic); Title: "Expressed Sequence Tags from the Samuel Roberts Noble Foundation *Medicago truncatula* nodulated root library" (Unpublished (2000)).

AW686992 NCBI acc. No. AW686992 (gi: 11930183) (Apr. 14, 2000); Watson,B.S., et al. "NFOO4GO7RT1F1055 Developing root *Medicago truncatula* cDNA clone NFOO4GO7RT 5', mRNA sequence"; source: *Medicago truncatula* (barrel medic); Title: "Expressed Sequence Tags from the Samuel Roberts Noble Foundation *Medicago truncatula* root library" (Unpublished (2000)).

AW706554 NCBI acc. No. AW706554 (gi: 7590810) (Apr. 18, 2000); Shoemaker,R., et al. "sj58h12.y1 Gm-c1033 *Glycine max* cDNA clone Genome Systems Clone ID: Gm-c1033-1536 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).

AW737966 NCBI acc. No. AW737966 (gi: 7646911) (Apr. 25, 2000); van der Hoeven,R.S., et al. "EST339393 tomato flower buds, anthesis, Cornell University *Solanum lycopersicum* cDNA clone cTOD4F22 5', mRNA sequence"; source: *Solanum lycopersicum* (*Lycopersicon esculentum*); Title: "Generation of ESTs from tomato flower tissue, anthesis" (Unpublished (1999)).

AW759181 NCBI acc. No. AW759181 (gi: 7691047) (May 4, 2000); Shoemaker,R., et al. "s138a09.y1 Gm-c1027 *Glycine max* cDNA clone Genome Systems Clone ID: Gm-c1027-3569 5' similar to TR:O80387 O80387 Ethylene Responsive Element Binding Factor. ;, mRNA sequence"; source: *Glycine max* (soybean); Title: "Public Soybean EST Project" (Unpublished (1999)).

AW760204 NCBI acc. No. AW760204 (gi: 7692089) (May 4, 2000); Shoemaker,R., et al. "s159d04.y1 Gm-c1027 *Glycine max* cDNA clone Genome Systems Clone ID: Gm-c1027-5600 5' similar to TR:O23143 O23143 Putative CKC2. ;, mRNA sequence"; source: *Glycine max* (soybean); Title: "Public Soybean EST Project" (Unpublished (1999)).

AW781602 NCBI acc. No. AW781602 (gi: 7796205) (May 12, 2000); Shoemaker,R., et al. "s182d06.y1 Gm-c1037 *Glycine max* cDNA clone Genome Systems Clone ID: Gm-c1037-516 5' similar to TR:Q40478 Q40478 EREBP-4. ;, mRNA sequence"; source: *Glycine max* (soybean); Title: "Public Soybean EST Project" (Unpublished (1999)).

AW782252 NCBI acc. No. AW782252 (gi: 7796858) (May 12, 2000); Shoemaker,R., et al. "sm03d11.y1 Gm-c1027 *Glycine max* cDNA clone Genome Systems Clone ID: Gm-c1027-7822 5' similar to TR:P93007 P93007 Cadmium-Induced Protein Isolog. ;, mRNA sequence"; source: *Glycine max* (soybean); Title: "Public Soybean EST Project" (Unpublished (1999)).

AW840600 NCBI acc. No. AW840600 (gi: 7934583) (May 18, 2000); Anderson,J.V., et al. "00058 leafy spurge Lambda HybriZAP 2.1 two-hybrid vector cDNA Library *Euphorbia esula* cDNA clone 16G 5' similar to DNA-binding Protein/AP2-Domain Containing Protein, mRNA sequence"; source: *Euphorbia esula* (leafy spurge); Title: "Identification of mRNAs expressed in underground adventitious buds of *Euphorbia esula* (leafy spurge)" (Unpublished (2000)).
AW840611 NCBI acc. No. AW840611 (gi: 7934594) (May 18, 2000); Anderson,J.V., et al. "00057 leafy spurge Lambda HybriZAP 2.1 two-hybrid vector cDNA Library *Euphorbia esula* cDNA clone 1G 5' similar to DNA-binding Protein/Ethylene Responsive Factor, mRNA sequence"; source: *Euphorbia esula* (leafy spurge); Title: "Identification of mRNAs expressed in underground adventitious buds of *Euphorbia esula* (leafy spurge)" (Unpublished (2000)).
AW930351 NCBI acc. No. AW930351 (gi: 8105848) (May 30, 2000); Alcala,J., et al. "EST340904 tomato fruit mature green, TAMU *Solanum lycopersicum* cDNA clone cLEF43H15 5', mRNA sequence"; source: *Solanum lycopersicum* (*Lycopersicon esculentum*); Title: "Generation of ESTs from tomato fruit tissue" (Unpublished (1999)).
AW931292 NCBI acc. No. AW931292 (gi: 8106693) (May 30, 2000); Alcala,J., et al. "EST357135 tomato fruit mature green, TAMU *Solanum lycopersicum* cDNA clone cLEF44J15 5', mRNA sequence"; source: *Solanum lycopersicum* (*Lycopersicon esculentum*); Title: "Generation of ESTs from tomato fruit tissue" (Unpublished (1999)).
AW933517 NCBI acc. No. AW933517 (gi: 8108834) (May 30, 2000); Alcala,J., et al. "EST359276 tomato fruit mature green, TAMU *Solanum lycopersicum* cDNA clone cLEF54C10 5', mRNA sequence"; source: *Solanum lycopersicum* (*Lycopersicon esculentum*); Title: "Generation of ESTs from tomato fruit tissue" (Unpublished (1999)).
AX033191 NCBI acc. No. AX033191 (gi: 10280046) (Sep. 22, 2000); Memelink,J., et al. "Sequence 2 from Patent WO0046383"; source: *Catharanthus roseus* (*Madagascar periwinkle*); Title: "Method of modulating metabolite biosynthesis in recombinant cells" (Patent: WO 0046383-A Aug. 10, 2000; Univ Leiden (NL) ; Memelink Johan (NL) ; Fits Cornelia Theodora Elisabe (NL) ; Kijne Jan Willem (NL) ; Menke Frank Leonardus Hendriku (NL)).
AX033192 NCBI acc. No. AX033192 (gi: 10280047) (Sep. 22, 2000); Memelink,J., et al. "Sequence 3 from Patent WO0046383"; source: *Catharanthus roseus* (*Madagascar periwinkle*); Title: "Method of modulating metabolite biosynthesis in recombinant cells" (Patent: WO 0046383-A Aug. 10, 2000; Univ Leiden (NL) ; Memelink Johan (NL) ; Fits Cornelia Theodora Elisabe (NL) ; Kijne Jan Willem (NL) ; Menke Frank Leonardus Hendriku (NL)).
AX573798 NCBI acc. No. AX573798 (gi: 27551457) (Jan. 9, 2003); Pages,M., et al. "Sequence 15 from Patent WO02079245"; source: *Oryza sativa*; Title: "Method for improving plant tolerance to environmental stress" (Patent: WO 02079245-A 15 Oct. 10, 2002; Consejo Superior Investigaciones Cientificas (CSIC) (ES)).
AY192370 NCBI acc. No. AY192370 (gi: 28274833) (Feb. 9, 2003); Tournier,B., et al. "*Lycopersicon esculentum* ethylene response factor 4 (ERF4) mRNA, complete cds"; source: *Lycopersicon esculentum* (tomato); Title: "LeERF2 defines a novel class of ethylene response factors and confers enhanced tolerance to cold stress when overexpressed in the tomato" (Unpublished).
BE057468 NCBI acc. No. BE057468 (gi: 8401834) (Jun. 9, 2000); Shoemaker,R., et al. "sm58e08.y1 Gm-c1028 *Glycine max* cDNA clone Genome Systems Clone ID: Gm-c1028-8127 5' similar to TR:O23105 O23105 AP2 Domain Containing Protein RAP2.3. ;, mRNA sequence"; source: *Glycine max* (soybean); Title: "Public Soybean EST Project" (Unpublished (1999)).
BE191029 NCBI acc. No. BE191029 (gi: 8669922) (Jun. 22, 2000); Shoemaker,R., et al. "sn83h08.y1 Gm-c1038 *Glycine max* cDNA clone Genome Systems Clone ID: Gm-c1038-1240 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).
BE203165 NCBI acc. No. BE203165 (gi: 8746436) (Jun. 27, 2000); VandenBosch,K., et al. "EST403187 KV1 *Medicago truncatula* cDNA clone pKV1-4L15, mRNA sequence"; source: *Medicago truncatula* (barrel medic); Title: "ESTs from roots of *Medicago truncatula* 24 hours after inoculation with *Sinorhizobium meliloti*" (Unpublished (1999)).

BE203296 NCBI acc. No. BE203296 (gi: 8746567) (Jun. 27, 2000); VandenBosch,K., et al. "EST403318 KV1 *Medicago truncatula* cDNA clone pKV1-5G15, mRNA sequence"; source: *Medicago truncatula* (barrel medic); Title: "ESTs from roots of *Medicago truncatula* 24 hours after inoculation with *Sinorhizobium meliloti*" (Unpublished (1999)).
BE318516 NCBI acc. No. BE318516 (gi: 11960607) (Jul. 14, 2000); Torres-Jerez,l., et al. "NF071G07LF1F1053 Developing leaf *Medicago truncatula* cDNA clone NF071G07LF 5', mRNA sequence"; source: *Medicago truncatula* (barrel medic); Title: "Expressed Sequence Tags from the Samuel Roberts Noble Foundation *Medicago truncatula* leaf library" (Unpublished (2000)).
BE325359 NCBI acc. No. BE325359 (gi: 11935917) (Jul. 14, 2000); He,X.-Z., et al. "NF087B10ST1F1077 Developing stem *Medicago truncatula* cDNA clone NF087B10ST 5', mRNA sequence"; source: *Medicago truncatula* (barrel medic); Title: "Expressed Sequence Tags from the Samuel Roberts Noble Foundation *Medicago truncatula* stem library" (Unpublished (2000)).
BE326131 NCBI acc. No. BE326131 (gi: 11934119) (Jul.14, 2000); He,X.-Z., et al. "NF085C08ST1F1055 Developing stem *Medicago truncatula* cDNA clone NF085C08ST 5', mRNA sequence"; source: *Medicago truncatula* (barrel medic); Title: "Expressed Sequence Tags from the Samuel Roberts Noble Foundation *Medicago truncatula* stem library" (Unpublished (2000)).
BE330726 NCBI acc. No. BE330726 (gi: 9204502) (Jul. 14, 2000); Shoemaker,R., et al. "so84a08.y1 Gm-c1041 *Glycine max* cDNA clone Genome Systems Clone ID: Gm-c1041-15 5' similar to TR:O81365 O81365 AP2 Domain Containing Protein ;, mRNA sequence"; source: *Glycine max* (soybean); Title: "Public Soybean EST Project" (Unpublished (1999)).
BE331593 NCBI acc. No. BE331593 (gi: 9205369) (Jul. 14, 2000); Shoemaker,R., et al. "sp16c03.y1 Gm-c1042 *Glycine max* cDNA clone Genome Systems Clone ID: Gm-c1042-701 5' similar to TR:Q40478 Q40478 EREBP-4. ;, mRNA sequence"; source: *Glycine max* (soybean); Title: "Public Soybean EST Project" (Unpublished (1999)).
BE427520 NCBI acc. No. BE427520 (gi: 9425363) (Jul. 24, 2000); Anderson,O.A., et al. "PSR7136 ITEC PSR Wheat Pericarp/Testa Library *Triticum aestivum* cDNA clone PSR7136, mRNA sequence"; source: *Triticum aestivum* (bread wheat); Title: "International Triticeae EST Cooperative (ITEC): Production of Expressed Sequence Tags for Species of the *Triticeae*" (Unpublished (2000)).
BE429439 NCBI acc. No. BE429439 (gi: 9427282) (Jul. 24, 2000); Anderson,O.A., et al. "TAS000.B08R990618 ITEC TAS Wheat cDNA Library *Triticum aestivum* cDNA clone TAS000.B08, mRNA sequence"; source: *Triticum aestivum* (bread wheat); Title: "International Triticeae EST Cooperative (ITEC): Production of Expressed Sequence Tags for Species of the *Triticeae*" (Unpublished (2000)).
BE432465 NCBI acc. No. BE432465 (gi: 9430308) (Jul. 24, 2000); Alcala,J., et al. "EST398994 tomato breaker fruit, TIGR *Solanum lycopersicum* cDNA clone cLEG8I18, mRNA sequence"; source: *Solanum lycopersicum* (*Lycopersicon esculentum*); Title: "Generation of ESTs from tomato fruit tissue, breaker stage" (Unpublished (2000)).
BE433462 NCBI acc. No. BE433462 (gi: 9431305) (Jul. 24, 2000); Alcala,J., et al. "EST399991 tomato breaker fruit, TIGR *Solanum lycopersicum* cDNA clone cLEG14M13, mRNA sequence"; source: *Solanum lycopersicum* (*Lycopersicon esculentum*); Title: "Generation of ESTs from tomato fruit tissue, breaker stage" (Unpublished (2000)).
BE435827 NCBI acc. No. BE435827 (gi: 9433670) (Jul. 24, 2000); Alcala,J., et al. "EST406905 tomato breaker fruit, TIGR *Solanum lycopersicum* cDNA clone cLEG29O9, mRNA sequence"; source: *Solanum lycopersicum* (*Lycopersicon esculentum*); Title: "Generation of ESTs from tomato fruit tissue, breaker stage" (Unpublished (2000)).
BE436333 NCBI acc. No. BE436333 (gi: 9434176) (Jul. 24, 2000); Alcala,J., et al. "EST407411 tomato breaker fruit, TIGR *Solanum lycopersicum* cDNA clone cLEG32E7, mRNA sequence"; source: *Solanum lycopersicum* (*Lycopersicon esculentum*); Title: "Generation of ESTs from tomato fruit tissue, breaker stage" (Unpublished (2000)).

BE436391 NCBI acc. No. BE436391 (gi: 9434234) (Jul. 24, 2000); Alcala,J., et al. "EST407469 tomato breaker fruit, TIGR *Solanum lycopersicum* cDNA clone cLEG32A16, mRNA sequence"; source: *Solanum lycopersicum* (*Lycopersicon esculentum*); Title: "Generation of ESTs from tomato fruit tissue, breaker stage" (Unpublished (2000)).

BE436556 NCBI acc. No. BE436556 (gi: 9434399) (Jul. 24, 2000); Alcala,J., et al. "EST407634 tomato breaker fruit, TIGR *Solanum lycopersicum* cDNA clone cLEG33I3, mRNA sequence"; source: *Solanum lycopersicum* (*Lycopersicon esculentum*); Title: "Generation of ESTs from tomato fruit tissue, breaker stage" (Unpublished (2000)).

BE449392 NCBI acc. No. BE449392 (gi: 9454895) (Jul. 26, 2000); van der Hoeven,R.S., et al. "EST356151 *L. hirsutum* trichome, Cornell University *Solanum habrochaites* cDNA clone cLHT31K6, mRNA sequence"; source: *Solanum habrochaites* (*Lycopersicon hirsutum*); Title: "Generation of ESTs from wild tomato (*Lycopersicon hirsutum*) trichomes" (Unpublished (2000)).

BE459781 NCBI acc. No. BE459781 (gi: 9504083) (Jul. 27, 2000); Alcala,J., et al. "EST415073 tomato developing/immature green fruit *Solanum lycopersicum* cDNA clone cLEM8C19, mRNA sequence"; source: *Solanum lycopersicum* (*Lycopersicon esculentum*); Title: "Generation of ESTs from tomato fruit tissue, immature green" (Unpublished (2000)).

BE461852 NCBI acc. No. BE461852 (gi: 9506154) (Jul. 27, 2000); Alcala,J., et al. "EST413271 tomato breaker fruit, TIGR *Solanum lycopersicum* cDNA clone cLEG40O17, mRNA sequence"; source: *Solanum lycopersicum* (*Lycopersicon esculentum*); Title: "Generation of ESTs from tomato fruit tissue, breaker stage" (Unpublished (2000)).

BE474049 NCBI acc. No. BE474049 (gi: 9564540) (Jul. 28, 2000); Shoemaker,R., et al. "sp58d12.y1 Gm-c1044 *Glycine max* cDNA clone Genome Systems Clone ID: Gm-c1044-144 5' similar to TR:O81365 O81365 AP2 Domain Containing Protein ;, mRNA sequence"; source: *Glycine max* (soybean); Title: "Public Soybean EST Project" (Unpublished (1999)).

BE494041 NCBI acc. No. BE494041 (gi: 9660634) (Aug. 2, 2000); Anderson,O.D., et al. "WHE1277__B09__D17ZS *Secale cereale* anther cDNA library *Secale cereale* cDNA clone WHE1277__B09__D17, mRNA sequence"; source: *Secale cereale* (rye); Title: "The structure and function of the expressed portion of the wheat genomes - Anther cDNA library from rye" (Unpublished (2000)).

BE554898 NCBI acc. No. BE554898 (gi: 9819385) (Aug. 15, 2000); Shoemaker,R., et al. "sp82c07.y1 Gm-c1045 *Glycine max* cDNA clone Genome Systems Clone ID: Gm-c1045-133 5' similar to TR:Q40478 Q40478 EREBP-4. ;, mRNA sequence"; source: *Glycine max* (soybean); Title: "Public Soybean EST Project" (Unpublished (1999)).

BE555398 NCBI acc. No. BE555398 (gi: 9819822) (Aug. 15, 2000); Shoemaker,R., et al. "sp88c01.y1 Gm-c1045 *Glycine max* cDNA clone Genome Systems Clone ID: Gm-c1045-697 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).

BE610114 NCBI acc. No. BE610114 (gi: 9901146) (Aug. 24, 2000); Shoemaker,R., et al. "sp80h02.y1 Gm-c1044 *Glycine max* cDNA clone Genome Systems Clone ID: Gm-c1044-2284 5' similar to TR:Q40478 Q40478 EREBP-4. ;, mRNA sequence"; source: *Glycine max* (soybean); Title: "Public Soybean EST Project" (Unpublished (1999)).

BE801560 NCBI acc. No. BE801560 (gi: 10232672) (Sep. 20, 2000); Shoemaker,R., et al. "sr16a08.y1 Gm-c1050 *Glycine max* cDNA clone Genome Systems Clone ID: Gm-c1050-495 5' similar to TR:O80387 O80387 Ethylene Responsive Element Binding Factor. ;, mRNA sequence"; source: *Glycine max* (soybean); Title: "Public Soybean EST Project" (Unpublished (1999)).

BE804368 NCBI acc. No. BE804368 (gi: 10235480) (Sep. 20, 2000); Shoemaker,R., et al. "sr78h05.y1 Gm-c1052 *Glycine max* cDNA clone Genome Systems Clone ID: Gm-c1052-1906 5' similar to TR:Q40478 Q40478 EREBP-4. ;, mRNA sequence"; source: *Glycine max* (soybean); Title: "Public Soybean EST Project" (Unpublished (1999)).

BE805304 NCBI acc. No. BE805304 (gi: 10236416) (Sep. 20, 2000); Shoemaker,R., et al. "ss40h06.y1 Gm-c1061 *Glycine max* cDNA clone Genome Systems Clone ID: Gm-c1061-1236 5' similar to TR:Q40478 Q40478 EREBP-4. ;, mRNA sequence"; source: *Glycine max* (soybean); Title: "Public Soybean EST Project" (Unpublished (1999)).

BE820195 NCBI acc. No. BE820195 (gi: 10252429) (Sep. 21, 2000); Vodkin,L., et al. "GM700006A11G12 Gm-r1070 *Glycine max* cDNA clone Gm-r1070-2231 3', mRNA sequence"; source: *Glycine max* (soybean); Title: "A Functional Genomics Program for Soybean (NSF 9872565)" (Unpublished (1999)).

BE941508 NCBI acc. No. BE941508 (gi: 10519339) (Oct. 3, 2000); Cote,F., et al. "EST421159 MGHG *Medicago truncatula* cDNA clone pMGHG-4M14, mRNA sequence"; source: *Medicago truncatula* (barrel medic); Title: "ESTs from seedling roots of *Medicago truncatula* after treatment with beta glucan elicitor preparation from *Phytophthora sojae*" (Unpublished (2000)).

BE941864 NCBI acc. No. BE941864 (gi: 10519623) (Oct. 3, 2000); Cote,F., et al. "EST421443 MGHG *Medicago truncatula* cDNA clone pMGHG-6D2, mRNA sequence"; source: *Medicago truncatula* (barrel medic); Title: "ESTs from seedling roots of *Medicago truncatula* after treatment with beta glucan elicitor preparation from *Phytophthora sojae*" (Unpublished (2000)).

BE942996 NCBI acc. No. BE942996 (gi: 10520755) (Oct. 3, 2000); Cote,F., et al. "EST422575 MGHG *Medicago truncatula* cDNA clone pMGHG-14B1, mRNA sequence"; source: *Medicago truncatula* (barrel medic); Title: "ESTs from seedling roots of *Medicago truncatula* after treatment with beta glucan elicitor preparation from *Phytophthora sojae*" (Unpublished (2000)).

BF008875 NCBI acc. No. BF008875 (gi: 10709151) (Oct. 6, 2000); Shoemaker,R., et al. "ss70e04.y1 Gm-c1062 *Glycine max* cDNA clone Genome Systems Clone ID: Gm-c1062-1783 5&pos; similar to TR:O81365 O81365 AP2 Domain Containing Protein ;, mRNA sequence"; source: *Glycine max* (soybean); Title: "Public Soybean EST Project" (Unpublished (1999)).

BF009446 NCBI acc. No. BF009446 (gi: 10709722) (Oct. 6, 2000); Shoemaker,R., et al. "ss78g12.y1 Gm-c1064 *Glycine max* cDNA clone Genome Systems Clone ID: Gm-c1064-287 5&pos; similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).

BF068784 NCBI acc. No. BF068784 (gi: 10845722) (Oct. 17, 2000); Shoemaker,R., et al. "st02e12.y1 Gm-c1065 *Glycine max* cDNA clone Genome Systems Clone ID: Gm-c1065-167 5&pos; similar to TR:P93589 P93589 DNA Binding Protein Homolog. ;, mRNA sequence"; source: *Glycine max* (soybean); Title: "Public Soybean EST Project" (Unpublished (1999)).

BF070873 NCBI acc. No. BF070873 (gi: 10843956) (Oct. 17, 2000); Shoemaker,R., et al. "st38c09.y1 Gm-c1067 *Glycine max* cDNA clone Genome Systems Clone ID: Gm-c1067-1266 5&pos; similar to TR:O23143 O23143 Putative CKC2. ;, mRNA sequence"; source: *Glycine max* (soybean); Title: "Public Soybean EST Project" (Unpublished (1999)).

BF096818 NCBI acc. No. BF096818 (gi: 10902528) (Oct. 19, 2000); van der Hoeven,R.S., et al. "EST360845 tomato nutrient deficient roots *Solanum lycopersicum* cDNA clone cLEW17110 5&pos; sequence, mRNA sequence"; source: *Solanum lycopersicum* (*Lycopersicon esculentum*); Title: "Generation of ESTs from tomato nutrient-deficient roots" (Unpublished (1999)).

BF112878 NCBI acc. No. BF112878 (gi: 10942568) (Oct. 20, 2000); Alcala,J., et al. "EST440468 tomato breaker fruit *Solanum lycopersicum* cDNA clone cLEG42N7 5&pos; sequence, mRNA sequence"; source: *Solanum lycopersicum* (*Lycopersicon esculentum*); Title: "Generation of ESTs from tomato fruit tissue, breaker stage" (Unpublished (2000)).

BF113172 NCBI acc. No. BF113172 (gi: 10942862) (Oct. 20, 2000); Alcala,J., et al. "EST440762 tomato breaker fruit *Solanum lycopersicum* cDNA clone cLEG43D8 5&pos; sequence, mRNA sequence"; source: *Solanum lycopersicum* (*Lycopersicon esculentum*); Title: "Generation of ESTs from tomato fruit tissue, breaker stage" (Unpublished (2000)).

BF263411 NCBI acc. No. BF263411 (gi: 13260800) (Nov. 17, 2000); Wing,R., et al. "HV__CEa0006K20f *Hordeum vulgare* seedling green leaf EST library HVcDNA0004 (Blumeria challenged) *Hordeum vulgare* subsp. vulgare cDNA clone HV_CEa0006K20f, mRNA sequence"; source: *Hordeum vulgare* subsp. vulgare; Title: "Development of a genetically and physically anchored EST resource for barley genomics: Blumeria infected incompatible (M1a13) seedling leaf cDNA library" (Unpublished (2001)).
BF275458 NCBI acc. No. BF275458 (gi: 11206528) (Nov. 17, 2000); Wing,R.A., et al. "GA_Eb0024B16f *Gossypium arboreum* 7-10 dpa fiber library *Gossypium arboreum* cDNA clone GA_Eb0024B16f, mRNA sequence"; source: *Gossypium arboreum*; Title: "An integrated analysis of the genetics, development, and evolution of the cotton fiber" (Unpublished (2000)).
BF275652 NCBI acc. No. BF275652 (gi: 11206722) (Nov. 17, 2000); Wing,R.A., et al. "GA_Eb0024J23f *Gossypium arboreum* 7-10 dpa fiber library *Gossypium arboreum* cDNA clone GA_Eb0024J23f, mRNA sequence"; source: *Gossypium arboreum*; Title: "An integrated analysis of the genetics, development, and evolution of the cotton fiber" (Unpublished (2000)).
BF277659 NCBI acc. No. BF277659 (gi: 11208729) (Nov. 17, 2000); Wing,R.A., et al. "GA_Eb0031C19f *Gossypium arboreum* 7-10 dpa fiber library *Gossypium arboreum* cDNA clone GA_Eb0031C19f, mRNA sequence"; source: *Gossypium arboreum*; Title: "An integrated analysis of the genetics, development, and evolution of the cotton fiber" (Unpublished (2000)).
BF324075 NCBI acc. No. BF324075 (gi: 11273699) (Nov. 21, 2000); Shoemaker,R., et al. "su22c11.y1 Gm-c1068 *Glycine max* cDNA clone Genome Systems Clone ID: Gm-c1068-117 5&pos; similar to TR:P93589 P93589 DNA Binding Protein Homolog. ;, mRNA sequence"; source: *Glycine max* (soybean); Title: "Public Soybean EST Project" (Unpublished (1999)).
BF596417 NCBI acc. No. BF596417 (gi: 11688741) (Dec. 12, 2000); Shoemaker,R., et al. "su51a06.y1 Gm-c1069 *Glycine max* cDNA clone Genome Systems Clone ID: Gm-c1069-396 5&pos; similar to TR:O81365 O81365 AP2 Domain Containing Protein ;, mRNA sequence"; source: *Glycine max* (soybean); Title: "Public Soybean EST Project" (Unpublished (1999)).
BF617601 NCBI acc. No. BF617604 (gi: 13109111) (Dec. 18, 2000); Wing,R., et al. "HVSMEc0018D19f *Hordeum vulgare* seedling shoot EST library HVcDNA0003 (Etiolated and unstressed) *Hordeum vulgare* subsp. vulgare cDNA clone HVSMEc0018D19f, mRNA sequence"; source: *Hordeum vulgare* subsp. vulgare; Title: "Development of a genetically and physically anchored EST resource for barley genomics: Morex unstressed seedling shoot cDNA library" (Unpublished (2001)).
BF618047 NCBI acc. No. BF618047 (gi: 13106669) (Dec. 18, 2000); Wing,R., et al. "HVSMEc0003G22f *Hordeum vulgare* seedling shoot EST library HVcDNA0003 (Etiolated and unstressed) *Hordeum vulgare* subsp. vulgare cDNA clone HVSMEc0003G22f, mRNA sequence"; source: *Hordeum vulgare* subsp. vulgare; Title: "Development of a genetically and physically anchored EST resource for barley genomics: Morex unstressed seedling shoot cDNA library" (Unpublished (2001)).
BF621655 NCBI acc. No. BF621655 (gi: 13083645) (Dec. 18, 2000); Wing,R., et al. "HVSMEa0011L23f *Hordeum vulgare* seedling shoot EST library HVcDNA0001 (Cold stress) *Hordeum vulgare* subsp. vulgare cDNA clone HVSMEa0011L23f, mRNA sequence"; source: *Hordeum vulgare* subsp. vulgare; Title: "Development of a genetically and physically anchored EST resource for barley genomics: Morex cold-stressed seedling shoot cDNA library" (Unpublished (2001)).
BF624177 NCBI acc. No. BF624177 (gi: 13083964) (Dec. 18, 2000); Wing,R., et al. "HVSMEa0012F2Of *Hordeum vulgare* seedling shoot EST library HVcDNA0001 (Cold stress) *Hordeum vulgare* subsp. vulgare cDNA clone HVSMEa0012F20f, mRNA sequence"; source: *Hordeum vulgare* subsp. vulgare; Title: "Development of a genetically and physically anchored EST resource for barley genomics: Morex cold-stressed seedling shoot cDNA library" (Unpublished (2001)).
BF634482 NCBI acc. No. BF634482 (gi: 11898640) (Dec. 19, 2000); Torrez-Jerez,I., et al. "NF074A12DT1F1088 Drought *Medicago truncatula* cDNA clone NF074A12DT 5&pos;, mRNA sequence"; source: *Medicago truncatula* (barrel medic); Title: "Expressed Sequence Tags from the Samuel Roberts Noble Foundation *Medicago truncatula* drought library" (Unpublished (2000)).
BF637755 NCBI acc. No. BF637755 (gi: 11901913) (Dec. 19, 2000); Liu,J., et al. "NF041B03PL1F1027 Phosphate starved leaf *Medicago truncatula* cDNA clone NF041B03PL 5&pos;, mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).
BF637999 NCBI acc. No. BF637999 (gi: 11902157) (Dec. 19, 2000); Liu,J., et al. "NF028F04PL1F1041 Phosphate starved leaf *Medicago truncatula* cDNA clone NF028F04PL 5&pos;, mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).
BF643225 NCBI acc. No. BF643225 (gi: 11908350) (Dec. 20, 2000); Torres-Jerez,I., et al. "NFOO1G02EC1F1017 Elicited cell culture *Medicago truncatula* cDNA clone NFOO1G02EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).
BF644716 NCBI acc. No. BF644716 (gi: 11909845) (Dec. 20, 2000); Torres-Jerez,I., et al. "NF019F07EC1F1062 Elicited cell culture *Medicago truncatula* cDNA clone NF019F07EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).
BF645474 NCBI acc. No. BF645474 (gi: 11910603) (Dec. 20, 2000); Torres-Jerez,I., et al. "NF019D04EC1F1041 Elicited cell culture *Medicago truncatula* cDNA clone NF019D04EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).
BF645999 NCBI acc. No. BF645999 (gi: 11911128) (Dec. 20, 2000); Torres-Jerez,I., et al. "NF043B08EC1F1064 Elicited cell culture *Medicago truncatula* cDNA clone NF043B08EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).
BF646324 NCBI acc. No. BF646324 (gi: 11911454) (Dec. 20, 2000); Torres-Jerez,I., et al. "NF074E05EC1F1038 Elicited cell culture *Medicago truncatula* cDNA clone NF074E05EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).
BF647222 NCBI acc. No. BF647222 (gi: 11912352) (Dec. 20, 2000); Torres-Jerez,I., et al. "NF033B03EC1F1028 Elicited cell culture *Medicago truncatula* cDNA clone NF033B03EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).
BF647376 NCBI acc. No. BF647376 (gi: 11912506) (Dec. 20, 2000); Torres-Jerez,I., et al. "NF033B02EC1F1016 Elicited cell culture *Medicago truncatula* cDNA clone NF033B02EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).
BF648210 NCBI acc. No. BF648210 (gi: 11913340) (Dec. 20, 2000); Torres-Jerez,I., et al. "NF045C04EC1F1033 Elicited cell culture *Medicago truncatula* cDNA clone NF045C04EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF648225 NCBI acc. No. BF648225 (gi: 11913355) (Dec. 20, 2000); Torres-Jerez,I., et al. "NF045D1OEC1F1089 Elicited cell culture *Medicago truncatula* cDNA clone NF045D1OEC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF648429 NCBI acc. No. BF648429 (gi: 11913559) (Dec. 20, 2000); Torres-Jerez,I., et al. "NF045H02EC1F1027 Elicited cell culture *Medicago truncatula* cDNA clone NF045H02EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF649047 NCBI acc. No. BF649047 (gi: 11914093) (Dec. 20, 2000); Torres-Jerez,I., et al. "NF053B11EC1F1091 Elicited cell culture *Medicago truncatula* cDNA clone NF053B11EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF649327 NCBI acc. No. BF649327 (gi: 11914457) (Dec. 20, 2000); Torres-Jerez,I., et al. "NF056E12EC1F1097 Elicited cell culture *Medicago truncatula* cDNA clone NF056E12EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF649790 NCBI acc. No. BF649790 (gi: 11914920) (Dec. 20, 2000); Torres-Jerez,I., et al. "NF084C07EC1F1052 Elicited cell culture *Medicago truncatula* cDNA clone NF084C07EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF649879 NCBI acc. No. BF649879 (gi: 11915009) (Dec. 20, 2000); Torres-Jerez,I., et al. "NF086A05EC1F1035 Elicited cell culture *Medicago truncatula* cDNA clone NF086A05EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF650089 NCBI acc. No. BF650089 (gi: 11915219) (Dec. 20, 2000); Torres-Jerez,I., et al. "NF088B12EC1F1095 Elicited cell culture *Medicago truncatula* cDNA clone NF088B12EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF650178 NCBI acc. No. BF650178 (gi: 11915308) (Dec. 20, 2000); Torres-Jerez,I., et al. "NF085H09EC1F1078 Elicited cell culture *Medicago truncatula* cDNA clone NF085H09EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF650547 NCBI acc. No. BF650547 (gi: 11915677) (Dec. 20, 2000); Torres-Jerez,I., et al. "NF097H02EC1F1026 Elicited cell culture *Medicago truncatula* cDNA clone NF097H02EC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF650930 NCBI acc. No. BF650930 (gi: 11916060) (Dec. 20, 2000); Torres-Jerez,I., et al. "NF098F1OEC1F1089 Elicited cell culture *Medicago truncatula* cDNA clone NF098F1OEC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BF651153 NCBI acc. No. BF651153 (gi: 11916283) (Dec. 20, 2000); Torres-Jerez,I., et al. "NF102B1OEC1F1079 Elicited cell culture *Medicago truncatula* cDNA clone NF102B1OEC 5&pos;, mRNA sequence"; source: *Medicago truncatula* (barrel medic); Title: "Expressed Sequence Tags from the Samuel Roberts Noble Foundation - Center for Medicago Genomics Research" (Unpublished (2000)).

BG046680 NCBI acc. No. BG046680 (gi: 12495682) (Jan. 25, 2001); Shoemaker,R., et al. "saa58c10.y1 Gm-c1060 *Glycine soja* cDNA clone Genome Systems Clone ID: Gm-c1060-884 5&pos; similar to TR:Q40478 Q40478 EREBP-4. ;, mRNA sequence"; source: *Glycine soja*; Title: "Public Soybean EST Project" (Unpublished (1999)).

BG128566 NCBI acc. No. BG128566 (gi: 12628754) (Jan. 31, 2001); van der Hoeven,R., et al. "EST474212 tomato shoot/meristem *Solanum lycopersicum* cDNA clone cT0F21K4 5&pos; sequence, mRNA sequence"; source: *Solanum lycopersicum (Lycopersicon esculentum)*; Title: "Generation of ESTs from tomato shoot/meristem tissue" (Unpublished (2001)).

BG129573 NCBI acc. No. BG129573 (gi: 12629761) (Jan. 31, 2001); van der Hoeven,R., et al. "EST475219 tomato shoot/meristem *Solanum lycopersicum* cDNA clone cT0F25A11 5&pos; sequence, mRNA sequence"; source: *Solanum lycopersicum (Lycopersicon esculentum)*; Title: "Generation of ESTs from tomato shoot/meristem tissue" (Unpublished (2001)).

BG155935 NCBI acc. No. BG155935 (gi: 12689599) (Feb. 6, 2001); Shoemaker,R., et al. "saa66d04.y1 Gm-c1060 *Glycine soja* cDNA clone Genome Systems Clone ID: Gm-c1060-1688 5' similar to TR:Q40478 Q40478 EREBP-4. ;, mRNA sequence"; source: *Glycine soja*; Title: "Public Soybean EST Project" (Unpublished (1999)).

BG239157 NCBI acc. No. BG239157 (gi: 12774230) (Feb. 13, 2001); Shoemaker,R., et al. "sab66d01.y1 Unknown Library Type *Glycine max* cDNA clone Genome Systems Clone ID: Gm-c1043-4369 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).

BG368839 NCBI acc. No. BG368839 (gi: 13257940) (Mar. 8, 2001); Wing,R., et al. "HVSMEi0020O12f *Hordeum vulgare* 20 DAP spike EST library HVcDNA0010 (20 DAP) *Hordeum vulgare* subsp. vulgare cDNA clone HVSMEi0020O12f, mRNA sequence"; source: *Hordeum vulgare* subsp. vulgare; Title: "Development of a genetically and physically anchored EST resource for barley genomics: Morex 20 DAP spike cDNA library" (Unpublished (2001)).

BG381764 NCBI acc. No. BG381764 (gi: 13306236) (Mar. 12, 2001); Anderson,J.V., et al. "00735 leafy spurge Lambda HybriZAP 2.1 two-hybrid vector cDNA Library *Euphorbia esula* cDNA clone 5AC 5&pos; similar to ethylene-responsive element binding factor, mRNA sequence"; source: *Euphorbia esula* (leafy spurge); Title: "Identification of mRNAs expressed in underground adventitious buds of *Euphorbia esula* (leafy spurge)" (Unpublished (2000)).

BG417325 NCBI acc. No. BG417325 (gi: 13322972) (Mar. 13, 2001); Wing,R., et al. "HVSMEk0017I08f *Hordeum vulgare* testa/pericarp EST library HVcDNA0013 (normal) *Hordeum vulgare* subsp. vulgare cDNA clone HVSMEk0017I08f, mRNA sequence"; source: *Hordeum vulgare* subsp. vulgare; Title: "Development of a genetically and physically anchored EST resource for barley genomics: Morex testa/pericarp cDNA library" (Unpublished (2001)).

BG444654 NCBI acc. No. BG444654 (gi: 13354306) (Mar. 15, 2001); Wing,R.A., et al. "GA_Ea0025B11f *Gossypium arboreum* 7-10 dpa fiber library *Gossypium arboreum* cDNA clone GA_Ea0025B11f, mRNA sequence"; source: *Gossypium arboreum*; Title: "An integrated analysis of the genetics, development, and evolution of the cotton fiber" (Unpublished (2000)).

BG447769 NCBI acc. No. BG447769 (gi: 13366548) (Mar. 16, 2001); Torres-Jerez,I., et al. "NF093H08EC1F1076 Elicited cell culture *Medicago truncatula* cDNA clone NF093H08EC 5', mRNA sequence"; source: *Medicago truncatula* (barrel medic); Title: "Expressed Sequence Tags from the Samuel Roberts Noble Foundation - Center for Medicago Genomics Research" (Unpublished (2000)).

BG448225 NCBI acc. No. BG448225 (gi: 13367006) (Mar. 16, 2001); Torres-Jerez,I., et al. "NF107H09EC1F1078 Elicited cell culture *Medicago truncatula* cDNA clone NF107H09EC 5', mRNA sequence"; source: *Medicago truncatula* (barrel medic);

Title: "Expressed Sequence Tags from the Samuel Roberts Noble Foundation - Center for Medicago Genomics Research" (Unpublished (2000)).

BG448686 NCBI acc. No. BG448686 (gi: 13367383) (Mar. 16, 2001); Watson,B.S., et al. "NF023A03NR1F1000 Nodulated root *Medicago truncatula* cDNA clone NF023A03NR 5', mRNA sequence"; source: *Medicago truncatula* (barrel medic); Title: "Expressed Sequence Tags from the Samuel Roberts Noble Foundation *Medicago truncatula* nodulated root library" (Unpublished (2000)).

BG449954 NCBI acc. No. BG449954 (gi: 13368736) (Mar. 16, 2001); Torrez-Jerez,I., et al. "NF013A1ODT1F1081 Drought *Medicago truncatula* cDNA clone NF013A1ODT 5&pos;, mRNA sequence"; source: *Medicago truncatula* (barrel medic); Title: "Expressed Sequence Tags from the Samuel Roberts Noble Foundation *Medicago truncatula* drought library" (Unpublished (2000)).

BG450588 NCBI acc. No. BG450588 (gi: 13369358) (Mar. 16, 2001); Torrez-Jerez,I., et al. "NF031F1ODT1F1091 Drought *Medicago truncatula* cDNA clone NF031F1ODT 5&pos;, mRNA sequence"; source: *Medicago truncatula* (barrel medic); Title: "Expressed Sequence Tags from the Samuel Roberts Noble Foundation *Medicago truncatula* drought library" (Unpublished (2000)).

BG451892 NCBI acc. No. BG451892 (gi: 13370674) (Mar. 16, 2001); Torrez-Jerez,I., et al. "NF101E12DT1F1088 Drought *Medicago truncatula* cDNA clone NF101E12DT 5&pos;, mRNA sequence"; source: *Medicago truncatula* (barrel medic); Title: "Expressed Sequence Tags from the Samuel Roberts Noble Foundation *Medicago truncatula* drought library" (Unpublished (2000)).

BG455325 NCBI acc. No. BG455325 (gi: 13378650) (Mar. 19, 2001); Liu,J., et al. "NF046F09PL1F1077 Phosphate starved leaf *Medicago truncatula* cDNA clone NF046F09PL 5', mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).

BG457772 NCBI acc. No. BG457772 (gi: 13381097) (Mar. 19, 2001); Liu,J., et al. "NF033D11PL1F1091 Phosphate starved leaf *Medicago truncatula* cDNA clone NF033D11PL 5', mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).

BG459073 NCBI acc. No. BG459073 (gi: 13382398) (Mar. 19, 2001); Anderson,J.V., et al. "00846 leafy spurge Lambda HybriZAP 2.1 two-hybrid vector cDNA Library *Euphorbia esula* cDNA clone 18AF 5' similar to putative Ckc2 [*Arabidopsis thaliana* ], accession# CAA05084, mRNA sequence"; source: *Euphorbia esula* (leafy spurge); Title: "Identification of mRNAs expressed in underground adventitious buds of *Euphorbia esula* (leafy spurge)" (Unpublished (2000)).

BG507541 NCBI acc. No. BG507541 (gi: 13477813) (Mar. 28, 2001); Shoemaker,R., et al. "sac60g11.y1 Gm-c1062 *Glycine max* cDNA clone Genome Systems Clone ID: Gm-c1062-4534 5' similar to TR:O81365 O81365 AP2 Domain Containing Protein ;, mRNA sequence"; source: *Glycine max* (soybean); Title: "Public Soybean EST Project" (Unpublished (1999)).

BG507761 NCBI acc. No. BG507761 (gi: 13478178) (Mar 28 2001); Shoemaker,R., et al. "sac89a05.y1 Gm-c1073 *Glycine max* cDNA clone Genome Systems Clone ID: Gm-c1073-33 5' similar to TR:P93392 P93392 S25-XP1 DNA Binding Protein. ;, mRNA sequence"; source: *Glycine max* (soybean); Title: "Public Soybean EST Project" (Unpublished (1999)).

BG508757 NCBI acc. No. BG508757 (gi: 13479414) (Mar 28 2001); Shoemaker,R., et al. "sac90a05.y1 Gm-c1073 *Glycine max* cDNA clone Genome Systems Clone ID: Gm-c1073-34 5' similar to TR:P93392 P93392 S25-XP1 DNA Binding Protein. ;, mRNA sequence"; source: *Glycine max* (soybean); Title: "Public Soybean EST Project" (Unpublished (1999)).

BG510218 NCBI acc. No. BG510218 (gi: 13480875) (Mar. 28, 2001); Shoemaker,R., et al. "sac64a08.y1 Gm-c1072 *Glycine max* cDNA clone Genome Systems Clone ID: Gm-c1072-16 5' similar to TR:O80387 O80387 Ethylene Responsive Element Binding Factor. ;, mRNA sequence"; source: *Glycine max* (soybean); Title: "Public Soybean EST Project" (Unpublished (1999)).

BG581520 NCBI acc. No. BG581520 (gi: 13596584) (Apr. 11, 2001); Fedorova,M., et al. "EST483254 GVN *Medicago truncatula* cDNA clone pGVN-6513 5' end, mRNA sequence"; source: *Medicago truncatula* (barrel medic); Title: "ESTs from one month old nitrogen-fixing root nodules of *Medicago truncatula* , 2001" (Unpublished (2001)).

BG581532 NCBI acc. No. BG581532 (gi: 13596584) (Apr. 11, 2001); Fedorova,M., et al. "EST483254 GVN *Medicago truncatula* cDNA clone pGVN-6513 5' end, mRNA sequence"; source: *Medicago truncatula* (barrel medic); Title: "ESTs from one month old nitrogen-fixing root nodules of *Medicago truncatula*, 2001" (Unpublished (2001)).

BG582281 NCBI acc. No. BG582281 (gi: 13597345) (Apr. 11, 2001); Fedorova,M., et al. "EST484022 GVN *Medicago truncatula* cDNA clone pGVN-69023 5' end, mRNA sequence"; source: *Medicago truncatula* (barrel medic); Title: "ESTs from one month old nitrogen-fixing root nodules of *Medicago truncatula*, 2001" (Unpublished (2001)).

BG582759 NCBI acc. No. BG582759 (gi: 13597823) (Apr. 11, 2001); Fedorova,M., et al. "EST484505 GVN *Medicago truncatula* cDNA clone pGVN-70J21 5' end, mRNA sequence"; source: *Medicago truncatula* (barrel medic); Title: "ESTs from one month old nitrogen-fixing root nodules of *Medicago truncatula*, 2001" (Unpublished (2001)).

BG582854 NCBI acc. No. BG582854 (gi: 13597918) (Apr. 11, 2001); Fedorova,M., et al. "EST484600 GVN *Medicago truncatula* cDNA clone pGVN-70L24 5' end, mRNA sequence"; source: *Medicago truncatula* (barrel medic); Title: "ESTs from one month old nitrogen-fixing root nodules of *Medicago truncatula*, 2001" (Unpublished (2001)).

BG582869 NCBI acc. No. BG582869 (gi: 13597933) (Apr. 11, 2001); Fedorova,M., et al. "EST484615 GVN *Medicago truncatula* cDNA clone pGVN-70P6 5' end, mRNA sequence"; source: *Medicago truncatula* (barrel medic); Title: "ESTs from one month old nitrogen-fixing root nodules of *Medicago truncatula*, 2001" (Unpublished (2001)).

BG583042 NCBI acc. No. BG583042 (gi: 13598098) (Apr. 11, 2001); Fedorova,M., et al. "EST484784 GVN *Medicago truncatula* cDNA clone pGVN-71O4 5' end, mRNA sequence"; source: *Medicago truncatula* (barrel medic); Title: "ESTs from one month old nitrogen-fixing root nodules of *Medicago truncatula*, 2001" (Unpublished (2001)).

BG583111 NCBI acc. No. BG583111 (gi: 13598175) (Apr. 11, 2001); Fedorova,M., et al. "EST484861 GVN *Medicago truncatula* cDNA clone pGVN-71N15 5' end, mRNA sequence"; source: *Medicago truncatula* (barrel medic); Title: "ESTs from one month old nitrogen-fixing root nodules of *Medicago truncatula*, 2001" (Unpublished (2001)).

BG583265 NCBI acc. No. BG583265 (gi: 13598329) (Apr. 11, 2001); Fedorova,M., et al. "EST485016 GVN *Medicago truncatula* cDNA clone pGVN-72M9 5' end, mRNA sequence"; source: *Medicago truncatula* (barrel medic); Title: "ESTs from one month old nitrogen-fixing root nodules of *Medicago truncatula*, 2001" (Unpublished (2001)).

BG583402 NCBI acc. No. BG583402 (gi: 13598466) (Apr. 11, 2001); Fedorova,M., et al. "EST485154 GVN *Medicago truncatula* cDNA clone pGVN-73K11 5' end, mRNA sequence"; source: *Medicago truncatula* (barrel medic); Title: "ESTs from one month old nitrogen-fixing root nodules of *Medicago truncatula*, 2001" (Unpublished (2001)).

BG583604 NCBI acc. No. BG583604 (gi: 13598668) (Apr. 11, 2001); Fedorova,M., et al. "EST485356 GVN *Medicago truncatula* cDNA clone pGVN-73L16 5' end, mRNA sequence"; source: *Medicago truncatula* (barrel medic); Title: "ESTs from one month old nitrogen-fixing root nodules of *Medicago truncatula*, 2001" (Unpublished (2001)).

BG583626 NCBI acc. No. BG583626 (gi: 13598690) (Apr. 11, 2001); Fedorova,M., et al. "EST485378 GVN *Medicago truncatula* cDNA clone pGVN-73P18 5' end, mRNA sequence"; source:

*Medicago truncatula* (barrel medic); Title: "ESTs from one month old nitrogen-fixing root nodules of *Medicago truncatula*, 2001" (Unpublished (2001)).

BG583711 NCBI acc. No. BG583711 (gi: 13598775) (Apr. 11, 2001); Fedorova,M., et al. "EST485464 GVN *Medicago truncatula* cDNA clone pGVN-74C14 5' end, mRNA sequence"; source: *Medicago truncatula* (barrel medic); Title: "ESTs from one month old nitrogen-fixing root nodules of *Medicago truncatula*, 2001" (Unpublished (2001)).

BG583745 NCBI acc. No. BG583745 (gi: 13598809) (Apr. 11, 2001); Fedorova,M., et al. "EST485500 GVN *Medicago truncatula* cDNA clone pGVN-74124 5' end, mRNA sequence"; source: *Medicago truncatula* (barrel medic); Title: "ESTs from one month old nitrogen-fixing root nodules of *Medicago truncatula*, 2001" (Unpublished (2001)).

BG583761 NCBI acc. No. BG583761 (gi: 13598825) (Apr. 11, 2001); Fedorova,M., et al. "EST485516 GVN *Medicago truncatula* cDNA clone pGVN-74M12 5' end, mRNA sequence"; source: *Medicago truncatula* (barrel medic); Title: "ESTs from one month old nitrogen-fixing root nodules of *Medicago truncatula*, 2001" (Unpublished (2001)).

BG587841 NCBI acc. No. BG587841 (gi: 13602905) (Apr. 11, 2001); Harrison,M.J., et al. "EST489616 KV3 *Medicago truncatula* cDNA clone pKV3-13E10 5' end, mRNA sequence"; source: *Medicago truncatula* (barrel medic); Title: "ESTs from roots of *Medicago truncatula* after colonization with *Glomus versiforme*, 2001" (Unpublished (2001)).

BG591632 NCBI acc. No. BG591632 (gi: 13609772) (Apr. 12, 2001); Zhang,P., et al. "EST499474 *P. infestans*-challenged leaf *Solanum tuberosum* cDNA clone BPLI9N11 5' sequence, mRNA sequence"; source: *Solanum tuberosum* (potato); Title: "Generation of ESTs from Potato Leaves Challenged with *Phytophthora infestans*, Incompatible Reaction" (Unpublished (2000)).

BG592132 NCBI acc. No. BG592132 (gi: 13610272) (Apr. 12, 2001); Zhang,P., et al. "EST499974 *P. infestans*-challenged leaf *Solanum tuberosum* cDNA clone BPLI11110 5' sequence, mRNA sequence"; source: *Solanum tuberosum* (potato); Title: "Generation of ESTs from Potato Leaves Challenged with *Phytophthora infestans*, Incompatible Reaction" (Unpublished (2000)).

BG606428 NCBI acc. No. BG606428 (gi: 13656411) (Apr. 17, 2001); Anderson,O.D., et al. "WHE2956_B01_C02ZS Wheat dormant embryo cDNA library *Triticum aestivum* cDNA clone WHE2956_B01_C02, mRNA sequence"; source: *Triticum aestivum* (bread wheat); Title: "The structure and function of the expressed portion of the wheat genomes - Dormant embryo cDNA library" (Unpublished (2001)).

BG642691 NCBI acc. No. BG642691 (gi: 13777572) (Apr. 24, 2001); van der Hoeven,R., et al. "EST510885 tomato shoot/meristem *Solanum lycopersicum* cDNA clone cTOF25K14 5' sequence, mRNA sequence"; source: *Solanum lycopersicum* (*Lycopersicon esculentum*); Title: "Generation of ESTs from tomato shoot/meristem tissue" (Unpublished (2001)).

BG643340 NCBI acc. No. BG643340 (gi: 13778565) (Apr. 24, 2001); van der Hoeven,R., et al. "EST511534 tomato shoot/meristem *Solanum lycopersicum* cDNA clone cTOF27E22 5' sequence, mRNA sequence"; source: *Solanum lycopersicum* (*Lycopersicon esculentum*); Title: "Generation of ESTs from tomato shoot/meristem tissue" (Unpublished (2001)).

BG644911 NCBI acc. No. BG644911 (gi: 13780023) (Apr. 24, 2001); VandenBosch,K., et al. "EST506530 KV3 *Medicago truncatula* cDNA clone pKV3-38P9 5' end, mRNA sequence"; source: *Medicago truncatula* (barrel medic); Title: "ESTs from roots of *Medicago truncatula* 72 h after Rhizobium inoculation, 2001" (Unpublished (2001)).

BG645028 NCBI acc. No. BG645028 (gi: 13780140) (Apr. 24, 2001); VandenBosch,K., et al. "EST506647 KV3 *Medicago truncatula* cDNA clone pKV3-39C23 5' end, mRNA sequence"; source: *Medicago truncatula* (barrel medic); Title: "ESTs from roots of *Medicago truncatula* 72 h after Rhizobium inoculation, 2001" (Unpublished (2001)).

BG646470 NCBI acc. No. BG646470 (gi: 13781582) (Apr. 24 , 2001); Hahn,M.G., et al. "EST508089 HOGA *Medicago truncatula* cDNA clone pHOGA-7L24 5' end, mRNA sequence"; source:

*Medicago truncatula* (barrel medic); Title: "ESTs from roots of *Medicago truncatula* treated with oligogalacturonides of DP 6-20" (Unpublished (2001)).

BG646567 NCBI acc. No. BG646567 (gi: 13781679) (Apr. 24, 2001); Hahn,M.G., et al. "EST508186 HOGA *Medicago truncatula* cDNA clone pHOGA-9M7 5' end, mRNA sequence"; source: *Medicago truncatula* (barrel medic); Title: "ESTs from roots of *Medicago truncatula* treated with oligogalacturonides of DP 6-20" (Unpublished (2001)).

BG646774 NCBI acc. No. BG646774 (gi: 13781886) (Apr. 24, 2001); Hahn,M.G., et al. "EST508393 HOGA *Medicago truncatula* cDNA clone pHOGA-9D12 5' end, mRNA sequence"; source: *Medicago truncatula* (barrel medic); Title: "ESTs from roots of *Medicago truncatula* treated with oligogalacturonides of DP 6-20" (Unpublished (2001)).

BG647592 NCBI acc. No. BG647592 (gi: 13782704) (Apr. 24, 2001); Hahn,M.G., et al. "EST509211 HOGA *Medicago truncatula* cDNA clone pHOGA-17G24 5' end, mRNA sequence"; source: *Medicago truncatula* (barrel medic); Title: "ESTs from roots of *Medicago truncatula* treated with oligogalacturonides of DP 6-20" (Unpublished (2001)).

BG647771 NCBI acc. No. BG647771 (gi: 13782883) (Apr. 24, 2001); Hahn,M.G., et al. "EST509390 HOGA *Medicago truncatula* cDNA clone pHOGA-17J8 5' end, mRNA sequence"; source: *Medicago truncatula* (barrel medic); Title: "ESTs from roots of *Medicago truncatula* treated with oligogalacturonides of DP 6-20" (Unpublished (2001)).

BG647799 NCBI acc. No. BG647799 (gi: 13782911) (Apr. 24, 2001); Hahn,M.G., et al. "EST509418 HOGA *Medicago truncatula* cDNA clone pHOGA-17N20 5' end, mRNA sequence"; source: *Medicago truncatula* (barrel medic); Title: "ESTs from roots of *Medicago truncatula* treated with oligogalacturonides of DP 6-20" (Unpublished (2001)).

BG647917 NCBI acc. No. BG647917 (gi: 13783029) (Apr. 24, 2001); Hahn,M.G., et al. "EST509536 HOGA *Medicago truncatula* cDNA clone pHOGA-18C12 5' end, mRNA sequence"; source: *Medicago truncatula* (barrel medic); Title: "ESTs from roots of *Medicago truncatula* treated with oligogalacturonides of DP 6-20" (Unpublished (2001)).

BG648548 NCBI acc. No. BG648548 (gi: 13783660) (Apr. 24, 2001); Hahn,M.G., et al. "EST510167 HOGA *Medicago truncatula* cDNA clone pHOGA-2311 5' end, mRNA sequence"; source: *Medicago truncatula* (barrel medic); Title: "ESTs from roots of *Medicago truncatula* treated with oligogalacturonides of DP 6-20" (Unpublished (2001)).

BG650102 NCBI acc. No. BG650102 (gi: 13787510) (Apr. 25, 2001); Shoemaker,R., et al. "sad79h09.y1 Gm-c1051 *Glycine max* cDNA clone Genome Systems Clone ID: Gm-c1051-6522 5' similar to TR:P93822 P93822 F19P19.18. ;, mRNA sequence"; source: *Glycine max* (soybean); Title: "Public Soybean EST Project" (Unpublished (1999)).

BG652103 NCBI acc. No. BG652103 (gi: 13789512) (Apr. 25, 2001); Shoemaker,R., et al. "sad74b10.y1 Gm-c1051 *Glycine max* cDNA clone Genome Systems Clone ID: Gm-c1051-5851 5' similar to TR:Q40477 Q40477 EREBP-3. ;, mRNA sequence"; source: *Glycine max* (soybean); Title: "Public Soybean EST Project" (Unpublished (1999)).

BG726262 NCBI acc. No. BG726262 (gi: 14011340) (May 9, 2001); Shoemaker,R., et al. "sae13f10.y1 Gm-c1067 *Glycine max* cDNA clone Genome Systems Clone ID: Gm-c1067-2947 5' similar to TR:Q9SJX3 Q9SJX3 Ethylene Reponse Factor-Like AP2 Domain Transcription Factor. ;, mRNA sequence"; source: *Glycine max* (soybean); Title: "Public Soybean EST Project" (Unpublished (1999)).

BG789540 NCBI acc. No. BG789540 (gi: 14125102) (May 16, 2001); Shoemaker,R., et al. "sae65a11.y1 Gm-c1064 *Glycine max* cDNA clone Genome Systems Clone ID: Gm-c1064-3093 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).

BG790680 NCBI acc. No. BG790680 (gi: 14126242) (May 16, 2001); Shoemaker,R., et al. "sae75d09.y1 Gm-c1064 *Glycine max* cDNA clone Genome Systems Clone ID: Gm-c1064-4025 5' similar to TR:P93822 P93822 F19P19.18. ;, mRNA sequence"; source: *Glycine max* (soybean); Title: "Public Soybean EST Project" (Unpublished (1999)).

BG790996 NCBI acc. No. BG790996 (gi: 14126558) (May 16, 2001); Shoemaker,R., et al. "sae72h12.y1 Gm-c1064 *Glycine max* cDNA clone Genome Systems Clone ID: Gm-c1064-3840 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).

BG886550 NCBI acc. No. BG886550 (gi: 14263636) (May 30, 2001); van der Hoeven,R., et al. "EST512401 cSTD *Solanum tuberosum* cDNA clone cSTD1K11 5' sequence similar to similar to *Prunus armeniaca* AP2 domain containing protein, mRNA sequence"; source: *Solanum tuberosum* (potato); Title: "Generations of ESTs from dormant potato tubers" (Unpublished (2001)).

BH454277 NCBI acc. No. BH454277 (gi: 17639988) (Dec. 12, 2001); Ayele,M., et al. "BOGSI45TR BOGS *Brassica oleracea* genomic clone BOGSI45, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BH460596 NCBI acc. No. BH460596 (gi: 17650341) (Dec. 13, 2001); Ayele,M., et al. "BOGWG8OTR BOGW *Brassica oleracea* genomic clone BOGWG80, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BH517030 NCBI acc. No. BH517030 (gi: 17725120) (Dec. 13, 2001); Ayele,M., et al. "BOHRB76TF BOHR *Brassica oleracea* genomic clone BOHRB76, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BH519444 NCBI acc. No. BH519444 (gi: 17727529) (Dec. 13, 2001); Ayele,M., et al. "BOGKI41TF BOGK *Brassica oleracea* genomic clone BOGKI41, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BH603154 NCBI acc. No. BH603154 (gi: 17855600) (Dec. 15, 2001); Ayele,M., et al. "BOGDP09TF BOGD *Brassica oleracea* genomic clone BOGDP09, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BH672011 NCBI acc. No. BH672011 (gi: 18737461) (Feb. 19, 2002); Ayele,M., et al. "BOHYF95TR BO_2_3_KB *Brassica oleracea* genomic clone BOHYF95, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BH683728 NCBI acc. No. BH683728 (gi: 18754171) (Feb. 19, 2002); Ayele,M., et al. "BOHTE23TR BO_2_3_KB *Brassica oleracea* genomic clone BOHTE23, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BH715240 NCBI acc. No. BH715240 (gi: 18809815) (Feb. 20, 2002); Ayele,M., et al. "BOHVQ41TR BO_2_3_KB *Brassica oleracea* genomic clone BOHVQ41, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

BI263133 NCBI acc. No. BI263133 (gi: 14864047) (Jul 18 2001); Liu,J., et al. "NF085D03PL1F1030 Phosphate starved leaf *Medicago truncatula* cDNA clone NF085D03PL 5&pos;, mRNA sequence"; source: *Medicago truncatula* (barrel medic); Title: "Expressed Sequence Tags from the Samuel Roberts Noble Foundation *Medicago truncatula* phosphate-starved leaf library" (Unpublished (2000)).

BI265074 NCBI acc. No. BI265074 (gi: 14867921) (Jul. 18, 2001); Korth,K., et al. "NF078F08IN1F1075 Insect herbivory *Medicago truncatula* cDNA clone NF078F08IN 5&pos;, mRNA sequence"; source: *Medicago truncatula* (barrel medic); Title: "Expressed Sequence Tags from the Samuel Roberts Noble Foundation *Medicago truncatula* insect herbivory library" (Unpublished (2000)).

BI265685 NCBI acc. No. BI265685 (gi: 14869141) (Jul. 18, 2001); Korth,K., et al. "NF083D07IN1F1062 Insect herbivory *Medicago truncatula* cDNA clone NF083D07IN 5&pos;, mRNA sequence"; source: *Medicago truncatula* (barrel medic); Title: "Expressed Sequence Tags from the Samuel Roberts Noble Foundation *Medicago truncatula* insect herbivory library" (Unpublished (2000)).

BI266358 NCBI acc. No. BI266358 (gi: 14870395) (Jul. 18, 2001); Korth,K., et al. "NF084D12IN1F1102 Insect herbivory *Medicago truncatula* cDNA clone NF084D12IN 5&pos;, mRNA sequence"; source: *Medicago truncatula* (barrel medic); Title: "Expressed Sequence Tags from the Samuel Roberts Noble Foundation *Medicago truncatula* insect herbivory library" (Unpublished (2000)).

BI271853 NCBI acc. No. BI271853 (gi: 14880681) (Jul. 18, 2001); Torres-Jerez,l., et al. "NF013E04FL1F1034 Developing flower *Medicago truncatula* cDNA clone NF013E04FL 5&pos;, mRNA sequence"; source: *Medicago truncatula* (barrel medic); Title: "Expressed Sequence Tags from the Samuel Roberts Noble Foundation *Medicago truncatula* flower library" (Unpublished (2001)).

BI305323 NCBI acc. No. BI305323 (gi: 14980645) (Jul. 20, 2001); Reddy,A.R., et al. "NRS2R_1_N04 Drought stress (root) *Oryza sativa* (indica cultivar-group) cDNA clone NRS2R_1_N04 3&pos;, mRNA sequence"; source: *Oryza sativa* (indica cultivar- group); Title: "Novel EST enrichment with normalized cDNA libraries from drought stressed rice (*Oryza sativa* L.cv Nagina 22)" (Unpublished (2001)).

BI305776 NCBI acc. No. BI305776 (gi: 14981085) (Jul. 20, 2001); Reddy,A.R., et al. "NL_1_L02 Drought stress (leaf) *Oryza sativa* (indica cultivar-group) cDNA clone NL_1_L02 3&pos;, mRNA sequence"; source: *Oryza sativa* (indica cultivar-group); Title: "Novel EST enrichment with normalized cDNA libraries from drought stressed rice (*Oryza sativa* L.cv Nagina 22)" (Unpublished (2001)).

BI321594 NCBI acc. No. BI321594 (gi: 15000780) (Jul. 23, 2001); Shoemaker,R., et al. "saf15b09.y3 Gm-c1076 *Glycine max* cDNA clone Genome Systems Clone ID: Gm-c1076-834 5' similar to TR:Q9ZR85 Q9ZR85 Ethylene-Responsive Element Binding Protein Homolog. ;, mRNA sequence"; source: *Glycine max* (soybean); Title: "Public Soybean EST Project" (Unpublished (1999)).

BI421270 NCBI acc. No. BI421270 (gi: 15194638) (Aug. 16, 2001); Alcala,J., et al. "EST531936 tomato callus, TAMU *Solanum lycopersicum* cDNA clone cLEC66M2 5' end, mRNA sequence"; source: *Solanum lycopersicum* (*Lycopersicon esculentum*); Title: "Generation of ESTs from tomato callus tissue" (Unpublished (1999)).

BI421507 NCBI acc. No. BI421507 (gi: 15195085) (Aug. 16, 2001); Alcala,J., et al. "EST532173 tomato callus, TAMU *Solanum lycopersicum* cDNA clone cLEC67G17 5' end, mRNA sequence"; source: *Solanum lycopersicum* (*Lycopersicon esculentum*); Title: "Generation of ESTs from tomato callus tissue" (Unpublished (1999)).

BI421558 NCBI acc. No. BI421558 (gi: 15195182) (Aug. 16, 2001); Alcala,J., et al. "EST532224 tomato callus, TAMU *Solanum lycopersicum* cDNA clone cLEC67A22 5' end, mRNA sequence"; source: *Solanum lycopersicum* (*Lycopersicon esculentum*); Title: "Generation of ESTs from tomato callus tissue" (Unpublished (1999)).

BI421895 NCBI acc. No. BI421895 (gi: 15195839) (Aug. 16, 2001); Alcala,J., et al. "EST532561 tomato callus, TAMU *Solanum lycopersicum* cDNA clone cLEC68E16 5' end, mRNA sequence"; source: *Solanum lycopersicum* (*Lycopersicon esculentum*); Title: "Generation of ESTs from tomato callus tissue" (Unpublished (1999)).

BI422101 NCBI acc. No. BI422101 (gi: 15196219) (Aug. 16, 2001); Alcala,J., et al. "EST532767 tomato callus, TAMU *Solanum lycopersicum* cDNA clone cLEC69A23 5' end, mRNA sequence"; source: *Solanum lycopersicum* (*Lycopersicon esculentum*); Title: "Generation of ESTs from tomato callus tissue" (Unpublished (1999)).

BI424734 NCBI acc. No. BI424734 (gi: 15201177) (Aug. 16, 2001); Shoemaker,R., et al. "sah48a08.y2 Gm-c1036 *Glycine max* cDNA clone Genome Systems Clone ID: Gm-c1036-4623 5' similar to TR:O81365 O81365 AP2 Domain Containing Protein ;, mRNA sequence"; source: *Glycine max* (soybean); Title: "Public Soybean EST Project" (Unpublished (1999)).

BI427468 NCBI acc. No. BI427468 (gi: 15204700) (Aug. 16, 2001); Shoemaker,R., et al. "sah80f02.y1 Gm-c1050 *Glycine max* cDNA clone Genome Systems Clone ID: Gm-c1050-2547 5' similar to Sw:ERF5_ARATH O80341 Ethylene Responsive Element Binding Factor 5 ;, mRNA sequence"; source: *Glycine max* (soybean); Title: "Public Soybean EST Project" (Unpublished (1999)).

BI468669 NCBI acc. No. BI468669 (gi: 15284778) (Aug. 24, 2001); Shoemaker,R., et al. "sai01h08.y1 Gm-c1050 *Glycine max* cDNA clone Genome Systems Clone ID: Gm-c1050-4575 5' similar to TR:Q40478 Q40478 EREBP-4. ;, mRNA sequence"; source: *Glycine max* (soybean); Title: "Public Soybean EST Project" (Unpublished (1999)).

BI469284 NCBI acc. No. BI469284 (gi: 15285393) (Aug. 24, 2001); Shoemaker,R., et al. "sai09h04.y1 Gm-c1053 *Glycine max* cDNA clone Genome Systems Clone ID: Gm-c1053-3031 5' similar to TR:O23143 O23143 Putative CKC2. ;, mRNA sequence"; source: *Glycine max* (soybean); Title: "Public Soybean EST Project" (Unpublished (1999)).

BI784879 NCBI acc. No. BI784879 (gi: 15812604) (Oct. 1, 2001); Shoemaker,R., et al. "saf94g11.y3 Gm-c1079 *Glycine max* cDNA clone Genome Systems Clone ID: Gm-c1079-1845 5' similar to TR:Q40478 Q40478 EREBP-4. ;, mRNA sequence"; source: *Glycine max* (soybean); Title: "Public Soybean EST Project" (Unpublished (1999)).

BI786168 NCBI acc. No. BI786168 (gi: 15813893) (Oct. 1, 2001); Shoemaker,R., et al. "sai33g03.y1 Gm-c1065 *Glycine max* cDNA clone Genome Systems Clone ID: Gm-c1065-5285 5' similar to TR:O80387 O80387 Ethylene Responsive Element Binding Factor. ;, mRNA sequence"; source: *Glycine max* (soybean); Title: "Public Soybean EST Project" (Unpublished (1999)).

BI787734 NCBI acc. No. BI787734 (gi: 15815459) (Oct. 1, 2001); Shoemaker,R., et al. "sag75b04.y1 Gm-c1084 *Glycine max* cDNA clone Genome Systems Clone ID: Gm-c1084-55 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BI893228 NCBI acc. No. BI893228 (gi: 16105488) (Oct. 12, 2001); Shoemaker,R., et al. "sai63b03.y1 Gm-c1068 *Glycine max* cDNA clone Genome Systems Clone ID: Gm-c1068-3149 5' similar to TR:O80387 O80387 Ethylene Responsive Element Binding Factor. ;, mRNA sequence"; source: *Glycine max* (soybean); Title: "Public Soybean EST Project" (Unpublished (1999)).

BI973708 NCBI acc. No. BI973708 (gi: 16348113) (Oct. 23, 2001); Shoemaker,R., et al. "sai91g09.y1 Gm-c1065 *Glycine max* cDNA clone Genome Systems Clone ID: Gm-c1065-8393 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BI973872 NCBI acc. No. BI973872 (gi: 16348277) (Oct. 23, 2001); Shoemaker,R., et al. "sai93h12.y1 Gm-c1065 *Glycine max* cDNA clone Genome Systems Clone ID: Gm-c1065-8807 5' similar to Sw:ERFI_ARATH O80337 Ethylene Responsive Element Binding Factor 1 ;, mRNA sequence"; source: *Glycine max* (soybean); Title: "Public Soybean EST Project" (Unpublished (1999)).

BM062245 NCBI acc. No. BM062245 (gi: 22782363) (Sep. 11, 2002); Lee,S., et al. "KS01040C11 KS01 *Capsicum annuum* cDNA, mRNA sequence"; source: *Capsicum annuum*; Title: "Generation of Expressed Sequence Tags from Hot Pepper (*Capsicum annuum L.*) and Sequence Analysis in Relation to Hypersensitive Response Against Pathogen" (Unpublished (2001)).

BM075553 NCBI acc. No. BM075553 (gi: 16922376) (Nov. 13, 2001); Wen,T.J., et al. "MEST357-A11.T3 ISUM5-RN *Zea mays* cDNA clone MEST357-A11 3&pos;, mRNA sequence"; source: *Zea mays*; Title: "Expressed Sequence Tags from B73 Maize: various stages and tissues including seedlings treated with a variety of hormones" (Unpublished (2001)).

BM093669 NCBI acc. No. BM093669 (gi: 17022635) (Nov. 20, 2001); Shoemaker,R., et al. "saj12f09.y1 Gm-c1066 *Glycine max* cDNA clone Genome Systems Clone ID: Gm-c1066-2585 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BM094577 NCBI acc. No. BM094577 (gi: 17023543) (Nov. 20, 2001); Shoemaker,R., et al. "saj17g07.y1 Gm-c1066 *Glycine max* cDNA clone Genome Systems Clone ID: Gm-c1066-3014 5' similar to TR:O80387 O80387 Ethylene Responsive Element Binding Factor. ;, mRNA sequence"; source: *Glycine max* (soybean); Title: "Public Soybean EST Project" (Unpublished (1999)).

BM110901 NCBI acc. No. BM110901 (gi: 17073001) (Nov. 26, 2001); van der Hoeven,R., et al. "EST558437 potato roots *Solanum tuberosum* cDNA clone cPRO9J5 5' end, mRNA sequence"; source: *Solanum tuberosum* (potato); Title: "Generation of ESTs from potato roots" (Unpublished (2001)).

BM143375 NCBI acc. No. BM143375 (gi: 17153433) (Nov. 29, 2001); Shoemaker,R., et al. "saj43b11.y1 Gm-c1072 *Glycine max* cDNA clone Soybean Clone ID: Gm-c1072-2374 5' similar to TR:Q40478 Q40478 EREBP-4. ;, mRNA sequence"; source: *Glycine max* (soybean); Title: "Public Soybean EST Project" (Unpublished (1999)).

BM178361 NCBI acc. No. BM178361 (gi: 17401579) (Dec. 6, 2001); Shoemaker,R., et al. "saj72a10.y1 Gm-c1072 *Glycine max* cDNA clone Soybean Clone ID: Gm-c1072-5035 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BM178875 NCBI acc. No. BM178875 (gi: 17402093) (Dec. 6, 2001); Shoemaker,R., et al. "saj60f01.y1 Gm-c1072 *Glycine max* cDNA clone Soybean Clone ID: Gm-c1072-4105 5' similar to TR:P93822 P93822 F19P19.18. ;, mRNA sequence"; source: *Glycine max* (soybean); Title: "Public Soybean EST Project" (Unpublished (1999)).

BM268956 NCBI acc. No. BM268956 (gi: 17931996) (Dec. 18, 2001); Wen,T.J., et al. "MEST402-H11.univ ISUM5-Rn *Zea mays* cDNA clone MEST402-H11 3&pos;, mRNA sequence"; source: *Zea mays*; Title: "Expressed Sequence Tags from B73 Maize: various stages and tissues including seedlings treated with a variety of hormones" (Unpublished (2001)).

BM271048 NCBI acc. No. BM271048 (gi: 17964311) (Dec. 20, 2001); Shoemaker,R., et al. "sak04f02.y1 Gm-c1074 *Glycine max* cDNA clone Soybean Clone ID: Gm-c1074-5236 5&pos; similar to TR:Q40478 Q40478 EREBP-4. ;, mRNA sequence"; source: *Glycine max* (soybean); Title: "Public Soybean EST Project" (Unpublished (1999)).

BM332316 NCBI acc. No. BM332316 (gi: 18162477) (Jan. 16, 2002); Wen,T.J., et al. "MEST167-B07.T3 ISUM5-RN *Zea mays* cDNA clone MEST167-B07 3&pos;, mRNA sequence"; source: *Zea mays*; Title: "Expressed Sequence Tags from B73 Maize: various stages and tissues including seedlings treated with a variety of hormones" (Unpublished (2001)).

BM332461 NCBI acc. No. BM332461 (gi: 18162622) (Jan. 16, 2002); Wen,T.J., et al. "MEST169-C11.T3 ISUM5-RN *Zea mays* cDNA clone MEST169-C11 3&pos;, mRNA sequence"; source: *Zea mays*; Title: "Expressed Sequence Tags from B73 Maize: various stages and tissues including seedlings treated with a variety of hormones" (Unpublished (2001)).

BM348130 NCBI acc. No. BM348130 (gi: 18172742) (Jan. 16, 2002); Wen,T.J., et al. "MEST286-H07.T3 ISUM5-RN *Zea mays* cDNA clone MEST286-H07 3&pos;, mRNA sequence"; source: *Zea mays*; Title: "Expressed Sequence Tags from B73 Maize: various stages and tissues including seedlings treated with a variety of hormones" (Unpublished (2001)).

BM348921 NCBI acc. No. BM348921 (gi: 18173533) (Jan. 16, 2002); Wen,T.J., et al. "MEST303-H12.T3 ISUM5-RN *Zea mays* cDNA clone MEST303-H12 3, mRNA sequence"; source: *Zea mays*;

Title: "Expressed Sequence Tags from B73 Maize: various stages and tissues including seedlings treated with a variety of hormones" (Unpublished (2001)).

BM403974 NCBI acc. No. BM403974 (gi: 18255379) (Jan. 22, 2002); Restrepo,S., et al. "EST578301 *P. infestans*-challenged potato leaf, compatible reaction *Solanum tuberosum* cDNA clone PPCCR61 5&pos; end, mRNA sequence"; source: *Solanum tuberosum* (potato); Title: "Generation of ESTs from Potato Leaves Challenged with *Phytophthora infestans*, Compatible Interaction" (Unpublished (2000)).

BM409157 NCBI acc. No. BM409157 (gi: 18260787) (Jan. 22, 2002); Alcala,J., et al. "EST583484 tomato breaker fruit *Solanum lycopersicum* cDNA clone cLEG47M16 5&pos; end, mRNA sequence"; source: *Solanum lycopersicum* (*Lycopersicon esculentum*); Title: "Generation of ESTs from tomato fruit tissue, breaker stage (2002)" (Unpublished (2002)).

BM411708 NCBI acc. No. BM411708 (gi: 18263338) (Jan. 22, 2002); Alcala,J., et al. "EST586035 tomato breaker fruit *Solanum lycopersicum* cDNA clone cLEG57L21 5' end, mRNA sequence"; source: *Solanum lycopersicum* (*Lycopersicon esculentum*); Title: "Generation of ESTs from tomato fruit tissue, breaker stage (2002)" (Unpublished (2002)).

BM412823 NCBI acc. No. BM412823 (gi: 18264453) (Jan. 22, 2002); Alcala,J., et al. "EST587150 tomato breaker fruit *Solanum lycopersicum* cDNA clone cLEG61C12 5' end, mRNA sequence"; source: *Solanum lycopersicum* (*Lycopersicon esculentum*); Title: "Generation of ESTs from tomato fruit tissue, breaker stage (2002)" (Unpublished (2002)).

BM412928 NCBI acc. No. BM412928 (gi: 18264558) (Jan. 22, 2002); Alcala,J., et al. "EST587255 tomato breaker fruit *Solanum lycopersicum* cDNA clone cLEG61N3 5' end, mRNA sequence"; source: *Solanum lycopersicum* (*Lycopersicon esculentum*); Title: "Generation of ESTs from tomato fruit tissue, breaker stage (2002)" (Unpublished (2002)).

BM436925 NCBI acc. No. BM436925 (gi: 18458647) (Jan. 31, 2002); Cramer,G.R., et al. "VVA011E03_53345 An expressed sequence tag database for abiotic stressed leaves of *Vitis vinifera* var. Chardonnay *Vitis vinifera* cDNA clone VVA011E03 5, mRNA sequence"; source: *Vitis vinifera*; Title: "An expressed sequence tag database for abiotic stressed leaves of *Vitis vinifera* var. Chardonnay" (Unpublished (2002)).

BM437083 NCBI acc. No. BM437083 (gi: 18458805) (Jan. 31, 2002); Cramer,G.R., et al. "VVA014A06_53661 An expressed sequence tag database for abiotic stressed leaves of *Vitis vinifera* var. Chardonnay *Vitis vinifera* cDNA clone VVA014A06 5, mRNA sequence"; source: *Vitis vinifera*; Title: "An expressed sequence tag database for abiotic stressed leaves of *Vitis vinifera* var. Chardonnay" (Unpublished (2002)).

BM437580 NCBI acc. No. BM437580 (gi: 18459302) (Jan. 31, 2002); Cramer,G.R., et al. "VVA021G02_54655 An expressed sequence tag database for abiotic stressed leaves of *Vitis vinifera* var. Chardonnay *Vitis vinifera* cDNA clone VVA021G02 5, mRNA sequence"; source: *Vitis vinifera*; Title: "An expressed sequence tag database for abiotic stressed leaves of *Vitis vinifera* var. Chardonnay" (Unpublished (2002)).

BM535956 NCBI acc. No. BM535956 (gi: 18814998) (Feb. 20, 2002); Alcala,J., et al. "EST588978 tomato breaker fruit *Solanum lycopersicum* cDNA clone cLEG70J23 5' end, mRNA sequence"; source: *Solanum lycopersicum* (*Lycopersicon esculentum*); Title: "Generation of ESTs from tomato fruit tissue, breaker stage (2002)" (Unpublished (2002)).

BM536165 NCBI acc. No. BM536165 (gi: 18815366) (Feb. 20, 2002); Alcala,J., et al. "EST589187 tomato breaker fruit *Solanum lycopersicum* cDNA clone cLEG71N23 5' end, mRNA sequence"; source: *Solanum lycopersicum* (*Lycopersicon esculentum*); Title: "Generation of ESTs from tomato fruit tissue, breaker stage (2002)" (Unpublished (2002)).

BM779603 NCBI acc. No. BM779603 (gi: 19109483) (Mar. 4, 2002); VandenBosch,K., et al. "EST590179 KV2 *Medicago truncatula* cDNA clone pKV2-52D13, mRNA sequence"; source: *Medicago truncatula* (barrel medic); Title: "ESTs from roots of *Medicago truncatula* 48 hr after inoculation with *Sinorhizobium meliloti*" (Unpublished (2002)).

BM779692 NCBI acc. No. BM779692 (gi: 19109604) (Mar. 4, 2002); VandenBosch,K., et al. "EST590268 KV2 *Medicago truncatula* cDNA clone pKV2-52D24, mRNA sequence"; source: *Medicago truncatula* (barrel medic); Title: "ESTs from roots of *Medicago truncatula* 48 hr after inoculation with *Sinorhizobium meliloti*" (Unpublished (2002)).

BM886268 NCBI acc. No. BM886268 (gi: 19270021) (Mar. 8, 2002); Shoemaker,R., et al. "sam14e12.y1 Gm-c1068 *Glycine max* cDNA clone Soybean Clone ID: Gm-c1068-4824 5&pos similar to TR:O80387 O80387 Ethylene Responsive Element Binding Factor. ;, mRNA sequence"; source: *Glycine max* (soybean); Title: "Public Soybean EST Project" (Unpublished (1999)).

BM891538 NCBI acc. No. BM891538 (gi: 19346658) (Mar. 11, 2002); Shoemaker,R., et al. "sam28e11.y1 Gm-c1068 *Glycine max* cDNA clone Soybean Clone ID: Gm-c1068-5998 5' similar to TR:O80387 O80387 Ethylene Responsive Element Binding Factor. ;, mRNA sequence"; source: *Glycine max* (soybean); Title: "Public Soybean EST Project" (Unpublished (1999)).

BM954448 NCBI acc. No. BM954448 (gi: 19453038) (Mar .14 , 2002); Shoemaker,R., et al. "san03e10.y1 Gm-c1084 *Glycine max* cDNA clone Soybean Clone ID: Gm-c1084-2900 5' similar to SW:ERF5_ARATH 080341 Ethylene Responsive Element Binding Factor 5 ;, mRNA sequence"; source: *Glycine max* (soybean); Title: "Public Soybean EST Project" (Unpublished (1999)).

BP174381 NCBI acc. No. BP174381 (gi: 29056877) (Mar. 18, 2003); Ujino-lhara,T., et al. "BP174381 *Cryptomeria japonica* inner bark *Cryptomeria japonica* cDNA clone CC1389R 3&pos;, mRNA sequence"; source: *Cryptomeria japonica* (Japanese cedar); Title: "Expression analysis of ESTs derived from the inner bark of *Cryptomeria japonica*" (Plant Mol. Biol. 43 (4), 451-457 (2000)).

BQ045702 NCBI acc. No. BQ045702 (gi: 19819688) (Mar. 29, 2002); Zhang,P., et al. "EST594820 *P. infestans*-challenged potato leaf, incompatible reaction *Solanum tuberosum* cDNA clone BPLI12L1 5' end, mRNA sequence"; source: *Solanum tuberosum* (potato); Title: "Generation of ESTs from Potato Leaves Challenged with *Phytophthora infestans*, incompatible Interaction (2002)" (Unpublished (2002)).

BQ047502 NCBI acc. No. BQ047502 (gi: 19821488) (Mar. 29, 2002); Zhang,P., et al. "EST596620 *P. infestans*-challenged potato leaf, incompatible reaction *Solanum tuberosum* cDNA clone BPLI17L16 5&pos; end, mRNA sequence"; source: *Solanum tuberosum* (potato); Title: "Generation of ESTs from Potato Leaves Challenged with *Phytophthora infestans*, incompatible Interaction (2002)" (Unpublished (2002)).

BQ080756 NCBI acc. No. BQ080756 (gi: 19936180) (Apr. 4, 2002); Shoemaker,R., et al. "san37g07.y1 Gm-c1084 *Glycine max* cDNA clone Soybean Clone ID: Gm-c1084-6086 5' similar to TR:Q9SJX3 Q9SJX3 Ethylene Reponse Factor-Like AP2 Domain Transcription Factor. ;, mRNA sequence"; source: *Glycine max* (soybean); Title: "Public Soybean EST Project" (Unpublished (1999)).

BQ081056 NCBI acc. No. BQ081056 (gi: 19936893) (Apr. 4, 2002); Shoemaker,R., et al. "san18g09.y1 Gm-c1084 *Glycine max* cDNA clone Soybean Clone ID: Gm-c1084-4529 5' similar to TR:P93822 P93822 F19P19.18. ;, mRNA sequence"; source: *Glycine max* (soybean); Title: "Public Soybean EST Project" (Unpublished (1999)).

BQ081073 NCBI acc. No. BQ081073 (gi: 19936936) (Apr. 4, 2002); Shoemaker,R., et al. "san19a08.y1 Gm-c1084 *Glycine max* cDNA clone Soybean Clone ID: Gm-c1084-4240 5' similar to TR:P93822 P93822 F19P19.18. ;, mRNA sequence"; source: *Glycine max* (soybean); Title: "Public Soybean EST Project" (Unpublished (1999)).

BQ081329 NCBI acc. No. BQ081329 (gi: 19937535) (Apr. 4, 2002); Shoemaker,R., et al. "san23a04.y1 Gm-c1084 *Glycine max* cDNA clone Soybean Clone ID: Gm-c1084-4616 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).

BQ138491 NCBI acc. No. BQ138491 (gi: 20274617) (Apr. 23, 2002); Watson,B.S., et al. "NF003G09PH1F1070 Phoma-infected *Medicago truncatula* cDNA clone NF003G09PH 5', mRNA sequence"; source: *Medicago truncatula* (barrel medic); Title:

"Expressed Sequence Tags from the Samuel Roberts Noble Foundation *Medicago truncatula* Phoma-infected library" (Unpublished (2002)).
BQ165291 NCBI acc. No. BQ165291 (gi: 20307557) (Apr. 25, 2002); VandenBosch,K., et al. "EST611160 KVKC *Medicago truncatula* cDNA clone pKVKC-7F4, mRNA sequence"; source: *Medicago truncatula* (barrel medic); Title: "The *Medicago truncatula* &pos;kiloclone&pos; set; ESTs selected and re-arrayed from various libraries" (Unpublished (2002)).
BQ452871 NCBI acc. No. BQ452871 (gi: 21255983) (May 29, 2002); Shoemaker,R., et al. "sao92e10.y1 Gm-c1081 *Glycine max* cDNA clone Soybean Clone ID: Gm-c1081-3284 5' similar to SW:ERFI_ARATH O80337 Ethylene Responsive Element Binding Factor 1 ;, mRNA sequence"; source: *Glycine max* (soybean); Title: "Public Soybean EST Project" (Unpublished (1999)).
BQ469024 NCBI acc. No. BQ469024 (gi: 21276806) (May 30, 2002); Zhang,H., et al. "HM03C08r HM *Hordeum vulgare* subsp. vulgare cDNA clone HM03C08 5-Prime, mRNA sequence"; source: *Hordeum vulgare* subsp. vulgare; Title: "Large-scale analysis of the barley transcriptome based on expressed sequence tags" (Plant J. 40 (2), 276-290 (2004)).
BQ514194 NCBI acc. No. BQ514194 (gi: 21373063) (Jun. 10, 2002); Buell,C.R., et al. "EST621609 Generation of a set of potato cDNA clones for microarray analyses mixed potato tissues *Solanum tuberosum* cDNA clone STMIK39 5&pos; end, mRNA sequence"; source: *Solanum tuberosum* (potato); Title: "Generation of a set of potato cDNA clones for microarray analyses" (Unpublished (2002)).
BQ514195 NCBI acc. No. BQ514195 (gi: 21373064) (Jun. 10, 2002); Buell,C.R., et al. "EST621610 Generation of a set of potato cDNA clones for microarray analyses mixed potato tissues *Solanum tuberosum* cDNA clone STMIK39 3&pos; end, mRNA sequence"; source: *Solanum tuberosum* (potato); Title: "Generation of a set of potato cDNA clones for microarray analyses" (Unpublished (2002)).
BQ517082 NCBI acc. No. BQ517082 (gi: 21375951) (Jun. 10, 2002); Buell,C.R., et al. "EST624497 Generation of a set of potato cDNA clones for microarray analyses mixed potato tissues *Solanum tuberosum* cDNA clone STMJB52 5&pos; end, mRNA sequence"; source: *Solanum tuberosum* (potato); Title: "Generation of a set of potato cDNA clones for microarray analyses" (Unpublished (2002)).
BQ517083 NCBI acc. No. BQ517083 (gi: 21375952) (Jun. 10, 2002); Buell,C.R., et al. "EST624498 Generation of a set of potato cDNA clones for microarray analyses mixed potato tissues *Solanum tuberosum* cDNA clone STMJB52 3&pos; end, mRNA sequence"; source: *Solanum tuberosum* (potato); Title: "Generation of a set of potato cDNA clones for microarray analyses" (Unpublished (2002)).
BQ592225 NCBI acc. No. BQ592225 (gi: 26121808) (Dec. 6, 2002); Herwig,R., et al. "E012698-024-021-H24-SP6 MPIZ-ADIS-024-developing root *Beta vulgaris* cDNA clone 024-021-H24 5-PRIME, mRNA sequence"; source: *Beta vulgaris*; Title: "Construction of a unigene cDNA clone set by oligonucleotide fingerprinting allows access to 25 000 potential sugar beet genes" (Plant J. 32 (5), 845857 (2002)).
BQ623351 NCBI acc. No. BQ623351 (gi: 21650520) (Jul. 1, 2002); Bausher,M., et al. "USDA-FP_00442 Ridge pineapple sweet orange entire seedling *Citrus sinensis* cDNA clone USDA-FP_00442 5&pos;, mRNA sequence"; source: Citrus sinensis; Title: "Expressed sequence tags isolated from entire sweet orange (*C. sinensis* L. Osbeck) seedling" (Unpublished (2003)).
BQ628375 NCBI acc. No. BQ628375 (gi: 21676024) (Jul. 2, 2002); Shoemaker,R., et al. "sap46b10.y1 Gm-c1087 *Glycine max* cDNA clone Soybean Clone ID: Gm-c10873547 5' similar to SW:ERF5_ARATH O80341 Ethylene Responsive Element Binding Factor 5 ;, mRNA sequence"; source: *Glycine max* (soybean); Title: "Public Soybean EST Project" (Unpublished (1999)).
BQ630661 NCBI acc. No. BQ630661 (gi: 21678310) (Jul. 2, 2002); Shoemaker,R., et al. "sap29e09.y1 Gm-c1082 *Glycine max* cDNA clone Soybean Clone ID: Gm-c10824050 5' similar to TR:Q40478 Q40478 EREBP-4. ;, mRNA sequence"; source: *Glycine max* (soybean); Title: "Public Soybean EST Project" (Unpublished (1999)).
BQ743147 NCBI acc. No. BQ743147 (gi: 21889934) (Jul. 17, 2002); Shoemaker,R., et al. "saq60g01.y1 Gm-c1076 *Glycine max* cDNA clone Soybean Clone ID: Gm-c1076-4154 5' similar to SW:ERFI_ARATH 080337 Ethylene Responsive Element Binding Factor 1 ;, mRNA sequence"; source:*Glycine max* (soybean); Title: "Public Soybean EST Project" (Unpublished (1999)).
BQ762577 NCBI acc. No. BQ762577 (gi: 21971049) (Jul. 26, 2002); Hedley,P., et al. "EBro02_SQ004_H12_R root, 3 week, hydroponic grown, low nitrogen, cv Optic, EBro02 *Hordeum vulgare* subsp. vulgare cDNA clone EBro02_SQ004_H12 5, mRNA sequence"; source: *Hordeum vulgare* subsp. vulgare; Title: "Development of Barley Transcriptome Resources" (Unpublished (2001)).
BQ785400 NCBI acc. No. BQ785400 (gi: 21993872) (Jul 26 2002); Shoemaker,R., et al. "saq77c02.y1 Gm-c1076 *Glycine max* cDNA clone Soybean Clone ID: Gm-c1076-5859 5' similar to TR:Q9ZNR2 Q9ZNR2 Ethylene Response Factor 1. ;, mRNA sequence"; source: *Glycine max* (soybean); Title: "Public Soybean EST Project" (Unpublished (1999)).
BQ786714 NCBI acc. No. BQ786714 (gi: 21995186) (Jul. 26, 2002); Shoemaker,R., et al. "saq72c10.y1 Gm-c1076 *Glycine max* cDNA clone Soybean Clone ID: Gm-c1076-5132 5' similar to SW:ERF5_ARATH 080341 Ethylene Responsive Element Binding Factor 5 ;, mRNA sequence"; source: *Glycine max* (soybean); Title: "Public Soybean EST Project" (Unpublished (1999)).
BQ991410 NCBI acc. No. BQ991410 (gi: 22210945) (Aug. 21, 2002); Kozik,A., et al. "QGF22M18.yg.ab1 QG_EFGHJ lettuce serriola *Lactuca serriola* cDNA clone QGF22M18, mRNA sequence"; source: *Lactuca serriola*; Title: "Lettuce and Sunflower ESTs from the Compositae Genome Project" (Unpublished (2002)).
BU763420 NCBI acc. No. BU763420 (gi: 23730658) (Oct. 10, 2002); Shoemaker,R., et al. "sas42d05.y1 Gm-c1080 *Glycine max* cDNA clone Soybean Clone ID: Gm-c1080-6322 5'similar to TR:Q40478 Q40478 EREBP-4. ;, mRNA sequence"; source: *Glycine max* (soybean); Title: "Public Soybean EST Project" (Unpublished (1999)).
BU765444 NCBI acc. No. BU765444 (gi: 23734437) (Oct. 10, 2002); Shoemaker,R., et al. "sas18g12.y1 Gm-c1080 *Glycine max* cDNA clone Soybean Clone ID: Gm-c1080-4176 5' similar to SW:ERF5_ARATH O80341 Ethylene Responsive Element Binding Factor 5 ;, mRNA sequence"; source: *Glycine max* (soybean); Title: "Public Soybean EST Project" (Unpublished (1999)).
BU765819 NCBI acc. No. BU765819 (gi: 23735106) (Oct. 10, 2002); Shoemaker,R., et al. "sas20d07.y1 Gm-c1080 *Glycine max* cDNA clone Soybean Clone ID: Gm-c1080-4382 5' similar to SW:ERF5_ARATH O80341 Ethylene Responsive Element Binding Factor 5 ;, mRNA sequence"; source: *Glycine max* (soybean); Title: "Public Soybean EST Project" (Unpublished (1999)).
BU765920 NCBI acc. No. BU765920 (gi: 23735288) (Oct. 10, 2002); Shoemaker,R., et al. "sar82b04.y1 Gm-c1074 *Glycine max* cDNA clone Soybean Clone ID: Gm-c1074-8887 5' similar to TR:Q40478 Q40478 EREBP-4. ;, mRNA sequence"; source: *Glycine max* (soybean); Title: "Public Soybean EST Project" (Unpublished (1999)).
BU765924 NCBI acc. No. BU765924 (gi: 23735295) (Oct. 10, 2002); Shoemaker,R., et al. "sar82c04.y1 Gm-c1074 *Glycine max* cDNA clone Soybean Clone ID: Gm-c1074-8935 5' similar to TR:Q40478 Q40478 EREPB-4. ;, mRNA sequence"; source: *Glycine max* (soybean); Title: "Public Soybean EST Project" (Unpublished (1999)).
BU814218 NCBI acc. No. BU814218 (gi: 23971351) (Oct. 15, 2002); Unneberg,P., et al. "N026E12 Populus bark cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BU830292 NCBI acc. No. BU830292 (gi: 24007304) (Oct. 15, 2002); Unneberg,P., et al. "T006E02 Populus apical shoot cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BU832225 NCBI acc. No. BU832225 (gi: 24011454) (Oct. 15, 2002); Unneberg,P., et al. "T031A05 Populus apical shoot cDNA library *Populus tremula* x Populus tremuloides cDNA 5 prime, mRNA sequence"; source: *Populus tremula* x Populus tremuloides;

Title: "The poplar tree transcriptome: Analysis of expressed sequence tags from multiple libraries" (Unpublished (2002)).
BU837816 NCBI acc. No. BU837816 (gi: 24020612) (Oct. 16, 2002); Unneberg,P., et al. "T106A05 Populus apical shoot cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BU871861 NCBI acc. No. BU871861 (gi: 24063385) (Oct. 16 , 2002); Unneberg,P., et al. "Q035D06 Populus flower cDNA library *Populus trichocarpa* cDNA 5 prime, mRNA sequence"; source: *Populus trichocarpa (Populus balsamifera* subsp. trichocarpa); Title: "The poplar tree transcriptome: Analysis of expressed sequence tags from multiple libraries" (Unpublished (2002)).
BU874000 NCBI acc. No. BU874000 (gi: 24065524) (Oct. 16, 2002); Unneberg,P., et al. "Q063CO2 Populus flower cDNA library *Populus trichocarpa* cDNA 5 prime, mRNA sequence"; source: *Populus trichocarpa (Populus balsamifera* subsp. trichocarpa); Title: "The poplar tree transcriptome: Analysis of expressed sequence tags from multiple libraries" (Unpublished (2002)).
BU884339 NCBI acc. No. BU884339 (gi: 24075856) (Oct. 17, 2002); Unneberg,P., et al. "R009C12 Populus root cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BU884448 NCBI acc. No. BU884448 (gi: 24075965) (Oct. 17, 2002); Unneberg,P., et al. "R010G08 Populus root cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BU887519 NCBI acc. No. BU887519 (gi: 24080231) (Oct. 17, 2002); Unneberg,P., et al. "R062F03 Populus root cDNA library *Populus tremula* x Populus tremuloides cDNA 5 prime, mRNA sequence"; source: *Populus tremula* x Populus tremuloides; Title: "The poplar tree transcriptome: Analysis of expressed sequence tags from multiple libraries" (Unpublished (2002)).
BZ332067 NCBI acc. No. BZ332067 (gi: 24720629) (Nov. 6, 2002); Rabinowicz,P.D., et al. "hx25b08.b1 WGS-SbicolorF (JM107 adapted methyl filtered) *Sorghum bicolor* genomic clone hx25b08 5&pos;, genomic survey sequence"; source: *Sorghum bicolor* (sorghum); Title: "Genomic shotgun sequences from *Sorghum bicolor* (methyl-filtered)" (Unpublished (2002)).
BZ337899 NCBI acc. No. BZ337899 (gi: 24733043) (Nov. 6, 2002); Rabinowicz,P.D., et al. "ia91f11.b1 WGS-SbicolorF (JM107 adapted methyl filtered) *Sorghum bicolor* genomic clone ia91f11 5&pos;, genomic survey sequence"; source: *Sorghum bicolor* (sorghum); Title: "Genomic shotgun sequences from *Sorghum bicolor* (methyl-filtered)" (Unpublished (2002)).
BZ359367 NCBI acc. No. BZ359367 (gi: 25059121) (Nov. 18, 2002); Rabinowicz,P.D., et al. "id72f11.b1 WGS-ZmaysF (JM107 adapted methyl filtered) *Zea mays* genomic clone id72f11 5&pos;, genomic survey sequence"; source: *Zea mays*; Title: "Genomic shotgun sequences from *Zea mays* (methyl-filtered)" (Unpublished (2002)).
BZ489256 NCBI acc. No. BZ489256 (gi: 26995806) (Dec. 16, 2002); Ayele,M., et al. "BOOAW09TF BO_1.6_2_KB_tot *Brassica oleracea* genomic clone BOOAW09, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
BZ489264 NCBI acc. No. BZ489264 (gi: 26995814) (Dec 16 2002); Ayele,M., et al. "BOOAW09TR BO_1.6_2_KB_tot *Brassica oleracea* genomic clone BOOAW09, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).
CA019696 NCBI acc. No. CA019696 (gi: 24297040) (Oct. 23, 2002); Zhang,H., et al. "HV12M24r HV *Hordeum vulgare* subsp. vulgare cDNA clone HV12M24 5-PRIME, mRNA sequence"; source: *Hordeum vulgare* subsp. vulgare; Title: "Large-scale analysis of the barley transcriptome based on expressed sequence tags" (Plant J. 40 (2), 276-290 (2004)).
CA514062 NCBI acc. No. CA514062 (gi: 25014619) (Nov. 15, 2002); Lee,S., et al. "KS09016D12 KS09 *Capsicum annuum* cDNA, mRNA sequence"; source:*Capsicum annuum*; Title: "Generation of Expressed Sequence Tags from Hot Pepper (*Capsicum annuum* L.) and Sequence Analysis in Relation to Hypersensitive Response Against Pathogen" (Unpublished (2001)).
CA522916 NCBI acc. No. CA522916 (gi: 25036961) (Nov. 15, 2002); Lee,S., et al. "KS12015D10 KS12 *Capsicum annuum* cDNA, mRNA sequence"; source: *Capsicum annuum*; Title: "Generation of Expressed Sequence Tags from Hot Pepper (*Capsicum annuum* L.) and Sequence Analysis in Relation to Hypersensitive Response Against Pathogen" (Unpublished (2001)).
CA783253 NCBI acc. No. CA783253 (gi: 26045764) (Dec. 4, 2002); Shoemaker,R., et al. "sat21f08.y1 Gm-c1036 *Glycine max* cDNA clone Soybean Clone ID: Gm-c1036-14464 5' similar to TR:Q40478 Q40478 EREPB-4. ;, mRNA sequence"; source: *Glycine max* (soybean); Title: "Public Soybean EST Project" (Unpublished (1999)).
CA783313 NCBI acc. No. CA783313 (gi: 26045880) (Dec. 4, 2002); Shoemaker,R., et al. "sat22e09.y1 Gm-c1036 *Glycine max* cDNA clone Soybean Clone ID: Gm-c1036-14441 5' similar to TR:Q40478 Q40478 EREBP-4. ;, mRNA sequence"; source: *Glycine max* (soybean); Title: "Public Soybean EST Project" (Unpublished (1999)).
CA799724 NCBI acc. No. CA799724 (gi: 26056810) (Dec. 5, 2002); Shoemaker,R., et al. "sat61h01.y1 Gm-c1056 *Glycine soja* cDNA clone Soybean Clone ID: Gm-c1056-6098 5' similar to TR:Q40478 Q40478 EREBP-4. ;, mRNA sequence"; source: *Glycine soja*; Title: "Public Soybean EST Project" (Unpublished (1999)).
CA801993 NCBI acc. No. CA801993 (gi: 26059079) (Dec. 5, 2002); Shoemaker,R., et al. "sau28c10.y1 Gm-c1062 *Glycine max* cDNA clone Soybean Clone ID: Gm-c1062-9356 5' similar to TR:Q40478 Q40478 EREBP-4. ;, mRNA sequence"; source: *Glycine max* (soybean); Title: "Public Soybean EST Project" (Unpublished (1999)).
CA918826 NCBI acc. No. CA918826 (gi: 27405756) (Dec. 27, 2002); VandenBosch,K., et al. "EST636544 MTUS *Medicago truncatula* cDNA clone MTUS-3F12, mRNA sequence"; source: *Medicago truncatula* (barrel medic); Title: "The *Medicago truncatula* 6K unigene set: cDNA clones selected and re-arrayed from various libraries" (Unpublished (2002)).
CB001513 NCBI acc. No. CB001513 (gi: 27578818) (Jan. 10, 2003); Cramer,G.R., et al. "VVB004H10_124488 An expressed sequence tag database for abiotic stressed leaves of *Vitis vinifera* var. Chardonnay *Vitis vinifera* cDNA clone VVB004H10 5, mRNA sequence"; source: *Vitis vinifera*; Title: "An expressed sequence tag database for abiotic stressed leaves of *Vitis vinifera* var. Chardonnay" (Unpublished (2002)).
CB002777 NCBI acc. No. CB002777 (gi: 27580082) (Jan.10 ,2003); Cramer,G.R., et al. "VVB020G03_132412 An expressed sequence tag database for abiotic stressed leaves of *Vitis vinifera* var. Chardonnay *Vitis vinifera* cDNA clone VVB020G03 5, mRNA sequence"; source: *Vitis vinifera*; Title: "An expressed sequence tag database for abiotic stressed leaves of *Vitis vinifera* var. Chardonnay" (Unpublished (2002)).
CB003172 NCBI acc. No. CB003172 (gi: 27580477) (Jan. 10, 2003); Cramer,G.R., et al. "VVB027C01_133202 An expressed sequence tag database for abiotic stressed leaves of *Vitis vinifera* var. Chardonnay *Vitis vinifera* cDNA clone VVB027C01 5, mRNA sequence"; source: *Vitis vinifera*; Title: "An expressed sequence tag database for abiotic stressed leaves of *Vitis vinifera* var. Chardonnay" (Unpublished (2002)).
CB003334 NCBI acc. No. CB003334 (gi: 27580639) (Jan. 10, 2003); Cramer,G.R., et al. "VVB029A07_133526 an expressed sequence tag database for abiotic stressed leaves of *Vitis vinifera* var. Chardonnay *Vitis vinifera* cDNA clone WB029A07 5, mRNA sequence"; source: *Vitis vinifera*; Title: "An expressed sequence tag database for abiotic stressed leaves of *Vitis vinifera* var. Chardonnay" (Unpublished (2002)).

CB003997 NCBI acc. No. CB003997 (gi: 27581302) (Jan. 10, 2003); Cramer,G.R., et al. "VVB034F08_134852 An expressed sequence tag database for abiotic stressed leaves of *Vitis vinifera* var. Chardonnay *Vitis vinifera* cDNA clone WB034F08 5, mRNA sequence"; source: *Vitis vinifera*; Title: "An expressed sequence tag database for abiotic stressed leaves of *Vitis vinifera* var. Chardonnay" (Unpublished (2002)).

CB007463 NCBI acc. No. CB007463 (gi: 27584768) (Jan. 10, 2003); Cushman,J.C., et al. "VVC045F10_141982 An expressed sequence tag database for abiotic stressed berries of *Vitis vinifera* var. Chardonnay *Vitis vinifera* cDNA clone VVC045F10 5, mRNA sequence"; source: *Vitis vinifera*; Title: "An expressed sequence tag database for abiotic stressed berries of *Vitis vinifera* var. Chardonnay" (Unpublished (2002)).

CB292286 NCBI acc. No. CB292286 (gi: 28617743) (Feb. 28, 2003); Close,T.J., et al. "UCRCS01_04ba10_g1 Washington Navel orange cold acclimated flavedo & albedo cDNA library *Citrus sinensis* cDNA clone UCRCS01_04ba10, mRNA sequence"; source: *Citrus sinensis*; Title: "Development of EST Resources and New Genetic Markers for California Citrus" (Unpublished (2003)).

CB322190 NCBI acc. No. CB322190 (gi: 28856848) (Mar. 5, 2003); Burns,J.K., et al. "EST0312 Mature leaf blade cDNA subtraction library *Citrus sinensis* cDNA clone 24LB271 similar to pathogenesis-related transcriptional activator PTI5 (acc# AAC49740), mRNA sequence"; source: *Citrus sinensis*; Title: "Expressed sequence tags of cDNA clones from a subtracted Valencia orange mature leaf blade library" (Unpublished (2000)).

CB341794 NCBI acc. No. CB341794 (gi: 28962761) (Mar. 14, 2003); Goes da Silva,F., et al. "CA32EN0002_IIIbF_A03 Cabernet Sauvignon Leaf - CA32EN *Vitis vinifera* cDNA clone CA32EN0002_IIIbF_A03 5&pos;, mRNA sequence"; source: *Vitis vinifera*; Title: "Transcriptional responses of *Vitis vinifera* to infection by the bacterial pathogen *Xylella fastidiosa*" (Unpublished (2003)).

CB342848 NCBI acc. No. CB342848 (gi: 28963815) (Mar. 14, 2003); Goes da Silva,F., et al. "CA32EN0004_IIIaF_C01 Cabernet Sauvignon Leaf - CA32EN *Vitis vinifera* cDNA clone CA32EN0004_IIIaF_C01 5&pos;, mRNA sequence"; source: *Vitis vinifera*; Title: "Transcriptional responses of *Vitis vinifera* to infection by the bacterial pathogen *Xylella fastidiosa*" (Unpublished (2003)).

CB342920 NCBI acc. No. CB342920 (gi: 28963887) (Mar. 14, 2003); Goes da Silva,F., et al. "CA32EN0004_IIIbR_C01 Cabernet Sauvignon Leaf - CA32EN *Vitis vinifera* cDNA clone CA32EN0004_IIIbR_C01 3&pos;, mRNA sequence"; source: *Vitis vinifera*; Title: "Transcriptional responses of *Vitis vinifera* to infection by the bacterial pathogen *Xylella fastidiosa*" (Unpublished (2003)).

CB350627 NCBI acc. No. CB350627 (gi: 28985410) (Mar. 17, 2003); Wen,T.J., et al. "MEST253-F08.univ ISUM5-RN *Zea mays* cDNA clone MEST253-F08 3&pos;, mRNA sequence"; source: *Zea mays*; Title: "Expressed Sequence Tags from B73 Maize: various stages and tissues including seedlings treated with a variety of hormones" (Unpublished (2001)).

CNS07EFR NCBI acc. No. AL513404 (gi: 12711302) (Feb. 7, 2001); Salse,J., et al. "*Oryza sativa* chromosome 12 clone OSJNBa0041K23, * Sequencing in Progress *"; source: *Oryza sativa*; Title: "*Oryza sativa* chromosome 12 sequencing" (Unpublished).

CRO238740 NCBI acc. No. AJ238740 (gi: 8346774) (Jun. 7, 2000); Menke,F.L.H., et al. "*Catharanthus roseus* mRNA for AP2-domain DNA-binding protein ORCA2"; source: *Catharanthus roseus* (Madagascar periwinkle); Title: "A jasmonate- and elicitor- responsive element in the periwinkle secondary metabolite biosynthetic gene Str interacts with a jasmonate- and elicitor-inducible AP2-domain transcription factor, ORCA2" (Unpublished).

CRO251249 NCBI acc. No. AJ251249 (gi: 8980312) (Jul. 8, 2000); van der Fits,L., et al. "*Catharanthus roseus* mRNA for AP2-domain DNA-binding protein (orca3 gene)"; source: *Catharanthus roseus* (Madagascar periwinkle); Title: "ORCA3, a jasmonate- responsive master regulator of multiple genes in plant primary and secondary metabolism" (Unpublished).

CRO251250 NCBI acc. No. AJ251250 (gi: 8980314) (Jul. 8, 2000); van der Fits,L., et al. "*Catharanthus roseus* orca3 gene for AP2-domain DNA-binding protein"; source: *Catharanthus roseus* (Madagascar periwinkle); Title: "ORCA3, a jasmonate-responsive master regulator of multiple genes in plant primary and secondary metabolism" (Unpublished).

LEU89255 NCBI acc. No. U89255 (gi: 2213780) (Jun. 25, 1997); Zhou,J., et al. "*Lycopersicon esculentum* DNA-binding protein Pti4 mRNA, complete cds"; source: *Lycopersicon esculentum* (tomato); Title: "The Pto Kinase Conferring Resistance to Tomato Bacterial Speck Disease Interacts with Proteins that Bind a Cis-Element of Pathogenesis-Related Genes" (EMBO J. 16, 3207-3218 (1997)).

LEU89256 NCBI acc. No. U89256 (gi: 2213782) (Jun. 25, 1997); Zhou,J., et al. "*Lycopersicon esculentum* DNA-binding protein PtiS mRNA, complete cds"; source: *Lycopersicon esculentum* (tomato); Title: "The Pto Kinase Conferring Resistance to Tomato Bacterial Speck Disease Interacts with Proteins that Bind a Cis-Element of Pathogenesis-Related Genes" (EMBO J. 16, 3207-3218 (1997)).

NP_171932 (gi: 15219717) (Aug. 21, 2001); Theologis,A., et al. "hypothetical protein [*Arabidopsis thaliana*]"; source: *Arabidopsis thaliana* (thale cress); Title: "Sequence and analysis of chromosome 1 of the plant *Arabidopsis thaliana*" (Nature 408 (6814), 816-820 (2000)).

NP_188963 (gi: 15229401) (Aug. 21, 2001); Salanoubat,M., et al. "ethylene responsive element binding protein, putative [*Arabidopsis thaliana*]"; source: *Arabidopsis thaliana* (thale cress); Title: "Sequence and analysis of chromosome 3 of the plant *Arabidopsis thaliana*" (Nature 408 (6814), 820-822 (2000)).

NCBI acc. No. NP_188964 (gi: 15229403) (Aug. 21, 2001); Salanoubat,M., et al. "ethylene responsive element binding protein, putative [*Arabidopsis thaliana*]"; source: *Arabidopsis thaliana* (thale cress); Title: "Sequence and analysis of chromosome 3 of the plant *Arabidopsis thaliana*" (Nature 408 (6814), 820-822 (2000)).

NCBI acc. No. NP_199154 (gi: 15239863) (Aug. 21, 2001); Tabata,S., et al. "Nicotiana EREPB-3 like [*Arabidopsis thaliana*]"; source: *Arabidopsis thaliana* (thale cress); Title: "Sequence and analysis of chromosome 5 of the plant *Arabidopsis thaliana*" (Nature 408 (6814), 823-826 (2000)).

NTU81157 NCBI acc. No. U81157 (gi: 1732405) (Dec. 16, 1996); Xu,P., et al. "*Nicotiana tabacum* S25-XP1 DNA binding protein mRNA, complete cds"; source: *Nicotiana tabacum* (common tobacco); Title: "Direct Submission" (Submitted (Dec. 6, 1996) Biotechnology Institute, Zhejiang Agriculture Unversity, Hangzhou, Zhejiang 310029, P.R.China).

OSA307662 NCBI acc. No. AJ307662 (gi: 14140112) (May 17, 2001); Mayer,K., et al. "*Oryza sativa* genomic DNA fragment, chromosome 2"; source: *Oryza sativa*; Title: "Conservation of microstructure bewtween a sequenced region of the genome of rice and multiple segments of the genome of *Arabidopsis thaliana*" (Unpublished).

OSJN00126 NCBI acc. No. AL607006 (gi: 15799247) (Sep. 27, 2001); Han,B., et al. "*Oryza sativa* chromosome 4 clone OSJNBA0079A21, * Sequencing in Progress *"; source: *Oryza sativa*; Title: "Direct Submission" (Submitted (Jul. 28, 2000) Han Bin, National Center for Gene Research, Chinese Academy of sciences, 500# Cao Bao Road, Shanghai 200233, China. E-mail enquiries: bhan@ncgr.ac.cn. Clone requests: bhan@ncgr.ac.cn).

OSJN00257 NCBI acc. No. AL731613 (gi: 20451722) (May 4, 2002); Han,B., et al. "*Oryza sativa* chromosome 4 clone OSJNBa0065H10, * Sequencing in Progress *"; source: *Oryza sativa*; Title: "Direct Submission" (Submitted (Apr. 2, 2002) Han Bin, National Center for Gene Research, Chinese Academy of sciences, 500# Cao Bao Road, Shanghai 200233, China.

AAG43545 NCBI acc. No. AAG43545 (gi: 12003376) (Jan. 2, 2001); Durrant,W.E., et al. "Avr9/Cf-9 rapidly elicited protein 1 [*Nicotiana tabacum*]"; source: *Nicotiana tabacum* (common tobacco); Title: "cDNA expression profiling reveals rapid, resistance gene-dependent, active oxygen-independent, gene induction during the plant defense response" (Unpublished).

BAA07324 NCBI acc. No. (gi: 1208498) (Feb. 28, 1996); Ohme-Takagi,M., et al. "EREPB-2"; source: *Nicotiana tabacum* (common tobacco); Title: "Direct Submission" (Submitted (Sep. 1, 1994)

Masaru Ohme-Takagi, National Institute of Bioscience and Human Thechnology, Plant Moplecular Biology Laboratory, 1-1 Higashi, Tsukuba, Ibaraki 305, Japan).

CAC39058 NCBI acc. No. CAC39058 (gi: 14140141) (May 17, 2001); Mayer,K., et al. "putative AP2-related transcription factor [*Oryza sativa*]"; source: *Oryza sativa*; Title: "Conservation of microstructure bewtween a sequenced region of the genome of rice and multiple segments of the genome of *Arabidopsis thaliana*" (Unpublished).

CAC39060 NCBI acc. No. CAC39060 (gi: 14140143) (May 17, 2001); Mayer,K., et al. "putative ethylene responsive element binding factor [*Oryza sativa*]"; source: *Oryza sativa*; Title: "Conservation of microstructure bewtween a sequenced region of the genome of rice and multiple segments of the genome of *Arabidopsis thaliana*" (Unpublished).

AAB38748 NCBI acc. No. AAB38748 (gi: 1732406) (Dec.16, 1996); Xu,P., et al. "S25- XP1 DNA binding protein [*Nicotiana tabacum*]"; source: *Nicotiana tabacum* (common tobacco); Title: "Direct Submission" (Submitted (Dec. 6, 1996) Biotechnology Institute, Zhejiang Agriculture Unversity, Hangzhou, Zhejiang 310029, P.R.China).

BAA87068 NCBI acc. No. BAA87068 (gi: 6478845) (Nov. 3,0 1999); Ashida,Y., et al. "ethylene-responsive element binding protein1 homolog [*Matricaria chamomilla*]"; source: *Matricaria chamomilla*; Title: "ethylene-responsive element binding protein1 (EREBP) homolog, *Matricaria chamomilla*" (Published Only in DataBase (1999) in press).

AAC49740 NCBI acc. No. (gi: 2213783) (Jun. 25, 1997); Zhou,J., et al. "PtiS [*Lycopersicon esculentum*]"; source: *Lycopersicon esculentum* (tomato); Title: "The Pto Kinase Conferring Resistance to Tomato Bacterial Speck Disease Interacts with Proteins that Bind a Cis-Element of Pathogenesis-Related Genes" (EMBO J. 16, 3207-3218 (1997)).

BAC21532 NCBI acc. No. BAC21532 (gi: 24060081) (Oct. 16, 2002); Sasaki,T., et al. "putative ethylene response factor ERF1 [*Oryza sativa* (japonica cultivar-group)]"; source: *Oryza sativa* (japonica cultivar-group); Title: "*Oryza sativa* nipponbare(GA3) genomic DNA, chromosome 7, PAC clone:P0710F09" (Published Only in Database (2002)).

AAN77067 NCBI acc. No. AAN77067 (gi: 25992126) (Dec. 2, 2002); Cheng,X.G., et al. "ethylene responsive element binding protein [*Lycopersicon esculentum*]"; source: *Solanum lycopersicum*(*Lycopersicon esculentum*); Title: "Direct Submission" (Submitted (Apr. 13, 2002) Department of Biological Science and Biotechnology, Tsinghua University, QinghuaYuan, Beijing 100084, China).

BAA87068 NCBI acc. No. BAA87068 (gi: 6478845) (Nov. 30, 1999); Ashida,Y., et al. "ethylene-responsive element binding protein1 homolog [*Matricaria chamomilla*]"; source: *Matricaria chamomilla*; Title: "ethylene-responsive element binding protein1 (EREPB) homolog, *Matricaria chamomilla*" (Published Only in DataBase (1999) in press).

T07689 NCBI acc. No. T07689 (gi: 7489078) (Apr. 6, 2000); Zhou,J., et al. "transcription factor Pti5 - tomato"; source: *Lycopersicon esculentum* (tomato); Title: "The Pto kinase conferring resistance to tomato bacterial speck disease interacts with proteins that bind a cis-element of pathogenesis-related genes" (EMBO J. 16 (11), 3207-3218 (1997)).

AAF63205 NCBI acc. No. AAF63205 (gi: 7528276) (Apr. 9, 2000); Scharte,J., et al. "AP2-related transcription factor [*Mesembryanthemum crystallinum*]"; source: *Mesembryanthemum crystallinum* (common iceplant); Title: "A stress induced transcription factor of the AP2 gene family from the inducible CAM-plant *Mesembryanthemum crystallinum* L." (Unpublished).

O04681 NCBI acc. No. O04681 (gi: 7531180) (Apr. 10, 2000); Zhou,J., et al. "Pathogenesis-Related Genes Transcriptional Activator PTI5"; source: *Lycopersicon esculentum* (tomato); Title: "The Pto kinase conferring resistance to tomato bacterial speck disease interacts with proteins that bind a cis-element of pathogenesis-related genes" (EMBO J. 16 (11), 3207-3218 (1997)).

BAA97122 NCBI acc. No. BAA97122 (gi: 8809571) (Jun 28 2000); Kitajima,S., et al. "ethylene-responsive element binding factor [*Nicotiana sylvestris*]"; source: *Nicotiana sylvestris* (wood tobacco);

Title: "Characterization of gene expression of NsERFs, transcription factors of basic PR genes from *Nicotiana sylvestriS*" (Plant Cell Physiol. 41, 817-824 (2000)).

CAB96899 NCBI acc. No. CAB96899 (gi: 8980313) (Jul. 8, 2000); van der Fits,L., et al. "AP2-domain DNA-binding protein [*Catharanthus roseus*]"; source: *Catharanthus roseus* (Madagascar periwinkle); Title: "ORCA3, a jasmonate-responsive master regulator of multiple genes in plant primary and secondary metabolism" (Unpublished).

CAB96900 NCBI acc. No. CAB96900 (gi: 8980315) (Jul. 8, 2000); van der Fits,L., et al. "AP2-domain DNA-binding protein [*Catharanthus roseus*]"; source: *Catharanthus roseus* (Madagascar periwinkle); Title: "ORCA3, a jasmonate-responsive master regulator of multiple genes in plant primary and secondary metabolism" (Unpublished).

BT009060 NCBI acc. No. BT009060 (gi: 32128611) (Jun. 20, 2003); Tingey,S.V., et al. "*Triticum aestivum* clone wdr1f.pk003.I5:fis, full insert mRNA sequence"; source: *Triticum aestivum* (bread wheat); Title: "Direct Submission" (Submitted (Jun. 20, 2003) Crop Genetics, E. I. DuPont de Nemours and Company, 1 Innovation Way, P.O. Box 6104, Newark, DE 19714-6104, USA).

CAE45639 NCBI acc. No. CAE45639 (gi: 34221729) (Aug. 25, 2003); Gong,W., et al. "putative ethylene responsive element binding protein [*Arabidopsis thaliana*]"; source: *Arabidopsis thaliana* (thale cress); Title: "*Arabidopsis thaliana* putative ethylene responsive element binding protein, similar to the At3g23230 protein encoded by chromosome 3" (Unpublished).

BAA95735 NCBI acc. No. BAA95735 (gi: 7939532) (May 19, 2000); Nakamura,Y., et al. "contains similarity to ethylene response element binding protein EREPB~gene_id:K14B15.13 [*Arabidopsis thaliana*]"; source: *Arabidopsis thaliana* (thale cress); Title: "Structural Analysis of *Arabidopsis thaliana* Chromosome 3. II" (Unpublished (1999)).

AB025608 EMBL acc. No. AB025608 (Apr. 9, 1999); "*Arabidopsis thaliana* genomic DNA, chromosme 3, TAC clone: K14B15".

Campbell, et al. (1998) Isolation of a cDNA from potato with structural similarity to the AP2 gene superfamily (Accession No. U77655) (PGR98-129). Plant Physiol. 117 (3), 1127.

Guo, H., and Ecker, J.R. (Feb. 2004). The ethylene signaling pathway: new insights. Curr Opin Plant Biol 7,40-49.

Lee, J.H., et al. (May 2004). The ethylene-responsive factor like protein 1 (CaERFLP1) of hot pepper (*Capsicum annuum* L.) interacts in vitro with both GCC and DRE/CRT sequences with different binding affinities: possible biological roles of CaERFLP1 in response to pathogen infection and high salinity conditions in transgenic tobacco plants. Plant Mol Biol 55, 61-81.

Riechmann, J.L., and Meyerowitz, E.M. (Jun. 1998). The AP2/EREBP family of plant transcription factors. Biol Chem 379, 633-646.

Aoyama, et al. (1995) Ectopic expression of the *Arabidopsis* transcriptional activator Athb-1 alters leaf cell fate in tobacco. Plant Cell. Nov. 1995;7(11):1773-1785.

Bowman et al. (1999) CRABS CLAW, a gene that regulates carpel and nectary development in *Arabidopsis*, encodes a novel protein with zinc finger and helix—loop—helix domains, Development 126:2387-2396.

Buchel, et al. (1999) Mutation of GT-1 binding sites in the PR-1A promoter influences the level of inducible gene expression in vivo. Plant Mol Biol. Jun. 1999;40(3):387-396.

Cao, et al. (2001) Effect of two conserved amino acid residues on DREB1A function. Biochemistry (Mosc). Jun. 2001;66(6):623-627.

Chao et al., Activation of the Ethylene Gas Response Pathway in Arabidopsis by the Nuclear Protein Ethylene-INSENSITIVE3 and Related Proteins, Cell (Jun. 27, 1997) 89:1133-1144.

Christiansen, et al. (1996) A novel type of DNA-binding protein interacts with a conserved sequence in an early nodulin ENOD12 promoter. Plant Mol Biol. Dec. 1996;32(5):809-821.

Collingwood, et al. (Dec. 1999). Nuclear receptors: coactivators, corepressors and chromatin remodeling in the control of transcription. J Mol Endocrinol. Dec. 1999;23(3):255-275.

Cubas, et al. (1999) The TCP domain: a motif found in proteins regulating plant growth and development. Plant J. Apr.;18(2):215-222.

Cvitanich, et al. (2000) CPP1, a DNA-binding protein involved in the expression of a soybean leghemoglobin c3 gene. Proc Natl Acad Sci U S A. 97(14):8163-8168.

Da Costa E Silva, et al. (1994) CG-1, a parsley light-induced DNA-binding protein. Plant Mol Biol. Aug. 1994;25(5):921-924.

Forsburg and Guarente. Identification and characterization of HAP4: a third component of the CCAAT-bound HAP2/HAP3 heteromer. Genes Dev. (Aug. 1989) 3:1166-1178.

Fromm, et al. (1989) An octopine synthase enhancer element directs tissue-specific expression and binds ASF-1, a factor from tobacco nuclear extracts. Plant Cell. Oct. 1989;1(10):977-984.

Gan and Amasino (1995) Inhibition of leaf senescence by autoregulated production of cytokinin. Science. Dec. 22, 1995;270(5244):1986-1988.

Giniger and Ptashne (1987) Transcription in yeast activated by a putative amphipathic alpha helix linked to a DNA binding unit. Nature. Dec. 17-23, 1987;330(6149):670-672.

Guevara-Garcia, et al. (1998) A 42 bp fragment of the pmas1' promoter containing an ocs-like element confers a developmental, wound- and chemically inducible expression pattern. Plant Mol Biol. Nov. 1998;38(5):743-753.

Guo, et al. (2004) Protein tolerance to random amino acid change. Proc Natl Acad Sci U S A. Jun. 22, 2004 22;101(25):9205-9210. Epub Jun. 14, 2004.

Hill et al. (1998) Functional analysis of conserved histidines in ADP-glucose pyro-phosphorylase from *Escherichia coli*. Biochem Biophys Res Commun. 244:573-577.

Hsieh et al. (1998). A PII-like protein in *Arabidopsis*: putative role in nitrogen sensing. Proc Natl Acad Sci U S A 95, 13965-13970.

Ishiguro et al. (1994) Characterization of cDNA encoding a novel DNA binding protein SPF1 that recognizes sp8 sequence in the 5'-upstream regions of genes coding for sporamin and beta-amylase from sweet potato. Mol. Gen. Genet. 244: 563-571.

Kaelin, et al. (1992) Expression cloning of a cDNA encoding a retinoblastoma-binding protein with E2F-like properties. Cell. Jul. 24, 1992;70(2):351-364.

Kaiser et al. (1995) Cis-acting elements of the CHS1 gene from white mustard controlling promoter activity and spatial patterns of expression. Plant Mol Biol. 28:231-243.

Kikuchi, et al. (2003); Collection, mapping, and annotation of over 28,000 cDNA clones from japonica rice. Science. Jul. 18, 2003;301(5631):376-379. Erratum in: Science. Sep. 2003;301(5641):1849.

Klein et al., A new family of DNA binding proteins includes putative transcriptional regulators of the *Antirrhinum majus* floral meristem identity gene SQUAMOSA. Mol. Gen. Genet. (Jan. 15, 1996) 250:7-16.

Lamb et al. (1992). Emerging strategies for enhancing crop resistance to microbial pathogens. Biotechnology (N Y) 10, 1436-1445.

Lazar, et al. (1988) Transforming growth factor alpha: mutation of aspartic acid 47 and leucine 48 results in different biological activities. Mol Cell Biol. Mar.;8(3):1247-1252.

Lee, et al. (Aug. 2004). Ectopic expression of a cold-inducible transcription factor, CBF1/DREB1b, in transgenic rice (*Oryza sativa* L.). Mol Cells 18, 107-114.

Lee, et al: "Derepression Of The Activity Of Genetically Engineered Heat Shock Factor Causes Constitutive Synthesis Of Heat Shock Proteins And Increased Thermotolerance In Transgenic *Arabidopsis*" Plant Journal, Blackwell Scientific Publications, Oxford, GB, vol. 8, No. 4, Oct. 1, 1995, pp. 603-612.

Ma and Ptashne (1987) A new class of yeast transcriptional activators. Cell. Oct. 9, 1987;51(1):113-119.

Manners, et al. (1998) The promoter of the plant defensin gene PDF1.2 from *Arabidopsis* is systemically activated by fungal pathogens and responds to methyl jasmonate but not to salicylic acid. Plant Mol Biol. Dec. 1998;38(6):1071-1080.

Millar, et al. (1999). CUT1, an *Arabidopsis* gene required for cuticular wax biosynthesis and pollen fertility, encodes a very-long-chain fatty acid condensing enzyme. Plant Cell 11, 825-838.

Moore, et al. (1998) A transcription activation system for regulated gene expression in transgenic plants. Proc Natl Acad Sci U S A. Jan. 6, 1998;95(1):376-381.

Odell, et al. (1985) Identification of DNA sequences required for activity of the cauliflower mosaic virus 35S promoter. Nature Feb. 28-Mar. 6, 1985;313(6005):810-812.

Odell, et al. (1994) Seed-specific gene activation mediated by the Cre/lox site-specific recombination system. Plant Physiol. Oct. 1994;106(2):447-458.

Ohl, et al. (1990) Functional properties of a phenylalanine ammonia-lyase promoter from *Arabidopsis*. Plant Cell. Sep. 1990;2(9):837-848.

Park et al. (2001). Overexpression of the tobacco Tsi1 gene encoding an EREBP/AP2-type transcription factor enhances resistance against pathogen attack and osmotic stress in tobacco. Plant Cell 13, 1035-1046.

Sasaki, et al. (2002) The genome sequence and structure of rice chromosome 1. Nature 420 (6913), 312-316.

Sato, et. al. (Apr. 28, 2000) Structural analysis of *Arabidopsis thaliana* chromosome 3. I. Sequence features of the regions of 4,504,864 by covered by sixty P1 and TAC clones. DNA Res. 7(2):131-135.

Schauser, et al. (1999) A plant regulator controlling development of symbiotic root nodules. Nature. Nov. 11, 1999;402(6758):191-195.

Seguin, et al. (1997) Characterization of a gene encoding a DNA-binding protein that interacts in vitro with vascular specific cis elements of the phenylalanine ammonia-lyase promoter. Plant Mol Biol. Oct. 1997;35(3):281-291.

Shi, et al. (1998) Gibberellin and abscisic acid regulate GAST1 expression at the level of transcription. Plant Mol Biol. Dec. 1998;38(6):1053-1060.

Siebertz et al. (1989) cis-analysis of the wound-inducible promoter wun1 in transgenic tobacco plants and histochemical localization of expression. Plant Cell 1:961-968.

Souer et al. (1996) The no apical meristem gene of Petunia is required for pattern formation in embryos and flowers and is expressed at meristem and primordia boundaries. Cell 85: 159-170.

Stemmer, et al. (1994) Rapid evolution of a protein in vitro by DNA shuffling. Nature. Aug. 4, 1994;370(6488):389-391.

Stemmer, et al. (1994) DNA shuffling by random fragmentation and reassembly: in vitro recombination for molecular evolution. Proc Natl Acad Sci U S A. Oct. 25, 1994;91(22):10747-10751.

Tournier et al. (2003) New members of the tomato ERF family show specific expression pattern and diverse DNA-binding capacity to the GCC box element. FEBS Lett 550:149-154.

Ulmasov, et al. (May 1999). Activation and repression of transcription by auxin-response factors. Proc Natl Acad Sci U S A. May 11, 1999;96(10):5844-5849.

Van Der Knaap et al. (2000) A novel gibberellin-induced gene from rice and its potential regulatory role in stem growth. Plant Physiol. Mar. 2000;122(3):695-704.

Van Der Kop, et al. (1999) Selection of *Arabidopsis* mutants overexpressing genes driven by the promoter of an auxin-inducible glutathione S-transferase gene. Plant Mol Biol. 39:979-990.

Vazquez, et al. (1999) The trithorax group gene osa encodes an ARID-domain protein that genetically interacts with the brahma chromatin-remodeling factor to regulate transcription. Development. Feb. 1999;126(4):733-742.

Willmott, et al. (1998) DNase1 footprints suggest the involvement of at least three types of transcription factors in the regulation of alpha-Amy2/A by gibberellin. Plant Mol Biol. Nov. 1998;38(5):817-825.

Wu, et al. (1995) Heat shock transcription factors: structure and regulation. Annu Rev Cell Dev Biol. 1995;11:441-469.

Xu et al. (1998) Identification of a novel DNA-binding protein to osmotin promoter, Science in China, Ser. C, 1998, 41: 657-663.

Yanagisawa et al: "Metabolic engineering with Dof1 transcription factor in plants: Improved nitrogen assimilation and growth under low-nitrogen conditions" PNAS of the USA, vol. 101, No. 20, May 18, 2004, pp. 7833-7838.

Yi, et al. (2004). The Pepper Transcription Factor CaPF1 Confers Pathogen and Freezing Tolerance in *Arabidopsis*. Plant Physiol. Sep. 2004;136(1):2862-2874.

Zhang et al. (1992) Expression of Antisense or Sense RNA of an Ankyrin Repeat-Containing Gene Blocks Chloroplast Differentiation in *Arabidopsis*. Plant Cell:1575-1588.

\* cited by examiner

|  | 90 | 100 | 110 | 120 |
|---|---|---|---|---|
| (42) G1752_At | | M E Y S - - Q S S M Y S | - - - S P - | - - - - - S |
| (4) G1791_At | | M E R I - - - - - - - - | - - - - - - - | - - - - - - |
| (6) G1795_At | | M D Q G - - - - - - - - | - - - - - - - | - - - - - - |
| (8) G30_At | | M D Q G - - - - - - - - | - - - - - - - | - - - - - - |
| (10) G3380_Os | | M D G - - - - - - - - - | - - - - - - - | - - - - - - |
| (36) G3794_Zm | | M D - - - - - - - - - - | - - - - - - - | - - - - - - |
| (30) G3736_Ta | | M E G G - - - - - - - - | - - - - - - - | - - - - - - |
| (12) G3381_Os | | M D H H - - - - - - - - | - - - - - - - | - - - - - - |
| (20) G3517_Zm | | M D G - - - - - - - - - | - - - - - - - | - - - - - - |
| (34) G3739_Zm | | M D G - - - - - - - - - | - - - - - - - | - - - - - - |
| (26) G3520_Gm | | M E E E - - - - - - - - | - - - - - - - | - - - - - - |
| (14) G3383_Os | | M E D - - - - - - - - - | - - - - - - - | - - - - - - |
| (32) G3737_Os | | M E D - - - - - - - - - | - - - - - - - | - - - - - - |
| (16) G3515_Os | | M E D - - - - - - - - - | - - - - - - - | - - - - - - |
| (18) G3516_Zm | | M E D - - - - - - - - - | - - - - - - - | - - - - - - |
| (2) G1792_At | - - - - - - - - - - - - - - - - - S | Q D D - - - - - - - - - | - - - - - - - | - - - - - - |
| (22) G3518_Gm | | M E G - - - - - - - - - | - - - - - - - | - - - - - - |
| (24) G3519_Gm | | M E G - - - - - - - - - | - - - - - - - | - - - - - - |
| (28) G3735_Mt | | M E G - - - - - - - - - | - - - - - - - | - - - - - - |
| (52) G26_At | - V S D F V S E L T G Q P I P S S I | D D Q - - - - - - - - - | - - - - - - - | - - - - - - |
| (50) G22_At | - - - I L N D N W S D L P - - L S V | D D S - - - - - - - - - | - - - - - - - | Q D M A I Y |
| (46) G1006_At | - - - C F T E S W G G L P - - L K E | N D S - - - - - - - - - | - - - - - - - | E D M L V Y |
| (48) G28_At | - Y P C F T E S W G D L P - - L K E | N D S - - - - - - - - - | - - - - - - - | E D M L V Y |
| (54) G1751_At | I E G C L G C N Y F F A P N - Q R I | E K N H Q - - - - - - - | - - - - - - - | - - - - - Q |
| (40) G45_At | - V P E V S R T W E A L P T L D D I | P E G - - - - - - - - - | - - - - - - - | - - - - - - |
| (38) G1266_At | | M D P F L I Q S P F S G | - - F S P E Y | S I G S |
| (44) G2512_At | | M E Y - - - Q T N F L S G E F | S P E N S | S S S |

FIG. 3C

|  |  | 130 | 140 | 150 | 160 |
|---|---|---|---|---|---|
| (42) G1752_At | S W S S S Q E S L | L W N E S C - F L | D Q S S E P Q A F F C - - | P N Y D Y S D D F |
| (4) G1791_At | E S - - - - - - - | Y N T N E M - - - | - - - - - - - - - - - - - | - - - - - - - - - |
| (6) G1795_At | G R - - - - - - G | V G A E H G - - - | - - - - - - - - - - - - - | - - - - - - - - - |
| (8) G30_At | G R S S G S - G G | G G A E Q G - - - | - - - - - - - - - - - - - | - - - - - - - - - |
| (10) G3380_Os | D G G G G W D D Q | G N G G G - - - - | - - - - - - - - - - - - - | - - - - - - - - - |
| (36) G3794_Zm | D G G - - - - - - | - - - - - - - - - | - - - - - - - - - - - - - | - - - - - - - - - |
| (30) G3736_Ta | E G S - - - - - - | - G G G G - - - - | - - - - - - - - - - - - - | - - - - - - - - - |
| (12) G3381_Os | H Q Q Q - - - - - | - Q Q E G - - - - | - - - - - - - - - - - - - | - - - - - - - - - |
| (20) G3517_Zm | E W S K - - D - - | - G G G G - - - - | - - - - - - - - - - - - - | - - - - - - - - - |
| (34) G3739_Zm | D W S K - - D - - | - G G G G - - - - | - - - - - - - - - - - - - | - - - - - - - - - |
| (26) G3520_Gm | S K E K - - - - - | - K K D T - - - - | - - - - - - - - - - - - - | - - - - - - - - - |
| (14) G3383_Os | N R S - - - - - - | - - K D T - - - - | - - - - - - - - - - - - - | - - - - - - - - - |
| (32) G3737_Os | D K - - - - - - - | - - K E A - - - - | - - - - - - - - - - - - - | - - - - - - - - - |
| (16) G3515_Os | D K S - - - - - - | - - K E G - - - - | - - - - - - - - - - - - - | - - - - - - - - - |
| (18) G3516_Zm | D K - - - - - - - | - - K E G - - - - | - - - - - - - - - - - - - | - - - - - - - - - |
| (2) G1792_At | - - - - - - - - - | - - - - - - - - - | - - - - - - - - - - - - - | - - - - - - - - - |
| (22) G3518_Gm | G R S S V S - - - | - - N G N - - - - | - - - - - - - - - - - - - | - - - - - - - - - |
| (24) G3519_Gm | G R S S V S - - - | - - N G N - - - - | - - - - - - - - - - - - - | - - - - - - - - - |
| (28) G3735_Mt | D H K L V S N S - | - T N G N G - - - | - - - - - - - - - - - - - | - - - - - - - - - |
| (52) G26_At | S S S - - - - L T | L Q E K S - - - - | - - - - - - - - - - - - - | - - - - - - - - - |
| (50) G22_At | N T L R D A V S S | G W T P S V P - - | - - P V T - - - - S P A E | E N K P P A T K A |
| (46) G1006_At | G L L K D A F H - | - F D T S S S - - | - - D L S C L F D F P A V | K V E P T E N F T |
| (48) G28_At | G I L N D A F H G | G W E P S S S S S | D E D R S - - - S F P S V | K I E T P E S F A |
| (54) G1751_At | E E E I T S S S N | R R R E S S P - - | - - - - - - - - - - - - - | - - - - - - - V A |
| (40) G45_At | S R E M L Q S L D | M S T E D Q E W T | E I L D A I A S F P N - - | K T N H D P L T N |
| (38) G1266_At | S P D S F S S S S | S N N Y S L P F N | E N D S E - E M F L Y G L | I E Q S T Q Q T Y |
| (44) G2512_At | S W S S - Q E S F | L W E E S - - F L | H Q S F D - Q S F L L S S | P T D N Y C D D F |

FIG. 3D

|           |                   | 170                   | 180                          | 190                   | 200       |
|-----------|-------------------|-----------------------|------------------------------|-----------------------|-----------|
| (42) G1752_At | F S F E S P E M M I | K E E I Q N G D V S | N S E E E E K V G I D E E R S | Y R G V R |
| (4) G1791_At  | - - - - - - - - - - | - - - - - - - - - - | - - - - - - - - - - - - - K | Y R G V R |
| (6) G1795_At  | - - - - - - - - - - | - - - - - - - - - - | - - - - - - - - - - - - - K | Y R G V R |
| (8) G30_At    | - - - - - - - - - - | - - - - - - - - - - | - - - - - - - - - - - - - K | Y R G V R |
| (10) G3380_Os | - - - E - T - - - T | K - - - - - - - - - | - - - - - - - - - - - - - - | Y R G V R |
| (36) G3794_Zm | - - - E - P - - - T | K - - - - - - - - - | - - - - - - - - - - - - - - | Y R G V R |
| (30) G3736_Ta | - - - E - P - - - T | K - - - - - - - - - | - - - - - - - - - - - - - - | Y R G V R |
| (12) G3381_Os | - - - E L V - - - A | K - - - - - - - - - | - - - - - - - - - - - - - - | Y R G V R |
| (20) G3517_Zm | - - - E - P - - - T | K - - - - - - - - - | - - - - - - - - - - - - - - | Y R G V R |
| (34) G3739_Zm | - - - E - P - - - T | K - - - - - - - - - | - - - - - - - - - - - - - - | Y R G V R |
| (26) G3520_Gm | - - - K E E - - - P | R - - - - - - - - - | - - - - - - - - - - - - - - | Y R G V R |
| (14) G3383_Os | - - - A T - - - - - | K - - - - - - - - - | - - - - - - - - - - - - - - | Y R G V R |
| (32) G3737_Os | - - - A S - - - - - | K - - - - - - - - - | - - - - - - - - - - - - - - | Y R G V R |
| (16) G3515_Os | - - - K S S - - - S | S - - - - - - - - - | - - - - - - - - - - - - - - | Y R G V R |
| (18) G3516_Zm | - - - K - - - - - - | - - - - - - - - - - | - - - - - - - - - - - - - - | Y R G V R |
| (2) G1792_At  | - - - - - - - - K Q | - - - - - - - - - - | - - - - - - - - - - - - A R | F R G V R |
| (22) G3518_Gm | - - - - - - - - - - | - - - - - - - - - - | - - - - - - - - - - V E V R | Y R G I R |
| (24) G3519_Gm | - - - - - - - - - - | - - - - - - - - - - | - - - - - - - - - - C E V R | Y R G I R |
| (28) G3735_Mt | - - - N G N G - - N | S - - - - - - - - - | - - - - - - - - - - D Q I K | Y R G I R |
| (52) G26_At   | - - - N S R - - - Q | R - - - - - - - - - | - - - - - - - - - - - - - N | Y R G V R |
| (50) G22_At   | S G S H A P - - - R | Q - - - - - - K - - | - - - - - - - - - - - G M Q | Y R G V R |
| (46) G1006_At | A M E E K P - - - K | K - - A I P V T - - | - - - - - - E T A V K A K H | Y R G V R |
| (48) G28_At   | A V D S V P V - - K | K E K T S P V S A A | - - - - - - V T A A K G K H | Y R G V R |
| (54) G1751_At | K K A E G G G K I R | K R K N K - - - - - | - - - - - - - - - - - K N G | Y R G V R |
| (40) G45_At   | P T I D S C S L S S | R V S C K - - - - - | - - - - - - - - - - - T R K | Y R G V R |
| (38) G1266_At | I D S D S Q D L P I | K - - - - - S V S - | S R K S - - - - - - - E K S | Y R G V R |
| (44) G2512_At | F A F E S S - - I I | K E E G K E A T V A | - A E E - - - - - - - E K S | Y R G V R |

FIG. 3E

|  |  | 210 |  | 220 | 230 | 240 |
|---|---|---|---|---|---|---|
| (42) G1752_At  | K R P W G K F A A E I R D | S T R N | G I R V W L G T F D K | A E E A A L A Y D Q | A A |
| (4) G1791_At   | K R P W G K Y A A E I R D | S A R H | G A R V W L G T F N T | A E D A A R A Y D R | A A |
| (6) G1795_At   | R R P W G K Y A A E I R D | S R K H | G E R V W L G T F D T | A E E A A R A Y D Q | A A |
| (8) G30_At     | R R P W G K Y A A E I R D | S R K H | G E R V W L G T F D T | A E D A A R A Y D R | A A |
| (10) G3380_Os  | R R P S G K F A A E I R D | S S R Q | S V R V W L G T F D T | A E E A A R A Y D R | A A |
| (36) G3794_Zm  | R R P S G K F A A E I R D | S S R Q | S V R M W L G T F D T | A E E A A R A Y D R | A A |
| (30) G3736_Ta  | R R P W G K F A A E I R D | S S R H | G V R M W L G T F D T | A E E A A A Y D R S | A |
| (12) G3381_Os  | R R P W G K F A A E I R D | S S R H | G V R V W L G T F D T | A E E A A R A Y D R S | A |
| (20) G3517_Zm  | R R P W G K Y A A E I R D | S S R H | G V R I W L G T F D T | A E E A A R A Y D R S | A |
| (34) G3739_Zm  | R R P W G K Y A A E I R D | S S R H | G V R I W L G T F D T | A E E A A R A Y D R S | A |
| (26) G3520_Gm  | R R P W G K F A A E I R D | P A R H | G A R V W L G T F L T | A E E A A R A Y D R A | A |
| (14) G3383_Os  | R R P W G K F A A E I R D | P E R G | G A R V W L G T F D T | A E E A A R A Y D R A | A |
| (32) G3737_Os  | R R P W G K F A A E I R D | P E R G | G S R V W L G T F D T | A E E A A R A Y D R A | A |
| (16) G3515_Os  | K R P W G K F A A E I R D | P E R G | G A R V W L G T F D T | A E E A A R A Y D R A | A |
| (18) G3516_Zm  | K R P W G K F A A E I R D | P E R G | G S R V W L G T F D T | A E E A A R A Y D R A | A |
| (2) G1792_At   | R R P W G K F A A E I R D | P S R N | G A R L W L G T F E T | A E E A A R A Y D R A | A |
| (22) G3518_Gm  | R R P W G K F A A E I R D | P T R K | G T R I W L G T F D T | A E Q A A R A Y D A A | A |
| (24) G3519_Gm  | R R P W G K F A A E I R D | P T R K | G T R I W L G T F D T | A E Q A A R A Y D A A | A |
| (28) G3735_Mt  | R R P W G K F A A E I R D | P T R K | G T R I W L G T F D T | A E Q A A R A Y D A A | A |
| (52) G26_At    | Q R P W G K W A A E I R D | P N K - | A A R V W L G T F D T | A E E A A L A Y D K A | A |
| (50) G22_At    | R R P W G K F A A E I R D | P K K N | G A R V W L G T Y E T P | E D A A V A Y D R A | A |
| (46) G1006_At  | Q R P W G K F A A E I R D | P A K N | G A R V W L G T F E T | A E D A A L A Y D I A | A |
| (48) G28_At    | Q R P W G K F A A E I R D | P A K N | G A R V W L G T F E T | A E D A A L A Y D R A | A |
| (54) G1751_At  | Q R P W G K F A A E I R D | P K R - | A T R V W L G T F E T | A E D A A R A Y D R A | A |
| (40) G45_At    | K R P W G K F A A E I R D | S T R N | G V R V W L G T F Q T | A E E A A M A Y D K A | A |
| (38) G1266_At  | R R P W G K F A A E I R D | S T R N | G I R V W L G T F E S | A E E A A L A Y D Q A | A |
| (44) G2512_At  | K R P W G K F A A E I R D | S T R K | G I R V W L G T F D T | A E A A A L A Y D Q A | A |

FIG. 3F

|     | 250 | 260 | 270 | 280 |
|---|---|---|---|---|
| (42) G1752_At | F A T K G - S L A T L N F P V E | V V R E S L K K M E N V N L H D G G S P V M A L |
| (4) G1791_At  | F G M R G - Q R A I L N F P H E | Y Q M M K D - - - - - - - - - - - G - - - - - |
| (6) G1795_At  | Y S M R G - Q A A I L N F P H E | Y N M G S G - - - - - - - - - - - V - - - - - |
| (8) G30_At    | Y S M R G - K A A I L N F P H E | Y N M G T - - - - - - - - - - - - - - - - - - |
| (10) G3380_Os | Y A M R G - H L A V L N F P A E | - - - - - - - - - - - - - - - - - A - - - - - |
| (36) G3794_Zm | Y A M R G - Q I A V L N F P A E | - - - - - - - - - - - - - - - - - A - - - - - |
| (30) G3736_Ta | Y S M R G - R N A V L N F P D R | - - - - - - - - - - - - - - - - - A - - - - - |
| (12) G3381_Os | Y S M R G - A N A V L N F P A D | - - - - - - - - - - - - - - - - - A - - - - - |
| (20) G3517_Zm | N S M R G - A N A V L N F P E D | - - - - - - - - - - - - - - - - - A - - - - - |
| (34) G3739_Zm | Y S M R G - A N A V L N F P E D | - - - - - - - - - - - - - - - - - A - - - - - |
| (26) G3520_Gm | Y E M R G - A L A V L N F P N E | - - - - - - - - - - - - - - - - - Y - - - - - |
| (14) G3383_Os | Y A Q R G - A A A V L N F P - - | - - - - - - - - - - - - - - - - - A - - - - - |
| (32) G3737_Os | F A M K G - A M A V L N F P - - | - - - - - - - - - - - - - - - - - - - - - - - |
| (16) G3515_Os | F A M K G - A T A M L N F P - - | - - - - - - - - - - - - - - - - - G - - - - - |
| (18) G3516_Zm | F A M K G - A T A V L N F P A S | - - - - - - - - - - - - - - - - - G - - - - - |
| (2) G1792_At  | F N L R G - H L A I L N F P N E | Y Y P - - - - - - - - - - - - - - - - - - - - |
| (22) G3518_Gm | F H F R G - H R A I L N F P N E | Y Q S H N P - - - - - - - - - - - N - - - - - |
| (24) G3519_Gm | F H F R G - H R A I L N F P N E | Y Q S H N P - - - - - - - - - - - N - - - - - |
| (28) G3735_Mt | F H F R G - H R A I L N F P N E | Y Q A P N S - - - - - - - - - - - S - - - - - |
| (52) G26_At   | F E F R G - H K A K L N F P E H | I R V N P T - - - - - - - - - - - - - - - - - |
| (50) G22_At   | F Q L R G - S K A K L N F P H L | I G S C - - - - - - - - - - - - - - - - - - - |
| (46) G1006_At | F R M R G - S R A L L N F P L R | V N S G - - - - - - - - - - - - - - - - - - - |
| (48) G28_At   | F R M R G - S R A L L N F P L R | V N S G - - - - - - - - - - - - - - - - - - - |
| (54) G1751_At | I G F R G - P R A K L N F P F V | D Y T S S - - - - - - - - - - - - - - - - - - |
| (40) G45_At   | V R I R G T Q K A H T N F Q L E | T V I K A M E M - - - - - - - D C N - - - - - |
| (38) G1266_At | F S M R G - S S A I L N F S A E | R V Q E S L S E I K - Y T Y E D G C S P V V A L |
| (44) G2512_At | F A L K G - S L A V L N F P A D | V V E E S L R K M E N V N L N D G E S P V I A L |

FIG. 3G

|  |  | 290 | 300 | 310 | 320 |
|---|---|---|---|---|---|
| (42) G1752_At | K R K H S L R N R P R | - - - - - G K K R | S S S S | S - - S S S - | S N S S S C S S S |
| (4) G1791_At | P N - - - - - G S H E | - - - - - N A V A | S S S S | G - - - - - - - | Y R G G G G G D |
| (6) G1795_At | S S S T A M A G S S S | - - - - - A S A S A | S S S | - - - - - - - - | - - - - - - - - |
| (8) G30_At | - - - - - - - G S S S | - - - - - T A A N | S S S S | - - - - - - - - | - - - - - - - - |
| (10) G3380_Os | R N Y V R G S - - - - | - - - - - G S - - - | S S S | S - - - - - - - | R Q - - - - H Q |
| (36) G3794_Zm | R N Y V R G - - - - - | - - - - - G S - - - | S S S | - - - - - - - - | R Q - - - - Q Q |
| (30) G3736_Ta | H V Y E A E A R R - Q | - - - - - G Q - G | S S S S | A - - - - - - - | R Q Q N Q Q Q Q |
| (12) G3381_Os | H I Y A R Q L H N - N | - - - - - N A A A G | S S S | S - - - - - - - | S S - - - - A A |
| (20) G3517_Zm | P A Y A A A A S R - - | - - - - - G S - A G G | S S | S - - - - - - - | R P - - - - - - |
| (34) G3739_Zm | H A Y A A A C - R - - | - - - - - G S G S | S S S S | S - - - - - - - | R H R - Q Q Q Q |
| (26) G3520_Gm | P S C S S M N S S - - | - - - - - S T L A P | S S S | S - - - - - - - | S N S M L K S D |
| (14) G3383_Os | A A A A G R G G G - - | - - - - - A G G A A | S G S | - - - - - - - - | S S S S S A Q |
| (32) G3737_Os | - - - - G R T S S - - | - - - - - T G S S | S S S S | S - - - - - - - | T P P A P V T |
| (16) G3515_Os | D H H H G A A S R - M | - - - - - T S T G | S S S S | S - - - - - - - | F T T P P P A N |
| (18) G3516_Zm | G S S A G A A P G G R | - - - - - T S G G | S S S S | - - - - - - - - | T T S A P A S |
| (2) G1792_At | R M D D Y S L R P P Y | - - - - - A S S S | S S S S | S - - - - - - - | G S T S T N V S |
| (22) G3518_Gm | S S L P M P L A V S A | - - - - - - P P S Y | S S S | S - - - - - - - | S T S N Y S G D |
| (24) G3519_Gm | S S L P M P L I V P - | - - - - - - P P S Y | S S S | - - - - - - - - | F T S N Y S A D |
| (28) G3735_Mt | S S L P M P L T M P P P P S S N P P P S | S S S S | S - - - - - - - | S F S S Y T V D |
| (52) G26_At | Q L Y P S P A T S H D R - I I V T P P S P P P P | I A P D I L L D Q Y G H F Q S R |
| (50) G22_At | K Y E P V R I R P R R | - - - - - R S P E P | S V S | - - - - - - - - | D Q L T S E Q K |
| (46) G1006_At | E P D P V R I T S K R | - - - - - S S S S | S S S S | S S S T S S - | S E N G K L K R R |
| (48) G28_At | E P D P V R I K S K R | - - - - - S S F S | S S N | - - - - - - - - | E N G A P K K R |
| (54) G1751_At | V S S P V A D D I G - | - - - - - A K A S A | S A S | V S - - - - - - | A T D S V E A E |
| (40) G45_At | P N Y Y R M N N S N T | - - - - - S D P L R | S S R | - - K I G L R - | G K E A V K A Y |
| (38) G1266_At | K R K H S M R R R - M | - - - - - T N K K | T K D S | D - - - - - - - - | F D H R |
| (44) G2512_At | K R K H S M R N R P R | - - - - - G K K K | S S S S | S T L T S S P S S S S S Y S S S |

|     |     | 370 |     |     |     |     |     |     |     |     |     |     |     |     |     |     | 380 |     |     |     |     |     |     |     |     |     |     |     |     |     | 390 |     |     |     |     |     |     |     |     |     | 400 |     |     |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| (42) G1752_At | - | - | - | - | - | - | - | T | - | - | - | - | S | R | S | S | S | K | Q | S | V | V | K | - | Q | E | S | G | - | T | L | V | V | F | E | D | L | G | A | E |
| (4) G1791_At | - | - | - | - | - | - | - | - | - | - | - | - | - | - | - | - | - | G | R | E | - | - | - | - | - | - | - | - | - | - | V | I | E | F | E | Y | L | D | D | S |
| (6) G1795_At | - | - | - | - | - | - | - | - | - | - | - | - | - | - | - | - | - | S | R | Q | - | - | - | - | - | - | - | - | - | - | V | F | E | F | E | Y | L | D | D | S |
| (8) G30_At | - | - | - | - | - | - | - | - | - | - | - | - | - | - | - | - | - | S | Q | Q | - | - | - | - | - | - | - | - | - | - | V | F | E | F | E | Y | L | D | D | S |
| (10) G3380_Os | - | - | - | - | - | - | - | - | - | - | - | - | - | - | - | - | - | - | R | Q | - | - | - | - | - | - | - | - | - | - | V | I | E | L | E | C | L | D | D | Q |
| (36) G3794_Zm | - | - | - | - | G | G | G | S | - | - | - | - | G | G | G | A | G | Q | Q | - | - | - | - | - | - | - | - | - | - | - | V | I | E | L | E | C | L | D | D | Q |
| (30) G3736_Ta | - | - | - | - | - | - | - | - | - | - | - | - | - | - | - | - | - | S | G | - | - | - | - | - | - | - | - | - | - | - | V | I | E | F | E | Y | L | D | D | D |
| (12) G3381_Os | - | - | - | - | - | - | - | - | - | - | - | - | - | - | - | - | - | A | A | R | P | P | - | - | - | - | - | - | - | - | P | I | E | F | E | Y | L | D | D | H |
| (20) G3517_Zm | - | - | - | - | - | - | - | - | - | - | - | - | - | - | - | - | - | S | G | R | D | - | - | - | - | - | - | - | - | - | V | I | E | F | E | Y | L | D | D | E |
| (34) G3739_Zm | - | - | - | - | - | - | - | - | - | - | - | - | - | - | - | - | - | S | G | R | D | - | - | - | - | - | - | - | - | - | V | I | E | L | E | Y | L | D | D | E |
| (26) G3520_Gm | - | - | - | - | - | - | - | - | - | - | - | - | - | - | - | - | - | - | G | K | Q | - | - | - | - | - | - | - | - | - | V | I | E | F | E | C | L | D | D | K |
| (14) G3383_Os | - | - | - | - | - | - | - | - | - | - | - | - | - | - | - | - | - | - | G | R | G | - | - | - | D | - | - | - | - | - | K | I | E | F | E | Y | L | D | D | K |
| (32) G3737_Os | - | - | - | - | - | - | - | - | - | - | - | - | - | - | - | - | - | S | R | H | C | A | - | D | - | - | - | T | T | E | K | V | E | L | V | Y | L | D | D | K |
| (16) G3515_Os | - | - | - | - | - | - | - | - | - | - | - | - | - | - | - | - | A | G | R | G | G | S | - | D | - | - | - | R | T | T | D | K | V | E | L | E | C | L | D | D | K |
| (18) G3516_Zm | - | - | - | - | - | - | - | - | - | - | - | - | - | - | - | - | - | G | R | A | R | V | P | D | - | - | - | - | - | S | E | K | V | E | L | E | C | L | D | D | R |
| (2) G1792_At | - | - | - | - | - | - | - | - | - | - | - | - | - | - | - | - | - | - | Q | N | Q | - | - | - | - | - | - | - | - | - | R | E | V | F | E | F | E | Y | L | D | D | K |
| (22) G3518_Gm | - | - | - | - | L | V | R | P | A | F | S | G | E | I | M | Q | G | G | D | H | - | - | - | - | - | - | - | D | D | D | T | F | E | L | E | Y | F | D | N | K |
| (24) G3519_Gm | - | - | - | - | L | V | R | P | - | - | - | G | E | I | M | Q | G | G | D | - | - | - | - | - | - | - | - | - | L | D | D | T | F | E | L | E | Y | L | D | N | K |
| (28) G3735_Mt | - | - | - | - | - | - | - | - | - | - | - | - | - | - | - | - | G | F | D | - | - | - | - | - | - | - | - | - | - | - | - | - | E | L | E | F | L | D | N | K |
| (52) G26_At | - | - | - | - | - | - | - | - | - | - | - | - | - | - | - | - | - | S | S | A | N | L | S | M | N | - | - | - | - | M | L | S | S | S | S | S | L | N | H | Q |
| (50) G22_At | - | - | - | - | - | - | - | - | - | - | - | - | - | - | - | H | V | D | D | G | E | S | S | - | - | - | - | - | - | L | V | V | P | E | L | D | F | T | V | D | Q | F | Y |
| (46) G1006_At | - | - | - | - | - | - | - | - | - | - | - | - | - | - | - | - | - | K | A | E | N | L | T | S | E | - | - | - | - | - | V | V | Q | V | K | C | E | V | - | G | D | E | T | R |
| (48) G28_At | - | - | - | - | - | - | - | - | - | - | - | - | - | - | - | - | - | A | A | G | G | G | M | D | K | - | - | - | - | - | - | - | - | G | L | T | V | K | C | E | - | V | E | V | A |
| (54) G1751_At | - | - | - | - | - | - | - | - | - | - | - | - | - | - | - | - | - | - | G | G | G | G | D | - | - | - | - | - | - | - | - | - | C | N | M | E | E | W | M | N | M | M |
| (40) G45_At | R | R | R | S | N | E | D | S | M | C | Q | E | V | E | M | Q | K | T | V | T | G | E | E | T | V | C | D | V | F | G | L | F | E | F | E | D | L | G | S | D |
| (38) G1266_At | - | - | - | - | - | - | - | - | - | - | - | - | - | - | - | - | - | - | - | - | - | - | V | K | - | - | L | D | N | - | - | V | V | V | F | E | D | L | G | E | Q |
| (44) G2512_At | - | - | - | - | - | - | - | - | L | - | - | - | - | S | S | R | S | R | K | Q | S | V | V | M | T | Q | E | S | N | T | T | L | V | V | L | E | D | L | G | A | E |

|       |       |       |       |
|-------|-------|-------|-------|
| 450   | 460   | 470   | 480   |

(42) G1752_At
(4) G1791_At
(6) G1795_At    - - - - G K K K
(8) G30_At
(10) G3380_Os
(36) G3794_Zm
(30) G3736_Ta
(12) G3381_Os
(20) G3517_Zm
(34) G3739_Zm
(26) G3520_Gm
(14) G3383_Os
(32) G3737_Os
(16) G3515_Os
(18) G3516_Zm
(2) G1792_At
(22) G3518_Gm
(24) G3519_Gm
(28) G3735_Mt
(52) G26_At
(50) G22_At
(46) G1006_At
(48) G28_At
(54) G1751_At
(40) G45_At
(38) G1266_At
(44) G2512_At

FIG. 3L

| | | | | | | | | | | | | | | | |
|---|---|---|---|---|---|---|---|---|---|---|---|---|---|---|---|
| G1752_At | (42) | L | V | V | F | E | D | L | G | A | E | Y | L | E | Q | L | L |
| G1791_At | (4) | V | I | E | F | E | Y | L | D | D | S | L | L | E | E | L | L |
| G1795_At | (6) | V | F | E | F | E | Y | L | D | D | S | V | L | E | E | L | L |
| G30_At | (8) | V | F | E | F | E | Y | L | D | D | S | V | L | D | E | L | L |
| G3380_Os | (10) | V | I | E | L | E | C | L | D | D | Q | V | L | Q | E | M | L |
| G3794_Zm | (36) | V | I | E | L | E | C | L | D | D | Q | V | L | Q | E | M | L |
| G3736_Ta | (30) | V | I | E | F | E | Y | L | D | D | D | V | L | Q | S | M | L |
| G3381_Os | (12) | P | I | E | F | E | Y | L | D | D | H | V | L | Q | E | M | L |
| G3517_Zm | (20) | V | I | E | F | E | Y | L | D | D | E | V | L | Q | E | M | L |
| G3739_Zm | (34) | V | I | E | L | E | Y | L | D | D | E | V | L | Q | E | M | L |
| G3520_Gm | (26) | V | I | E | F | E | C | L | D | D | K | L | L | E | D | L | L |
| G3383_Os | (14) | K | I | E | F | E | Y | L | D | D | K | V | L | D | D | L | L |
| G3737_Os | (32) | K | V | E | L | V | Y | L | D | D | K | V | L | D | E | L | L |
| G3515_Os | (16) | K | V | E | L | E | C | L | D | D | K | V | L | E | D | L | L |
| G3516_Zm | (18) | K | V | E | L | E | C | L | D | D | R | V | L | E | E | L | L |
| G1792_At | (2) | V | F | E | F | E | Y | L | D | D | K | V | L | E | E | L | L |
| G3518_Gm | (22) | T | F | E | L | E | Y | F | D | N | K | L | L | E | E | L | L |
| G3519_Gm | (24) | T | F | E | L | E | Y | L | D | N | K | L | L | E | E | L | L |
| G3735_Mt | (28) | - | - | E | L | E | F | L | D | N | K | L | L | Q | E | L | L |
| G26_At | (52) | S | S | S | S | S | S | L | N | H | Q | G | L | R | P | N | L |
| G22_At | (50) | E | L | D | F | T | V | D | Q | F | Y | F | D | G | S | L | L |
| G1006_At | (46) | K | C | E | V | - | G | D | E | T | R | V | D | - | E | L | L |
| G28_At | (48) | T | V | K | C | E | - | V | E | V | A | R | G | - | R | L | L |
| G1751_At | (54) | C | N | M | E | E | W | M | N | M | M | M | M | D | F | L | G |
| G45_At | (40) | L | F | E | F | E | D | L | G | S | D | Y | L | E | T | L | L |
| G1266_At | (38) | V | V | V | F | E | D | L | G | E | Q | Y | L | E | E | L | L |
| G2512_At | (44) | L | V | V | L | E | D | L | G | A | E | Y | L | E | E | L | - |
| | | | | | | E | | D | | | | | L | | | L | |

G1792 clade (brace covering G1791_At through G3735_Mt)

FIG. 4

CONFERRING BIOTIC AND ABIOTIC STRESS TOLERANCE IN PLANTS

RELATIONSHIP TO CO-PENDING APPLICATIONS

This application (the "present application") claims the benefit of U.S. provisional application 60/961,403, filed 20 Jul. 2007; and, the present application is a continuation-in-part of U.S. non-provisional application Ser. No. 11/479,226, filed 30 Jun. 2006 (pending), which is a continuation-in-part of U.S. non-provisional application Ser. No. 09/713,994, filed 16 Nov. 2007 (abandoned), which claims the benefit of U.S. provisional application 60/166,228, filed 17 Nov. 1999; and, the present application is a continuation-in-part of U.S. non-provisional application Ser. No. 11/725,235, filed 16 Mar. 2007 (pending), which is a divisional of U.S. non-provisional application Ser. No. 10/225,068, filed 9 Aug. 2002 (issued as U.S. Pat. No. 7,193,129), which is a continuation-in-part of U.S. non-provisional application Ser. No. 09/837,944, filed 18 Apr. 2001 (abandoned), and U.S. non-provisional application Ser. No. 10/225,068 is also a continuation-in-part of U.S. non-provisional application Ser. No. 10/171,468, filed 14 Jun. 2002 (abandoned), and U.S. non-provisional application Ser. No. 10/225,068 claims the benefit of each of U.S. provisional application 60/310,847, filed 9 Aug. 2001, U.S. provisional application 60/336,049, filed 19 Nov. 2001, and U.S. provisional application 60/338,692, filed 11 Dec. 2001; and, the present application is a continuation-in-part of U.S. non-provisional application Ser. No. 11/728,567, filed 26 Mar. 2007 (pending), which is a divisional of U.S. non-provisional application Ser. No. 10/225,066, filed 9 Aug. 2002 (issued as U.S. Pat. No. 7,238,860), which is a continuation-in-part of U.S. non-provisional application Ser. No. 09/837,944, filed 18 Apr. 2001 (abandoned), and U.S. non-provisional application Ser. No. 10/225,066 is also a continuation-in-part of U.S. non-provisional application Ser. No. 10/171,468, filed 14 Jun. 2002 (abandoned), and U.S. non-provisional application Ser. No. 10/225,066 also claims the benefit of each of U.S. provisional application 60/310,847, filed 9 Aug. 2001, U.S. provisional application 60/336,049, filed 19 Nov. 2001, and U.S. provisional application 60/338,692, filed 11 Dec. 2001; and, the present application is a continuation-in-part of U.S. non-provisional application Ser. No. 10/374,780, filed 25 Feb. 2003 (pending), which is a continuation-in-part of U.S. non-provisional application Ser. No. 10/225,068, filed 9 Aug. 2002 (issued as U.S. Pat. No. 7,193,129), and U.S. non-provisional application Ser. No. 10/374,780 is a continuation-in-part of U.S. non-provisional application Ser. No. 10/225,066, filed 9 Aug. 2002 (issued as U.S. Pat. No. 7,238,860), and U.S. non-provisional application Ser. No. 10/374,780 is a continuation-in-part of U.S. non-provisional application Ser. No. 09/934,455, filed 22 Aug. 2001 (abandoned), which is a continuation-in-part of U.S. non-provisional application Ser. No. 09/713,994, filed 16 Nov. 2007 (abandoned), and U.S. non-provisional application Ser. No. 09/934,455 is a continuation-in-part of U.S. non-provisional application Ser. No. 09/837,944, filed 18 Apr. 2001 (abandoned); and, the present application is a continuation-in-part of U.S. non-provisional application Ser. No. 10/546,266, filed 19 Aug. 2005 (pending), which is a '371 National Stage filing of PCT application PCT/US2004005654, filed 25 Feb. 2004 (expired), which is a continuation-in-part of U.S. non-provisional application Ser. No. 10/374,780, filed 25 Feb. 2003 (pending); and, the present application is a continuation-in-part of U.S. non-provisional application Ser. No. 10/559,441, filed 2 Dec. 2005 (pending), which is a '371 National Stage filing of PCT application PCT/US2004/017768, filed 4 Jun. 2004 (expired), which is a continuation-in-part of U.S. non-provisional application Ser. No. 10/456,882, filed 6 Jun. 2003 (abandoned); and, the present application is a continuation-in-part of U.S. non-provisional application Ser. No. 11/642,814, filed 20 Dec. 2006 (pending), which is a divisional application of U.S. non-provisional application Ser. No. 10/666,642, filed 18 Sep. 2003 (issued as U.S. Pat. No. 7,196,245), which claims the benefit of each of U.S. provisional application 60/411,837, filed 18 Sep. 2002, and U.S. provisional application 60/465,809, filed 24 Apr. 2003; and, the present application is a continuation-in-part of U.S. non-provisional application Ser. No. 10/714,887, filed 13 Nov. 2003 (pending), which is a continuation-in-part of U.S. non-provisional application Ser. No. 10/456,882, filed 6 Jun. 2003 (abandoned), and U.S. non-provisional application Ser. No. 10/714,887 is also a continuation-in-part of U.S. non-provisional application Ser. No. 10/666,642, filed 18 Sep. 2003 (issued as U.S. Pat. No. 7,196,245), which claims the benefit of each of U.S. provisional application 60/411,837, filed 18 Sep. 2002, and U.S. provisional application 60/465,809, filed 24 Apr. 2003; and, the present application is a continuation-in-part of U.S. non-provisional application Ser. No. 11/435,388, filed 15 May 2006 (pending), which is a continuation-in-part of PCT application PCT/US04/37584, filed 12 Nov. 2004 (expired), which is a continuation-in-part of U.S. non-provisional application Ser. No. 10/714,887, filed 13 Nov. 2003 (pending); and, the present application is a continuation-in-part of U.S. non-provisional application Ser. No. 11/632,390, filed 11 Jan. 2007 (pending), which is a '371 National Stage filing of PCT application PCT/US2005/025010, filed 14 Jul. 2005 (expired), which claims the benefit of U.S. provisional application 60/588,405, filed 14 Jul. 2004; and, the present application is a continuation-in-part of PCT application PCT/US2006/34615, filed 31 Aug. 2006 (pending), which claims the benefit of U.S. provisional application 60/713,952, filed 31 Aug. 2005; and, the present application is a continuation-in-part of U.S. non-provisional application Ser. No. 10/903,236, filed 30 Jul. 2004 (pending); which is a continuation-in-part of U.S. non-provisional application Ser. No. 10/456,882, filed 6 Jun. 2003 (abandoned) and U.S. non-provisional application Ser. No. 10/903,236 is also a continuation-in-part of U.S. non-provisional application Ser. No. 10/666,642, filed 18 Sep. 2003 (issued as U.S. Pat. No. 7,196,245), which claims the benefit of each of U.S. provisional application 60/411,837, filed 18 Sep. 2002, and U.S. provisional application 60/465,809, filed 24 Apr. 2003; and, the present application is a continuation-in-part of U.S. non-provisional application Ser. No. 11/699,973, filed 29 Jan. 2007 (pending), which is a continuation-in-part of PCT application PCT/US2005-027151, filed 29 Jul. 2005 (expired), which is a continuation-in-part of U.S. non-provisional application Ser. No. 10/903,236, filed 30 Jul. 2004 (pending). The entire contents of each of these applications are hereby incorporated by reference.

FIELD OF THE INVENTION

The present invention relates to increasing a plant's tolerance to abiotic stress and resistance to disease and the yield that may be obtained from a plant.

BACKGROUND OF THE INVENTION

The Effects of Various Factors on Plant Yield.

Yield of commercially valuable species in the natural environment may be suboptimal as plants often grow under unfavorable conditions, such as at an inappropriate temperature or with a limited supply of soil nutrients, light, or water. Increased tolerance to abiotic stresses, such as water deprivation, salt, freezing and other hyperosmotic stresses, and cold, and heat, may improve germination, early establishment of developing seedlings, and plant development. In water-limited environments, crop yield is a function of water use, water use efficiency (WUE; defined as aerial biomass yield/water use) and the harvest index (HI; the ratio of yield biomass to the total cumulative biomass at harvest). WUE is a complex trait that involves water and $CO_2$ uptake, transport and exchange at the leaf surface (transpiration). Improved WUE has been proposed as a criterion for yield improvement under drought. Water deficit can also have adverse effects in the form of increased susceptibility to disease and pests, reduced plant growth and reproductive failure. Genes that improve WUE and tolerance to water deficit thus promote plant growth, fertility, and disease resistance. Enhanced tolerance to these stresses would lead to yield increases in conventional varieties and reduce yield variation in hybrid varieties.

Fortunately, a plant's traits, including its biochemical, developmental, or phenotypic characteristics that enhance yield or tolerance to various abiotic or biotic stresses, may be controlled through a number of cellular processes. One important way to manipulate that control is through transcription factors—proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties.

We have identified polynucleotides encoding transcription factors, including *Arabidopsis* sequences G1792, G1791, G1795, G30, soy sequences G3518, G3519 and G3520, rice sequences G3380, G3381, G3383, G3515, G3737, corn sequences G3516, G3517, G3739, and G3794, *Medicago* sequence G3735, and *Triticum* sequence G3736 (SEQ ID NOs: 2, 4, 6, 8, 22, 24, 26, 10, 12, 14, 16, 32, 18, 20, 34, 36, 28, and 30, respectively) and equivalogs listed in the Sequence Listing from a variety of other species, developed transgenic plants using almost all of these polynucleotides from diverse species, and analyzed the plants for their tolerance to low nitrogen conditions, tolerance to cold, tolerance to water deficit conditions, and/or resistance to disease. In so doing, we have identified important polynucleotide and polypeptide sequences for producing commercially valuable plants and crops as well as the methods for making them and using them. Other aspects and embodiments of the invention are described below and can be derived from the teachings of this disclosure as a whole.

SUMMARY OF THE INVENTION

The present invention describes polynucleotides that may be introduced into plants. The polynucleotides encode transcription factor polypeptides that have the useful properties of increasing increased abiotic or biotic stress tolerance, increased tolerance to low nitrogen, and/or altered sensing of carbon-nitrogen (C/N) balance. The present invention thus may be used to increase a plant's tolerance to resistance to biotic stress, or tolerance to abiotic stress, including multiple abiotic stresses, which may further include hyperosmotic stresses such as high salt or drought. This method is accomplished by first providing a nucleic acid construct such as an expression vector, an expression cassette, a plasmid or other DNA preparation and then introducing the expression vector into a plant to produce a transformed plant. The expression vector contains both a regulatory element and a polynucleotide sequence. The regulatory element controls the expression of the polynucleotide sequence. The polynucleotide encodes a member of the G1792 clade of transcription factor polypeptides, which are shown in the present invention to comprise two distinct conserved domains: an AP2 domain and an EDLL domain, in order from N-terminal to C-terminal. The EDLL domain is characterized by, in order from N-terminal to C-terminal, a glutamic acid residue, an aspartic acid residue, and two leucine residues. The consensus sequence for the EDLL domain is represented by SEQ ID NO: 63. After a target plant is transformed with the nucleic acid construct, which confers increased tolerance to low nitrogen conditions, cold, or water deficit conditions, and/or resistance to disease by virtue of the overexpression of the G1792 clade member, the transformed plant is grown.

The invention also pertains to a method for producing a plant with greater tolerance to low nitrogen conditions, cold, or water deficit conditions, and/or resistance to disease, than a control plant. This method is performed by providing the nucleic acid construct just described. After transforming a target plant with this expression vector, a transformed plant with greater tolerance to low nitrogen conditions, cold, or water deficit conditions, and/or greater resistance to disease than a control plant is the result. Water deficit conditions may include various hyperosmotic stresses such as salt, mannitol, sucrose, heat, water deprivation, dehydration, drought, or freezing. Tolerance to cold, which has been shown to be increased by overexpression of a sizable number of G1792 clade member polypeptides, may be conferred during germination or growth. Disease pathogens may include fungal pathogens such as *Botrytis, Erysiphe, Fusarium* or *Sclerotinia*.

The invention also encompasses transgenic plants that have greater tolerance to multiple abiotic stress tolerances than a control plant, wherein the transgenic plants are produced by the above methods.

The invention is further directed to a seed produced from any of the transformed plants produced by the methods disclosed or claimed herein.

The methods encompassed by the invention may be extended to propagation techniques used to generate plants. For example, a target plant that has been transformed with a polynucleotide encoding a G1792 polypeptide clade member and that has greater tolerance to low nitrogen conditions, cold, water deficit, or resistance to disease, than a control plant may be "selfed" (i.e., self-pollinated) or crossed with another plant to produce seed. A progeny plant may be grown from this seed, thus generating a transformed progeny plant with greater resistance to disease or greater tolerance to low nitrogen conditions, cold, water deficit, as compared to the control plant.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

CD-ROM No. 1: Sequence Listing in Computer Readable Form (37 CFR §1.821(c), CD-ROM No. 2: Sequence Listing in Computer Readable Form (37 CFR §1.821(c), and CD-ROM No. 3: Computer Readable Form of Sequence Listing under 37 CFR §1.821(e) & 37 CFR §1.824, are identical read-only memory computer-readable compact discs and each contains a copy of the Sequence Listing in ASCII text format. The Sequence Listing is named "MBI-0063CIP.ST25.txt", is 187 kilobytes in size, and the Sequence Listing files were created on 30 Oct. 2007. The copies of the Sequence Listing on the CD-ROM discs are hereby incorporated by reference in their entirety.

FIG. 1 shows a conservative estimate of phylogenetic relationships among the orders of flowering plants (modified from Angiosperm Phylogeny Group (1998) *Ann. Missouri Bot. Gard.* 84: 1-49). Those plants with a single cotyledon (monocots) are a monophyletic clade nested within at least two major lineages of eudicots; the eudicots are further divided into rosids and asterids. *Arabidopsis* is a rosid eudicot classified within the order Brassicales; rice is a member of the monocot order Poales. FIG. 1 was adapted from Daly et al. (2001) *Plant Physiol.* 127: 1328-1333.

Figure 2:
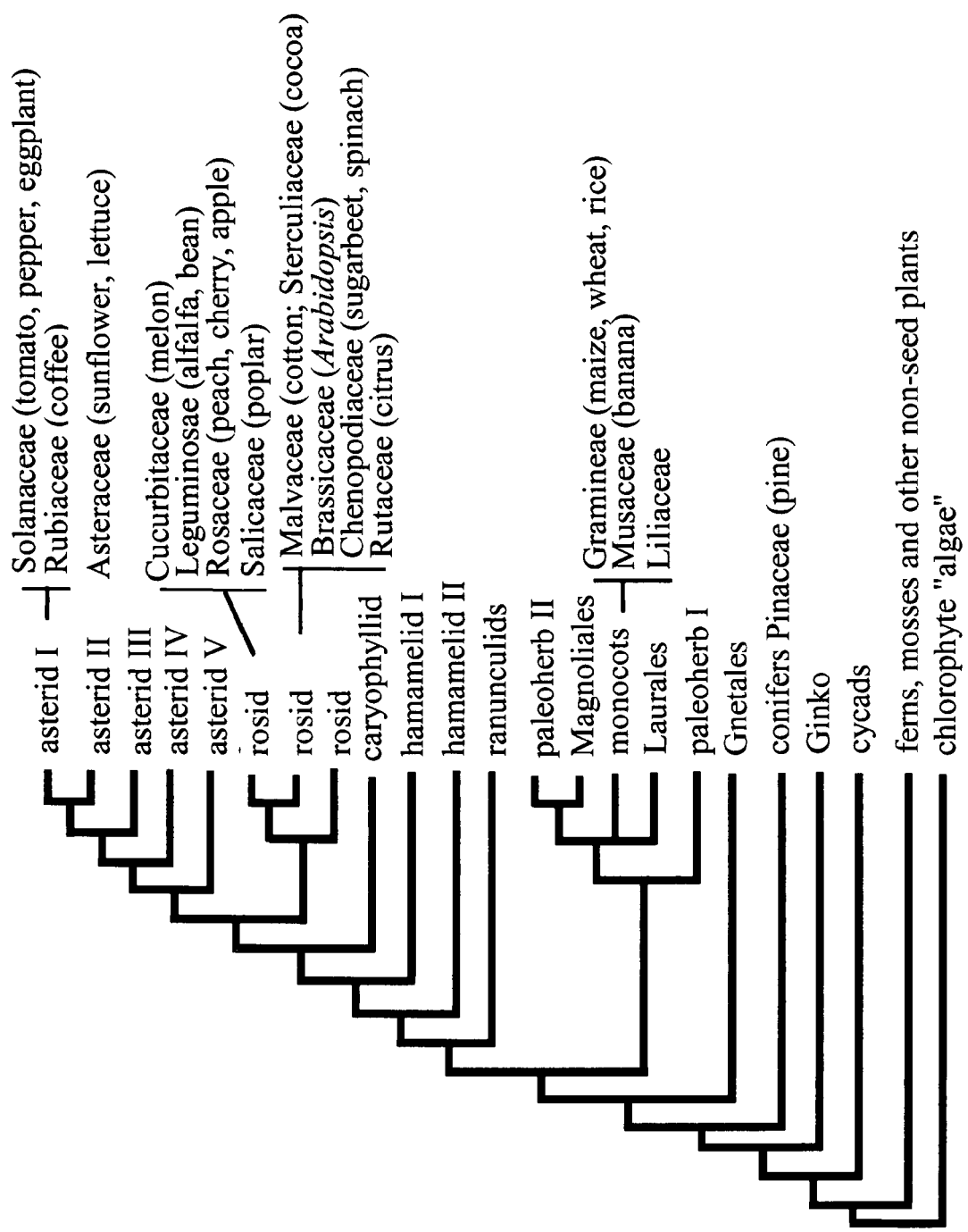

FIG. 2 shows a phylogenic dendogram depicting phylogenetic relationships of higher plant taxa, including clades containing tomato and *Arabidopsis*; adapted from Ku et al. (2000) *Proc. Natl. Acad. Sci. USA* 97: 9121-9126; and Chase et al. (1993) *Ann. Missouri Bot. Gard.* 80: 528-580.

Figure 3I:
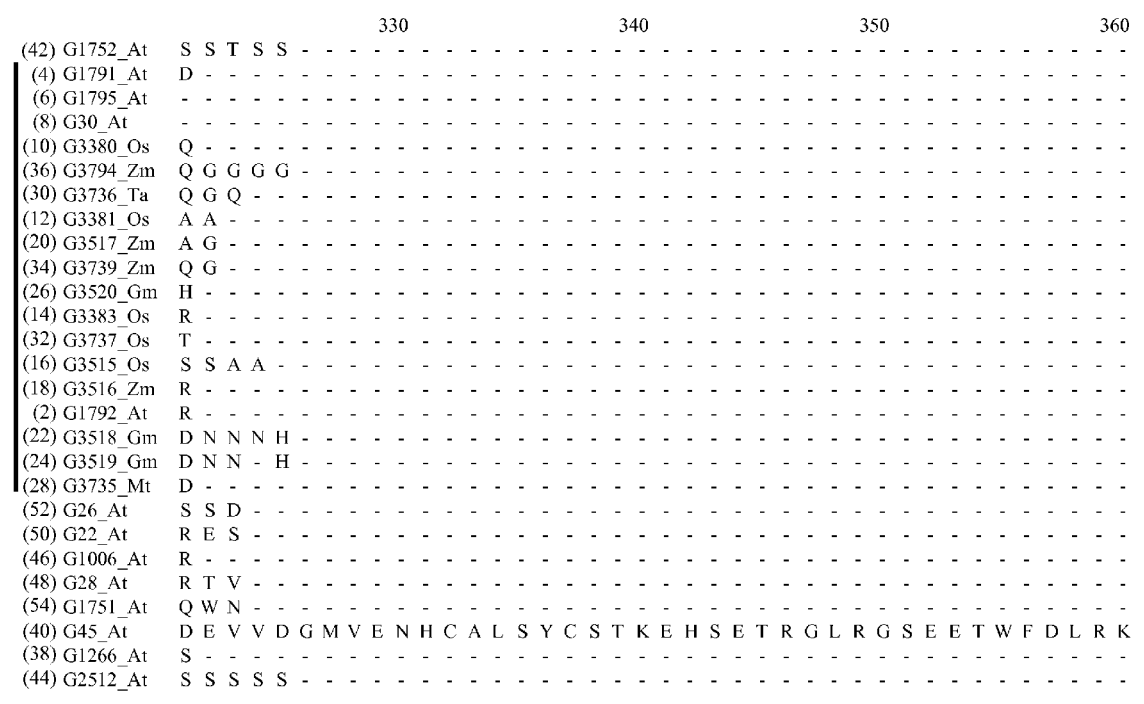
Figure 3K:
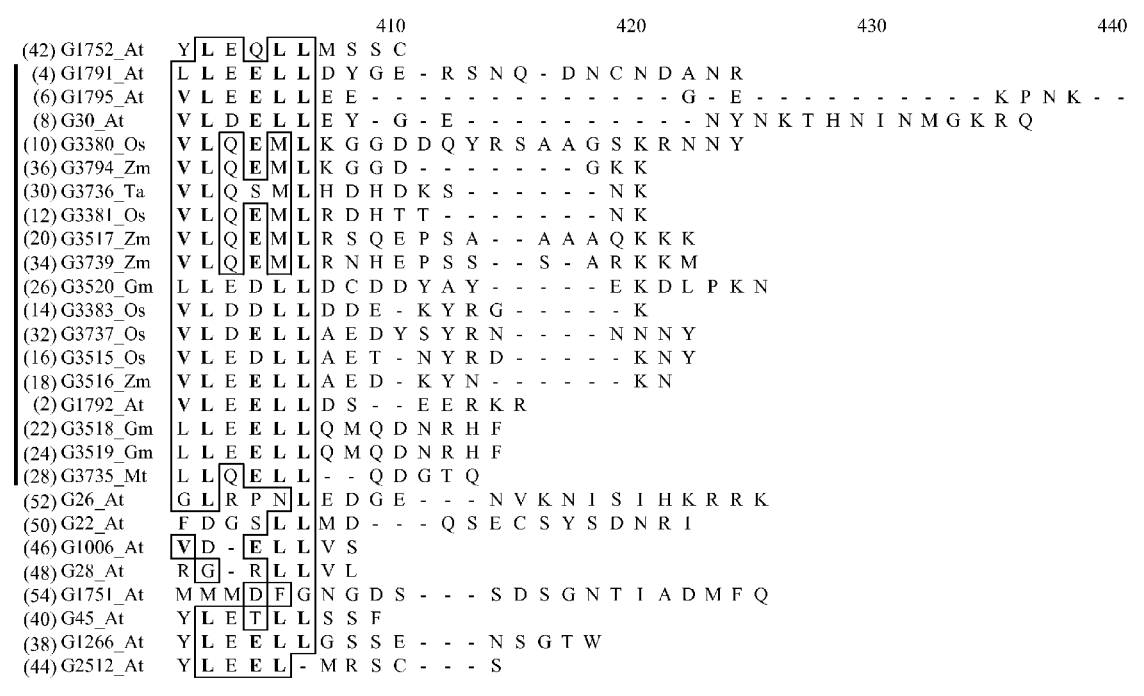

FIGS. 3A-3L represent a multiple amino acid sequence alignment of G1792 orthologs and paralogs. Clade orthologs and paralogs are indicated by the black bar on the left side of the figure. Conserved regions of identity are boxed and appear in boldface, while conserved sequences of similarity are boxed and appear as plain text. The AP2 conserved domains span alignment coordinates 196-254. The S conserved domain spans alignment coordinates of 301-304. The EDLL conserved domain (SEQ ID NO: 63) spans the alignment coordinates of 391-406 (FIGS. 3J-3K; see also FIG. 4). Abbreviations in this figure include: At *Arabidopsis thaliana*; Os *Oryza sativa*; Zm *Zea mays*; Ta *Triticum aestivum*; Gm *Glycine max*; Mt *Medicago truncatula*. SEQ ID NOs: appear in parentheses in these Figures.

FIG. 4 shows a novel conserved domain for the G1792 Glade, herein referred to as the "EDLL domain" (SEQ ID NO: 63). All Glade members contain a glutamic acid residue at position 3, an aspartic acid residue at position 8, and leucine residues at positions 12 and 16 of the domain. SEQ ID NOs: appear in parentheses in this Figure.

Figure 5:
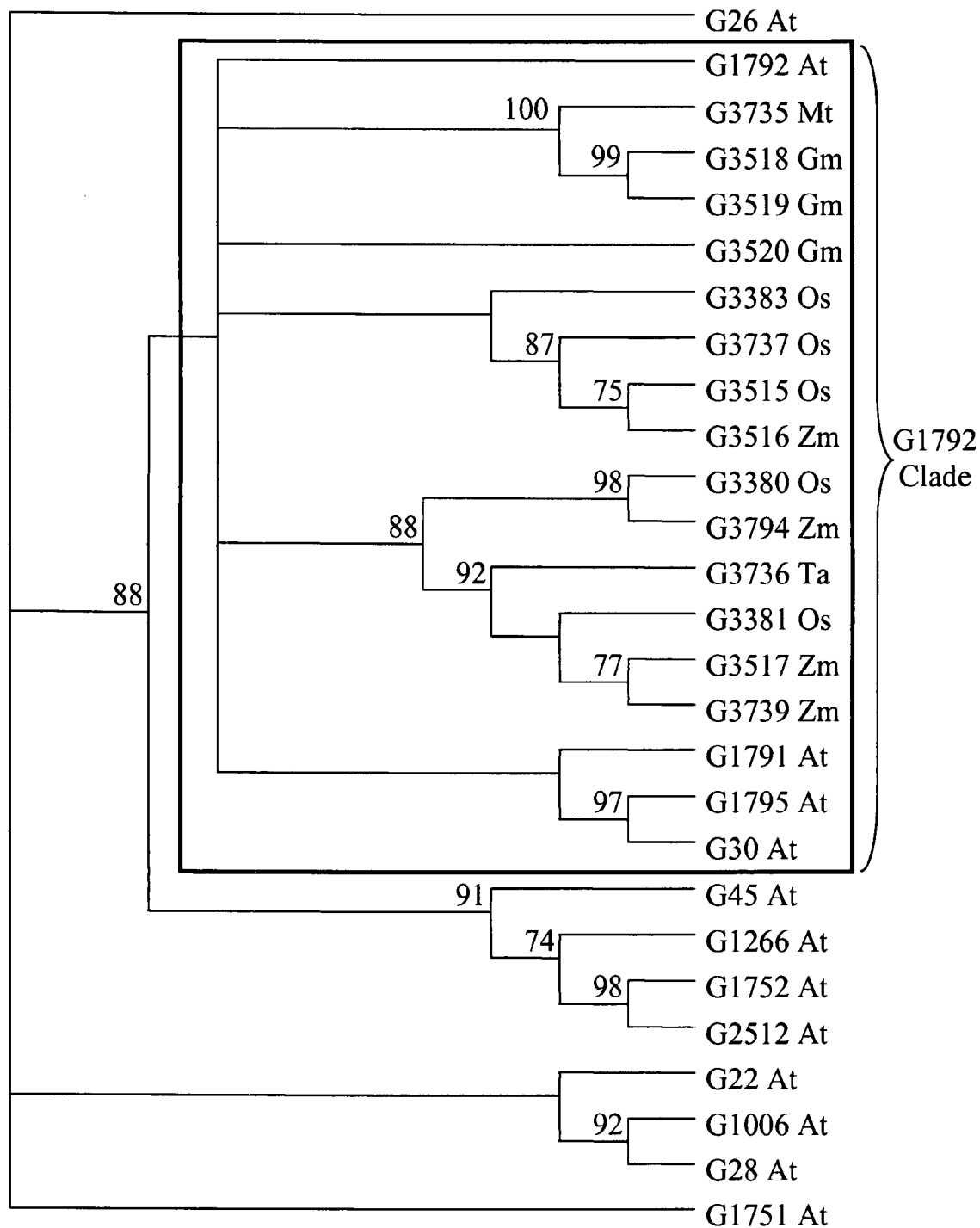

FIG. 5 illustrates the relationship of G1792 and related sequences in this phylogenetic tree of the G1792 clade. The tree building method used was "Neighbor Joining" with "Systematic Tie-Breaking" and Bootstrapping with 1000 replicates. The AP2 domains (as listed in Table 1) were used to build the phylogeny. The members of the G1792 clade are shown within the large box.

DETAILED DESCRIPTION

The present invention relates to polynucleotides and polypeptides for modifying phenotypes of plants, particularly those associated with increased tolerance to low nitrogen and abiotic stress. Throughout this disclosure, various information sources are referred to and/or are specifically incorporated. The information sources include scientific journal articles, patent documents, textbooks, and World Wide Web browser-inactive page addresses, for example. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides, optionally at least about 30 consecutive nucleotides, at least about 50 consecutive nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single stranded.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as splicing and folding to obtain a functional protein or polypeptide. A gene may be isolated, partially isolated, or be found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and which may be used to determine the limits of the genetically active unit (Rieger et al. (1976) *Glossary of Genetics and Cytogenetics: Classical and Molecular,* 4th ed., Springer Verlag, Berlin). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a nucleic acid construct such as an expression vector, an expression cassette, a plasmid or other DNA preparation, or otherwise recombined with one or more additional nucleic acid.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise 1) a localization domain, 2) an activation domain, 3) a repression domain, 4) an oligomerization domain, or 5) a DNA-binding domain, or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Hybridization complex" refers to a complex between two nucleic acid molecules by virtue of the formation of hydrogen bonds between purines and pyrimidines.

"Identity" or "similarity" refers to sequence similarity between two or more polynucleotide sequences, or two or more polypeptide sequences, with identity being a more strict comparison. The phrases "percent identity" and "% identity" refer to the percentage of identical bases or residues at corresponding positions found in a comparison of two or more sequences (when a position in the compared sequence is occupied by the same nucleotide base or amino acid, then the molecules are identical at that position). "Sequence similarity" refers to the percentage of bases that are similar in the corresponding positions of two or more polynucleotide sequences. A degree of homology or similarity of polypeptide sequences is a function of the number of similar amino acid residues at positions shared by the polypeptide sequences. Two or more sequences can be anywhere from 0-100% similar, or any integer value therebetween. Identity or similarity can be determined by comparing a position in each sequence that may be aligned for purposes of comparison.

"Alignment" refers to a number of nucleotide bases or amino acid residue sequences aligned by lengthwise comparison so that components in common (i.e., nucleotide bases or amino acid residues) may be visually and readily identified. The fraction or percentage of components in common is related to the homology or identity between the sequences. Alignments such as those of FIGS. 3A-L or FIG. 4 may be used to identify conserved domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. An "AP2 domain", such as is found in a member of AP2 transcription factor family, is an example of a conserved domain. With respect to polynucleotides encoding presently disclosed transcription factors, a conserved domain is preferably at least 10 base pairs (bp) in length. A "conserved domain", with respect to presently disclosed AP2 polypeptides refers to a domain within a transcription factor family that exhibits a higher degree of sequence homology, such as at least 56.3% or at least 67.7% sequence identity including conservative substitutions, to the conserved AP2 domain of a G1792 clade member polypeptide. A fragment or domain can be referred to as outside a conserved domain, outside a consensus sequence, or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (for example, Riechmann et al. (2000) *Science* 290: 2105-2110). Thus, by using alignment methods well known in the art, the conserved domains of the plant transcription factors for the AP2 proteins may be determined.

Conserved domains for members of the G1792 clade of transcription factor polypeptides (or simply the "G1792 clade"), including SEQ ID NO: 2, 4, 6, 8, 10, 12, 14, 16, 18, 20, 22, 24, 26, 28, 30, 32, 34 and 36, are listed in Table 1. A comparison of these conserved domains with other sequences would allow one of skill in the art to identify AP2 or EDLL domains in the polypeptides listed or referred to in this disclosure, as well as other polypeptides not presented in this disclosure, but which comprise these domains.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of the hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985) *Nature* 313:402-404, and Sambrook et al. (1989) *Molecular Cloning: A Laboratory Manual*, 2nd Ed., Cold Spring Harbor Laboratory, Cold Spring Harbor, N.Y.; and by Haymes et al. "*Nucleic Acid Hybridization: A Practical Approach*", IRL Press, Washington, D.C. (1985), which references are incorporated herein by reference.

In general, stringency is determined by the temperature, ionic strength, and concentration of denaturing agents (e.g., formamide) used in a hybridization and washing procedure (a more detailed description of establishing and determining stringency is disclosed below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, encoded transcription factors having about 67.7% or greater identity with the AP2 domain of disclosed transcription factors.

Regarding the terms "paralog" and "ortholog", homologous polynucleotide sequences and homologous polypeptide sequences may be paralogs or orthologs of the claimed polynucleotide or polypeptide sequence. Orthologs and paralogs are evolutionarily related genes that have similar sequence and similar functions. Orthologs are structurally related genes in different species that are derived by a speciation event. Paralogs are structurally related genes within a single species that are derived by a duplication event. Sequences that are sufficiently similar to one another will be appreciated by those of skill in the art and may be based upon percentage identity of the complete sequences, percentage identity of a conserved domain or sequence within the complete sequence, percentage similarity to the complete sequence, percentage similarity to a conserved domain or sequence within the complete sequence, and/or an arrangement of contiguous nucleotides or peptides particular to a conserved domain or complete sequence. Sequences that are sufficiently similar to one another will also bind in a similar manner to the same DNA binding sites of transcriptional regulatory elements using methods well known to those of skill in the art.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

The term "variant", as used herein, may refer to polynucleotides or polypeptides that differ from the presently disclosed polynucleotides or polypeptides, respectively, in sequence from each other, and as set forth below.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the term refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the transcription factors and transcription factor homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/ or a deletion of one or more cysteine residues. Guidance in determining which and how many amino acid residues may be substituted, inserted or deleted without abolishing functional or biological activity may be found using computer programs well known in the art, for example, DNASTAR software (U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about nine consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing. Exemplary fragments also include fragments that comprise a region that encodes an AP2 domain of a transcription factor. Exemplary fragments also include fragments that comprise a conserved domain of a transcription factor. Exemplary fragments include fragments that comprise an AP2 conserved domain, for example, amino acid residues 16-80 of G1792 (SEQ ID NO: 2), or an EDLL domain (SEQ ID NO: 63), amino acid residues 117-132, as noted in Table 1.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode transcription factors and transcription factor derivatives, or fragments thereof, entirely by synthetic chemistry. After production, the synthetic sequence may be inserted into any of the many available expression vectors, expression cassettes or plasmids and cell systems using reagents well known in the art. Moreover, synthetic chemistry may be used to introduce mutations into a sequence encoding transcription factors or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat), fruit (the mature ovary), plant tissue (for example, vascular tissue or ground tissue), cells (for example, guard cells, egg cells, and the like), and progeny of plants. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (as shown in FIG. 1, adapted from Daly et al. (2001) *Plant Physiol.* 127: 1328-1333; FIG. 2, adapted from Ku et al. (2000) *Proc. Natl. Acad. Sci. USA* 97: 9121-9126; and also Tudge in *The Variety of Life*, Oxford University Press, New York, N.Y. (2000) pp. 547-606).

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain a nucleic acid construct such as an expression vector, an expression cassette, a plasmid or other DNA preparation. The nucleic acid construct typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as osmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% or greater increase or decrease in an observed trait compared with a wild-type or control plant. It is known that there can be a natural variation in the modified trait. Therefore, the trait modification observed entails a change of the normal distribution of the trait in the plants compared with the distribution observed in wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell knocking out or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factors are under the control of a strong expression signal, such as one of the promoters described herein (e.g., the cauliflower mosaic virus 35S transcription initiation region). Overexpression may occur throughout a plant or in specific tissues of the plant, depending on the promoter used, as described below.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention possess an AP2 domain. Examples of AP2 or EDLL conserved domains of the sequences of the invention may be found in Table 1. The transcription factors of the invention also comprise an amino acid subsequence that forms a transcription activation domain that regulates expression of one or more abiotic stress or low nitrogen tolerance genes in a plant when the transcription factor binds to the regulating region.

"Substantially purified" refers to nucleic acid molecules or proteins that are removed from their natural environment and are isolated or separated, and are at least about 60% free, preferably about 75% free, and most preferably about 90% free, from other components with which they are naturally associated.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding site or DNA-binding site motif (for example, Riechmann et al. (2000) supra). The plant transcription factors of the present invention belong to the AP2 transcription factor family (Riechmann and Meyerowitz (1998) *Biol. Chem.* 379: 633-646).

Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semisynthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) *Genes Development* 11: 3194-3205, and Peng et al. (1999) *Nature,* 400: 256-261. In addition, many others have demonstrated that an *Arabidopsis* transcription factor expressed in an exogenous plant species elicits the same or very similar phenotypic response (for example, Fu et al. (2001) *Plant Cell* 13: 1791-1802; Nandi et al. (2000) *Curr. Biol.* 10: 215-218; Coupland (1995) *Nature* 377: 482-483; and Weigel and Nilsson (1995) *Nature* 377: 482-500).

In another example, a transcription factor expressed in another plant species elicits the same or very similar phenotypic response of the endogenous sequence, as often predicted in earlier studies of *Arabidopsis* transcription factors in *Arabidopsis* (Mandel et al. (1992) *Cell* 71-133-143) and Suzuki et al. (2001) *Plant J.* 28: 409-418). Other examples include Müller et al. (2001) *Plant J.* 28:169-179; Kim et al. (2001) *Plant J.* 25: 247-259; Kyozuka and Shimamoto (2002) *Plant Cell Physiol.* 43: 130-135; Boss and Thomas (2002) *Nature,* 416: 847-850; He et al. (2000) *Transgenic Res.* 9: 223-227; and Robson et al. (2001) *Plant J.* 28: 619-631.

In yet another example, Gilmour et al. ((1998) *Plant J.* 16: 433-442) teach an *Arabidopsis* AP2 transcription factor, CBF1, that increases plant freezing tolerance when overexpressed in transgenic plants. Jaglo et al. ((2001) *Plant Physiol.* 127: 910-917) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues, PKK/RPAGRxKFxETRHP and DSAWR, which bracket the AP2/EREBP DNA binding domains of the proteins and distinguish them from other members of the AP2/EREBP protein family (Jaglo et al. (2001) supra).

Transcription factors mediate cellular responses and control traits through altered expression of genes containing cis-acting nucleotide sequences that are targets of the introduced transcription factor. It is well appreciated in the Art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al. (2000) *Plant Cell* 12: 65-79; and Borevitz et al. (2000) *Plant Cell* 12: 2383-2393). Further, global transcript profiles have been used successfully as diagnostic tools for specific cellular states (e.g., cancerous vs. non-cancerous; Bhattacharjee et al. (2001) *Proc. Natl. Acad. Sci. USA* 98: 13790-13795; and Xu et al. (2001) *Proc. Natl. Acad. Sci. USA* 98: 15089-15094). Consequently, it is evident to one skilled in the art that similarity of transcript profile upon overexpression of different transcription factors would indicate similarity of transcription factor function.

Polypeptides and Polynucleotides of the Invention. The present invention provides, among other things, transcription factors (TFs), and transcription factor homolog polypeptides, and isolated or recombinant polynucleotides encoding the polypeptides, or novel sequence variant polypeptides or polynucleotides encoding novel variants of transcription factors derived from the specific sequences provided in the Sequence Listing. Also provided are methods for increasing a plant's tolerance to one or conditions of abiotic stress, including low nitrogen, cold, heat, or hyperosmotic stress such as high salt or drought. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer tolerance to one or more abiotic stresses, including low nitrogen, high salt, drought, heat and/or cold, in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

These sequences and others derived from diverse species and found in the sequence listing have been ectopically expressed in overexpressor plants. The changes in the characteristic(s) or trait(s) of the plants were then observed and found to confer increased abiotic stress or low nitrogen tolerance. Therefore, the polynucleotides and polypeptides can be used to improve desirable characteristics of plants.

The polynucleotides of the invention were also ectopically expressed in overexpressor plant cells and the changes in the expression levels of a number of genes, polynucleotides, and/or proteins of the plant cells observed. Therefore, the polynucleotides and polypeptides can be used to change expression levels of a genes, polynucleotides, and/or proteins of plants.

The AP2 family, including the G1792 clade. AP2 (APETALA2) and EREBPs (Ethylene-Responsive Element Binding Proteins) are the prototypic members of a family of transcription factors unique to plants, whose distinguishing characteristic is that they contain AP2 DNA-binding domain (a review appears in Riechmann and Meyerowitz (1998) *Biol. Chem.* 379: 633-646). The AP2 domain was first recognized as a repeated motif within the *Arabidopsis thaliana* AP2 protein (Jofuku et al. (1994) *Plant Cell* 6: 1211-1225). Shortly afterwards, four DNA-binding proteins from tobacco were identified that interact with a sequence that is essential for the responsiveness of some promoters to the plant hormone ethylene, and were designated as ethylene-responsive element binding proteins (EREBPs; Ohme-Takagi et al. (1995) *Plant Cell* 7: 173-182). The DNA-binding domain of EREBP-2 was mapped to a region that was common to all four proteins (Ohme-Takagi et al (1995) supra), and that was found to be closely related to the AP2 domain (Weigel (1995) *Plant Cell* 7: 388-389) but that did not bear sequence similarity to previously known DNA-binding motifs.

AP2/EREBP genes form a large family, with many members known in several plant species (Okamuro et al. (1997) *Proc. Natl. Acad. Sci. USA* 94: 7076-7081; Riechmann and Meyerowitz (1998) supra). The number of AP2/EREBP genes in the *Arabidopsis thaliana* genome is approximately 145 (Riechmann et al. (2000) *Science* 290: 2105-2110). The APETALA2 class is characterized by the presence of two AP2 DNA binding domains, and contains 14 genes. The AP2/ERF is the largest subfamily, and includes 125 genes which are involved in abiotic (DREB subgroup) and biotic (ERF subgroup) stress responses and the RAV subgroup includes 6 genes which all have a B3 DNA binding domain in addition to the AP2 DNA binding domain (Kagaya et al. (1999) *Nucleic Acids Res.* 27: 470-478).

The attack of a plant by a pathogen may induce defense responses that lead to resistance to the invasion, and these responses are associated with transcriptional activation of defense-related genes, among them those encoding pathogenesis-related (PR) proteins. The involvement of EREBP-like genes in controlling the plant defense response is based on the observation that many PR gene promoters contain a short cis-acting element that mediates their responsiveness to ethylene (ethylene appears to be one of several signal molecules controlling the activation of defense responses). Tobacco EREBP-1, -2, -3, and -4, and tomato Pti4, Pti5 and Pti6 proteins have been shown to recognize such cis-acting elements (Ohme-Takagi (1995) supra; Zhou et al. (1997) *EMBO J.* 16: 3207-3218). In addition, Pti4, Pti5, and Pti6 proteins have been shown to directly interact with Pto, a protein kinase that confers resistance against *Pseudomonas syringae* pv tomato (Zhou et al. (1997) supra). Plants are also challenged by adverse environmental conditions like cold or drought, and EREBP-like proteins appear to be involved in the responses to these abiotic stresses as well. COR (for cold-regulated) gene expression is induced during cold acclimation, the process by which plants increase their resistance to freezing in response to low unfreezing temperatures. The *Arabidopsis* EREBP-like gene CBF1 (Stockinger et al. (1997) *Proc. Natl. Acad. Sci. USA* 94: 1035-1040) is a regulator of the cold acclimation response, because ectopic expression of CBF1 in *Arabidopsis* transgenic plants induced COR gene expression in the absence of a cold stimulus, and the plant freezing tolerance was increased (Jaglo-Ottosen et al. (1998) *Science* 280: 104-106). Finally, another *Arabidopsis* EREBP-like gene, ABI4, is involved in abscisic acid (ABA) signal transduction, because abi4 mutants are insensitive to ABA (ABA is a plant hormone that regulates many agronomically important aspects of plant development; Finkelstein et al. (1998) *Plant Cell* 10: 1043-1054).

*Arabidopsis* AP2 is involved in the specification of sepal and petal identity through its activity as a homeotic gene that forms part of the combinatorial genetic mechanism of floral organ identity determination and it is also required for normal ovule and seed development (Bowman et al. (1991) *Development* 112: 1-20; Jofuku et al. (1994) supra). *Arabidopsis* ANT is required for ovule development and it also plays a role in floral organ growth (Elliott et al. (1996) *Plant Cell* 8: 155-168; Klucher et al. (1996) *Plant Cell* 8: 137-153). Finally, maize G115 regulates leaf epidermal cell identity (Moose et al. (1996) *Genes Dev.* 10: 3018-3027).

We first identified G1792 (AT3G23230) as a putative transcription factor in the sequence of BAC clone K14B15 (AB025608, gene K14B15.14). We have assigned the name TRANSCRIPTIONAL REGULATOR OF DEFENSE RESPONSE 1 (TDR1) to this gene, based on its apparent role in disease responses. The G1792 protein and other polypeptides within the G1792 clade contain a single AP2 domain and belong to the ERF class of AP2 proteins. The primary amino acid sequence of G1792 and other members of the G1792 clade, showing the relative positions of the AP2 domain, are presented in FIGS. 3A-3L. As can be seen from Table 1, the putative orthologs of G1792 possess AP2 domains that are at least about 67.7% identical to the AP2 domain of G1792.

Sequences that possess or encode for conserved domains that meet these criteria of percentage identity, and that have comparable biological activity to the present polypeptide sequences, thus being members of the G1792 clade of polypeptides, are encompassed by the invention. The AP2 domains are required for DNA binding and are thus required for conferring similar functions in the transcription factors of the invention and in the plants of the invention. Overexpression in a transformed plant of a polypeptide that comprises and AP2 domain of the invention (and an EDLL domain of the invention, as noted below) results in the transformed plant having greater tolerance to low nitrogen conditions, greater tolerance to cold, greater tolerance to water deficit conditions, and/or greater resistance to disease, as compared to a control plant.

In addition to the AP2 domain, the G1792 clade of transcription factor polypeptides contains a putative activation domain designated the "EDLL domain". Four amino acids are highly conserved in the paralogs and orthologs of G1792 within this domain. These conserved residues comprise glutamic acid, aspartic acid, and two leucine residues (hence the "EDLL" designation) in the subsequence:

Glu-(Xaa)$_{2-4}$-Asp-(Xaa)$_3$-Leu-(Xaa)$_3$-Leu (SEQ ID NO: 63)

where Xaa can be any amino acid, including those represented in FIG. 4.

Residues within a highly conserved region of a protein may be so conserved because of their importance to the function of that protein. Alignments of the sequences in the G1792 clade (FIGS. 3A-3L) indicate a high degree of conservation of the AP2 and EDLL domains, and particular residues, in clade members.

AtERF type transcription factors respond to abiotic stress. While ERF type transcription factors are primarily recognized for responding to a variety of biotic stresses (such as pathogen infection), some ERFs have been characterized as being responsive to abiotic stress. Fujimoto et. al. (2000) *Plant Cell* 12: 393-404 have shown that AtERF1-5, corresponding to G28 (SEQ ID NO: 48), G1006 (SEQ ID NO: 46), G1005 (SEQ ID NO: 62), G6 (SEQ ID NO: 58), and G1004 (SEQ ID NO: 60), respectively, can respond to various abiotic stresses, including cold, heat, drought, ABA, CHX, and wounding. Genes normally associated with the plant defense response (PR1, PR2, PR5, and peroxidases) have also been shown to be regulated by water stress (Zhu et. al. (1995) *Plant Physiol.* 108: 929-937; Ingram and Bartels (1996). *Annu Rev. Plant Physiol. Plant Mol. Biol.* 47:377-403) suggesting some overlap between the two responses. A target sequence for ERF-type transcription factors has been identified and extensively studied (Hao et al. (1998) *J. Biol. Chem.* 273: 26857-26861). This target sequence consists of AGCCGCC and has been found in the 5' upstream regions of genes responding to disease and regulated by ERFs. However, it is also certainly the case that several genes (ARSK1 and dehydrin) known to be induced by ABA, NaCl, cold and wounding, also possess a GCC box regulatory element in their 5' upstream regions (Hwang and Goodman (1995) *Plant J.* 8: 37-43) suggesting that ERF type transcription factors may regulate also regulate abiotic stress associated genes.

ERF type transcription factors in other species. ERF-type transcription factors are well known to be transcriptional activators of disease responses (Fujimoto et. al. (2000) supra; Gu et al. (2000) *Plant Cell* 12: 771-786; Chen et al. (2002) *Plant Cell* 14: 559-574; Cheong et al. (2002) *Plant Physiol.* 129: 661-677; Onate-Sanchez and Singh (2002) *Plant Physiol.* 128: 1313-1322; Brown et al. (2003) *Plant Physiol.* 132: 1020-1032; Lorenzo et al. (2003) *Plant Cell* 15: 165-178) but have not been well characterized as being involved in response to abiotic stress conditions such as drought. Other AP2 transcription factors (DREBs), including the CBF class, are known to bind DRE elements in genes responding to abiotic stresses such as drought, high salt, and cold (Haake et al. (2002) *Plant Physiol.* 130: 639-648; Thomashow (2001) *Plant Physiol.* 125: 89-93, Liu et al. (1998) *Plant Cell* 10: 1391-1406; Gilmour et al. (2000) *Plant Physiol.* 124: 1854-1865; and Shinozaki and Yamaguchi-Shinozaki (2000) *Curr. Opin. Plant Biol.* 3: 217-223).

Protein structure and properties: DNA binding motifs. Two positions have been identified as defining ERF class transcription factors. These consist of amino acids Ala-14 and Asp-19 in the AP2 domain (Sakuma et. al. (2002) *Biochem. Biophys. Res. Commun.* 290: 998-1009). Recent work indicates that these two amino acids (Ala-14 and Asp-19) have a key function in determining the target specificity (Sakuma et. al. (2002) supra; Hao et al. (2002) *Biochemistry* 41: 4202-4208) and interact directly with the DNA. The 3-dimensional structure/GCC box complex indicates the interaction of the second strand of the β-sheet with the DNA. The GCC box binding motif of ERF type transcription factors consists of a core sequence of AGCCCGCC.

Table 1 shows the polypeptides identified by: polypeptide SEQ ID NO (first column); the Gene ID (GID) No. and species (second column); the conserved domain coordinates for the AP2 and EDLL domains in amino acid residue coordinates (third column); AP2 domain sequences of the respective polypeptides (fourth column); the identity in percentage terms of the respective AP2 domains to the AP2 domain of G1792 determined using the AP2 domains listed in this table and manual comparison of the complete domains (fifth column); EDLL domain sequences of the respective polypeptides (sixth column); and the percent identity of the respective EDLL domains to the EDLL domain of G1792 determined using the EDLL domains listed in this table and direct manual comparison of the complete domains (seventh column). Polypeptide sequences that are shown herein to confer low nitrogen or abiotic stress tolerance include *Arabidopsis* G30, G1791, and G1792, soybean G3518 and G3520, rice G3380, G3381, G3383, G3515, and G3737, and corn G3516 and G3517. These sequences have AP2 domains with about 67.7% or greater identity to the AP2 domain of G1792, and about 56.3% or greater identity to the EDLL domain of G1792.

TABLE 1

Gene families and conserved domains of G1792 clade members

| SEQ ID NO: | GID No./ Species | AP2 and EDLL Domains in AA Coordinates | AP2 domain | SEQ ID NO: of AP2 domain | % ID to AP2 Domain of G1792* | EDLL Domain | SEQ ID NO:/ of EDLL domain | % ID to EDLL Domain of G1792* |
|---|---|---|---|---|---|---|---|---|
| 2 | G1792 At | 16-80; 117-132 | KQARFRGVRRRPW GKFAAEIRDPSRN GARLWLGTFETAE EAARAYDRAAFNL RGHLAILNFPNEY | 94 | 100% | VFEFEYL DDKVLEE LL | 112 | 100% |
| 26 | G3520 Gm | 14-78; 109-124 | EEPRYRGVRRRPWG KFAAEIRDPARHGA RVWLGTFLTAEEAA RAYDRAAYEMRGA LAVLNFPNEY | 95 | 80.0% | VIEFECLD DKLLEDLL | 113 | 75.0% |
| 24 | G3519 Gm | 13-77; 128-143 | CEVRYRGIRRRPWG KFAAEIRDPTRKGT RIWLGTFDTAEQAA RAYDAAAFHFRGH RAILNFPNEY | 96 | 76.9% | TFELEYLD NKLLEELL | 114 | 75.0% |
| 22 | G3518 Gm | 13-77; 135-150 | VEVRYRGIRRRPWG KFAAEIRDPTRKGT RIWLGTFDTAEQAA RAYDAAAFHFRGH RAILNFPNEY | 97 | 76.9% | TFELEYFD NKLLEELL | 115 | 68.8% |
| 28 | G3735 Mt | 23-87; 131-144 | DQIKYRGIRRRPWG KFAAEIRDPTRKGT RIWLGTFDTAEQAA RAYDAAAFHFRGHR AILNFPNEY | 98 | 75.4% | ELEFLDN KLLQELL | 116 | 56.3% |
| 4 | G1791 At | 10-74; 108-123 | NEMKYRGVRKRPW GKYAAEIRDSARH GARVWLGTFNTAE DAARAYDRAAFGM RGQRAILNIFPHE Y | 99 | 72.3% | VIEFEYLD DSLLEELL | 117 | 81.3% |
| 14 | G3383 Os | 9-73; 101-116 | TATKYRGVRRRPW GKFAAEIRDPERG GARVWLGTFDTAE EAARAYDRAAYAQ RGAAAVLNFPAAA | 100 | 72.3% | KIEFEYLD DKVLDDLL | 118 | 75.0% |
| 10 | G3380 Os | 18-62; 103-118 | ETTKYRGVRRRPSG KFAAEIRDSSRQSV RVWLGTFDTAEEAA RAYDRAAYAMRGHL AVLNFPAEA | 101 | 72.3% | VIELECLD DQVLQEML | 119 | 62.5% |

TABLE 1-continued

Gene families and conserved domains of G1792 clade members

| SEQ ID NO: | GID No./ Species | AP2 and EDLL Domains in AA Coordinates | AP2 domain | SEQ ID NO: of AP2 domain | % ID to AP2 Domain of G1792* | EDLL Domain | SEQ ID NO:/ of EDLL domain | % ID to EDLL Domain of G1792* |
|---|---|---|---|---|---|---|---|---|
| 8 | G30 At | 16-80; 100-115 | EQGKYRGVRRRPW GKYAAEIRDSRKHG ERVWLGTFDTAEDA ARAYDRAAYSMRGK AAILNFPHEY | 102 | 70.8% | VFEFEYL DDSVLDE LL | 120 | 87.5% |
| 12 | G3381 Os | 14-78; 109-124 | LVAKYRGVRRRPW GKFAAEIRDSSRH GVRVWLGTFDTAE EAARAYDRSAYMR GANAVLNFPADA | 103 | 70.8% | FIEFEYLD DHVLQEML | 121 | 68.8% |
| 32 | G3737 Os | 8-37; 101-116 | AASKYRGVRRRPW GKFAAEIRDPERG GSRVWLGTFDTAE EAARAYDRAAFAM KGAMAVLNFPGRT | 104 | 70.8% | KVELVYL DDKVLDE LL | 122 | 68.8% |
| 16 | G3515 Os | 11-75; 116-131 | SSSSYRGVRKRPWG KFAAEIRDPERGGA RVWLGTFDTAEEAA RAYDRAAFAMKGAT TAMLNFPGDH | 105 | 70.8% | KVELECL DDKVLED LL | 123 | 68.8% |
| 18 | G3516 Zm | 6-70; 107-122 | KEGKYRGVRKRPW GKFAAEIRDPERG GSRVWLGTFDTAE EAARAYDRAAFAM KGATAVLNFPASG | 106 | 70.8% | KVELECL DDRVLEE LL | 124 | 68.8% |
| 6 | G1795 At | 11-75; 104-119 | EHGKYRGVRRRPW GKYAAEIRDSRKH GERVWLGTFDTAE EAARAYDQAAYSM RGQAAILNFPHEY | 107 | 69.2% | VFEFEYL DDSVLEE LL | 125 | 93.8% |
| 36 | G3794 Zm | 6-70; 102-117 | EPTKYRGVRRRPSG KFAAEIRDSSRQSV RMWLGTFDTAEEAA RAYDRAAYAMRGQI AVLNFPAEA | 108 | 69.2% | VIELECLD DQVLQEML | 126 | 62.5% |
| 20 | G3517 Zm | 13-77; 103-118 | EPTKYRGVRRIRPWG KYAAEIRDSSRIIGV RIWLGTFDTAEEAAR AYDRSANSMRGANAV LNFPEDA | 109 | 67.7% | VIEFEYLD DEVLQEML | 127 | 75.0% |
| 34 | G3739 Zm | 13-77; 107-122 | EPTKYRGVRRRPWG KYAAEIRDSSRHGV RIWLGTFDTAEEAA RAYDRSAYSMRGAN AVLNFPEDA | 110 | 67.7% | VIELEYLD DEVLQEML | 128 | 75.0% |
| 30 | G3736 Ta | 12-76; 108-123 | EPTKYRGVRRRPWG KFAAEIRDSSRHGV RMWLGTFDTAEEAA AAYDRSAYSMRGRN AVLNFPDRA | 111 | 67.7% | VIEFEYLD DDVLQSML | 129 | 68.8% |

Abbreviations for Table 1:
At - *Arabidopsis thaliana*;
Gm - *Glycine max*;
Mt - *Medicago truncatula*;
Os - *Oryza sativa*;
Ta - *Triticum aestivum*;
Zm - *Zea mays*
* based on direct comparison of the optimally aligned AP2 and EDLL complete domains found in this table The transcription factors of the invention each possess an AP2 domain and an EDLL domain, and include paralogs and orthologs of G1792 found by BLAST analysis, as described below. The AP2 domains of G1792 clade members are at least about 67.7% identical to the AP2 domain of G1792, and the EDLL domains of G1792 clade members are at least about 56.3% identical to the EDLL domain of G1792 (Table 1). These transcription factors rely on the binding specificity and functions of their conserved domains.

Producing Polypeptides. The polynucleotides of the invention include sequences that encode transcription factors and transcription factor homolog polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homolog polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homolog polypeptide is an endogenous or exogenous gene.

A variety of methods exist for producing the polynucleotides of the invention. Procedures for identifying and isolating DNA clones are well known to those of skill in the art and are described in, e.g., Berger and Kimmel (1987) *Guide to Molecular Cloning Techniques, Methods Enzymol.* vol. 152, Academic Press, Inc., San Diego, Calif.; Sambrook et al. (1989) supra, vol. 1-3, Cold Spring Harbor Laboratory, Cold Spring Harbor, N.Y., and Ausubel et al. (supplemented through 2000), eds., *Current Protocols in Molecular Biology*, Greene Publishing Associates, Inc. and John Wiley & Sons, Inc.

Alternatively, polynucleotides of the invention, can be produced by a variety of in vitro amplification methods adapted to the present invention by appropriate selection of specific or degenerate primers. Examples of protocols sufficient to direct persons of skill, through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger and Kimmel (1987) supra, Sambrook (1989) supra, and Ausubel (2000) supra, as well as Mullis et al. (1990) *PCR Protocols A Guide to Methods and Applications* (Innis et al., eds) Academic Press Inc. San Diego, Calif. Improved methods for cloning in vitro amplified nucleic acids are described in Wallace et al. U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase (e.g., Ausubel (2000) supra, Sambrook (1989) supra, and Berger and Kimmel (1987) supra).

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) *Tetrahedron Letters* 22: 1859-1869; and Matthes et al. (1984) *EMBO J.* 3: 801-805. According to such methods, oligonucleotides are synthesized, purified, annealed to their complementary strand, ligated and then optionally cloned into suitable nucleic acid constructs. And if so desired, the polynucleotides and polypeptides of the invention can be custom ordered from any of a number of commercial suppliers.

Homologous Sequences. Sequences homologous to those provided in the Sequence Listing derived from *Arabidopsis thaliana* or from other plants of choice, are also an aspect of the invention. Homologous sequences can be derived from any plant including monocots and eudicots and in particular agriculturally important plant species, including but not limited to, crops such as soybean, wheat, corn (maize), potato, cotton, rice, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such as pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen (1998) Genome Res. 8: 163-167, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, supra). In fact, many specific examples exist in which gene function has been shown to correlate well with gene phylogeny (Eisen, supra). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994); Higgins et al. (1996)). Groups of similar genes can also be identified with pair-wise BLAST analysis (Feng and Doolittle (1987)). For example, a clade of very similar MADS domain transcription factors from *Arabidopsis* all share a common function in flowering time (Ratcliffe et al. (2001)), and a group of very similar AP2 domain transcription factors from *Arabidopsis* are involved in tolerance of plants to freezing (Gilmour et al. (1998)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001))

Transcription factor gene sequences are conserved across diverse eukaryotic species lines (Goodrich et al. (1993); Lin et al. (1991); Sadowski et al. (1988)). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994); Higgins et al. (1996)) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to deduce similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in U.S. Pat. No. 7,135,616), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from eudicots and monocots can confer greater tolerance to drought-related stress as compared to control plants;

(iii) Myb-related *Arabidopsis* G682 (found in U.S. Pat. Nos. 7,223,904 and 7,193,129) and numerous phylogenetically-related sequences from eudicots and monocots can confer greater tolerance to heat, drought-related stress, cold, and salt as compared to control plants;

(iv) WRKY family *Arabidopsis* G1274 (found in U.S. Pat. No. 7,196,245) and numerous closely-related sequences from eudicots and monocots have been shown to confer increased water deprivation tolerance, and (v) AT-hook family soy sequence G3456 (found in US patent publication 20040128712A1) and numerous phylogenetically-related sequences from eudicots and monocots, increased biomass compared to control plants when these sequences are overexpressed in plants.

The polypeptides sequences belong to distinct clades of polypeptides that include members from diverse species. In each case, most or all of the clade member sequences derived from both eudicots and monocots have been shown to confer increased yield or tolerance to one or more abiotic stresses when the sequences were overexpressed. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

Polypeptides that are phylogenetically related to the polypeptides of the invention may be at least, or may have conserved AP2 domains that share at least:

about 67.7%, at least about 68%, at least about 69%, at least about 69.2%, at least about 70%, at least about 71%, at least about 72%, at least about 72.3%, at least about 73%, at least about 74%, at least about 75%, at least about 75.4%, at least about 76%, at least about 76.9%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% amino acid sequence identity with an AP2 domain of the invention (SEQ ID NOs: 94-111);

or may have EDLL domains that share at least about 56.3%, at least about 62.5%, at least about 68.8%, at least about 75.0%, at least about 81.3%, at least about 87.5%, at least about 93.8%, or about 100% amino acid sequence identity with an EDLL domain of the invention (SEQ ID NOs: 112-129);

and have similar functions in the polypeptides in that the polypeptides of the invention may, when overexpressed, regulate transcription and confer at least one regulatory activity selected from the group consisting of greater tolerance to cold, water deficit, or low nitrogen conditions, or greater resistance to disease, as compared to a control plant.

At the nucleotide level, the sequences of the invention will typically share at least about 30% or 40% nucleotide sequence identity, preferably at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990); Altschul et al. (1993)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989, 1991)). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at http://www.ncbi.nlm.nih.gov/).

Other techniques for alignment are described by Doolittle (1996). Preferably, an alignment program that permits gaps in the sequence is utilized to align the sequences. The Smith-Waterman is one type of algorithm that permits gaps in sequence alignments (see Shpaer (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein (1990)) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997)), PFAM, and other databases which contain previously identified and annotated motifs, sequences and gene functions. Methods that search for primary sequence patterns with secondary structure gap penalties (Smith et al. (1992)) as well as algorithms such as Basic Local Alignment Search Tool (BLAST; Altschul (1990); Altschul et al. (1993)), BLOCKS (Henikoff and Henikoff (1991)), Hidden Markov Models (HMM; Eddy (1996); Sonnhammer et al. (1997)), and the like, can be used to manipulate and analyze polynucleotide and polypeptide sequences encoded by polynucleotides. These databases, algorithms and other methods are well known in the art and are described in Ausubel et al. (1997), and in Meyers (1995).

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow (2002) have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and B-box zinc finger domains. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in Table 1 and the Sequence Listing. In addition to the sequences in Table 1 and the Sequence Listing, the invention encompasses isolated nucleotide sequences that are phylogenetically and structurally similar to sequences listed in the Sequence Listing) and can function in a plant by increasing yield and/or and abiotic stress tolerance when ectopically expressed in a plant.

Transcription factors that are homologous to the listed AP2 transcription factors will typically share at least about 67.7% and 56.3% amino acid sequence identity in their AP2 and EDLL domains, respectively, as seen by the examples shown to confer low nitrogen or abiotic stress tolerance in Table 1. Transcription factors that are homologous to the listed sequences should share at least 40% amino acid sequence identity over the entire length of the polypeptide.

Since a significant number of these sequences are phylogenetically and sequentially related to each other and have been shown to increase yield from a plant and/or abiotic stress tolerance, one skilled in the art would predict that other similar, phylogenetically related sequences falling within the present clades of polypeptides would also perform similar functions when ectopically expressed.

Identifying, Polynucleotides or Nucleic Acids by Hybridization. Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above.

Encompassed by the invention are polynucleotide sequences that are capable of hybridizing to the claimed polynucleotide sequences, including any of the transcription factor polynucleotides within the Sequence Listing, and fragments thereof under various conditions of stringency (for example, Wahl and Berger, in Berger and Kimmel (1987) supra, pages 399407, and Kimmel, in and Berger and Kimmel (1987) supra, pages 507-511). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art (for example, in Sambrook et al. (1989) supra; Berger and Kimmel (1987) supra, pages 467-469; and Anderson and Young (1985) "Quantitative Filter Hybridisation." In: Hames and Higgins, ed., *Nucleic Acid Hybridisation. A Practical Approach*, Oxford, IRL Press, 73-111.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

(I) DNA-DNA:

$$T_m(°C.)=81.5+16.6(\log[Na^+])+0.41(\% G+C)-0.62(\% \text{formamide})-500/L$$

(II) DNA-RNA:

$$T_m(°C.)=79.8+18.5(\log[Na^+])+0.58(\% G+C)+0.12(\% G+C)^2-0.5(\% \text{formamide})-820/L$$

(III) RNA-RNA:

$$T_m(°C.)=79.8+18.5(\log[Na^+])+0.58(\% G+C)+0.12(\% G+C)^2-0.35(\% \text{formamide})-820/L$$

where L is the length of the duplex formed, [Na$^+$] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson et al. (1985) supra). In addition, one or more of the following may be used to reduce non-specific hybridization: sonicated salmon sperm DNA or another non-complementary DNA, bovine serum albumin, sodium pyrophosphate, sodium dodecyl sulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guideline, high stringency is typically performed at $T_m$–5° C. to $T_m$–20° C., moderate stringency at $T_m$–20° C. to $T_m$–35° C. and low stringency at $T_m$–35° C. to $T_m$–50° C. for duplex>150 base pairs. Hybridization may be performed at low to moderate stringency (25-50° C. below $T_m$), followed by post-hybridization washes at increasing stringencies. Maximum rates of hybridization in solution are determined empirically to occur at $T_m$–25° C. for DNA-DNA duplex and $T_m$–15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present transcription factors include, for example:

0.5×, 1.0×, 1.5×, or 2×SSC, 0.1% SDS at 50°, 55°, 60° or 65° C., or 6×SSC at 65° C.;

50% formamide, 4×SSC at 42° C.; or 0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Sequence Variations. It will readily be appreciated by those of skill in the art, that any of a variety of polynucleotide sequences are capable of encoding the transcription factors and transcription factor homolog polypeptides of the invention. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the Sequence Listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Those skilled in the art would recognize that, for example, G1792, SEQ ID NO: 2, represents a single transcription factor; allelic variation and alternative splicing may be expected to occur. Allelic variants of SEQ ID NO: 1 can be cloned by probing cDNA or genomic libraries from different individual organisms according to standard procedures. Allelic variants of the DNA sequence shown in SEQ ID NO: 1, including those containing silent mutations and those in which mutations result in amino acid sequence changes, are within the scope of the present invention, as are proteins which are allelic variants of SEQ ID NO: 2. cDNAs generated from alternatively spliced mRNAs, which retain the properties of the transcription factor are included within the scope of the present invention, as are polypeptides encoded by such cDNAs and mRNAs. Allelic variants and splice variants of these sequences can be cloned by probing cDNA or genomic libraries from different individual organisms or tissues according to standard procedures known in the art (U.S. Pat. No. 6,388,064).

Thus, in addition to the sequences set forth in the Sequence Listing, the invention also encompasses related nucleic acid molecules that include allelic or splice variants, and sequences that are complementary. Related nucleic acid molecules also include nucleotide sequences encoding a polypeptide comprising a substitution, modification, addition and/or deletion of one or more amino acid residues. Such related polypeptides may comprise, for example, additions and/or deletions of one or more N-linked or O-linked glycosylation sites, or an addition and/or a deletion of one or more cysteine residues.

Expression and Modification of Polypeptides. Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homolog.

The transgenic plants of the present invention comprising recombinant polynucleotide sequences are generally derived from parental plants, which may themselves be non-transformed (or non-transgenic) plants. These transgenic plants may either have a transcription factor gene "knocked out" (for example, with a genomic insertion by homologous recombination, an antisense or ribozyme construct) or expressed to a normal or wild-type extent. However, overexpressing transgenic "progeny" plants will exhibit greater mRNA levels, wherein the mRNA encodes a transcription factor, that is, a DNA-binding protein that is capable of binding to a DNA regulatory sequence and inducing transcription, and preferably, expression of a plant trait gene. Preferably, the mRNA expression level will be at least three-fold greater than that of the parental plant, or more preferably at least ten-fold greater mRNA levels compared to said parental plant, and most preferably at least fifty-fold greater compared to said parental plant.

Vectors, Promoters and Expression Systems. The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, cassettes, plasmids, promoters and many other relevant topics, include Berger and Kimmel (1987) supra, Sambrook (1989) supra, and Ausubel (1997, 2000) supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach (1989) *Methods for Plant Molecular Biology*, Academic Press, and Gelvin et al. (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucleic Acids Res.* 12: 8711-8721, Klee (1985) *Bio/Technology* 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957-962) and corn (Gordon-Kamm (1990) *Plant Cell* 2: 603-618) can be produced. An immature embryo can also be a good target tissue for monocots for direct DNA delivery techniques by using the particle gun (Weeks et al. (1993) *Plant Physiol.* 102: 1077-1084; Vasil (1993) *Bio/Technology* 10: 667-674; Wan and Lemeaux (1994) *Plant Physiol.* 104: 37-48, and for *Agrobacterium*-mediated DNA transfer (Ishida et al. (1996) *Nature Biotechnol.* 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

A potential utility for the transcription factor polynucleotides disclosed herein is the isolation of promoter elements from these genes that can be used to program expression in plants of any genes. Each transcription factor gene disclosed herein is expressed in a unique fashion, as determined by promoter elements located upstream of the start of translation, and additionally within an intron of the transcription factor gene or downstream of the termination codon of the gene. As is well known in the art, for a significant portion of genes, the promoter sequences are located entirely in the region directly upstream of the start of translation. In such cases, typically the promoter sequences are located within 2.0 kb of the start of translation, or within 1.5 kb of the start of translation, frequently within 1.0 kb of the start of translation, and sometimes within 0.5 kb of the start of translation.

The promoter sequences can be isolated according to methods known to one skilled in the art.

Examples of constitutive plant promoters which can be useful for expressing the TF sequence include: the cauliflower mosaic virus (CaMV) 35S promoter, which confers constitutive, high-level expression in most plant tissues (for example, Odell et al. (1985) *Nature* 313: 810-812); the nopaline synthase promoter (An et al. (1988) *Plant Physiol.* 88: 547-552); and the octopine synthase promoter (Fromm et al. (1989) *Plant Cell* 1: 977-984).

The transcription factors of the invention may be operably linked with a specific promoter that causes the transcription factor to be expressed in response to environmental, tissue-specific or temporal signals. A variety of plant gene promoters are known to regulate gene expression in response to environmental, hormonal, chemical, developmental signals, and in a tissue-active manner; many of these may be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening, such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11: 651-662), root-specific promoters, such as ARSK1, and those disclosed in U.S. Pat. Nos. 5,618,988, 5,837,848 and 5,905,186, epidermis-specific promoters, including CUT1 (Kunst et al. (1999) *Biochem. Soc. Trans.* 28: 651-654), pollen-active promoters such as PTA29, PTA26 and PTA13 (U.S. Pat. No. 5,792,929), promoters active in vascular tissue (Ringli and Keller (1998) *Plant Mol. Biol.* 37: 977-988), flower-specific (Kaiser et al. (1995) *Plant Mol. Biol.* 28: 231-243), pollen (Baerson et al. (1994) *Plant Mol. Biol.* 26: 1947-1959), carpels (Ohl et al. (1990) *Plant Cell* 2: 837-848), pollen and ovules (Baerson et al. (1993) *Plant Mol. Biol.* 22: 255-267), auxin-inducible promoters (such as that described in van der Kop et al. (1999) *Plant Mol. Biol.* 39: 979-990 or Baumann et al. (1999) *Plant Cell* 11: 323-334), cytokinin-inducible promoter (Guevara-Garcia (1998) *Plant Mol. Biol.* 38: 743-753), promoters responsive to gibberellin (Shi et al. (1998) *Plant Mol. Biol.* 38: 1053-1060, Willmott et al. (1998) *Plant Mol. Biol.* 38: 817-825) and the like. Additional promoters are those that elicit expression in response to heat (Ainley et al. (1993) *Plant Mol. Biol.* 22: 13-23), light (e.g., the pea rbcS-3A promoter, described in Kuhlemeier et al. (1989) *Plant Cell* 1: 471-478, and the maize rbcS promoter, described in Schaffner and Sheen (1991) *Plant Cell* 3: 997-1012); wounding (e.g., wunI, described in Siebertz et al. (1989) *Plant Cell* 1: 961-968), pathogens (such as the PR-1 promoter described in Buchel et al. (1999) Plant Mol. Biol. 40: 387-396, and the PDF1.2 promoter described in Manners et al. (1998) *Plant Mol. Biol.* 38: 1071-1080), and chemicals such as methyl jasmonate or salicylic acid (Gatz (1997) *Annu. Rev. Plant Physiol. Plant Mol. Biol.* 48: 89-108). In addition, the timing of the expression can be controlled by using promoters such as those acting at senescence (Gan and Amasino (1995) *Science* 270: 1986-1988); or late seed development (Odell et al. (1994) *Plant Physiol.* 106: 447-458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Production of Transgenic Plants

Modification of Traits. The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologs) of the invention, as compared with the levels of the same protein found in a wild-type plant, can be used to modify a plant's traits. An illustrative example of trait modification, improved characteristics, by altering expression levels of a particular transcription factor is described further in the Examples and the Sequence Listing.

*Arabidopsis* as a model system. *Arabidopsis thaliana* is the object of rapidly growing attention as a model for genetics and metabolism in plants. *Arabidopsis* has a small genome, and well-documented studies are available. It is easy to grow in large numbers and mutants defining important genetically controlled mechanisms are either available, or can readily be obtained. Various methods to introduce and express isolated homologous genes are available (Koncz et al., editors, *Methods in Arabidopsis Research* (1992) World Scientific, New Jersey NJ, in "Preface"). Because of its small size, short life cycle, obligate autogamy and high fertility, *Arabidopsis* is also a choice organism for the isolation of mutants and studies in morphogenetic and development pathways, and control of these pathways by transcription factors (Koncz (1992) supra, p. 72). A number of studies introducing transcription factors into *A. thaliana* have demonstrated the utility of this plant for understanding the mechanisms of gene regulation and trait alteration in plants (for example, Koncz (1992) supra, and U.S. Pat. No. 6,417,428).

*Arabidopsis* genes in transgenic plants. Expression of genes encoding transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) et al. *Genes and Development* 11: 3194-3205, and Peng et al. (1999) *Nature* 400: 256-261. In addition, many others have demonstrated that an *Arabidopsis* transcription factor expressed in an exogenous plant species elicits the same or very similar phenotypic response (for example, Fu et al. (2001) *Plant Cell* 13: 1791-1802; Nandi et al. (2000) *Curr. Biol.* 10: 215-218; Coupland (1995) *Nature* 377: 482-483; and Weigel and Nilsson (1995) *Nature* 377: 482-500).

Homologous genes introduced into transgenic plants. Homologous genes that may be derived from any plant, or from any source whether natural, synthetic, semi-synthetic or recombinant, and that share significant sequence identity or similarity to those provided by the present invention, may be introduced into plants, for example, crop plants, to confer desirable or improved traits. Consequently, transgenic plants may be produced that comprise a recombinant a nucleic acid construct such as an expression vector, an expression cassette, a plasmid or other nucleic acid preparation with a promoter operably linked to one or more sequences homologous to presently disclosed sequences. The promoter may be, for example, a plant or viral promoter.

The invention thus provides for methods for preparing transgenic plants, and for modifying plant traits. These methods include introducing into a plant a recombinant nucleic acid construct comprising a functional promoter operably linked to one or more sequences homologous to presently disclosed sequences. Plants and kits for producing these plants that result from the application of these methods are also encompassed by the present invention.

Transcription factors of interest for the modification of plant traits. Currently, the existence of a series of maturity groups for different latitudes represents a major barrier to the introduction of new valuable traits. Any trait (e.g. increased tolerance to an abiotic or biotic stress) has to be bred into each of the different maturity groups separately, a laborious and costly exercise. The availability of single strain, which could be grown at any latitude, would therefore greatly increase the potential for introducing new traits to crop species such as soybean and cotton.

For the specific effects, traits and utilities conferred to plants, one or more transcription factor genes of the present invention may be used to increase or decrease, or improve or prove deleterious to a given trait. For example, knocking out a transcription factor gene that naturally occurs in a plant, or suppressing the gene (with, for example, antisense suppression), may cause decreased tolerance to an osmotic stress relative to non-transformed or wild-type plants. By overexpressing this gene, the plant may experience increased tolerance to the same stress. More than one transcription factor gene may be introduced into a plant, either by transforming the plant with one or more nucleic acid constructs comprising two or more transcription factors, or by selective breeding of plants to yield hybrid crosses that comprise more than one introduced transcription factor.

Genes, traits and utilities that affect plant characteristics. Plant transcription factors can modulate gene expression, and, in turn, be modulated by the environmental experience of a plant. Significant alterations in a plant's environment invariably result in a change in the plant's transcription factor gene expression pattern. Altered transcription factor expression patterns generally result in phenotypic changes in the plant. Transcription factor gene product(s) in transgenic plants then differ(s) in amounts or proportions from that found in wild-type or non-transformed plants, and those transcription factors likely represent polypeptides that are used to alter the response to the environmental change. By way of example, it is well accepted in the art that analytical methods based on altered expression patterns may be used to screen for phenotypic changes in a plant far more effectively than can be achieved using traditional methods.

Plants overexpressing members of the G1792 clade of transcription factor polypeptides, including sequences from diverse species of monocots and eudicots, such as *Arabidopsis thaliana* polypeptides G1792, G1791, G1795 and G30, *Oryza sativa* polypeptide G3381, and *Glycine max* polypeptide G3520, were shown to be more tolerant to low nitrogen conditions than control plants (Example VIII).

The invention also provides polynucleotides that encode G1792 clade polypeptides, fragments thereof, conserved domains thereof, paralogs, orthologs, equivalogs, and fragments thereof. Examples of these sequences are listed in the Sequence Listing, and due to the high degree of structural similarity to the sequences of the invention, it is expected that many of the sequences for which data have not been generated will also function to increase abiotic stress and/or low nitrogen tolerance. The invention also encompasses the complements of the polynucleotides. The polynucleotides are also useful for screening libraries of molecules or compounds for specific binding and for identifying other sequences of G1792 clade member by identifying orthologs having similar sequences, particularly in the conserved domains.

Antisense and Co-suppression. In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) Antisense Technology: A Practical Approach IRL Press at Oxford University Press, Oxford, U.K. Antisense regulation is also described in Crowley et al. (1985) Cell 43: 633-641; Rosenberg et al. (1985) Nature 313: 703-706; Preiss et al. (1985) Nature 313: 27-32; Melton (1985) Proc. Natl. Acad. Sci. USA 82: 144-148; Izant and Weintraub (1985) Science 229: 345-352; and Kim and Wold (1985) Cell 42: 129-138. Additional methods for antisense regulation are known in the art. Antisense regulation has been used to reduce or inhibit expression of plant genes in, for example in European Patent Publication No. 271988. Antisense RNA may be used to reduce gene expression to produce a visible or biochemical phenotypic change in a plant (Smith et al. (1988) Nature 334: 724-726; Smith et al. (1990) Plant Mol. Biol. 14: 369-379). In general, sense or anti-sense sequences are introduced into a cell, where they are optionally amplified, for example, by transcription. Such sequences include both simple oligonucleotide sequences and catalytic sequences such as ribozymes.

For example, a reduction or elimination of expression (i.e., a "knock-out") of a transcription factor or transcription factor homolog polypeptide in a transgenic plant, e.g., to modify a plant trait, can be obtained by introducing an antisense construct corresponding to the polypeptide of interest as a cDNA. For antisense suppression, the transcription factor or homolog cDNA is arranged in reverse orientation (with respect to the coding sequence) relative to the promoter sequence in the nucleic acid construct. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective anti-sense suppression. While antisense sequences of various lengths can be utilized, preferably, the introduced antisense sequence in the nucleic acid construct will be at least 30 nucleotides in length, and improved antisense suppression will typically be observed as the length of the antisense sequence increases. Preferably, the length of the antisense sequence in the nucleic acid construct will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Nucleic acid constructs in which RNA encoded by a transcription factor or transcription factor homolog cDNA is over-expressed can also be used to obtain co-suppression of a corresponding endogenous gene, for example, in the manner disclosed in U.S. Pat. No. 5,231,020. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Nucleic acid constructs expressing an untranslatable form of the transcription factor mRNA (e.g., sequences comprising one or more stop codon, or nonsense mutation) can also be used to suppress expression of an endogenous transcription factor, thereby reducing or eliminating its activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-stranded RNA (Sharp (1999) Genes and Development 13: 139-141). Another method for abolishing the expression of a gene is by insertion mutagenesis using the T-DNA of Agrobacterium tumefaciens. After generating the insertion mutants, the mutants can be screened to identify those containing the insertion in a transcription factor or transcription factor homolog gene. Plants containing a single transgene insertion event at the desired gene can be crossed to generate homozygous plants for the mutation. Such methods are well known to those of skill in the art (for example, in Koncz et al. (1992) supra).

Suppression of endogenous transcription factor gene expression can also be achieved using RNA interference, or RNAi. RNAi is a post-transcriptional, targeted gene-silencing technique that uses double-stranded RNA (dsRNA) to incite degradation of messenger RNA (mRNA) containing the same sequence as the dsRNA (Constans (2002) The Scientist 16:36). Small interfering RNAs, or siRNAs are produced in at least two steps: an endogenous ribonuclease cleaves longer dsRNA into shorter, 21-23 nucleotide-long RNAs. The siRNA segments then mediate the degradation of the target mRNA (Zamore (2001) Nature Struct. Biol. 8: 746-50). RNAi has been used for gene function determination in a manner similar to antisense oligonucleotides (Constans (2002) supra). Nucleic acid constructs that continually express siRNAs in transiently and stably-transfected cells have been engineered to express small hairpin RNAs (shRNAs), which get processed in vivo into siRNAs-like molecules capable of carrying out gene-specific silencing (Brummelkamp et al. (2002) Science 296:550-553, and Paddison et al. (2002) Genes & Dev. 16:948-958). Post-transcriptional gene silencing by double-stranded RNA is discussed in further detail by Hammond et al. (2001) *Nature Rev Gen* 2: 110-119, Fire et al. (1998) *Nature* 391: 806-811 and Timmons and Fire (1998) *Nature* 395: 854.

Alternatively, a plant phenotype can be altered by eliminating an endogenous gene, such as a transcription factor or transcription factor homolog, e.g., by homologous recombination (Kempin et al. (1997) *Nature* 389: 802-803).

A plant trait can also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means, such as, for example, by ectopically expressing a gene by T-DNA activation tagging (Ichikawa et al. (1997) *Nature* 390 698-701; Kakimoto et al. (1996) *Science* 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (for example, in PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example, by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a nucleic acid construct, most typically an expression vector an expression cassette, or a plasmid, including a polynucleotide, e.g., encoding a transcription factor or transcription factor homolog, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. Examples of these protocols are described in Ammirato et al. eds., (1984) *Handbook of Plant Cell Culture—Crop Species*, Macmillan Publ. Co., New York N.Y.; Shimamoto et al. (1989) *Nature* 338: 274-276; Fromm et al. (1990) *Bio/Technol.* 8: 833-839; and Vasil et al. (1990) *Bio/Technol.* 8: 429-434.

Transformation and regeneration of both monocotyledonous and dicotyledonous plant cells are now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens*-mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the nucleic acid construct. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems—Sequence Identity. In addition to providing compositions and methods to improve plant traits, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FIND-PATTERNS or the like (GCG, Madison, Wis.). Public sequence databases such as GenBank, EMBL, Swiss-Prot and PIR or private sequence databases such as PHYTOSEQ sequence database (Incyte Genomics, Wilmington, Del.) can be searched.

Alignment of sequences for comparison can be conducted by the local homology algorithm of Smith and Waterman (1981) *Adv. Appl. Math.* 2: 482-489, by the homology alignment algorithm of Needleman and Wunsch (1970) *J. Mol. Biol.* 48: 443-453, by the search for similarity method of Pearson and Lipman (1988) *Proc. Natl. Acad. Sci. USA* 85: 2444-2448, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al. (1997, 2000) supra.

A variety of methods for determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. (1990) supra. Software for performing BLAST analyses is publicly available, e.g., through the National Library of Medicine's National Center for Biotechnology Information (National Institutes of Health US government website at www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990, 1993) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (Henikoff and Henikoff (1992) *Proc. Natl. Acad. Sci. USA* 89: 10915-10919). Unless otherwise indicated, "sequence identity" here refers to the % sequence identity generated from a tblastx using the NCBI version of the algorithm at the default settings using gapped alignments with the filter "off" (for example, at the NIH website at www.ncbi.nlm.nih.gov, supra).

In addition to calculating percent sequence identity, the BLAST algorithm also performs a statistical analysis of the similarity between two sequences (for example, Karlin and Altschul (1993) *Proc. Natl. Acad. Sci. USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001.

An additional example of a useful sequence alignment algorithm is PILEUP. PILEUP creates a multiple sequence alignment from a group of related sequences using progressive, pairwise alignments. The program can align, for example, up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element that displays an alignment produced by the alignment instruction set.

The methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

Any sequence herein can be used to identify a similar, homologous, paralogous, or orthologous sequence in another plant. This provides means for identifying endogenous sequences in other plants that may be useful to alter a trait of progeny plants, which results from crossing two plants of different strain. For example, sequences that encode an ortholog of any of the sequences herein that naturally occur in a plant with a desired trait can be identified using the sequences disclosed herein. The plant is then crossed with a second plant of the same species but which does not have the desired trait to produce progeny which can then be used in further crossing experiments to produce the desired trait in the second plant. Therefore the resulting progeny plant contains no transgenes; expression of the endogenous sequence may also be regulated by treatment with a particular chemical or other means, such as EMR. Some examples of such compounds well known in the art include: ethylene; cytokinins; phenolic compounds, which stimulate the transcription of the genes needed for infection; specific monosaccharides and acidic environments that potentiate vir gene induction; acidic polysaccharides which induce one or more chromosomal genes; and opines; other mechanisms include light or dark treatment (reviews of such treatments appears in Winans (1992) *Microbiol. Rev.* 56: 12-31; Eyal et al. (1992) *Plant*

Mol. Biol. 19: 589-599; Chrispeels et al. (2000) Plant Mol. Biol. 42: 279-290; and Piazza et al. (2002) Plant Physiol. 128: 1077-1086).

EXAMPLES

This invention is not limited to the particular devices, machines, materials and methods described. Although particular embodiments are described, equivalent embodiments may be used to practice the invention. The examples below are provided to enable the subject invention and are not included for the purpose of limiting the invention.

The invention being generally described will be more readily understood by reference to the following examples, which are included merely for purposes of illustration of certain aspects and embodiments of the present invention and are not intended to limit the invention. It will be recognized by one of skill in the art that a transcription factor associated with a particular first trait may also be associated with at least one other, unrelated and inherent second trait which was not predicted by the first trait.

Example I

Full Length Gene Identification and Cloning

Arabidopsis transcription factor clones used in these studies were made in one of three ways: isolation from a library, amplification from cDNA, or amplification from genomic DNA. The ends of the Arabidopsis transcription factor coding sequences were generally confirmed by RACE PCR or by comparison with public cDNA sequences before cloning.

Putative transcription factor sequences (genomic or ESTs) related to known transcription factors were identified in the Arabidopsis thaliana GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, Arabidopsis thaliana cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Roche Diagnostics Corp., Indianapolis, Ind.). Purified radiolabelled probes were added to filters immersed in Church hybridization medium (0.5 M $NaPO_4$ pH 7.0, 7% SDS, 1% w/v bovine serum albumin) and hybridized overnight at 60° C. with shaking. Filters were washed two times for 45 to 60 minutes with 1×SSC, 1% SDS at 60° C.

To identify additional sequence 5' or 3' of a partial cDNA sequence in a cDNA library, 5' and 3' rapid amplification of cDNA ends (RACE) was performed using the MARATHON cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the MARATHON Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Clones of transcription factor orthologs from rice, maize, and soybean presented in this report were all made by amplification from cDNA. The ends of the coding sequences were predicted based on homology to Arabidopsis or by comparison to public and proprietary cDNA sequences; RACE PCR was not done to confirm the ends of the coding sequences. For cDNA amplification, we used KOD Hot Start DNA Polymerase (Novagen), in combination with 1M betaine and 3% DMSO. This protocol was found to be successful in amplifying cDNA from GC-rich species such as rice and corn, along with some non-GC-rich species such as soybean and tomato, where traditional PCR protocols failed. Primers were designed using at least 30 bases specific to the target sequence, and were designed close to, or overlapping, the start and stop codons of the predicted coding sequence.

Clones were fully sequenced. In the case of rice, high-quality public genomic sequence is available for comparison, and clones with sequence changes that result in changes in amino acid sequence of the encoded protein were rejected. For corn and soy, however, it was often unclear whether sequence differences represented an error or polymorphism in the source sequence or a PCR error in the clone. Therefore, in the cases where the sequence of the clone we obtained differed from the source sequence, a second clone was created from an independent PCR reaction. If the sequences of the two clones agreed, then the clone was accepted as a legitimate sequence variant.

Example II

Construction of Expression Nucleic Acid Constructs

The sequence was amplified from a genomic or cDNA library using primers specific to sequences upstream and downstream of the coding region. The nucleic acid construct was pMEN20 or pMEN65 (SEQ ID NO: 68), which are both derived from pMON316 (Sanders et al. (1987) Nucleic Acids Res. 15:1543-1558) and contain the CaMV 35S promoter to express transgenes (pMEN20 is an earlier version of pMEN65 in which the kanamycin resistance gene is driven by the 35S promoter rather than the nos promoter. It is the base vector for P5381 and P5375). To clone the sequence into the constructs, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a QIAQUICK gel extraction kit (Qiagen, Valencia, Calif.). The fragments of interest were ligated at a ratio of 3:1 (vector to insert). Ligation reactions using T4 DNA ligase (New England Biolabs, Beverly Mass.) were carried out at 16° C. for 16 hours. The ligated DNAs were transformed into competent cells of the E. coli strain DH5alpha by using the heat shock method. The transformations were plated on LB plates containing 50 mg/l kanamycin (Sigma Chemical Co. St. Louis Mo.). Individual colonies were grown overnight in five milliliters of LB broth containing 50 mg/l kanamycin at 37° C. Plasmid DNA was purified by using Qiaquick Mini Prep kits (Qiagen, Valencia, Calif.).

Two-component vectors. P5381 (pMEN53; SEQ ID NO: 64) is the 2-component base vector that is used to express genes under the control of the LexA operator. It contains eight tandem LexA operators from plasmid p8op-lacZ (Clontech) followed by a polylinker. The plasmid carries a sulfonamide resistance gene driven by the 35S promoter.

GAL4 fusion vectors. P21195 (SEQ ID NO: 65) is the backbone vector for creation of N-terminal GAL4 activation domain protein fusions. It was created by inserting the GAL4 activation domain into the BglII and KpnI sites of pMEN65. To create gene fusions, the transcription factor gene of interest is amplified using a primer that starts at the second amino acid and has added the KpnI or SalI and NotI sites. The PCR product is then cloned into the KpnI or SalI and NotI sites of P21195, taking care to maintain the reading frame.

P21378 (SEQ ID NO: 66) was constructed to serve as a backbone vector for creation of C-terminal GAL4 activation domain fusions. However, P5425 was also used as a backbone construct. P21378 was constructed by amplification of the GAL4 activation domain and insertion of this domain into the NotI and XbaI sites of pMEN65. To create gene fusions, the transcription factor gene of interest is amplified using a 3' primer that ends at the last amino acid codon before the stop codon. The PCR product can then be cloned into the SalI and NotI sites.

P5425 (also called pMEN201) is a derivative of pMEN20 that carries a CBF1:GAL4 fusion. To construct other GAL4 fusions, the CBF1 gene was removed with SalI or KpnI and EcoRI. The gene of interest was amplified using a 3' primer that ended at the last amino acid codon before the stop codon and contained an EcoRI or MfeI site. The product was inserted into these SalI or KpnI and EcoRI sites, taking care to maintain the reading frame.

Example III

Transformation of *Agrobacterium* with the Nucleic Acid Construct

Direct promoter fusion. After the nucleic acid construct containing the gene was constructed, the construct was used to transform *Agrobacterium tumefaciens* cells expressing the gene products. The stock of *Agrobacterium tumefaciens* cells for transformation was made as described by Nagel et al. (1990) *FEMS Microbiol Letts.* 67: 325-328. *Agrobacterium* strain ABI was grown in 250 ml LB medium (Sigma Chemical Co., St. Louis, Mo.) overnight at 28° C. with shaking until an absorbance over 1 cm at 600 nm ($A_{600}$) of 0.5-1.0 was reached. Cells were harvested by centrifugation at 4,000×g for 15 minutes at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

*Agrobacterium* cells were transformed with plasmids prepared as described above following the protocol described by Nagel et al. (supra). For each nucleic acid construct to be transformed, 50-100 ng DNA (generally resuspended in 10 mM Tris-HCl, 1 mM EDTA, pH 8.0) was mixed with 40 µl of *Agrobacterium* cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad, Hercules, Calif.). After electroporation, cells were immediately resuspended in 1.0 ml LB and allowed to recover without antibiotic selection for 2-4 hours at 28° C. in a shaking incubator. After recovery, cells were plated onto selective medium of LB broth containing 100 µg/ml spectinomycin (Sigma Chemical Co., St. Louis, Mo.) and incubated for 24-48 hours at 28° C. Single colonies were then picked and inoculated in fresh medium. The presence of the plasmid construct was verified by PCR amplification and sequence analysis.

As an alternative to plant transformation with a direct fusion construct, some plant lines were transformed with a two component expression system in which a kanamycin resistant 35S::LexA-GAL4-TA driver line was established and then supertransformed with an opLexA::transcription factor construct carrying a sulfonamide resistance gene for each of the transcription factors of interest.

The first component vector contained a transgene carrying a 35S::LexA-GAL4-transactivation (TA) domain along with a kanamycin resistance selectable marker. Having established a driver line containing the 35S::LexA-GAL4-transactivation domain component, the transcription factors of the invention could be expressed by super-transforming or crossing in a second construct carrying a sulphonamide resistance selectable marker and the transcription factor polynucleotide of interest cloned behind a LexA operator site (opLexA::TF). For example, two constructs, P6506 (SEQ ID NO: 80) and a second construct comprising a G1792 clade polynucleotide cloned behind a LexA operator site (e.g., opLexA::G1792) together constitute a two-component system for expression of a G1792 polynucleotide from the 35S promoter. A kanamycin resistant transgenic line containing P6506 is established, and this is then supertransformed with the second construct containing a genomic clone of the G1792 clade polynucleotide and a resistance marker. For each transcription factor that was overexpressed with this two component system, the second construct carried a sulfonamide selectable marker and was contained within the vector backbone.

Promoters used to control regulation of the polynucleotides of the invention are listed in Table 2. Compilations of the sequences of promoter fragments and the expressed transgene sequences within the PIDs are provided in the Sequence Listing.

TABLE 2

Promoters combined with G1792 clade polynucleotides

| Promoter | Promoter SEQ ID NO: | Construct (PID) used to generate vectors | SEQ ID NO: of PID |
|---|---|---|---|
| Cauliflower mosaic 35S ("CaMV35S" or "35S") constitutive promoter | 69 | P6506 (35S::m35S::oEnh::LexAGal4) | 80 |
| AS1 emergent leaf primordia-expressed promoter | 79 | P5319 (prAS1::m35S::oEnh::LexAGal4(GFP)) | 81 |
| CUT1 epidermal-expressed promoter | 76 | P5288 (prCUT1::m35S::oEnh::LexAGal4(GFP)) | 82 |

TABLE 2-continued

Promoters combined with G1792 clade polynucleotides

| Promoter | Promoter SEQ ID NO: | Construct (PID) used to generate vectors | SEQ ID NO: of PID |
|---|---|---|---|
| LTP1 epidermal-expressed promoter | 70 | P5287 (prLTP1::m35S::oEnh::LexAGal4(GFP)) | 83 |
| AP1 floral meristem-expressed promoter | 78 | P5326 (prAP1::m35S::oEnh::LexAGal4(GFP)) | 84 |
| RBCS3 leaf and green tissue-expressed promoter | 71 | P5284 (prRBCS3::m35S::oEnh::LexAGal4(GFP)) | 85 |
| ARSK1 root-expressed promoter | 75 | P5311 (prARSK1::m35S::oEnh::LexAGal4(GFP)) | 86 |
| RSI1 root-expressed promoter | 77 | P5310 (prRSI1::m35S::oEnh::LexAGal4(GFP)) | 87 |
| STM shoot apical meristem-expressed promoter | 72 | P5318 (prSTM::m35S::oEnh::LexAGal4(GFP)) | 88 |
| RD29a stress-inducible promoter | 73 | P9002 (prRD29a::m35S::oEnh::LexAGal4(GFP)) | 89 |
| SUC2 vascular tissue-expressed promoter | 74 | P5290 (prSUC2::m35S::oEnh::LexAGal4(GFP)) | 90 |
| prAT5G62150 | | P26707 (prAT5G62150::G1795) | 91 |
| prAT5G24090 | | P26708 (prAT5G24090::G1795) | 92 |
| prAT1G35230 | | P26467 (AT1G35230::G1795) | 93 |

Example IV

Transformation of *Arabidopsis* Plants with *Agrobacterium tumefaciens*

*Agrobacterium* strain ABI was used for all plant transformations. This strain is chloramphenicol, kanamycin and gentamycin resistant. After transformation of *Agrobacterium tumefaciens* with plasmid vectors containing the gene, single *Agrobacterium* colonies were identified, propagated, and used to transform *Arabidopsis* plants. Briefly, 500 ml cultures of LB medium containing 50 mg/l kanamycin were inoculated with the colonies and grown at 28° C. with shaking for 2 days until an optical absorbance at 600 nm wavelength over 1 cm ($A_{600}$) of >2.0 is reached. Cells were then harvested by centrifugation at 4,000×g for 10 minutes, and resuspended in infiltration medium (½ X Murashige and Skoog salts (Sigma Chemical Co., St. Louis, Mo.), 1× Gamborg's B-5 vitamins (Sigma Chemical Co., St. Louis, Mo.), 5.0% (w/v) sucrose, 0.044 µM benzylamino purine (Sigma Chemical Co., St. Louis, Mo.), 200 µl/l Silwet L-77 (Lehle Seeds, Round Rock, Tex.) until an $A_{600}$ of 0.8 was reached).

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50-75 µE/m²/second) at 22-23° C. with 65-70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of *Agrobacterium* infiltration medium as described above for 30 seconds, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of *Arabidopsis* Primary Transformants

Seeds collected from the transformation pots were sterilized essentially as follows. Seeds were dispersed into in a solution containing 0.1% (v/v) Triton X-100 (Sigma Chemical Co., St. Louis, Mo.) and sterile water and washed by shaking the suspension for 20 minutes. The wash solution was then drained and replaced with fresh wash solution to wash the seeds for 20 minutes with shaking. After removal of the ethanol/detergent solution, a solution containing 0.1% (v/v) Triton X-100 and 30% (v/v) bleach (CLOROX; Clorox Corp. Oakland, Calif.) was added to the seeds, and the suspension was shaken for 10 minutes. After removal of the bleach/detergent solution, seeds were then washed five times in sterile distilled water. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50-75 µE/m²/second) at 22-23° C. After 7-10 days of growth under these conditions, kanamycin-resistant primary transformants ($T_1$ generation) were visible and obtained. These seedlings were transferred first to fresh selection plates where the seedlings continued to grow for 3-5 more days, and then to soil (Pro-Mix BX potting medium).

Primary transformants were crossed and progeny seeds ($T_2$) collected; kanamycin-resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of *Arabidopsis* Plants with Transcription Factor Gene Knockouts The screening of insertion mutagenized *Arabidopsis* collections for null mutants in a known target gene was essentially as described in Krysan et al. (1999) *Plant Cell* 11: 2283-2290. Briefly, gene-specific primers, nested by 5-250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Modified Phenotypes in Overexpressing Plants Morpholoyical Analysis Experiments were performed to identify those transformants that exhibited a morphological difference relative to control plants, i.e., a modified structure, physiology, and/or development characteristics relative to, for example, a wild-type plant, a non-transformed plant or a plant transformed with an "empty" expression vector lacking the DNA encoding a polypeptide of the invention. For such studies, the transformants were exposed to various assay conditions and novel structural, physiological responses, or developmental characteristics associated with the ectopic expression of the polynucleotides or polypeptides of the invention were observed. Examples of genes and equivalogs that confer significant improvements to overexpressing plants are noted.

Assays to Measure Increased Tolerance to Abiotic Stresses, Including Cold, Hyperosmotic Stresses and Low Nitrogen Conditions.

Modified phenotypes observed for particular overexpressing plants may include increased abiotic tolerance, that is, greater tolerance than would be found in a control plant, such as a wild-type plant, an untransformed plant from a parental line, or a plant transformed with an "empty" expression vector. For a particular overexpressor that shows a less beneficial characteristic, such as reduced abiotic stress resistance or tolerance, it may be more useful to select a plant with a decreased expression of the particular transcription factor, for example, in a knockout plant. For a particular knockout plant that shows a less beneficial characteristic, such as abiotic stress resistance or tolerance, it may be more useful to select a plant with an increased expression of the particular transcription factor.

The germination assays in Example VIII followed modifications of the same basic protocol. Sterile seeds were sown on the conditional media listed below. Plates were incubated at 22° C. under 24-hour light (120-130 µEin/m$^2$/s) in a growth chamber. Evaluation of germination and seedling vigor was conducted 3 to 15 days after planting. The basal media was 80% Murashige-Skoog medium (MS)+vitamins.

For stress experiments conducted with more mature plants, seeds were germinated and grown for seven days on MS+vitamins+1% sucrose at, 22° C. and then transferred to cold and heat stress conditions. The plants were either exposed to cold stress (6 hour exposure to 8° C.), or heat stress (32° C. was applied for five days, after which the plants were transferred back 22° C. for recovery and evaluated after 5 days relative to controls not exposed to the depressed or elevated temperature).

The salt stress assays were intended to find genes that confer better germination, seedling vigor or growth in high salt. Evaporation from the soil surface causes upward water movement and salt accumulation in the upper soil layer where the seeds are placed. Thus, germination normally takes place at a salt concentration much higher than the mean salt concentration of the whole soil profile. Plants differ in their tolerance to NaCl depending on their stage of development, therefore seed germination, seedling vigor, and plant growth responses were evaluated.

Hyperosmotic stress assays (including NaCl and mannitol assays) were conducted to determine if an osmotic stress phenotype was NaCl-specific or if it was a general hyperosmotic stress related phenotype. Plants tolerant to hyperosmotic stress could also have more tolerance to drought and/or freezing.

For salt and hyperosmotic stress germination experiments, the medium was supplemented with 150 mM NaCl or 300 mM mannitol. Growth regulator sensitivity assays were performed in MS media, vitamins, and either 0.3 µM ABA, 9.4% sucrose, or 5% glucose.

Desiccation and drought assays were performed to find genes that mediate better plant survival after short-term, severe water deprivation. Ion leakage was measured if needed.

For plate-based desiccation assays (plate-based water deficit assays), wild-type and control seedlings were grown for 14 days on MS+Vitamins+1% Sucrose at 22° C. The plates were then left open in the sterile laminar flow hood for 3 hr for hardening, and the seedlings were removed from the media and dried for 1.5 h in the sterile hood. The seedlings were transferred back to plates and incubated at 22° C. for recovery. The plants were then evaluated after another five days.

Polyethylene glycol (PEG) hyperosmotic stress tolerance screens involved sterilizing plant seeds with chlorine gas for 2 hrs. The seeds were plated on each plate containing 3% PEG, ½× MS salts, 1% phytagel, and 10 µg/ml glufosinate-ammonium (BASTA). Two replicate plates per seed line were planted. The plates were placed at 4° C. for 3 days to stratify seeds. The plates were held vertically for 11 additional days at temperatures of 22° C. (day) and 20° C. (night). The photoperiod was 16 hours with an average light intensity of about 120 µmol/m2/s. The racks holding the plates were rotated daily within the shelves of the growth chamber carts. At 11 days, root length measurements are made. At 14 days, seedling status was determined, root length was measured, growth stage was recorded, the visual color was assessed, pooled seedling fresh weight was measured, and a whole plate photograph was taken.

Sugar sensing assays were intended to find genes involved in sugar sensing by germinating seeds on high concentrations of sucrose and glucose and looking for degrees of hypocotyl elongation. The germination assay on mannitol controlled for responses related to osmotic stress. Sugars are key regulatory molecules that affect diverse processes in higher plants including germination, growth, flowering, senescence, sugar metabolism and photosynthesis. Sucrose is the major transport form of photosynthate and its flux through cells has been shown to affect gene expression and alter storage compound accumulation in seeds (source-sink relationships). Glucose-specific hexose-sensing has also been described in plants and is implicated in cell division and repression of "famine" genes (photosynthetic or glyoxylate cycles).

Temperature stress assays were carried out to find genes that confer better germination, seedling vigor or plant growth under temperature stress (cold, freezing and heat). Temperature stress cold germination experiments were carried out at 8° C. Heat stress germination experiments were conducted at 32° C. to 37° C. for 6 hours of exposure.

For nitrogen utilization assays, sterile seeds were sown onto plates containing media based on 80% MS without a nitrogen source ("low N germ" assay). For carbon/nitrogen balance (C/N) sensing assays, the media also contained 3% sucrose (−N/+G). The −"low N w/gln germ" media was identical but was supplemented with 1 mM glutamine. Plates were incubated in a 24-hour light C (120-130 µEins$^{-2}$ m$^{-1}$) growth chamber at 22° C. Evaluation of germination and seedling vigor was done five days after planting for C/N assays. The production of less anthocyanin on these media is generally associated with increased tolerance to nitrogen limitation, and a transgene responsible for the altered response is likely involved in the plant's ability to perceive their carbon and nitrogen status. For example, in the germination assay that monitors the effect of carbon on nitrogen signaling through anthocyanin production on media with high sucrose and with or without glutamine (Hsieh et al. (1998) *Proc. Natl. Acad. Sci. USA* 95: 13965-13970), 35S::G1792 lines made less anthocyanin on high sucrose with glutamine, indicating that this sequence is likely involved in monitoring carbon and nitrogen status in plants.

Soil Drought (Clay Pot)

The soil drought assay (performed in clay pots) was based on that described by Haake et al. (2002).

Experimental Procedure.

Previously, we have performed clay-pot assays on segregating T2 populations, sown directly to soil. However, in the current procedure, seedlings were first germinated on selection plates containing either kanamycin or sulfonamide.

Seeds were sterilized by a 2 minute ethanol treatment followed by 20 minutes in 30% bleach/0.01% Tween and five washes in distilled water. Seeds were sown to MS agar in 0.1% agarose and stratified for three days at 4° C., before transfer to growth cabinets with a temperature of 22° C. After seven days of growth on selection plates, seedlings were transplanted to 3.5 inch diameter clay pots containing 80 g of a 50:50 mix of vermiculite:perlite topped with 80 g of Pro-Mix. Typically, each pot contained 14 seedlings, and plants of the transgenic line being tested were in separate pots to the wild-type controls. Pots containing the transgenic line versus control pots were interspersed in the growth room, maintained under 24-hour light conditions (18-23° C., and 90-100 µE m−2 s−1) and watered for a period of 14 days. Water was then withheld and pots were placed on absorbent paper for a period of 8-10 days to apply a drought treatment. After this period, a visual qualitative "drought score" from 0-6 was assigned to record the extent of visible drought stress symptoms. A score of "6" corresponded to no visible symptoms whereas a score of "0" corresponded to extreme wilting and the leaves having a "crispy" texture. At the end of the drought period, pots were re-watered and scored after 5-6 days; the number of surviving plants in each pot was counted, and the proportion of the total plants in the pot that survived was calculated.

A variation of the above method was sometimes used, whereby plants for a given transgenic line were compared to wild-type controls in the same pot. For those studies, 7 wild-type seedlings were transplanted into one half of a 3.5 inch pot and 7 seedlings of the line being tested were transplanted into the other half of the pot.

Analysis of results. In a given experiment, we typically compared 6 or more pots of a transgenic line with 6 or more pots of the appropriate control. The mean drought score and mean proportion of plants surviving (survival rate) were calculated for both the transgenic line and the wild-type pots. In each case a p-value* was calculated, which indicated the significance of the difference between the two mean values. The results for each transgenic line across each planting for a particular project were then presented in a results table.

Calculation of p-values. For the assays where control and experimental plants were in separate pots, survival was analyzed with a logistic regression to account for the fact that the random variable is a proportion between 0 and 1. The reported p-value was the significance of the experimental proportion contrasted to the control, based upon regressing the logit-transformed data.

Drought score, being an ordered factor with no real numeric meaning, was analyzed with a non-parametric test between the experimental and control groups. The p-value was calculated with a Mann-Whitney rank-sum test.

The transcription factor sequences of the Sequence Listing, or those in the present Tables or Figures, and their equivalogs, can be used to prepare transgenic plants and plants with increased abiotic stress tolerance. The specific transgenic plants listed below are produced from the sequences of the Sequence Listing, as noted. The Sequence Listing, Table 3 and Examples VIII and IX provide exemplary polynucleotide and polypeptide sequences of the invention.

Example VIII

Genes that Confer Significant Abiotic Stress Tolerance or Biotic Stress Resistance This example provides experimental evidence for increased tolerance to various abiotic stresses or resistance to disease controlled by the transcription factor polypeptides and polypeptides of the invention, indicating that sequences found within the G1792 clade of transcription factor polypeptides are functionally related. As shown below in Table 3 and the descriptions that follow, members of the G1792 clade of transcription factor polypeptides from diverse plant species, including G30, G1791, and G1792, soybean G3518 and G3520, rice G3380, G3381, G3383, G3515, and G3737, and corn G3516 and G3517 (SEQ ID NO: 7, 3, 1, 21, 25, 9, 11, 13, 15, 31, 17, and 19, respectively) increase tolerance to cold, water deficit, and/or low nitrogen conditions, and clade member polypeptides also tended to increase resistance to disease when these sequences are overexpressed in plants. From these experimental results, it may be inferred that a considerable number of sequences within the G1792 clade from diverse plant species may be used to impart increased environmental stress tolerance. Many of these genes conferred increased tolerance to multiple abiotic stresses. Not all assays were performed with every sequence and plant combination, but in general these results do demonstrate the ability of a significant number of clade sequences to confer the improved traits listed in Table 3.

TABLE 3

Improved traits produced by overexpressing G1792 clade polypeptides in plants

| GID (SEQ ID NO:) Species | Percent identity to G1792 AP2 domain | Improved trait (greater tolerance or resistance) to: | | | |
|---|---|---|---|---|---|
| | | Low nitrogen conditions | Disease | Water deficit | Cold |
| G1792 (2) At | 100.0 | +[1,2,3,4,6,7,8,9,12,13,14,15] | +[1,2,3,6,7,14] (B, E, F, S) | +[1,3,5,6,7,8,10,11,12,13,14,15] (dhyd, drt, NaCl, man, suc) | +[1,3,8,10,11,13,14,15] (germ, grth) |
| G3520 (26) Gm | 80.0 | +[1] | +[1] (S, E) | +[1] (heat) | +[1] (grth) |
| G3519 (24) Gm | 76.9 | | +[1] (E) | +[1] (dhyd) | +[1] (germ) |
| G3518 (22) Gm | 76.9 | +[1] | +[1] (E) | +[1] (drt, NaCl) | +[1] (germ, grth) |
| G1791 (4) At | 72.3 | +[2,12,15] | +[2,3,4,6] (B, E, S) | +[3,7,12] (dhyd, drt, NaCl) | +[2,7] (germ, grth) |
| G3380 (10) Os | 72.3 | | +[1] (E) | +[1] (drt, man) | +[1] (grth) |
| G3383 (14) Os | 72.3 | | | +[1] (dhyd, man) | +[1] (germ, grth) |
| G3515 (16) Os | 70.8 | +[1] | | +[1] (drt, man) | +[1] (grth) |
| G3737 (32) Os | 70.8 | | +[1] (E) | +[1] (dhyd, drt, NaCl) | +[1] (germ, grth) |
| G3381 (12) Os | 70.8 | +[1] | + (S, E) | +[1] (drt, man) | +[1] (germ) |
| G3516 (18) Zm | 70.8 | +[1] | | +[1] (dhyd) | +[1] (germ) |
| G30 (8) At | 70.8 | +[4,12,15] | +[2,4,6,7] (B, E, S) | +[6,12,15] (dhyd, heat, man, NaCl) | +[2,3,4,10,12,15] (germ) |
| G3794 (36) Zm | 69.2 | | | +[1] (dhyd) | +[1] (germ) |
| G1795 (6) At | 69.2 | +[15,18] | +[1,3,4,6,7,15,16,17,18] (B, E, S) | +[3,4,15,16] (dhyd, drt, man) | +[16,17] (germ) |
| G3739 (34) Zm | 67.7 | +[1] | +[1] (E) | +[1] (dhyd, man) | +[1] (germ) |

TABLE 3-continued

Improved traits produced by overexpressing G1792 clade polypeptides in plants

| GID (SEQ ID NO:) Species | Percent identity to G1792 AP2 domain | Low nitrogen conditions | Improved trait (greater tolerance or resistance) to: | | |
|---|---|---|---|---|---|
| | | | Disease | Water deficit | Cold |
| G35I7 (20) Zm | 67.7 | | +[1] (S, E) | +[1] (dhyd, heat) | +[1] (germ, grth) |

Notes for Table 3:
[1] with 35S promoter
[2] with AS 1 promoter
[3] with CUT1 promoter
[4] with LTP1 promoter
[5] with AP1 promoter
[6] GR fusion
[7] with RBCS3 promoter
[8] promoter reporter
[9] with ARSK1 promoter
[10] with RSI1 promoter
[11] with STM promoter
[12] with RD29a promoter
[13] C-terminal GAL4 activation domain fusion
[14] N-terminal GAL4 activation domain fusion
[15] with SUC2 promoter
[16] with AT5G62150 promoter
[17] with AT5G24090 promoter
[18] with AT1G35230 promoter
At = *Arabidopsis thaliana*, Gm = *Glycine max*, Os = *Oryza sativa*, Zm = *Zea mays*
Disease abbreviations: B = Botrytis, E = Erysiphe, F = Fusarium, S = Sclerotinia
Water deficit abbreviations: dhyd = dehydration, drt = drought, man = mannitol, suc = sucrose
Cold treatment abbreviations: germ = observed during germination, grth = during growth of seedlings
NaCl = germination assay in 150 mM NaCl
Man = germination assay in 300 mM mannitol
Suc = germination assay in 9.4% sucrose
ABA = germination assay in 0.3 μM abscisic acid
Dhyd = severe dehydration assay where seedlings are dried 1.5 h, transferred to 22° C., evaluated 5 days later
Cold germ = germination at 8° C.
Cold growth = growth of plants at 8° C. until a stress response is evident
Heat = germination or growth at 32° C.
Low N conditions = rate of germination under low nitrogen conditions
+ greater tolerance compared to controls; the response was consistent and was moderately above the normal levels of variability observed for that assay (for ABA, less sensitive to ABA than controls)

Constitutive overexpression of G1792 clade members often produced small plants that may have exhibited darker green leaves than were observed in control plants. Because of the generally undesirable (but not universally undesirable) nature of smaller size, transgenic plants were generated that over-expressed G1792 clade members with a variety of regulatory schemes, as indicated below. In many cases, inducible or tissue-specific expression of G1792 clade polypeptides produced plants that were more tolerant to cold, low nitrogen conditions, water deficit, or more resistant to pathogens, yet were more similar or morphologically similar to control plants, thus demonstrating that improved traits can be retained without the adverse morphological or developmental characteristics sometimes found in constitutive over-expressors of this clade.

G1792 (*Arabidopsis thaliana*; SEQ ID NO: 1 and 2) Overexpression, Effects on Morphology and Alleviation of Adverse Morphological Characteristics Plants overexpressing G1792 under the regulatory control of the constitutive 35S promoter were generally smaller than wild-type controls, were rather dark and shiny and in some cases showed delayed flowering.

The majority of the *Arabidopsis* lines overexpressing G1792 under the regulatory control of the SUC2 promoter were similar to controls in their development and morphology. Most lines performed better than wild-type controls in at least one plate-based physiological and/or nitrogen utilization assay.

The majority of the *Arabidopsis* lines overexpressing G1792 under the regulatory control of the RBCS3 promoter were slightly smaller, darker green, and later developing than controls, but these phenotypes were much less severe than those of 35S::G1792 plants.

Some epidermal-specific LTP1::G1792 T1 lines flowered slightly early, but otherwise LTP1::G1792 plants were not consistently different from controls. LTP1::G1792 lines showed a better performance than wild-type controls in a low N growth assay on plates.

A number of *Arabidopsis* lines overexpressing G1792 under the regulatory control of the STM (shoot apical meristem-specific) promoter were smaller than wild-type controls. Other lines showed no consistent developmental or morphological differences with respect to the controls. Three lines were more tolerant to ABA, and three lines were more tolerant to germination under cold conditions than wild-type controls.

N-GAL4-TA G1792 plants exhibited comparable phenotypes to 35S::G1792 lines and all (to varying extents) were dwarfed, late flowering, dark in coloration, and had a shiny appearance. These plants showed a better performance than controls in severe dehydration and cold germination assays performed on plates. Three lines also showed a better performance than controls in a plate based low N growth assay. The phenotype seen was less potent than with overexpression lines for the native form of G1792, suggesting that the GAL4-G1792 fusion might have a reduction in activity relative to the native form.

G30 (*Arabidopsis thaliana*: SEQ ID NO: 7 and 8) Overexpression, Effects on Morphology and Alleviation of Adverse Morphological Characteristics Plants overexpressing G30 under the regulatory control of the epidermal-specific LTP1 were small in size and dark in color, with curling upright leaves compared to controls. All lines also flowered and developed late. The small, dark green, and late flowering phenotypes are typical of members of the G1792 clade, though much less severe than seen in 35S::G30 plants.

Most of the *Arabidopsis* lines overexpressing G30 under the regulatory control of the RD29A promoter (line 5; stress inducible) were similar to wild-type controls in their development and morphology. This promoter-gene combination conferred greater tolerance to salt, ABA, germination in cold and low nitrogen conditions than the controls.

Most *Arabidopsis* lines overexpressing G30 under the regulatory control of the SUC2 promoter (vascular-specific) were dark, shiny, and small. However, this promoter-gene combination conferred greater tolerance to mannitol, sucrose, desiccation, and germination in cold than wild-type controls. The overexpressors also performed better than controls in low nitrogen and nitrogen utilization assays.

Most of the *Arabidopsis* lines over-expressing G30 under the regulatory control of the RBCS3 promoter were dark green and slightly small in size, but were more similar to wild-type morphology than 35S::G30 lines.

G1791 (*Arabidopsis thaliana*: SEQ ID NO: 3 and 4) Overexpression, Effects on Morphology and Alleviation of Adverse Morphological Characteristics In general, two-component G1791 lines under the regulatory control of the leaf-specific G1791 promoter (RBCS3::G1791) were smaller than control plants. Several lines were slightly late flowering. The lines were tested in plate based assays and showed a better performance than controls in ABA germination and cold growth assays.

Some of the *Arabidopsis* lines overexpressing G1791 under the regulatory control of the RD29A promoter (line 5; stress inducible) were small and late developing. Other lines were similar to wild-type controls in their development and morphology. This promoter-gene combination conferred greater tolerance to salt, ABA, and low nitrogen conditions than the controls.

G1266 (*Arabidopsis thaliana*: SEQ ID NO: 37 and 38) Abiotic Stress Assay Results G1266 is an *Arabidopsis* sequence related to G1792 (FIG. 5). Many of the 35S::G1266 lines were small and spindly. Five out of ten 35S::G1266 (direct promoter fusion) lines were insensitive to ABA in a germination assay. Two of these lines were also tolerant to NaCl and mannitol in a germination assay. Two other lines were more tolerant to cold in another germination assay.

G1752 (*Arabidopsis thaliana*; SEQ ID NO: 41 and 42) Abiotic Stress Assay Results G1752 is an *Arabidopsis* sequence related to G1792 (FIG. 5). Three out of seven 35S::G1752 (direct promoter fusion) lines were tolerant to mannitol in a germination assay. These three lines were a darker green than control seedlings, but appeared somewhat smaller. Several lines were small, chlorotic, and had less root growth than wild-type controls.

G1792 and related genes respond in baseline microarray experiments. G1792 and related genes have been identified as responding to abiotic stresses in microarray experiments in which wild-type Columbia plants were been treated with various abiotic stresses. G1792 transcript in roots peaks four hours after mannitol treatment, reaching an expression level approximately 24-fold higher than mock treated plants. G1792 transcript levels in roots in NaCl treated plants reach levels eight-fold higher than mock treated plants at eight hours. Interestingly, G1792 expression is down-regulated in both soil-based drought experiments and upon treatment with ABA. Expression levels in both cases are down-regulated approximately three-fold.

Utilities for G1792 clade members under constitutive and non-constitutive regulatory control. The results of these studies with the constitutive and non-constitutive regulatory control of many G1792 clade members indicate that the polynucleotide and polypeptide sequences can be used to improve abiotic stress tolerance, and in a number of cases can do so without conferring severe adverse morphological or developmental defects to the plants. These data confirm our conclusions that G1792 and other G1792 clade members may be valuable tools for the purpose of increasing yield and quality of plant products.

Example IX

Disease Resistance and Abiotic Stress Tolerance without Severe Developmental or Morphological Defects As noted in this example and in the results presented above, overexpression of G1792 and its closely-related homologs using non-constitutive regulatory schemes produced plants that were similar in their development and morphology to wild type, but which retained disease resistance and abiotic stress tolerant phenotypes.

A number of RBCS3:G1792 lines were late flowering, slightly small in size and slightly dark in coloration. All other lines were equivalent in development and morphology to control lines.

Overall, LTP1::G1792 lines were not consistently different from control plants in their development and morphology.

RBCS3::G1791 and LTP1::G1791 lines were generally similar to control lines in their development and morphology.

RBCS3::G1795 and LTP1::G1795 lines were small at the rosette stage of development, had dark green leaves, and all lines flowered late.

Most of the RBCS3::G30 lines were marginally small and somewhat late in their development. All of these lines were at least marginally late flowering, and had dark green/slightly wrinkled leaves. At late stages of development almost all plants showed no consistent differences relative to wild-type controls. LTP1::G30 plants were similar in their development; all were dark in color, late developing and slightly small in size at early stages, slightly smaller than wild type at the rosette stage, and very similar to controls at late stages of development.

Example X

Identification of Homologous Sequences by Computer Homology Search

This example describes identification of genes that are orthologous to *Arabidopsis thaliana* G1792 clade member transcription factors from a computer homology search.

Homologous sequences, including those of paralogs and orthologs from *Arabidopsis* and other plant species, were identified using database sequence search tools, such as the Basic Local Alignment Search Tool (BLAST) (Altschul et al. (1990) supra; and Altschul et al. (1997) *Nucleic Acid Res.* 25: 3389-3402). The tblastx sequence analysis programs were employed using the BLOSUM-62 scoring matrix (Henikoff and Henikoff (1992) *Proc. Natl. Acad. Sci. USA* 89: 10915-10919). The entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*).

These sequences are compared to sequences representing transcription factor genes presented in the Sequence Listing, using the Washington University TBLASTX algorithm (version 2.0a19 MP) at the default settings using gapped alignments with the filter "off". For each transcription factor gene in the Sequence Listing, individual comparisons were ordered by probability score (P-value), where the score reflects the probability that a particular alignment occurred by chance. For example, a score of 3.6e−59 is 3.6×10−59. In addition to P-values, comparisons were also scored by percentage identity. Percentage identity reflects the degree to which two segments of DNA or protein are identical over a particular length. Examples of sequences so identified are presented in, for example, the Sequence Listing and Table 1. Paralogous or orthologous sequences may be readily identified and available in GenBank by Accession number (Sequence Identifier or Accession Number). The percent sequence identity among these sequences can be as low as 49%, or even lower sequence identity.

Candidate paralogous sequences were identified among *Arabidopsis* transcription factors through alignment, identity, and phylogenic relationships. G1791, G1795 and G30 (SEQ ID NO: 4, 6, and 8, respectively), paralogs of G1792, may be found in the Sequence Listing.

Candidate orthologous sequences were identified from proprietary unigene sets of plant gene sequences in *Zea mays*, *Glycine max* and *Oryza sativa* based on significant homology to *Arabidopsis* transcription factors. These candidates were reciprocally compared to the set of *Arabidopsis* transcription factors. If the candidate showed maximal similarity in the protein domain to the eliciting transcription factor or to a paralog of the eliciting transcription factor, then it was considered to be an ortholog. Identified non-*Arabidopsis* sequences that were shown in this manner to be orthologous to the *Arabidopsis* sequences are provided in, for example, Table 1.

Example XI

Transformation of Eudicots to Produce Increased Yield, Abiotic Stress Tolerance and/or Disease Resistance Crop species overexpressing members of the G1792 clade of transcription factor polypeptides have been shown experimentally to produce plants with increased tolerance to low nitrogen conditions and other abiotic stresses, including hyperosmotic stress and/or heat and/or cold. This observation indicates that these genes, when overexpressed, will result in larger yields of various plant species, particularly during conditions of abiotic stress or low nitrogen.

Thus, transcription factor sequences listed in the Sequence Listing recombined into pMEN20 or pMEN65 nucleic acid constructs may be transformed into a plant for the purpose of modifying plant traits. The construct may be introduced into a variety of cereal plants by means well known in the art such as, for example, direct DNA transfer or *Agrobacterium tumefaciens*-mediated transformation. It is now routine to produce transgenic plants using most dicot or eudicot plants (see Weissbach and Weissbach, (1989) supra; Gelvin et al. (1990) supra; Herrera-Estrella et al. (1983) supra; Bevan (1984) supra; and Klee (1985) supra). Methods for analysis of traits are routine in the art and examples are disclosed above.

Methods for transforming cotton may be found in U.S. Pat. Nos. 5,004,863, 5,159,135 and 5,518,908; for transforming *brassica* species may be found in U.S. Pat. No. 5,463,174; for transforming peanut plants may be found in Cheng et al. (1996) *Plant Cell Rep.* 15: 653-657, and McKently et al. (1995) *Plant Cell Rep.* 14: 699-703; and for transforming pea may be found in Grant et al. (1995) *Plant Cell Rep.* 15: 254-258.

Numerous protocols for the transformation of tomato and soy plants have been previously described, and are well known in the art. Gruber et al. ((1993) in *Methods in Plant Molecular Biology and Biotechnology*, p. 89-119, Glick and Thompson, eds., CRC Press, Inc., Boca Raton) describe several expression vectors and culture methods that may be used for cell or tissue transformation and subsequent regeneration. For soybean transformation, methods are described by Miki et al. (1993) in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., (1987) *Part. Sci. Technol.* 5:27-37; Christou et al. (1992) *Plant. J.* 2: 275-281; Sanford (1993) *Methods Enzymol.* 217: 483-509; Klein et al. (1987) *Nature* 327: 70-73; U.S. Pat. No. 5,015,580 (Christou et al), issued May 14, 1991; and U.S. Pat. No. 5,322,783 (Tomes et al.), issued Jun. 21, 1994.

Alternatively, sonication methods (see, for example, Zhang et al. (1991) *Bio/Technology* 9: 996-997); direct uptake of DNA into protoplasts using $CaCl_2$ precipitation, polyvinyl alcohol or poly-L-ornithine (see, for example, Hain et al. (1985) *Mol. Gen. Genet.* 199: 161-168; Draper et al., *Plant Cell Physiol.* 23: 451-458 (1982)); liposome or spheroplast fusion (see, for example, Deshayes et al. (1985) *EMBO J.*, 4: 2731-2737; Christou et al. (1987) *Proc. Natl. Acad. Sci. USA* 84: 3962-3966); and electroporation of protoplasts and whole cells and tissues (see, for example, Donn et al.(1990) in *Abstracts of VIIth International Congress on Plant Cell and Tissue Culture IAPTC*, A2-38: 53; D'Halluin et al. (1992) *Plant Cell* 4: 1495-1505; and Spencer et al. (1994) *Plant Mol. Biol.* 24: 51-61) have been used to introduce foreign DNA and expression vectors into plants.

After a eudicot plant, monocot plant or plant cell (and the latter regenerated into a plant), the transformed plant may be crossed with itself or a plant from the same line, a nontransformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986) In *Tomato Biotechnology*: Alan R. Liss, Inc., 169-178, and in U.S. Pat. No. 6,613,962, the latter method described in brief here. Eight day old cotyledon explants are precultured for 24 hours in Petri dishes containing a feeder layer of suspension cells plated on MS medium with 2% (w/v) sucrose and 0.8% agar supplemented with 10 μM α-naphthalene acetic acid and 4.4 μM 6-benzylaminopurine. The explants are then infected with a diluted overnight culture of *Agrobacterium tumefaciens* containing a nucleic acid construct comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 μM zeatin, 67.3 μM vancomycin, 418.9 μM cefotaxime and 171.6 μM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055. In this method, soybean seed is surface sterilized by exposure to chlorine gas evolved in a glass bell jar. Seeds are germinated by plating on ⅒ strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the nucleic acid construct comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XII

Increased Biotic and Abiotic Stress Tolerance in Monocots

Cereal plants such as, but not limited to, corn, wheat, rice, sorghum, or barley, or other grasses such as switchgrass or *Miscanthus*, may be transformed with the present polynucleotide sequences, including monocot or eudicot-derived sequences such as those presented in Table 3, cloned into an expression vector and containing a kanamycin-resistance marker, and expressed constitutively under, for example, the CaMV 35S or COR15 promoters. pMEN20 or pMEN65 and other nucleic acid constructs may also be used for the purpose of modifying plant traits. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The nucleic acid construct may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the nucleic acid construct.

The sample tissues are immersed in a suspension of $3\times10^{-9}$ cells of *Agrobacterium* containing the nucleic acid construct for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994) *Plant Mol. Biol.* 25: 925-937) such as corn, wheat, rice, sorghum (Cassas et al. (1993) *Proc. Natl. Acad. Sci. USA* 90: 11212-11216, and barley (Wan and Lemeaux (1994) *Plant Physiol.* 104:37-48). DNA transfer methods such as the microprojectile method can be used for corn (Fromm et al. (1990) *Bio/Technol.* 8: 833-839); Gordon-Kamm et al. (1990) *Plant Cell* 2: 603-618; Ishida (1990) *Nature Biotechnol.* 14:745-750), wheat (Vasil et al. (1992) *Bio/Technol.* 10:667-674; Vasil et al. (1993) *Bio/Technol.* 11:1553-1558; Weeks et al. (1993) *Plant Physiol.* 102:1077-1084), and rice (Christou (1991) *Bio/Technol.* 9:957-962; Hiei et al. (1994) *Plant J.* 6:271-282; Aldemita and Hodges (1996) *Planta* 199:612-617; and Hiei et al. (1997) *Plant Mol. Biol.* 35:205-218). For most cereal plants, embryogenic cells derived from immature scutellum tissues are the preferred cellular targets for transformation (Hiei et al. (1997) *Plant Mol. Biol.* 35:205-218; Vasil (1994) *Plant Mol. Biol.* 25: 925-937). For transforming corn embryogenic cells derived from immature scutellar tissue using microprojectile bombardment, the A188XB73 genotype is the preferred genotype (Fromm et al. (1990) *Bio/*

Technol. 8: 833-839; Gordon-Kamm et al. (1990) Plant Cell 2: 603-618). After microprojectile bombardment the tissues are selected on phosphinothricin to identify the transgenic embryogenic cells (Gordon-Kamm et al. (1990) Plant Cell 2: 603-618). Transgenic plants are regenerated by standard corn regeneration techniques (Fromm et al. (1990) Bio/Technol. 8: 833-839; Gordon-Kamm et al. (1990) Plant Cell 2: 603-618).

Northern blot analysis, RT-PCR or microarray analysis of the regenerated, transformed plants may be used to show expression of G1792 and related genes that are capable of conferring tolerance to biotic or abiotic stress.

To verify the ability to confer abiotic stress tolerance, mature plants overexpressing a G1792 clade member, or alternatively, seedling progeny of these plants, may be challenged by low nitrogen conditions or another abiotic stress such as heat, cold, or the hyperosmotic stresses of drought, high salt or freezing. Alternatively, these plants may be challenged in an osmotic stress condition that may also measure altered sugar sensing, such as a high sugar condition. By comparing wild type and transgenic plants similarly treated, the transgenic plants may be shown to have greater tolerance to biotic and or abiotic stress.

By comparing wild type and transgenic plants similarly treated, the transgenic plants may be shown to have greater tolerance to low nitrogen conditions and/or abiotic stress, or also fewer adverse effects from low nitrogen conditions and/or abiotic stresses including hyperosmotic (e.g., high salt and drought), heat, and cold stresses.

The transgenic plants may also have greater yield relative to a control plant when both are faced with the same low nitrogen or abiotic stress. Since plants overexpressing members of the G1792 clade may be tolerant to one or more abiotic stresses, plants overexpressing a member of the G1792 clade may incur a smaller yield loss and better quality than control plants when the overexpressors and control plants are faced with similar abiotic stress challenges. Better yield or quality may be obtained by, for example, reducing distortions, lesion size or number, defoliation, stunting, necrosis or pathogen susceptibility (e.g., pathogen growth or sporulation) by at least about 5%, or at least 10%, or at least 20% or more, up to 100%, relative to a control plant exposed to the same abiotic stress, or increasing chlorophyll content or photosynthesis by at least about 5%, or at least 10%, or at least 20% or more relative to a control plant subjected to the same abiotic stress. As indicated in Example VIII, a number of plants overexpressing members of the G1792 clade showed significantly better turgor and greater mass (up to and including 100%) and significantly fewer or reduced stress-related symptoms compared to control plants.

After a monocot plant or plant cell has been transformed (and the latter regenerated into a plant) and shown to have greater tolerance to low nitrogen and/or abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

Example XIII

Sequences that Confer Significant Improvements to non-*Arabidopsis* Species

The function of specific orthologs of G1792 has been analyzed and may be further characterized by incorporation into crop plants. The ectopic overexpression of these orthologs may be regulated using constitutive, inducible, or tissue specific regulatory elements, as disclosed above. Genes that have been examined and have been shown to modify plant traits (including increasing tolerance to an abiotic stress or multiple abiotic stresses) encode members of the G1792 clade of transcription factor polypeptides, such as those found in *Arabidopsis thaliana* (SEQ ID NO: 2, 4, 6 and 8), *Glycine max* (22, 24, and 26), *Medicago truncatula* (28), *Oryza sativa* (SEQ ID NO: 10, 12, 14, 16, and 32), *Triticum aestivum* (30), and *Zea mays* (SEQ ID NO: 18, 20, 34 and 36). In addition to these sequences, it is expected that related polynucleotide sequences encoding polypeptides found in the Sequence Listing can also induce increased tolerance to abiotic stresses, when transformed into a considerable variety of plants of different species, and including higher plants. The polynucleotide and polypeptide sequences in the sequence listing may be used to transform any higher plant. For example, sequences derived from monocots (e.g., the rice or corn sequences) may be used to transform both monocot and eudicot plants, and those derived from eudicots (e.g., the *Arabidopsis* and soy genes) may be used to transform either group, although it is expected that some of these sequences will function best if the gene is transformed into a plant from the same group as that from which the sequence is derived.

In addition to the constitutive 35S promoter, G1792 clade members may be overexpressed under the regulatory control of inducible or tissue-specific promoters. For example, ARSK1 and RSI1 (root-specific), RBCS3 (photosynthetic tissue-specific), CUT1 and LTP1 (epidermal-specific), SUC2 (vascular-specific) STM (shoot apical meristem-specific), AP1 (floral meristem-specific), AS1 (emergent leaf primordia-specific) and RD29A (stress-inducible) promoters may be used to confer abiotic stress tolerance in plants. Typically, these promoter-gene combinations may be readily achieved via the two-component system, although direct promoter fusions may also be considered. To date, we have found the use of alternative tissue-specific promoters to be a particular valuable approach in dissecting and optimizing gene function. In a number of cases, we have found that a stress-tolerance phenotype could be achieved without undesirable morphological changes (e.g., stunting, low fertility) that may be conferred when using a constitutive promoter.

These experiments demonstrate that a number of G1792 clade members, including G30, G1791, and G1792, soybean G3518 and G3520, rice G3380, G3381, G3383, G3515, and G3737, and corn G3516 and G3517 (SEQ ID NO: 8, 4, 2, 22, 26, 10, 12, 14, 16, 32, 18, and 20, respectively) can be identified and shown to confer increased abiotic stress tolerance in a plant relative to a control plant. It is expected that the same methods may be applied to identify and eventually make use of other members of the clade from a diverse range of species.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the Claims. Modifications that become apparent from the foregoing description and accompanying figures fall within the scope of the following Claims.

What is claimed is:

1. A nucleic acid construct comprising a recombinant nucleic acid sequence encoding a polypeptide that regulates transcription in a plant, wherein the polypeptide has an AP2 domain with at least 83% amino acid identity to amino acids 6-70 of SEQ ID NO: 18, the polypeptide comprises an EDLL domain of SEQ ID NO: 63, and expression of the polypeptide in a plant confers greater tolerance to water deficit or nitrogen-limited conditions than a control plant.

2. The nucleic acid construct of claim 1, wherein the polypeptide has at least 85% amino acid identity to SEQ ID NO: 18.

3. The nucleic acid construct of claim 1, wherein the polypeptide has at least 96% amino acid identity to SEQ ID NO: 18.

4. The nucleic acid construct of claim 1, wherein the polypeptide is overexpressed under the regulatory control of a constitutive, inducible, or tissue-specific promoter.

5. A recombinant host cell comprising the nucleic acid construct of claim 1.

6. A transgenic seed comprising the nucleic acid construct of claim 1.

7. A target plant transformed with the nucleic acid construct of claim 1, wherein the target plant produces greater yield than a control plant, said greater yield resulting from expression of the polypeptide in the target plant.

8. A transformed plant that has greater tolerance to nitrogen-limited conditions than a control plant;
wherein the transformed plant is transformed with a nucleic acid construct comprising a recombinant polynucleotide encoding a polypeptide;
wherein the polypeptide has an AP2 domain with at least 83% amino acid identity to amino acids 6-70 of SEQ ID NO: 18, the polypeptide comprises an EDLL domain of SEQ ID NO: 63, and expression of the polypeptide in the transgenic plant confers to the transgenic plant greater tolerance to nitrogen-limited conditions than the tolerance to nitrogen-limited conditions of the control plant.

9. The transformed plant of claim 8, wherein the polypeptide has at least 85% amino acid identity to SEQ ID NO: 18.

10. The transformed plant of claim 8, wherein the polypeptide has at least 96% amino acid identity to SEQ ID NO: 18.

11. The transformed plant of claim 8, wherein the polypeptide is overexpressed under the regulatory control of a constitutive, inducible, or tissue-specific promoter.

12. A transgenic seed derived from the transformed plant of claim 8, wherein the transgenic seed comprises the nucleic acid construct of claim 8.

13. The transformed plant of claim 8, wherein the transformed plant produces greater yield than the control plant, said greater yield resulting from expression of the polypeptide in the transformed plant.

14. A transformed plant that has greater tolerance to water deficit than a control plant;
wherein the transformed plant is transformed with a nucleic acid construct comprising a recombinant polynucleotide encoding a polypeptide;
wherein the polypeptide has an AP2 domain with at least 83% amino acid identity to amino acids 6-70 of SEQ ID NO: 18, the polypeptide comprises an EDLL domain of SEQ ID NO: 63, and expression of the polypeptide in the transgenic plant confers to the transgenic plant greater tolerance to water deficit than the control plant.

15. The transformed plant of claim 14, wherein the polypeptide has at least 85% amino acid identity to SEQ ID NO: 18.

16. The transformed plant of claim 14, wherein the polypeptide has at least 96% amino acid identity to SEQ ID NO: 18.

17. The transformed plant of claim 14, wherein the polypeptide is overexpressed under the regulatory control of a constitutive, inducible, or tissue-specific promoter.

18. A transgenic seed derived from the transformed plant of claim 14, wherein the transgenic seed comprises the nucleic acid construct of claim 8.

19. The transformed plant of claim 14, wherein the transformed plant produces greater yield than the control plant, said greater yield resulting from expression of the polypeptide in the transformed plant.

20. The transformed plant of claim 14, wherein the transformed plant is a monocot.

* * * * *

SEQUENCE LISTING

<160> NUMBER OF SEQ ID NOS: 129

<210> SEQ ID NO 1
<211> LENGTH: 696
<212> TYPE: DNA
<213> ORGANISM: Arabidopsis thaliana
<220> FEATURE:
<223> OTHER INFORMATION: G1792

<400> SEQUENCE: 1

```
aatccataga tctcttatta aataacagtg ctgaccaagc tcttacaaag caaaccaatc      60
tagaacacca aagttaatgg agagctcaaa caggagcagc aacaaccaat cacaagatga     120
caagcaagct cgtttccggg gagttcgaag aaggccttgg ggaaagtttg cagcagagat     180
tcgagacccg tcgagaaacg gtgcccgtct ttggctcggg acatttgaga ccgctgagga     240
ggcagcaagg gcttatgacc gagcagcctt aaccttaggg gtcatctcg  ctatactcaa     300
cttccctaat gagtattatc cacgtatgga cgactactcg cttcgccctc cttatgcttc     360
ttcttcttcg tcgtcgtcat cgggttcaac ttctactaat gtgagtcgac aaaaccaaag     420
agaagttttc gagtttgagt atttggacga taaggttctt gaagaacttc ttgattcaga     480
agaaaggaag agataatcac gattagtttt gttttgatat tttatgtggc actgttgtgg     540
ctacctacgt gcattatgtg catgtatagg tcgcttgatt agtactttat aacatgcatg     600
ccacgaccat aaattgtaag agaagacgta ctttgcgttt tcatgaaata tgaatgttag     660
atggtttgag tacaaaaaaa aaaaaaaaaa aaaaaa                              696
```

<210> SEQ ID NO 2
<211> LENGTH: 139
<212> TYPE: PRT
<213> ORGANISM: Arabidopsis thaliana
<220> FEATURE:
<223> OTHER INFORMATION: G1792 polypeptide

<400> SEQUENCE: 2

```
Met Glu Ser Ser Asn Arg Ser Asn Asn Gln Ser Gln Asp Asp Lys
  1               5                  10                  15

Gln Ala Arg Phe Arg Gly Val Arg Arg Arg Pro Trp Gly Lys Phe Ala
                 20                  25                  30

Ala Glu Ile Arg Asp Pro Ser Arg Asn Gly Ala Arg Leu Trp Leu Gly
             35                  40                  45

Thr Phe Glu Thr Ala Glu Glu Ala Arg Ala Tyr Asp Arg Ala Ala
         50                  55                  60

Phe Asn Leu Arg Gly His Leu Ala Ile Leu Asn Phe Pro Asn Glu Tyr
 65                  70                  75                  80

Tyr Pro Arg Met Asp Asp Tyr Ser Leu Arg Pro Pro Tyr Ala Ser Ser
                 85                  90                  95

Ser Ser Ser Ser Ser Gly Ser Thr Ser Thr Asn Val Ser Arg Gln
            100                 105                 110

Asn Gln Arg Glu Val Phe Glu Phe Glu Tyr Leu Asp Asp Lys Val Leu
        115                 120                 125

Glu Glu Leu Leu Asp Ser Glu Glu Arg Lys Arg
    130                 135
```

<210> SEQ ID NO 3
<211> LENGTH: 549
<212> TYPE: DNA

<213> ORGANISM: Arabidopsis thaliana
<220> FEATURE:
<223> OTHER INFORMATION: G1791

<400> SEQUENCE: 3

```
atgtacatgc aaaacaaaa accttaaaag ctttcatgga acgtatagag tcttataaca      60
cgaatgagat gaaatacaga ggcgtacgaa agcgtccatg gggaaaatat gcggcggaga    120
ttcgcgactc agctagacac ggtgctcgtg tttggcttgg acgtttaac  acagcggaag    180
acgcggctcg ggcttatgat agagcagctt tcggcatgag aggccaaagg gccattctca    240
attttcctca cgagtatcaa atgatgaagg acggtccaaa tggcagccac gagaatgcag    300
tggcttcctc gtcgtcggga tatagaggag aggtggtgg  tgatgatggg agggaagtta    360
ttgagttcga gtatttggat gatagtttat tggaggagct tttagattat ggtgagagat    420
ctaaccaaga caattgtaac gacgcaaacc gctagatcat cactacttac ttacagtgta    480
atgtttttgg agtaaagagt aataatcaat ataatatact ttagtttagg aaaaaaaaa    540
aaaaaaaaa                                                            549
```

<210> SEQ ID NO 4
<211> LENGTH: 139
<212> TYPE: PRT
<213> ORGANISM: Arabidopsis thaliana
<220> FEATURE:
<223> OTHER INFORMATION: G1791 polypeptide

<400> SEQUENCE: 4

```
Met Glu Arg Ile Glu Ser Tyr Asn Thr Asn Glu Met Lys Tyr Arg Gly
1               5                   10                  15
Val Arg Lys Arg Pro Trp Gly Lys Tyr Ala Ala Glu Ile Arg Asp Ser
            20                  25                  30
Ala Arg His Gly Ala Arg Val Trp Leu Gly Thr Phe Asn Thr Ala Glu
        35                  40                  45
Asp Ala Ala Arg Ala Tyr Asp Arg Ala Ala Phe Gly Met Arg Gly Gln
    50                  55                  60
Arg Ala Ile Leu Asn Phe Pro His Glu Tyr Gln Met Met Lys Asp Gly
65                  70                  75                  80
Pro Asn Gly Ser His Glu Asn Ala Val Ala Ser Ser Ser Gly Tyr
                85                  90                  95
Arg Gly Gly Gly Gly Asp Gly Arg Glu Val Ile Glu Phe Glu
            100                 105                 110
Tyr Leu Asp Asp Ser Leu Leu Glu Glu Leu Leu Asp Tyr Gly Glu Arg
        115                 120                 125
Ser Asn Gln Asp Asn Cys Asn Asp Ala Asn Arg
    130                 135
```

<210> SEQ ID NO 5
<211> LENGTH: 450
<212> TYPE: DNA
<213> ORGANISM: Arabidopsis thaliana
<220> FEATURE:
<223> OTHER INFORMATION: G1795

<400> SEQUENCE: 5

```
acaaacacgc aaaaagtcat taatatatgg atcaaggagg tcgaggtgtc ggtgccgagc     60
atggaaagta ccggggagtt cggagacgac cttggggaaa atatgcagca gagatacgag    120
attcgaggaa gcacggtgaa cgtgtgtggc ttggaacgtt cgatacggca gaggaagcgg    180
```

```
ctagagccta tgaccaagct gcttactcca tgagaggcca agcagcaatc cttaacttcc      240
ctcatgagta taacatgggg agtggtgtct cttcttccac cgccatggct ggatcttcct      300
ccgcctccgc ctccgcttct tcttcttcta ggcaagtttt tgaatttgag tacttggatg      360
atagtgtttt ggaggagctc cttgaggaag gagagaaacc taacaagggc aagaagaaat      420
gagcgagata taattcatga ttatttctaa                                       450

<210> SEQ ID NO 6
<211> LENGTH: 131
<212> TYPE: PRT
<213> ORGANISM: Arabidopsis thaliana
<220> FEATURE:
<223> OTHER INFORMATION: G1795 polypeptide

<400> SEQUENCE: 6

Met Asp Gln Gly Gly Arg Gly Val Gly Ala Glu His Gly Lys Tyr Arg
1               5                   10                  15

Gly Val Arg Arg Arg Pro Trp Gly Lys Tyr Ala Ala Glu Ile Arg Asp
            20                  25                  30

Ser Arg Lys His Gly Glu Arg Val Trp Leu Gly Thr Phe Asp Thr Ala
        35                  40                  45

Glu Glu Ala Ala Arg Ala Tyr Asp Gln Ala Ala Tyr Ser Met Arg Gly
    50                  55                  60

Gln Ala Ala Ile Leu Asn Phe Pro His Glu Tyr Asn Met Gly Ser Gly
65                  70                  75                  80

Val Ser Ser Ser Thr Ala Met Ala Gly Ser Ser Ala Ser Ala Ser
                85                  90                  95

Ala Ser Ser Ser Arg Gln Val Phe Glu Phe Glu Tyr Leu Asp Asp
            100                 105                 110

Ser Val Leu Glu Glu Leu Leu Glu Glu Gly Glu Lys Pro Asn Lys Gly
        115                 120                 125

Lys Lys Lys
    130

<210> SEQ ID NO 7
<211> LENGTH: 553
<212> TYPE: DNA
<213> ORGANISM: Arabidopsis thaliana
<220> FEATURE:
<223> OTHER INFORMATION: G30

<400> SEQUENCE: 7
ctcttctgac gcacaacagt atatacacat acacagatat atggatcaag gaggtcgtag       60
cagtggtagt ggaggaggag gagccgagca agggaagtac cgtggagtaa ggagacgacc      120
ttggggtaaa tacgccgcgg aaataagaga ttcgaggaag cacggagagc gtgtgtggct      180
agggacattc gacactgcgg aagacgcggc tcgagcctat gaccgagccg cctattcaat      240
gagaggcaaa gctgccattc tcaacttccc tcacgagtat aacatgggaa ccggatcctc      300
atccactgcg gctaattctt cttcctcgtc gcagcaagtt tttgagtttg agtacttgga      360
cgatagcgtt ttggatgaac ttcttgaata tggagagaac tataacaaga ctcataatat      420
caacatgggc aagaggcaat aaagggaata caatcggtat taactgaaag ttatgtgaaa      480
gaccattttc agttataaca aataaaataa atcccaagc gtacaaagct gtttctaaaa       540
aaaaaaaaaa aaa                                                         553

<210> SEQ ID NO 8
```

```
<211> LENGTH: 133
<212> TYPE: PRT
<213> ORGANISM: Arabidopsis thaliana
<220> FEATURE:
<223> OTHER INFORMATION: G30 polypeptide

<400> SEQUENCE: 8

Met Asp Gln Gly Gly Arg Ser Gly Ser Gly Gly Gly Ala Glu
1               5                   10                  15

Gln Gly Lys Tyr Arg Gly Val Arg Arg Pro Trp Gly Lys Tyr Ala
            20                  25                  30

Ala Glu Ile Arg Asp Ser Arg Lys His Gly Glu Arg Val Trp Leu Gly
        35                  40                  45

Thr Phe Asp Thr Ala Glu Asp Ala Ala Arg Ala Tyr Asp Arg Ala Ala
    50                  55                  60

Tyr Ser Met Arg Gly Lys Ala Ala Ile Leu Asn Phe Pro His Glu Tyr
65                  70                  75                  80

Asn Met Gly Thr Gly Ser Ser Ser Thr Ala Ala Asn Ser Ser Ser
                85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
        115                 120                 125

Met Gly Lys Arg Gln
    130

<210> SEQ ID NO 9
<211> LENGTH: 579
<212> TYPE: DNA
<213> ORGANISM: Oryza sativa
<220> FEATURE:
<223> OTHER INFORMATION: G3380

<400> SEQUENCE: 9
ggtccgatcc gtaacagtag tagctagtta atttgattat tgtccgtccg cggccggtca       60
gtggtcgcaa tcgatcgatc gatatcatgg acggcgacgg cggcggcgga tgggacgatc      120
agggcaacgg cggcggcgag acgaccaagt accgtggcgt gcgtcgccgg ccttctggca      180
agttcgcggc ggagatccgt gactccagca ggcagagctc ccgcgtctgg ctgggaacct      240
tcgacaccgc cgaggaggct gcgcgggctt acgaccgcgc cgcctacgcc atgcgcggcc      300
acctcgccgt cctcaacttc cctgctgagg cgcgcaacta cgtgcgggga tcaggctcgt      360
cgtcctcgtc ccgacagcat cagcagcggc aggtgatcga gctggagtgc ctagacgacc      420
aagtgctgca agagatgctc aagggtggcg acgatcagta caggtcagca gctgggagca      480
agaggaataa ctactagcta tatatgctgc taacctactt acaatcgcga tacatatcga      540
ggtttgggga tttcttctc acctgtgtgc agaggctgc                             579

<210> SEQ ID NO 10
<211> LENGTH: 136
<212> TYPE: PRT
<213> ORGANISM: Oryza sativa
<220> FEATURE:
<223> OTHER INFORMATION: G3380 polypeptide

<400> SEQUENCE: 10

Met Asp Gly Asp Gly Gly Gly Trp Asp Asp Gln Gly Asn Gly Gly
1               5                   10                  15

Gly Glu Thr Thr Lys Tyr Arg Gly Val Arg Arg Arg Pro Ser Gly Lys
```

-continued

```
                    20                  25                  30
Phe Ala Ala Glu Ile Arg Asp Ser Ser Arg Gln Ser Val Arg Val Trp
             35                  40                  45
Leu Gly Thr Phe Asp Thr Ala Glu Glu Ala Ala Arg Ala Tyr Asp Arg
         50                  55                  60
Ala Ala Tyr Ala Met Arg Gly His Leu Ala Val Leu Asn Phe Pro Ala
 65                  70                  75                  80
Glu Ala Arg Asn Tyr Val Arg Gly Ser Gly Ser Ser Ser Ser Ser Arg
                 85                  90                  95
Gln His Gln Gln Arg Gln Val Ile Glu Leu Cys Leu Asp Asp Gln
                100                 105                 110
Val Leu Gln Glu Met Leu Lys Gly Gly Asp Asp Gln Tyr Arg Ser Ala
             115                 120                 125
Ala Gly Ser Lys Arg Asn Asn Tyr
         130                 135
```

<210> SEQ ID NO 11
<211> LENGTH: 514
<212> TYPE: DNA
<213> ORGANISM: Oryza sativa
<220> FEATURE:
<223> OTHER INFORMATION: G3381

<400> SEQUENCE: 11

```
atcgatcatc tgctacgaac tcaccctata tatatatact ccatcttagg agctgcttga    60
tcgatcgaca tatatataac taatggatca tcatcatcag cagcagcagc aggagggtga   120
gctggtggcc aagtacaggg gcgtgcggcg gcggccgtgg ggcaaattcg cggcagagat   180
ccgcgactcg agccggcacg gcgtccgcgt gtggctgggc accttcgaca cagccgagga   240
ggccgctcgc gcctacgacc gctccgccta ctccatgcgc ggcgccaacg ccgtcctcaa   300
cttccccgcc gacgcccaca tctacgcccg tcaactacaa ataataacg ccgctgctgg   360
ctcttcatct tcctcttccg ccgccgccgc agcagccagg ccgccgccga tcgagttcga   420
gtacctcgat gaccacgtcc tgcaggagat gctccgagac cacaccacca acaagtagct   480
tactactcca ctatatatgc tgcctgctgc ttgt                               514
```

<210> SEQ ID NO 12
<211> LENGTH: 131
<212> TYPE: PRT
<213> ORGANISM: Oryza sativa
<220> FEATURE:
<223> OTHER INFORMATION: G3381 polypeptide
<400> SEQUENCE: 12

```
Met Asp His His His Gln Gln Gln Gln Glu Gly Glu Leu Val Ala
 1               5                  10                  15
Lys Tyr Arg Gly Val Arg Arg Arg Pro Trp Gly Lys Phe Ala Ala Glu
                 20                  25                  30
Ile Arg Asp Ser Ser Arg His Gly Val Arg Val Trp Leu Gly Thr Phe
             35                  40                  45
Asp Thr Ala Glu Glu Ala Ala Arg Ala Tyr Asp Arg Ser Ala Tyr Ser
         50                  55                  60
Met Arg Gly Ala Asn Ala Val Leu Asn Phe Pro Ala Asp Ala His Ile
 65                  70                  75                  80
Tyr Ala Arg Gln Leu His Asn Asn Ala Ala Gly Ser Ser Ser
                 85                  90                  95
```

```
Ser Ser Ser Ala Ala Ala Ala Ala Arg Pro Pro Ile Glu Phe
            100                 105                 110

Glu Tyr Leu Asp Asp His Val Leu Gln Glu Met Leu Arg Asp His Thr
            115                 120                 125

Thr Asn Lys
    130

<210> SEQ ID NO 13
<211> LENGTH: 375
<212> TYPE: DNA
<213> ORGANISM: Oryza sativa
<220> FEATURE:
<223> OTHER INFORMATION: G3383

<400> SEQUENCE: 13
atggaggaca accggagcaa ggacacggcg accaagtacc gcggcgtgag gaggcggccg      60
tggggcaagt tcgcggcgga gatccgcgac ccggagcgcg gcggggcgcg cgtctggctc     120
ggcaccttcg acaccgccga ggaggcggcg cgtgcctacg accgcgcggc ctacgcccag     180
cgcggcgccg ccgccgtgct caacttcccg gccgccgccg ccgccggcag gggtggagga     240
gccggcggcg ccgcttccgg gtcgtcgtcg tcgtcgtccg cgcagcgcgg caggggcgac     300
aagatcgagt cgagtacct cgacgacaag gtgctcgacg atctcctcga cgacgagaag     360
taccgtggta aatga                                                     375

<210> SEQ ID NO 14
<211> LENGTH: 124
<212> TYPE: PRT
<213> ORGANISM: Oryza sativa
<220> FEATURE:
<223> OTHER INFORMATION: G3383 polypeptide

<400> SEQUENCE: 14

Met Glu Asp Asn Arg Ser Lys Asp Thr Ala Thr Lys Tyr Arg Gly Val
1               5                   10                  15

Arg Arg Arg Pro Trp Gly Lys Phe Ala Ala Glu Ile Arg Asp Pro Glu
            20                  25                  30

Arg Gly Gly Ala Arg Val Trp Leu Gly Thr Phe Asp Thr Ala Glu Glu
        35                  40                  45

Ala Ala Arg Ala Tyr Asp Arg Ala Ala Tyr Ala Gln Arg Gly Ala Ala
    50                  55                  60

Ala Val Leu Asn Phe Pro Ala Ala Ala Ala Gly Arg Gly Gly Gly
65                  70                  75                  80

Ala Gly Gly Ala Ala Ser Gly Ser Ser Ser Ser Ser Ala Gln Arg
            85                  90                  95

Gly Arg Gly Asp Lys Ile Glu Phe Glu Tyr Leu Asp Asp Lys Val Leu
            100                 105                 110

Asp Asp Leu Leu Asp Asp Glu Lys Tyr Arg Gly Lys
        115                 120

<210> SEQ ID NO 15
<211> LENGTH: 466
<212> TYPE: DNA
<213> ORGANISM: Oryza sativa
<220> FEATURE:
<223> OTHER INFORMATION: G3515

<400> SEQUENCE: 15
gtgtgcgagc ggttgcgtcc gcatggagga cgacaagagt aaggagggga atcgtcgtc      60
```

```
gtcgtaccgc ggcgtgcgga agcggccgtg gggcaagttc gcggcggaga tccgcgaccc    120
ggagcgcggg ggagcccgcg tgtggctcgg cacgttcgac accgcggagg aggccgcgcg    180
ggcgtacgac cgcgccgcat tcgccatgaa gggcgccacg gccatgctca acttcccggg    240
agatcatcat cacggcgccg caagcaggat gaccagcacc ggctcttctt cgtcctcctt    300
caccacgcct cctccggcga actcctccgc ggcggcgggc cgcggcggct ccgatcggac    360
gacggacaag gtggagctgg agtgcctcga cgacaaggtc ctggaggacc tcctcgcgga    420
gaccaactat cgtgataaga actactagct agctagctac tatggc                   466

<210> SEQ ID NO 16
<211> LENGTH: 141
<212> TYPE: PRT
<213> ORGANISM: Oryza sativa
<220> FEATURE:
<223> OTHER INFORMATION: G3515 polypeptide

<400> SEQUENCE: 16

Met Glu Asp Asp Lys Ser Lys Glu Gly Lys Ser Ser Ser Tyr Arg
1               5                   10                  15

Gly Val Arg Lys Arg Pro Trp Gly Lys Phe Ala Ala Glu Ile Arg Asp
            20                  25                  30

Pro Glu Arg Gly Gly Ala Arg Val Trp Leu Gly Thr Phe Asp Thr Ala
        35                  40                  45

Glu Glu Ala Ala Arg Ala Tyr Asp Arg Ala Ala Phe Ala Met Lys Gly
    50                  55                  60

Ala Thr Ala Met Leu Asn Phe Pro Gly Asp His His Gly Ala Ala
65                  70                  75                  80

Ser Arg Met Thr Ser Thr Gly Ser Ser Ser Ser Phe Thr Thr Pro
                85                  90                  95

Pro Pro Ala Asn Ser Ser Ala Ala Ala Gly Arg Gly Gly Ser Asp Arg
            100                 105                 110

Thr Thr Asp Lys Val Glu Leu Glu Cys Leu Asp Asp Lys Val Leu Glu
        115                 120                 125

Asp Leu Leu Ala Glu Thr Asn Tyr Arg Asp Lys Asn Tyr
    130                 135                 140

<210> SEQ ID NO 17
<211> LENGTH: 393
<212> TYPE: DNA
<213> ORGANISM: Zea mays
<220> FEATURE:
<223> OTHER INFORMATION: G3516

<400> SEQUENCE: 17
atggaggacg acaagaagga gggcaagtac cgcggcgtgc ggaagcggcc gtggggcaag     60
ttcgccgcgg agatccggga cccggagcgc ggcggctccc cgtctggct cggcaccttc    120 gacaccgccg aggaggccgc cagggcctac gaccgcgccg cattcgccat gaagggcgcc    180
acggccgtgc tcaacttccc cgccagcgga ggatcgtcag ctggcgcggc tcccggcggc    240
cggaccagcg gcggctcctc ctcgtccacc acgtcggctc cggccagcag ggggagggcc    300
cgtgttcccg actcggagaa ggtggagctg gagtgcctcg acgacagggt cttggaagag    360
ctgctcgcgg aagacaagta caacaagaac taa                                 393

<210> SEQ ID NO 18
<211> LENGTH: 130
<212> TYPE: PRT
```

<213> ORGANISM: Zea mays
<220> FEATURE:
<223> OTHER INFORMATION: G3516 polypeptide

<400> SEQUENCE: 18

```
Met Glu Asp Asp Lys Lys Glu Gly Lys Tyr Arg Gly Val Arg Lys Arg
1               5                   10                  15

Pro Trp Gly Lys Phe Ala Ala Glu Ile Arg Asp Pro Glu Arg Gly Gly
            20                  25                  30

Ser Arg Val Trp Leu Gly Thr Phe Asp Thr Ala Glu Glu Ala Ala Arg
        35                  40                  45

Ala Tyr Asp Arg Ala Ala Phe Ala Met Lys Gly Ala Thr Ala Val Leu
    50                  55                  60

Asn Phe Pro Ala Ser Gly Gly Ser Ser Ala Gly Ala Ala Pro Gly Gly
65                  70                  75                  80

Arg Thr Ser Gly Gly Ser Ser Ser Thr Thr Ser Ala Pro Ala Ser
                85                  90                  95

Arg Gly Arg Ala Arg Val Pro Asp Ser Glu Lys Val Glu Leu Glu Cys
            100                 105                 110

Leu Asp Asp Arg Val Leu Glu Glu Leu Leu Ala Glu Asp Lys Tyr Asn
            115                 120                 125

Lys Asn
    130
```

<210> SEQ ID NO 19
<211> LENGTH: 477
<212> TYPE: DNA
<213> ORGANISM: Zea mays
<220> FEATURE:
<223> OTHER INFORMATION: G3517

<400> SEQUENCE: 19

```
tacgtccgat ccacagccat catcgccacc cgcgcgctta tggatggcga gtggtccaag      60
gacggcggag gcggcgagcc gaccaagtac cgcggcgtgc ggcgtcggcc ctggggcaag     120
tacgcggcgg agatccgcga ctcgagccgg cacggcgtcc gcatctggct cggcacgttc     180
gacaccgccg aggaggccgc cagggcgtac gaccgctccg ccaactccat gcgcggcgcc     240
aacgccgtgc tcaacttccc ggaggacgcg cccgcctacg ccgccgccgc ctcccgtggc     300
tccgccggcg gatcctcgtc cagaccggcg ggctccggcc gggacgtgat cgagtttgag     360
tacctcgacg acgaggtgct gcaggagatg ctcaggagcc aggagccgtc ggcggcggcg     420
gcgcagaaga agaagtagcg cgagcgccac aggtggcgaa acggccgctt ttccaaa       477
```

<210> SEQ ID NO 20
<211> LENGTH: 132
<212> TYPE: PRT
<213> ORGANISM: Zea mays
<220> FEATURE:
<223> OTHER INFORMATION: G3517 polypeptide

<400> SEQUENCE: 20

```
Met Asp Gly Glu Trp Ser Lys Asp Gly Gly Gly Glu Pro Thr Lys
1               5                   10                  15

Tyr Arg Gly Val Arg Arg Arg Pro Trp Gly Lys Tyr Ala Ala Glu Ile
            20                  25                  30

Arg Asp Ser Ser Arg His Gly Val Arg Ile Trp Leu Gly Thr Phe Asp
        35                  40                  45

Thr Ala Glu Glu Ala Ala Arg Ala Tyr Asp Arg Ser Ala Asn Ser Met
```

```
              50                  55                  60
Arg Gly Ala Asn Ala Val Leu Asn Phe Pro Glu Asp Ala Pro Ala Tyr
 65                  70                  75                  80

Ala Ala Ala Ala Ser Arg Gly Ser Ala Gly Gly Ser Ser Ser Arg Pro
                 85                  90                  95

Ala Gly Ser Gly Arg Asp Val Ile Glu Phe Glu Tyr Leu Asp Asp Glu
                100                 105                 110

Val Leu Gln Glu Met Leu Arg Ser Gln Glu Pro Ser Ala Ala Ala Ala
                115                 120                 125

Gln Lys Lys Lys
    130

<210> SEQ ID NO 21
<211> LENGTH: 717
<212> TYPE: DNA
<213> ORGANISM: Glycine max
<220> FEATURE:
<223> OTHER INFORMATION: G3518

<400> SEQUENCE: 21
ctaacacaca taacaataac ttagcaacat tttttccttc cttctttctt tctttctata     60 cttttttgttg ttaattctaa gttctaagag aagaaaaatg gagggtggaa gatcatcagt    120
ttcaaatggg aatgttgagg ttcgttatag agggattaga agaaggccat ggggaaagtt    180
tgcagcagag attcgtgacc ctacaaggaa aggaacaagg atatggcttg gaacatttga    240
cactgctgaa caagctgcac gagcttatga tgctgctgct tttcattttc gtggccacag    300
agcaattctc aacttcccaa atgagtatca atctcataat ccaaactctt ctttgcctat    360
gcctctagct gtgtcagctc ctccttctta ttcttcttct tcttccactt ctaattattc    420
cggtgatgat aataataacc accttgtgag accagctttt tctggagaaa taatgcaagg    480
tggtgatcat gatgatgata cttttgagtt ggagtacttc gataataagt tgctcgagga    540
actccttcag atgcaagata acagacactt ctaaaagtaa aatataacac aagccagcta    600
tgttgtgtta gtcactggca tgaaataaaa tgcaagaaaa tattgttgat tttatttaat    660
atattttgtt tgatttttttt tttttttttt gtagctgatc aaagttcttc gaaatga       717

<210> SEQ ID NO 22
<211> LENGTH: 158
<212> TYPE: PRT
<213> ORGANISM: Glycine max
<220> FEATURE:
<223> OTHER INFORMATION: G3518 polypeptide

<400> SEQUENCE: 22

Met Glu Gly Gly Arg Ser Ser Val Ser Asn Gly Asn Val Glu Val Arg
  1               5                  10                  15

Tyr Arg Gly Ile Arg Arg Arg Pro Trp Gly Lys Phe Ala Ala Glu Ile
                 20                  25                  30

Arg Asp Pro Thr Arg Lys Gly Thr Arg Ile Trp Leu Gly Thr Phe Asp
             35                  40                  45

Thr Ala Glu Gln Ala Ala Arg Ala Tyr Asp Ala Ala Ala Phe His Phe
     50                  55                  60

Arg Gly His Arg Ala Ile Leu Asn Phe Pro Asn Glu Tyr Gln Ser His
 65                  70                  75                  80

Asn Pro Asn Ser Ser Leu Pro Met Pro Leu Ala Val Ser Ala Pro Pro
                 85                  90                  95
```

```
Ser Tyr Ser Ser Ser Ser Thr Ser Asn Tyr Ser Gly Asp Asp Asn
            100                 105                 110

Asn Asn His Leu Val Arg Pro Ala Phe Ser Gly Glu Ile Met Gln Gly
        115                 120                 125

Gly Asp His Asp Asp Asp Thr Phe Glu Leu Glu Tyr Phe Asp Asn Lys
    130                 135                 140

Leu Leu Glu Glu Leu Leu Gln Met Gln Asp Asn Arg His Phe
145                 150                 155

<210> SEQ ID NO 23
<211> LENGTH: 609
<212> TYPE: DNA
<213> ORGANISM: Glycine max
<220> FEATURE:
<223> OTHER INFORMATION: G3519

<400> SEQUENCE: 23
tttctttctt tctatacttt ttgtggttct gattattaag ttctaagaga ataacaatgg     60
agggtggaag atcatctgtt tcaaatggga attgtgaggt tcggtataga gggattagaa    120
gaaggccatg gggcaagttt gcagcagaga ttcgtgaccc tacgaggaaa gggacaagga    180
tatggcttgg aacatttgac actgcggaac aagctgctcg agcttatgat gctgctgctt    240
ttcattttcg tggtcataga gcaattctca acttcccaaa tgagtaccaa tctcataatc    300
caaactcttc tttgcctatg cctctaattg tgcctcctcc ttcttattct tcttctttca    360
cttctaatta ttctgctgat gataataacc accttgtgag acctggagaa ataatgcaag    420
gtggtgatct tgatgacact tttgagttgg agtacttgga taataagttg ctcgaggaac    480
tccttcagat gcaagataac agacacttct aaaagtaaaa tataacacaa gccagctatg    540
ttgtgttagt cactggcatg aaataaaatg caaagaaata ttgttgattt tatttaatat    600
attttgttt                                                            609

<210> SEQ ID NO 24
<211> LENGTH: 151
<212> TYPE: PRT
<213> ORGANISM: Glycine max
<220> FEATURE:
<223> OTHER INFORMATION: G3519 polypeptide

<400> SEQUENCE: 24

Met Glu Gly Gly Arg Ser Ser Val Ser Asn Gly Asn Cys Glu Val Arg
1               5                   10                  15

Tyr Arg Gly Ile Arg Arg Arg Pro Trp Gly Lys Phe Ala Ala Glu Ile
            20                  25                  30

Arg Asp Pro Thr Arg Lys Gly Thr Arg Ile Trp Leu Gly Thr Phe Asp
        35                  40                  45

Thr Ala Glu Gln Ala Ala Arg Ala Tyr Asp Ala Ala Phe His Phe
    50                  55                  60

Arg Gly His Arg Ala Ile Leu Asn Phe Pro Asn Glu Tyr Gln Ser His
65                  70                  75                  80

Asn Pro Asn Ser Ser Leu Pro Met Pro Leu Ile Val Pro Pro Pro Ser
                85                  90                  95

Tyr Ser Ser Ser Phe Thr Ser Asn Tyr Ser Ala Asp Asp Asn Asn His
            100                 105                 110

Leu Val Arg Pro Gly Glu Ile Met Gln Gly Gly Asp Leu Asp Asp Thr
        115                 120                 125

Phe Glu Leu Glu Tyr Leu Asp Asn Lys Leu Leu Glu Glu Leu Leu Gln
```

```
                   130                 135                 140
Met Gln Asp Asn Arg His Phe
145                 150

<210> SEQ ID NO 25
<211> LENGTH: 440
<212> TYPE: DNA
<213> ORGANISM: Glycine max
<220> FEATURE:
<223> OTHER INFORMATION: G3520

<400> SEQUENCE: 25
aaggcacaca atgaagagg agtcaaagga gaaaagaag gacactaagg aggaaccacg      60 ttatagaga gtgcggcggc ggccgtgggg gaagttcgcg gccgagattc gggacccggc    120
ccggcacggt gcccgagtgt ggctggggac atttctcacg gcggaggagg ctgctagggc    180
ttatgaccga gctgcctatg agatgagggg cgctttagcc gttctcaatt ttccaaatga    240
gtatccttca tgctcttcta tgaactcatc ttcaacatta gcaccttcat cttcttcttc    300
aaattcaatg cttaaaagtg atcatggtaa acaagttatt gagttcgagt gcttggatga    360
caaattgtta gaggaccttc ttgattgtga tgactatgcc tacgagaaag acttgcctaa    420
gaactgaacg gtttgatcaa                                                440

<210> SEQ ID NO 26
<211> LENGTH: 138
<212> TYPE: PRT
<213> ORGANISM: Glycine max
<220> FEATURE:
<223> OTHER INFORMATION: G3520 polypeptide

<400> SEQUENCE: 26

Met Glu Glu Glu Ser Lys Glu Lys Lys Asp Thr Lys Glu Glu Pro
1               5                   10                  15

Arg Tyr Arg Gly Val Arg Arg Pro Trp Gly Lys Phe Ala Ala Glu
                20                  25                  30

Ile Arg Asp Pro Ala Arg His Gly Ala Arg Val Trp Leu Gly Thr Phe
            35                  40                  45

Leu Thr Ala Glu Glu Ala Ala Arg Ala Tyr Asp Arg Ala Ala Tyr Glu
        50                  55                  60

Met Arg Gly Ala Leu Ala Val Leu Asn Phe Pro Asn Glu Tyr Pro Ser
65                  70                  75                  80

Cys Ser Ser Met Asn Ser Ser Ser Thr Leu Ala Pro Ser Ser Ser Ser
                85                  90                  95

Ser Asn Ser Met Leu Lys Ser Asp His Gly Lys Gln Val Ile Glu Phe
                100                 105                 110

Glu Cys Leu Asp Asp Lys Leu Leu Glu Asp Leu Leu Asp Cys Asp Asp
            115                 120                 125

Tyr Ala Tyr Glu Lys Asp Leu Pro Lys Asn
        130                 135

<210> SEQ ID NO 27
<211> LENGTH: 653
<212> TYPE: DNA
<213> ORGANISM: Medicago truncatula
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
```

```
<222> LOCATION: (610)..(610)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<223> OTHER INFORMATION: G3735

<400> SEQUENCE: 27
ctaatccttc atactaaaga aaacatagac ttataacaaa atatattatta tttacttcgt      60 atatttttgt gtttcaaatt aatggaggga gatcataaat tagtttcaaa ttcaacaaat     120
ggaaatggaa atggaaatgg aaattcagat caaataaagt atagaggaat tcgtagaaga     180
ccatggggaa aatttgcagc agaaattcgt gacccaacaa ggaaagggac aagaatatgg     240
cttggaacat ttgatactgc tgaacaagct gcaagagctt atgatgctgc tgcttttcat     300
tttcgtggtc atagagctat tctcaatttc cctaatgaat atcaagctcc taattcatct     360
tcttcattac ctatgcctct tactatgcct ccaccacctt cttctaatcc acctccttct     420
tcttcttctt cttcctcttt ttcttcttac accgttgatg atggttttga tgagcttgaa     480
ttcttggata taagttgct tcaagaactt cttcaagatg aaacacaata gttaactatt     540
gaagatcaag tggcatgaaa tgtattggtg gtcatttaat tttctcttca ttaatttatt     600
ttggnttggn tatgnatctc atttntatga ataaatgaga atggggnatt ana            653

<210> SEQ ID NO 28
<211> LENGTH: 149
<212> TYPE: PRT
<213> ORGANISM: Medicago truncatula
<220> FEATURE:
<223> OTHER INFORMATION: G3735 polypeptide

<400> SEQUENCE: 28

Met Glu Gly Asp His Lys Leu Val Ser Asn Ser Thr Asn Gly Asn Gly
1               5                   10                  15

Asn Gly Asn Gly Asn Ser Asp Gln Ile Lys Tyr Arg Gly Ile Arg Arg
            20                  25                  30

Arg Pro Trp Gly Lys Phe Ala Ala Glu Ile Arg Asp Pro Thr Arg Lys
        35                  40                  45

Gly Thr Arg Ile Trp Leu Gly Thr Phe Asp Thr Ala Glu Gln Ala Ala
    50                  55                  60

Arg Ala Tyr Asp Ala Ala Ala Phe His Phe Arg Gly His Arg Ala Ile
65                  70                  75                  80

Leu Asn Phe Pro Asn Glu Tyr Gln Ala Pro Asn Ser Ser Ser Ser Leu
                85                  90                  95

Pro Met Pro Leu Thr Met Pro Pro Pro Ser Ser Asn Pro Pro
            100                 105                 110

Ser Ser Ser Ser Ser Ser Ser Phe Ser Ser Tyr Thr Val Asp Asp Gly
        115                 120                 125
```

Phe Asp Glu Leu Glu Phe Leu Asp Asn Lys Leu Leu Gln Glu Leu Leu
130                 135                 140

Gln Asp Gly Thr Gln
145

<210> SEQ ID NO 29
<211> LENGTH: 859
<212> TYPE: DNA
<213> ORGANISM: Triticum aestivum
<220> FEATURE:
<223> OTHER INFORMATION: G3736

<400> SEQUENCE: 29

| | | | | | |
|---|---|---|---|---|---|
| gcacgaggct | tcattctccc | tcgttccatc | caagctccac | catccatcac | tgatttgcac | 60 |
| ttacctagct | actccgcaac | ccccacttcc | ggcttcttca | tttctcacta | ctagtacgta | 120 |
| gttgagatta | tggagggcgg | agaaggatcc | ggtggcggcg | gcgagccgac | caagtaccgc | 180 |
| ggggtgcgcc | gcaggccgtg | gggcaagttc | gccgcggaga | tccgggactc | gagccggcac | 240 |
| ggcgtgcgca | tgtggctcgg | caccttcgac | accgccgagg | aggccgcggc | cgcctacgac | 300 |
| cgctccgcct | actccatgcg | cggccgcaac | gccgtgctca | acttccccga | ccgggcgcac | 360 |
| gtctacgagg | ccgaggccag | gcgccagggc | cagggctctt | cgtcgtcggc | gaggcagcag | 420 |
| aatcagcagc | agcagcaggg | gcagagcggg | gtgatcgagt | tcgagtacct | ggacgacgac | 480 |
| gtgctgcagt | ccatgctcca | cgaccacgac | aaatccaaca | gtagatcga | tggatcatcc | 540 |
| atccatccat | ccatggatcg | atccataata | cctactgtat | catcccggcc | cggccggcaa | 600 |
| catcgacctg | cgtgcatgcg | cgggcgcgga | tgcaatctac | actacctacc | tatgcattcc | 660 |
| ggccatatat | taggtacgta | gattatatgt | gtacgagagc | ctacgagctc | gatgaagatc | 720 |
| gtacgtggtg | cattctgatg | catgaggatt | ccatcgacac | gaccctctac | catatatttg | 780 |
| atgggtcgat | cgagtaattt | gcagccagta | atccaatcga | tgatatgggg | ttttcaaaaa | 840 |
| aaaaaaaaaa | aaaaaaaaa | | | | | 859 |

<210> SEQ ID NO 30
<211> LENGTH: 131
<212> TYPE: PRT
<213> ORGANISM: Triticum aestivum
<220> FEATURE:
<223> OTHER INFORMATION: G3736 polypeptide

<400> SEQUENCE: 30

Met Glu Gly Gly Glu Gly Ser Gly Gly Gly Glu Pro Thr Lys Tyr
1               5                   10                  15

Arg Gly Val Arg Arg Pro Trp Gly Lys Phe Ala Ala Glu Ile Arg
                20                  25                  30

Asp Ser Ser Arg His Gly Val Arg Met Trp Leu Gly Thr Phe Asp Thr
            35                  40                  45

Ala Glu Glu Ala Ala Ala Tyr Asp Arg Ser Ala Tyr Ser Met Arg
        50                  55                  60

Gly Arg Asn Ala Val Leu Asn Phe Pro Asp Arg Ala His Val Tyr Glu
65                  70                  75                  80

Ala Glu Ala Arg Arg Gln Gly Gln Gly Ser Ser Ser Ala Arg Gln
                85                  90                  95

Gln Asn Gln Gln Gln Gln Gly Gln Ser Gly Val Ile Glu Phe Glu
            100                 105                 110

Tyr Leu Asp Asp Asp Val Leu Gln Ser Met Leu His Asp His Asp Lys
            115                 120                 125

Ser Asn Lys
    130

<210> SEQ ID NO 31
<211> LENGTH: 882
<212> TYPE: DNA
<213> ORGANISM: Oryza sativa
<220> FEATURE:
<223> OTHER INFORMATION: G3737

<400> SEQUENCE: 31

```
acacatgcat cgatcattca tggatgccga attgccgcga tccgggcatt atttcgcgcc        60
aggagaccca agatcatcgt gtcgcccacg ctataaatag ctagctagct tgcctttatg       120
ttgcatatgc caactgctac atgcaggacg tctgaaacta tcattagtga cctgcagcgc       180
ctgcagtata tatatacaag tagtagtgag catggaggac gacaagaagg aggcggcgag       240
caagtaccgc ggcgtacgga ggcggccgtg gggcaaattc gcggcggaga tccgcgaccc       300
ggagcgcggc ggctcacgcg tctggcttgg cacgttcgac accgccgagg aggccgcgcg       360
agcgtacgac cgcgccgcat cgccatgaa gggcgctatg ccgtgctca acttcccagg         420
caggacgagc agcaccggct cttcgtcgtc atcgtcatcc acgccgccag ctccggtgac       480
gacgagccgc cactgcgccg acacgacgga aaggtggag cttgtgtacc ttgacgacaa        540
ggtgctcgac gagctccttg cggaggacta cagctaccgc aacaacaaca actactgatc       600
cggccgtcga tgaactgaga cggatcgaca tggggccggt cgtcggtacg ctcgctgaaa       660
cgagacccgg attgctatca ataagcaagc agaagaaaac cgtctcctat atatagcttc       720
ttctgttggc acaagcatat atgggcatgc atgacacatg ctactgtgaa ttgacgggtg       780
tgtgctgtgt gcagactact aaaccacgct tgcaagttgc acgtacgacg tggttgtcaa       840
gagcatgcag tccacgaagc agagaaaaac acctggttta tc                          882
```

<210> SEQ ID NO 32
<211> LENGTH: 128
<212> TYPE: PRT
<213> ORGANISM: Oryza sativa
<220> FEATURE:
<223> OTHER INFORMATION: G3737 polypeptide

<400> SEQUENCE: 32

Met Glu Asp Asp Lys Lys Glu Ala Ala Ser Lys Tyr Arg Gly Val Arg
1               5                   10                  15

Arg Arg Pro Trp Gly Lys Phe Ala Ala Glu Ile Arg Asp Pro Glu Arg
            20                  25                  30

Gly Gly Ser Arg Val Trp Leu Gly Thr Phe Asp Thr Ala Glu Glu Ala
        35                  40                  45

Ala Arg Ala Tyr Asp Arg Ala Ala Phe Ala Met Lys Gly Ala Met Ala
    50                  55                  60

Val Leu Asn Phe Pro Gly Arg Thr Ser Ser Thr Gly Ser Ser Ser Ser
65                  70                  75                  80

Ser Ser Ser Thr Pro Pro Ala Pro Val Thr Thr Ser Arg His Cys Ala
                85                  90                  95

Asp Thr Thr Glu Lys Val Glu Leu Val Tyr Leu Asp Asp Lys Val Leu
            100                 105                 110

Asp Glu Leu Leu Ala Glu Asp Tyr Ser Tyr Arg Asn Asn Asn Asn Tyr
        115                 120                 125

<210> SEQ ID NO 33
<211> LENGTH: 899
<212> TYPE: DNA
<213> ORGANISM: Zea mays
<220> FEATURE:
<223> OTHER INFORMATION: G3739

<400> SEQUENCE: 33

```
cgatataatt cactcctctc aacgctcgct gcacacacac accagtgaac ctagccagcc      60
atttgccgca tcgatcatca gtcgctgtca cgcgcgccaa accaaaccaa agcccaaacc     120
cagctgcaag tgctactgac agcagctagc aaacacacac ccgtcgccat cgctatggac     180
ggcgactggt ccaaggacgg cggaggtgga gagccgacca aatatcgcgg cgtgcggcgg     240
cggccctggg gcaagtacgc ggccgagatc cgcgactcga gccgccacgg cgtccgcatc     300
tggctgggca ccttcgacac cgccgaggag gccgccaggg cgtacgaccg gagcgcctac     360
tccatgcgcg cgccaacgc cgtcctcaac ttcccggagg acgcgcacgc ctacgccgcc     420
gcctgccgcg gctccggatc ctcctcatcc tcgtccaggc ataggcagca gcagcagcag     480
ggctccggca gggacgtgat cgagctcgag tacctcgacg acgaggtgct gcaggagatg     540
ctcaggaacc acgagccgtc gtcgtctgcg aggaagaaga tgtaatgcaa gacgactggt     600
acacgtggcg aatgcacgtt gcacatcaga atgccatgta tgcgtggggg gttacgttca     660
attgtatgca tgcagtgcag tgactaccgg ccggctctcc tggatatgtc ggccatctct     720
ctctatatat tattaaaatg tcagctccct tctctaattt ggcgggagtt acatcagtgg     780
tactatgcag agttgcatac ttgcatatat atgcacatta ttaattaata actcgatctc     840
tcgtggacgg tggaacagtg ataatcatct cattgtcaat taattttgat caaagaaat      899
```

<210> SEQ ID NO 34
<211> LENGTH: 136
<212> TYPE: PRT
<213> ORGANISM: Zea mays
<220> FEATURE:
<223> OTHER INFORMATION: G3739 polypeptide

<400> SEQUENCE: 34

```
Met Asp Gly Asp Trp Ser Lys Asp Gly Gly Gly Glu Pro Thr Lys
1               5                   10                  15

Tyr Arg Gly Val Arg Arg Pro Trp Gly Lys Tyr Ala Ala Glu Ile
            20                  25                  30

Arg Asp Ser Ser Arg His Gly Val Arg Ile Trp Leu Gly Thr Phe Asp
        35                  40                  45

Thr Ala Glu Glu Ala Ala Arg Ala Tyr Asp Arg Ser Ala Tyr Ser Met
    50                  55                  60

Arg Gly Ala Asn Ala Val Leu Asn Phe Pro Glu Asp Ala His Ala Tyr
65                  70                  75                  80

Ala Ala Ala Cys Arg Gly Ser Gly Ser Ser Ser Ser Ser Arg His
                85                  90                  95

Arg Gln Gln Gln Gln Gly Ser Gly Arg Asp Val Ile Glu Leu Glu
            100                 105                 110

Tyr Leu Asp Asp Glu Val Leu Gln Glu Met Leu Arg Asn His Glu Pro
        115                 120                 125

Ser Ser Ser Ala Arg Lys Lys Met
    130                 135
```

<210> SEQ ID NO 35
<211> LENGTH: 918

<212> TYPE: DNA
<213> ORGANISM: Zea mays
<220> FEATURE:
<223> OTHER INFORMATION: G3794

<400> SEQUENCE: 35

```
attacttgtg cacttgggtg cagtgcctgc agtataatca agttagggtt taaaagaacc      60
tcgaccgcga tcgtatatag atccagatta tcattagtta ttagaccact gtgatatcga     120
tggacgacgg cggcgagcca accaagtacc gcggcgtgcg gcgccggccg tcggggaagt     180
tcgccgccga gatccgcgac tccagccggc agagcgtgcg catgtggctg ggcaccttcg     240
acacggccga ggaggccgca agggcgtacg accgcgcggc ctacgccatg cgcggccaaa     300
tcgccgtgct caacttcccc gccgaggcgc gcaactacgt gcgcgcgggg tcgtcgtcgt     360
cccgccagca gcagcaggga ggaggaggag gaggaggaag tggcggcggc gccggtcagc     420
aggtgatcga gctggagtgc ctggacgatc aggtgctgca ggagatgctc aagggcggcg     480
acgggaaaaa atagttgtta gcgtatctga tcacaggtgc acgtgttgaa actgattatg     540
accaggcgat cgatcccatc ttgtgcatgc ggcctgccaa agttgctggg tcttctcatc     600
gacctatata tatgcttc tcgatccata tatatcat aaatgcatgc agggtgcatg        660
catgtaccaa gtttggaatt ataatgctct tggtgctgaa ttgaagtata ctagtatata     720
tagtgtgatc catgtattga aaaggttgtt ttgcttaatc gcgtcatgat tgcacacgtg     780
cttgtttctg cttaaacaac ccatatatat agccggctct ggcctttgtc aagtctgcaa     840
tccttataca tcgttggtaa ttcatgcatg agttctatgt aactgcaatt tagataaatt     900
gtagctaata taatagtc                                                   918
```

<210> SEQ ID NO 36
<211> LENGTH: 124
<212> TYPE: PRT
<213> ORGANISM: Zea mays
<220> FEATURE:
<223> OTHER INFORMATION: G3794 polypeptide

<400> SEQUENCE: 36

```
Met Asp Asp Gly Gly Glu Pro Thr Lys Tyr Arg Gly Val Arg Arg Arg
1               5                   10                  15

Pro Ser Gly Lys Phe Ala Ala Glu Ile Arg Asp Ser Ser Arg Gln Ser
            20                  25                  30

Val Arg Met Trp Leu Gly Thr Phe Asp Thr Ala Glu Glu Ala Ala Arg
        35                  40                  45

Ala Tyr Asp Arg Ala Ala Tyr Ala Met Arg Gly Gln Ile Ala Val Leu
    50                  55                  60

Asn Phe Pro Ala Glu Ala Arg Asn Tyr Val Arg Gly Gly Ser Ser Ser
65                  70                  75                  80

Ser Arg Gln Gln Gln Gln Gly Gly Gly Gly Gly Gly Ser Gly Gly
            85                  90                  95

Gly Ala Gly Gln Gln Val Ile Glu Leu Glu Cys Leu Asp Asp Gln Val
            100                 105                 110

Leu Gln Glu Met Leu Lys Gly Gly Asp Gly Lys Lys
            115                 120
```

<210> SEQ ID NO 37
<211> LENGTH: 859
<212> TYPE: DNA
<213> ORGANISM: Arabidopsis thaliana
<220> FEATURE:

<223> OTHER INFORMATION: G1266

<400> SEQUENCE: 37

```
caatccacta acgatcccta accgaaaaca gagtagtcaa gaaacagagt attttttcta      60
catggatcca tttttaattc agtccccatt ctccggcttc tcaccggaat attctatcgg     120
atcttctcca gattctttct catcctcttc ttctaacaat tactctcttc ccttcaacga     180
gaacgactca gaggaaatgt ttctctacgg tctaatcgag cagtccacgc aacaaaccta     240
tattgactcg gatagtcaag accttccgat caaatccgta agctcaagaa agtcagagaa     300
gtcttacaga ggcgtaagac gacggccatg ggggaaattc gcggcggaga taagagattc     360
gactagaaac ggtattaggg tttggctcgg gacgttcgaa agcgcggaag aggcggcttt     420
agcctacgat caagctgctt tctcgatgag agggtcctcg gcgattctca attttttcggc     480
ggagagagtt caagagtcgc tttcggagat taaatatacc tacgaggatg gttgttctcc     540
ggttgtggcg ttgaagagga aacactcgat gagacggaga atgaccaata agaagacgaa     600
agatagtgac tttgatcacc gctccgtgaa gttagataat gtagttgtct ttgaggattt     660
gggagaacag taccttgagg agcttttggg gtcttctgaa aatagtggga cttggtgaaa     720
gattaggatt tgtattaggg accttaagtt tgaagtggtt gattaatttt aaccctaata     780
tgttttttgt ttgcttaaat atttgattct attgagaaac atcgaaaaca gtttgtatgt     840
acttttgtga tacttggcg                                                  859
```

<210> SEQ ID NO 38
<211> LENGTH: 218
<212> TYPE: PRT
<213> ORGANISM: Arabidopsis thaliana
<220> FEATURE:
<223> OTHER INFORMATION: G1266 polypeptide

<400> SEQUENCE: 38

```
Met Asp Pro Phe Leu Ile Gln Ser Pro Phe Ser Gly Phe Ser Pro Glu
1               5                   10                  15

Tyr Ser Ile Gly Ser Ser Pro Asp Ser Phe Ser Ser Ser Ser Ser Asn
            20                  25                  30

Asn Tyr Ser Leu Pro Phe Asn Glu Asn Asp Ser Glu Glu Met Phe Leu
        35                  40                  45

Tyr Gly Leu Ile Glu Gln Ser Thr Gln Gln Thr Tyr Ile Asp Ser Asp
    50                  55                  60

Ser Gln Asp Leu Pro Ile Lys Ser Val Ser Ser Arg Lys Ser Glu Lys
65                  70                  75                  80

Ser Tyr Arg Gly Val Arg Arg Pro Trp Gly Lys Phe Ala Ala Glu
                85                  90                  95

Ile Arg Asp Ser Thr Arg Asn Gly Ile Arg Val Trp Leu Gly Thr Phe
            100                 105                 110

Glu Ser Ala Glu Glu Ala Ala Leu Ala Tyr Asp Gln Ala Ala Phe Ser
        115                 120                 125

Met Arg Gly Ser Ser Ala Ile Leu Asn Phe Ser Ala Glu Arg Val Gln
    130                 135                 140

Glu Ser Leu Ser Glu Ile Lys Tyr Thr Tyr Glu Asp Gly Cys Ser Pro
145                 150                 155                 160

Val Val Ala Leu Lys Arg Lys His Ser Met Arg Arg Met Thr Asn
                165                 170                 175

Lys Lys Thr Lys Asp Ser Asp Phe Asp His Arg Ser Val Lys Leu Asp
            180                 185                 190
```

-continued

```
Asn Val Val Val Phe Glu Asp Leu Gly Glu Gln Tyr Leu Glu Glu Leu
        195                 200                 205

Leu Gly Ser Ser Glu Asn Ser Gly Thr Trp
    210                 215

<210> SEQ ID NO 39
<211> LENGTH: 1262
<212> TYPE: DNA
<213> ORGANISM: Arabidopsis thaliana
<220> FEATURE:
<223> OTHER INFORMATION: G45

<400> SEQUENCE: 39
attaatactc tgcatctagt ccttttcaag agtacacaat ctgcactttt ttaatgaaaa     60
tagtacacaa tctttatact tcaaactgag gtaacattat taaattaatt tattgaagtt    120
gacttaagat gatctattca cataatggta cgtgtgtgtg tgtatacaca gaaaacccct    180
gattttatgt ggaacctaaa accctccatg aaatgcggtc agtaccttag aacacaagtt    240
tcaccaactg tacttcccaa ttatcctgcc gcagattcaa caatggcttt tggcaatatc    300
caagaactag acggcgagat cctaaagaac gtttgggcga attacatcgg aacaccacaa    360
accgatacaa gatcaattca agttccagaa gtttctagaa cttgggaagc gttgcctacc    420
cttgatgaca taccagaagg ttctagagaa atgcttcaaa gcctagatat gtcgacggag    480
gaccaggaat ggacagagat tctcgatgct attgcttctt tcccaaacaa aaccaatcat    540
gatccattaa ccaaccctac cattgattca tgttctttgt cttctcgggt ttcttgcaaa    600
acaagaaaat acaggggagt acggaagcgt ccgtggggga aatttgcagc cgaaatcagg    660
gattcgacga gaaacggtgt tagggtttgg ctcggaacgt tccaaactgc agaggaagca    720
gctatggctt acgataaagc cgcggttaga attagaggta ctcaaaaagc tcacacaaat    780
tttcagctcg aaacagttat aaaagctatg gaaatggatt gcaacccaaa ctactaccgg    840
atgaacaact caaatacgtc cgatccatta agaagcagcc gcaaaatcgg attgagaaca    900 ggaaaaagagg cggttaaggc ttatgatgaa gtcgttgatg ggatggttga aaaccattgt    960
gcccttagct attgttcaac taaggagcac tcggagactc gtggtttgcg tgggagtgaa   1020
gaaacttggt tcgatttaag aaagagacga aggagtaatg aagattctat gtgtcaagaa   1080
gttgaaatgc agaagacggt tactggagaa gagacagtat gtgatgtgtt tggtttgttt   1140
gagtttgagg atttgggaag tgattatttg gagacgttat tatcttcttt ttgacagaaa   1200
tacattgaaa actaccgttg ctaatttgat aggtatacat atatagacat gtatatattg   1260
ta                                                                  1262

<210> SEQ ID NO 40
<211> LENGTH: 349
<212> TYPE: PRT
<213> ORGANISM: Arabidopsis thaliana
<220> FEATURE:
<223> OTHER INFORMATION: G45 polypeptide

<400> SEQUENCE: 40

Met Val Arg Val Cys Val Tyr Thr Gln Lys Thr Pro Asp Phe Met Trp
1               5                   10                  15

Asn Leu Lys Pro Ser Met Lys Cys Gly Gln Tyr Leu Arg Thr Gln Val
            20                  25                  30

Ser Pro Thr Val Leu Pro Asn Tyr Pro Ala Ala Asp Ser Thr Met Ala
        35                  40                  45

```

```
Phe Gly Asn Ile Gln Glu Leu Asp Gly Glu Ile Leu Lys Asn Val Trp
 50                  55                  60

Ala Asn Tyr Ile Gly Thr Pro Gln Thr Asp Thr Arg Ser Ile Gln Val
 65                  70                  75                  80

Pro Glu Val Ser Arg Thr Trp Glu Ala Leu Pro Thr Leu Asp Asp Ile
                 85                  90                  95

Pro Glu Gly Ser Arg Glu Met Leu Gln Ser Leu Asp Met Ser Thr Glu
                100                 105                 110

Asp Gln Glu Trp Thr Glu Ile Leu Asp Ala Ile Ala Ser Phe Pro Asn
                115                 120                 125

Lys Thr Asn His Asp Pro Leu Thr Asn Pro Thr Ile Asp Ser Cys Ser
130                 135                 140

Leu Ser Ser Arg Val Ser Cys Lys Thr Arg Lys Tyr Arg Gly Val Arg
145                 150                 155                 160

Lys Arg Pro Trp Gly Lys Phe Ala Ala Glu Ile Arg Asp Ser Thr Arg
                165                 170                 175

Asn Gly Val Arg Val Trp Leu Gly Thr Phe Gln Thr Ala Glu Glu Ala
                180                 185                 190

Ala Met Ala Tyr Asp Lys Ala Ala Val Arg Ile Arg Gly Thr Gln Lys
                195                 200                 205

Ala His Thr Asn Phe Gln Leu Gly Thr Val Ile Lys Ala Met Glu Met
210                 215                 220

Asp Cys Asn Pro Asn Tyr Tyr Arg Met Asn Asn Ser Asn Thr Ser Asp
225                 230                 235                 240

Pro Leu Arg Ser Ser Arg Lys Ile Gly Leu Arg Thr Gly Lys Glu Ala
                245                 250                 255

Val Lys Ala Tyr Asp Glu Val Val Asp Gly Met Val Glu Asn His Cys
                260                 265                 270

Ala Leu Ser Tyr Cys Ser Thr Lys Glu His Ser Glu Thr Arg Gly Leu
                275                 280                 285

Arg Gly Ser Glu Glu Thr Trp Phe Asp Leu Arg Lys Arg Arg Arg Ser
290                 295                 300

Asn Glu Asp Ser Met Cys Gln Glu Val Glu Met Gln Lys Thr Val Thr
305                 310                 315                 320

Gly Glu Glu Thr Val Cys Asp Val Phe Gly Leu Phe Glu Phe Glu Asp
                325                 330                 335

Leu Gly Ser Asp Tyr Leu Glu Thr Leu Leu Ser Ser Phe
                340                 345

<210> SEQ ID NO 41
<211> LENGTH: 933
<212> TYPE: DNA
<213> ORGANISM: Arabidopsis thaliana
<220> FEATURE:
<223> OTHER INFORMATION: G1752

<400> SEQUENCE: 41
aaaaaaaaaa aaaaaaaaaa acttatggaa tattcccaat cttccatgta ttcatctcca      60
agttcttgga gctcatcaca agaatcactc ttatggaacg agagctgttt cttggatcaa     120
tcatctgaac ctcaagcctt cttttgccct aattatgatt actccgatga cttttttctca    180 tttgagtcac cggagatgat gattaaggaa gaaattcaaa acggcgacgt ttctaactcc     240
gaagaagaag aaaaggttgg aattgatgaa gaaagatcat acagaggagt gaggaaaagg     300
ccgtggggga aatttgcagc ggagataaga gattcaacga ggaatggaat tagggtttgg     360
```

-continued

```
ctcgggacat tgacaaagc cgaggaagcc gctcttgctt atgatcaagc ggctttcgcc    420
acaaaaggat ctcttgcaac acttaatttc ccggtggaag tggttagaga gtcgctaaag    480
aaaatggaga atgtgaatct tcatgatgga ggatctccgg ttatggcctt gaagagaaaa    540
cattctcttc gaaaccggcc tagagggaaa aagcgatcct cttcttcttc ttcttcttct    600
tctaattctt cttcttgctc ttcttcttcg tctacttctt caacatcaag aagtagtagt    660
aagcagagtg ttgtgaagca agaaagtggt acacttgtgg ttttgaaga tttaggtgct     720 gagtatttag aacaacttct tatgagctca tgttgatctt gtaattgatt tcagcaaaag    780
ccactattaa actttaattt tgtgataatt aatcttgaaa tttgttttgt tcattctgca    840
atttctttgg ttctcttatt ttttgtttgt tgtatccaaa tgaaattatt ggaagagatg    900
gtgatgttaa agtgtatata tataaaaaaa aaa                                 933
```

<210> SEQ ID NO 42
<211> LENGTH: 243
<212> TYPE: PRT
<213> ORGANISM: Arabidopsis thaliana
<220> FEATURE:
<223> OTHER INFORMATION: G1752 polypeptide

<400> SEQUENCE: 42

```
Met Glu Tyr Ser Gln Ser Ser Met Tyr Ser Ser Pro Ser Ser Trp Ser
1               5                   10                  15

Ser Ser Gln Glu Ser Leu Leu Trp Asn Glu Ser Cys Phe Leu Asp Gln
            20                  25                  30

Ser Ser Glu Pro Gln Ala Phe Phe Cys Pro Asn Tyr Asp Tyr Ser Asp
        35                  40                  45

Asp Phe Phe Ser Phe Glu Ser Pro Glu Met Met Ile Lys Glu Glu Ile
    50                  55                  60

Gln Asn Gly Asp Val Ser Asn Ser Glu Glu Glu Lys Val Gly Ile
65                  70                  75                  80

Asp Glu Glu Arg Ser Tyr Arg Gly Val Arg Lys Arg Pro Trp Gly Lys
                85                  90                  95

Phe Ala Ala Glu Ile Arg Asp Ser Thr Arg Asn Gly Ile Arg Val Trp
            100                 105                 110

Leu Gly Thr Phe Asp Lys Ala Glu Glu Ala Ala Leu Ala Tyr Asp Gln
        115                 120                 125

Ala Ala Phe Ala Thr Lys Gly Ser Leu Ala Thr Leu Asn Phe Pro Val
    130                 135                 140

Glu Val Val Arg Glu Ser Leu Lys Lys Met Glu Asn Val Asn Leu His
145                 150                 155                 160

Asp Gly Gly Ser Pro Val Met Ala Leu Lys Arg Lys His Ser Leu Arg
                165                 170                 175

Asn Arg Pro Arg Gly Lys Lys Arg Ser Ser Ser Ser Ser Ser Ser Ser
            180                 185                 190

Ser Asn Ser Ser Ser Cys Ser Ser Ser Ser Thr Ser Ser Thr Ser
        195                 200                 205

Arg Ser Ser Ser Lys Gln Ser Val Val Lys Gln Glu Ser Gly Thr Leu
    210                 215                 220

Val Val Phe Glu Asp Leu Gly Ala Glu Tyr Leu Glu Gln Leu Leu Met
225                 230                 235                 240

Ser Ser Cys
```

<210> SEQ ID NO 43
<211> LENGTH: 832
<212> TYPE: DNA
<213> ORGANISM: Arabidopsis thaliana
<220> FEATURE:
<223> OTHER INFORMATION: G2512

<400> SEQUENCE: 43

```
aacttagtgc cacttagaca caataagaaa accgttaaca agaagaaaaa aaaaagatcg      60
aaaatggaat atcaaactaa cttcttaagt ggagagtttt ccccggagaa ctcttcttca     120
agctcatgga gctcacaaga atcattcttg tgggaagaga gtttcttaca tcaatcattt     180
gaccaatcct tccttttatc tagccctact gataactact gtgatgactt ctttgcattt     240
gaatcatcaa tcataaaaga agaaggaaaa gaagccaccg tggcggccga ggaggaggag     300
aagtcataca gaggagtgag gaaacggccg tgggggaaat tcgcggccga gataagagac     360
tcaacgagga aagggataag agtgtggctt gggacattcg acaccgcgga ggcggcggct     420
ctcgcttatg atcaggcggc tttcgctttg aaaggcagcc tcgcagtact caatttcccc     480
gcggatgtcg ttgaagaatc tctccggaag atggagaatg tgaatctcaa tgatggagag     540
tctccggtga tagccttgaa gagaaaacac tccatgagaa accgtcctag aggaaagaag     600
aaatcttctt cttcttcgac gttgacatct tctccttctt cctcctcctc ctattcatct     660
tcttcgtctt cttcttcttt gtcgtcaaga agtagaaaac agagtgttgt tatgacgcaa     720
gaaagtaata caacacttgt ggttcttgag gatttaggtg ctgaatactt agaagagctt     780
atgagatcat gttcttgata atctctgctt ctacaatttt tatgtaattt ga             832
```

<210> SEQ ID NO 44
<211> LENGTH: 244
<212> TYPE: PRT
<213> ORGANISM: Arabidopsis thaliana
<220> FEATURE:
<223> OTHER INFORMATION: G2512 polypeptide

<400> SEQUENCE: 44

Met Glu Tyr Gln Thr Asn Phe Leu Ser Gly Glu Phe Ser Pro Glu Asn
1               5                   10                  15

Ser Ser Ser Ser Ser Trp Ser Ser Gln Glu Ser Phe Leu Trp Glu Glu
            20                  25                  30

Ser Phe Leu His Gln Ser Phe Asp Gln Ser Phe Leu Leu Ser Ser Pro
        35                  40                  45

Thr Asp Asn Tyr Cys Asp Asp Phe Phe Ala Phe Glu Ser Ser Ile Ile
    50                  55                  60

Lys Glu Glu Gly Lys Glu Ala Thr Val Ala Ala Glu Glu Glu Glu Lys
65                  70                  75                  80

Ser Tyr Arg Gly Val Arg Lys Arg Pro Trp Gly Lys Phe Ala Ala Glu
                85                  90                  95

Ile Arg Asp Ser Thr Arg Lys Gly Ile Arg Val Trp Leu Gly Thr Phe
            100                 105                 110

Asp Thr Ala Glu Ala Ala Ala Leu Ala Tyr Asp Gln Ala Ala Phe Ala
        115                 120                 125

Leu Lys Gly Ser Leu Ala Val Leu Asn Phe Pro Ala Asp Val Val Glu
    130                 135                 140

Glu Ser Leu Arg Lys Met Glu Asn Val Asn Leu Asn Asp Gly Glu Ser
145                 150                 155                 160

Pro Val Ile Ala Leu Lys Arg Lys His Ser Met Arg Asn Arg Pro Arg
                165                 170                 175

Gly Lys Lys Lys Ser Ser Ser Ser Thr Leu Thr Ser Ser Pro Ser
            180                 185                 190

Ser Ser Ser Ser Tyr Ser Ser Ser Ser Ser Ser Leu Ser Ser
            195                 200                 205

Arg Ser Arg Lys Gln Ser Val Val Met Thr Gln Glu Ser Asn Thr Thr
    210                 215                 220

Leu Val Val Leu Glu Asp Leu Gly Ala Glu Tyr Leu Glu Glu Leu Met
225                 230                 235                 240

Arg Ser Cys Ser

<210> SEQ ID NO 45
<211> LENGTH: 913
<212> TYPE: DNA
<213> ORGANISM: Arabidopsis thaliana
<220> FEATURE:
<223> OTHER INFORMATION: G1006

<400> SEQUENCE: 45
gataaatcaa tcaacaaaac aaaaaaaact ctatagttag tttctctgaa aatgtacgga      60
cagtgcaata tagaatccga ctacgctttg ttggagtcga taacacgtca cttgctagga     120
ggaggaggag agaacgagct gcgactcaat gagtcaacac cgagttcgtg tttcacagag     180
agttggggag gtttgccatt gaaagagaat gattcagagg acatgttggt gtacggactc     240
ctcaaagatg ccttccattt tgacacgtca tcatcggact tgagctgtct ttttgatttt     300
ccggcggtta aagtcgagcc aactgagaac tttacggcga tggaggagaa accaaagaaa     360
gcgataccgg ttacggagac ggcagtgaag gcgaagcatt acagaggagt gaggcagaga     420
ccgtggggga aattcgcggc ggagatacgt gatccggcga agaatggagc tagggtttgg     480
ttagggacgt tgagacggc ggaagatgcg gctttagctt acgatatagc tgcttttagg     540
atgcgtggtt cccgcgcttt attgaatttt ccgttgaggg ttaattccgg tgaacctgac     600
ccggttcgga tcacgtctaa gagatcttct tcgtcgtcgt cgtcgtcgtc ctcttctacg     660
tcgtcgtctg aaaacgggaa gttgaaacga aggagaaaag cagagaatct gacgtcggag     720
gtggtgcagg tgaagtgtga ggttggtgat gagacacgtg ttgatgagtt attggtttca     780
taagtttgat cttgtgtgtt ttgtagttga atagttttgc tataaatgtt gaggcaccaa     840
gtaaaagtgt tcccgtgatg taaattagtt actaaacaga gccatatatc ttcaatcaaa     900
aaaaaaaaaa aaa                                                         913

<210> SEQ ID NO 46
<211> LENGTH: 243
<212> TYPE: PRT
<213> ORGANISM: Arabidopsis thaliana
<220> FEATURE:
<223> OTHER INFORMATION: G1006 polypeptide

<400> SEQUENCE: 46

Met Tyr Gly Gln Cys Asn Ile Glu Ser Asp Tyr Ala Leu Leu Glu Ser
1               5                   10                  15

Ile Thr Arg His Leu Leu Gly Gly Gly Glu Asn Glu Leu Arg Leu
            20                  25                  30

Asn Glu Ser Thr Pro Ser Ser Cys Phe Thr Glu Ser Trp Gly Gly Leu
            35                  40                  45

Pro Leu Lys Glu Asn Asp Ser Glu Asp Met Leu Val Tyr Gly Leu Leu
    50                  55                  60

```
Lys Asp Ala Phe His Phe Asp Thr Ser Ser Asp Leu Ser Cys Leu
 65                  70                  75                  80

Phe Asp Phe Pro Ala Val Lys Val Glu Pro Thr Glu Asn Phe Thr Ala
                 85                  90                  95

Met Glu Glu Lys Pro Lys Lys Ala Ile Pro Val Thr Glu Thr Ala Val
            100                 105                 110

Lys Ala Lys His Tyr Arg Gly Val Arg Gln Arg Pro Trp Gly Lys Phe
        115                 120                 125

Ala Ala Glu Ile Arg Asp Pro Ala Lys Asn Gly Ala Arg Val Trp Leu
    130                 135                 140

Gly Thr Phe Glu Thr Ala Glu Asp Ala Ala Leu Ala Tyr Asp Ile Ala
145                 150                 155                 160

Ala Phe Arg Met Arg Gly Ser Arg Ala Leu Leu Asn Phe Pro Leu Arg
                165                 170                 175

Val Asn Ser Gly Glu Pro Asp Pro Val Arg Ile Thr Ser Lys Arg Ser
            180                 185                 190

Ser Ser Ser Ser Ser Ser Ser Ser Ser Thr Ser Ser Ser Glu Asn
        195                 200                 205

Gly Lys Leu Lys Arg Arg Arg Lys Ala Glu Asn Leu Thr Ser Glu Val
    210                 215                 220

Val Gln Val Lys Cys Glu Val Gly Asp Glu Thr Arg Val Asp Glu Leu
225                 230                 235                 240

Leu Val Ser

<210> SEQ ID NO 47
<211> LENGTH: 964
<212> TYPE: DNA
<213> ORGANISM: Arabidopsis thaliana
<220> FEATURE:
<223> OTHER INFORMATION: G28

<400> SEQUENCE: 47
gaaatctcaa caagaaccaa accaaacaac aaaaaaacat tcttaataat tatctttctg      60
ttatgtcgat gacggcggat tctcaatctg attatgcttt tcttgagtcc atacgacgac     120
acttactagg agaatcggag ccgatactca gtgagtcgac agcgagttcg gttactcaat     180
cttgtgtaac cggtcagagc attaaaccgg tgtacgacg aaaccctagc tttagcaaac      240
tgtatccttg cttcaccgag agctggggag atttgccgtt gaaagaaaac gattctgagg     300
atatgttagt ttacggtatc ctcaacgacg cctttcacgg cggttgggag ccgtcttctt     360
cgtcttccga cgaagatcgt agctctttcc cgagtgttaa gatcgagact ccggagagtt     420
tcgcggcggt ggattctgtt ccggtcaaga aggagaagac gagtcctgtt tcggcggcgg     480
tgacggcggc gaagggaaag cattatagag gagtgagaca aaggccgtgg gggaaatttg     540
cggcggagat tagagatccg gcgaagaacg gagctagggt ttggttagga acgtttgaga     600
cggcggagga cgcggcgttg gcttacgaca gagctgcttt caggatgcgt ggttccgcg      660
ctttgttgaa ttttccgttg agagttaatt caggagaacc cgacccggtt cgaatcaagt     720
ccaagagatc ttcttttttct tcttctaacg agaacggagc tccgaagaag aggagaacgg     780
tggccgccgg tggtggaatg gataagggat tgacggtgaa gtgcgaggtt gttgaagtgg     840
cacgtggcga tcgtttattg gttttataat tttgattttt ctttgttgga tgattatatg     900
attcttcaaa aagaagaac gttaataaaa aaattcgttt attattaaaa aaaaaaaaa       960
aaaa                                                                  964
```

<210> SEQ ID NO 48
<211> LENGTH: 268
<212> TYPE: PRT
<213> ORGANISM: Arabidopsis thaliana
<220> FEATURE:
<223> OTHER INFORMATION: G28 polypeptide

<400> SEQUENCE: 48

```
Met Ser Met Thr Ala Asp Ser Gln Ser Asp Tyr Ala Phe Leu Glu Ser
1               5                   10                  15

Ile Arg Arg His Leu Leu Gly Glu Ser Glu Pro Ile Leu Ser Glu Ser
            20                  25                  30

Thr Ala Ser Ser Val Thr Gln Ser Cys Val Thr Gly Gln Ser Ile Lys
        35                  40                  45

Pro Val Tyr Gly Arg Asn Pro Ser Phe Ser Lys Leu Tyr Pro Cys Phe
    50                  55                  60

Thr Glu Ser Trp Gly Asp Leu Pro Leu Lys Glu Asn Asp Ser Glu Asp
65                  70                  75                  80

Met Leu Val Tyr Gly Ile Leu Asn Asp Ala Phe His Gly Gly Trp Glu
                85                  90                  95

Pro Ser Ser Ser Ser Asp Glu Asp Arg Ser Ser Phe Pro Ser Val
            100                 105                 110

Lys Ile Glu Thr Pro Gly Ser Phe Ala Ala Val Asp Ser Val Pro Val
            115                 120                 125

Lys Lys Glu Lys Thr Ser Pro Val Ser Ala Ala Val Thr Ala Ala Lys
130                 135                 140

Gly Lys His Tyr Arg Gly Val Arg Gln Arg Pro Trp Gly Lys Phe Ala
145                 150                 155                 160

Ala Glu Ile Arg Asp Pro Ala Lys Asn Gly Ala Arg Val Trp Leu Gly
                165                 170                 175

Thr Phe Glu Thr Ala Glu Asp Ala Ala Leu Ala Tyr Asp Arg Ala Ala
            180                 185                 190

Phe Arg Met Arg Gly Ser Arg Ala Leu Leu Asn Phe Pro Leu Arg Val
        195                 200                 205

Asn Ser Gly Glu Pro Asp Pro Val Arg Ile Lys Ser Lys Arg Ser Ser
    210                 215                 220

Phe Ser Ser Asn Glu Asn Gly Ala Pro Lys Lys Arg Arg Thr Val
225                 230                 235                 240

Ala Ala Gly Gly Gly Met Asp Lys Gly Leu Thr Val Lys Cys Glu Val
                245                 250                 255

Val Glu Val Ala Arg Gly Asp Arg Leu Leu Val Leu
            260                 265
```

<210> SEQ ID NO 49
<211> LENGTH: 913
<212> TYPE: DNA
<213> ORGANISM: Arabidopsis thaliana
<220> FEATURE:
<223> OTHER INFORMATION: G22

<400> SEQUENCE: 49

```
agaaaacatc tctcactctc taaaatacac actctcatca aaaaccttct cttcggttca      60
gaagcattca agaatccatt atgagctcat ctgattccgt taataacggc gttaactcac     120
ggatgtactt ccgtaacccg agtttcagca acgttatctt aaacgataac tggagcgact     180
tgccgttaag tgtcgacgat tctcaagaca tggctattta caacactctc cgtgatgccg     240
```

```
ttagctccgg ctggacaccc tccgttcctc ccgttacctc tccggcgag gaaaataagc    300 ctccggcgac gaaggcgagt ggctcacacg cgccgaggca gaaggggatg cagtacagag    360
gagtgaggag gaggccgtgg gggaaattcg cggcggagat tagggatccg aagaagaacg    420
gagctagggt ttggctcggg acttacgaga cgccggagga cgcggcggtg gcgtacgacc    480
gagcggcgtt tcagctcaga ggatcgaaag ctaagctgaa ttttccgcat ttgattggtt    540
cttgtaagta tgagccggtt aggattaggc ctcgccgtcg ctcgccggaa ccgtcagtct    600
ccgatcagtt aacgtcggag cagaagaggg aaagccacgt ggatgacggc gagtctagtt    660
tggttgtacc ggagttggat ttcacggtgg atcagtttta cttcgatggt agtttattaa    720
tggaccaatc agaatgttct tattctgata atcggatata attagtttta agattaagca    780
aaatttgtcc aacgagtttt gctgtatgaa atatctatcg atgactcaac aggttttgat    840
catgatcata tgtaatgtga tggaaattaa atattgacgt ttgttttttt gttgtaaaaa    900
aaaaaaaaaa aaa                                                       913
```

<210> SEQ ID NO 50
<211> LENGTH: 226
<212> TYPE: PRT
<213> ORGANISM: Arabidopsis thaliana
<220> FEATURE:
<223> OTHER INFORMATION: G22 polypeptide

<400> SEQUENCE: 50

```
Met Ser Ser Ser Asp Ser Val Asn Asn Gly Val Asn Ser Arg Met Tyr
1               5                   10                  15

Phe Arg Asn Pro Ser Phe Ser Asn Val Ile Leu Asn Asp Asn Trp Ser
            20                  25                  30

Asp Leu Pro Leu Ser Val Asp Ser Gln Asp Met Ala Ile Tyr Asn
        35                  40                  45

Thr Leu Arg Asp Ala Val Ser Ser Gly Trp Thr Pro Ser Val Pro Pro
    50                  55                  60

Val Thr Ser Pro Ala Glu Glu Asn Lys Pro Ala Thr Lys Ala Ser
65                  70                  75                  80

Gly Ser His Ala Pro Arg Gln Lys Gly Met Gln Tyr Arg Gly Val Arg
                85                  90                  95

Arg Arg Pro Trp Gly Lys Phe Ala Ala Glu Ile Arg Asp Pro Lys Lys
            100                 105                 110

Asn Gly Ala Arg Val Trp Leu Gly Thr Tyr Glu Thr Pro Glu Asp Ala
        115                 120                 125

Ala Val Ala Tyr Asp Arg Ala Ala Phe Gln Leu Arg Gly Ser Lys Ala
    130                 135                 140

Lys Leu Asn Phe Pro His Leu Ile Gly Ser Cys Lys Tyr Glu Pro Val
145                 150                 155                 160

Arg Ile Arg Pro Arg Arg Ser Pro Glu Pro Ser Val Ser Asp Gln
                165                 170                 175

Leu Thr Ser Glu Gln Lys Arg Glu Ser His Val Asp Asp Gly Glu Ser
            180                 185                 190

Ser Leu Val Val Pro Glu Leu Asp Phe Thr Val Asp Gln Phe Tyr Phe
        195                 200                 205

Asp Gly Ser Leu Leu Met Asp Gln Ser Glu Cys Ser Tyr Ser Asp Asn
    210                 215                 220

Arg Ile
225
```

<210> SEQ ID NO 51
<211> LENGTH: 1084
<212> TYPE: DNA
<213> ORGANISM: Arabidopsis thaliana
<220> FEATURE:
<223> OTHER INFORMATION: G26

<400> SEQUENCE: 51

```
ttggcttgta cccaaaccca tctttgactt caaaaataaa ataaaaataa tcataattga      60
catcatcgga taatgcatag cgggaagaga cctctatcac cagaatcaat ggccggaaat     120
agagaagaga aaaagagtt gtgttgttgc tcaactttgt cggaatctga tgtgtctgat     180
tttgtctctg aactcactgg tcaacccatc ccatcatcca tgatgatca atcttcgtcg     240
cttactcttc aagaaaaaag taactcgagg caacgaaact acagaggcgt gaggcaaaga     300
ccgtggggaa atgggcggc tgagattcgt gacccgaaca aggcagctcg tgtgtggctt     360
gggacgttcg acactgcaga agaagccgcc ttagcgtatg ataaagctgc atttgagttt     420
agaggtcaca aggccaagct taacttcccc gagcatattc gtgtcaaccc tactcaactc     480
tatccatcgc ccgctacttc ccatgatcgc attatcgtga caccacctag tccacctcca     540
ccaattgctc ctgacatact tcttgatcaa tatggccact tcaatctcg aagtagtgat     600
tccagtgcca acttgtccat gaatatgctg tcttcttcgt cttcatcttt gaatcatcaa     660
gggctaagac caaatttgga ggatggtgaa aacgtgaaga acattagtat ccacaaacga     720
cgaaaataac atgttaatgg cataaatatc tcttcgtcca agttatcaaa cgcattgacc     780
tccggctttg atcattttag gcgcttaatc tctttacgac ttcattttgg tagtctttaa     840
agagtctatg gagtggattt agctaggaat caggccttat ggatgaaaaa tatataaatt     900
ttgaacatga ctatgcaaga atgggatgaa gactacttag cttggaaaac gtcctgatag     960
gtcatgacga ctatatccac agaagatgac cgacggagac aacaacatgc ctcacctgat    1020
cgaccgatca aatgagataa tgtgttgacc ggaccggtcg gatcaggttg ggtcgagtat    1080
atca                                                                 1084
```

<210> SEQ ID NO 52
<211> LENGTH: 218
<212> TYPE: PRT
<213> ORGANISM: Arabidopsis thaliana
<220> FEATURE:
<223> OTHER INFORMATION: G26 polypeptide

<400> SEQUENCE: 52

```
Met His Ser Gly Lys Arg Pro Leu Ser Pro Glu Ser Met Ala Gly Asn
1               5                   10                  15

Arg Glu Glu Lys Lys Glu Leu Cys Cys Cys Ser Thr Leu Ser Glu Ser
            20                  25                  30

Asp Val Ser Asp Phe Val Ser Glu Leu Thr Gly Gln Pro Ile Pro Ser
        35                  40                  45

Ser Ile Asp Asp Gln Ser Ser Ser Leu Thr Leu Gln Glu Lys Ser Asn
    50                  55                  60

Ser Arg Gln Arg Asn Tyr Arg Gly Val Arg Gln Arg Pro Trp Gly Lys
65                  70                  75                  80

Trp Ala Ala Glu Ile Arg Asp Pro Asn Lys Ala Ala Arg Val Trp Leu
                85                  90                  95

Gly Thr Phe Asp Thr Ala Glu Glu Ala Ala Leu Ala Tyr Asp Lys Ala
            100                 105                 110
```

```
Ala Phe Glu Phe Arg Gly His Lys Ala Lys Leu Asn Phe Pro Glu His
        115                 120                 125

Ile Arg Val Asn Pro Thr Gln Leu Tyr Pro Ser Pro Ala Thr Ser His
    130                 135                 140

Asp Arg Ile Ile Val Thr Pro Ser Pro Pro Pro Ile Ala Pro
145                 150                 155                 160

Asp Ile Leu Leu Asp Gln Tyr Gly His Phe Gln Ser Arg Ser Ser Asp
                165                 170                 175

Ser Ser Ala Asn Leu Ser Met Asn Met Leu Ser Ser Ser Ser Ser Ser
            180                 185                 190

Leu Asn His Gln Gly Leu Arg Pro Asn Leu Glu Asp Gly Glu Asn Val
        195                 200                 205

Lys Asn Ile Ser Ile His Lys Arg Arg Lys
    210                 215
```

<210> SEQ ID NO 53
<211> LENGTH: 1123
<212> TYPE: DNA
<213> ORGANISM: Arabidopsis thaliana
<220> FEATURE:
<223> OTHER INFORMATION: G1751

<400> SEQUENCE: 53

```
aaacacaaac aaaactcata ttttcaatct ccaggtgctt tacaccaaca gagtcgcaag       60
aaaacaaaaa ccaaactcgg atttagtttg acagaagaag gaatcgagag tcgggtatgc      120
attatcctaa aacagaacc gaattcgtcg gagctccagc cccaacccgg tatcaaaagg       180
agcagttgtc accggagcaa gagctttcag ttattgtctc tgctttgcaa cacgtgatct      240
caggggaaaa cgaaacggcg ccgtgtcagg gtttttccag tgacagcaca gtgataagcg      300
cgggaatgcc tcggttggat tcagacactt gtcaagtctg taggatcgaa ggatgtctcg      360
gctgtaacta cttttcgcg ccaaatcaga gaattgaaaa gaatcatcaa caagaagaag       420
agattactag tagtagtaac agaagaagag agagctctcc cgtggcgaag aaagcggaag      480
gtggcgggaa aatcaggaag aggaagaaca agaagaatgg ttacagagga gttaggcaaa      540
gaccttgggg aaaatttgca gctgagatca gagatcctaa aagagccaca cgtgtttggc      600
ttggtacttt cgaaaccgcc gaagatgcgg ctcgagctta tgatcgagcc gcgattggat      660
tccgtgggcc aagggctaaa ctcaacttcc cctttgtgga ttacacgtct tcagtttcat      720
ctcctgttgc tgctgatgat ataggagcaa aggcaagtgc aagcgccagt gtgagcgcca      780
cagattcagt tgaagcagag caatggaacg gaggaggagg ggattgcaat atggaggagt      840
ggatgaatat gatgatgatg atggattttg ggaatggaga ttcttcagat tcaggaaata      900
caattgctga tatgttccag tgataaatga gctctttctt gttggcgttt tttggagtta      960
agtgcaagaa gagattgaca ctgtggcttg tttaaagtga acaagaacaa gaaagcatgt     1020
aattagtagt ctcattcttt tgtttgtggt caattctatg tttatctcat ataaaatctg     1080
agttaaaccct atctgaggag agagtaaata aagaggttaa gaa                      1123
```

<210> SEQ ID NO 54
<211> LENGTH: 268
<212> TYPE: PRT
<213> ORGANISM: Arabidopsis thaliana
<220> FEATURE:
<223> OTHER INFORMATION: G1751 polypeptide

<400> SEQUENCE: 54

```
Met His Tyr Pro Asn Asn Arg Thr Glu Phe Val Gly Ala Pro Ala Pro
 1               5                  10                  15

Thr Arg Tyr Gln Lys Glu Gln Leu Ser Pro Glu Gln Glu Leu Ser Val
                20                  25                  30

Ile Val Ser Ala Leu Gln His Val Ile Ser Gly Glu Asn Glu Thr Ala
            35                  40                  45

Pro Cys Gln Gly Phe Ser Ser Asp Ser Thr Val Ile Ser Ala Gly Met
        50                  55                  60

Pro Arg Leu Asp Ser Asp Thr Cys Gln Val Cys Arg Ile Glu Gly Cys
65                  70                  75                  80

Leu Gly Cys Asn Tyr Phe Phe Ala Pro Asn Gln Arg Ile Glu Lys Asn
                85                  90                  95

His Gln Gln Glu Glu Glu Ile Thr Ser Ser Ser Asn Arg Arg Arg Glu
            100                 105                 110

Ser Ser Pro Val Ala Lys Lys Ala Glu Gly Gly Lys Ile Arg Lys
        115                 120                 125

Arg Lys Asn Lys Lys Asn Gly Tyr Arg Gly Val Arg Gln Arg Pro Trp
    130                 135                 140

Gly Lys Phe Ala Ala Glu Ile Arg Asp Pro Lys Arg Ala Thr Arg Val
145                 150                 155                 160

Trp Leu Gly Thr Phe Glu Thr Ala Glu Asp Ala Ala Arg Ala Tyr Asp
                165                 170                 175

Arg Ala Ala Ile Gly Phe Arg Gly Pro Arg Ala Lys Leu Asn Phe Pro
            180                 185                 190

Phe Val Asp Tyr Thr Ser Ser Val Ser Ser Pro Val Ala Ala Asp Asp
        195                 200                 205

Ile Gly Ala Lys Ala Ser Ala Ser Ala Ser Val Ser Ala Thr Asp Ser
    210                 215                 220

Val Glu Ala Glu Gln Trp Asn Gly Gly Gly Asp Cys Asn Met Glu
225                 230                 235                 240

Glu Trp Met Asn Met Met Met Met Asp Phe Gly Asn Gly Asp Ser
                245                 250                 255

Ser Asp Ser Gly Asn Thr Ile Ala Asp Met Phe Gln
            260                 265

<210> SEQ ID NO 55
<211> LENGTH: 1200
<212> TYPE: DNA
<213> ORGANISM: Arabidopsis thaliana
<220> FEATURE:
<223> OTHER INFORMATION: G589

<400> SEQUENCE: 55
aaaaaaacag aagccatgaa ctcctcgtct cttctaactc cttcatcatc tccttctcca      60
catcttcaat ctcctgcaac attcgaccac gatgatttcc tccaccacat cttctcctcc     120
actccttggc cctcatccgt tctcgacgac actcctccac caacttccga ttgtgccccc     180
gtcactggat tccaccacca cgacgccgat tcaagaaacc agatcactat gattcctttg     240
tcacataacc atcctaatga cgctctcttc aatggcttct ccaccggatc tctcccttc      300 cacctccctc aaggatcggg aggtcaaacg caaacgcagt cgcaggcgac ggcgtcagcc     360
accaccggtg gtgcaacggc gcaacctcag acaaagccta aagtccgagc taggagaggt     420
caagccactg atcctcacag tatcgccgaa cggttacgga gagagaggat agcggaaaga     480
atgaaatctc ttcaagaact tgtccctaat ggtaacaaga cagacaaagc atcaatgctc     540
```

-continued

```
gatgagatta tcgattatgt caagttctta cagctccaag tcaaggtact aagcatgagt      600
agactgggcg gtgctgcttc tgcttcttct caaatctctg aggatgccgg tggatcccac      660
gaaaacacct cctcctccgg cgaggcgaag atgacggagc accaagttgc aaagctaatg      720
gaagaggaca tgggatcagc catgcaatat ctacaaggca aaggtctttg cctcatgccc      780
atctcgttag ccaccaccat ctccaccgcc acgtgtcctt ctcgtagccc cttcgttaaa      840
gataccggcg ttcctttgtc tcctaaccta tccactacaa tagttgctaa cggtaatggc      900
tcatcgttgg tcaccgttaa agacgctccc tccgtttcca agccgtgata acggccattt      960
gtccatttca ttttcccttt tttgggtggg aagagagaa aaaagtttag aagacaaaga     1020
caagtgggat aggtggtttt ggtcaaagtt tagaaagaat aaggtcgtgt tttcggatac     1080
gacaccgtat ttgcgtacac tttggttttc tgtctttacc tactacaaac cacccataag     1140
cacactcatg ttatcatgtt tttttttttt tggtttataa agatataaaa aaaaaaaaaa     1200
```

<210> SEQ ID NO 56
<211> LENGTH: 310
<212> TYPE: PRT
<213> ORGANISM: Arabidopsis thaliana
<220> FEATURE:
<223> OTHER INFORMATION: G589 polypeptide

<400> SEQUENCE: 56

```
Met Asn Ser Ser Ser Leu Leu Thr Pro Ser Ser Pro Ser Pro His
1               5                   10                  15

Leu Gln Ser Pro Ala Thr Phe Asp His Asp Asp Phe Leu His His Ile
            20                  25                  30

Phe Ser Ser Thr Pro Trp Pro Ser Ser Val Leu Asp Asp Thr Pro Pro
        35                  40                  45

Pro Thr Ser Asp Cys Ala Pro Val Thr Gly Phe His His Asp Ala
    50                  55                  60

Asp Ser Arg Asn Gln Ile Thr Met Ile Pro Leu Ser His Asn His Pro
65                  70                  75                  80

Asn Asp Ala Leu Phe Asn Gly Phe Ser Thr Gly Ser Leu Pro Phe His
                85                  90                  95

Leu Pro Gln Gly Ser Gly Gly Gln Thr Gln Thr Gln Ser Gln Ala Thr
            100                 105                 110

Ala Ser Ala Thr Thr Gly Gly Ala Thr Ala Gln Pro Gln Thr Lys Pro
        115                 120                 125

Lys Val Arg Ala Arg Arg Gly Gln Ala Thr Asp Pro His Ser Ile Ala
    130                 135                 140

Glu Arg Leu Arg Arg Glu Arg Ile Ala Glu Arg Met Lys Ser Leu Gln
145                 150                 155                 160

Glu Leu Val Pro Asn Gly Asn Lys Thr Asp Lys Ala Ser Met Leu Asp
                165                 170                 175

Glu Ile Ile Asp Tyr Val Lys Phe Leu Gln Leu Gln Val Lys Val Leu
            180                 185                 190

Ser Met Ser Arg Leu Gly Gly Ala Ala Ser Ala Ser Gln Ile Ser
        195                 200                 205

Glu Asp Ala Gly Gly Ser His Glu Asn Thr Ser Ser Ser Gly Glu Ala
    210                 215                 220

Lys Met Thr Glu His Gln Val Ala Lys Leu Met Glu Glu Asp Met Gly
225                 230                 235                 240

Ser Ala Met Gln Tyr Leu Gln Gly Lys Gly Leu Cys Leu Met Pro Ile
                245                 250                 255
```

```
Ser Leu Ala Thr Thr Ile Ser Thr Ala Thr Cys Pro Ser Arg Ser Pro
            260                 265                 270

Phe Val Lys Asp Thr Gly Val Pro Leu Ser Pro Asn Leu Ser Thr Thr
        275                 280                 285

Ile Val Ala Asn Gly Asn Gly Ser Ser Leu Val Thr Val Lys Asp Ala
    290                 295                 300

Pro Ser Val Ser Lys Pro
305             310
```

<210> SEQ ID NO 57
<211> LENGTH: 1023
<212> TYPE: DNA
<213> ORGANISM: Arabidopsis thaliana
<220> FEATURE:
<223> OTHER INFORMATION: G6

<400> SEQUENCE: 57

```
tatctatccg agaatggcca agatgggctt gaaacccgac ccggctacta ctaaccagac    60
ccacaataat gccaaggaga ttcgttacag aggcgttagg aagcgtcctt ggggccgtta   120
tgccgccgag atccgagatc cgggcaagaa aacccgcgtc tggcttggca ctttcgatac   180
ggctgaagag gcggcgcgtg cttacgatac ggcggcgcgt gattttcgtg gtgctaaggc   240
taagaccaat ttcccaactt ttctcgagct gagtgaccaa aaggtcccta ccggtttcgc   300
gcgtagccct agccagagca gcacgctcga ctgtgcttct cctccgacgt tagttgtgcc   360
ttcagcgacg gctgggaatg ttccccccgca gctcgagctt agtctcggcg gaggaggcgg   420
cggctcgtgt tatcagatcc cgatgtcgcg tcctgtctac tttttggacc tgatggggat   480
cggtaacgta ggtcgtggtc agcctcctcc tgtgacatcg gcgtttagat cgccggtggt   540
gcatgttgcg acgaagatgg cttgtggtgc ccaaagcgac tctgattcgt catcggtcgt   600
tgatttcgaa ggtgggatgg agaagagatc tcagctgtta gatctagatc ttaatttgcc   660
tcctccatcg gaacaggcct gagcttttaa cggtgtcgtt tcaattcgaa gcgcatgcgt   720
ttcttcttct ttttgagctg tgaaaattcg ttttctcata gttttttctc tctctctct   780
tcagtctaaa tttattacca gttttttagaa agaaaaaaca gattaaatct gagagagaaa   840
aatataattt tagctgacat ggatcgttat gtacatatta ttacataacc ggagatctga   900
acttttgttg tgtgctttta atttttttgcg acttggtttc accccatgtt gtttctctat   960
ttttttttact acttttttttt tttttgttct tccaaatttt caatcaataa tttggtaatc  1020
ttc                                                                  1023
```

<210> SEQ ID NO 58
<211> LENGTH: 222
<212> TYPE: PRT
<213> ORGANISM: Arabidopsis thaliana
<220> FEATURE:
<223> OTHER INFORMATION: G6 polypeptide

<400> SEQUENCE: 58

```
Met Ala Lys Met Gly Leu Lys Pro Asp Pro Ala Thr Thr Asn Gln Thr
1               5                   10                  15

His Asn Asn Ala Lys Glu Ile Arg Tyr Arg Gly Val Arg Lys Arg Pro
            20                  25                  30

Trp Gly Arg Tyr Ala Ala Glu Ile Arg Asp Pro Gly Lys Lys Thr Arg
        35                  40                  45

Val Trp Leu Gly Thr Phe Asp Thr Ala Glu Glu Ala Ala Arg Ala Tyr
```

```
                50                  55                  60
Asp Thr Ala Ala Arg Asp Phe Arg Gly Ala Lys Ala Lys Thr Asn Phe
 65                  70                  75                  80

Pro Thr Phe Leu Glu Leu Ser Asp Gln Lys Val Pro Thr Gly Phe Ala
                 85                  90                  95

Arg Ser Pro Ser Gln Ser Ser Thr Leu Asp Cys Ala Ser Pro Pro Thr
            100                 105                 110

Leu Val Val Pro Ser Ala Thr Ala Gly Asn Val Pro Pro Gln Leu Glu
        115                 120                 125

Leu Ser Leu Gly Gly Gly Gly Gly Ser Cys Tyr Gln Ile Pro Met
130                 135                 140

Ser Arg Pro Val Tyr Phe Leu Asp Leu Met Gly Ile Gly Asn Val Gly
145                 150                 155                 160

Arg Gly Gln Pro Pro Pro Val Thr Ser Ala Phe Arg Ser Pro Val Val
                165                 170                 175

His Val Ala Thr Lys Met Ala Cys Gly Ala Gln Ser Asp Ser Asp Ser
            180                 185                 190

Ser Ser Val Val Asp Phe Glu Gly Gly Met Glu Lys Arg Ser Gln Leu
        195                 200                 205

Leu Asp Leu Asp Leu Asn Leu Pro Pro Pro Ser Glu Gln Ala
    210                 215                 220

<210> SEQ ID NO 59
<211> LENGTH: 1059
<212> TYPE: DNA
<213> ORGANISM: Arabidopsis thaliana
<220> FEATURE:
<223> OTHER INFORMATION: G1004

<400> SEQUENCE: 59
atggcgactc ctaacgaagt atctgcactt tggttcatcg agaaacatct actcgacgag     60
gcttctcctg tggctacaga tccatggatg aagcacgaat catcatcagc aacagaatct    120
agctctgact cttcttctat catcttcgga tcatcgtcct cttctttcgc cccaattgat    180
ttctctgaat ccgtatgcaa acctgaaatc atcgatctcg atactcccag atctatggaa    240
tttctatcga ttccatttga atttgactca gaagtttctg tttctgattt cgattttaaa    300
ccttctaatc aaaatcaaaa tcagtttgaa ccggagctta atctcaaat tcgtaaaccg    360
ccattgaaga tttcgcttcc agctaaaaca gagtggattc aattcgcagc tgaaaacacc    420
aaaccggaag ttactaaacc ggtttcggaa gaagagaaga agcattacag aggagtaaga    480
caaagaccgt gggggaaatt cgcggcggag attcgtgacc cgaataaacg cggatctcgc    540
gtttggcttg gacgtttgga tacagcgatt gaagcggcta gagcttatga cgaagcagcg    600
tttagactac gaggatcgaa agcgattttg aatttccctc ttgaagttgg gaagtggaaa    660
ccacgcgccg atgaaggtga agaaaacgg aagagagacg atgatgagaa agtgactgtg    720
gttgagaaag tgttgaagac ggaacagagc gttgacgtta acggtggaga cgtttccg    780
tttgtaacgt cgaatttaac ggaattatgt gactgggatt taacgggggtt tcttaacttt    840
ccgcttctgt cgccgttatc tcctcatcca ccgtttggtt attcccagtt gaccgttgtt    900
tgattagttt tttttgagtt tttgaacgat gtgtatgctg acgtggacgt acacgtaggt    960
gcatgcgatg aaaaaaacat ctatttgttc atattttgc gtttttctat tgttcattc    1020
tttttcacaa ttcacaatac attatttcag ttaatgatc                           1059
```

```
<210> SEQ ID NO 60
<211> LENGTH: 300
<212> TYPE: PRT
<213> ORGANISM: Arabidopsis thaliana
<220> FEATURE:
<223> OTHER INFORMATION: G1004 polypeptide

<400> SEQUENCE: 60

Met Ala Thr Pro Asn Glu Val Ser Ala Leu Trp Phe Ile Glu Lys His
1               5                  10                  15

Leu Leu Asp Glu Ala Ser Pro Val Ala Thr Asp Pro Trp Met Lys His
            20                  25                  30

Glu Ser Ser Ser Ala Thr Glu Ser Ser Asp Ser Ser Ile Ile
        35                  40                  45

Phe Gly Ser Ser Ser Ser Phe Ala Pro Ile Asp Phe Ser Glu Ser
    50                  55                  60

Val Cys Lys Pro Glu Ile Ile Asp Leu Asp Thr Pro Arg Ser Met Glu
65                  70                  75                  80

Phe Leu Ser Ile Pro Phe Glu Phe Asp Ser Glu Val Ser Val Ser Asp
                85                  90                  95

Phe Asp Phe Lys Pro Ser Asn Gln Asn Gln Asn Gln Phe Glu Pro Glu
            100                 105                 110

Leu Lys Ser Gln Ile Arg Lys Pro Pro Leu Lys Ile Ser Leu Pro Ala
        115                 120                 125

Lys Thr Glu Trp Ile Gln Phe Ala Ala Glu Asn Thr Lys Pro Glu Val
    130                 135                 140

Thr Lys Pro Val Ser Glu Glu Glu Lys Lys His Tyr Arg Gly Val Arg
145                 150                 155                 160

Gln Arg Pro Trp Gly Lys Phe Ala Ala Glu Ile Arg Asp Pro Asn Lys
                165                 170                 175

Arg Gly Ser Arg Val Trp Leu Gly Thr Phe Asp Thr Ala Ile Glu Ala
            180                 185                 190

Ala Arg Ala Tyr Asp Glu Ala Ala Phe Arg Leu Arg Gly Ser Lys Ala
        195                 200                 205

Ile Leu Asn Phe Pro Leu Glu Val Gly Lys Trp Lys Pro Arg Ala Asp
    210                 215                 220

Glu Gly Glu Lys Lys Arg Lys Arg Asp Asp Glu Lys Val Thr Val
225                 230                 235                 240

Val Glu Lys Val Leu Lys Thr Glu Gln Ser Val Asp Val Asn Gly Gly
                245                 250                 255

Glu Thr Phe Pro Phe Val Thr Ser Asn Leu Thr Glu Leu Cys Asp Trp
            260                 265                 270

Asp Leu Thr Gly Phe Leu Asn Phe Pro Leu Leu Ser Pro Leu Ser Pro
        275                 280                 285

His Pro Pro Phe Gly Tyr Ser Gln Leu Thr Val Val
    290                 295                 300

<210> SEQ ID NO 61
<211> LENGTH: 1281
<212> TYPE: DNA
<213> ORGANISM: Arabidopsis thaliana
<220> FEATURE:
<223> OTHER INFORMATION: G1005

<400> SEQUENCE: 61 gcttttgtg ttgaagagag agtttcctat cttctccatt cctcccacca tctccctcat       60
cttcatcttc ctctctcttt ctctctttct caacaatctc tattagatct ttctccatta     120
```

```
ccattacctc tggctttctc ttaaatccac catcatgagg agaggaagag gctcttccgc    180
cgtcgccgga cctaccgtcg ttgccgccat caacggatct gtaaaagaaa tcagattcag    240
aggcgtaagg aagagacctt ggggacgatt cgcagctgag atccgtgatc catggaaaaa    300
agctcgtgtt tggttaggta ctttcgattc cgccgaagaa gctgctcgcg cttacgactc    360
cgccgctcgt aacctccgtg gtcctaaagc caaaactaat ttccccatcg attcttcttc    420
tcctcctcct cctaatctcc gatttaatca gattcgtaat caaaatcaaa accaagtcga    480
tccgtttatg gaccaccggt tattcaccga ccatcaacaa cagttcccga ttgttaaccg    540
gcctactagt agcagcatga gcagcaccgt tgaatcgttt agcggaccca gacctacgac    600
gatgaaaccg gccacgacga agagatatcc tagaactcca ccggttgttc cggaggattg    660
tcacagcgat tgcgattcgt cgtcgtctgt aatcgacgac gacgacgata tcgcatcgtc    720
ttcacggcga cggaatccgc cgtttcaatt cgatcttaat tttccaccgt tggattgtgt    780
tgacttgttc aatggcgctg atgatcttca ctgtaccgat ctacgtctct aatgaattgg    840
taaaatcaaa ctcaaaatca cagatccgtg atcggtttga ttttaatcga aaacacacaa    900
caaaatcctt ttttttttt ttttaaattt tctgtttcgt tgatctcata taattttac     960
tatgcgggag aaatagaaag acaaagaaac gaagaagaag aagaagatgg tgatgagctt    1020
gagagagctt gagctggttc tgtgtttctt ctgtgatgat attgtaagag tattattatt    1080
ttactattat tactaaatct tcaaaaccaa gaagaagaag accgaacacg atgatctgtt    1140
gtgtctgttt gttttactgt aagaaaaacg cagatctggg tttcgttttt ttcttgagat    1200
agatcaaaca accccccatct ttgtaacata tacatttgga acactcatga ttctaaataa    1260
aaaatctaga atctttttttt c                                            1281
```

<210> SEQ ID NO 62
<211> LENGTH: 225
<212> TYPE: PRT
<213> ORGANISM: Arabidopsis thaliana
<220> FEATURE:
<223> OTHER INFORMATION: G1005 polypeptide

<400> SEQUENCE: 62

```
Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Ala Arg Val Trp Leu Gly Thr Phe Asp Ser Glu Glu Ala Ala
    50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Pro Pro Pro Asn Leu Arg
                85                  90                  95

Phe Asn Gln Ile Arg Asn Gln Asn Gln Asn Val Asp Pro Phe Met
            100                 105                 110

Asp His Arg Leu Phe Thr Asp His Gln Gln Gln Phe Pro Ile Val Asn
        115                 120                 125

Arg Pro Thr Ser Ser Ser Met Ser Ser Thr Val Glu Ser Phe Ser Gly
    130                 135                 140

Pro Arg Pro Thr Thr Met Lys Pro Ala Thr Thr Lys Arg Tyr Pro Arg
```

```
                145                 150                 155                 160
Thr Pro Pro Val Val Pro Glu Asp Cys His Ser Asp Cys Asp Ser Ser
                    165                 170                 175
Ser Ser Val Ile Asp Asp Asp Asp Ile Ala Ser Ser Ser Arg Arg
                180                 185                 190
Arg Asn Pro Pro Phe Gln Phe Asp Leu Asn Phe Pro Pro Leu Asp Cys
        195                 200                 205
Val Asp Leu Phe Asn Gly Ala Asp Asp Leu His Cys Thr Asp Leu Arg
    210                 215                 220
Leu
225

<210> SEQ ID NO 63
<211> LENGTH: 12
<212> TYPE: PRT
<213> ORGANISM: Arabidopsis thaliana
<220> FEATURE:
<221> NAME/KEY: misc_feature
<222> LOCATION: (2)..(3)
<223> OTHER INFORMATION: Xaa can be any naturally occurring amino acid,
      second Xaa is 1 to 3 residues in length
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<223> OTHER INFORMATION: EDLL Domain

<400> SEQUENCE: 63

Glu Xaa Xaa Asp Xaa Xaa Xaa Leu Xaa Xaa Xaa Leu
1               5                   10

<210> SEQ ID NO 64
<211> LENGTH: 333
<212> TYPE: DNA
<213> ORGANISM: Artificial sequence
<220> FEATURE:
<223> OTHER INFORMATION: P5381 LexAOP and polylinker sequence

<400> SEQUENCE: 64
acatatccat atctaatctt acctcgactg ctgtatataa aaccagtggt tatatgtcca      60
gtactgctgt atataaaacc agtggttata tgtacagtac gtcgatcgat cgacgactgc     120
tgtatataaa accagtggtt atatgtacag tactgctgta tataaaacca gtggttatat     180
gtacagtacg tcgaggggat gatcaagacc cttcctctat ataaggaagt tcatttcatt     240
tggagaggac acgctgacaa gctgactcta gcagatctgg taccgtcgac ggtgagctcc     300
gcggccgctc tagacaggcc tcgtaccgga tcc                                  333

<210> SEQ ID NO 65
<211> LENGTH: 406
<212> TYPE: DNA
<213> ORGANISM: Artificial sequence
<220> FEATURE:
<223> OTHER INFORMATION: P21195 GAL4 and polylinker sequence

<400> SEQUENCE: 65
agatctatgc ccaattttaa tcaaagtggg aatattgctg atagctcatt gtccttcact      60
ttcactaaca gtagcaacgg tccgaacctc ataacaactc aaacaaattc tcaagcgctt     120
```

```
tcacaaccaa ttgcctcctc taacgttcat gataacttca tgaataatga aatcacggct    180
agtaaaattg atgatggtaa taattcaaaa ccactgtcac ctggttggac ggaccaaact    240
gcgtataacg cgtttggaat cactacaggg atgtttaata ccactacaat ggatgatgta    300
tataactatc tattcgatga tgaagatacc ccaccaaacc caaaaaaaga gggtaccgtc    360
gacggtgagc tccgcggccg ctctagacag gcctcgtacc ggatcc                   406

<210> SEQ ID NO 66
<211> LENGTH: 411
<212> TYPE: DNA
<213> ORGANISM: Artificial sequence
<220> FEATURE:
<223> OTHER INFORMATION: P21378 GAL4 and polylinker

<400> SEQUENCE: 66
agatctggta ccgtcgacgg tgagctccgc ggccgcccca attttaatca aagtgggaat     60
attgctgata gctcattgtc cttcactttc actaacagta gcaacggtcc gaacctcata    120
acaactcaaa caaattctca agcgctttca caaccaattg cctcctctaa cgttcatgat    180
aacttcatga ataatgaaat cacggctagt aaaattgatg atggtaataa ttcaaaacca    240
ctgtcacctg gttggacgga ccaaactgcg tataacgcgt ttggaatcac tacagggatg    300
tttaatacca ctacaatgga tgatgtatat aactatctat cgatgatga agataccca     360 ccaaacccaa aaaagagta gtaagctcta gacaggcctc gtaccggatc c             411

<210> SEQ ID NO 67
<211> LENGTH: 3523
<212> TYPE: DNA
<213> ORGANISM: Artificial sequence
<220> FEATURE:
<221> NAME/KEY: misc_feature
<222> LOCATION: (1)..(4)
<223> OTHER INFORMATION: n is a, c, g, or t
<220> FEATURE:
<223> OTHER INFORMATION: P5375 pMEN48 insert

<400> SEQUENCE: 67
nnnnaagctt tgagctccgc ggccgcaaga cccttcctct atataaggaa gttcatttca     60
tttggagagg acacgctcga gtataagagc tcatttttac aacaattacc acaacaaca    120 aacaacaaac aacattacaa ttacatttac aattaccatg gaagcgttaa cggccaggca    180
acaagaggtg tttgatctca tccgtgatca catcagccag acaggtatgc cgccgacgcg    240
tgcggaaatc gcgcagcgtt tggggttccg ttccccaaac gcggctgaag aacatctgaa    300
ggcgctggca cgcaaaggcg ttattgaaat tgtttccggc gcatcacgcg ggattcgtct    360
gttgcaggaa gaggaagaag ggttgccgct ggtaggtcgt gtggctgccg gtgaaccact    420
tctggcgcaa cagcatattg aaggtcatta tcaggtcgat ccttccttat tcaagccgaa    480
tgctgatttc ctgctgcgcg tcagcggat gtcgatgaaa gatatcggca ttatggatgg    540
tgacttgctg gcagtgcata aaactcagga tgtacgtaac ggtcaggtcg ttgtcgcacg    600
tattgatgac gaagttaccg ttaagcgcct gaaaaacag gcaataaag tcgaactgtt    660 gccagaaaat agcgagttta aaccaattgt cgtagatctt cgtcagcaga gcttcaccat    720
tgaagggctg gcggttgggg ttattcgcaa cggcgactgg ctggaattcc caattttaa    780 tcaaagtggg aatattgctg atagctcatt gtccttcact ttcactaaca gtagcaacgg    840
tccgaacctc ataacaactc aaacaaattc tcaagcgctt tcacaaccaa ttgcctcctc    900
taacgttcat gataacttca tgaataatga aatcacggct agtaaaattg atgatggtaa    960
```

```
taattcaaaa ccactgtcac ctggttggac ggaccaaact gcgtataacg cgtttggaat    1020
cactacaggg atgtttaata ccactacaat ggatgatgta tataactatc tattcgatga    1080
tgaagatacc ccaccaaacc caaaaaaaga gtagctagag ctttcgttcg tatcatcggt    1140
ttcgacaacg ttcgtcaagt tcaatgcatc agtttcattg cgcacacacc agaatcctac    1200
tgagtttgag tattatggca ttgggaaaac tgttttcctt gtaccatttg ttgtgcttgt    1260
aatttactgt gttttttatt cggttttcgc tatcgaactg tgaaatggaa atggatggag    1320
aagagttaat gaatgatatg gtccttttgt tcattctcaa attaatatta tttgtttttt    1380
ctcttatttg ttgtgtgttg aatttgaaat tataagagat atgcaaacat tttgttttga    1440
gtaaaaatgt gtcaaatcgt ggcctctaat gaccgaagtt aatatgagga gtaaaacact    1500
tgtagttgta ccattatgct tattcactag gcaacaaata tattttcaga cctagaaaag    1560
ctgcaaatgt tactgaatac aagtatgtcc tcttgtgttt tagacattta tgaactttcc    1620
tttatgtaat tttccagaat ccttgtcaga ttctaatcat tgctttataa ttatagttat    1680
actcatggat ttgtagttga gtatgaaaat attttttaat gcattttatg acttgccaat    1740
tgattgacaa catgcatcaa tctagaacat atccatatct aatcttacct cgactgctgt    1800
atataaaacc agtggttata tgtccagtac tgctgtatat aaaaccagtg gttatatgta    1860
cagtacgtcg atcgatcgac gactgctgta tataaaacca gtggttatat gtacagtact    1920
gctgtatata aaaccagtgg ttatatgtac agtacgtcga ggggatgatc aagacccttc    1980
ctctatataa ggaagttcat ttcatttgga gaggacacgc tcgagtataa gagctcattt    2040
ttacaacaat taccaacaac aacaaacaac aaacaacatt acaattacat ttacaattac    2100
catggtgagc aagggcgagg agctgttcac cggggtggtg cccatcctgg tcgagctgga    2160
cggcgacgta aacggccaca agttcagcgt gtccggcgag ggcgagggcg atgccaccta    2220
cggcaagctg accctgaagt tcatctgcac caccggcaag ctgcccgtgc cctggcccac    2280
cctcgtgacc accctgacct acggcgtgca gtgcttcagc cgctaccccg accacatgaa    2340
gcagcacgac ttcttcaagt ccgccatgcc cgaaggctac gtccaggagc gcaccatctt    2400
cttcaaggac gacggcaact acaagacccg cgccgaggtg aagttcgagg gcgacaccct    2460
ggtgaaccgc atcgagctga agggcatcga cttcaaggag gacggcaaca tcctggggca    2520
caagctggag tacaactaca acagccacaa cgtctatatc atggccgaca gcagaagaa    2580 cggcatcaag gtgaacttca gatccgcca acatcgag gacggcagcg tgcagctcgc    2640
cgaccactac cagcagaaca cccccatcgg cgacggcccc gtgctgctgc ccgacaacca    2700
ctacctgagc acccagtccg ccctgagcaa agacccaaac gagaagcgcg atcacatggt    2760
cctgctggag ttcgtgaccg ccgccgggat cactctcggc atggacgagc tgtacaagtc    2820
cggagggatc ctctagctag agctttcgtt cgtatcatcg gtttcgacaa cgttcgtcaa    2880
gttcaatgca tcagtttcat tgcgcacaca ccagaatcct actgagtttg agtattatgg    2940
cattgggaaa actgttttc ttgtaccatt tgttgtgctt gtaatttact gtgttttta    3000 ttcggttttc gctatcgaac tgtgaaatgg aaatggatgg agaagagtta atgaatgata    3060
tggtcctttt gttcattctc aaattaatat tatttgtttt ttctcttatt tgttgtgtgt    3120
tgaatttgaa attataagag atatgcaaac attttgtttt gagtaaaaat gtgtcaaatc    3180
gtggcctcta atgaccgaag ttaatatgag gagtaaaaca cttgtagttg taccattatg    3240
cttattcact aggcaacaaa tatattttca gacctagaaa agctgcaaat gttactgaat    3300
```

-continued

```
acaagtatgt cctcttgtgt tttagacatt tatgaacttt cctttatgta attttccaga      3360
atccttgtca gattctaatc attgctttat aattatagtt atactcatgg atttgtagtt      3420
gagtatgaaa atattttta atgcatttta tgacttgcca attgattgac aacatgcatc       3480
aatcgacctg cagccactcg aagcggccgg ccgccactcg aga                       3523
```

<210> SEQ ID NO 68
<211> LENGTH: 3158
<212> TYPE: DNA
<213> ORGANISM: Artificial sequence
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (17)..(52)
<223> OTHER INFORMATION: n is a, c, g, or t
<220> FEATURE:
<223> OTHER INFORMATION: pMEN065 overexpression vector

<400> SEQUENCE: 68

```
aagcttnnnn ctgcagnnnn nnnnnnnnnn nnnnnnnnnn nnnnnnnnnn nntcggattc      60
cattgcccag ctatctgtca ctttattgtg aagatagtga aaagaaggt ggctcctaca      120 aatgccatca ttgcgataaa ggaaaggcca tcgttgaaga tgcctctgcc gacagtggtc      180
ccaaagatgg accccacccc acgaggagca tcgtggaaaa agaagacgtt ccaaccacgt      240
cttcaaagca agtggattga tgtgatggtc cgattgagac ttttcaacaa agggtaatat      300
ccggaaacct cctcggattc cattgcccag ctatctgtca ctttattgtg aagatagtgg      360
aaaaggaagg tggctcctac aaatgccatc attgcgataa aggaaaggcc atcgttgaag      420
atgcctctgc cgacagtggt cccaaagatg gacccccacc cacgaggagc atcgtggaaa      480
aagaagacgt tccaaccacg tcttcaaagc aagtggattg atgtgatatc tccactgacg      540
taagggatga cgcacaatcc cactatcctt cgcaagaccc ttcctctata taggaagtt       600 catttcattt ggagaggaca cgctgacaag ctgactctag cagatctggt accgtcgacg      660
gtgagctccg cggccgctct agacaggcct cgtaccggat cctctagcta gagctttcgt      720
tcgtatcatc ggtttcgaca acgttcgtca agttcaatgc atcagtttca ttgcgcacac      780
accagaatcc tactgagttt gagtattatg gcattgggaa aactgttttt cttgtaccat      840
ttgttgtgct tgtaatttac tgtgtttttt attcggtttt cgctatcgaa ctgtgaaatg      900
gaaatggatg gagaagagtt aatgaatgat atggtccttt tgttcattct caaattaata      960
ttatttgttt tttctcttat ttgttgtgtg ttgaatttga aattataaga gatatgcaaa     1020
cattttgttt tgagtaaaaa tgtgtcaaat cgtggcctct aatgaccgaa gttaatatga     1080
ggagtaaaac acttgtagtt gtaccattat gcttattcac taggcaacaa atatattttc     1140
agacctagaa aagctgcaaa tgttactgaa tacaagtatg tcctcttgtg ttttagacat     1200
ttatgaactt cctttatgt aattttccag atccttgtc agattctaat cattgcttta      1260
taattatagt tatactcatg gatttgtagt tgagtatgaa atattttttt aatgcatttt     1320
atgacttgcc aattgattga acatgcatca atcgacctg cagccactc gaagcggccg      1380 gccgccactc gagatcatga gcggagaatt aaggagtca cgttatgacc ccgccgatg      1440 acgcgggaca agccgtttta cgtttggaac tgacagaacc gcaacgttga aggagccact     1500
cagccgcggg tttctggagt ttaatgagct aagcacatac gtcagaaacc attattgcgc     1560
gttcaaaagt cgcctaaggt cactatcagc tagcaaatat ttcttgtcaa aaatgctcca     1620
```

```
ctgacgttcc ataaattccc ctcggtatcc aattagagtc tcatattcac tctcaatcca    1680
aataatctgc accggatctg gatcgtttcg catgattgaa caagatggat tgcacgcagg    1740
ttctccggcc gcttgggtgg agaggctatt cggctatgac tgggcacaac agacaatcgg    1800
ctgctctgat gccgccgtgt tccggctgtc agcgcagggg cgcccggttc ttttttgtcaa   1860
gaccgacctg tccggtgccc tgaatgaact gcaggacgag gcagcgcggc tatcgtggct    1920
ggccacgacg ggcgttcctt gcgcagctgt gctcgacgtt gtcactgaag cgggaaggga    1980
ctggctgcta ttgggcgaag tgccggggca ggatctcctg tcatctcacc ttgctcctgc    2040
cgagaaagta tccatcatgg ctgatgcaat gcggcggctg catacgcttg atccggctac    2100
ctgcccattc gaccaccaag cgaaacatcg catcgagcga gcacgtactc ggatggaagc    2160
cggtcttgtc gatcaggatg atctggacga agagcatcag gggctcgcgc cagccgaact    2220
gttcgccagg ctcaaggcgc gcatgcccga cggcgaggat ctcgtcgtga cccatggcga    2280
tgcctgcttg ccgaatatca tggtggaaaa tggccgcttt tctggattca tcgactgtgg    2340
ccggctgggt gtggcggacc gctatcagga catagcgttg gctacccgtg atattgctga    2400
agagcttggc ggcgaatggg ctgaccgctt cctcgtgctt tacggtatcg ccgctcccga    2460
ttcgcagcgc atcgccttct atcgccttct tgacgagttc ttctgagcgg gactctgggg    2520
ttcgaaatga ccgaccaagc gacgcccaac ctgccatcac gagatttcga ttccaccgcc    2580
gccttctatg aaaggttggg cttcggaatc gttttccggg acgccggctg atgatcctc    2640
cagcgcgggg atctcatgct ggagttcttc gcccacggga tctctgcgga acaggcggtc    2700
gaaggtgccg atatcattac gacagcaacg gccgacaagc acaacgccac gatcctgagc    2760
gacaatatga tcgggcccgg cgtccacatc aacggcgtcg gcggcgactg cccaggcaag    2820
accgagatgc accgcgatat cttgctgcgt tcggatattt tcgtggagtt cccgccacag    2880
acccggatga tccccgatcg ttcaaacatt tggcaataaa gtttcttaag attgaatcct    2940
gttgccggtc ttgcgatgat tatcatataa tttctgttga attacgttaa gcatgtaata    3000
attaacatgt aatgcatgac gttatttatg agatgggttt ttatgattag agtcccgcaa    3060
ttatacattt aatacgcgat agaaaacaaa atatagcgcg caaactagga taaattatcg    3120
cgcgcggtgt catctatgtt actagatcgg gctcgaga                            3158
```

<210> SEQ ID NO 69
<211> LENGTH: 574
<212> TYPE: DNA
<213> ORGANISM: Cauliflower mosaic virus
<220> FEATURE:
<223> OTHER INFORMATION: CaMV 35S promoter

<400> SEQUENCE: 69

```
gcggattcca ttgcccagct atctgtcact ttattgtgaa gatagtgaaa aagaaggtgg      60
ctcctacaaa tgccatcatt gcgataaagg aaaggccatc gttgaagatg cctctgccga    120
cagtggtccc aaagatggac ccccacccac gaggagcatc gtggaaaaag aagacgttcc    180
aaccacgtct tcaaagcaag tggattgatg tgatggtccg attgagactt ttcaacaaag    240
ggtaatatcc ggaaacctcc tcggattcca ttgcccagct atctgtcact ttattgtgaa    300
gatagtggaa aaggaaggtg gctcctacaa atgccatcat tgcgataaag gaaaggccat    360
cgttgaagat gcctctgccg acagtggtcc caaagatgga cccccaccca cgaggagcat    420
cgtggaaaaa gaagacgttc caaccacgtc ttcaaagcaa gtggattgat gtgatatctc    480
```

```
cactgacgta agggatgacg cacaatccca ctatccttcg caagacccctt cctctatata    540 aggaagttca tttcatttgg agaggacacg ctga                                574
```

<210> SEQ ID NO 70
<211> LENGTH: 1183
<212> TYPE: DNA
<213> ORGANISM: Arabidopsis thaliana
<220> FEATURE:
<223> OTHER INFORMATION: LTP1 (Lipid Transfer Protein 1) promoter

<400> SEQUENCE: 70

```
gatatgacca aaatgattaa cttgcattac agttgggaag tatcaagtaa acaacatttt      60
gtttttgttt gatatcggga atctcaaaac caaagtccac actagttttt ggactatata    120
atgataaaag tcagatatct actaatacta gttgatcagt atattcgaaa acatgacttt    180
ccaaatgtaa gttatttact ttttttttgc tattataatt aagatcaata aaaatgtcta    240
agttttaaat ctttatcatt atatccaaac aatcataatc ttattgttaa tctctcatca    300
acacacagtt tttaaaataa attaattacc ctttgcatga taccgaagag aaacgaattc    360
gttcaaataa ttttataaca ggaaataaaa tagataaccg aaataaacga tagaatgatt    420
tcttagtact aactcttaac aacagtttta tttaaatgac ttttgtaaaa aaaacaaagt    480
taacttatac acgtacacgt gtcgaaaata ttattgacaa tggatagcat gattcttatt    540
agagtcatgt aaaagataaa cacatgcaaa tatatatatg aataatatgt tgttaagata    600
aactagacga ttagaatata tagcacatct atagtttgta aaataactat ttctcaacta    660
gacttaagtc ttcgaaatac ataaataaac aaaactataa aaattcagaa aaaaacatga    720
gagtacgtta gtaaaatgta ttttttttggt aaaataatca cttttcatca ggtcttttgt    780
aaagcagttt tcatgttaga taaacgagat tttaattttt tttaaaaaaa gaagtaaact    840
aactatgttc ctatctacac acctataatt ttgaacaatt acaaaacaac aatgaaatgc    900
aaagaagacg tagggcactg tcacactaca atacgattaa taaatgtatt ttggtcgaat    960
taataacttt ccatacgata aagttgaatt aacatgtcaa acaaaagaga tgagtggtcc   1020
tatacatagt taggaattag gaacctctaa attaaatgag tacaaccacc aactactcct   1080
tccctctata atctatcgca ttcacaccac ataacatata cgtacctact ctatataaca   1140
ctcactcccc aaactctctt catcatccat cactacacac atc                     1183
```

<210> SEQ ID NO 71
<211> LENGTH: 1009
<212> TYPE: DNA
<213> ORGANISM: Lycopersicon esculentum
<220> FEATURE:
<223> OTHER INFORMATION: RBCS3 (Ribulose 1,5-bisphosphate carboxylase,
      small subunit 3) promoter

<400> SEQUENCE: 71

```
aaatggagta atatggataa tcaacgcaac tatatagaga aaaataata gcgctaccat       60 atacgaaaaa tagtaaaaaa ttataataat gattcagaat aaattattaa taactaaaaa    120
gcgtaaagaa ataaattaga gaataagtga tacaaaattg gatgttaatg gatacttctt    180
ataattgctt aaaaggaata caagatggga aataatgtgt tattattatt gatgtataaa    240
gaatttgtac aatttttgta tcaataaagt tccaaaaata atctttaaaa aataaaagta    300
cccttttatg aacttttttat caaataaatg aaatccaata ttagcaaaac attgatatta    360
ttactaaata tttgttaaat taaaaaatat gtcatttat ttttttaacag atattttta    420
```

| | |
|---|---|
| aagtaaatgt tataaattac gaaaaaggga ttaatgagta tcaaaacagc ctaaatggga | 480 |
| ggagacaata acagaaattt gctgtagtaa ggtggcttaa gtcatcattt aatttgatat | 540 |
| tataaaaatt ctaattagtt tatagtcttt cttttcctct tttgtttgtc ttgtatgcta | 600 |
| aaaaaggtat attatatcta taaattatgt agcataatga ccacatctgg catcatcttt | 660 |
| acacaattca cctaaatatc tcaagcgaag ttttgccaaa actgaagaaa agatttgaac | 720 |
| aacctatcaa gtaacaaaaa tcccaaacaa tatagtcatc tatattaaat cttttcaatt | 780 |
| gaagaaattg tcaaagacac atacctctat gagttttttc atcattttt ttttcttttt | 840 |
| taaactgtat ttttaaaaaa atattgaata aaacatgtcc tattcattag tttgggaact | 900 |
| ttaagataag gagtgtgtaa tttcagaggc cattaatttt gaaatgtcaa gagccacata | 960 |
| atccaatggt tatggttgct cttagatgag gttattgctt taggtgaaa | 1009 |

<210> SEQ ID NO 72
<211> LENGTH: 4361
<212> TYPE: DNA
<213> ORGANISM: Arabidopsis thaliana
<220> FEATURE:
<223> OTHER INFORMATION: STM (Shoot Meristemless) promoter

<400> SEQUENCE: 72

| | |
|---|---|
| agaatgtagc aatacaaata tatgacggta ccgttatcca tcaccattat atgtatatat | 60 |
| gtataatttg ataaatattc actttgtgtt tcgtcgtttg cttaataaac agctcatttc | 120 |
| catggtattg agtcttctat atgcgagaga atcagattcc cgctgggata caaaagaac | 180 |
| aaggtactga aaaaaataga caaaactttt ttttaaatta tataagctat aaaagaaaag | 240 |
| agtatagaga gagattagcc ctactgttta agagggagag agtagggtca ttagggcttt | 300 |
| agagagagaa gacattcgga ctgtccccac ttgcttttct gtagaataac attatttaaa | 360 |
| tcttattttt aattaaatat tacaactaaa agaagaaacc aacttttaaa ataaatgcag | 420 |
| attatatgct ctgacttgga ctaaataaaa cttgcaagta acagtttcaa gtccttttgt | 480 |
| tttagaactt tttctttcgt agaagtgata aatgattgcc ctagacctga tagattctct | 540 |
| aaaattctac gtattacagc ataagttacc tcctttattt gactattaga ccatccatat | 600 |
| tggtgggctt ttagcaaatg ttcttaacaa taatttata atttatttta atgttaagag | 660 |
| gtttgataat ttttttttt taagagtgta ttttgtttat taaaatgtgt tttgtttctt | 720 |
| atataagaac caaatcttaa ctatttacc aattaaacat taaatttaaa ttttaatatc | 780 |
| tctaagaatt atattaagag ccaatataga tgcttttaaa accattggtt gaataaataa | 840 |
| atctaacctt cttaattatt tctgtgtgaa tattttctaa attttcattt taatttagca | 900 |
| caatataatc catgttctaa aaagaacaat taacataata tttacaaacc taaaaagatt | 960 |
| ataaaacaca atttttatttt ttacagctta taatgtttta agttcaggt ttattttta | 1020 |
| aaagttcagg tttattacat taggtttgac ttgtaatcat catttatcac aacgatcaaa | 1080 |
| ctattattac aatcacaata gtagacaaaa tttaggatat atatatatat atataattat | 1140 |
| gtataaacta tgaacattta aagtgagatt tttcaaaata atatataaat tcaaatagaa | 1200 |
| atagactatt tggttcttaa atgagagacc cccgaaaaaa tctttttttt tttctcatca | 1260 |
| agctgtttac atttttagat ataaaatcat attcttata gtttagaata tgaattaaat | 1320 |
| agttttatat gttattaact tatcataaga tatgcgtgag gttggccaaa aactcatcaa | 1380 |
| ttaaccaaat aagaaaagta aaattgtatt ttgctttgct aaaaatgtaa atatttcatt | 1440 |
| gaaaaatgaa aaaggtttag gtaatacaat taagtaaatc ctacaatttt ggttccatgg | 1500 |

```
caaaagaata aaattgtatt gctttggtaa aagttgatcc aactaatata ttcagtagaa    1560
actgcaaaac tgaagaaata agtttgttta gtagaattgc tttcggttat gtaatgaata    1620
tacatccaaa atggcttttt agtaatgatg tcttttcata ctctttccaa tccctactac    1680
tttcagatta tttgtcctac tattatagag atatacgttc gttttcaata atatgaaaag    1740
tgatatatat ttaaatagtg tgatatatat ataagttttg caagtgcatc acttcccaaa    1800
atcgcataaa tcattaatca tattgtcgaa aacagtataa taacttctta aacgaaaacg    1860
cagcgcaatt aaaaataaca actagagata attgacaaaa cattgattaa tatttaccta    1920
taagttaatt attgtatttta aaatttattt aaagttcata aggaaaacat atgcaaaaat    1980
atttatatct aatattttgc tatgttatcc tttttttttt ttacgttatc ctaattttgt    2040
ttatcctaat ttgttgtggt taaaatctta ttattgataa aaagagaact ttttttttttg    2100 tcatcataaa aaagagaact tattacttcg atttttaaaat tctatgagcg taggagacaa    2160
agaaaaaaaa aataaaaaaa aaaagaagag aaaaatcact tcttttcttc tttttagtcc    2220
agatccaaca tattttggat aactaaatga agattttttta aaaaaatata ttttagggta    2280
tatataaatc ataatttgaa gcaaatgaaa taaaatccag tttggtaata tataaatatg    2340
atttgatggg ttccttgtaa tctctctcta tctattagtt tctcagttat cttttctttg    2400
ccagaaatgg cagtgaaggc agtggctgag gagagagttt ttttcttct ttcatgggga    2460 aagtaaaact ttgccttgaa gatttctctc ttcaatattt ttctaagact tttgatttca    2520
acgaatcact gtccttaacc taaaagcaag aaaaattagc tttatactgg tctttacttt    2580
tttttaacat atttatttt atatagttta cttataaaca tagacatacg agtatgggaa    2640
tatatagtat atccaacttc taaataatat ttcgaatagt gataacaaaa ttagcaatac    2700
atacggctag tgaaatgttg atcgaataaa cggcactgat gtaatgtact tatcaatttt    2760
gataatttta attgtattgt ttttcttttt ttcccacagt attgaactag acaattaaat    2820
ttaaagtaaa attatacatt tctttcgttg tgtattaaag taacatgcat aatatcattt    2880
tccttcgtac aatcctccaa attgacaatt gatgaattac tttgtcaatc gtaaatgaat    2940
ttttctcaag tctgtatact attttcaggg ataaacaggt acaggtgtcc catgcttatt    3000
ctcttgatag taacatgtgt cctatgttga gtcaattcta cgttcgaaga agtgctaaca    3060
attgttaata gcctcgtata ttattctaat taaaatgcct cgatagattt ggttagtggt    3120
ctgaatgtga ttggttattt tttcaagtgg caagaggtct accatctaat attacaatca    3180
atcgaccaaa aaggtcgaga acatgataat ggtggcaaat acaaatggtt cattgttgtc    3240
taatataaca agccatcagt tgtcactttt taaaaacaat acagaataca agatactttt    3300
tttttaaggt aaaatgtgtg tttaatatt tcgtttatat aacaaataaa cagttacatg    3360
ttttactcta tgattatatt tatgacattt ttcttcttct taacaacatt ttttttccat    3420
aagaacattt acaatagtat taaaactttg attgcaatca aatgttagat cacttattat    3480
aaaattacta agactgctat cttttcctat tgacaaaagc gaatccaata tatgttactg    3540
aaacaaatgc gtaaattata ctatatggag atctatcggt taattattga gagaatctaa    3600
gaaagttttt gagtacaaca gtcctaataa tatcttcaca taccatataa tatacatata    3660
tacatataca caaatgtact ttttaaacca acatcagcat acgtatatcc catcaggaaa    3720
cttagacttt tgggaattca tggtatgaaa accaaaacca aatgacaaca ttcgatttga    3780
tactcccgac ccatggtaaa gaaataacaa attccaatat atctttcact ggactttccg    3840
```

```
aggcacattc cggttttctc catttcaaga aattgtcaaa aataaattga gatccggttt    3900
attacctcaa aaagaagaa  gagaaattac aacattaatt tccgaaaagg cataaatgag    3960
aaatcatatt tcagcagaag aacacaaaag agttaagaac ccacagatca cacaacctct    4020
gtccatgtct gcttttaca  ctttttttaaa ataagtttct cctaaaaagt tatttcctat   4080
ttataataat ttccttagat ttatcttcct ggtctctctt ctgctgcttc cctctccccc    4140
ataactatca ctatttagaa ttttcaatgt ggaaaaggaa gctgattgtt gaagcataaa    4200
tcccgggaga ccacttttgc attttcaaat aattaaatta aaccatagat acacacacac    4260
agttacttac tcttttaggg tttcccaata aatttatagt actttaatgt gtttcatgat    4320
attgatgata aatgctagct gtatttacaa tgggggctcc t                       4361
```

<210> SEQ ID NO 73
<211> LENGTH: 1510
<212> TYPE: DNA
<213> ORGANISM: Arabidopsis thaliana
<220> FEATURE:
<223> OTHER INFORMATION: RD29A (Desiccation-responsive 29a) promoter

<400> SEQUENCE: 73

```
ggttgctatg gtagggacta tggggttttc ggattccggt ggaagtgagt ggggaggcag      60
tggcggaggt aagggagttc aagattctgg aactgaagat ttggggtttt gcttttgaat     120
gtttgcgttt ttgtatgatg cctctgtttg tgaactttga tgtatttat ctttgtgtga     180 aaaagagatt gggttaataa aatatttgct ttttggata agaaactctt ttagcggccc     240
attaataaag gttacaaatg caaaatcatg ttagcgtcag atatttaatt attcgaagat     300
gattgtgata gatttaaaat tatcctagtc aaaagaaag agtaggttga gcagaaacag      360
tgacatctgt tgtttgtacc atacaaatta gtttagatta ttggttaaca tgttaaatgg     420
ctatgcatgt gacatttaga ccttatcgga attaatttgt agaattatta attaagatgt     480
tgattagttc aaacaaaaat tttatattaa aaaatgtaaa cgaatatttt gtatgttcag     540
tgaaagtaaa acaaattaaa ttaacaagaa acttatagaa gaaattttt actatttaag     600 agaaagaaaa aaatctatca tttaatctga gtcctaaaaa ctgttatact taacagttaa     660
cgcatgattt gatggaggag ccatagatgc aattcaatca aactgaaatt tctgcaagaa     720
tctcaaacac ggagatctca aagtttgaaa gaaaatttat ttcttcgact caaaacaaac     780
ttacgaaatt taggtagaac ttatatacat tatattgtaa ttttttgtaa caaaatgttt     840
ttattattat tatagaattt tactggttaa attaaaaatg aatagaaaag gtgaattaag     900
aggagagagg aggtaaacat tttcttctat tttttcatat tttcaggata aattattgta     960
aaagtttaca agatttccat ttgactagtg taaatgagga atattctcta gtaagatcat    1020
tatttcatct acttcttta tcttctacca gtagaggaat aaacaatatt tagctccttt     1080
gtaaatacaa attaattttc cttcttgaca tcattcaatt ttaattttac gtataaaata    1140
aaagatcata cctattagaa cgattaagga gaaatacaat tcgaatgaga aggatgtgcc    1200
gtttgttata ataaacagcc acacgacgta acgtaaaat gaccacatga tgggccaata    1260
gacatggacc gactactaat aatagtaagt tacattttag gatggaataa atatcatacc    1320
gacatcagtt ttgaaagaaa agggaaaaaa agaaaaaata aataaagat atactaccga    1380 catgagttcc aaaaagcaaa aaaaagatc aagccgacac agacacgcgt agagagcaaa    1440
atgactttga cgtcacacca cgaaaacaga cgcttcatac gtgtcccttt atctctctca    1500
gtctctctat                                                          1510
```

<210> SEQ ID NO 74
<211> LENGTH: 2244
<212> TYPE: DNA
<213> ORGANISM: Arabidopsis thaliana
<220> FEATURE:
<223> OTHER INFORMATION: SUC2 (Sucrose-proton Symporter) promoter

<400> SEQUENCE: 74

| | | | | | |
|---|---|---|---|---|---|
| aactagggt | gcataatgat | ggaacaaagc | acaaatcttt | taacgcaaac | taactacaac | 60 |
| cttcttttgg | ggtccccatc | cccgaccca | atgttttgga | attaataaaa | ctacaatcac | 120 |
| ttaccaaaaa | ataaaagttc | aaggccacta | taatttctca | tatgaaccta | catttataaa | 180 |
| taaaatctgg | tttcatatta | atttcacaca | ccaagttact | ttctattatt | aactgttata | 240 |
| atggaccatg | aaatcatttg | catatgaact | gcaatgatac | ataatccact | ttgttttgtg | 300 |
| ggagacattt | accagatttc | ggtaaattgg | tattccccct | tttatgtgat | tggtcattga | 360 |
| tcattgttag | tggccagaca | tttgaactcc | cgttttttg | tctataagaa | ttcggaaaca | 420 |
| tatagtatcc | tttgaaaacg | gagaaacaaa | taacaatgtg | gacaaactag | atataatttc | 480 |
| aacacaagac | tatgggaatg | attttaccca | ctaattataa | tccgatcaca | aggtttcaac | 540 |
| gaactagttt | tccagatatc | aaccaaattt | actttggaat | taaactaact | taaaactaat | 600 |
| tggttgttcg | taaatggtgc | tttttttttt | tgcggatgtt | agtaaagggt | tttatgtatt | 660 |
| ttatattatt | agttatctgt | tttcagtgtt | atgttgtctc | atccataaag | tttatatgtt | 720 |
| ttttctttgc | tctataactt | atatatatat | atgagtttac | agttatattt | atacatttca | 780 |
| gatacttgat | cggcatttt | tttggtaaaa | aatatatgca | tgaaaaactc | aagtgtttct | 840 |
| tttttaagga | atttttaaat | ggtgattata | tgaatataat | catatgtata | tccgtatata | 900 |
| tatgtagcca | gatagttaat | tatttggggg | atatttgaat | tattaatgtt | ataatattct | 960 |
| ttcttttgac | tcgtctggtt | aaattaaaga | acaaaaaaaa | cacatacttt | tactgtttta | 1020 |
| aaaggttaaa | ttaacataat | ttattgatta | caagtgtcaa | gtccatgaca | ttgcatgtag | 1080 |
| gttcgagact | tcagagataa | cggaagagat | cgataattgt | gatcgtaaca | tccagatatg | 1140 |
| tatgtttaat | tttcatttag | atgtggatca | gagaagataa | gtcaaactgt | cttcataatt | 1200 |
| taagacaacc | tcttttaata | ttttcccaaa | acatgttta | tgtaactact | ttgcttatgt | 1260 |
| gattgcctga | ggatactatt | attctctgtc | tttattctct | tcacaccaca | tttaaatagt | 1320 |
| ttaagagcat | agaaattaat | tattttcaaa | aaggtgatta | tatgcatgca | aaatagcaca | 1380 |
| ccatttatgt | ttatatttc | aaattattta | atacatttca | atatttcata | agtgtgattt | 1440 |
| tttttttttt | tgtcaatttc | ataagtgtga | tttgtcattt | gtattaaaca | attgtatcgc | 1500 |
| gcagtacaaa | taacagtgg | gagaggtgaa | aatgcagtta | taaaactgtc | caataattta | 1560 |
| ctaacacatt | taaatatcta | aaaagagtgt | ttcaaaaaaa | attctttga | aataagaaaa | 1620 |
| gtgatagata | ttttttacgct | ttcgtctgaa | aataaaacaa | taatagttta | ttagaaaaat | 1680 |
| gttatcaccg | aaaattattc | tagtgccact | cgctcggatc | gaaattcgaa | agttatattc | 1740 |
| tttctctta | cctaatataa | aaatcacaag | aaaaatcaat | ccgaatatat | ctatcaacat | 1800 |
| agtatatgcc | cttacatatt | gtttctgact | tttctctatc | cgaatttctc | gcttcatggt | 1860 |
| tttttttaa | catattctca | tttaattttc | attactatta | tataactaaa | agatggaaat | 1920 |
| aaaataaagt | gtctttgaga | atcgaacgtc | catatcagta | agatagtttg | tgtgaaggta | 1980 |
| aaatctaaaa | gatttaagtt | ccaaaaacag | aaaataatt | attacgctaa | aaagaagaa | 2040 |

```
aataattaaa tacaaaacag aaaaaaataa tatacgacag acacgtgtca cgaagatacc    2100
ctacgctata gacacagctc tgttttctct tttctatgcc tcaaggctct cttaacttca    2160
ctgtctcctc ttcggataat cctatccttc tcttcctata aatacctctc cactcttcct    2220
cttcctccac cactacaacc acca                                           2244

<210> SEQ ID NO 75
<211> LENGTH: 2365
<212> TYPE: DNA
<213> ORGANISM: Arabidopsis thaliana
<220> FEATURE:
<223> OTHER INFORMATION: ARSK1 (Root-specific Kinase 1) promoter

<400> SEQUENCE: 75
ggcgagtgat ggtatattta ttggttgggc ttaaatatat ttcagatgca aaaccatatt      60
gaatcaataa attataaata catagcttcc ctaaccactt aaaccaccag ctacaaaacc     120
aataaacccg atcaatcatt atgttttcat aggatttcct gaacatacat taaattattt     180
ttcattttct tggtgctctt ttctgtctta ttcacgtttt aatggacata atcggtttca     240
tattgtaaat ctctttaacc taacgaacaa tttaatgacc ctagtaatag gataagaagg     300
tcgtgaaaaa tgaacgagaa aaacccacc aaaacactat ataagaaaga ccgaaaaagt     360
aaaaagggtg agccataaac caaaaacctt accagatgtt gtcaaagaac aaaaatcatc     420
atccatgatt aacctacgct tcactactaa gacaaggcga ttgtgtcccg gttgaaaagg     480
ttgtaaaaca gtttgaggat gctacaaaag tggatgttaa gtatgaagcg ctaaggttt     540 tggatttggt ctaggagcac attggttaag caatatcttc ggtggagatt gagtttttag     600
agatagtaga tactaattca tctatggaga catgcaaatt catcaaaatg cttggatgaa     660
ttagaaaaac taggtggaga atacagtaaa aaaattcaaa aagtgcatat tgtttggaca     720
acattaatat gtacaaatag tttacattta aatgtattat tttactaatt aagtacatat     780
aaagttgcta aactaaacta atataatttt tgcataagta aatttatcgt taaaagtttt     840
ctttctagcc actaaacaac aatacaaaat cgcccaagtc acccattaat taatttagaa     900
gtgaaaaaca aaatcttaat tatatggacg atcttgtcta ccatatttca agggctacag     960
gcctacagcc gccgaataaa tcttaccagc cttaaaccag aacaacggca aataagttca    1020
tgtggcggct ggtgatgatt cacaatttcc ccgacagttc tatgataatg aaactatata    1080
attattgtac gtacatacat gcatgcgacg aacaacactt caatttaatt gttagtatta    1140
aattacattt atagtgaagt atgttgggac gattagacgg atacaatgca cttatgttct    1200
ccggaaaatg aatcatttgt gttcagagca tgactccaag agtcaaaaaa gttattaaat    1260
ttatttgaat ttaaaactta aaaatagtgt aattttaac cacccgctgc cgcaaacgtt    1320
ggcggaagaa tacgcggtgt taaacaattt ttgtgatcgt tgtcaaacat ttgtaaccgc    1380
aatctctact gcacaatctg ttacgtttac aatttacaag ttagtataga agaacgttcg    1440
tacctgaaga ccaaccgacc tttagttatt gaataaatga ttatttagtt aagagtaaca    1500
aaatcaatgg ttcaaatttg tttctcttcc ttacttctta aattttaatc atggaagaaa    1560
caaagtcaac ggacatccaa ttatggccta atcatctcat tctcctttca acaaggcgaa    1620
tcaaatcttc tttatacgta atattttattt gccagcctga aatgtatacc aaatcatttt    1680
taaattaatt gcctaaatta ttagaacaaa aactattagt aaataactaa ttagtcttat    1740
gaaactagaa atcgagatag tggaatatag agagacacca ttaaattcac aaaatcatttt   1800 ttaaattacc taaattatta caacaaaaac tattagacag aactaagtct ataatgaaac    1860
```

```
gagagatcgt atttggaatg tagagcgaga gacaattttc aattcattga atatataagc    1920
aaaattatat agcccgtaga ctttggtgag atgaagtcta agtacaaaca actgaatgaa    1980
tttataatca ataatattga ttatattgtg attagaaaaa gaaacaact tgcgttattt    2040 ttcaatatta ttgtgaggat taatgtgaac atggaatcgt gtttctcctg aaaaaaatat    2100
cagcatagag cttagaacaa tataaatata tccaccaaaa ataacttcaa cattttata    2160 caactaatac aaaaaaaaaa aagcaaactt tttgtatata taaataaatt tgaaaactca    2220
aaggtcggtc agtacgaata agacacaaca actactataa attagaggac tttgaagaca    2280
agtaggttaa ctagaacatc cttaatttct aaacctacgc actctacaaa agattcatca    2340
aaaggagtaa aagactaact ttctc                                          2365

<210> SEQ ID NO 76
<211> LENGTH: 1176
<212> TYPE: DNA
<213> ORGANISM: Arabidopsis thaliana
<220> FEATURE:
<223> OTHER INFORMATION: CUT1 (Cuticular Wax Condensing Enzyme1)
      promoter

<400> SEQUENCE: 76
tgtgaattat attttactct tcgatatcgg ttgttgacga ttaaccatgc aaaaaagaaa      60
cattaattgc gaatgtaaat aacaaaacat gtaactcttg tagatataca tgtatcgaca     120
tttaaacccg aatatatatg tatacctata atttctctga ttttcacgct acctgccacg     180
tacatgggtg ataggtccaa actcacaagt aaaagtttac gtacagtgaa ttcgtctttt     240
tgggtataaa cgtacattta atttacacgt aagaaaggat taccaattct ttcatttatg     300
gtaccagaca gagttaaggc aaacaagaga aacatataga gttttgatat gttttcttgg     360
ataaatatta aattgatgca atatttaggg atggacacaa ggtaatatat gccttttaag     420
gtatatgtgc tatatgaatc gtttcgcatg ggtactaaaa ttatttgtcc ttactttata     480
taaacaaatt ccaacaaaat caagtttttg ctaaaactag tttatttgcg ggttatttaa     540
ttacctatca tattacttgt aatatcattc gtatgttaac gggtaaacca aaccaaaccg     600
gatattgaac tattaaaaat cttgtaaatt tgacacaaac taatgaatat ctaaattatg     660
ttactgctat gataacgacc attttttgttt ttgagaacca taatataaat tacaggtacg     720
tgacaagtac taagtattta tatccaccctt tagtcacagt accaatattg cgcctaccgg     780
gcaacgtgaa cgtgatcatc aaatcaaagt agttaccaaa cgctttgatc tcgataaaac     840
taaaagctga cacgtcttgc tgtttcttaa tttatttctc ttacaacgac aattttgaga     900
aatatgaaat ttttatatcg aaagggaaca gtccttatca tttgctccca tcacttgctt     960
ttgtctagtt acaactggaa atcgaagaga agtattacaa aaacattttt ctcgtcattt    1020 ataaaaaat gacaaaaaat taaatagaga gcaaagcaag agcgttgggt gacgttggtc    1080
tcttcattaa ctcctctcat ctacccctttc ctctgttcgc ctttatatcc ttcaccttcc    1140
ctctctcatc ttcattaact catcttcaaa aatacc                              1176

<210> SEQ ID NO 77
<211> LENGTH: 922
<212> TYPE: DNA
<213> ORGANISM: Lycopersion esculentum
<220> FEATURE:
<223> OTHER INFORMATION: RSI1 (Root System Inducible 1) promoter

<400> SEQUENCE: 77
```

| | |
|---|---|
| caatcaacta aatggacttt tcttgtgcat tggtcccatt tttacgccct aatattcgct | 60 |
| tacttgcttt tttgtatttt atttatttta gttttaattt tatctacctc caaattgata | 120 |
| gaaataatta cacttatagt cctttttgaaa aattataatt atagcattca agtaaataaa | 180 |
| aatacgtatt tttagtcact ttgtaatgta taattttgag ttgaaaatgt atcaaaagta | 240 |
| aatttatatt cttaagatat ggataaagtt tacatataca ttatccgttt catacccctat | 300 |
| ttatagtatt acattgcata agttattgta gatcttgatc gaaagtatgt gatattaata | 360 |
| ctattttttag aattatgtta ttctcagtta tggagtgata tttaaaatca atatagtata | 420 |
| tcgataatca gatagtttaa ttcttatttt ctccatccaa tttatataat gatattataa | 480 |
| tcaattttac gaatgagatg gatattttga aattttttagt ttaaaataaa ttttaaattt | 540 |
| tttgtgggtc tataaattat ctaattaaga ggtaaaatag aaagtttgaa attaattatt | 600 |
| acttactaaa tatataaata tgtcattttt tcttaaactg atttagaaga aaagagtgtc | 660 |
| atatacatgg acagaacgaa tataatttga taattaaatt tgtaaagatt catagttaat | 720 |
| agggatcaaa attgcacgta tccattacta taaggtcata tttgcttcat aaaaatcatc | 780 |
| aggatcaaaa atcagaattt atattatatt tgagggacta aaaatgctaa tatcacaaat | 840 |
| taaaattagt ctataaatat tcacacttta ctcttctaat tccatcaaat atttccattt | 900 |
| atcttctctt cttcttaaat at | 922 |

<210> SEQ ID NO 78
<211> LENGTH: 3446
<212> TYPE: DNA
<213> ORGANISM: Arabidopsis thaliana
<220> FEATURE:
<223> OTHER INFORMATION: AP1 (floral meristem-specific) promoter

<400> SEQUENCE: 78

| | |
|---|---|
| cacggaccctt ggatctgaag ttatgaacaa taacatattt ggcaaaacaa agaaaaaaga | 60 |
| aacaacaata ctaacatatt ttggtaaaag aacattgaga agtctcaaaa attaacttct | 120 |
| tcttattttg tttcctaata agaccgtttg cttcatttca agttcttagg aaataaatttc | 180 |
| atgtaacgtg tatgtagata tgtttatgta cagataaaga gagatctgaa aatgatatat | 240 |
| agagcttttg tggtgataag tgcaacaagc aggatatata tatcgaacgt ggtggttaga | 300 |
| agatagcgtc aaaatagatg ctagctgctg cgtatacatc atattcatat catatgtact | 360 |
| tctcttttgt gatttctcat gtgattgaac atactacata aatcttgata gatttataaa | 420 |
| aatgcaacaa attgttgttt atataagaaa aataaaacac tgatatgata tttcattagt | 480 |
| tattatcaaa tttgcaatat aatgtttaac atccaagatt tgttttacat aatcgttacg | 540 |
| gttactaaag tttaatttat gatgtttttaa aacaaattga gactaaatttt ctaaaagaaa | 600 |
| catatacgta catgtgtgta gctgcgtata tatatagaat ggtggggcta aaagctaatg | 660 |
| atgtgtacat taattggaca tttgatgtgg ctggattgga cccaacttgc tctttgatag | 720 |
| agacctaact aagacaattt tgctcttcat tcatttctcc cgtatacata attgaattaa | 780 |
| ctgtacataa tgtttcacaa caagcgatct agctatatat ttcaaaataa cagagactga | 840 |
| tattttaatc tggtcttcta agctctaacg tcaaattaaa aaaaaaatcc gatcttctaa | 900 |
| ttaattagaa gaaatcaatt atagaacctc tctctttaat ttcattttatt taaaactgct | 960 |
| tggaaattta attattcact aaagactcac tattctcctt aatttatgat aatttgtaga | 1020 |
| tcatatgttc agttttttatt tatttgccat tcgaatgttg agttttaatt aaaccaatat | 1080 |

```
gttaatattc gaattaaaaa aacttaccta taattcactt atttaaaaac ataaaataat    1140
aataattgca tcaccgtgat acaaagcaac ctcacaagtc acaactctcg tgactacaaa    1200
gatcactcat taaacaaacc ttcctgcctt ctttttttct acttgggcac ctcgaccgat    1260
cgaagactat tcttgggatc tgcttcaaaa acgactatat gttctaaatc cacttcgtat    1320
gatgacgaac atttggttta ctactgaaga tagagattac gtccttctaa ttagaagtaa    1380
ttaattattt tagtatttgg aagctaatgg tggagatgta accgtatctt agtggatcga    1440
gatattgtat ataaaatatg tatgctacat cgaataataa actgaaagag agtaaaaagg    1500
gatatttaat gggaagaaaa gaagggtgga gatgtaacaa aggcgaagat aatggatatt    1560
cttgggatgt tgtcttcaag gccacgagct tagattcttt tagttttgct caatttgtta    1620
agtttctact tttcctttttg ttgcttacta cttttgctca tgatctccat atacatatca    1680
tacatatata tagtatacta tctttagact gatttctcta tacactatct tttaacttat    1740
gtatcgtttc aaaactcagg acgtacatgt ttaaatttgg ttatataacc acgaccattt    1800
caagtatata tgtcatacca taccagattt aatataactt ctatgaagaa aatacataaa    1860
gttggattaa aatgcaagtg acatctttt agcataggtt catttggcat agaagaaata    1920
tataactaaa aatgaacttt aacttaaata gattttacta tattacaatt ttttcttttt    1980
acatggtcta atttatttt ctaaaattag tataattgtt gttttgatga aacaataata    2040
ccgtaagcaa tagttgctaa agatgtcca aatatttata aattacaaag taaatcaaat    2100
aaggaagaag acacgtggaa aacaccaaat aagagaagaa atggaaaaaa cagaaagaaa    2160
ttttttaaca agaaaaatca attagtcctc aaacctgaga tatttaaagt aatcaactaa    2220
aacaggaaca cttgactaac aaagaaattt gaaacgtggt ccaactttca cttaattata    2280
ttgttttctc taaggcttat gcaatatatg ccttaagcaa atgccgaatc tgttttttt    2340 tttttttgtta ttggatattg actgaaaata aggggttttt tcacacttga agatctcaaa    2400
agagaaaact attacaacgg aaattcattg taaaagaagt gattaagcaa attgagcaaa    2460 ggttttatg tggtttattt cattatatga ttgacatcaa attgtatata tatggttgtt    2520
ttatttaaca atatatatgg atataacgta caaactaaat atgtttgatt gacgaaaaaa    2580
aatatatgta tgtttgatta acaacatagc acatattcaa ctgatttttg tcctgatcat    2640
ctacaactta ataagaacac acaacattga acaaatcttt gacaaaatac tatttttggg    2700
tttgaaattt tgaatactta caattattct tctcgatctt cctctctttc cttaaatcct    2760
gcgtacaaat ccgtcgacgc aatacattac acagttgtca attggttctc agctctacca    2820
aaaacatcta ttgccaaaag aaaggtctat ttgtacttca ctgttacagc tgagaacatt    2880
aaatataata agcaaatttg ataaaacaaa gggttctcac cttattccaa aagaatagtg    2940 taaaatagg taatagagaa atgttaataa aaggaaatta aaaatagata ttttggttgg    3000
ttcagatttt gtttcgtaga tctacaggga atctccgcc gtcaatgcaa agcgaaggtg    3060
acacttgggg aaggaccagt ggtccgtaca atgttactta cccatttctc ttcacgagac    3120
gtcgataatc aaattgttta ttttcatatt tttaagtccg cagtttttatt aaaaaatcat    3180 ggacccgaca ttagtacgag ataccaat gagaagtcga cacgcaaatc ctaaagaaac    3240
cactgtggtt tttgcaaaca agagaaacca gctttagctt ttccctaaaa ccactcttac    3300
ccaaatctct ccataaataa agatcccgag actcaaacac aagtcttttt ataaaggaaa    3360
gaaagaaaaa ctttcctaat tggttcatac caaagtctga gctcttcttt atatctctct    3420
tgtagtttct tattgggggt ctttgt                                        3446
```

<210> SEQ ID NO 79
<211> LENGTH: 4801
<212> TYPE: DNA
<213> ORGANISM: Arabidopsis thaliana
<220> FEATURE:
<223> OTHER INFORMATION: AS1 (emergent leaf primordia-specific) promoter

<400> SEQUENCE: 79

```
ggaccgtgta atgggccatt gggccaagtt ttcttgatat aaaatctgaa atactactaa      60
attacaattt ttcttaaact cgatttcata attcatgtgg gactcagttc tccgcgtctt     120
atgacttaag agttaagagt aaagacaatt gattgtagtt tgcattatta aggttgtgat     180
tttaaaggct atattggccc aggcaaagtg gttatgaaag ttaaaaggta ttattaaatg     240
tcgttatgga ctagctaaag aaaagagatg gatatagaaa cggatttgcc agtttgtgag     300
gttacgtact cgttactttc tattgcattt tgtgtgtca ttgtgcttgt gatttcttta      360
gtatatgttt ttcttttgt caaactcttt agtacatgtt atgctttatt ttcttgttta      420
gcattgttat tgttattttg atccatgttc ttttacttaa tgtgtagagt gttcacgtac     480
gactctttat gatcgctata ctaatatact atgaaactcg aatgagaaca tgcatgtcat     540
aaatcaataa aacataacat acgacactta acctaaatca tacattcatt gattcatact     600
atcatgatcc tcatcacatt agtatcattt gtctttattt attacttagc tacttcgtta     660
tcttattata tctttacctg ttctgctggt catttgccat aaacaccaag tacaagcaac     720
tctttagtcc aatatcagac caaattaaca aacatttccc caatccaaaa cggaaattta     780
attataatta gcatttaaat aggttcgatt acaaaaaaaa atcaacaaag gaacaagtca     840
atttcataat ggtttgtcaa ttgtcacaca acgaaatggc tagccggatc aagcatgcat     900
gatccaaatt tcaacatttc catgataacc tgaattataa cgtctacata aaccatattt     960
aaataaatag gatggtcgaa agatatcatt aaaagaacga ttcaatattc tttattgttc    1020
aattgataca catgttattc tccttaacca gttatgaaca tgtcctacaa gtttcttgac    1080
ccaaactcat aatttcatat accataatcc caagttaagt ttttttttt tggggatcaa     1140
aatctcaagt taagttaagt tcaattattt agctgtaatg ctcggaaaaa agatcggatg    1200
aatatccaat tggttcaata tatccccaa tccggccaat ctccctatct ttatagctta    1260
attattagag aatggtcaat tcacgccatc agaaccagtt tcatatcttc atgaaccaaa    1320
acgcctacaa ccctattatt caagaaatca ctataattgt ccaagtaaaa ccattaatta    1380
accgagtcga ttttctatg gtcctatagg catgttgtta ctcaaactac tgattaatta     1440
ataagaagtt gtagtttgaa aaagaatcta gctgaaaaat actcctactc taagaattta    1500
agttagaata aaacatatta atacaaatat aaaaatttag ttattaaaaa agcgctacta    1560
ccaagacgtc ctaaagaaaa actagctttg tcttctaaaa gaaaacctag cttaactacc    1620
caaaaaaatc tagttttaca aacactaaag acaaatttta tttttcaaca aatttaccaa    1680
ttaaagaaaa ttccatgtag gaatgtatcc aaattgaaaa tatccctaca tatttttgtag   1740
gaaaaaaggt tttataaat attaaaaaaa cgagaaaaag aaaagagaaa agagaaaaaa     1800
aaaagccgga gagaatggag cacatgaggt aaaaggcaag agatggcaga gagaagatca    1860
gagaagggat ctgcctcaat ttgacaactc atatgtcatg tcatttccct cactactatt    1920
attttcctat ttcaaaaaca cctttctctg ataccatcac cttttacctt ctctttttt     1980
ttactgtctt tgctctgttt cacattccct tctatatata cagtatagta tattttatcc    2040
```

```
ttcttttatt gttttgctta ctaaaagttt ttttcctccg gaatcaaaat tctaaaatgt    2100
atatcatgtt aggtcgcgag ggccatgcaa tattatgaac tatgcatgat gattaatgtc    2160
tgtggatcca tcacaaatat tattgaaggt tgatcagaga ctatggacca aaatggtccg    2220
aatcgcctga taataaaaaa ctattcattt ttattttttta ttttttttat taaacatgtg    2280
attaatgata gatcttacga ttcgcaactg ggaaacatgc actaactcaa acttaaaaca    2340
cacaatacta aaagttctat taaattttga atgtaaagag aaatatatta ggcaatcaaa    2400
cggtcaagta aatcatacac atcgataatt tatttttta tccttcaaag caggcccatc     2460
caaggcccac cactattctc atatcaacat acttttcttg ttttggttaa atcaacctac    2520
catgttggct gttctctccg ctcctctgtg taagatcaca ccaacaccac tgcataattt    2580
cttgtattat tttgagactt gagagtaaac tgattgacaa aaaaaaaaaa aaaaaaaaa     2640 aattgagagt aaactagttt cttgaatatt gattttttca gcttaatttg ttggggaaag   2700
atattactac tattgctgta aaaaaaaaaa aaaaaaaaa agatattatt actatatttg    2760
tagtgatttt attttgaaaa ttctcttcac tttttttgtag ttaacattct aattttgtga   2820
aaagaacttt taatgtcagg tcatgtctct taaaaagttt gcatgatgaa atgatttaca    2880
aattacaata gaaaatggaa accattgcaa actaaatttt tatcaaaaaa aatcgaaaat    2940
aaaatgtatt gacttagtaa tgctgtgtct gctacgatta actattacac ataatgcaac    3000
actgaattat ccaaatacat tattagaata atagtattac agtatcacta ttacaacaac    3060
aatgtcaaca ataatcttat tataataata tataaataga ccttagtgac atcatatatt    3120
atagaaaaca tgtggttgcc taatttgtat aagctagata cttgggggtg atgagtgact    3180
agttgatgca atgataaaag agtgaaagtt ttgtctgcct gattatagac gtcggagaaa    3240
tactaaaata cgctatgaag attttggcgc atggtagcag aaaaaaaaaa cggagggtgt    3300
gagtgagtag tggtagtcgg atgtgatgga acaaagaaaa gtattttttgg tagggttatg   3360 ggagagagaa ggggaccatt attacacact tacatgcttt ccccaaaaga taccattccc    3420 atttctgac acgtgtcccc ctcatcccca attactcata cgtcaaatcc aattttagc      3480 ctaaaagttt tttttatttg tttagccaaa tctattttac taattaaagt tttcaaatgg    3540
caaatagaaa gatcttctaa ggttttataa aattacttga ttatttctag ttttgctcat    3600
tttttaaata aaatttctct ttttttttctt gcaacattat tgattttttt tttgataggg   3660
agtaacatta gtgatgttct atctcttctc attgcaaaaa ctttattttc tcatctctat    3720
ttgatcatca ttgcgaaatc ttccattttc aacaaatact tttccatgtt aatatgctgt    3780
ttcaaaatat aagtgtttgg aaaataaatc aacaagttta aatgttaact atttttatgc    3840
tattataatt attttttctta tgggtaagtg gaaattaatg ttactcaaat tggacataaa   3900
attctattgt ttgagtgaag gagtttataa atggagcatt attttcttga atggttagtt    3960
tttcttctat cattttgaca agtaaatgac ttttcagcca ctaaagtaca cactttttc    4020 atttaaattt aaagcatccc ctacattaga ttgtcatttt atttctcata atgttataga    4080
aaaatgaatt ttgagatccc aatgtagtaa atatatataa aaaaggttt aatattgtca     4140 atgacaaaca acgaacttat ggaatttcaa cttttcacct ccacgcgcct ctgtcagagt    4200 ttttttttc cccacttgtg atgtaaaaag gggaaacgt ctgtgtctca gtcggtaaac      4260 ttttctctc tttttttttt taaagatttt attttaatta tgccgtctct gtggtctaat     4320
cgtgtacgtc gtctggtttt aaaagcctct ctcactttgg tcttttcgtt ttctctcttc    4380 catttctcc aactatataa aaaaaaaaaa gtgagagaga gagcaaatct gtgtgatgga     4440
```

```
agttgctctt gagtttggga ttatttatct tttcaatatc atttggtaag catttttatt    4500
ttgttttata gtaataattt taactctctt atcttcttaa taagtctttg cttaatagtg    4560
ttttggggtc agcattaatt tcccctgttt ggtttccaga atataggttg tatagtgtga    4620
taataacaaa ttattccaag ttttgcttca aacattgtca aagttttttgt catttttcatt    4680 tcttgaaacg gaaatttttc agactttgta aatttctaatt cgaaaattcg acagatcttg    4740
tagatttgtt tcgatctttt agagttttga attggagaga tttatgaaac gggttgattt    4800
t                                                                     4801

<210> SEQ ID NO 80
<211> LENGTH: 4276
<212> TYPE: DNA
<213> ORGANISM: artificial sequence
<220> FEATURE:
<223> OTHER INFORMATION: P6506(35S::m35S::oEnh::LexAGal4)

<400> SEQUENCE: 80
catgcctgca ggtccccaga ttagccttttt caatttcaga aagaatgcta acccacagat      60
ggttagagag gcttacgcag caggtctcat caagacgatc tacccgagca ataatctcca     120
ggaaatcaaa taccttccca agaaggttaa agatgcagtc aaaagattca ggactaactg     180
catcaagaac acagagaaag atatatttct caagatcaga agtactattc cagtatggac     240
gattcaaggc ttgcttcaca aaccaaggca agtaatagag attggagtct ctaaaaaggt     300
agttcccact gaatcaaagg ccatggagtc aaagattcaa atagaggacc taacagaact     360
cgccgtaaag actggcgaac agttcataca gagtctctta cgactcaatg acaagaagaa     420
aatcttcgtc aacatggtgg agcacgacac acttgtctac tccaaaaata tcaaagatac     480
agtctcagaa gaccaaaggg caattgagac ttttcaacaa agggtaatat ccggaaacct     540
cctcggattc cattgcccag ctatctgtca ctttattgtg aagatagtgg aaaaggaagg     600
tggctcctac aaatgccatc attgcgataa aggaaaggcc atcgttgaag atgcctctgc     660
cgacagtggt cccaaagatg gacccccacc cacgaggagc atcgtggaaa agaagacgt      720 tccaaccacg tcttcaaagc aagtggattg atgtgatatc tccactgacg taagggatga     780
cgcacaatcc cactatcctt cggcggccgc aagacccttc ctctatataa ggaagttcat     840
ttcatttgga gaggacacgc tcgagtataa gagctcattt ttacaacaat taccaacaac     900
aacaaacaac aaacaacatt acaattacat ttacaattac catggaagcg ttaacggcca     960
ggcaacaaga ggtgtttgat ctcatccgtg atcacatcag ccagacaggt atgccgccga    1020
cgcgtgcgga atcgcgcag cgtttggggt tccgttcccc aaacgcggct gaagaacatc    1080
tgaaggcgct ggcacgcaaa ggcgttattg aaattgtttc cggcgcatca cgcgggattc    1140
gtctgttgca ggaagaggaa gaagggttgc cgctggtagg tcgtgtggct gccggtgaac    1200
cacttctggc gcaacagcat attgaaggtc attatcaggt cgatcccttc ctattcaagc    1260
cgaatgctga tttcctgctg cgcgtcagcg ggatgtcgat gaaagatatc ggcattatgg    1320
atggtgactt gctggcagtg cataaaactc aggatgtacg taacggtcag gtcgttgtcg    1380
cacgtattga tgacgaagtt accgttaagc gcctgaaaaa acagggcaat aaagtcgaac    1440
tgttgccaga aaatagcgag tttaaaccaa ttgtcgtaga tcttcgtcag cagagcttca    1500
ccattgaagg gctggcggtt ggggttattc gcaacggcga ctggctggaa ttccccaatt    1560
ttaatcaaag tgggaatatt gctgatagct cattgtcctt cactttcact aacagtagca    1620
```

```
acggtccgaa cctcataaca actcaaacaa attctcaagc gctttcacaa ccaattgcct      1680
cctctaacgt tcatgataac ttcatgaata atgaaatcac ggctagtaaa attgatgatg      1740
gtaataattc aaaaccactg tcacctggtt ggacggacca aactgcgtat aacgcgtttg      1800
gaatcactac agggatgttt aataccacta caatggatga tgtatataac tatctattcg      1860
atgatgaaga tacccacca aacccaaaaa aagagtagct agagcttccg ttcgtatcat       1920
cggtttcgac aacgttcgtc aagttcaatg catcagtttc attgcgcaca caccagaatc      1980
ctactgagtt tgagtattat ggcattggga aaactgtttt tcttgtacca tttgttgtgc      2040
ttgtaattta ctgtgttttt tattcggttt tcgctatcga actgtgaaat ggaaatggat      2100
ggagaagagt taatgaatga tatggtcctt ttgttcattc tcaaattaat attatttgtt      2160
ttttctctta tttgttgtgt gttgaatttg aaattataag agatatgcaa acattttgtt      2220
ttgagtaaaa atgtgtcaaa tcgtggcctc taatgaccga agttaatatg aggagtaaaa      2280
cacttgtagt tgtaccatta tgcttattca ctaggcaaca aatatatttt cagacctaga      2340
aaagctgcaa atgttactga atacaagtat gtcctcttgt gttttagaca tttatgaact      2400
ttcctttatg taattttcca gaatccttgt cagattctaa tcattgcttt ataattatag      2460
ttatactcat ggatttgtag ttgagtatga aaatattttt taatgcattt tatgacttgc      2520
caattgattg acaacatgca tcaatctaga acatatccat atctaatctt acctcgactg      2580
ctgtatataa aaccagtggt tatatgtcca gtactgctgt atataaaacc agtggttata      2640
tgtacagtac gtcgatcgat cgacgactgc tgtatataaa accagtggtt atatgtacag      2700
tactgctgta tataaaacca gtggttatat gtacagtacg tcgagggat gatcaagacc       2760 cttcctctat ataaggaagt tcatttcatt tggagaggac acgctcgagt ataagagctc      2820 attttacaa caattaccaa caacaacaaa caacaaacaa cattacaatt acatttacaa       2880
ttaccatggt gagcaagggc gaggagctgt tcaccggggt ggtgcccatc ctggtcgagc      2940
tggacggcga cgtaaacggc cacaagttca gcgtgtccgg cgagggcgag ggcgatgcca      3000
cctacggcaa gctgaccctg aagttcatct gcaccaccgg caagctgccc gtgccctggc      3060
ccaccctcgt gaccaccctg acctacggcg tgcagtgctt cagccgctac cccgaccaca      3120
tgaagcagca cgacttcttc aagtccgcca tgcccgaagg ctacgtccag gagcgcacca      3180
tcttcttcaa ggacgacggc aactacaaga cccgcgccga ggtgaagttc gagggcgaca      3240
ccctggtgaa ccgcatcgag ctgaagggca tcgacttcaa ggaggacggc aacatcctgg      3300
ggcacaagct ggagtacaac tacaacagcc acaacgtcta tatcatggcc gacaagcaga      3360
agaacggcat caaggtgaac ttcaagatcc gccacaacat cgaggacggc agcgtgcagc      3420
tcgccgacca ctaccagcag aacaccccca tcggcgacgg ccccgtgctg ctgcccgaca      3480
accactacct gagcacccag tccgccctga gcaaagaccc caacgagaag cgcgatcaca      3540
tggtcctgct ggagttcgtg accgccgccg ggatcactct cggcatggac gagctgtaca      3600
agtccggagg gatcctctag ctagagcttt cgttcgtatc atcggtttcg acaacgttcg      3660
tcaagttcaa tgcatcagtt tcattgcgca cacaccagaa tcctactgag tttgagtatt      3720
atggcattgg gaaaactgtt tttcttgtac catttgttgt gcttgtaatt tactgtgttt      3780
tttattcggt tttcgctatc gaactgtgaa atggaaatgg atggagaaga gttaatgaat      3840
gatatggtcc ttttgttcat tctcaaatta atattatttg ttttttctct tatttgttgt      3900
gtgttgaatt tgaaattata agagatatgc aaacattttg ttttgagtaa aatgtgtca       3960 aatcgtggcc tctaatgacc gaagttaata tgaggagtaa aacacttgta gttgtaccat      4020
```

```
tatgcttatt cactaggcaa caaatatatt ttcagaccta gaaaagctgc aaatgttact    4080
gaatacaagt atgtcctctt gtgttttaga catttatgaa cttccttta tgtaattttc     4140 cagaatcctt gtcagattct aatcattgct ttataattat agttatactc atggatttgt    4200
agttgagtat gaaaatattt tttaatgcat tttatgactt gccaattgat tgacaacatg    4260
catcaatcga cctgca                                                    4276

<210> SEQ ID NO 81
<211> LENGTH: 4801
<212> TYPE: DNA
<213> ORGANISM: artificial sequence
<220> FEATURE:
<223> OTHER INFORMATION: P5319 (prAS1::m35S::oEnh::LexAGal4(GFP))

<400> SEQUENCE: 81
ggaccgtgta atgggccatt gggccaagtt ttcttgatat aaaatctgaa atactactaa      60
attacaattt ttcttaaact cgatttcata attcatgtgg gactcagttc tccgcgtctt     120
atgacttaag agttaagagt aaagacaatt gattgtagtt tgcattatta aggttgtgat     180
tttaaaggct atattggccc aggcaaagtg gttatgaaag ttaaaggta ttattaaatg      240 tcgttatgga ctagctaaag aaaagagatg gatatagaaa cggatttgcc agtttgtgag     300
gttacgtact cgttactttc tattgcattt ttgtgtgtca ttgtgcttgt gatttcttta    360
gtatatgttt tcttttttgt caaactcttt agtacatgtt atgctttatt ttcttgttta    420
gcattgttat tgttatttg atccatgttc ttttacttaa tgtgtagagt gttcacgtac     480
gactctttat gatcgctata ctaatatact atgaaactcg aatgagaaca tgcatgtcat    540
aaatcaataa aacataacat acgacactta acctaaatca tacattcatt gattcatact    600
atcatgatcc tcatcacatt agtatcattt gtctttattt attacttagc tacttcgtta    660
tcttattata tctttacctg ttctgctggt catttgccat aaacaccaag tacaagcaac    720
tctttagtcc aatatcagac caaattaaca acatttccc caatccaaaa cggaaattta     780
attataatta gcatttaaat aggttcgatt acaaaaaaaa atcaacaaag gaacaagtca    840
atttcataat ggtttgtcaa ttgtcacaca acgaaatggc tagccggatc aagcatgcat    900
gatccaaatt tcaacatttc catgataacc tgaattataa cgtctacata accatatt     960 aaataaatag gatggtcgaa agatatcatt aaaagaacga ttcaatattc tttattgttc    1020
aattgataca catgttattc tccttaacca gttatgaaca tgtcctacaa gtttcttgac    1080
ccaaactcat aatttcatat accataatcc caagttaagt ttttttttt tggggatcaa     1140 aatctcaagt taagtaagt tcaattattt agctgtaatg ctcggaaaaa agatcggatg     1200
aatatccaat tggttcaata tatcccccaa tccggccaat ctccctatct ttatagctta    1260
attattagag aatggtcaat tcacgccatc agaaccagtt tcatatcttc atgaaccaaa    1320
acgcctacaa cccattatt caagaaatca ctataattgt ccaagtaaaa ccattaatta     1380
accgagtcga tttttctatg gtcctatagg catgttgtta ctcaaactac tgattaatta    1440
ataagaagtt gtagtttgaa aaagaatcta gctgaaaaat actcctactc taagaattta    1500
agttagaata aacatatta atacaaatat aaaaatttag ttattaaaaa agcgctacta     1560
ccaagacgtc ctaaagaaaa actagctttg tcttctaaaa gaaaacctag cttaactacc    1620 caaaaaatc tagttttaca aacactaaag acaaatttta ttttcaaca aatttaccaa      1680 ttaagaaaa ttccatgtag gaatgtatcc aaattgaaaa tatccctaca tattttgtag    1740
```

```
gaaaaaaggt ttttataaat attaaaaaaa cgagaaaaag aaaagagaaa agagaaaaaa    1800
aaaagccgga gagaatggag cacatgaggt aaaaggcaag agatggcaga gagaagatca    1860
gagaagggat ctgcctcaat tgacaactc atatgtcatg tcatttccct cactactatt     1920
attttcctat ttcaaaaaca cctttctctg ataccatcac cttttaccttt ctcttttttt   1980 ttactgtctt tgctctgttt cacattccct tctatatata cagtatagta tattttatcc   2040
ttcttttatt gttttgctta ctaaaagttt ttttcctccg gaatcaaaat tctaaaatgt   2100
atatcatgtt aggtcgcgag ggccatgcaa tattatgaac tatgcatgat gattaatgtc   2160
tgtggatcca tcacaaatat tattgaaggt tgatcagaga ctatggacca aaatggtccg   2220
aatcgcctga taataaaaaa ctattcattt ttattttta tttttttat taaacatgtg     2280 attaatgata gatcttacga ttcgcaactg ggaaacatgc actaactcaa acttaaaaca   2340
cacaatacta aaagttctat taaattttga atgtaaagag aaatatatta ggcaatcaaa   2400
cggtcaagta aatcatacac atcgataatt tattttttta tccttcaaag caggcccatc   2460
caaggcccac cactattctc atatcaacat acttttcttg ttttggttaa atcaacctac   2520
catgttggct gttctctccg ctcctctgtg taagatcaca ccaacaccac tgcataattt   2580
cttgtattat tttgagactt gagagtaaac tgattgacaa aaaaaaaaa aaaaaaaaa     2640 aattgagagt aaactagttt cttgaatatt gatttttca gcttaatttg ttggggaaag   2700
atattactac tattgctgta aaaaaaaaa aaaaaaaaa agatattatt actatatttg    2760
tagtgatttt attttgaaaa ttctcttcac ttttttgtag ttaacattct aattttgtga   2820
aaagaacttt taatgtcagg tcatgtctct taaaaagttt gcatgatgaa atgatttaca   2880
aattacaata gaaaatggaa accattgcaa actaaatttt tatcaaaaaa aatcgaaaat   2940
aaaatgtatt gacttagtaa tgctgtgtct gctacgatta actattacac ataatgcaac   3000
actgaattat ccaaatacat tattagaata atagtattac agtatcacta ttacaacaac   3060
aatgtcaaca ataatcttat tataataata tataaataga ccttagtgac atcatattat   3120
atagaaaaca tgtggttgcc taatttgtat aagctagata cttgggggtg atgagtgact   3180
agttgatgca atgataaaag agtgaaagtt ttgtctgcct gattatagac gtcggagaaa   3240
tactaaaata cgctatgaag attttggcgc atggtagcag aaaaaaaaaa cggagggtgt   3300
gagtgagtag tggtagtcgg atgtgatgga acaaagaaaa gtattttggg tagggttatg   3360
ggagagagaa ggggaccatt attacacact tacatgcttt ccccaaaaga taccattccc   3420
attttctgac acgtgtcccc ctcatcccca attactcata cgtcaaatcc aatttttagc   3480
ctaaaagttt tttttatttg tttagccaaa tctatttac taattaaagt ttcaaatgg    3540 caaatagaaa gatcttctaa ggtttataa aattacttga ttatttctag ttttgctcat   3600
tttttaaata aaatttctct tttttttctt gcaacattat tgattttttt tttgataggg   3660
agtaacatta gtgatgttct atctcttctc attgcaaaaa ctttattttc tcatctctat   3720
ttgatcatca ttgcgaaatc ttccattttc aacaaatact tttccatgtt aatatgctgt   3780
ttcaaaatat aagtgtttgg aaaataaatc aacaagttta aatgttaact ttttttatgc   3840
tattataatt attttctta tgggtaagtg gaaattaatg ttactcaaat tggacataaa    3900
attctattgt ttgagtgaag gagtttataa atggagcatt attttcttga atggttagtt   3960
tttcttctat cattttgaca agtaaatgac ttttcagcca ctaaagtaca cacttttc     4020 atttaaattt aaagcatccc ctacattaga ttgtcatttt atttctcata atgttataga   4080
aaaatgaatt ttgagatccc aatgtagtaa atatatataa aaaaaggttt aatattgtca   4140
```

```
atgacaaaca acgaacttat ggaatttcaa cttttcacct ccacgcgcct ctgtcagagt    4200 ttttttttc cccacttgtg atgtaaaaag gggaaaacgt ctgtgtctca gtcggtaaac     4260
tttttctctc tttttttttt taaagatttt attttaatta tgccgtctct gtggtctaat    4320
cgtgtacgtc gtctggtttt aaaagcctct ctcactttgg tcttttcgtt ttctctcttc    4380
cattttctcc aactatataa aaaaaaaaaa gtgagagaga gagcaaatct gtgtgatgga    4440
agttgctctt gagtttggga ttatttatct tttcaatatc atttggtaag cattttattt    4500
ttgttttata gtaataattt taactctctt atcttcttaa taagtctttg cttaatagtg    4560
ttttggggtc agcattaatt tccctgtttt ggtttccaga atataggttg tatagtgtga    4620
taataacaaa ttattccaag ttttgcttca aacattgtca aagtttttgt cattttcatt    4680
tcttgaaacg gaaatttttc agactttgta atttctaatt cgaaaattcg acagatcttg    4740
tagatttgtt tcgatctttt agagttttga attggagaga tttatgaaac gggttgattt    4800
t                                                                    4801

<210> SEQ ID NO 82
<211> LENGTH: 1176
<212> TYPE: DNA
<213> ORGANISM: artificial sequence
<220> FEATURE:
<223> OTHER INFORMATION: P5288 (prCUT1::m35S::oEnh::LexAGal4(GFP))

<400> SEQUENCE: 82
tgtgaattat attttactct tcgatatcgg ttgttgacga ttaaccatgc aaaaaagaaa      60
cattaattgc gaatgtaaat aacaaaacat gtaactcttg tagatataca tgtatcgaca    120
tttaaacccg aatatatatg tatacctata atttctctga ttttcacgct acctgccacg    180
tacatgggtg ataggtccaa actcacaagt aaaagtttac gtacagtgaa ttcgtctttt    240
tgggtataaa cgtacattta atttacacgt aagaaaggat taccaattct ttcatttatg    300
gtaccagaca gagttaaggc aaacaagaga acatataga gttttgatat gttttcttgg     360
ataaatatta aattgatgca atatttaggg atggacacaa ggtaatatat gccttttaag    420
gtatatgtgc tatatgaatc gtttcgcatg ggtactaaaa ttatttgtcc ttactttata    480
taaacaaatt ccaacaaaat caagtttttg ctaaaactag tttatttgcg ggttatttaa    540
ttacctatca tattacttgt aatatcattc gtatgttaac gggtaaacca aaccaaaccg    600
gatattgaac tattaaaaat cttgtaaatt tgacacaaac taatgaatat ctaaattatg    660
ttactgctat gataacgacc attttgttt tgagaacca taatataaat tacaggtacg      720
tgacaagtac taagtattta tatccaccct tagtcacagt accaatattg cgcctaccgg    780
gcaacgtgaa cgtgatcatc aaatcaaagt agttaccaaa cgctttgatc tcgataaaac    840
taaaagctga cacgtcttgc tgtttcttaa tttatttctc ttacaacgac aattttgaga    900
aatatgaaat tttttatatcg aaagggaaca gtccttatca tttgctccca tcacttgctt    960
ttgtctagtt acaactggaa atcgaagaga agtattacaa aaacattttt ctcgtcattt   1020
ataaaaaaat gacaaaaaat taaatagaga gcaaagcaag agcgttgggt gacgttggtc   1080
tcttcattaa ctcctctcat ctacccccttc tctgttcgc ctttatatcc ttcaccttcc   1140
ctctctcatc ttcattaact catcttcaaa aatacc                             1176

<210> SEQ ID NO 83
<211> LENGTH: 1183
<212> TYPE: DNA
```

<213> ORGANISM: artificial sequence
<220> FEATURE:
<223> OTHER INFORMATION: P5287 (prLTP1::m35S::oEnh::LexAGal4(GFP))

<400> SEQUENCE: 83

```
gatatgacca aaatgattaa cttgcattac agttgggaag tatcaagtaa acaacatttt      60
gtttttgttt gatatcggga atctcaaaac caaagtccac actagttttt ggactatata     120
atgataaaag tcagatatct actaatacta gttgatcagt atattcgaaa acatgacttt     180
ccaaatgtaa gttatttact ttttttttgc tattataatt aagatcaata aaaatgtcta     240
agttttaaat ctttatcatt atatccaaac aatcataatc ttattgttaa tctctcatca     300
acacacagtt tttaaaataa attaattacc ctttgcatga taccgaagag aaacgaattc     360
gttcaaataa ttttataaca ggaaataaaa tagataaccg aaataaacga tagaatgatt     420
tcttagtact aactcttaac aacagttttta tttaaatgac ttttgtaaaa aaaacaaagt     480
taacttatac acgtacacgt gtcgaaaata ttattgacaa tggatagcat gattcttatt     540
agagtcatgt aaaagataaa cacatgcaaa tatatatg aataatatgt tgttaagata       600
aactagacga ttagaatata tagcacatct atagtttgta aaataactat ttctcaacta     660
gacttaagtc ttcgaaatac ataaatacaa aaactataa aaattcagaa aaaacatga      720 gagtacgtta gtaaaatgta ttttttttggt aaaataatca ctttcatca ggtcttttgt     780 aaagcagttt tcatgttaga taaacgagat tttaatttttt tttaaaaaaa gaagtaaact    840
aactatgttc ctatctacac acctataatt ttgaacaatt acaaacaac aatgaaatgc     900 aaagaagacg tagggcactg tcacactaca atacgattaa taaatgtatt ttggtcgaat    960
taataacttt ccatacgata aagttgaatt aacatgtcaa acaaagaga tgagtggtcc    1020 tatacatagt taggaattag gaacctctaa attaaatgag tacaaccacc aactactcct   1080
tccctctata atctatcgca ttcacaccac ataacatata cgtacctact ctatataaca   1140
ctcactcccc aaactctctt catcatccat cactacacac atc                     1183
```

<210> SEQ ID NO 84
<211> LENGTH: 3446
<212> TYPE: DNA
<213> ORGANISM: artificial sequence
<220> FEATURE:
<223> OTHER INFORMATION: P5326 (prAP1::m35S::oEnh::LexAGal4(GFP))

<400> SEQUENCE: 84

```
cacggacctt ggatctgaag ttatgaacaa taacatattt ggcaaaacaa agaaaaaaga     60
aacaacaata ctaacatatt ttggtaaaag aacattgaga agtctcaaaa attaacttct    120
tcttattttg tttcctaata agaccgtttg cttcatttca agttcttagg aaataatttc    180
atgtaacgtg tatgtagata tgtttatgta cagataaaga gagatctgaa aatgatatat    240
agagcttttg tggtgataag tgcaacaagc aggatatata tatcgaacgt ggtggttaga    300
agatagcgtc aaaatagatg ctagctgctg cgtatacatc atattcatat catatgtact    360
tctcttttgt gatttctcat gtgattgaac atactacata aatcttgata gatttataaa    420
aatgcaacaa attgttgttt atataagaaa aataaaacac tgatatgata tttcattagt    480
tattatcaaa tttgcaatat aatgtttaac atccaagatt tgttttacat aatcgttacg    540
gttactaaag tttaatttat gatgttttaa aacaaattga gactaaattt ctaaaagaaa    600
catatacgta catgtgtgta gctgcgtata tatatagaat ggtggggcta aaagctaatg    660
atgtgtacat taattggaca tttgatgtgg ctggattgga cccaacttgc tctttgatag    720
```

```
agacctaact aagacaattt tgctcttcat tcatttctcc cgtatacata attgaattaa    780
ctgtacataa tgtttcacaa caagcgatct agctatatat ttcaaaataa cagagactga    840
tattttaatc tggtcttcta agctctaacg tcaaattaaa aaaaaaatcc gatcttctaa    900
ttaattagaa gaaatcaatt atagaacctc tctctttaat ttcatttatt taaaactgct    960
tggaaattta attattcact aaagactcac tattctcctt aatttatgat aatttgtaga   1020
tcatatgttc agttttatt tatttgccat tcgaatgttg agttttaatt aaaccaatat    1080
gttaatattc gaattaaaaa aacttaccta taattcactt atttaaaaac ataaaataat   1140
aataattgca tcaccgtgat acaaagcaac ctcacaagtc acaactctcg tgactacaaa   1200
gatcactcat taaacaaacc ttcctgcctt cttttttttct acttgggcac ctcgaccgat   1260
cgaagactat tcttgggatc tgcttcaaaa acgactatat gttctaaatc cacttcgtat   1320
gatgacgaac atttggttta ctactgaaga tagagattac gtccttctaa ttagaagtaa   1380
ttaattattt tagtatttgg aagctaatgg tggagatgta accgtatctt agtggatcga   1440
gatattgtat ataaaatatg tatgctacat cgaataataa actgaaagag agtaaaaagg   1500
gatatttaat gggaagaaaa gaagggtgga gatgtaacaa aggcgaagat aatggatatt   1560
cttgggatgt tgtcttcaag gccacgagct tagattcttt tagttttgct caatttgtta   1620
agtttctact tttccttttg ttgcttacta cttttgctca tgatctccat atacatatca   1680
tacatatata tagtatacta tctttagact gatttctcta tacactatct tttaacttat   1740
gtatcgtttc aaaactcagg acgtacatgt ttaaatttgg ttatataacc acgaccattt   1800
caagtatata tgtcatacca taccagattt aatataactt ctatgaagaa atacataaa    1860
gttggattaa aatgcaagtg acatcttttt agcataggtt catttggcat agaagaaata   1920
tataactaaa aatgaacttt aacttaaata gattttacta tattacaatt ttttcttttt   1980
acatggtcta atttattttt ctaaaattag tataattgtt gttttgatga acaataata    2040
ccgtaagcaa tagttgctaa agatgtccaa atatttata aattacaaag taaatcaaat    2100
aaggaagaag acacgtggaa acaccaaat aagagaagaa atggaaaaaa cagaaagaaa    2160
ttttttaaca agaaaaatca attagtcctc aaacctgaga tatttaaagt aatcaactaa   2220
aacaggaaca cttgactaac aaagaaattt gaacgtggt ccaactttca cttaattata    2280
ttgttttctc taaggcttat gcaatatatg ccttaagcaa atgccgaatc tgttttttt    2340
tttttttgtta ttggatattg actgaaaata aggggttttt tcacacttga agatctcaaa   2400
agagaaaact attacaacgg aaattcattg taaaagaagt gattaagcaa attgagcaaa   2460
ggttttatg tggtttattt cattatatga ttgacatcaa attgtatata tatggttgtt    2520
ttatttaaca atatatatgg atataacgta caaactaaat atgtttgatt gacgaaaaaa   2580
aatatatgta tgtttgatta acaacatagc acatattcaa ctgatttttg tcctgatcat   2640
ctacaactta ataagaacac acaacattga acaaatcttt gacaaaatac tattttggg    2700
tttgaaattt tgaatactta caattattct tctcgatctt cctctctttc cttaaatcct   2760
gcgtacaaat ccgtcgacgc aatacattac acagttgtca attggttctc agctctacca   2820
aaacatctca ttgccaaaag aaaggtctat ttgtacttca ctgttacagc tgagaacatt   2880
aaatataata agcaaatttg ataaaacaaa gggttctcac cttattccaa aagaatagtg   2940
taaaataggg taatagagaa atgttaataa aaggaaatta aaaatagata ttttggttgg   3000
ttcagatttt gtttcgtaga tctacaggga aatctccgcc gtcaatgcaa agcgaaggtg   3060
```

-continued

```
acacttgggg aaggaccagt ggtccgtaca atgttactta cccatttctc ttcacgagac      3120
gtcgataatc aaattgttta ttttcatatt tttaagtccg cagttttatt aaaaaatcat      3180
ggacccgaca ttagtacgag atataccaat gagaagtcga cacgcaaatc ctaaagaaac      3240
cactgtggtt tttgcaaaca agagaaacca gctttagctt ttccctaaaa ccactcttac      3300
ccaaatctct ccataaataa agatcccgag actcaaacac aagtcttttt ataaggaaa       3360 gaaagaaaaa ctttcctaat tggttcatac caaagtctga gctcttcttt atatctctct      3420
tgtagtttct tattgggggt ctttgt                                           3446
```

<210> SEQ ID NO 85
<211> LENGTH: 1009
<212> TYPE: DNA
<213> ORGANISM: artificial sequence
<220> FEATURE:
<223> OTHER INFORMATION: P5284 (prRBCS3::m35S::oEnh::LexAGal4(GFP))

<400> SEQUENCE: 85

```
aaatggagta atatggataa tcaacgcaac tatatagaga aaaataata gcgctaccat         60 atacgaaaaa tagtaaaaaa ttataataat gattcagaat aaattattaa taactaaaaa        120
gcgtaaagaa ataaattaga gaataagtga tacaaaattg gatgttaatg gatacttctt        180
ataattgctt aaaaggaata caagatggga aataatgtgt tattattatt gatgtataaa        240
gaatttgtac aatttttgta tcaataaagt tccaaaaata atctttaaaa aataaaagta        300 ccctttatg aactttttat caaatatatg aaatccaata ttagcaaaac attgatatta        360
ttactaaata tttgttaaat taaaaaatat gtcatttat tttttaacag atatttttta        420
aagtaaatgt tataaattac gaaaaaggga ttaatgagta tcaaaacagc ctaaatggga       480
ggagacaata acagaaattt gctgtagtaa ggtggcttaa gtcatcattt aatttgatat        540
tataaaaatt ctaattagtt tatagtcttt cttttcctct tttgtttgtc ttgtatgcta        600
aaaaaggtat attatatcta taaattatgt agcataatga ccacatctgg catcatcttt        660
acacaattca cctaaatatc tcaagcgaag ttttgccaaa actgaagaaa agatttgaac        720
aacctatcaa gtaacaaaaa tcccaaacaa tatagtcatc tatattaaat cttttcaatt        780
gaagaaattg tcaaagacac ataccctcat gagttttttc atcaattttt ttttcttttt        840
taaactgtat ttttaaaaaa atattgaata aaacatgtcc tattcattag tttgggaact        900
ttaagataag gagtgtgtaa tttcagaggc tattaatttt gaaatgtcaa gagccacata        960
atccaatggt tatggttgct cttagatgag gttattgctt taggtgaaa                   1009
```

<210> SEQ ID NO 86
<211> LENGTH: 2365
<212> TYPE: DNA
<213> ORGANISM: artificial sequence
<220> FEATURE:
<223> OTHER INFORMATION: P5311 (prARSK1::m35S::oEnh::LexAGal4(GFP))

<400> SEQUENCE: 86

```
ggcgagtgat ggtatattta ttggttgggc ttaaatatat ttcagatgca aaaccatatt         60
gaatcaataa attataaata catagcttcc ctaaccactt aaaccaccag ctacaaaacc       120
aataaacccg atcaatcatt atgttttcat aggattccct gaacatacat taaattattt       180
ttcattttct tggtgctctt ttctgtctta ttcacgtttt aatggacata atcggtttca       240
tattgtaaat ctctttaacc taacgaacaa tttaatgacc ctagtaatag gataagaagg       300
tcgtgaaaaa tgaacgagaa aaaacccacc aaaaacactat ataagaaaga ccgaaaagt       360
```

```
aaaaagggtg agccataaac caaaaacctt accagatgtt gtcaaagaac aaaaatcatc    420
atccatgatt aacctacgct tcactactaa gacaaggcga ttgtgtcccg gttgaaaagg    480
ttgtaaaaca gtttgaggat gctacaaaag tggatgttaa gtatgaagcg gctaaggttt    540
tggatttggt ctaggagcac attggttaag caatatcttc ggtggagatt gagttttag    600
agatagtaga tactaattca tctatggaga catgcaaatt catcaaaatg cttggatgaa    660
ttagaaaaac taggtggaga atacagtaaa aaaattcaaa aagtgcatat tgtttggaca    720
acattaatat gtacaaatag tttacattta aatgtattat tttactaatt aagtacatat    780
aaagttgcta aactaaacta ataatttt tgcataagta aatttatcgt taaaagtttt      840
ctttctagcc actaaacaac aatacaaaat cgcccaagtc acccattaat taatttagaa    900
gtgaaaaaca aaatcttaat tatatggacg atcttgtcta ccatatttca agggctacag    960
gcctacagcc gccgaataaa tcttaccagc cttaaaccag aacaacggca ataagttca    1020
tgtggcggct ggtgatgatt cacaatttcc ccgacagttc tatgataatg aaactatata   1080
attattgtac gtacatacat gcatgcgacg aacaacactt caatttaatt gttagtatta   1140
aattacattt atagtgaagt atgttgggac gattagacgg atacaatgca cttatgttct   1200
ccggaaaatg aatcatttgt gttcagagca tgactccaag agtcaaaaaa gttattaaat   1260
ttatttgaat ttaaaactta aaaatagtgt aattttaac cacccgctgc cgcaaacgtt    1320
ggcggaagaa tacgcggtgt taaacaattt ttgtgatcgt tgtcaaacat ttgtaaccgc   1380
aatctctact gcacaatctg ttacgtttac aattacaag ttagtataga agaacgttcg    1440
tacctgaaga ccaaccgacc tttagttatt gaataaatga ttatttagtt aagagtaaca   1500
aaatcaatgg ttcaaatttg tttctcttcc ttacttctta aattttaatc atggaagaaa   1560
caaagtcaac ggacatccaa ttatggccta atcatctcat tctcctttca acaaggcgaa   1620
tcaaatcttc tttatacgta atatttattt gccagcctga aatgtatacc aaatcatttt   1680
taaattaatt gcctaaatta ttagaacaaa aactattagt aaataactaa ttagtcttat   1740
gaaactagaa atcgagatag tggaatatag agagacacca ttaaattcac aaaatcattt   1800
ttaaattacc taaattatta caacaaaaac tattagacag aactaagtct ataatgaaac   1860
gagagatcgt atttggaatg tagagcgaga gacaattttc aattcattga atatataagc   1920
aaaattatat agcccgtaga ctttggtgag atgaagtcta agtacaaaca actgaatgaa   1980
tttataatca ataatattga ttatattgtg attagaaaaa gaaacaact tgcgttattt     2040
ttcaatatta ttgtgaggat taatgtgaac atggaatcgt gtttctcctg aaaaaaatat   2100
cagcatagag cttagaacaa tataaatata tccaccaaaa ataacttcaa cattttata    2160
caactaatac aaaaaaaaaa aagcaaactt tttgtatata taaataaatt tgaaaactca   2220
aaggtcggtc agtacgaata agacacaaca actactataa attagaggac tttgaagaca   2280
agtaggttaa ctagaacatc cttaatttct aaacctacgc actctacaaa agattcatca   2340
aaaggagtaa aagactaact ttctc                                         2365
```

<210> SEQ ID NO 87
<211> LENGTH: 922
<212> TYPE: DNA
<213> ORGANISM: artificial sequence
<220> FEATURE:
<223> OTHER INFORMATION: P5310 (prRSI1::m35S::oEnh::LexAGal4(GFP))

<400> SEQUENCE: 87

```
caatcaacta aatggacttt tcttgtgcat tggtcccatt tttacgccct aatattcgct      60
tacttgcttt tttgtatttt atttatttta gttttaattt tatctacctc caaattgata     120
gaaataatta cacttatagt cctttttgaaa aattataatt atagcattca agtaaataaa    180
aatacgtatt tttagtcact ttgtaatgta taattttgag ttgaaaatgt atcaaaagta     240
aatttatatt cttaagatat ggataaagtt tacatataca ttatccgttt catacccctat    300 ttatagtatt acattgcata agttattgta gatcttgatc gaaagtatgt gatattaata    360
ctatttttag aattatgtta ttctcagtta tggagtgata tttaaaatca atatagtata    420
tcgataatca gatagtttaa ttcttatttt ctccatccaa tttatataat gatattataa    480
tcaattttac gaatgagatg gatattttga aattttttagt ttaaaataaa ttttaaattt    540
tttgtgggtc tataaattat ctaattaaga ggtaaaatag aaagtttgaa attaattatt    600
acttactaaa tatataaata tgtcattttt tcttaaactg atttagaaga aaagagtgtc    660
atatacatgg acagaacgaa tataaatttga taattaaatt tgtaaagatt catagttaat    720
agggatcaaa attgcacgta tccattacta aaggtcata tttgcttcat aaaaatcatc     780
aggatcaaaa atcagaattt atattatatt tgagggacta aaaatgctaa tatcacaaat    840
taaaattagt ctataaatat tcacacttta ctcttctaat tccatcaaat atttccattt    900
atcttctctt cttcttaaat at                                              922

<210> SEQ ID NO 88
<211> LENGTH: 4361
<212> TYPE: DNA
<213> ORGANISM: artificial sequence
<220> FEATURE:
<223> OTHER INFORMATION: P5318 (prSTM::m35S::oEnh::LexAGal4(GFP))

<400> SEQUENCE: 88
agaatgtagc aatacaaata tatgacggta ccgttatcca tcaccattat atgtatatat     60
gtataatttg ataaatattc actttgtgtt tcgtcgtttg cttaataaac agctcatttc    120
catggtattg agtcttctat atgcgagaga atcagattcc cgctgggata acaaaagaac    180
aaggtactga aaaaaataga caaaactttt ttttaaatta tataagctat aaaagaaaag    240
agtatagaga gagattagcc ctactgttta agagggagag agtagggtca ttagggctttt    300 agagagagaa gacattcgga ctgtccccac ttgcttttct gtagaataac attatttaaa    360 tcttatttttt aattaaatat tacaactaaa agaagaaacc aacttttaaa ataaatgcag    420
attatatgct ctgacttgga ctaaataaaa cttgcaagta acagtttcaa gtcctttttgt   480 tttagaactt tttctttcgt agaagtgata aatgattgcc ctagacctga tagattctct    540
aaaattctac gtattacagc ataagttacc tcctttattt gactattaga ccatccatat    600
tggtgggctt ttagcaaatg ttcttaacaa taatttata atttatttta atgttaagag     660
gtttgataat tttttttttt taagagtgta ttttgtttat taaaatgtgt tttgtttctt    720 ataaagaac caaatcttaa ctatttttacc aattaaacat taaatttaaa ttttaatatc    780
tctaagaatt atattaagag ccaatataga tgcttttaaa accattggtt gaataaataa    840
atctaacctt cttaattatt tctgtgtgaa tattttctaa atttcattt taatttagca     900 caatataatc catgttctaa aaagaacaat taacataata tttacaaacc taaaaagatt    960
ataaaacaca atttttattttt ttacagctta taatgtttta aagttcaggt ttatttttta  1020
aaagttcagg tttattacat taggtttgac ttgtaatcat catttatcac aacgatcaaa   1080
ctattattac aatcacaata gtagacaaaa tttaggatat atatatatat ataaattat    1140
```

```
gtataaacta tgaacattta aagtgagatt tttcaaaata atatataaat tcaaatagaa    1200
atagactatt tggttcttaa atgagagacc cccgaaaaaa tctttttttt tttctcatca    1260
agctgtttac attttagat ataaaatcat attctttata gtttagaata tgaattaaat     1320
agttttatat gttattaact tatcataaga tatgcgtgag gttggccaaa aactcatcaa    1380
ttaaccaaat aagaaaagta aaattgtatt ttgctttgct aaaaatgtaa atatttcatt    1440
gaaaaatgaa aaaggtttag gtaatacaat taagtaaatc ctacaattttt ggttccatgg   1500 caaaagaata aaattgtatt gctttggtaa aagttgatcc aactaatata ttcagtagaa    1560
actgcaaaac tgaagaaata agtttgttta gtagaattgc tttcggttat gtaatgaata    1620
tacatccaaa atggcttttt agtaatgatg tcttttcata ctctttccaa tccctactac    1680
tttcagatta tttgtcctac tattatagag atatacgttc gttttcaata atatgaaaag    1740
tgatatatat ttaaatagtg tgatatatat ataagttttg caagtgcatc acttcccaaa    1800
atcgcataaa tcattaatca tattgtcgaa aacagtataa taacttctta aacgaaaacg    1860
cagcgcaatt aaaaataaca actagagata attgacaaaa cattgattaa tatttaccta    1920
taagttaatt attgtattta aaatttattt aaagttcata aggaaaacat atgcaaaaat    1980
atttatatct aatattttgc tatgttatcc tttttttttt ttacgttatc ctaattttgt    2040
ttatcctaat ttgttgtggt taaaatctta ttattgataa aaagagaact ttttttttg     2100 tcatcataaa aaagagaact tattacttcg attttaaaat tctatgagcg taggagacaa    2160
agaaaaaaaa aataaaaaaa aaaagaagag aaaaatcact tcttttcttc tttttagtcc    2220
agatccaaca tattttggat aactaaatga agatttttta aaaaaatata ttttagggta    2280
tatataaatc ataatttgaa gcaaatgaaa taaaatccag tttggtaata tataaatatg    2340
atttgatggg ttccttgtaa tctctctcta tctattagtt tctcagttat cttttctttg    2400
ccagaaatgg cagtgaaggc agtggctgag gagagagttt ttttcttct ttcatgggga    2460 aagtaaaact ttgccttgaa gatttctctc ttcaatattt ttctaagact tttgatttca    2520
acgaatcact gtccttaacc taaaagcaag aaaaattagc tttatactgg tctttacttt    2580
tttttaacat atttattttt atatagttta cttataaaca tagacatacg agtatgggaa    2640
tatatagtat atccaacttc taaataatat ttcgaatagt gataacaaaa ttagcaatac    2700
atacggctag tgaaatgttg atcgaataaa cggcactgat gtaatgtact tatcaatttt    2760
gataatttta attgtattgt ttttctttt ttcccacagt attgaactag acaattaaat     2820
ttaaagtaaa attatacatt tctttcgttg tgtattaaag taacatgcat aatatcattt    2880
tccttcgtac aatcctccaa attgacaatt gatgaattac tttgtcaatc gtaaatgaat    2940
ttttctcaag tctgtatact attttcaggg ataaacaggt acaggtgtcc catgcttatt    3000
ctcttgatag taacatgtgt cctatgttga gtcaattcta cgttcgaaga agtgctaaca    3060
attgttaata gcctcgtata ttattctaat taaaatgcct cgatagattt ggttagtggt    3120
ctgaatgtga ttggttattt tttcaagtgg caagaggtct accatctaat attacaatca    3180
atcgaccaaa aaggtcgaga acatgataat ggtggcaaat acaaatggtt cattgttgtc    3240
taatataaca agccatcagt tgtcactttt taaaaacaat acagaataca agatactttt    3300
tttttaaggt aaaatgtgtg tttaatattt tcgtttatat aacaaataaa cagttacatg    3360
ttttactcta tgattatatt tatgacattt ttcttcttct taacaacatt ttttcccat     3420 aagaacattt acaatagtat taaaactttg attgcaatca aatgttagat cacttattat    3480
```

```
aaaattactga agactgctat cttttcctat tgacaaaagc gaatccaata tatgttactg    3540
aaacaaatgc gtaaattata ctatatggag atctatcggt taattattga gagaatctaa    3600
gaaagttttt gagtacaaca gtcctaataa tatcttcaca taccatataa tatacatata    3660
tacatataca caaatgtact ttttaaacca acatcagcat acgtatatcc catcaggaaa    3720
cttagacttt tgggaattca tggtatgaaa accaaaacca aatgacaaca ttcgatttga    3780
tactcccgac ccatggtaaa gaataacaa attccaatat atctttcact ggactttccg     3840
aggcacattc cggttttctc catttcaaga aattgtcaaa ataaattga gatccggttt     3900 attacctcaa aaagaagaa gagaaattac aacattaatt tccgaaaagg cataaatgag     3960
aaatcatatt tcagcagaag aacacaaaag agttaagaac ccacagatca cacaacctct    4020
gtccatgtct gctttttaca cttttttaaa ataagtttct cctaaaaagt tatttcctat    4080
ttataataat ttccttagat ttatcttcct ggtctctctt ctgctgcttc cctctccccc    4140
ataactatca ctatttagaa ttttcaatgt ggaaaggaa gctgattgtt gaagcataaa     4200
tcccgggaga ccacttttgc attttcaaat aattaaatta aaccatagat acacacacac    4260
agttacttac tcttttaggg tttcccaata aatttatagt actttaatgt gtttcatgat    4320
attgatgata aatgctagct gtatttacaa tgggggctcc t                        4361
```

<210> SEQ ID NO 89
<211> LENGTH: 1510
<212> TYPE: DNA
<213> ORGANISM: artificial sequence
<220> FEATURE:
<223> OTHER INFORMATION: P9002 (prRD29a::m35S::oEnh::LexAGal4(GFP))

<400> SEQUENCE: 89

```
ggttgctatg gtagggacta tggggttttc ggattccggt ggaagtgagt ggggaggcag      60
tggcggaggt aagggagttc aagattctgg aactgaagat ttgggggtttt gcttttgaat    120 gtttgcgttt ttgtatgatg cctctgtttg tgaactttga tgtattttat ctttgtgtga    180
aaaagagatt gggttaataa aatatttgct ttttttggata agaaactctt ttagcggccc    240
attaataaag gttacaaatg caaaatcatg ttagcgtcag atatttaatt attcgaagat    300
gattgtgata gatttaaaat tatcctagtc aaaaagaaag agtaggttga gcagaaacag    360
tgacatctgt tgtttgtacc atacaaatta gtttagatta ttggttaaca tgttaaatgg    420
ctatgcatgt gacatttaga ccttatcgga attaatttgt agaattatta attaagatgt    480
tgattagttc aaacaaaaat tttatattaa aaaatgtaaa cgaatatttt gtatgttcag    540
tgaaagtaaa acaaattaaa ttaacaagaa acttatagaa gaaattttt actatttaag    600 agaagaaaa aaatctatca tttaatctga gtcctaaaaa ctgttatact taacagttaa     660
cgcatgattt gatggaggag ccatagatgc aattcaatca aactgaaatt tctgcaagaa    720
tctcaaacac ggagatctca aagtttgaaa gaaaatttat ttcttcgact caaaacaaac    780
ttacgaaatt taggtagaac ttatatacat tatattgtaa ttttttgtaa caaaatgttt    840
ttattattat tatagaattt tactggttaa attaaaatg aatagaaaag gtgaattaag     900
aggagagagg aggtaaacat tttcttctat tttttcatat tttcaggata aattattgta    960
aaagtttaca agatttccat ttgactagtg taaatgagga atattctcta gtaagatcat   1020
tatttcatct acttctttta tcttctacca gtagaggaat aaacaatatt tagctccttt   1080
gtaaatacaa attaatttc cttccttgaca tcattcaatt ttaattttac gtataaaata    1140
aaagatcata cctattagaa cgattaagga gaaatacaat tcgaatgaga aggatgtgcc   1200
```

```
gtttgttata ataaacagcc acacgacgta aacgtaaaat gaccacatga tgggccaata    1260
gacatggacc gactactaat aatagtaagt tacattttag gatggaataa atatcatacc    1320
gacatcagtt ttgaaagaaa agggaaaaaa agaaaaaata aataaaagat atactaccga    1380
catgagttcc aaaaagcaaa aaaaaagatc aagccgacac agacacgcgt agagagcaaa    1440
atgactttga cgtcacacca cgaaaacaga cgcttcatac gtgtcccttt atctctctca    1500
gtctctctat                                                          1510

<210> SEQ ID NO 90
<211> LENGTH: 2244
<212> TYPE: DNA
<213> ORGANISM: artificial sequence
<220> FEATURE:
<223> OTHER INFORMATION: P5290 (prSUC2::m35S::oEnh::LexAGal4(GFP))

<400> SEQUENCE: 90 aactagggt gcataatgat ggaacaaagc acaaatcttt taacgcaaac taactacaac     60
cttcttttgg ggtccccatc cccgacccta atgttttgga attaataaaa ctacaatcac    120
ttaccaaaaa ataaaagttc aaggccacta taatttctca tatgaaccta catttataaa    180
taaaatctgg tttcatatta atttcacaca ccaagttact ttctattatt aactgttata    240
atggaccatg aaatcatttg catatgaact gcaatgatac ataatccact tgttttgtg     300 ggagacattt accagatttc ggtaaattgg tattccccct tttatgtgat tggtcattga    360
tcattgttag tggccagaca tttgaactcc cgttttttg tctataagaa ttcggaaaca    420
tatagtatcc tttgaaaacg gagaaacaaa taacaatgtg gacaaactag atataatttc    480
aacacaagac tatgggaatg attttaccca ctaattataa tccgatcaca aggtttcaac    540
gaactagttt tccagatatc aaccaaattt actttggaat taaactaact taaaactaat    600
tggttgttcg taaatggtgc tttttttttt tgcggatgtt agtaaagggt tttatgtatt    660
ttatattatt agttatctgt tttcagtgtt atgttgtctc atccataaag tttatatgtt    720
ttttctttgc tctataactt atatatatat atgagtttac agttatattt atacatttca    780
gatacttgat cggcattttt tttggtaaaa aatatatgca tgaaaaactc aagtgtttct    840
tttttaagga atttttaaat ggtgattata tgaatataat catatgtata tccgtatata    900
tatgtagcca gatagttaat tatttggggg atatttgaat tattaatgtt ataatattct    960
ttcttttgac tcgtctggtt aaattaaaga acaaaaaaaa cacatacttt tactgtttta   1020
aaaggttaaa ttaacataat ttattgatta caagtgtcaa gtccatgaca ttgcatgtag   1080
gttcgagact tcagagataa cggaagagat cgataattgt gatcgtaaca tccagatatg   1140
tatgtttaat tttcatttag atgtggatca gagaagataa gtcaaactgt cttcataatt   1200
taagacaacc tcttttaata ttttcccaaa acatgtttta tgtaactact ttgcttatgt   1260
gattgcctga ggatactatt attctctgtc tttattctct tcacaccaca tttaaatagt   1320
ttaagagcat agaaattaat tattttcaaa aaggtgatta tatgcatgca aaatagcaca   1380
ccatttatgt ttatattttc aaattattta atacatttca atatttcata agtgtgattt   1440 ttttttttt tgtcaatttc ataagtgtga tttgtcattt gtattaaaca attgtatcgc    1500
gcagtacaaa taaacagtgg gagaggtgaa aatgcagtta taaaactgtc caataattta   1560
ctaacacatt taaatatcta aaagagtgt ttcaaaaaaa attctttga aataagaaaa     1620 gtgatagata tttttacgct ttcgtctgaa aataaaacaa taatagttta ttagaaaaat   1680
```

-continued

```
gttatcaccg aaaattattc tagtgccact cgctcggatc gaaattcgaa agttatattc    1740
tttctcttta cctaatataa aaatcacaag aaaaatcaat ccgaatatat ctatcaacat    1800
agtatatgcc cttacatatt gtttctgact tttctctatc cgaatttctc gcttcatggt    1860 tttttttttaa catattctca tttaattttc attactatta tataactaaa agatggaaat   1920
aaaataaagt gtctttgaga atcgaacgtc catatcagta agatagtttg tgtgaaggta    1980
aaatctaaaa gatttaagtt ccaaaaacag aaaataatat attacgctaa aaagaagaa     2040 ataattaaaa tacaaaacag aaaaaaataa tatacgacag acacgtgtca cgaagatacc    2100
ctacgctata gacacagctc tgttttctct tttctatgcc tcaaggctct cttaacttca    2160
ctgtctcctc ttcggataat cctatccttc tcttcctata aatacctctc cactcttcct    2220
cttcctccac cactacaacc acca                                           2244
```

<210> SEQ ID NO 91
<211> LENGTH: 1207
<212> TYPE: DNA
<213> ORGANISM: artificial sequence
<220> FEATURE:
<223> OTHER INFORMATION: P26707 (prAT5G62150::G1795) (G1795 is from A. thaliana)

<400> SEQUENCE: 91

```
tggtatatgc acgacaggac aaccgataca atgacagttg gttccaaaaa aaaagtttaa     60
tcctaaatat atgaataatc gaatcgatca ataacacgtt gacaaaaaac gaacaaataa    120
tcacactgat gaaccacttt ataatgaaca gagaattttg taatctgaaa attttgaaag    180
tcaagaggtt aatcaagtaa ttatagaaag gtagttgtaa cgttggcttt tgtggaacta    240
ataacttacg tgtctttaaa cggcggctac tttggaaggc tacgtttctt aatttgaacc    300
tcattttctc cattttcctt cgtttatacg atatctttt caaaaaagtg acccaataac     360
cacacatata acatatttag tataactttg aatataaacg aatcaatgat atctgaattt    420
tattttgatt ttgatcttga tttttgttgt tttttgtcga ggctattgcc ttgccacttt    480
ggatgaagga acccggctaa ggtaagaccc cctgcctaat attagcctcc ggcgaatttt    540
gcactcagaa attacattat gttatagttt tggaattta gtttaaattt gtaaaagtat     600
taaaacaatt ggtcaactat tatattaatt agctcaagag tgctttcaaa aacatatctt    660
aaatttaata agaaatatt ccaatatctt aaccagtact aaaagagaag atcagaaaat     720
ttcttataaa actttaatct aataaaatca tctacgactc taccattcaa tatttttttg    780
ttattgtttt atttacatat ttcttttaat atttacatat ctctttttcct ttttgctaaa   840 aaaaagttgg cataaaaatt actaaatttt aagcgtaaaa aaataaaatt aattattgtc    900
tattgccatt tttggaggat ggatatgatt tggaggaata gttaaagaaa gtgctaaaat    960
ctcctttagt gagtcacaac cgttgacctt caccgcaagg cacaagagac caagtctcta   1020
acccaacaca acacaaaacc cataaactga aaagactaac ctaccctatc ttgccatata   1080
aatccctctc gagcaacgca tgttaaataa acctaattta tacattcatt ctcaaagtca   1140
aaaggagaca gggagagaga gagagagaga gagaattcaa agcgtttttt ttttataaat   1200
taaaggc                                                             1207
```

<210> SEQ ID NO 92
<211> LENGTH: 1216
<212> TYPE: DNA
<213> ORGANISM: artificial sequence
<220> FEATURE:

<223> OTHER INFORMATION: P26708 (prAT5G24090::G1795) (G1795 is from A. thaliana)

<400> SEQUENCE: 92

| | | | | | |
|---|---|---|---|---|---|
| aaatggtcca | gttttggccc | aaatatttaa | caacatttgg | gttacgagta | tttgcccttt | 60 |
| acaaatggat | caacaatctc | cctggatcaa | tatttagtgg | ccggtttcat | gaatcaacat | 120 |
| attcttttt | ttttttgtc | taaagaatca | acatattcta | aatcaccaaa | acactttggt | 180 |
| caacaatttt | cgacaatata | tggaaattag | gttggattat | catgcgactt | ttttctgatt | 240 |
| aattttatgt | attttaatt | tacgatgaa | ttcggactac | taatttgtat | tatgataact | 300 |
| ttacattttc | catactactc | aagtccaagt | aaaatactat | tgtatatata | tctttggatt | 360 |
| ttacataaat | taatggggag | gcctaataaa | atatactcgg | agtatatcat | ttgactttga | 420 |
| aatttatcga | gtcaaatcaa | tgattgtatt | tttggtaaaa | acaattatta | tgaagacttt | 480 |
| gaaagttttt | aatgattta | atttcaaaaa | ttagtaaatg | ctggtctggt | tatccatcca | 540 |
| ttggaagaga | aataagacc | ttttcaaagc | tagttgataa | aaaaagttct | cggtcctatc | 600 |
| cctcatctta | taaagaaatt | attaatacgt | ttagggattc | aattcacaga | agatttaaaa | 660 |
| acaaatggaa | aataggatat | taccataata | attatggttc | aacaacaatt | tcgatttcta | 720 |
| atttgaataa | tggaaattta | gatcaaaaat | agttccgact | catagataaa | ttgaaatgtg | 780 |
| ccaaatgtca | cgtaaaccag | caagaggaca | aagtcaacac | cacaagagac | gacgacgagc | 840 |
| acagtgtgag | gttatgatat | ataccctctg | cgagactgcg | actgctatta | ctgatttgat | 900 |
| cccaagtttt | ttttttttt | ttgaaattta | ttttttcttt | atacacaatt | acatagtggt | 960 |
| aagagattct | agatggcttc | ttaatgtttg | agatttatat | ctagtttaag | taggaaagct | 1020 |
| atattatttg | aagaaagaaa | aaaacaacca | atcaaagtca | tgcaatgtgt | gtgagagaca | 1080 |
| ttataacata | catagataag | atataaaaat | taaagcaaac | aaaagtcata | ttttacttct | 1140 |
| tttataaaaa | aagaagttaa | gcaataacaa | acaaacacat | aaccacaaag | aagacaaaac | 1200 |
| atctttaacc | aaaaac | | | | | 1216 |

<210> SEQ ID NO 93
<211> LENGTH: 1199
<212> TYPE: DNA
<213> ORGANISM: artificial sequence
<220> FEATURE:
<223> OTHER INFORMATION: P26467 (AT1G35230::G1795) (G1795 is from A. thaliana)

<400> SEQUENCE: 93

| | | | | | |
|---|---|---|---|---|---|
| cttctaagaa | tagttgcaag | cctttaaata | ctccgacaaa | tctggcatta | gccgaaagat | 60 |
| attccaaact | caaaatcgga | tcagatagtg | tggtggtcta | attttacctg | gatcgggaga | 120 |
| tgtccactct | gtaccacctt | gatgcatttt | tactgatact | gatcagatca | accgatataa | 180 |
| tatatatata | aaaaagaaa | gttcgtccaa | aggaatcat | tattttctta | accaatagaa | 240 |
| tataggaaat | aataggataa | atctatatta | gtggacaggt | aatagaatgc | tttcattcac | 300 |
| attgaaatca | tattgtaata | agcacacttt | tcttatcaaa | aaaaaaggc | aaaaagaaat | 360 |
| ggccacgcaa | taaatcatt | agggtaagtt | gaattttggt | ccataatatt | ataaattaat | 420 |
| ttaatctcga | aagcttaatc | ttatgatctc | atgtgatctt | tattgaattt | acttacttcc | 480 |
| atagagtttt | gtattttgtc | taaggaaaga | aaaaaaagt | ctgccagctt | tggaacgccg | 540 |
| cccattcctc | tagactttct | tggaaacaac | gcgttgttct | tgttgggtc | gacgaagact | 600 |
| cactaaatcc | atccgacgac | tcagattta | tcttggcttc | ttttgatgtg | tacacatatc | 660 |

```
caccctgatt tgattcccaa agccaaaagc ctgaacaatg tagtgtagaa gaagtgacgg    720
gaaaaaacgg taatgaatcc acaatggata tttacagaaa gaaataaaat tatatagatt    780
atagagaagc aaaattatgc aaataatctt tatttaatac tattaaaaga gtagctgttg    840
gaaactataa caggtaattt aaaatatttt acaagttcaa catataataa ttttgaaatt    900
cagtccaaca taactatcag tatggaaata agccaaacaa attactcaaa ataagaaata    960
tgttttcaca ttattattta aacatttta gtcatttgtt tggcttattt ccaaaacgat    1020
atttatgttg gacttgtttt caaaagtatt atgttgaact tgtaaaaaaa atttatatag    1080
ctgttgaaat ttccaagaaa ataaggtttt acacctaaac ccttccacta tatatataaa    1140
ccccactttt gtctctatat ctttactaat ttcttaaacc ctctcaacaa tacgtaaca     1199
```

<210> SEQ ID NO 94
<211> LENGTH: 65
<212> TYPE: PRT
<213> ORGANISM: Arabidopsis thaliana
<220> FEATURE:
<223> OTHER INFORMATION: G1792 AP2 domain

<400> SEQUENCE: 94

Lys Gln Ala Arg Phe Arg Gly Val Arg Arg Pro Trp Gly Lys Phe
1               5                   10                  15

Ala Ala Glu Ile Arg Asp Pro Ser Arg Asn Gly Ala Arg Leu Trp Leu
                20                  25                  30

Gly Thr Phe Glu Thr Ala Glu Glu Ala Ala Arg Ala Tyr Asp Arg Ala
            35                  40                  45

Ala Phe Asn Leu Arg Gly His Leu Ala Ile Leu Asn Phe Pro Asn Glu
        50                  55                  60

Tyr
65

<210> SEQ ID NO 95
<211> LENGTH: 65
<212> TYPE: PRT
<213> ORGANISM: Glycine max
<220> FEATURE:
<223> OTHER INFORMATION: G3520 AP2 domain

<400> SEQUENCE: 95

Glu Glu Pro Arg Tyr Arg Gly Val Arg Arg Pro Trp Gly Lys Phe
1               5                   10                  15

Ala Ala Glu Ile Arg Asp Pro Ala Arg His Gly Ala Arg Val Trp Leu
                20                  25                  30

Gly Thr Phe Leu Thr Ala Glu Glu Ala Ala Arg Ala Tyr Asp Arg Ala
            35                  40                  45

Ala Tyr Glu Met Arg Gly Ala Leu Ala Val Leu Asn Phe Pro Asn Glu
        50                  55                  60

Tyr
65

<210> SEQ ID NO 96
<211> LENGTH: 65
<212> TYPE: PRT
<213> ORGANISM: Glycine max
<220> FEATURE:
<223> OTHER INFORMATION: G3519 AP2 domain

<400> SEQUENCE: 96

```
Cys Glu Val Arg Tyr Arg Gly Ile Arg Arg Pro Trp Gly Lys Phe
1               5                   10                  15

Ala Ala Glu Ile Arg Asp Pro Thr Arg Lys Gly Thr Arg Ile Trp Leu
            20                  25                  30

Gly Thr Phe Asp Thr Ala Glu Gln Ala Ala Arg Ala Tyr Asp Ala Ala
        35                  40                  45

Ala Phe His Phe Arg Gly His Arg Ala Ile Leu Asn Phe Pro Asn Glu
    50                  55                  60

Tyr
65

<210> SEQ ID NO 97
<211> LENGTH: 65
<212> TYPE: PRT
<213> ORGANISM: Glycine max
<220> FEATURE:
<223> OTHER INFORMATION: G3518 AP2 domain

<400> SEQUENCE: 97

Val Glu Val Arg Tyr Arg Gly Ile Arg Arg Pro Trp Gly Lys Phe
1               5                   10                  15

Ala Ala Glu Ile Arg Asp Pro Thr Arg Lys Gly Thr Arg Ile Trp Leu
            20                  25                  30

Gly Thr Phe Asp Thr Ala Glu Gln Ala Ala Arg Ala Tyr Asp Ala Ala
        35                  40                  45

Ala Phe His Phe Arg Gly His Arg Ala Ile Leu Asn Phe Pro Asn Glu
    50                  55                  60

Tyr
65

<210> SEQ ID NO 98
<211> LENGTH: 65
<212> TYPE: PRT
<213> ORGANISM: Medicago truncatula
<220> FEATURE:
<223> OTHER INFORMATION: G3735 AP2 domain

<400> SEQUENCE: 98

Asp Gln Ile Lys Tyr Arg Gly Ile Arg Arg Pro Trp Gly Lys Phe
1               5                   10                  15

Ala Ala Glu Ile Arg Asp Pro Thr Arg Lys Gly Thr Arg Ile Trp Leu
            20                  25                  30

Gly Thr Phe Asp Thr Ala Glu Gln Ala Ala Arg Ala Tyr Asp Ala Ala
        35                  40                  45

Ala Phe His Phe Arg Gly His Arg Ala Ile Leu Asn Phe Pro Asn Glu
    50                  55                  60

Tyr
65

<210> SEQ ID NO 99
<211> LENGTH: 65
<212> TYPE: PRT
<213> ORGANISM: Arabidopsis thaliana
<220> FEATURE:
<223> OTHER INFORMATION: G1791 AP2 domain

<400> SEQUENCE: 99

Asn Glu Met Lys Tyr Arg Gly Val Arg Lys Arg Pro Trp Gly Lys Tyr
1               5                   10                  15

Ala Ala Glu Ile Arg Asp Ser Ala Arg His Gly Ala Arg Val Trp Leu
```

```
                    20                  25                  30
Gly Thr Phe Asn Thr Ala Glu Asp Ala Ala Arg Ala Tyr Asp Arg Ala
            35                  40                  45
Ala Phe Gly Met Arg Gly Gln Arg Ala Ile Leu Asn Phe Pro His Glu
        50                  55                  60
Tyr
65

<210> SEQ ID NO 100
<211> LENGTH: 65
<212> TYPE: PRT
<213> ORGANISM: Oryza sativa
<220> FEATURE:
<223> OTHER INFORMATION: G3383 AP2 domain

<400> SEQUENCE: 100

Thr Ala Thr Lys Tyr Arg Gly Val Arg Arg Pro Trp Gly Lys Phe
1               5                   10                  15

Ala Ala Glu Ile Arg Asp Pro Glu Arg Gly Ala Arg Val Trp Leu
                20                  25                  30

Gly Thr Phe Asp Thr Ala Glu Glu Ala Ala Arg Ala Tyr Asp Arg Ala
            35                  40                  45

Ala Tyr Ala Gln Arg Gly Ala Ala Ala Val Leu Asn Phe Pro Ala Ala
        50                  55                  60

Ala
65

<210> SEQ ID NO 101
<211> LENGTH: 65
<212> TYPE: PRT
<213> ORGANISM: Oryza sativa
<220> FEATURE:
<223> OTHER INFORMATION: G3380 AP2 domain

<400> SEQUENCE: 101

Glu Thr Thr Lys Tyr Arg Gly Val Arg Arg Pro Ser Gly Lys Phe
1               5                   10                  15

Ala Ala Glu Ile Arg Asp Ser Ser Arg Gln Ser Val Arg Val Trp Leu
                20                  25                  30

Gly Thr Phe Asp Thr Ala Glu Glu Ala Ala Arg Ala Tyr Asp Arg Ala
            35                  40                  45

Ala Tyr Ala Met Arg Gly His Leu Ala Val Leu Asn Phe Pro Ala Glu
        50                  55                  60

Ala
65

<210> SEQ ID NO 102
<211> LENGTH: 65
<212> TYPE: PRT
<213> ORGANISM: Arabidopsis thaliana
<220> FEATURE:
<223> OTHER INFORMATION: G30 AP2 domain

<400> SEQUENCE: 102

Glu Gln Gly Lys Tyr Arg Gly Val Arg Arg Pro Trp Gly Lys Tyr
1               5                   10                  15

Ala Ala Glu Ile Arg Asp Ser Arg Lys His Gly Glu Arg Val Trp Leu
                20                  25                  30

Gly Thr Phe Asp Thr Ala Glu Asp Ala Ala Arg Ala Tyr Asp Arg Ala
            35                  40                  45
```

```
Ala Tyr Ser Met Arg Gly Lys Ala Ala Ile Leu Asn Phe Pro His Glu
    50                  55                  60

Tyr
65

<210> SEQ ID NO 103
<211> LENGTH: 65
<212> TYPE: PRT
<213> ORGANISM: Oryza sativa
<220> FEATURE:
<223> OTHER INFORMATION: G3381 AP2 domain

<400> SEQUENCE: 103

Leu Val Ala Lys Tyr Arg Gly Val Arg Arg Pro Trp Gly Lys Phe
1                5                  10                  15

Ala Ala Glu Ile Arg Asp Ser Ser Arg His Gly Val Arg Val Trp Leu
                20                  25                  30

Gly Thr Phe Asp Thr Ala Glu Ala Ala Arg Ala Tyr Asp Arg Ser
                35                  40                  45

Ala Tyr Ser Met Arg Gly Ala Asn Ala Val Leu Asn Phe Pro Ala Asp
    50                  55                  60

Ala
65

<210> SEQ ID NO 104
<211> LENGTH: 65
<212> TYPE: PRT
<213> ORGANISM: Oryza sativa
<220> FEATURE:
<223> OTHER INFORMATION: G3737 AP2 domain

<400> SEQUENCE: 104

Ala Ala Ser Lys Tyr Arg Gly Val Arg Arg Pro Trp Gly Lys Phe
1                5                  10                  15

Ala Ala Glu Ile Arg Asp Pro Glu Arg Gly Gly Ser Arg Val Trp Leu
                20                  25                  30

Gly Thr Phe Asp Thr Ala Glu Ala Ala Arg Ala Tyr Asp Arg Ala
                35                  40                  45

Ala Phe Ala Met Lys Gly Ala Met Ala Val Leu Asn Phe Pro Gly Arg
    50                  55                  60

Thr
65

<210> SEQ ID NO 105
<211> LENGTH: 65
<212> TYPE: PRT
<213> ORGANISM: Oryza sativa
<220> FEATURE:
<223> OTHER INFORMATION: G3515 AP2 domain

<400> SEQUENCE: 105

Ser Ser Ser Ser Tyr Arg Gly Val Arg Lys Arg Pro Trp Gly Lys Phe
1                5                  10                  15

Ala Ala Glu Ile Arg Asp Pro Glu Arg Gly Gly Ala Arg Val Trp Leu
                20                  25                  30

Gly Thr Phe Asp Thr Ala Glu Ala Ala Arg Ala Tyr Asp Arg Ala
                35                  40                  45

Ala Phe Ala Met Lys Gly Ala Thr Ala Met Leu Asn Phe Pro Gly Asp
    50                  55                  60
```

His
65

<210> SEQ ID NO 106
<211> LENGTH: 65
<212> TYPE: PRT
<213> ORGANISM: Zea mays
<220> FEATURE:
<223> OTHER INFORMATION: G3516 AP2 domain

<400> SEQUENCE: 106

Lys Glu Gly Lys Tyr Arg Gly Val Arg Lys Arg Pro Trp Gly Lys Phe
1               5                   10                  15

Ala Ala Glu Ile Arg Asp Pro Glu Arg Gly Gly Ser Arg Val Trp Leu
            20                  25                  30

Gly Thr Phe Asp Thr Ala Glu Ala Ala Arg Ala Tyr Asp Arg Ala
        35                  40                  45

Ala Phe Ala Met Lys Gly Ala Thr Ala Val Leu Asn Phe Pro Ala Ser
    50                  55                  60

Gly
65

<210> SEQ ID NO 107
<211> LENGTH: 65
<212> TYPE: PRT
<213> ORGANISM: Arabidopsis thaliana
<220> FEATURE:
<223> OTHER INFORMATION: G1795 AP2 domain

<400> SEQUENCE: 107

Glu His Gly Lys Tyr Arg Gly Val Arg Arg Arg Pro Trp Gly Lys Tyr
1               5                   10                  15

Ala Ala Glu Ile Arg Asp Ser Arg Lys His Gly Glu Arg Val Trp Leu
            20                  25                  30

Gly Thr Phe Asp Thr Ala Glu Ala Ala Arg Ala Tyr Asp Gln Ala
        35                  40                  45

Ala Tyr Ser Met Arg Gly Gln Ala Ala Ile Leu Asn Phe Pro His Glu
    50                  55                  60

Tyr
65

<210> SEQ ID NO 108
<211> LENGTH: 65
<212> TYPE: PRT
<213> ORGANISM: Zea mays
<220> FEATURE:
<223> OTHER INFORMATION: G3794 AP2 domain

<400> SEQUENCE: 108

Glu Pro Thr Lys Tyr Arg Gly Val Arg Arg Arg Pro Ser Gly Lys Phe
1               5                   10                  15

Ala Ala Glu Ile Arg Asp Ser Ser Arg Gln Ser Val Arg Met Trp Leu
            20                  25                  30

Gly Thr Phe Asp Thr Ala Glu Ala Ala Arg Ala Tyr Asp Arg Ala
        35                  40                  45

Ala Tyr Ala Met Arg Gly Gln Ile Ala Val Leu Asn Phe Pro Ala Glu
    50                  55                  60

Ala
65

```
<210> SEQ ID NO 109
<211> LENGTH: 65
<212> TYPE: PRT
<213> ORGANISM: Zea mays
<220> FEATURE:
<223> OTHER INFORMATION: G3517 AP2 domain

<400> SEQUENCE: 109
```

Glu Pro Thr Lys Tyr Arg Gly Val Arg Arg Pro Trp Gly Lys Tyr
1               5                   10                  15

Ala Ala Glu Ile Arg Asp Ser Ser Arg His Gly Val Arg Ile Trp Leu
            20                  25                  30

Gly Thr Phe Asp Thr Ala Glu Ala Ala Arg Ala Tyr Asp Arg Ser
            35                  40                  45

Ala Asn Ser Met Arg Gly Ala Asn Ala Val Leu Asn Phe Pro Glu Asp
        50                  55                  60

Ala
65

```
<210> SEQ ID NO 110
<211> LENGTH: 65
<212> TYPE: PRT
<213> ORGANISM: Zea mays
<220> FEATURE:
<223> OTHER INFORMATION: G3739 AP2 domain

<400> SEQUENCE: 110
```

Glu Pro Thr Lys Tyr Arg Gly Val Arg Arg Pro Trp Gly Lys Tyr
1               5                   10                  15

Ala Ala Glu Ile Arg Asp Ser Ser Arg His Gly Val Arg Ile Trp Leu
            20                  25                  30

Gly Thr Phe Asp Thr Ala Glu Ala Ala Arg Ala Tyr Asp Arg Ser
            35                  40                  45

Ala Tyr Ser Met Arg Gly Ala Asn Ala Val Leu Asn Phe Pro Glu Asp
        50                  55                  60

Ala
65

```
<210> SEQ ID NO 111
<211> LENGTH: 65
<212> TYPE: PRT
<213> ORGANISM: Triticum aestivum
<220> FEATURE:
<223> OTHER INFORMATION: G3736 AP2 domain

<400> SEQUENCE: 111
```

Glu Pro Thr Lys Tyr Arg Gly Val Arg Arg Pro Trp Gly Lys Phe
1               5                   10                  15

Ala Ala Glu Ile Arg Asp Ser Ser Arg His Gly Val Arg Met Trp Leu
            20                  25                  30

Gly Thr Phe Asp Thr Ala Glu Ala Ala Arg Ala Tyr Asp Arg Ser
            35                  40                  45

Ala Tyr Ser Met Arg Gly Arg Asn Ala Val Leu Asn Phe Pro Asp Arg
        50                  55                  60

Ala
65

```
<210> SEQ ID NO 112
<211> LENGTH: 16
<212> TYPE: PRT
<213> ORGANISM: Arabidopsis thaliana
```

```
<220> FEATURE:
<223> OTHER INFORMATION: G1792 EDLL domain

<400> SEQUENCE: 112

Val Phe Glu Phe Glu Tyr Leu Asp Asp Lys Val Leu Glu Glu Leu Leu
1               5                   10                  15

<210> SEQ ID NO 113
<211> LENGTH: 16
<212> TYPE: PRT
<213> ORGANISM: Glycine max
<220> FEATURE:
<223> OTHER INFORMATION: G3520 EDLL domain

<400> SEQUENCE: 113

Val Ile Glu Phe Glu Cys Leu Asp Asp Lys Leu Leu Glu Asp Leu Leu
1               5                   10                  15

<210> SEQ ID NO 114
<211> LENGTH: 16
<212> TYPE: PRT
<213> ORGANISM: Glycine max
<220> FEATURE:
<223> OTHER INFORMATION: G3519 EDLL domain

<400> SEQUENCE: 114

Thr Phe Glu Leu Glu Tyr Leu Asp Asn Lys Leu Leu Glu Glu Leu Leu
1               5                   10                  15

<210> SEQ ID NO 115
<211> LENGTH: 16
<212> TYPE: PRT
<213> ORGANISM: Glycine max
<220> FEATURE:
<223> OTHER INFORMATION: G3518 EDLL domain

<400> SEQUENCE: 115

Thr Phe Glu Leu Glu Tyr Phe Asp Asn Lys Leu Leu Glu Glu Leu Leu
1               5                   10                  15

<210> SEQ ID NO 116
<211> LENGTH: 14
<212> TYPE: PRT
<213> ORGANISM: Medicago truncatula
<220> FEATURE:
<223> OTHER INFORMATION: G3735 EDLL domain

<400> SEQUENCE: 116

Glu Leu Glu Phe Leu Asp Asn Lys Leu Leu Gln Glu Leu Leu
1               5                   10

<210> SEQ ID NO 117
<211> LENGTH: 16
<212> TYPE: PRT
<213> ORGANISM: Arabidopsis thaliana
<220> FEATURE:
<223> OTHER INFORMATION: G1791 EDLL domain

<400> SEQUENCE: 117

Val Ile Glu Phe Glu Tyr Leu Asp Asp Ser Leu Leu Glu Glu Leu Leu
1               5                   10                  15

<210> SEQ ID NO 118
<211> LENGTH: 16
<212> TYPE: PRT
<213> ORGANISM: Oryza sativa
<220> FEATURE:
```

<223> OTHER INFORMATION: G3383 EDLL domain

<400> SEQUENCE: 118

Lys Ile Glu Phe Glu Tyr Leu Asp Asp Lys Val Leu Asp Asp Leu Leu
1               5                   10                  15

<210> SEQ ID NO 119
<211> LENGTH: 16
<212> TYPE: PRT
<213> ORGANISM: Oryza sativa
<220> FEATURE:
<223> OTHER INFORMATION: G3380 EDLL domain

<400> SEQUENCE: 119

Val Ile Glu Leu Glu Cys Leu Asp Asp Gln Val Leu Gln Glu Met Leu
1               5                   10                  15

<210> SEQ ID NO 120
<211> LENGTH: 16
<212> TYPE: PRT
<213> ORGANISM: Arabidopsis thaliana
<220> FEATURE:
<223> OTHER INFORMATION: G30 EDLL domain

<400> SEQUENCE: 120

Val Phe Glu Phe Glu Tyr Leu Asp Asp Ser Val Leu Asp Glu Leu Leu
1               5                   10                  15

<210> SEQ ID NO 121
<211> LENGTH: 16
<212> TYPE: PRT
<213> ORGANISM: Oryza sativa
<220> FEATURE:
<223> OTHER INFORMATION: G3381 EDLL domain

<400> SEQUENCE: 121

Pro Ile Glu Phe Glu Tyr Leu Asp Asp His Val Leu Gln Glu Met Leu
1               5                   10                  15

<210> SEQ ID NO 122
<211> LENGTH: 16
<212> TYPE: PRT
<213> ORGANISM: Oryza sativa
<220> FEATURE:
<223> OTHER INFORMATION: G3737 EDLL domain

<400> SEQUENCE: 122

Lys Val Glu Leu Val Tyr Leu Asp Asp Lys Val Leu Asp Glu Leu Leu
1               5                   10                  15

<210> SEQ ID NO 123
<211> LENGTH: 16
<212> TYPE: PRT
<213> ORGANISM: Oryza sativa
<220> FEATURE:
<223> OTHER INFORMATION: G3515 EDLL domain

<400> SEQUENCE: 123

Lys Val Glu Leu Glu Cys Leu Asp Asp Lys Val Leu Glu Asp Leu Leu
1               5                   10                  15

<210> SEQ ID NO 124
<211> LENGTH: 16
<212> TYPE: PRT
<213> ORGANISM: Zea mays
<220> FEATURE:
<223> OTHER INFORMATION: G3516 EDLL domain

```
<400> SEQUENCE: 124

Lys Val Glu Leu Glu Cys Leu Asp Asp Arg Val Leu Glu Glu Leu Leu
1               5                   10                  15

<210> SEQ ID NO 125
<211> LENGTH: 16
<212> TYPE: PRT
<213> ORGANISM: Arabidopsis thaliana
<220> FEATURE:
<223> OTHER INFORMATION: G1795 EDLL domain

<400> SEQUENCE: 125

Val Phe Glu Phe Glu Tyr Leu Asp Asp Ser Val Leu Glu Glu Leu Leu
1               5                   10                  15

<210> SEQ ID NO 126
<211> LENGTH: 16
<212> TYPE: PRT
<213> ORGANISM: Zea mays
<220> FEATURE:
<223> OTHER INFORMATION: G3794 EDLL domain

<400> SEQUENCE: 126

Val Ile Glu Leu Glu Cys Leu Asp Asp Gln Val Leu Gln Glu Met Leu
1               5                   10                  15

<210> SEQ ID NO 127
<211> LENGTH: 16
<212> TYPE: PRT
<213> ORGANISM: Zea mays
<220> FEATURE:
<223> OTHER INFORMATION: G3517 EDLL domain

<400> SEQUENCE: 127

Val Ile Glu Phe Glu Tyr Leu Asp Asp Glu Val Leu Gln Glu Met Leu
1               5                   10                  15

<210> SEQ ID NO 128
<211> LENGTH: 16
<212> TYPE: PRT
<213> ORGANISM: Zea mays
<220> FEATURE:
<223> OTHER INFORMATION: G3739 EDLL domain

<400> SEQUENCE: 128

Val Ile Glu Leu Glu Tyr Leu Asp Asp Glu Val Leu Gln Glu Met Leu
1               5                   10                  15

<210> SEQ ID NO 129
<211> LENGTH: 16
<212> TYPE: PRT
<213> ORGANISM: Triticum aestivum
<220> FEATURE:
<223> OTHER INFORMATION: G3736 EDLL domain

<400> SEQUENCE: 129

Val Ile Glu Phe Glu Tyr Leu Asp Asp Asp Val Leu Gln Ser Met Leu
1               5                   10                  15
```